US012773496B2

(12) United States Patent
Lanigan et al.

(10) Patent No.: US 12,773,496 B2
(45) Date of Patent: Oct. 27, 2026

(54) INFUSION SET AND INSERTER ASSEMBLY APPARATUSES, SYSTEMS, AND METHODS

(71) Applicant: DEKA Products Limited Partnership, Manchester, NH (US)

(72) Inventors: Richard J. Lanigan, Concord, NH (US); David D. B. Cannan, Manchester, NH (US); Yashi D. Sanghvi, Nashua, NH (US); Cornelis Plomp, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 653 days.

(21) Appl. No.: 18/237,601

(22) Filed: Aug. 24, 2023

(65) Prior Publication Data

US 2024/0066217 A1 Feb. 29, 2024

Related U.S. Application Data

(60) Provisional application No. 63/401,279, filed on Aug. 26, 2022.

(51) Int. Cl.
*A61M 5/158* (2006.01)
*A61M 5/14* (2006.01)

(52) U.S. Cl.
CPC .......... *A61M 5/158* (2013.01); *A61M 5/1413* (2013.01); *A61M 2207/10* (2013.01); *A61M 2210/04* (2013.01)

(58) Field of Classification Search
CPC .. A61M 2005/1585; A61M 2005/1586; A61M 2005/1587; A61M 5/158;
(Continued)

(56) References Cited

U.S. PATENT DOCUMENTS

| | | | |
|---|---|---|---|
| 1,934,046 | A | 11/1933 | Demarchi |
| 2,512,568 | A | 6/1950 | Saffir |

(Continued)

FOREIGN PATENT DOCUMENTS

| | | |
|---|---|---|
| CA | 225208 | 10/2023 |
| CA | 219028 | 1/2025 |

(Continued)

OTHER PUBLICATIONS

MiniMed Mio Advance Infusion Set, announced in YouTube on May 7, 2019 [Online]. [Retrieved on Aug. 2, 2023], Available from the internet URL:https://www.youtube.com/watch?v=2For6SAvxRQ (Year: 2022).

(Continued)

*Primary Examiner* — Jason E Flick
(74) *Attorney, Agent, or Firm* — Toohey Law Group, LLC; Kevin D. Mandro

(57) ABSTRACT

A care assembly placement system may comprise an inserter including a port with a coupling interface and a receptacle body including tracks partially swept around the axis of the port. The system may further comprise a cartridge including a retainer with a care assembly coupled thereto and a sharp holder having a first end bearing a sharp. The retainer may include projections. The sharp holder may include a coupling interface opposite the first end. When the cartridge is placed in an aligned position relative the receptacle body and rotated to a coupled state, the projections may each displace along a ramp of a respective track in a first displacement range translationally driving the cartridge to a position in which sharp holder and port coupling interfaces are aligned. The sharp holder coupling interface may be rotated into engagement with the port coupling interface in a second displacement range of the cartridge.

23 Claims, 156 Drawing Sheets

(58) Field of Classification Search
CPC .... A61M 2005/14252; A61M 39/1011; A61M 5/3287; A61M 39/20; A61M 2210/04; A61M 2207/10; A61M 5/1413; A61M 2005/1581
See application file for complete search history.

(56) References Cited

U.S. PATENT DOCUMENTS

| | | | |
|---|---|---|---|
| 2,743,723 | A | 5/1956 | Hein |
| 2,945,496 | A | 7/1960 | Fosdal |
| 3,122,138 | A | 2/1964 | Geary |
| 3,856,009 | A | 12/1974 | Winnie |
| 4,284,077 | A | 8/1981 | Wagner |
| 4,299,219 | A | 11/1981 | Norris, Jr. |
| D265,590 | S | 7/1982 | Gauvry |
| 4,723,940 | A | 2/1988 | Wiegerinck |
| 4,755,173 | A | 7/1988 | Konopka et al. |
| 4,838,863 | A | 6/1989 | Allard et al. |
| 5,176,662 | A | 1/1993 | Bartholomew et al. |
| 5,257,980 | A | 11/1993 | Van Antwerp et al. |
| 5,320,607 | A | 6/1994 | Ishibashi |
| 5,395,379 | A | 3/1995 | Deutchman |
| D363,542 | S | 10/1995 | Parris et al. |
| 5,478,315 | A | 12/1995 | Brothers et al. |
| 5,522,803 | A | 6/1996 | Teissen-Simony |
| 5,584,813 | A | 12/1996 | Livingston et al. |
| 5,743,891 | A | 4/1998 | Tolkoff et al. |
| D395,501 | S | 6/1998 | Erskine et al. |
| 5,782,871 | A | 7/1998 | Fujiwara et al. |
| D403,398 | S | 12/1998 | Guala et al. |
| 5,851,197 | A | 12/1998 | Marano et al. |
| D405,882 | S | 2/1999 | Yale |
| 5,879,311 | A | 3/1999 | Duchon et al. |
| 5,968,011 | A | 10/1999 | Larsen et al. |
| D416,086 | S | 11/1999 | Parris et al. |
| 5,980,506 | A | 11/1999 | Mathiasen |
| D417,733 | S | 12/1999 | Howell et al. |
| 6,017,328 | A | 1/2000 | Fischell et al. |
| 6,056,718 | A | 5/2000 | Funderburk et al. |
| 6,086,545 | A | 7/2000 | Roe |
| 6,086,575 | A | 7/2000 | Mejslov |
| 6,093,172 | A | 7/2000 | Funderburk et al. |
| 6,123,690 | A | 9/2000 | Mejslov |
| 6,183,446 | B1 | 2/2001 | Jeanbourquin |
| 6,254,580 | B1 | 7/2001 | Svedman |
| 6,261,272 | B1 | 7/2001 | Gross et al. |
| 6,293,925 | B1 | 9/2001 | Safabash et al. |
| 6,302,866 | B1 | 10/2001 | Marggi |
| 6,355,021 | B1 | 3/2002 | Nielsen et al. |
| 6,379,339 | B1 | 4/2002 | Klitgaard et al. |
| 6,461,329 | B1 | 10/2002 | Van Antwerp et al. |
| D465,845 | S | 11/2002 | Swenson |
| D465,846 | S | 11/2002 | Hwang |
| 6,482,176 | B1 | 11/2002 | Wich |
| D472,630 | S | 4/2003 | Douglas et al. |
| 6,558,402 | B1 | 5/2003 | Chelak et al. |
| D476,418 | S | 6/2003 | Sprieck et al. |
| 6,579,267 | B2 | 6/2003 | Lynch et al. |
| 6,582,403 | B1 | 6/2003 | Bierman et al. |
| 6,589,229 | B1 | 7/2003 | Connelly et al. |
| 6,605,058 | B1 | 8/2003 | Wich |
| 6,607,509 | B2 | 8/2003 | Bobroff et al. |
| D484,242 | S | 12/2003 | Wilkinson |
| D484,976 | S | 1/2004 | Wilkinson |
| 6,685,674 | B2 | 2/2004 | Douglas et al. |
| 6,699,218 | B2 | 3/2004 | Flaherty et al. |
| D488,230 | S | 4/2004 | Ignotz et al. |
| 6,736,797 | B1 | 5/2004 | Larsen et al. |
| 6,749,589 | B1 | 6/2004 | Douglas et al. |
| 6,830,562 | B2 | 12/2004 | Mogensen et al. |
| 6,835,190 | B2 | 12/2004 | Nguyen |
| 6,887,417 | B1 | 5/2005 | Gawreluk et al. |
| D507,833 | S | 7/2005 | Coss |
| 6,923,791 | B2 | 8/2005 | Douglas |
| 6,926,694 | B2 | 8/2005 | Marano-Ford et al. |
| 6,949,084 | B2 | 9/2005 | Marggi et al. |
| 6,994,691 | B2 | 2/2006 | Ejlersen |
| 7,056,302 | B2 | 6/2006 | Douglas |
| 7,060,054 | B2 | 6/2006 | Nissels |
| 7,066,885 | B2 | 6/2006 | Erickson et al. |
| 7,066,922 | B2 | 6/2006 | Angel et al. |
| 7,070,580 | B2 | 7/2006 | Nielsen |
| 7,083,597 | B2 | 8/2006 | Lynch et al. |
| 7,115,111 | B2 | 10/2006 | Haindl |
| 7,147,623 | B2 | 12/2006 | Mathiasen |
| 7,147,624 | B2 | 12/2006 | Hirsiger et al. |
| 7,214,207 | B2 | 5/2007 | Lynch et al. |
| D547,859 | S | 7/2007 | Choi |
| 7,258,678 | B2 | 8/2007 | Wilkinson |
| D554,253 | S | 10/2007 | Kornerup |
| 7,303,543 | B1 | 12/2007 | Maule et al. |
| 7,303,544 | B2 | 12/2007 | Bütikofer et al. |
| 7,309,326 | B2 | 12/2007 | Fangrow, Jr. |
| 7,338,465 | B2 | 3/2008 | Patton |
| 7,377,908 | B2 | 5/2008 | Buetikofer et al. |
| 7,407,493 | B2 | 8/2008 | Cane’ |
| D576,267 | S | 9/2008 | Mogensen et al. |
| 7,431,876 | B2 | 10/2008 | Mejlhede et al. |
| 7,455,663 | B2 | 11/2008 | Bikovsky |
| 7,481,794 | B2 | 1/2009 | Jensen |
| 7,494,481 | B2 | 2/2009 | Moberg et al. |
| 7,510,543 | B2 | 3/2009 | Michels et al. |
| 7,513,887 | B2 | 4/2009 | Halseth et al. |
| 7,520,867 | B2 | 4/2009 | Bowman et al. |
| 7,524,309 | B2 | 4/2009 | McConnell et al. |
| D592,310 | S | 5/2009 | Leatt |
| 7,549,976 | B2 | 6/2009 | Michels et al. |
| 7,569,034 | B2 | 8/2009 | Lynch et al. |
| 7,578,807 | B2 | 8/2009 | Wyss et al. |
| D600,341 | S | 9/2009 | Loerwald |
| 7,585,287 | B2 | 9/2009 | Bresina et al. |
| 7,594,902 | B2 | 9/2009 | Horisberger et al. |
| D604,836 | S | 11/2009 | Crawford et al. |
| D604,837 | S | 11/2009 | Crawford et al. |
| D604,838 | S | 11/2009 | Crawford et al. |
| D604,839 | S | 11/2009 | Crawford et al. |
| 7,621,395 | B2 | 11/2009 | Mogensen et al. |
| D605,287 | S | 12/2009 | Crawford et al. |
| D605,300 | S | 12/2009 | Mazzarolo |
| 7,648,494 | B2 | 1/2010 | Kornerup et al. |
| D609,804 | S | 2/2010 | Uchida et al. |
| D609,806 | S | 2/2010 | Uchida et al. |
| 7,666,150 | B2 | 2/2010 | Douglas et al. |
| 7,678,079 | B2 | 3/2010 | Shermer et al. |
| 7,682,338 | B2 | 3/2010 | Griffin |
| 7,699,807 | B2 | 4/2010 | Faust et al. |
| 7,699,808 | B2 | 4/2010 | Marrs et al. |
| 7,704,229 | B2 | 4/2010 | Moberg et al. |
| D616,094 | S | 5/2010 | Boone, III et al. |
| 7,731,691 | B2 | 6/2010 | Cote et al. |
| 7,736,338 | B2 | 6/2010 | Kavazov et al. |
| 7,740,600 | B2 | 6/2010 | Slatkine et al. |
| 7,758,516 | B2 | 7/2010 | Perez |
| 7,766,867 | B2 | 8/2010 | Lynch et al. |
| 7,766,874 | B2 | 8/2010 | Liniger |
| 7,771,393 | B2 | 8/2010 | Liniger et al. |
| 7,789,857 | B2 | 9/2010 | Moberg et al. |
| 7,815,607 | B2 | 10/2010 | Rutti et al. |
| D627,459 | S | 11/2010 | Uchida et al. |
| 7,841,991 | B2 | 11/2010 | Douglas et al. |
| 7,850,652 | B2 | 12/2010 | Liniger et al. |
| 7,850,658 | B2 | 12/2010 | Faust et al. |
| 7,867,199 | B2 | 1/2011 | Mogensen et al. |
| 7,867,200 | B2 | 1/2011 | Mogensen et al. |
| 7,879,010 | B2 | 2/2011 | Hunn et al. |
| 7,887,737 | B2 | 2/2011 | Mejlhede et al. |
| 7,892,216 | B2 | 2/2011 | Fangrow, Jr. |
| 7,896,844 | B2 | 3/2011 | Thalmann et al. |
| 7,901,382 | B2 | 3/2011 | Daily et al. |
| 7,909,791 | B2 | 3/2011 | Liniger et al. |
| 7,931,615 | B2 | 4/2011 | Fangrow, Jr. |
| 7,935,104 | B2 | 5/2011 | Yodfat et al. |
| 7,946,984 | B2 | 5/2011 | Brister et al. |
| 7,951,080 | B2 | 5/2011 | Taub |

(56) References Cited

U.S. PATENT DOCUMENTS 7,951,122 B2 5/2011 Shekalim
7,955,297 B2 6/2011 Radmer
7,981,085 B2 7/2011 Ethelfeld
7,985,199 B2 7/2011 Kornerup et al.
7,985,203 B2 7/2011 Haueter et al.
7,993,306 B2 8/2011 Marrs et al.
8,002,752 B2 8/2011 Yodfat et al.
8,012,126 B2 9/2011 Tipsmark et al.
8,025,658 B2 9/2011 Chong et al.
8,043,262 B2 10/2011 Streit et al.
8,043,317 B2 10/2011 Fritz et al.
8,062,250 B2 11/2011 Mogensen et al.
8,062,253 B2 11/2011 Nielsen et al.
8,152,771 B2 4/2012 Mogensen et al.
8,157,773 B2 4/2012 Tashjian
8,162,892 B2 4/2012 Mogensen et al.
8,167,841 B2 5/2012 Teisen-Simony et al.
8,172,803 B2 5/2012 Morrissey et al.
8,172,805 B2 5/2012 Mogensen et al.
8,221,355 B2 7/2012 Kornerup et al.
8,226,614 B2 7/2012 Turner et al.
8,246,588 B2 8/2012 Gyrn
8,262,618 B2 9/2012 Scheurer
8,287,516 B2 10/2012 Kornerup et al.
8,292,849 B2 10/2012 Bobroff et al.
8,298,172 B2 10/2012 Nielsen et al.
8,303,545 B2 11/2012 Schraga
8,303,549 B2 11/2012 Mejlhede et al.
8,317,759 B2 11/2012 Moberg et al.
8,323,250 B2 12/2012 Chong et al.
8,343,115 B2 1/2013 Lynch et al.
8,409,145 B2 4/2013 Raymond et al.
8,430,850 B2 4/2013 Gyrn et al.
8,435,211 B2 5/2013 Yodfat et al.
8,439,838 B2 5/2013 Mogensen et al.
8,449,479 B2 5/2013 Radzuinas et al.
D685,496 S 7/2013 Lee
8,475,410 B2 7/2013 Kaufmann et al.
8,486,003 B2 7/2013 Nielsen
8,506,585 B2 8/2013 Kube
8,529,515 B2 9/2013 Woehr et al.
8,551,047 B2 10/2013 Burns
8,562,567 B2 10/2013 Gundberg
8,571,624 B2 10/2013 Stafford
D693,114 S 11/2013 Lemanski
8,579,863 B2 11/2013 Scherr
8,617,126 B2 12/2013 Gross et al.
8,628,498 B2 1/2014 Safabash et al.
8,641,674 B2 2/2014 Bobroff et al.
8,679,132 B2 3/2014 Deck
8,690,775 B2 4/2014 Brister et al.
8,696,570 B2 4/2014 Yodfat et al.
8,709,033 B2 4/2014 Kim et al.
8,715,232 B2 5/2014 Yodfat et al.
8,734,391 B2 5/2014 Yodfat et al.
8,740,851 B2 6/2014 Ethelfeld
8,747,363 B2 6/2014 Neilsen et al.
D709,186 S 7/2014 Boaz et al.
8,790,311 B2 7/2014 Gryn
8,795,230 B2 8/2014 Schoonmaker et al.
8,795,234 B2 8/2014 Kadamus et al.
8,795,309 B2 8/2014 Lacy
D713,957 S 9/2014 Woehr et al.
8,858,498 B2 10/2014 West
8,882,710 B2 11/2014 Chong et al.
8,882,711 B2 11/2014 Saulenas et al.
D720,466 S 12/2014 Edding
8,900,190 B2 12/2014 Chong et al.
8,920,381 B2 12/2014 Ejlersen
8,945,050 B2 2/2015 Wei
8,945,057 B2 2/2015 Gyrn et al.
8,956,330 B2 2/2015 Fangrow, Jr.
8,961,469 B2 2/2015 Sonderegger et al.
9,011,388 B2 4/2015 Schwartz et al.
9,101,389 B2 8/2015 Havel et al.
9,119,913 B2 9/2015 Lanigan
9,211,379 B2 12/2015 Mejlhede et al.
9,215,992 B2 12/2015 Donnay et al.
9,220,833 B2 12/2015 Robert et al.
9,220,838 B2 12/2015 Soma et al.
D747,456 S 1/2016 Sonderegger et al.
D747,459 S 1/2016 Sonderegger et al.
D747,472 S 1/2016 Bradley et al.
9,227,013 B2 1/2016 Lacy
9,238,123 B2 1/2016 Weadock et al.
9,254,373 B2 2/2016 Hørdum
9,265,881 B2 2/2016 Montalvo et al.
9,278,173 B2 3/2016 Mejlhede et al.
9,295,786 B2 3/2016 Gottlieb et al.
D754,842 S 4/2016 Sonderegger et al.
D754,843 S 4/2016 Sonderegger et al.
9,308,354 B2 4/2016 Farrell et al.
D756,504 S 5/2016 Sonderegger et al.
9,327,098 B2 5/2016 Kelvered et al.
9,339,603 B2 5/2016 Gray et al.
9,375,529 B2 6/2016 Searle et al.
9,375,537 B2 6/2016 Montalvo et al.
9,427,180 B2 8/2016 DiCesare et al.
9,433,757 B2 9/2016 Constantineau et al.
9,440,051 B2 9/2016 Gyrn
9,480,792 B2 11/2016 Constantineau et al.
9,511,189 B2 12/2016 O'Connor et al.
9,522,228 B2 12/2016 Teutsch et al.
9,522,229 B2 12/2016 Sonderegger et al.
9,545,477 B2 1/2017 Chong et al.
9,566,384 B2 2/2017 Gyrn et al.
9,597,461 B2 3/2017 Aasmul
9,610,401 B2 4/2017 Antonio et al.
9,649,053 B2 5/2017 DiCesare et al.
D790,691 S 6/2017 Davis et al.
9,675,750 B2 6/2017 Grant et al.
9,675,785 B2 6/2017 Constantineau et al.
9,724,127 B2 8/2017 Gyrn
9,731,069 B2 8/2017 Benéet al.
9,744,295 B2 8/2017 Wyss et al.
D801,522 S 10/2017 Shalom
9,782,538 B2 10/2017 Cole et al.
9,789,250 B2 10/2017 Hwang
9,795,777 B2 10/2017 Sonderegger et al.
9,821,113 B2 11/2017 Cole et al.
9,844,330 B2 12/2017 Wilkinson
9,872,642 B2 1/2018 Deck
9,878,110 B2 1/2018 Cole et al.
9,901,675 B2 2/2018 Ella et al.
9,901,681 B2 2/2018 Sweeney et al.
D812,223 S 3/2018 Evans et al.
D815,279 S 4/2018 Darras
9,943,332 B2 4/2018 Chong et al.
9,943,643 B2 4/2018 Constantineau et al.
D817,482 S 5/2018 Howell et al.
9,968,742 B2 5/2018 Van Antwerp et al.
9,987,476 B2 6/2018 Montalvo et al.
10,071,209 B2 9/2018 Solomon et al.
10,076,356 B2 9/2018 Hadvary et al.
10,076,606 B2 9/2018 Ambruzs et al.
10,080,582 B2 9/2018 Hadvary et al.
10,080,839 B2 9/2018 Cole et al.
10,105,484 B2 10/2018 Sonderegger et al.
10,117,989 B2 11/2018 Hadvary et al.
10,130,761 B2 11/2018 Searle et al.
D836,769 S 12/2018 Kabel-Eckes
D839,423 S 1/2019 Großer et al.
10,194,938 B2 2/2019 Byager
10,195,342 B2 2/2019 Cole et al.
D842,464 S 3/2019 Davis et al.
10,220,137 B2 3/2019 Sonderegger
10,279,108 B2 5/2019 Teoh et al.
10,369,277 B2 8/2019 Mogensen et al.
10,413,661 B2 9/2019 Kamen et al.
D863,546 S 10/2019 Converse
D883,474 S 5/2020 Tipsmark
D884,160 S 5/2020 Adams
10,646,643 B2 5/2020 Cabiri et al.
10,682,462 B2 6/2020 Howell et al.

(56) References Cited

U.S. PATENT DOCUMENTS

| | | | |
|---|---|---|---|
| D893,707 S | 8/2020 | Burkholz et al. | |
| D900,308 S | 10/2020 | Burkholz et al. | |
| 10,792,419 B2 | 10/2020 | Kamen et al. | |
| D913,487 S | 3/2021 | Orofino | |
| 10,933,191 B2 | 3/2021 | Lawrence et al. | |
| D961,782 S | 8/2022 | Locke et al. | |
| 11,458,292 B2 | 10/2022 | Erichsen | |
| D973,202 S | 12/2022 | Schuepbach | |
| D975,845 S | 1/2023 | Kobayashi et al. | |
| 11,617,827 B2 | 4/2023 | Mogensen et al. | |
| D995,103 S | 8/2023 | Smith | |
| 11,786,653 B2 | 10/2023 | Gyrn et al. | |
| D1,008,452 S | 12/2023 | Lanigan | |
| D1,013,864 S | 2/2024 | Lanigan | |
| D1,043,975 S | 9/2024 | Cox et al. | |
| D1,043,976 S | 9/2024 | Cannan et al. | |
| D1,057,941 S | 1/2025 | Cannan et al. | |
| D1,064,312 S | 2/2025 | Chae | |
| D1,077,238 S | 5/2025 | Filgate et al. | |
| D1,090,862 S | 8/2025 | Furtado et al. | |
| 2002/0055711 A1 | 5/2002 | Lavi et al. | |
| 2002/0072720 A1 | 6/2002 | Hague et al. | |
| 2002/0173769 A1 | 11/2002 | Gray et al. | |
| 2004/0116866 A1 | 6/2004 | Gorman et al. | |
| 2004/0158207 A1 | 8/2004 | Hunn et al. | |
| 2005/0101932 A1 | 5/2005 | Cote et al. | |
| 2005/0107743 A1 | 5/2005 | Fangrow, Jr. | |
| 2005/0113761 A1 | 5/2005 | Faust et al. | |
| 2005/0245956 A1 | 11/2005 | Steinemann et al. | |
| 2005/0256460 A1 | 11/2005 | Rome et al. | |
| 2005/0273076 A1 | 12/2005 | Beasley et al. | |
| 2006/0184104 A1 | 8/2006 | Cheney, II et al. | |
| 2006/0247574 A1 | 11/2006 | Maule et al. | |
| 2007/0088254 A1 | 4/2007 | DeStefano | |
| 2007/0191772 A1 | 8/2007 | Wojcik | |
| 2007/0191773 A1 | 8/2007 | Wojcik | |
| 2008/0154205 A1 | 6/2008 | Wojcik | |
| 2008/0208139 A1 | 8/2008 | Scheurer et al. | |
| 2008/0215006 A1 | 9/2008 | Thorkild | |
| 2008/0249471 A1 | 10/2008 | DeStefano et al. | |
| 2009/0012472 A1 | 1/2009 | Ahm et al. | |
| 2009/0012473 A1 | 1/2009 | Stettler et al. | |
| 2009/0076451 A1 | 3/2009 | Teisen-Simony et al. | |
| 2009/0143763 A1 | 6/2009 | Wyss et al. | |
| 2009/0198190 A1 | 8/2009 | Jensen et al. | |
| 2009/0216215 A1 | 8/2009 | Thalmann et al. | |
| 2009/0218243 A1 | 9/2009 | Gyrn et al. | |
| 2009/0326472 A1 | 12/2009 | Carter et al. | |
| 2010/0004597 A1 | 1/2010 | Gyrn et al. | |
| 2010/0036323 A1 | 2/2010 | Smith | |
| 2010/0137695 A1 | 6/2010 | Yodfat et al. | |
| 2010/0160851 A1 | 6/2010 | Dimalanta et al. | |
| 2010/0198157 A1 | 8/2010 | Gyrn et al. | |
| 2011/0009703 A1 | 1/2011 | Smith | |
| 2011/0034883 A1 | 2/2011 | Gyrn et al. | |
| 2011/0040263 A1 | 2/2011 | Hørdum et al. | |
| 2011/0087159 A1 | 4/2011 | Parihar et al. | |
| 2011/0098652 A1 | 4/2011 | Hasted et al. | |
| 2011/0137257 A1 | 6/2011 | Gyrn et al. | |
| 2012/0022461 A1 | 1/2012 | Schubert et al. | |
| 2012/0046533 A1 | 2/2012 | Voskanyan et al. | |
| 2012/0095406 A1 | 4/2012 | Gyrn et al. | |
| 2012/0143135 A1 | 6/2012 | Cole | |
| 2012/0150123 A1 | 6/2012 | Lawrence et al. | |
| 2012/0265166 A1 | 10/2012 | Yodfat | |
| 2012/0283646 A1 | 11/2012 | Kouyoumijian | |
| 2013/0066293 A1* | 3/2013 | Garfield | A61J 1/10 604/408 |
| 2013/0197439 A1 | 8/2013 | Melvin et al. | |
| 2013/0338594 A1 | 12/2013 | De Ros et al. | |
| 2014/0039453 A1 | 2/2014 | Sonderegger | |
| 2014/0058353 A1 | 2/2014 | Politis et al. | |
| 2014/0058360 A1 | 2/2014 | Schoonmaker et al. | |
| 2014/0074028 A1 | 3/2014 | Sonderegger et al. | |
| 2014/0094756 A1 | 4/2014 | Bobroff et al. | |
| 2014/0155679 A1 | 6/2014 | Pesach et al. | |
| 2014/0155819 A1 | 6/2014 | Amirouche et al. | |
| 2014/0275773 A1 | 9/2014 | Tarazona et al. | |
| 2014/0276557 A1 | 9/2014 | Vaishya | |
| 2014/0296782 A1 | 10/2014 | Ulrich et al. | |
| 2015/0025478 A1 | 1/2015 | Hibdon et al. | |
| 2015/0051583 A1 | 2/2015 | Horvath et al. | |
| 2015/0112302 A1 | 4/2015 | Chattaraj et al. | |
| 2015/0164545 A1 | 6/2015 | Gyrn | |
| 2016/0015303 A1 | 1/2016 | Bernstein et al. | |
| 2016/0129203 A1 | 5/2016 | Chong et al. | |
| 2016/0339186 A1 | 11/2016 | Hagy et al. | |
| 2017/0281863 A1 | 10/2017 | Kamen et al. | |
| 2017/0303831 A1 | 10/2017 | Tsubouchi et al. | |
| 2018/0200412 A1 | 7/2018 | Dang et al. | |
| 2019/0009019 A1 | 1/2019 | Shor et al. | |
| 2019/0060562 A1 | 2/2019 | Olivas et al. | |
| 2019/0216397 A1 | 7/2019 | Yavorsky et al. | |
| 2019/0336078 A1 | 11/2019 | Dang et al. | |
| 2020/0164159 A1 | 5/2020 | Chattaraj et al. | |
| 2020/0289748 A1 | 9/2020 | Lanigan et al. | |
| 2020/0368515 A1 | 11/2020 | Erichsen | |
| 2021/0268179 A1 | 9/2021 | Schøndorff et al. | |
| 2021/0386930 A1 | 12/2021 | Lanigan et al. | |
| 2022/0117627 A1* | 4/2022 | Garai | A61B 17/3468 |
| 2022/0125346 A1 | 4/2022 | Stafford | |
| 2022/0202366 A1 | 6/2022 | Mitchell et al. | |
| 2022/0379019 A1 | 12/2022 | Lanigan et al. | |
| 2023/0060176 A1 | 3/2023 | Lanigan | |
| 2023/0062738 A1 | 3/2023 | Lanigan et al. | |
| 2024/0066217 A1 | 2/2024 | Lanigan et al. | |
| 2024/0216605 A1 | 7/2024 | Lanigan | |
| 2024/0216606 A1 | 7/2024 | Lanigan | |
| 2024/0261498 A1 | 8/2024 | Lanigan | |
| 2024/0261499 A1 | 8/2024 | Lanigan | |
| 2024/0293615 A1 | 9/2024 | Lanigan | |
| 2024/0382674 A1 | 11/2024 | Lanigan | |
| 2025/0082271 A1 | 3/2025 | Oakes | |
| 2025/0107939 A1 | 4/2025 | Gardner et al. | |

FOREIGN PATENT DOCUMENTS

| | | | |
|---|---|---|---|
| CN | 203494005 | U | 3/2014 |
| CN | 203609736 | U | 5/2014 |
| CN | 203815967 | U | 9/2014 |
| CN | 104302333 | A | 1/2015 |
| CN | 109069734 | A | 12/2018 |
| CN | 202230824756.3 | | 9/2023 |
| CN | 202330222706.2 | | 11/2023 |
| DE | 3708031 | A1 | 11/1987 |
| DE | 29905072 | U1 | 9/1999 |
| EM | 71109IL | | 7/2023 |
| EP | 1539281 | B1 | 5/2007 |
| EP | 1691877 | B1 | 12/2013 |
| EP | 2712642 | A1 | 4/2014 |
| EP | 2713879 | B1 | 7/2017 |
| JP | 2014510574 | A | 5/2014 |
| JP | D2021-01054 | | 7/2022 |
| WO | WO2004020035 | A1 | 3/2004 |
| WO | WO2012/134588 | A1 | 10/2012 |
| WO | WO2013/070715 | A1 | 5/2013 |
| WO | WO2018018164 | A1 | 2/2018 |

OTHER PUBLICATIONS

Neria Guard Infusion Set, announced in You Tube on May 17, 2022 [Online]. [Retrieved on Aug. 2, 2023], Available from the internet URL:https://www.youtube.com/watch?v=VUoLi-_gcyE (Year: 2023).

Autosoft XC Infusion Set. Product Support Page[Online]. Tandemdiabetes.com 2023. [Retrieved on Aug. 2, 2023]. Retrieved from the Internet: URL:https://support.tandemdiabetes.com/hc/en-us/articles/360039015054/ (Year: 2023).

Tapecon. using Adhesive Constructions to Improve Chain of Custody Sleep Apnea Tests. No Publication Date. Retrieved Feb. 19, 2025. https://www.tapecon.com/blog/adhesive-constructions-chain-of-custody-sleep-apnea-tests Medical Design & Outsourcing. new 3M Durapore Advanced Surgical Tape Offers Adhesive Innovation. Oct. 25, 2018. https://

(56) References Cited

OTHER PUBLICATIONS www.medicaldesignandoutsourcing.com/new-3m-durapore-advanced-surgical-tape-offers-adhesive-innovation/.
"*Cleo 90 Infusion Set Training Guide*" [online] Smiths Medical MD, Inc. pp.1, https://manualzz.com/doc/6784816/to-the-cleo-training-guide (Retrieved Sep. 1, 2021).
Heinemann, Lutz and Lars Krinelke "Insulin Infusion Set: The Achilles Heel of Continuous Subcutaneous Insulin Infusion" [online] Journal of Diabetes Science and Technology vol. 6, No. 4, Jul. 2012. pp. 954-964 doi: 10.1177/193229681200600429.
"*Spring Universal Infusion Set Quick Guide*" [online] Spring-set Health Solutions Ltd. pp. 1-2, https://www.slideshare net/springnow1/spring-universal-guide?from_action=save (Retrieved Sep. 8, 2021).
International Search Report and Written Opinion date of mailing Jul. 31, 2020 received in International patent application PCT/US2020/019287 from the European Patent Office as International Searching Authority, European Patent Office, P.B. 5818 Patentlaan 2 NL—2280 HV Rijswijk (pp. 1-16).
International Search Report and Written Opinion date of mailing Jan. 13, 2023 received in International patent application PCT/US2022/041649 from the European Patent Office as International Searching Authority, European Patent Office, P.B. 5818 Patentlaan 2 NL—2280 HV Rijswijk (pp. 1-26).
PharmaSens seeks FDA Approval for new insulin pump. Online, published date Jan. 2, 2024. Retrieved on May 8, 2024 from URL:https://www.medicaldevice-network.com/news/pharmasens-fda-approval-insulin-pump/.
MIT jet-injector provides a needle-free alternative to medicine delivery. Online, published date May 24, 2012. Retrieved on May 8, 2024 from URL: https://newatlas.com/jet-injection-system-mit/22673/.
Tandem Varisoft Infusion Sets. 2024. Retrieived Nov. 16, 2024. https://doubekmedical.com/product/tandem-varisoft-infusion-sets/.
Tandem Autosoft 90 Infusion Sets. 2024. Retrieved Nov. 16, 2024. https://tinyurl.com/y38tt4fu.
International Search Report and Written Opinion dated Jan. 25, 2024, received in International patent application PCT/US2023/031046 from the European Patent Office as International Searching Authority, European Patent Office, P.B. 5818 Patentlaan 2 NL—2280 HV Rijswijk (pp. 1-17).

* cited by examiner

INFUSION SET AND INSERTER ASSEMBLY APPARATUSES, SYSTEMS, AND METHODS

CROSS REFERENCE TO RELATED APPLICATIONS

This application claims the benefit of U.S. Provisional Application Ser. No. 63/401,279 filed Aug. 26, 2022 and entitled Infusion Set and Inserter Assembly, Apparatuses, Systems, and Methods, which is hereby incorporated herein by reference in its entirety.

BACKGROUND

Field of Disclosure

This application relates generally to infusion sets and inserter assemblies for infusion sets, and more particularly, to infusion sets and inserter assemblies as well as methods for the use thereof.

Description of Related Art

Many potentially valuable medicines or compounds, including biologicals, are not orally active due to poor absorption, hepatic metabolism or other pharmacokinetic factors. Additionally, some therapeutic compounds, although they can be orally administered, are sometimes required to be taken so often that it is difficult for a patient to maintain the desired schedule. In these cases, parenteral delivery is often employed or could be employed.

Effective parenteral delivery routes of drugs, other fluid, and compounds such as subcutaneous injection, intramuscular injection, and intravenous (IV) administration include puncture of the skin with a needle or stylet. Insulin is an example of a therapeutic fluid that is self-injected by millions of diabetic patients. Users of parenterally delivered drugs may benefit from a wearable device that would automatically deliver needed drugs/compound over a period of time.

To this end, there have been efforts to design portable and wearable devices for the controlled release of therapeutics. Such devices are known to have a reservoir such as a cartridge, syringe, or bag, and to be electronically controlled. These devices suffer from a number of drawbacks including the malfunction rate. Reducing the size, weight, and cost of these devices is also an ongoing challenge. Additionally, these devices often apply to the skin and pose the challenge of frequent relocation for application.

SUMMARY

In accordance with an example embodiment of the present disclosure an inserter assembly may comprise a housing having an insertion driver latch defined thereon. The inserter assembly may further comprise an insertion driver displaceable between an initial position and a forward position. The insertion driver may be engaged with the insertion driver latch in the initial position. The inserter assembly may further comprise a release finger displaceable relative to the housing from a first position to a ready position and from the ready position to a triggering position. The release finger may be configured to press a portion of the insertion driver in a setting direction and hold the insertion driver in engagement with the insertion driver latch when the release finger is displaced from the first position to the ready position. The release finger may be configured to displace a portion of the insertion driver in a release direction dislodging the insertion driver from the insertion driver latch when the release finger is displaced from the ready position to the triggering position. The inserter assembly may further comprise a latch arrangement. The inserter assembly may further comprise an insertion bias member configured to be held in a distorted state by the latch arrangement and engagement of the insertion driver with the insertion driver latch when the release finger reaches the ready position. The insertion bias member configured to be freed from the distorted state when the insertion driver is dislodged from the insertion driver latch.

In some embodiments, the latch arrangement may include a set of opposing retainer arms and a retainer displaceable therebetween. The retainer arms may have ledges defined thereon which overhang the retainer when the latch arrangement is engaged. In some embodiments, the retainer may be configured to displace as the release finger is displaced from the first position to the ready position. The latch arrangement may be engaged as the release finger is displaced to the ready position. In some embodiments, the inserter assembly may further comprise a retraction bias member configured to distort when the release finger is displaced to the ready position. The retraction bias member may be configured to be held in a distorted state by the latch arrangement. In some embodiments, the insertion driver may be configured to disengage the latch arrangement when displaced from the initial position to the forward position. The retraction bias member may be configured to displace the insertion driver to the initial position upon disengagement of the latch arrangement. In some embodiments, the insertion driver may include a port configured to couple to an insertion sharp bearing body. In some embodiments, the housing may include a receptacle configured to couple to a care assembly cartridge. In some embodiments, the housing may include a receptacle including a set of receiving shoes for retainer pins of a care assembly cartridge. In some embodiments, the release finger may be configured to collide with and deflect around a portion of the insertion driver as the release finger is displaced to the ready position. In some embodiments, the housing may block deflection of the release finger in a direction toward the housing when the release finger is displaced from the ready position to the trigger position. In some embodiments, the insertion driver may include a cantilevered arm including a catch body which is configured to engage the insertion driver latch. The housing may block deflection of the cantilevered arm in a direction toward the housing. In some embodiments, the release finger may be configured to collide with a portion of the cantilevered arm deflecting the cantilevered arm out of the path of the release finger while the release finger is displaced from the ready position to the trigger position. Deflection of the cantilevered arm may dislodge the catch body from the inserter driver latch.

In accordance with another exemplary embodiment of the present disclosure an inserter assembly may comprise a casing including an exterior housing and an end cap. The inserter assembly may further comprise an interior housing. The inserter assembly may further comprise an insertion driver included in the interior housing. The insertion driver may be displaceable from an initial position, in which the insertion driver is engaged with an insertion driver latch defined on the interior sidewall of the interior housing, to a forward position. The inserter assembly may further comprise an insertion bias member between the insertion driver and the end cap. The inserter assembly may further comprise a retainer configured to engage a first latch upon displacement of the casing in a first direction to a ready position. The insertion bias member may be held in a distorted state when the retainer is engaged with the first latch and the insertion driver is engaged with the insertion driver latch. The inserter assembly may further comprise a release finger included on the casing and configured to hold the insertion driver in engagement with the insertion driver latch when the casing is displaced to the ready position. The release finger may be configured to dislodge the insertion driver from the insertion driver latch when the casing is displaced from the ready position to a trigger position in a second direction. The insertion bias member may be configured to urge the insertion driver to the forward position upon release of the insertion driver latch. The insertion driver may disengage the retainer from the first latch when displaced toward the forward position.

In some embodiments, the inserter assembly may further comprise a retraction bias member configured to distort when the casing is displaced to the ready state. The retraction bias member may be configured to be held in a distorted state when the retainer is in engagement with the first latch. In some embodiments, the retraction bias member may be freed from the distorted state when the retainer is disengaged from the first latch. The retraction bias member may be configured to displace retainer away from the first latch and displace the insertion driver to the initial position upon disengagement of the retainer from the first latch. In some embodiments, the insertion driver may include a port configured to couple to an insertion sharp holder bearing an insertion sharp. In some embodiments, the interior housing may include a receptacle opposite the end cap, the receptacle may be configured to couple to a care assembly cartridge. In some embodiments, the release finger may be configured to collide with and deflect around a portion of the insertion driver as the casing is displaced to the ready position. In some embodiments, the interior housing may block deflection of the release finger in a direction toward the interior housing when the casing is displaced from the ready position to the trigger position. In some embodiments, the insertion driver may include a cantilevered arm including a catch body. The catch body may be configured to engage the insertion driver latch. The interior housing may block deflection of the cantilevered arm in a direction toward the interior housing. In some embodiments, the release finger may be configured to collide with a portion of the cantilevered arm deflecting the cantilevered arm out of the path of the release finger while the casing is displaced from the ready position to the trigger position. Deflection of the cantilevered arm may dislodge the catch body from the inserter driver latch. In some embodiments, the retainer may comprise a reset body and a retraction spring retainer. A portion of the insertion driver may be disposed between the retraction spring retainer and the reset body. The insertion bias member may be captured between the portion of the insertion driver and the reset body. In some embodiments, the end cap may include a post which extends into a passage defined in the reset body. The end cap may be configured to push against the reset body as the casing is displaced to the ready position.

In accordance with another example embodiment of the present disclosure an inserter assembly may comprise a casing including an exterior housing and an end cap. The inserter assembly may further comprise an interior housing. The casing may be displaceable relative to the interior housing. The inserter assembly may further comprise a retainer configured to engage a first latch when the casing is displaced in a first direction toward the interior housing beyond a first threshold distance. The inserter assembly may further comprise an insertion driver included in the interior housing and displaceable from a first position to a second position and including a routing body. The inserter assembly may further comprise a release finger included on the casing. The release finger may be configured press against the routing body in a setting direction which reinforces engagement of the insertion driver with an insertion driver latch when the casing is displaced in the first direction. The release finger may be configured to displace the routing body in a release direction which dislodges the insertion driver from the insertion driver latch when the casing is pulled in a second direction opposite the first direction beyond a second threshold distance. The inserter assembly may further comprise a first bias member maintained in a distorted state when the retainer is engaged to the first latch and the insertion driver is engaged with the insertion driver latch. The first bias member may urge the insertion driver toward the second position when the insertion driver is dislodged from the insertion driver latch. The insertion driver may disengage the retainer from the first latch when displaced toward the second position.

In some embodiments, the insertion driver may include a cantilevered arm including a catch body which engages with the insertion driver latch. In some embodiments, the routing body may be disposed on the cantilevered arm. In some embodiments, the routing body may include opposing first and second faces each including a sloped portion. In some embodiments, the release finger may include a paddle body having opposing first and second paddle body sides each including a sloped portion. The sloped portion of the first paddle body side may be configured to advance into the sloped portion of the second face of the routing body as the casing is displaced in the first direction. The release finger may deflect around the second face of the routing body with further advancement of the casing in the first direction. The sloped portion of the second paddle body side may be configured to advance into the sloped portion of the first face of the routing body when the casing is displaced in the second direction. The cantilevered arm displacing in the release direction out of the path of the paddle body with further advancement of the casing in the second direction. In some embodiments, the cantilevered arm may extend along an axis and the routing body may project from the cantilevered arm in a direction substantially perpendicular to the axis. In some embodiments, the insertion driver latch may be provided by at least one shelf defined on an interior surface of the interior housing. In some embodiments, the interior housing may inhibit deflection of the release finger in a direction opposite the release direction when the casing is displaced in the second direction. In some embodiments, the insertion driver may include a port configured to mate with an insertion sharp holder. In some embodiments, the inserter assembly may further comprise a second bias member. In some embodiments, the second bias member may be configured to transition to a distorted state when the casing is displaced in the first direction. The second bias member may be held in the distorted state when the retainer is engaged with the first latch. In some embodiments, the second bias member may be configured to urge retainer away from the first latch and may be configured urge the insertion driver toward the first position and into engagement with the insertion driver latch when the first latch is disengaged. In some embodiments, a shaft of the insertion driver may extend through the second bias member.

In accordance with yet another example embodiment of the present disclosure a cartridge for a reusable inserter assembly may comprise a housing having a bay recessed into an end of the housing. The housing may include a set of retention members projecting into the bay. The cartridge may further comprise a retainer including a flange. The flange may be captured between a rim at an end of the bay and respective ends of the retention members. A set of cantilevered arms may project from a first face of the flange. The cartridge may further comprise a first patient care assembly portion coupled to the retainer by the set of cantilevered arms. The cartridge may further comprise a sharp holder having an insertion sharp coupled thereto. The cartridge may further comprise a second patient care assembly portion carried on the insertion sharp.

In some embodiments, the cartridge may further comprise a set of mating bodies which extend proud of a surface of the rim most distal to the flange. In some embodiments, the mating bodies may be mating pins. In some embodiments, the mating bodies may project from a second face of the flange opposite the first face. In some embodiments, the retention members may be cantilevered sections of a side wall of the bay. In some embodiments, the cantilevered arms may define guides. The sharp holder may be configured to displace along the guides. In some embodiments, the rim may form a stop which limits the displacement range of the sharp holder in a first direction. In some embodiments, the guides may be formed by slots extending through each of the cantilevered arms. In some embodiments, the first patient care assembly portion may be an infusion set base and the second patient care assembly portion may be a cannula subassembly. In some embodiments, the housing may be disposed within and releaseably coupled to a container.

In accordance with another example embodiment of the present disclosure, a cartridge for a reusable inserter assembly may comprise a housing having a bay recessed into an end of the housing. The housing may include a set of retention members projecting into the bay. The cartridge may further comprise a retainer including a flange. The flange may be captured between a rim at an end of the bay and respective ends of the retention members. A set of cantilevered arms may project from a first face of the flange. The cantilevered arms may each include a guide passage along a section of the cantilevered arm which extends through the cantilevered arm. The cartridge may further comprise a first patient care assembly portion coupled to the retainer by the set of cantilevered arms. The cartridge may further comprise a sharp holder having an insertion sharp coupled thereto. The sharp holder may include fins extending from a main portion of the sharp holder through the guide passages. The cartridge may further comprise a second patient care assembly portion carried on the insertion sharp.

In some embodiments, the cartridge may further comprise a set of mating bodies which extend proud of a surface of the rim most distal to the flange. In some embodiments, the mating bodies may be mating pins. In some embodiments, the mating bodies may project from a second face of the flange opposite the first face. In some embodiments, the retention members may be cantilevered sections of a side wall of the bay. In some embodiments, the section of each cantilevered arm including the guide passage may extend from a supported end of each cantilevered arm to a point shy of an unsupported end of each cantilever arm. In some embodiments, the rim may form a stop which limits the displacement range of the sharp holder in a first direction along the guide passages. In some embodiments, the first patient care assembly portion may be an infusion set base and the second patient care assembly portion may be a cannula subassembly. In some embodiments, the housing may be disposed within and releaseably coupled to a container. In some embodiments, a barrier may be attached to the container. The barrier and container may completely enclose the housing, retainer, first patient care assembly portion, second patient care assembly portion, and sharp holder.

In accordance with another example embodiment of the present disclosure a method of assembling a cartridge for a reusable inserter assembly may comprise placing an insertion sharp extending from a sharp holder through a septum and cannula of a cannula assembly. The method may further comprise locating the sharp holder within a set of guides of a retainer. The method may further comprise advancing the retainer into a bay of a housing through a first displacement range in which a flange of the retainer deflects a set of retention members and to a retained position in which the flange is advanced against a rim at an end of the bay and clear of the retention members. The retention members may restore to a resting state blocking movement of the retainer into positions in the first displacement range. The method may further comprise releasably coupling an infusion set base to a set of cantilevered arms included in the retainer.

In some embodiments, advancing the retainer into the bay may further comprise blocking displacement of the sharp holder along a portion of the guides with the rim. In some embodiments, the method may further comprise passing a set of mating bodies defined on the retainer through at least one opening in the rim. In some embodiments, the method may further comprise placing the housing into a container. In some embodiments, the method may further comprise releasably coupling the housing to the container. In some embodiments, the method may further comprise sealing an opening in the container with a barrier. The barrier and container together may completely surround the housing. In some embodiments, locating the sharp holder within the guides may comprise placing fins on the sharp holder within slots defined through the cantilevered arms. In some embodiments, locating the sharp holder within the guides may comprise introducing portions of the sharp holder into slots extending through the cantilevered arms. The portions of the sharp holder may be introduced into sections of the slots most distal to unsupported ends of the cantilevered arms.

In accordance with still another example embodiment of the present disclosure an inserter assembly may comprise a casing having an open end and an opposing closed end. The inserter assembly may further comprise a care assembly base holder having a care assembly base releasably coupled thereto. The inserter assembly may further comprise a trigger body held in place relative to the care assembly base holder via an insertion latch arrangement. The inserter assembly may further comprise a sharp shuttle bearing an insertion sharp. The sharp shuttle may be coupled to the trigger body via a retraction latch arrangement. The inserter assembly may further comprise a first bias member configured to urge the trigger body, sharp shuttle, and insertion sharp toward the open end of the casing when the insertion latch arrangement is transitioned to a released state. The inserter assembly may further comprise a second bias member configured to urge the sharp shuttle and insertion sharp toward the closed end upon the retraction latch arrangement being displaced into a trigger when the trigger body and sharp shuttle are displaced to a retraction release position by the first bias member.

In some embodiments, the insertion latch arrangement may be configured to transition to the insertion release state when a force pressing a portion of the trigger body and a portion of the casing against one another exceeds a threshold. In some embodiments, the insertion latch arrangement may comprise a ledge of the trigger body releasably engaged with a catch defined on the care assembly base holder. In some embodiments, the trigger body may include an arm having a ledge defined thereon. The insertion latch arrangement formed by engagement of the ledge with a catch defined on the care assembly base holder. In some embodiments, the care assembly base holder may include an aperture through which a terminal portion of the arm extends. In some embodiments, the terminal portion of the arm may be disposed in line with a trigger protrusion on the casing. Displacement of the casing relative to the trigger body may be inhibited by abutment of the terminal portion with the trigger protrusion. In some embodiments, the arm may be configured to deflect to a deflected state when a force pressing the trigger protrusion and terminal portion of the arm against one another exceeds a threshold. The ledge may be displaced out of engagement with the catch transitioning the insertion latch arrangement to the released state when the arm is in the deflected state. In some embodiments, the trigger may be defined on the care assembly base holder. In some embodiments, the retraction latch arrangement may comprise a ledge of the sharp shuttle releasably engaged with a catch defined on the trigger body. In some embodiments, the retraction release position may be at an end of a displacement range of the trigger body. In some embodiments, the retraction release position may be at an intermediate point in a displacement range of the trigger body. The first bias member may be configured to continue propelling the trigger body toward the open end in an insertion direction through a terminal portion of the displacement range of the trigger body after the trigger body reaches the intermediate point. In some embodiments, a cannula subassembly may be carried by the insertion sharp and the trigger body may be configured to displace the cannula subassembly toward the open end in the terminal portion of the displacement range of the trigger body. In some embodiments, a cannula subassembly may be carried by the insertion sharp. In some embodiments, the insertion latch arrangement may be configured to transition to the released state by displacement of the casing relative to at least the care assembly base in a direction away from the care assembly base. In some embodiments, an adhesive configured to anchor the care assembly base to a biological barrier may be coupled to the care assembly base. The biological barrier may be lifted from a resting position as the casing is displaced relative to the care assembly base.

In accordance with yet another example embodiment of the present disclosure, an inserter assembly may comprise a casing. The inserter assembly may further comprise a care assembly base holder having a care assembly base releasably coupled thereto. The inserter assembly may further comprise an insertion unit held in place relative to the care assembly base holder via an insertion latch arrangement. The insertion unit may comprise a trigger body. The insertion unit may further comprise a retraction unit including an insertion sharp. The retraction unit may be releasably coupled to the trigger body via a retraction latch arrangement. The inserter assembly may further comprise a first bias member configured to urge the insertion unit to displace in an insertion direction when the insertion latch arrangement is transitioned to a first released state. The inserter assembly may further comprise a second bias member configured to urge the retraction unit to displace in a retraction direction upon the retraction latch arrangement being displaced into a trigger when insertion unit is displaced to a retraction release position by the first bias member.

In some embodiments, the second bias member may be maintained in a distorted state between the trigger body and a portion of the retraction unit while the retraction latch arrangement is in an engaged state. In some embodiments, the retraction release position may be at an end of a displacement range of the trigger body. In some embodiments, the retraction release position may be at an intermediate point in a displacement range of the trigger body. The first bias member may be configured to propel the trigger body beyond the retraction release point toward the open end. In some embodiments, a cannula subassembly may be carried by the insertion sharp. The trigger body may be configured to push the cannula subassembly in the insertion direction as the trigger body is displaced in the insertion direction by the first bias member. In some embodiments, a care assembly portion separate from the care assembly base may be carried by the insertion sharp. In some embodiments, the insertion unit may be configured to displace together with the casing until more than a threshold force is applied to pull the casing and insertion unit apart. In some embodiments, the care assembly base may be coupled to an adhesive. Withdrawal of the casing away from a patch of a biological barrier when the adhesive is adhered to the patch may generate the threshold force and lift the patch from a resting state. In some embodiments, the insertion latch arrangement may comprise a resilient member releasably engaged with a catch. The casing may be configured to deflect the resilient member out of engagement with the catch to transition the insertion latch arrangement to the released state when the casing is pulled in a direction away from the care assembly base. In some embodiments, the retraction release arrangement may comprise a resilient member of the retraction unit releasably engaged with a catch defined on the trigger body.

In accordance with another example embodiment of the present disclosure an inserter assembly may comprise an insertion unit constrained from displacing in an insertion direction by an insertion latch arrangement. The inserter assembly may further comprise a retraction unit including an insertion sharp. The retraction unit may be releasably coupled to the insertion unit by a retraction latch arrangement. The inserter assembly may further comprise a first bias member configured to urge the insertion unit and retraction unit to displace in an insertion direction upon release of the insertion latch arrangement. The inserter assembly may further comprise a second bias member configured to urge the retraction unit to displace in a retraction direction. The inserter assembly may further comprise a retraction trigger. The retraction latch arrangement may be configured transition to a disengaged state upon displacement into the retraction trigger at an intermediate point in a displacement path of the insertion unit.

In some embodiments, a transcutaneous access assembly may be carried by the insertion sharp. In some embodiments, an infusion cannula assembly may be carried by the insertion sharp. In some embodiments, the insertion unit may be configured to drive a transcutaneous access assembly carried by the insertion sharp in an insertion direction after passing the intermediate point. In some embodiments, the insertion unit may be configured to press a transcutaneous access assembly carried by the insertion sharp in the insertion direction after passing the intermediate point. In some embodiments, the inserter assembly may further comprise a holder and a first patient care assembly portion coupled to the holder. The inserter assembly may also comprise a second patient care assembly portion carried by the insertion sharp. In some embodiments, the second patient care assembly portion may be coupled to the first patient care assembly portion as the insertion unit is displaced along the displacement path. In some embodiments, the second patient care assembly portion may be coupled to the first patient care assembly portion once the insertion unit is displaced beyond the intermediate point. In some embodiments, the inserter assembly may comprise an access assembly carried by the insertion sharp. The insertion sharp may have a lead length extending beyond the access assembly. In some embodiments, the access assembly may be positioned in the displacement path of the insertion unit and the intermediate point may be selected such that the insertion unit drives the access assembly, in the insertion direction, a distance at least equal to the lead length after passing the intermediate point.

In accordance with another example embodiment of the present disclosure, an inserter for placing a device may comprise a casing. The inserter may further comprise a device base having an adhesive thereon configured to anchor the base to a portion of a barrier. The inserter may further comprise a spring biased insertion unit maintained in an initial state by an insertion latch arrangement. The base may be releasably coupled to the insertion unit and anchor the insertion unit from displacing relative to the portion of the barrier when the base is anchored to the portion of the barrier by the adhesive. The casing may be displaceable, in a direction opposite an insertion displacement direction of the insertion unit, from an initial position to a triggered position. The casing may be configured to transition the insertion latch arrangement to a disengaged state as the casing is displaced to the triggered position. The insertion latch arrangement may inhibit relative motion of the casing and insertion unit until a force threshold is exceeded.

In some embodiments, the force threshold may be greater than a threshold necessary to lift the portion of the barrier from a resting position when the base is anchored to the portion of the barrier via the adhesive. In some embodiments, the inserter assembly may further comprise a transcutaneous access assembly. The insertion unit spring may be biased to displace in the insertion direction and couple the transcutaneous access assembly into the base upon release of the insertion latch arrangement. In some embodiments, the insertion unit may comprise a spring biased retraction unit including an insertion sharp. The retraction unit may be releasably coupled to a remainder of the insertion unit by a retraction latch arrangement and constrained to displace in tandem with the remainder of the insertion unit while the retraction latch arrangement is in an engaged state. In some embodiments, the insertion unit may be spring biased to displace in the insertion direction along a displacement path. The retraction latch arrangement may be configured to displace into a triggering protrusion as the insertion unit is displaced along the displacement path. In some embodiments, the retraction latch arrangement may be configured to displace into the triggering protrusion as the insertion unit reaches an intermediate point in the displacement path. In some embodiments, the retraction unit may be spring biased to displace in a retraction direction opposite the insertion direction. In some embodiments, the retraction unit may comprise a tipping projection.

In accordance with a further example embodiment of the present disclosure, a method of placing a care assembly on a biological barrier may comprise adhering a portion of the care assembly coupled to an inserter assembly to the barrier. The method may further comprise pulling the inserter assembly away from the barrier. The method may further comprise lifting the barrier, via adhesion of the portion of the care assembly, from a resting position to a lifted position. The method may further comprise disengaging an insertion latch arrangement and propelling an insertion unit and an access assembly in an insertion direction after lifting the barrier. The method may further comprise disengaging a retraction latch arrangement and propelling a retraction unit including an insertion sharp in a retraction direction once the insertion unit reaches a retraction release position. Displacement of the access assembly in the insertion direction and displacement of the retraction unit in the retraction direction may at least partially temporally overlap.

In some embodiments, the method may further comprise coupling the access assembly to the portion of the patient care assembly. In some embodiments, propelling the retraction unit in the retraction direction may further comprise tilting the insertion sharp. In some embodiments, disengaging the insertion latch arrangement may comprise displacing a portion of a casing of the inserter assembly into a portion of the insertion latch arrangement and deflecting the portion of the insertion latch arrangement. In some embodiments, disengaging the retraction latch arrangement may comprise driving the retraction unit in the insertion direction and into a trigger. In some embodiments, driving the retraction unit in the insertion direction and into the trigger may comprise displacing the retraction unit and insertion unit in tandem with one another when the insertion latch arrangement is disengaged. In some embodiments, disengaging the retraction latch arrangement may comprise decoupling the retraction unit from the insertion unit as the insertion unit is displaced in the insertion direction. In some embodiments, disengaging the insertion latch arrangement may further comprise freeing a first bias member held in a first distorted state while the insertion latch arrangement is in an engaged state and disengaging the retraction latch arrangement may comprise freeing a second bias member held in a second distorted state while the retraction latch arrangement is in an engaged state. In some embodiments, the method may further comprise removing a lock member from the inserter assembly.

In accordance with another exemplary embodiment of the present disclosure, a method of placing an access device with an inserter assembly may comprise coupling the inserter assembly to a biological barrier. The method may further comprise lifting the biological barrier coupled to the inserter assembly from a resting state to a lifted state by displacing the inserter assembly in a direction away from the barrier. The method may further comprise automatically disengaging an insertion latch arrangement after the skin has been lifted at least a certain distance and propelling an insertion unit including a retraction unit with an insertion sharp in an insertion direction. The method may further comprise automatically disengaging a retraction latch arrangement coupling the retraction unit to the remainder of the insertion unit once the insertion unit is displaced to a retraction release position and propelling the retraction unit in a retraction direction. The method may further comprise propelling the remainder of the insertion unit in the insertion direction from the retraction release position to a forward position.

In some embodiments, the method may further comprise blocking displacement of the insertion unit in the retraction direction after the insertion unit reaches the forward position. In some embodiments, the method may further comprise tilting the retraction unit as the retraction unit is propelled in the retraction direction. In some embodiments, the method may further comprise coupling an access assembly to an access assembly base as at least the remainder of the insertion unit is displaced in the insertion direction. In some embodiments, the retraction release point may be reached before the access assembly is coupled to the access assembly base. In some embodiments, the access assembly may be a cannula subassembly and the access assembly base is an infusion set base. In some embodiments, coupling the inserter assembly to the biological barrier may comprise adhering an access assembly base to the biological barrier. In some embodiments, the method may further comprise releasing the access assembly base from the inserter assembly.

In accordance with another example embodiment of the present disclosure an example inserter assembly may comprise a casing including an exterior housing and an end cap. The inserter assembly may further comprise an interior housing. The inserter assembly may further comprise an insertion driver included in the interior housing and displaceable from an initial position, in which the insertion driver is engaged with an insertion driver latch defined on the interior sidewall of the interior housing, to a forward position. The inserter assembly may further comprise an insertion bias member between the insertion driver and the end cap. The inserter assembly may further comprise a retainer configured to engage a first latch upon displacement of the casing in a first direction to a ready position. The insertion bias member may be held in a distorted state when the retainer is engaged with the first latch and the insertion driver is engaged with the insertion driver latch. The insertion bias member may be configured to urge the insertion driver to the forward position upon release of the insertion driver latch. The inserter assembly may further comprises a disarming lock. The disarming lock may be configured to displace between an inactive position and an active position. The disarming lock may block release of the insertion driver latch in the active position.

In some embodiments, the insertion driver may disengage the retainer from the first latch when displaced toward the forward position. In some embodiments, the insertion driver may include a cantilevered arm including a catch body which is configured to engage the insertion driver latch. The interior housing may block deflection of the cantilevered arm in a direction toward the interior housing. In some embodiments, the disarming lock may include a body which blocks deflection of the cantilevered arm in a direction away from the interior housing when the disarming lock is in the active position. In some embodiments, the disarming lock may include a base portion from which a set of barrier bodies project. The barrier bodies may be configured to extend through passages in the end cap. In some embodiments, the disarming lock may be configured to rotationally displace between the inactive position and active position. In some embodiments, the inserter assembly may further comprise a retraction bias member configured to distort when the casing is displaced to the ready state. The retraction bias member may be configured to be held in a distorted state when the retainer is in engagement with the first latch. In some embodiments, the insertion driver may disengage the retainer from the first latch when displaced toward the forward position. The retraction bias member may be freed from the distorted state when the retainer is disengaged from the first latch. The retraction bias member may be configured to displace the retainer away from the first latch and displace the insertion driver to the initial position upon disengagement of the retainer from the first latch. In some embodiments, the insertion driver may include a port configured to couple to an insertion sharp holder bearing an insertion sharp. In some embodiments, the interior housing may include a receptacle opposite the end cap, the receptacle configured to couple to a care assembly cartridge.

In accordance with another example embodiment of the present disclosure, an inserter assembly may comprise a casing. The inserter assembly may further comprise a disarming lock displaceable between an inactive position and a disarming position. The inserter assembly may further comprise an interior housing. The casing may be displaceable relative to the interior housing when the disarming lock is in the inactive position and blocked from displacement relative to the interior housing when the disarming lock is in the disarming position. The inserter assembly may further comprise a retainer configured to engage a first latch when the casing is displaced in a first direction toward the interior housing. The inserter assembly may further comprise an insertion driver included within the interior housing and displaceable from a first position to a second position and including a routing body. The inserter assembly may further comprise a release finger included on the casing. The release finger may be configured deflect around the routing body when the casing is displaced in the first direction and configured to displace the routing body in a release direction which disengages the insertion driver from an insertion driver latch when the casing is pulled in a second direction. The inserter assembly may further comprise a first bias member maintained in a distorted state when the retainer is engaged to the first latch and the insertion driver is engaged with the insertion driver latch. The first bias member may urge the insertion driver toward the second position when the insertion driver is disengaged from the insertion driver latch.

In some embodiments, the disarming lock and exterior housing may be a continuous monolithic component. In some embodiments, the disarming lock may be deflectable relative to the exterior housing to displace the disarming lock between the inactive position and the active position. In some embodiments, at least a portion of the disarming lock may be disposed in a window defined in the interior housing when the disarming lock is in the disarming position. In some embodiments, the insertion driver may include a cantilevered arm including a catch body which engages with the insertion driver latch, the routing body being disposed on the cantilevered arm. In some embodiments, the insertion driver latch may be provided by at least one shelf defined on an interior surface of the interior housing. In some embodiments, the insertion driver may include a port configured to mate with an insertion sharp holder. In some embodiments, the inserter assembly further may comprises a second bias member. In some embodiments, the second bias member may be configured to transition to a distorted state when the casing is displaced in the first direction. The second bias member may be held in the distorted state when the retainer is engaged with the first latch. In some embodiments, the second bias member may be configured to urge the retainer away from the first latch and urge the insertion driver toward the first position and into engagement with the insertion driver latch when the first latch is disengaged.

In accordance with another example embodiment of the present disclosure, an inserter assembly may comprise a casing including an exterior housing and an end cap. The inserter assembly may further comprise an interior housing. The inserter assembly may further comprise an insertion driver included in the interior housing and displaceable from an initial position, in which the insertion driver is engaged with an insertion driver latch defined on the interior sidewall of the interior housing, to a forward position. The inserter assembly may further comprise an insertion bias member between the insertion driver and the end cap. The inserter assembly may further comprise a retainer configured to distort a second bias member and engage a first latch upon displacement with the casing in a first direction from an unarmed state to a ready state. The insertion bias member may be held in a distorted state when the retainer is engaged with the first latch and the insertion driver is engaged with the insertion driver latch. The insertion bias member may be configured to urge the insertion driver to the forward position upon release of the insertion driver latch. The inserter assembly may further comprise a disarming actuator configured to disengage the retainer from the first latch when displaced from an inactive state to an actuated state. The second bias member may be configured to propel the casing and retainer to the unarmed state upon disengagement of the retainer from the first latch.

In some embodiments, the first bias member may be in abutment with the insertion driver and a face of the retainer in abutment with the casing and is configured to urge the retainer and casing to the unarmed state upon disengagement of the retainer from the first latch. In some embodiments, the insertion driver may include a cantilevered arm including a catch body which engages with the insertion driver latch. In some embodiments, the insertion driver latch may be provided by at least one shelf defined on an interior surface of the interior housing. In some embodiments, the insertion driver may include a port configured to mate with an insertion sharp holder. In some embodiments, the interior housing may include a receptacle opposite the end cap. The receptacle may be configured to couple to a care assembly cartridge. In some embodiments, a release finger may be defined on the casing and configured to hold the insertion driver in engagement with the insertion driver latch when the casing is displaced toward the ready state. In some embodiments, the release finger may be further configured to dislodge the insertion driver from the insertion driver latch when the casing is displaced in a second direction opposite the first direction from the ready state to a trigger position when the disarming actuator is in the inactive state. In some embodiments, the disarming actuator may be configured to deflect the release finger to a deflected state when transitioned from the inactive state to the active state. In some embodiments, when the casing is displaced from the ready state to the trigger position and the release finger is in the deflected state, the release finger may not contact the insertion driver. In some embodiments, the release finger may be configured to dislodge the insertion driver from the insertion driver latch when the casing is displaced in a second direction opposite the first direction from the ready state to a trigger position. In some embodiments, when the casing is displaced through the trigger position as the retainer and casing are propelled toward the unarmed state by the second bias member, the retainer may be configured to collide with the insertion driver and reverse progress of the insertion driver toward the forward state engendered by the release of the insertion driver latch.

In accordance with another example embodiment of the present disclosure an inserter assembly may comprise a casing including an exterior housing and an end cap. The inserter assembly may further comprise an interior housing. The inserter assembly may further comprise an insertion driver included in the interior housing and displaceable from an initial position, in which the insertion driver is engaged with an insertion driver latch defined on the interior sidewall of the interior housing, to a forward position. The inserter assembly may further comprise an insertion bias member between the insertion driver and the end cap. The inserter assembly may further comprise a retainer configured to distort a second bias member and engage a first latch upon displacement with the casing in a first direction from an unarmed state to a ready state. The insertion bias member may be held in a distorted state when the retainer is engaged with the first latch and the insertion driver is engaged with the insertion driver latch. The insertion bias member may be configured to urge the insertion driver to the forward position upon release of the insertion driver latch. The inserter assembly may further comprise a disarming actuator configured to disengage the retainer from the first latch when displaced from an inactive state to an actuated state. The second bias member may be configured to propel the casing and retainer through a retraction stroke in a second direction opposite the first direction upon disengagement of the retainer from the first latch.

In some embodiments, the first bias member may be in abutment with the insertion driver and a face of the retainer in abutment with the casing and is configured to urge the retainer and casing through the retraction stroke upon disengagement of the retainer from the first latch. In some embodiments, the insertion driver may include a cantilevered arm including a ledge which engages with the insertion driver latch. In some embodiments, the insertion driver latch may include a shelf defined on the interior housing. In some embodiments, the insertion driver may include a port configured to mate with an insertion sharp holder. In some embodiments, the interior housing may include a receptacle opposite the end cap. The receptacle may be configured to couple to a care assembly cartridge. In some embodiments, a release finger may be defined on the casing and may be configured to reinforce engagement of the insertion driver with the insertion driver latch when the casing is displaced toward the ready state. In some embodiments, the release finger may be further configured to dislodge the insertion driver from the insertion driver latch when the casing is displaced in the second direction from the ready state to a trigger position and the disarming actuator is in the inactive state. In some embodiments, the disarming actuator may be configured to deflect the release finger to a deflected state when transitioned from the inactive state to the active state. In some embodiments, when the casing is displaced through the retraction stroke, the release finger may be in the deflected state and is maintained out of contact with the insertion driver. In some embodiments, the release finger may be configured to dislodge the insertion driver from the insertion driver latch when the casing is displaced through the retraction stroke. In some embodiments, when the casing and retainer are displaced through the retraction stroke, the retainer may be configured to collide with and reverse progress of the insertion driver toward the forward state engendered by the release of the insertion driver latch.

In accordance with another embodiment of the present disclosure a method of disarming an inserter having a spring loaded insertion driver and a spring loaded retractor may comprise adhering a portion of a patient care assembly to a barrier. The method may further comprise displacing a disarming actuator of the inserter from an inactive state to an active state. The method may further comprise dislodging a first latch holding the retractor in place as the disarming actuator is displaced to the active state. The method may further comprise releasing a spring of the spring loaded retractor and driving the spring loaded retractor and a casing of the inserter through a retraction stroke. The method may further comprise disassociating the portion of the patient care assembly from the barrier.

In some embodiments, the method may further comprise maintaining a second latch holding the spring loaded insertion driver in place as the spring loaded retractor and casing are driven through the retraction stroke. In some embodiments, the method may further comprise releasing a spring of the spring loaded insertion driver during the retraction stroke, the spring of the spring loaded insertion driver may urge the insertion driver a forward direction. In some embodiments, the method further may comprise colliding into the spring loaded insertion driver with the spring loaded retractor and reversing progress of the insertion driver toward the forward direction as the spring loaded retractor displaces through the retraction stroke. In some embodiments, displacing the disarming actuator may comprise depressing a button. In some embodiments, displacing the disarming actuator may comprise depressing at least one tab coupled to the first latch. In some embodiments, dislodging the first latch may comprise deflecting a latch arm out of engagement with the spring loaded retractor. In some embodiments, the method may further comprise deflecting a release finger of the casing out of alignment with a fin on a cantilevered arm of the insertion driver upon displacement of the disarming actuator from the inactive to the active state. In some embodiments, the method further may comprise automatically returning the disarming actuator to the inactive state during the retraction stroke. In some embodiments, automatically returning the disarming actuator to the inactive state may comprise displacing a ramped face on the disarming actuator into the insertion driver. In some embodiments, the method may further comprise driving the disarming actuator with the retainer and the casing through the retraction stroke.

In accordance with another example embodiment of the present disclosure, an example inserter assembly may comprise a casing. The inserter assembly may further comprise a body including a cavity flanked by a set of arms. The inserter assembly may further comprise a patient care assembly including a base releasably engaged with the set of arms and a second portion. The inserter assembly may further comprise a spring biased unit including sharp holder on which an insertion sharp and the second portion of the patient care assembly are borne. The inserter assembly may further comprise a spring for the spring biased unit. The inserter assembly may further comprise a trigger having a first state in which the spring is maintained in an energy storing state and a second state in which the spring is released from the energy storing state. The spring may propel the spring biased unit toward the base when the trigger is actuated. The inserter assembly may further comprise a yoke having at least a portion adjacent each of the set of arms. The yoke may restrain at least a portion of each of the set of arms from deflecting. The arms may include a set of nubs. A portion of the spring biased unit may collide with the nubs and splay the set of arms apart to release the base when the insertion sharp and second portion of the patient care assembly are displaced to toward the base.

In some embodiments, the yoke may be an open centered member which surrounds the arms. In some embodiments, the yoke may include a split section and rests upon a sill defined on the set of arms. In some embodiments, the yoke may rest upon a sill defined on the set of arms and a portion of the spring biased unit may include a set of projections. The projections may collide with and distort the yoke around the sill when the spring propels the spring bias unit toward the base. In some embodiments, the yoke may include a set of pads. Each of the pads may be adjacent a respective arm of the set of arms. The pads may connect to a section of the body via a flexure. In some embodiments, the portion of the spring biased unit may collide with each pad when the spring biased unit is propelled toward the base and the spring biased unit may exert a force on that causes the flexures to yield. In some embodiments, the yoke may be provided by a set of lobes on the sharp holder through which the arms extend. Each of the set of arms may have a thick region and a thin region. Each lobe may block deflection of a respective arm of the set of arms when the lobe is adjacent the thick region of the respective arm. The lobe may be sized to permit deflection of the respective arm when adjacent the thin region of the respective arm. In some embodiments, the base may be an infusion set base and the second portion of the patient care assembly may be a cannula subassembly. In some embodiments, the patient care assembly may be an analyte sensor. In some embodiments, the base and second portion of the patient care assembly may couple together when the spring biased unit is propelled toward the base.

In accordance with another example embodiment of the present disclosure, an example patient care assembly placement system may comprise an inserter assembly including a port and a receptacle body. The port may have a central slot flanked on opposing sides by segments of a port rim. The receptacle body may include a set of shoes each swept about a portion of an axis of the port from a closed shoe end to an open shoe end. The shoes may each have an overhang region most distal a main section of the receptacle body. The system may further comprise a cartridge including a retainer, a patient care assembly coupled to the retainer, and a sharp bearing body from which an insertion sharp projects. The retainer may include a set of mating pins each having a stem portion and a wider head portion. The sharp bearing body may include a first end opposite a second end from which the insertion sharp projects. The sharp bearing body including a thinned region intermediate the first and second end. When the cartridge is placed in an aligned position relative the receptacle body and rotated to a coupled state, each mating pin may displace from the open shoe end to the closed shoe end of a respective shoe. The cartridge may translationally displace to a position in which the first end of the sharp bearing body is advanced into the port to a depth where thinned region is aligned with the port rim over a mating pin capture displacement range. The head portion of each mating pin may displace along a ramp of the overhang region of the respective shoe in the mating pin capture displacement range. The first end of the sharp bearing body may subsequently be rotated over the port rim in a sharp bearing body capture displacement range.

In accordance with another example embodiment of the present disclosure an example patient care assembly placement system may comprise an inserter assembly including a port flanked on opposing sides by shelves and a receptacle body including a set of mating tracks partially swept around the axis of the port. The inserter may further comprise a cartridge including a retainer, a patient care assembly coupled to the retainer, and a sharp holder from which an insertion sharp projects. The retainer may include a set of mating projections. The sharp holder may include a thinned region intermediate a first end opposite a second end from which the insertion sharp projects. When the cartridge is placed in an aligned position relative the receptacle body and rotated to a coupled state, the mating projections may displace along a ramped region of a respective mating track in a mating projection capture displacement range translationally driving the cartridge to a position in which the first end of the sharp holder is advanced into the port to a depth where thinned region is aligned with the shelves. The first end of the sharp holder may subsequently be rotated over the shelves in a sharp holder capture displacement range of the cartridge.

In some embodiments, the mating tracks may include shoes with overhanging shoulder segments at a portion of each mating track most distal a main section of the receptacle body. In some embodiments, the mating projections may each be mating pins having a head portion and a relatively thinner stem portion connecting the head portion to the rest of the retainer. In some embodiments, the port may be shaped to accept the first end of the sharp holder when the cartridge is within a rotational position within the mating projection capture displacement range. In some embodiments, the first end of the sharp holder may have an elongate cross-sectional shape and the thinned region may have a cross-sectional shape which is less elongate than that of the first end. In some embodiments, the thinned region may be formed by a notch recessed into the sharp holder at an angle which is substantially perpendicular to the axis of the insertion sharp. In some embodiments, the shelves may have a thickness sufficient to substantially fill the notch when the cartridge has been rotated through the sharp holder capture displacement range. In some embodiments, the ramped region of each respective mating track may begin at an open end of that mating track. The mating projections may be at a closed end of respective mating tracks when the cartridge is rotated to the coupled state. In some embodiments, the ramped region of each respective mating track may include a steepest portion along a segment of the ramped region most proximal the open end. In some embodiments, the patient care assembly may be selected from a list consisting of an infusion set and an analyte sensor. In some embodiments, the patient care assembly may include a first portion and a second portion spaced from the first portion within the cartridge.

BRIEF DESCRIPTION OF THE DRAWINGS

These and other aspects will become more apparent from the following detailed description of the various embodiments of the present disclosure with reference to the drawings wherein:

FIG. 86 depicts a bottom view of an example inserter assembly;

FIG. 87 depicts a cross-sectional view taken at the indicated cut plane of FIG. 86;

FIGS. 88A-88B depict cross-sectional views of another exemplary inserter assembly about to be applied to a user's skin;

FIG. 89A depicts a side view of an alternative embodiment of a sharp holder;

FIG. 89B depicts a perspective view of the sharp holder shown in FIG. 89A;

FIG. 89C depicts another side view of the sharp holder illustrated in FIG. 89A;

FIG. 90 depicts a perspective view of an exemplary retainer cap;

FIG. 91 depicts a cross-sectional view of an example retainer cap and sharp holder;

FIG. 92 depicts a detailed view of a portion of FIG. 91;

FIG. 93A depicts a perspective view of an exemplary sharp retractor;

FIG. 93B depicts another perspective view of the sharp retractor shown in FIG. 93A;

FIG. 94 depicts a perspective view of an example inserter assembly including a button;

Figure 94:
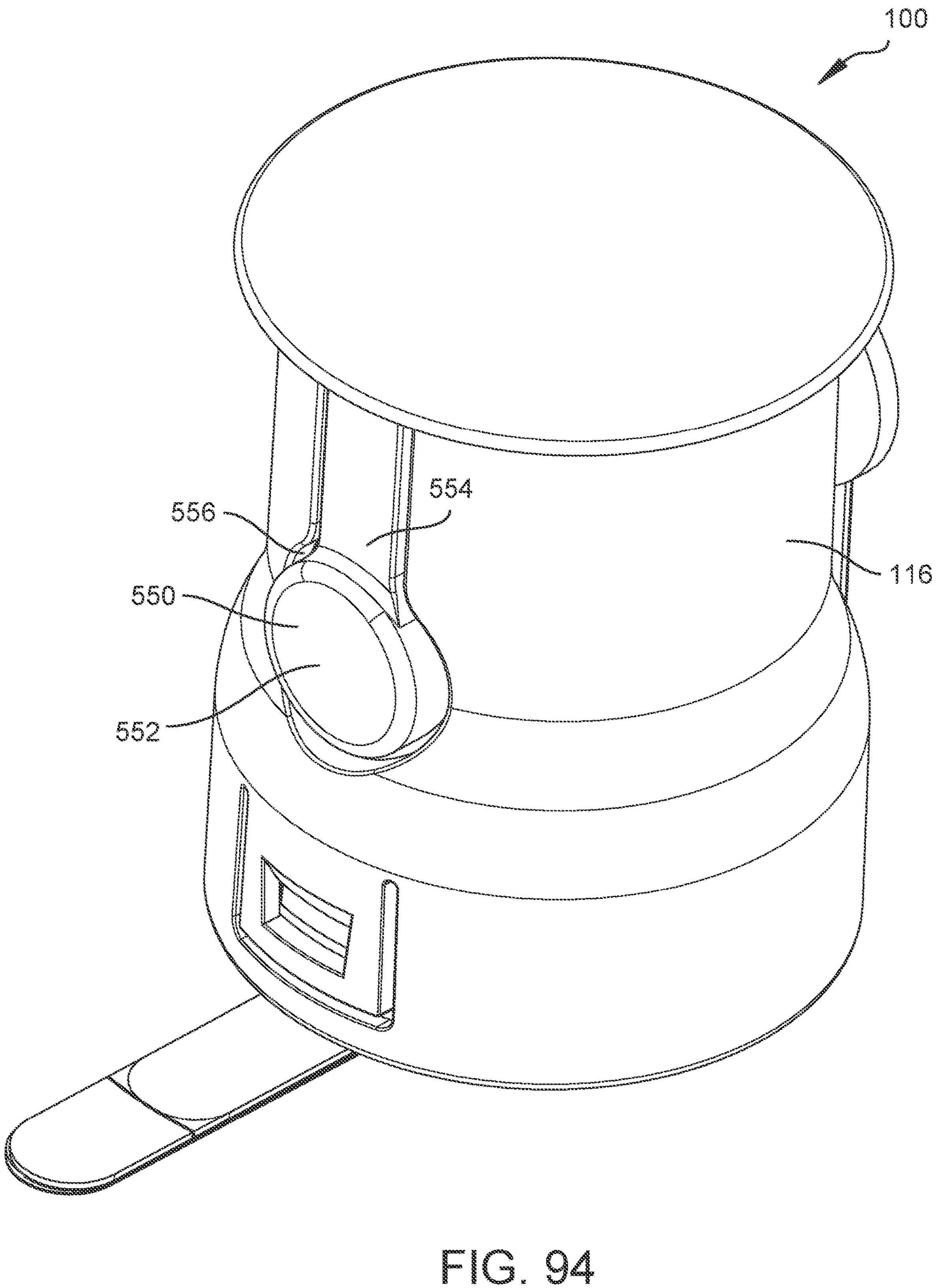
Figure 95C:
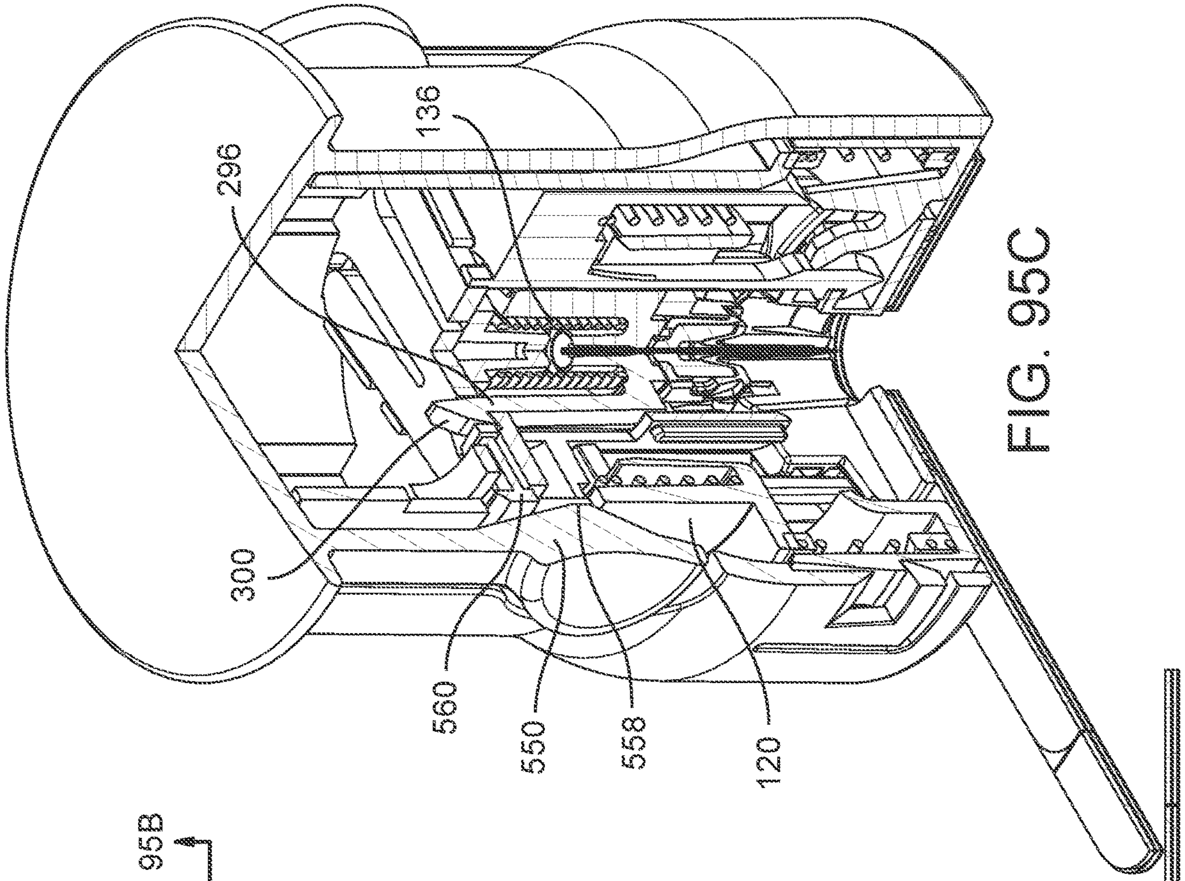
Figure 95A:
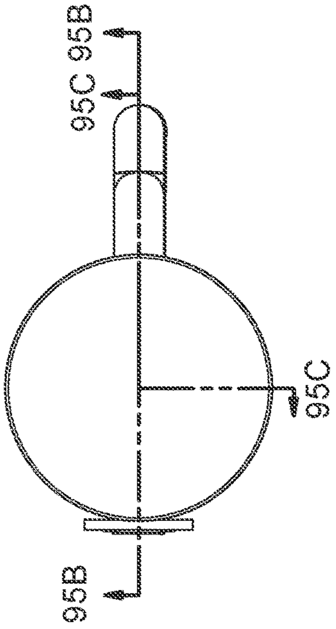
Figure 95B:
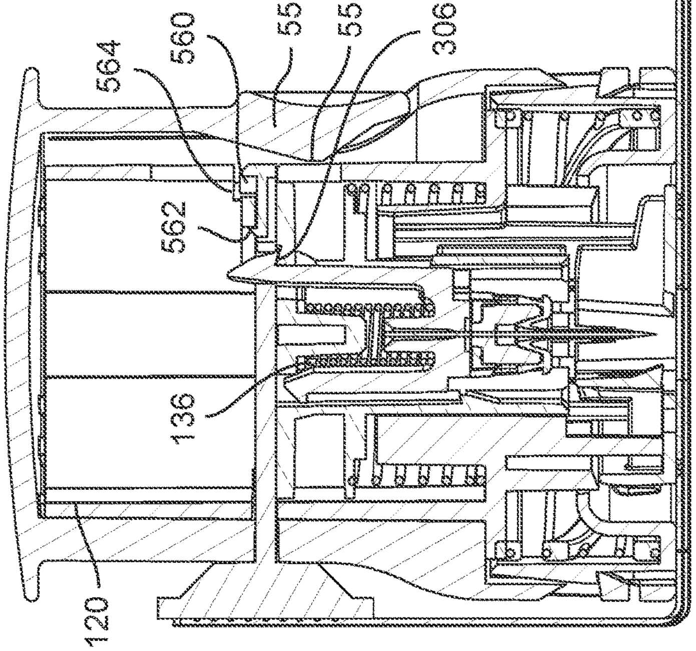
Figure 96:
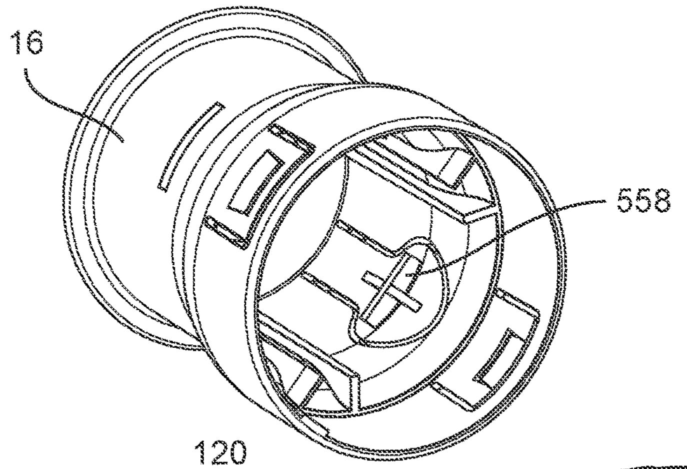
Figure 98:
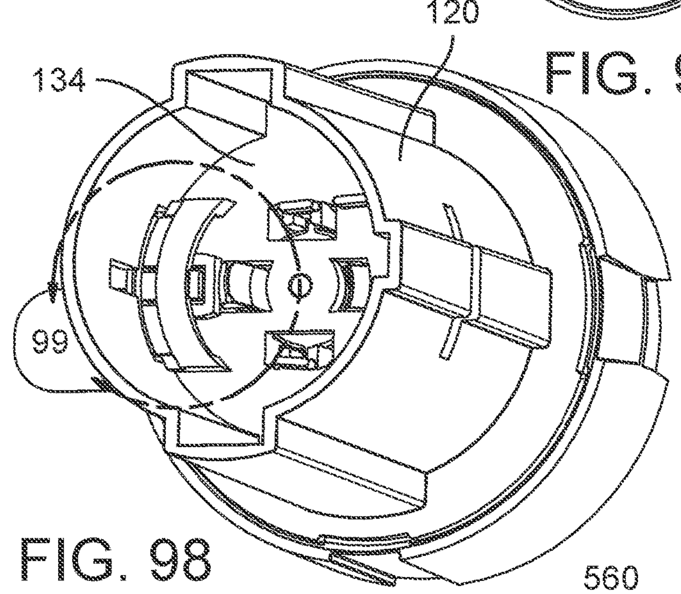
Figure 97:
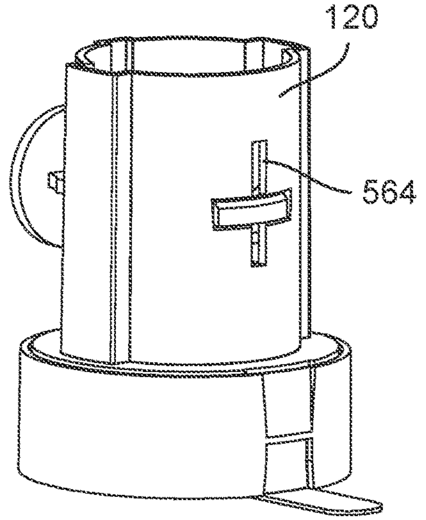
Figure 100:
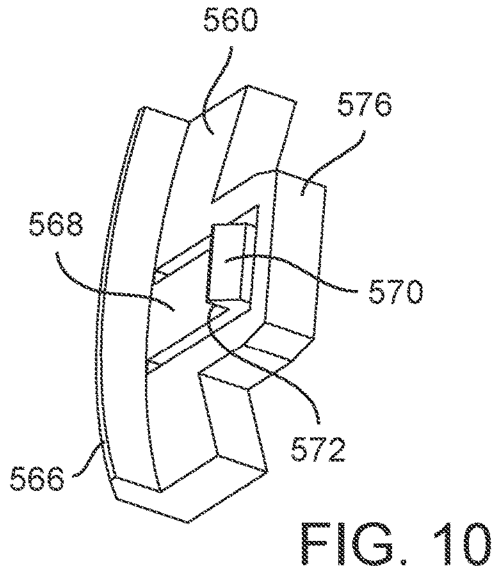
Figure 99:
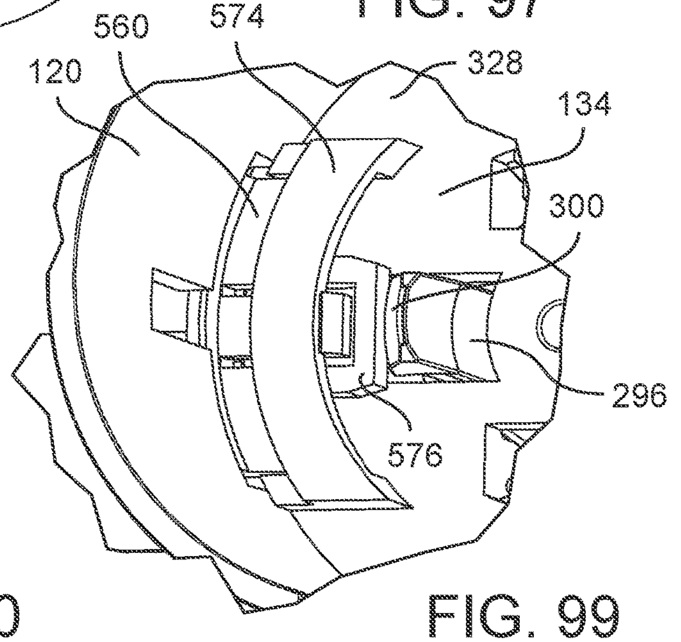
Figure 101:
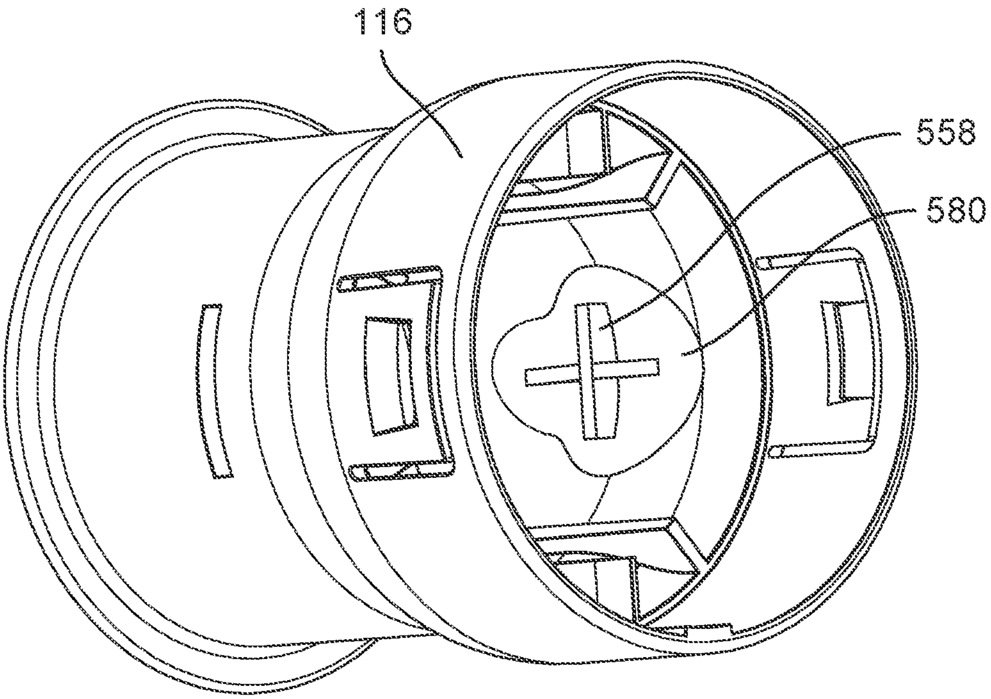
Figure 102:
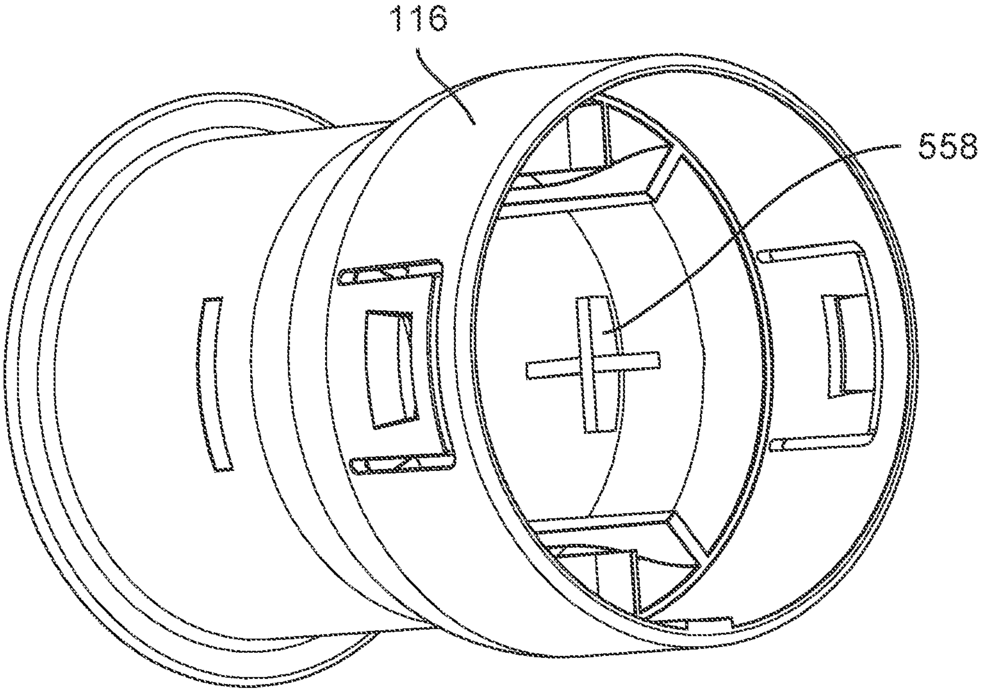
Figure 103:
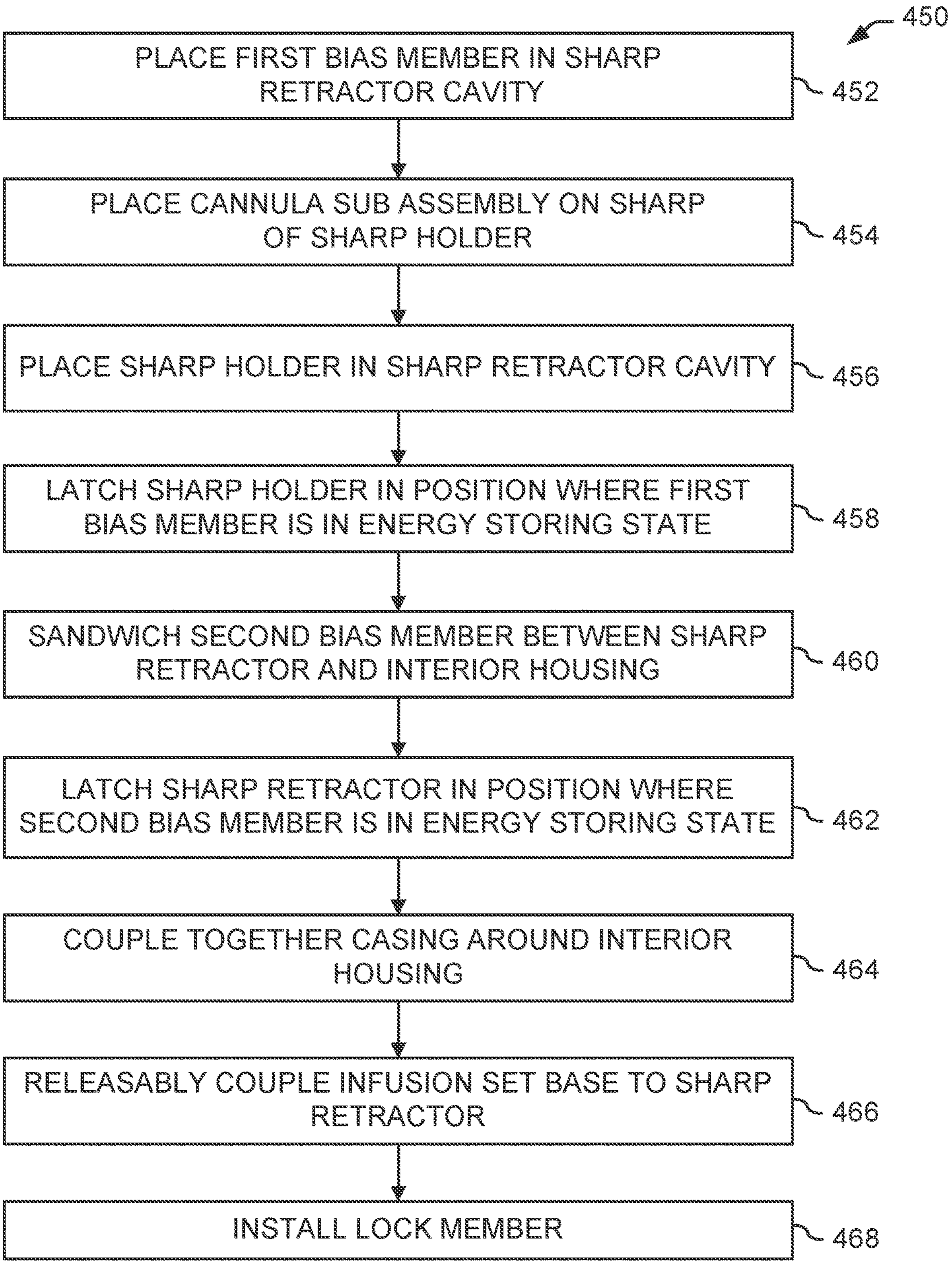
Figure 104:
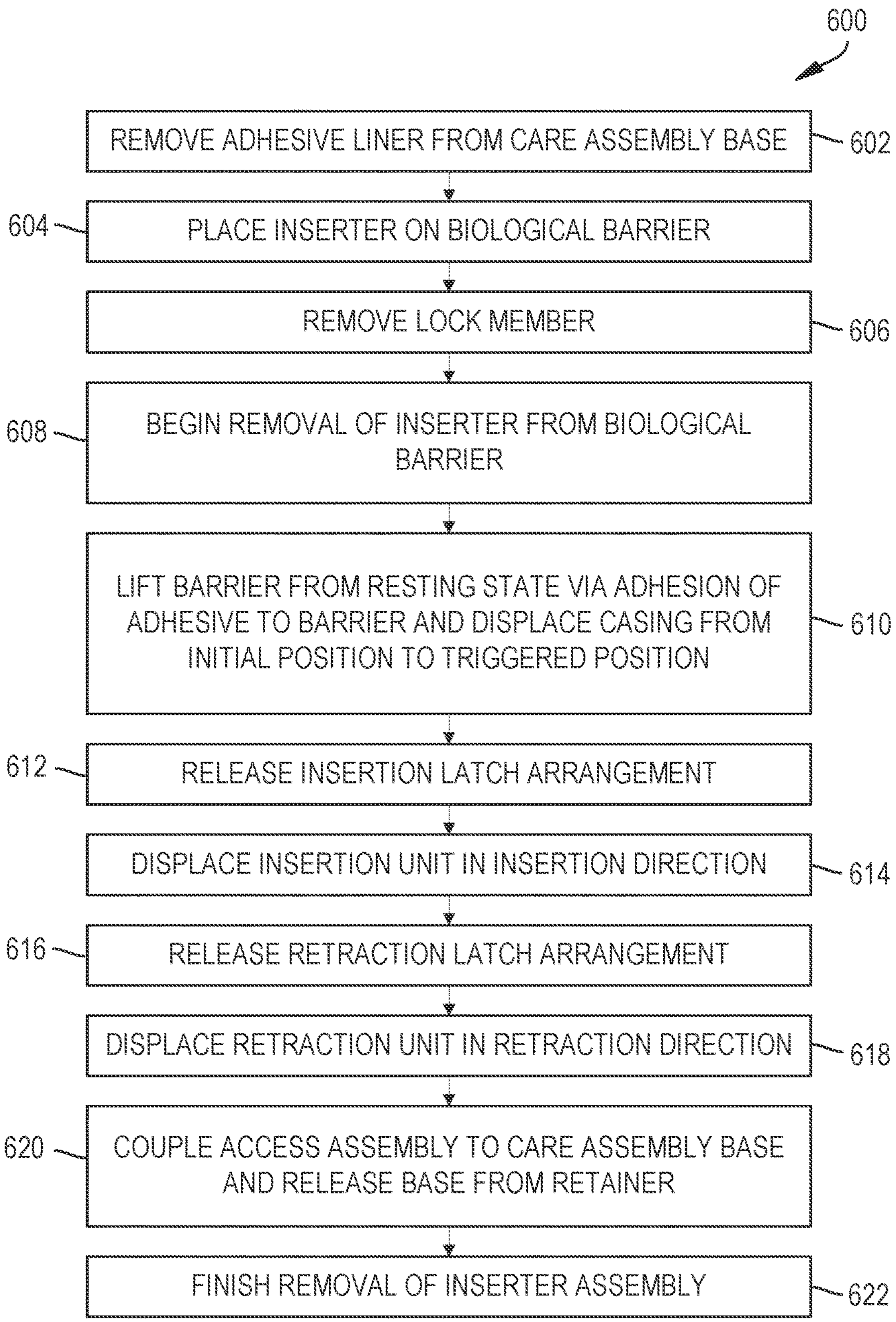
Figure 105:
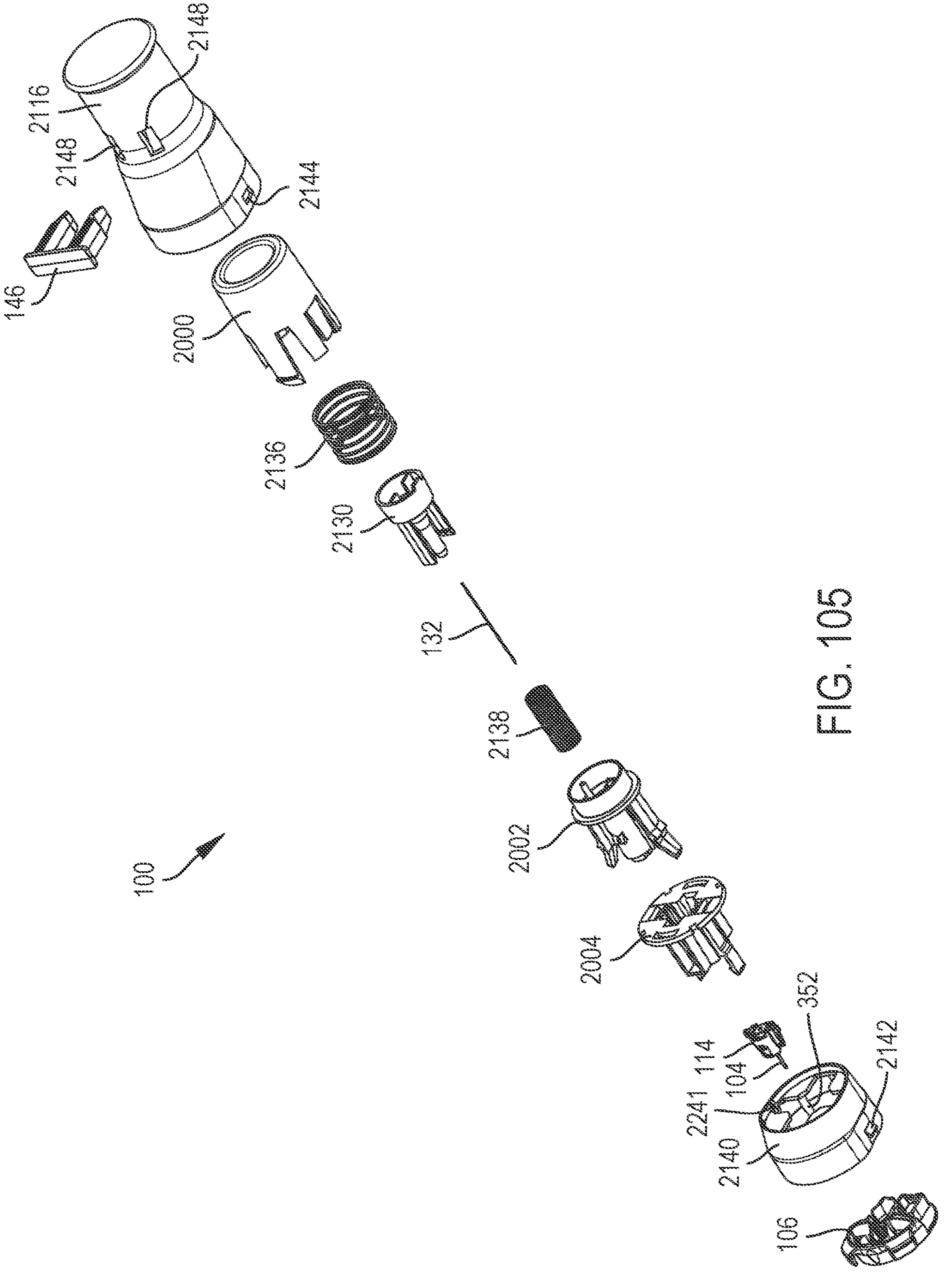
Figure 106:
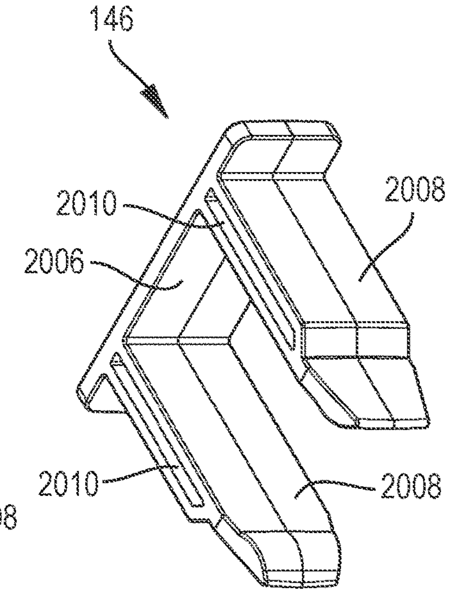
Figure 107:
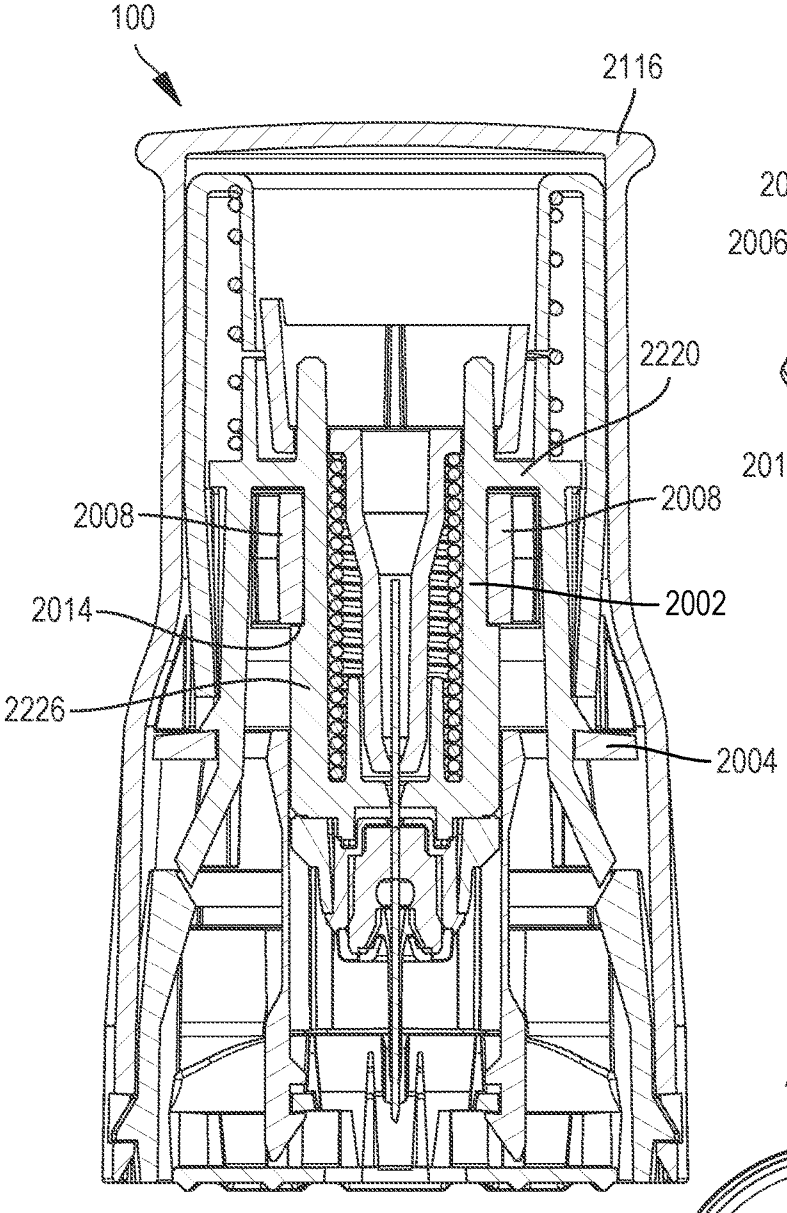
Figure 108:
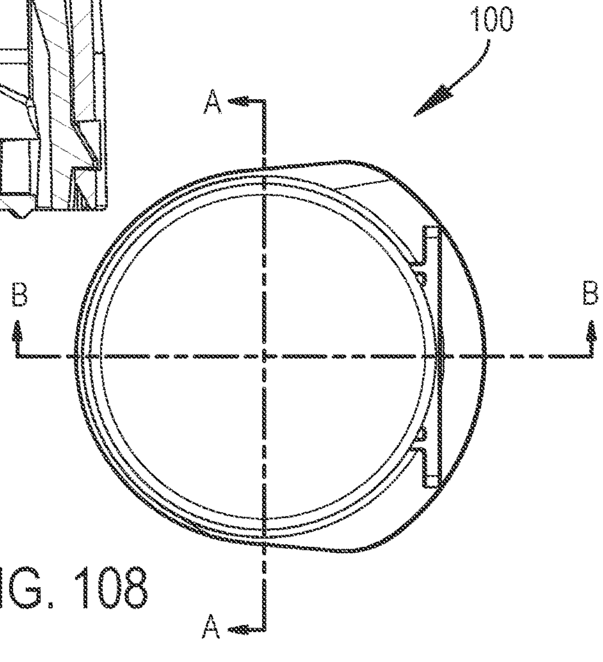
Figure 109A:
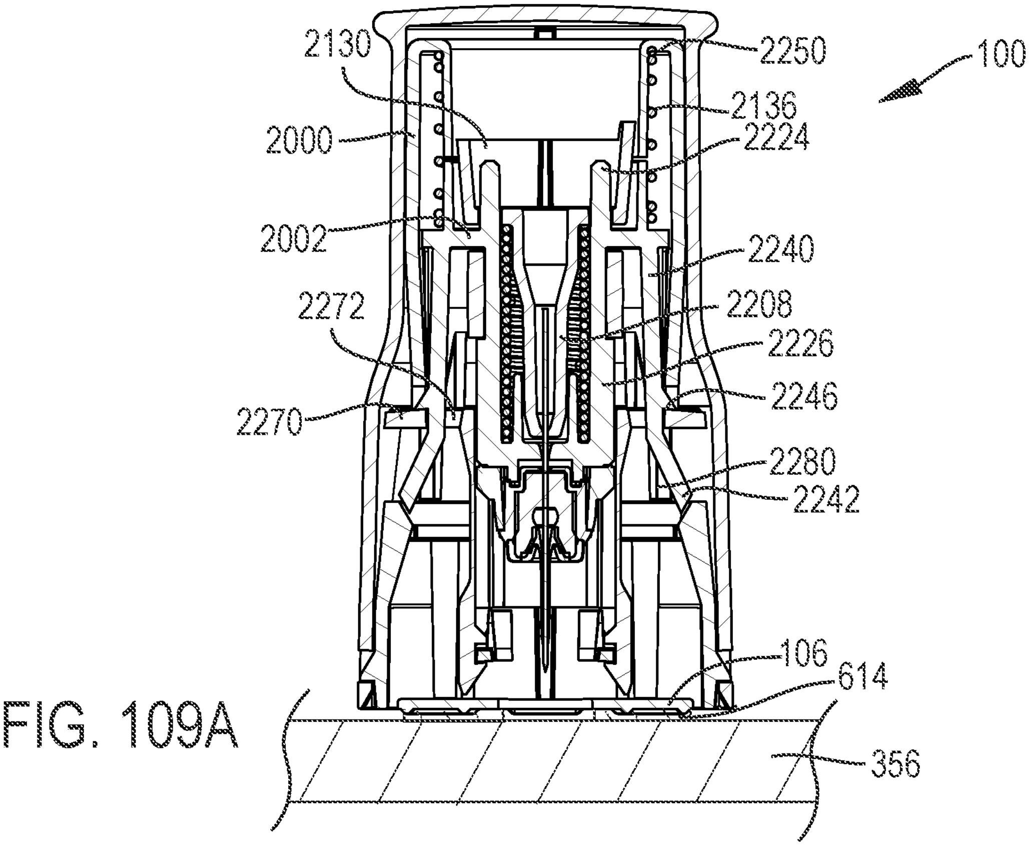
Figure 109B:
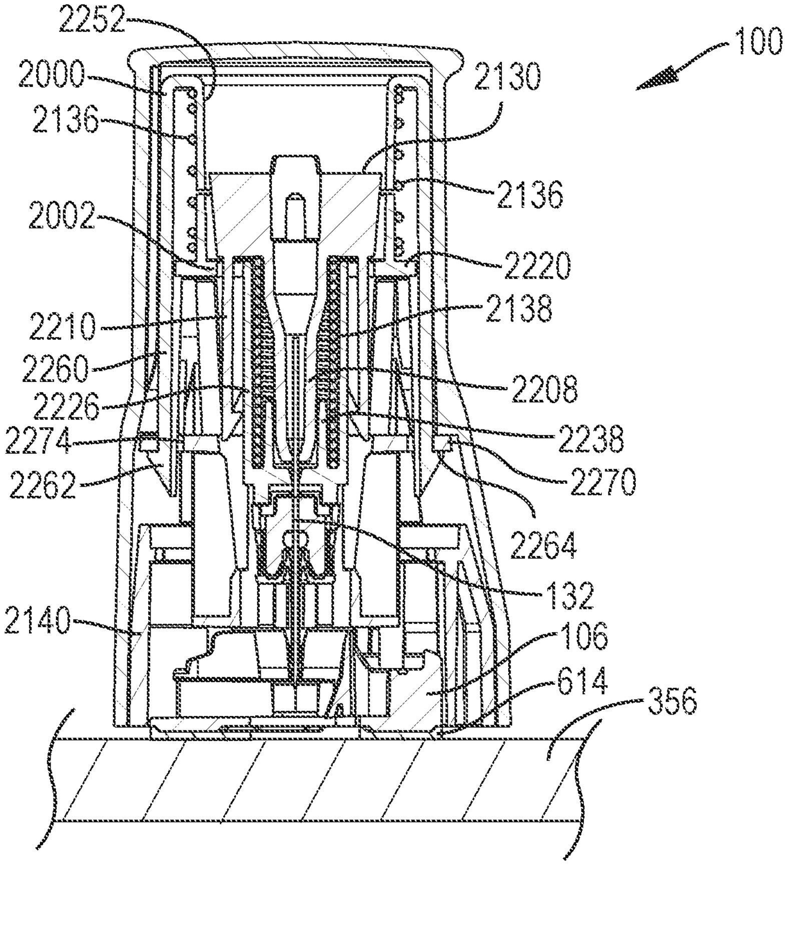
Figure 110:
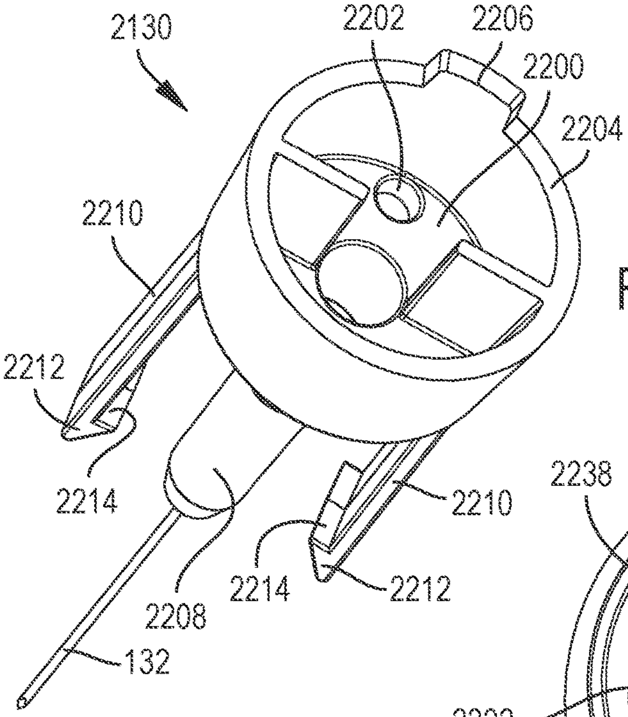
Figure 111A:
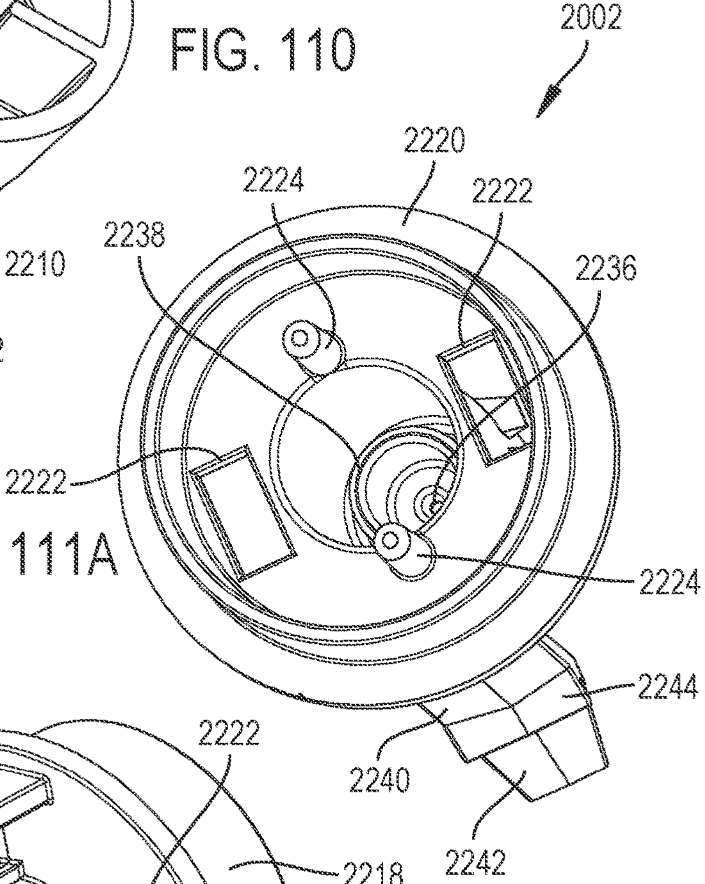
Figure 111B:
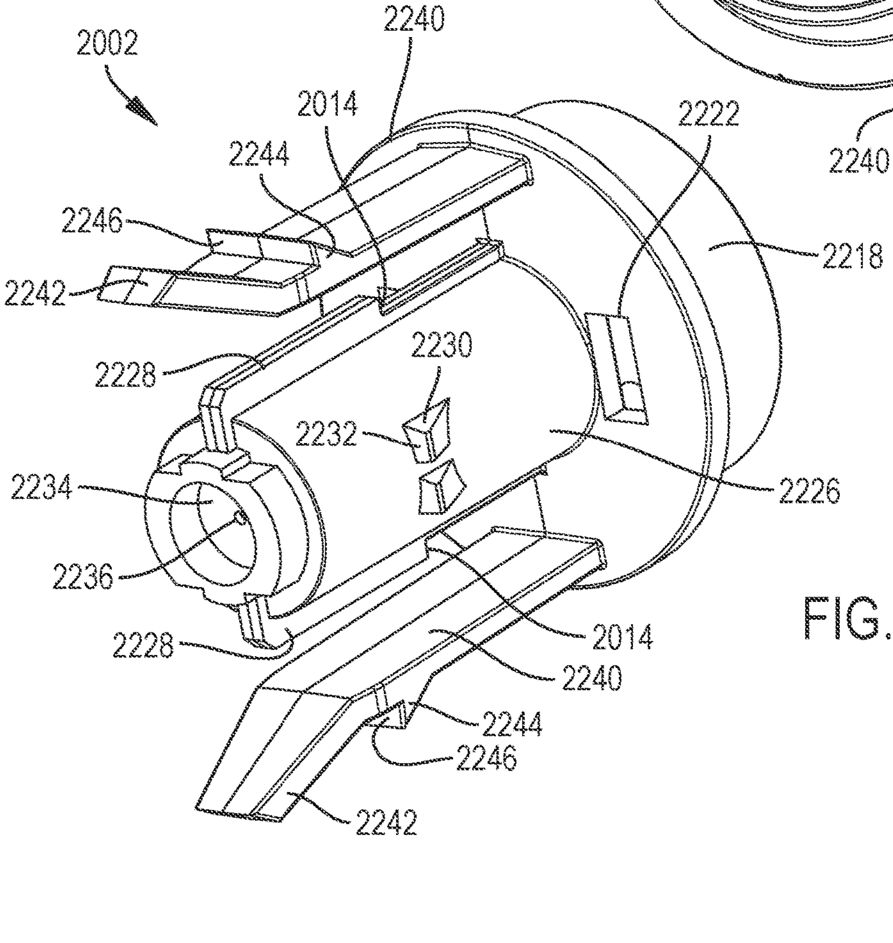
Figure 112:
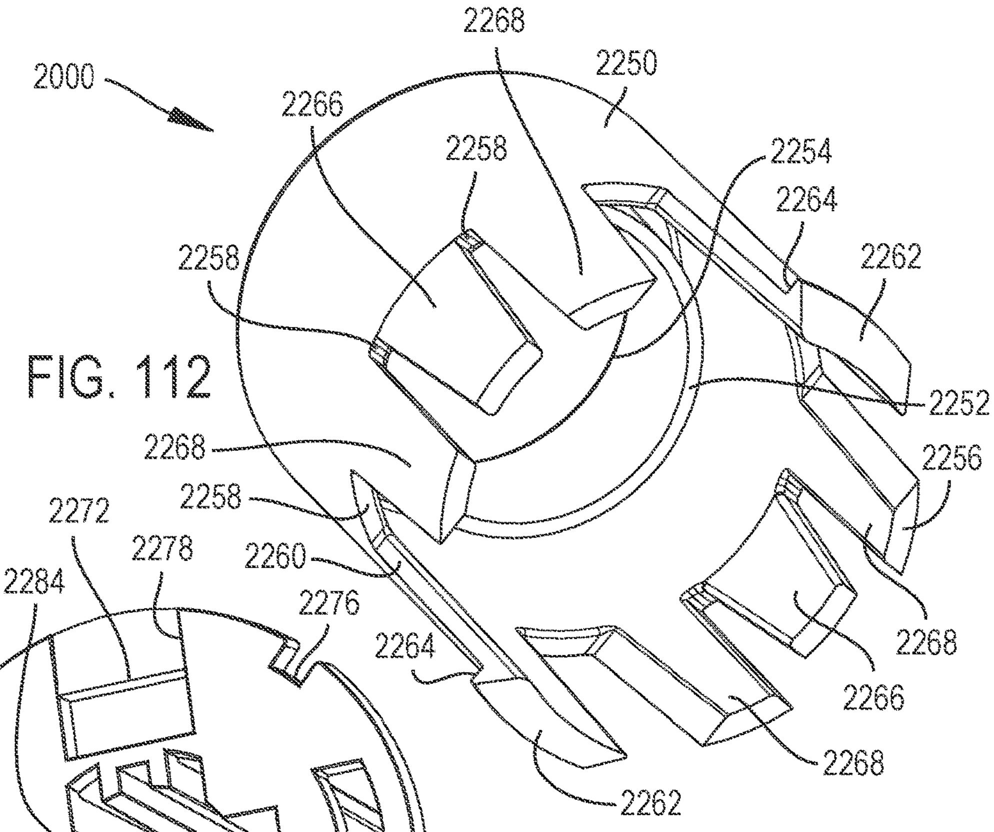
Figure 113A:
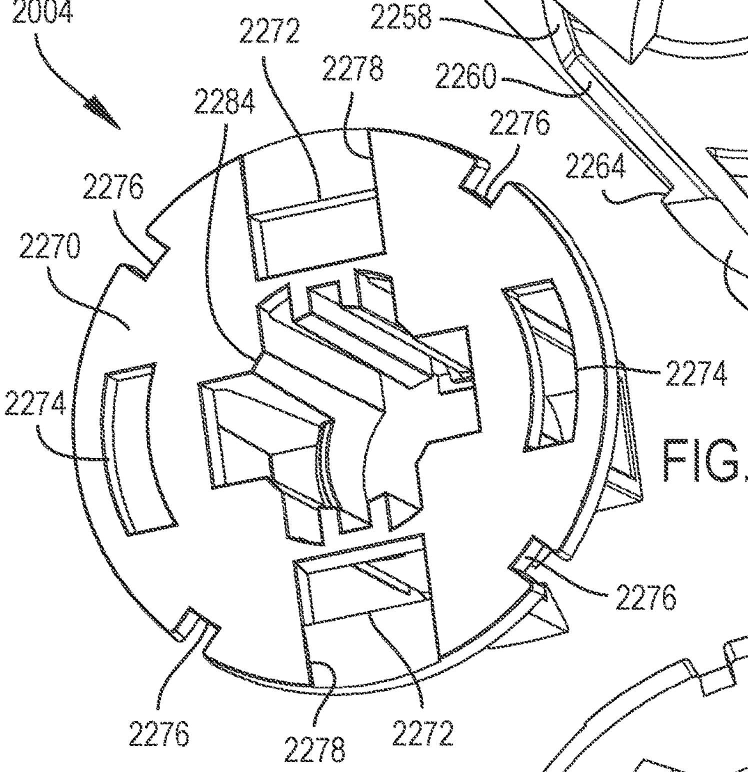
Figure 113B:
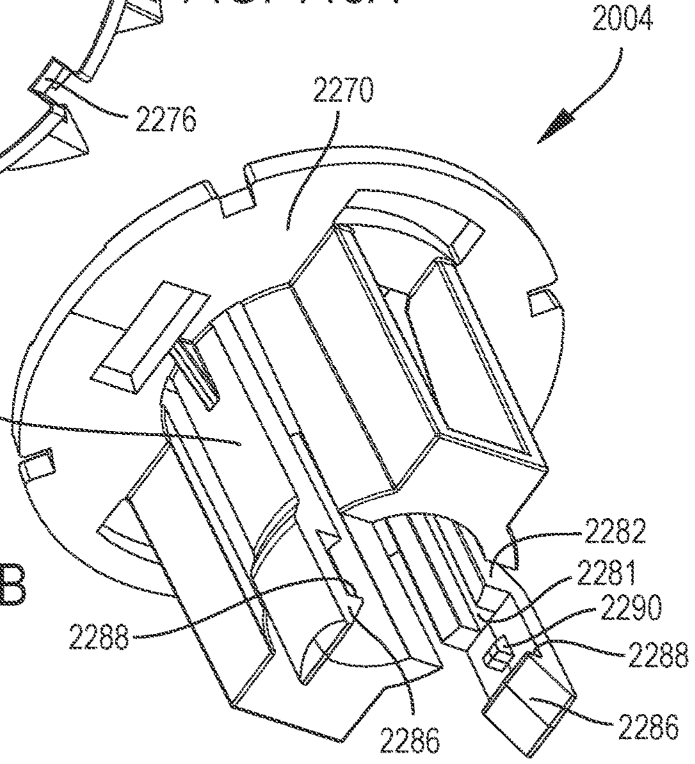
Figure 114A:
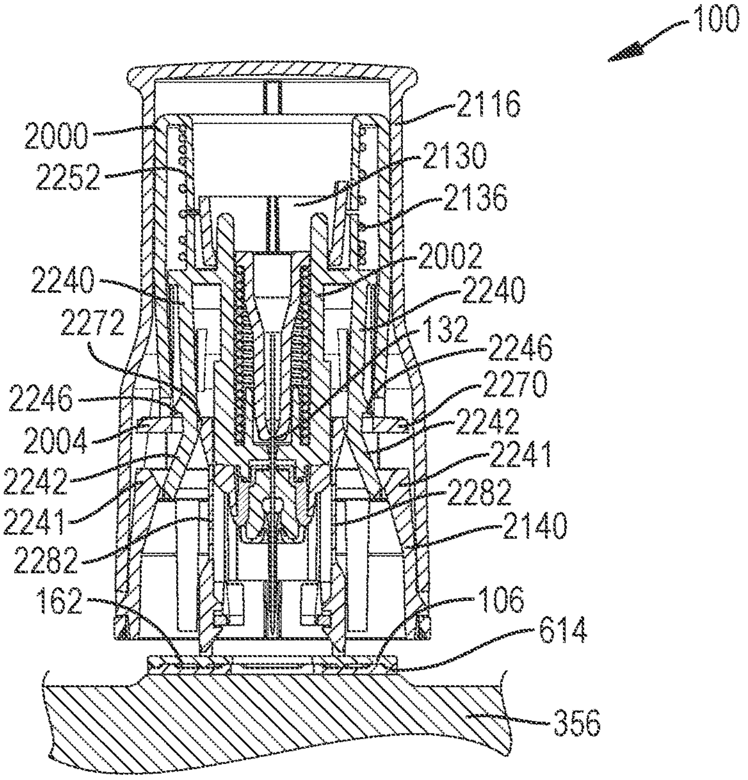
Figure 114B:
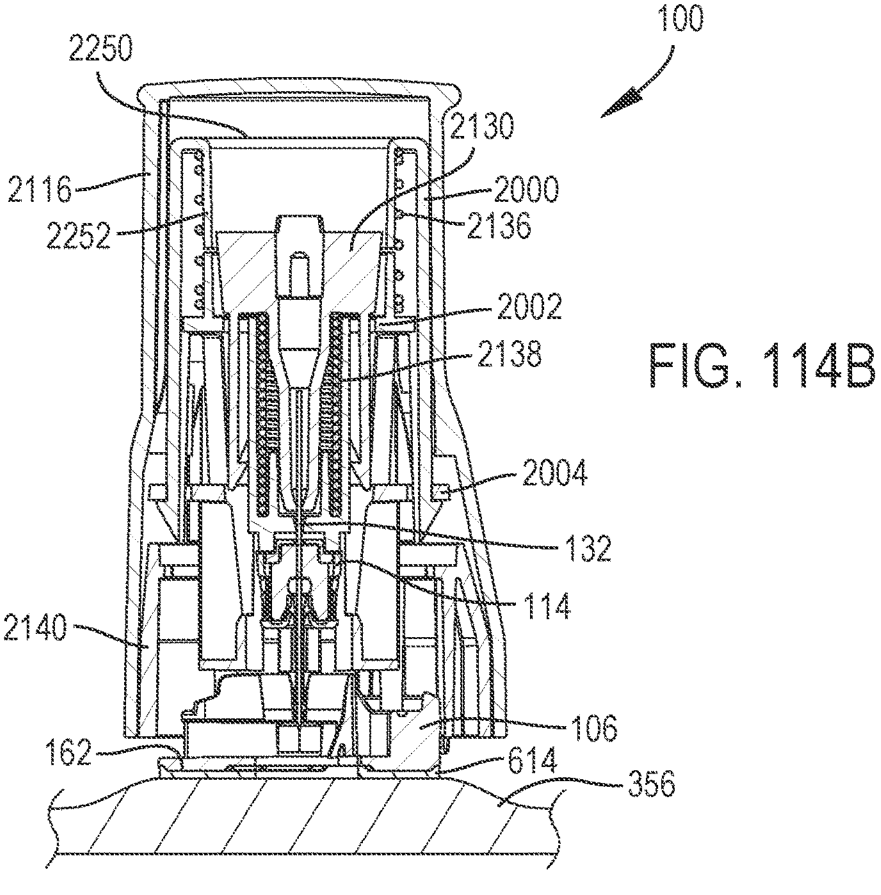
Figure 115A:
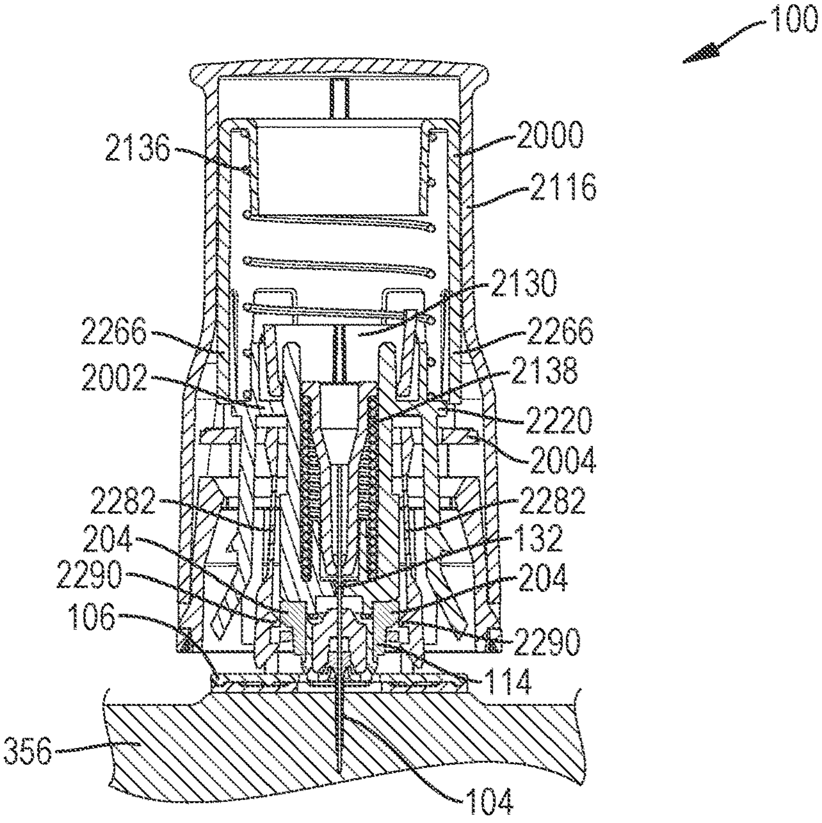
Figure 115B:
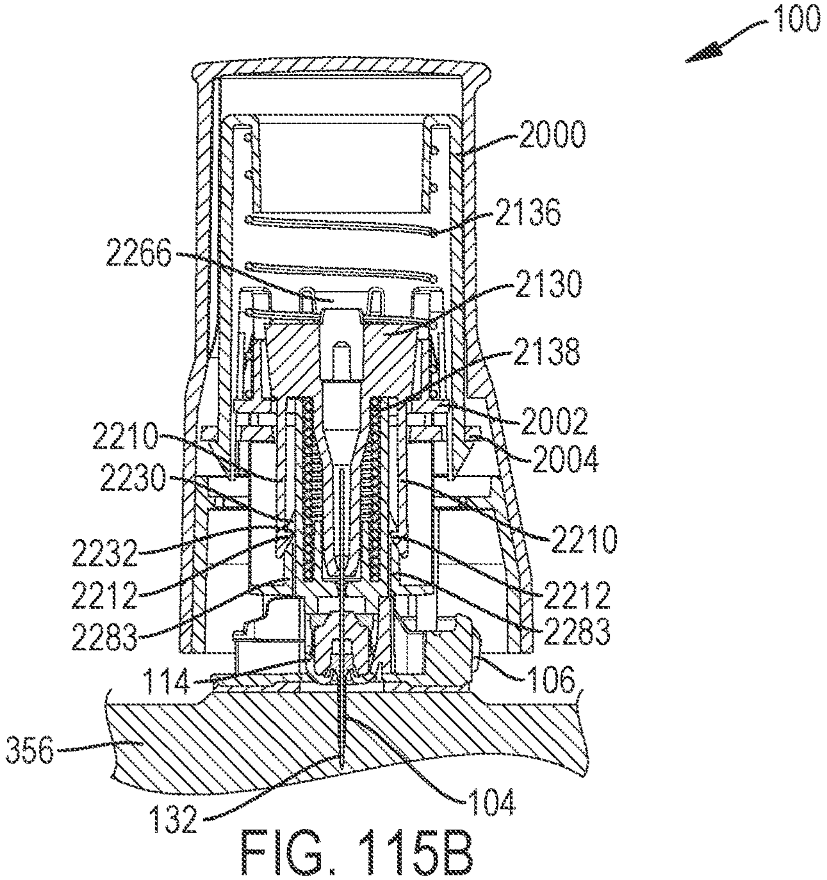
Figure 116A:
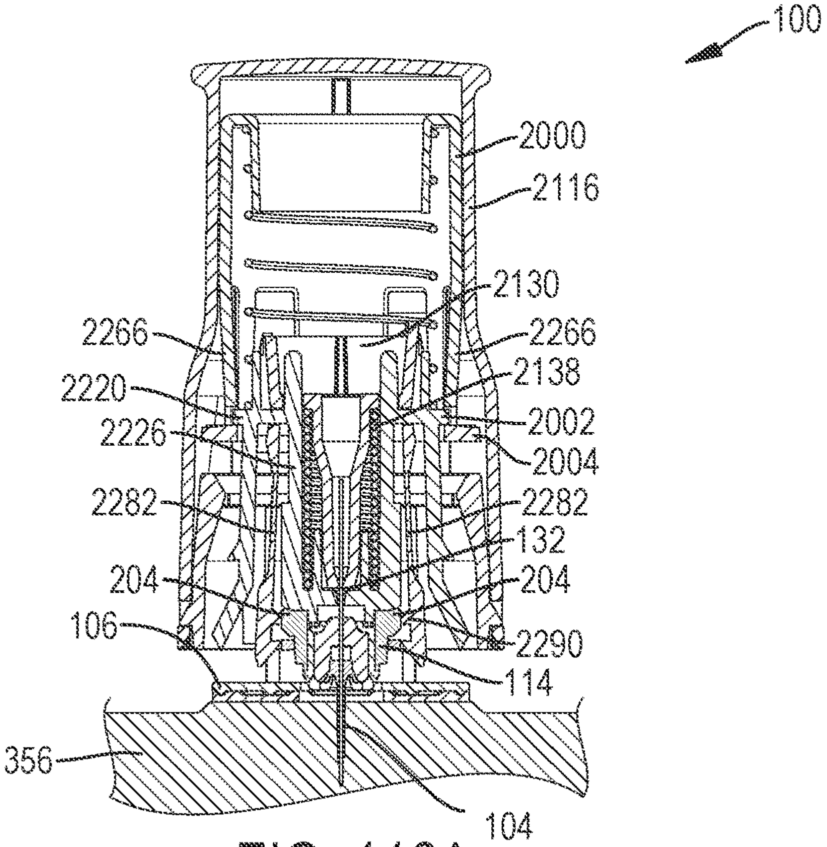
Figure 116B:
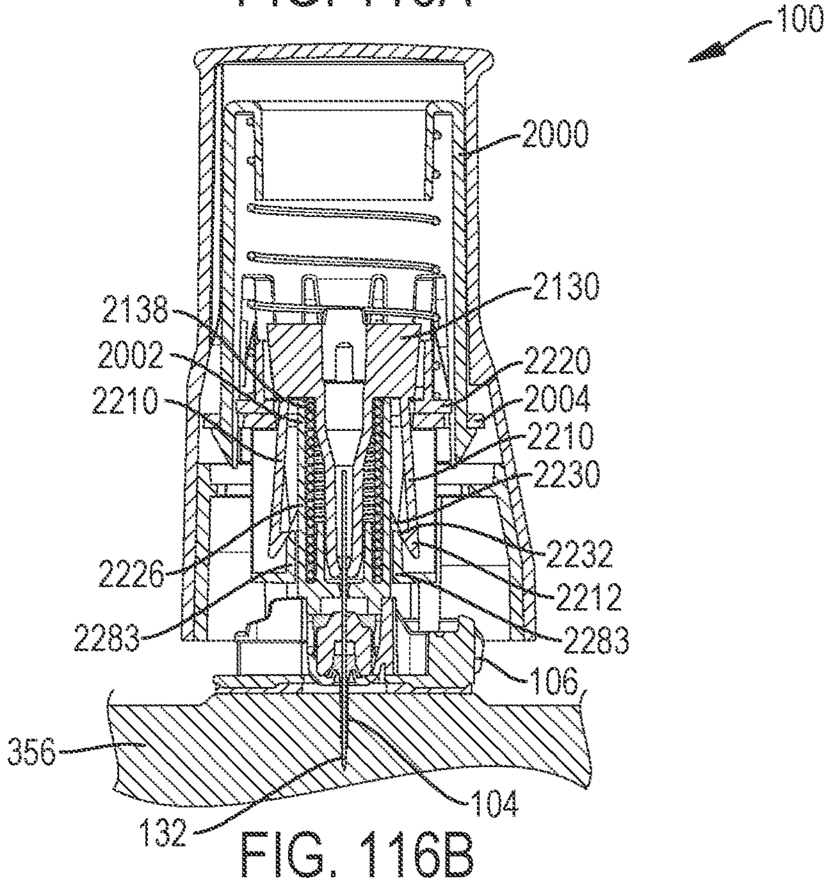
Figure 117A:
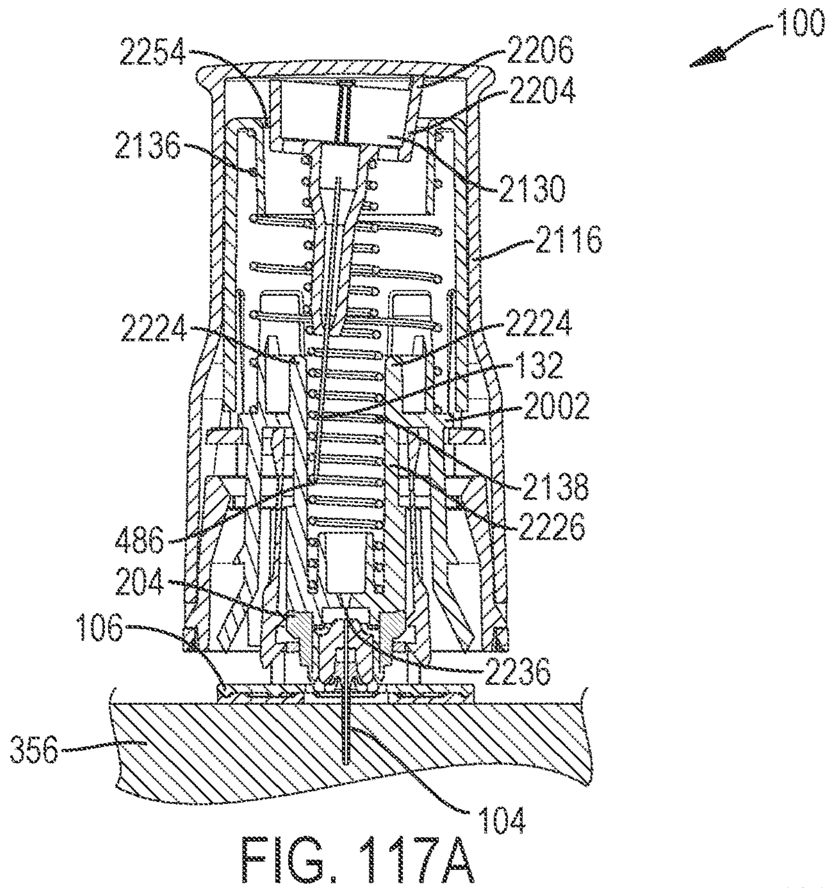
Figure 117B:
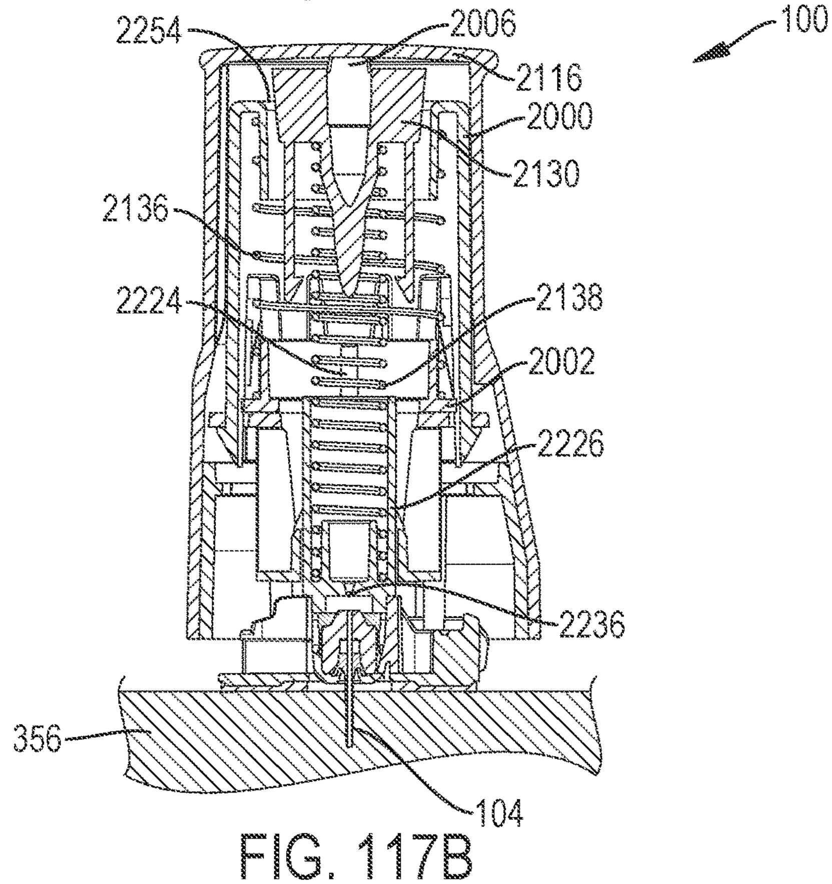
Figure 118:
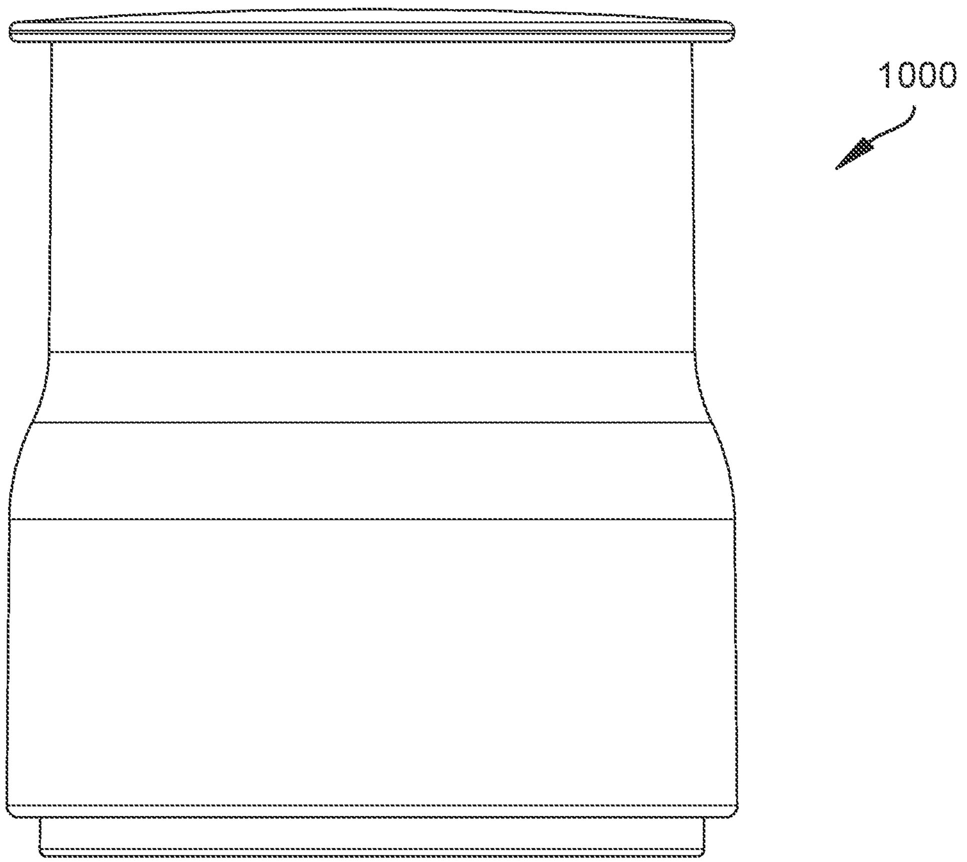
Figure 118:
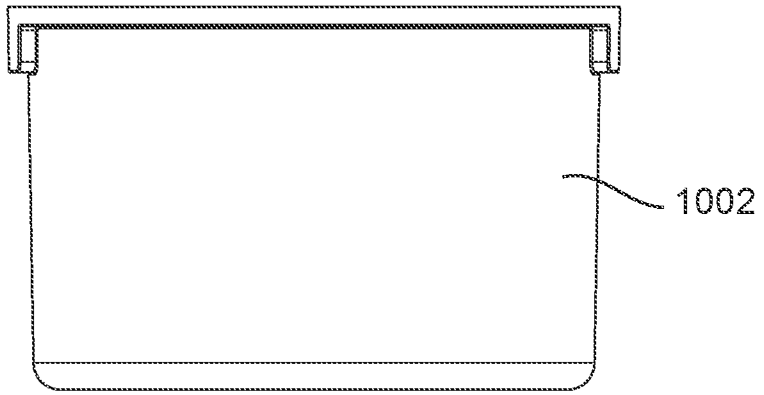
Figure 119A:
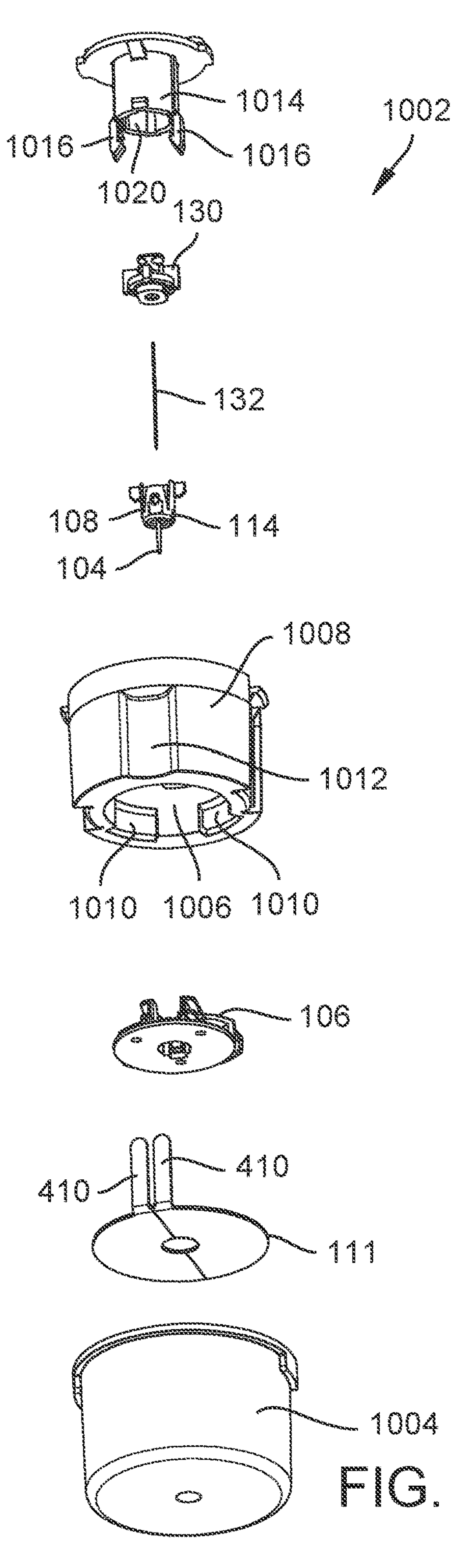
Figure 119B:
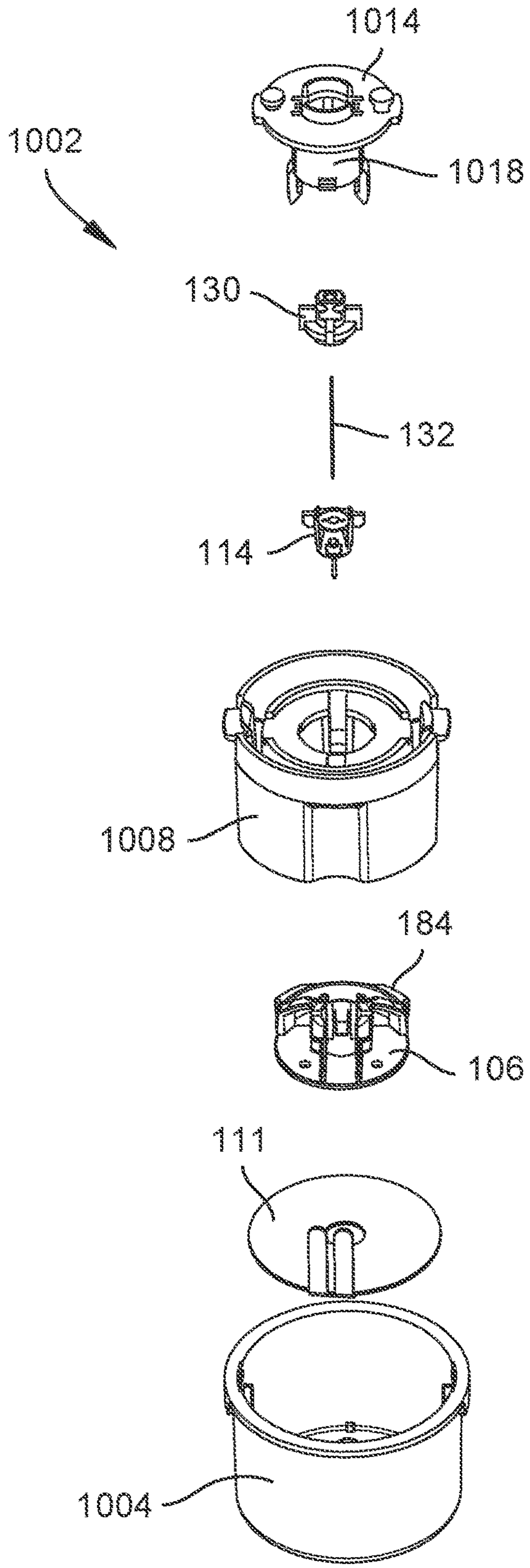
Figure 120A:
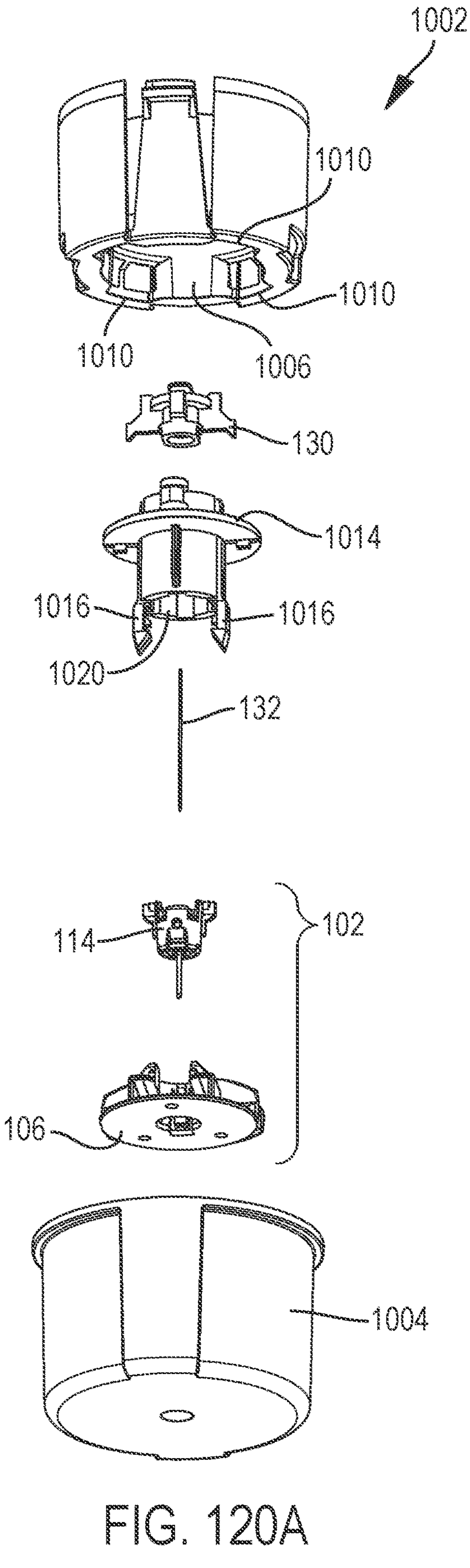
Figure 120B:
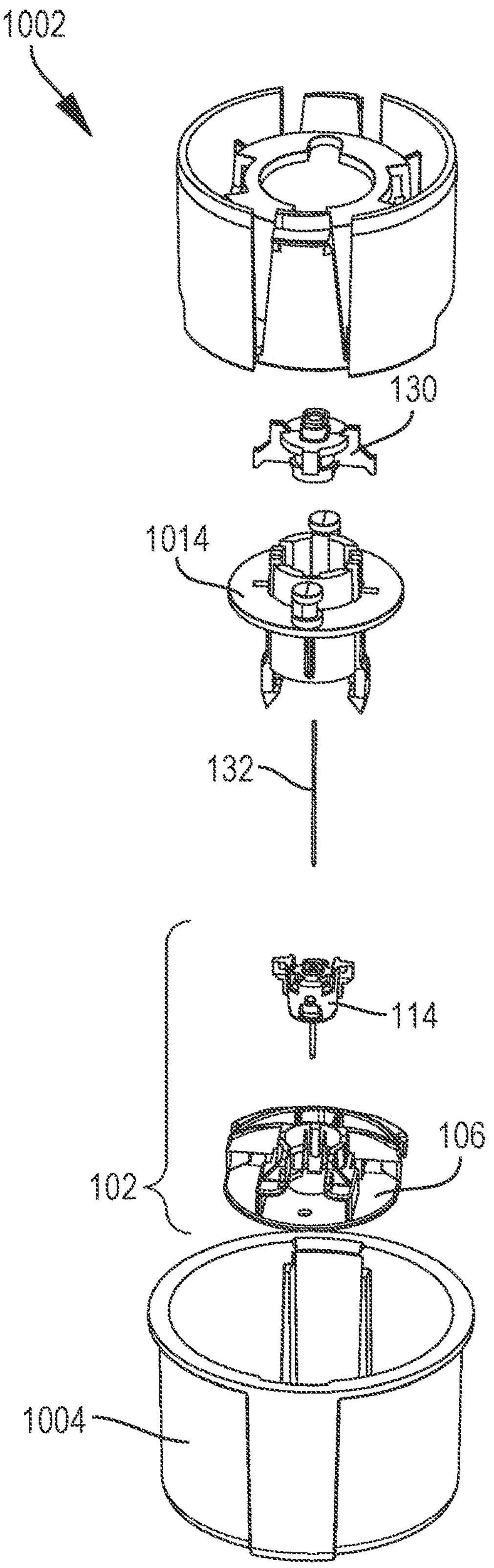
Figure 121:
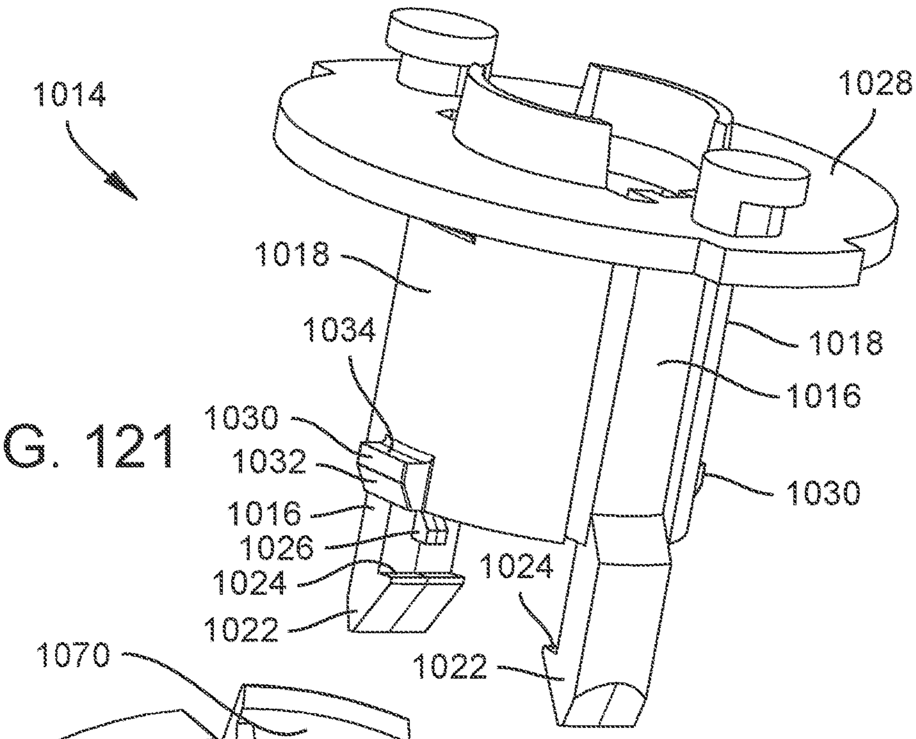
Figure 122:
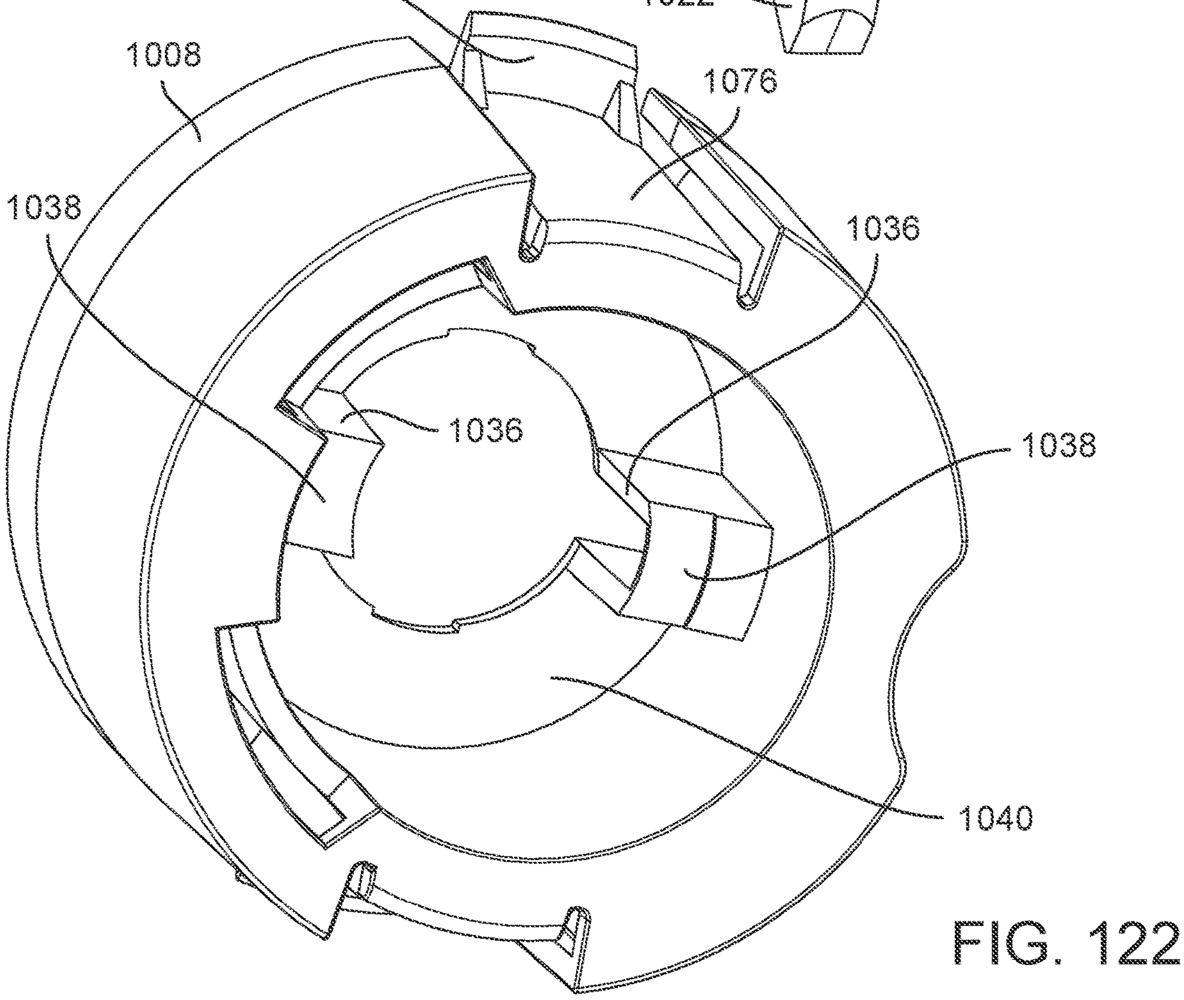
Figure 123:
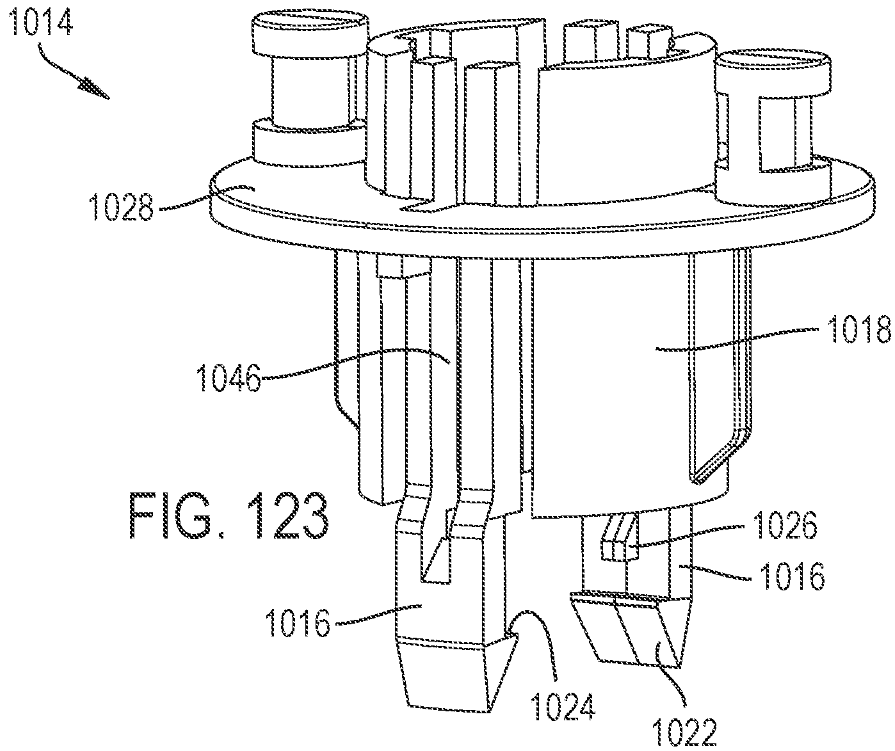
Figure 124:
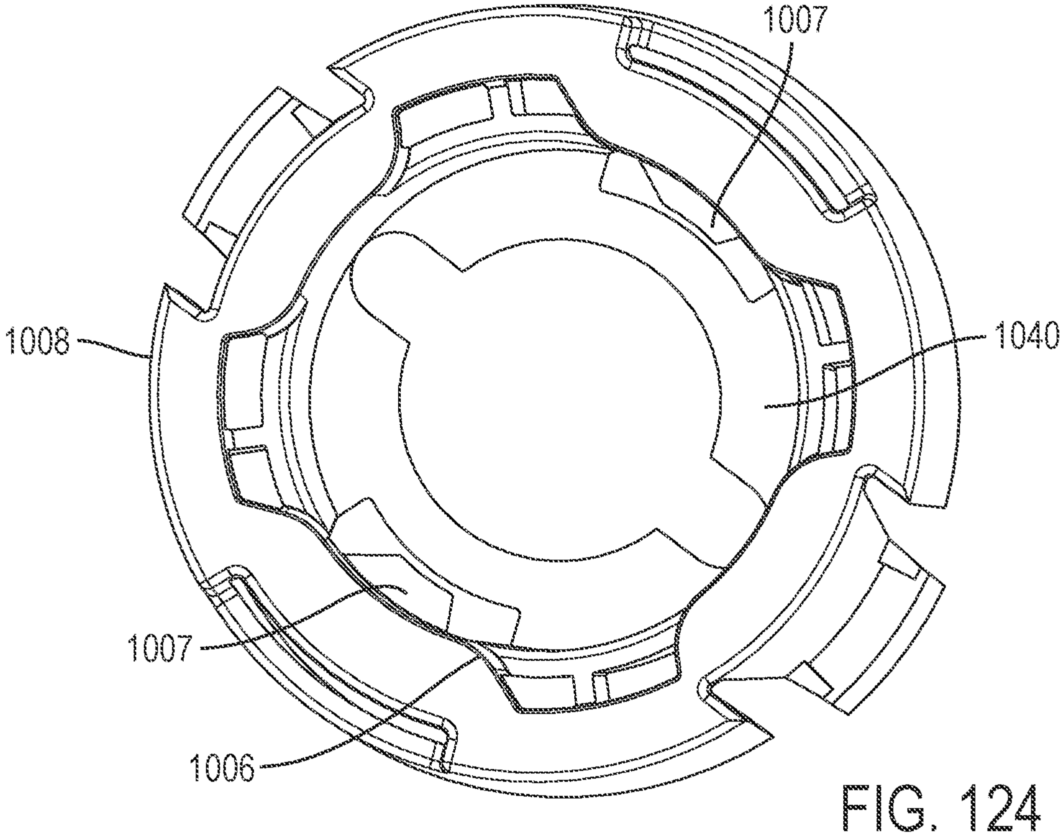
Figure 125:
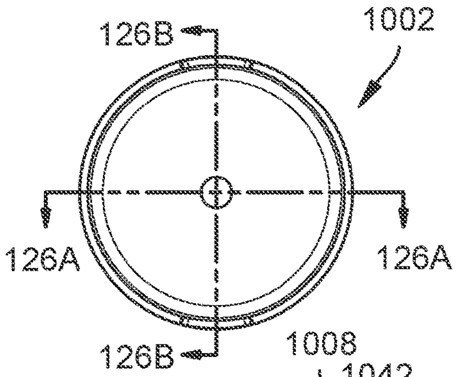
Figure 126A:
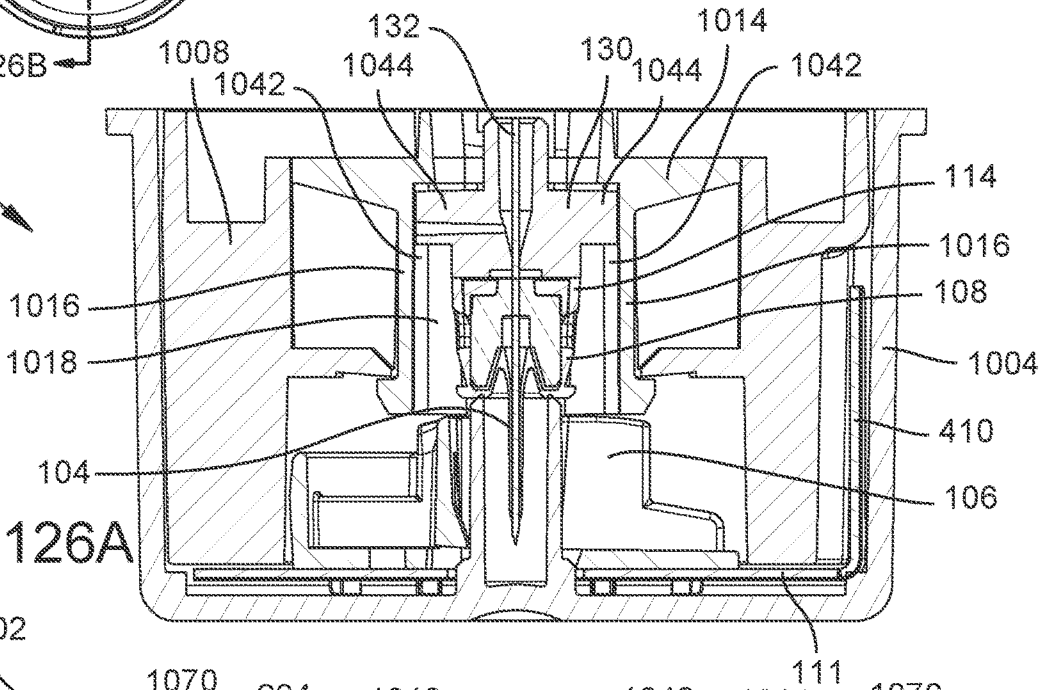
Figure 126B:
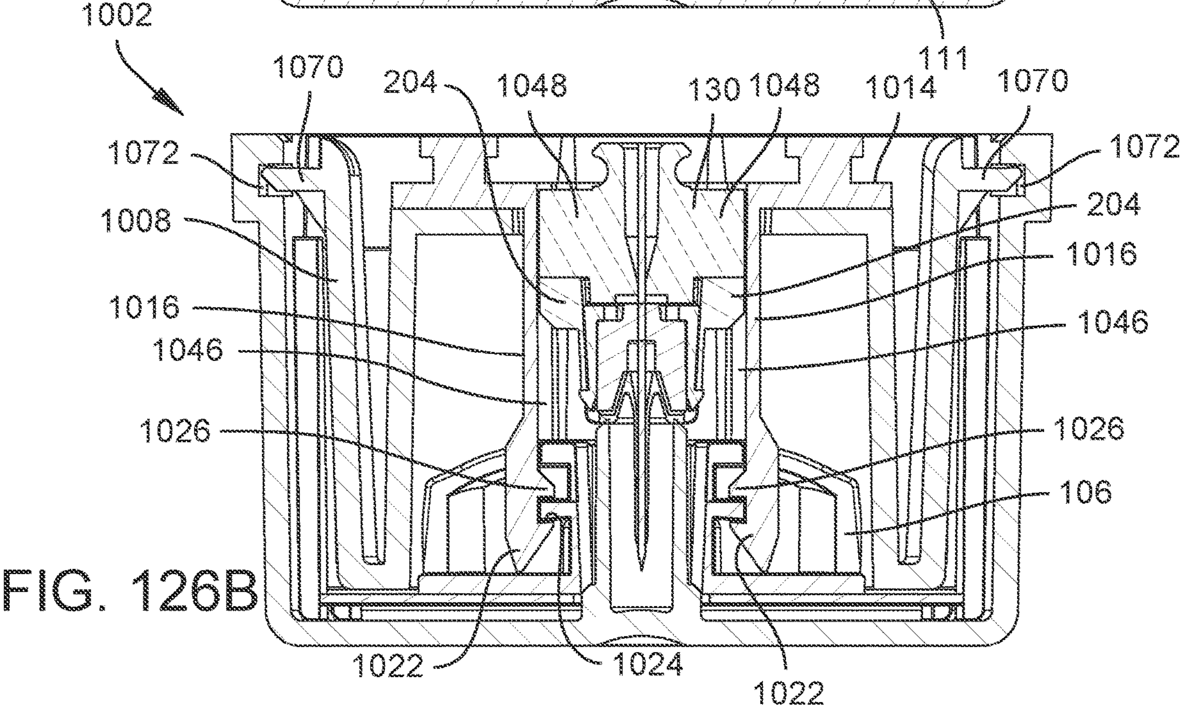
Figure 127:
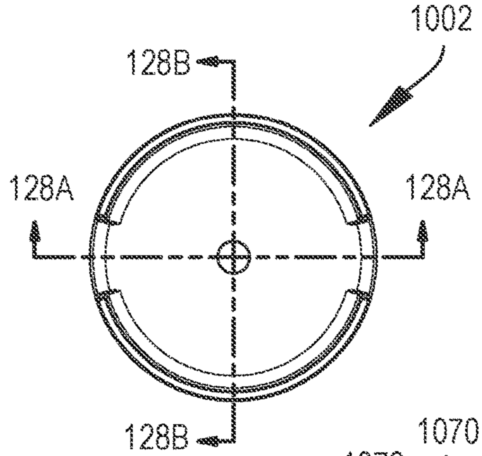
Figure 128A:
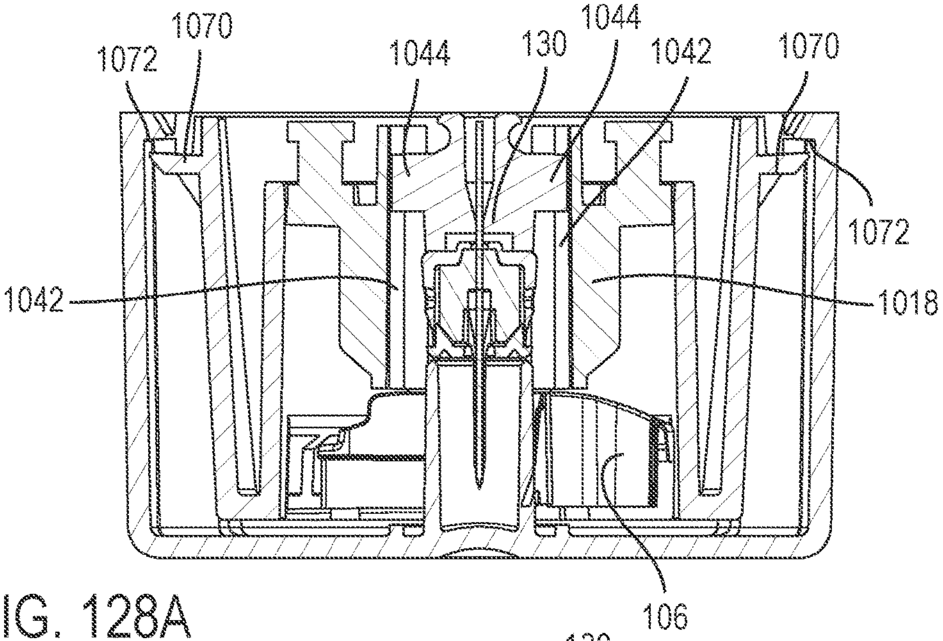
Figure 128B:
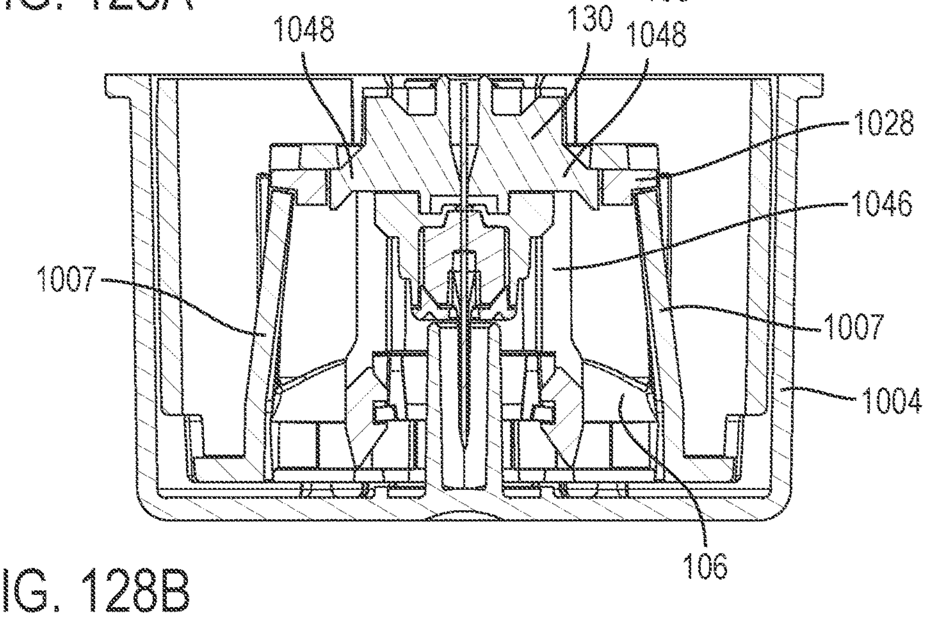
Figure 129A:
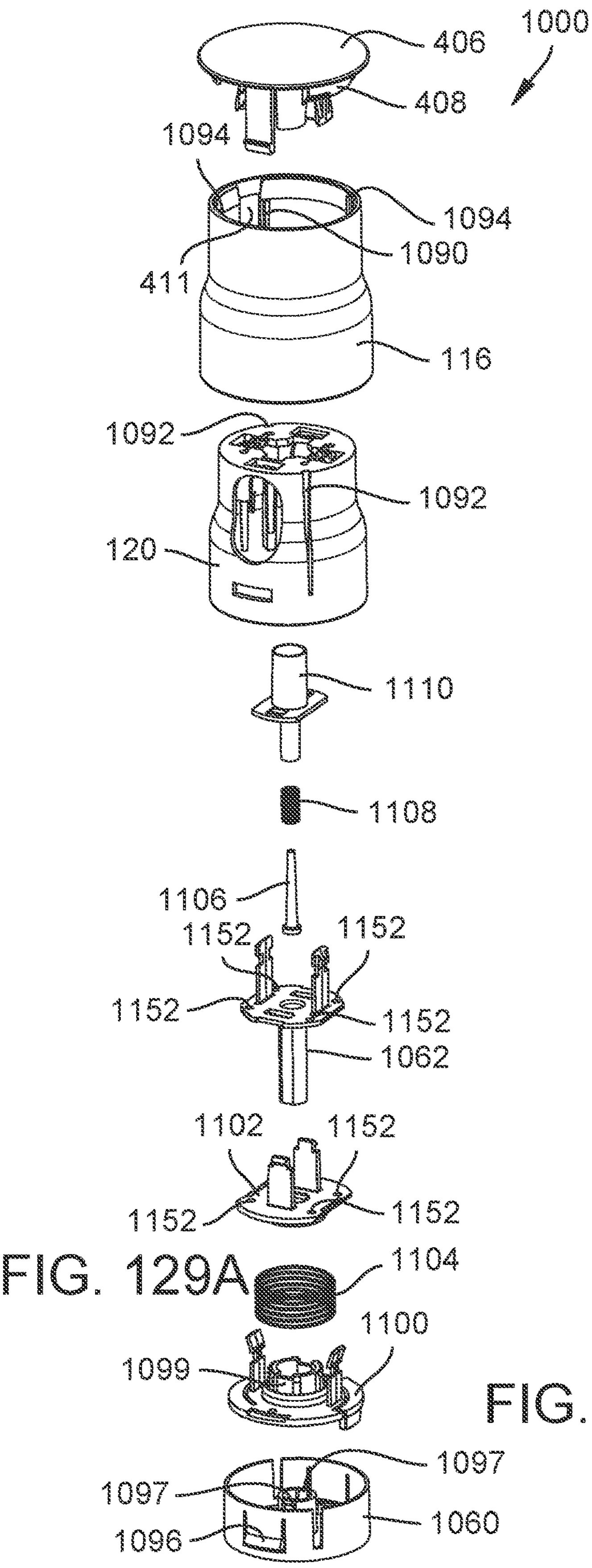
Figure 129B:
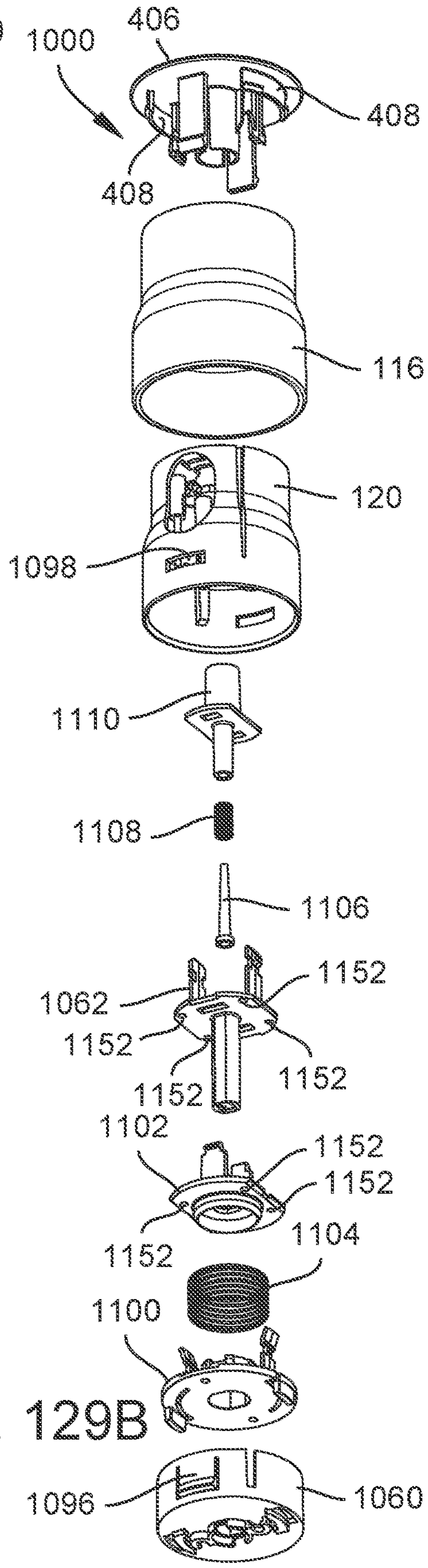
Figure 130A:
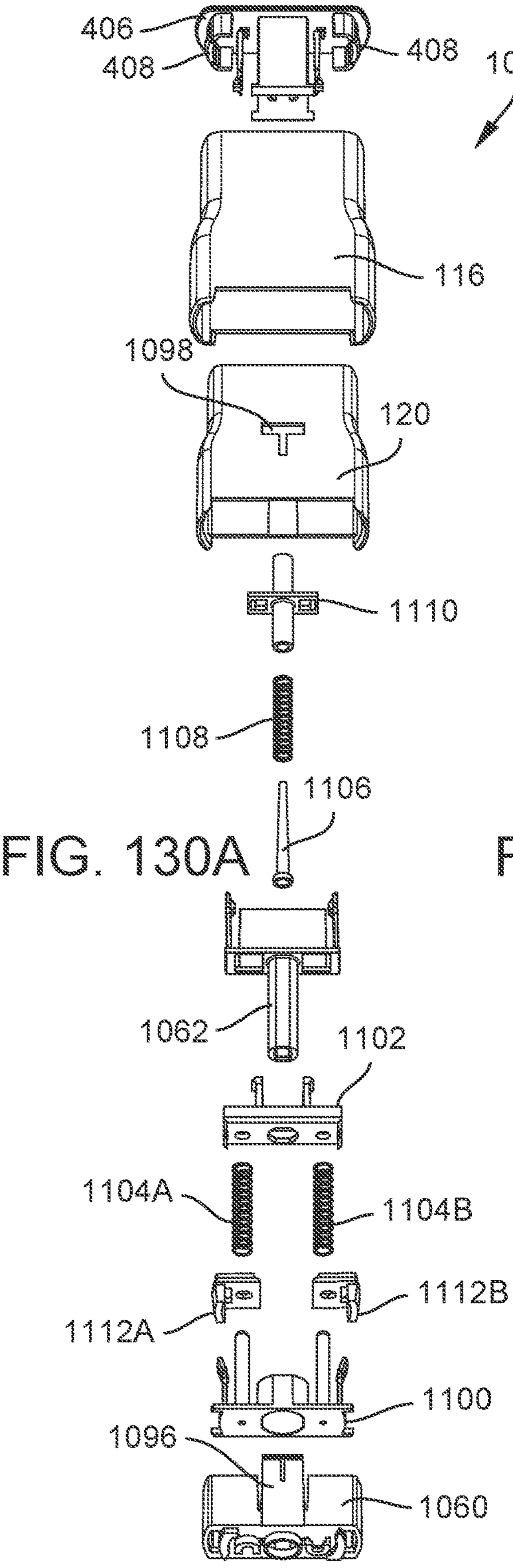
Figure 130B:
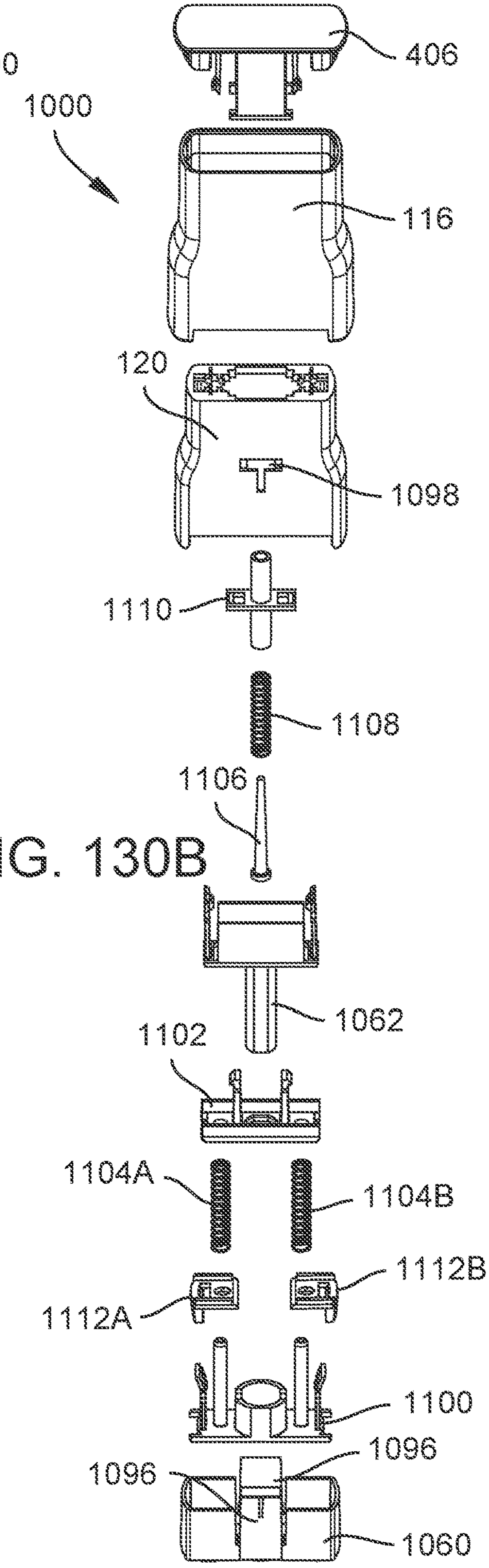
Figure 131A:
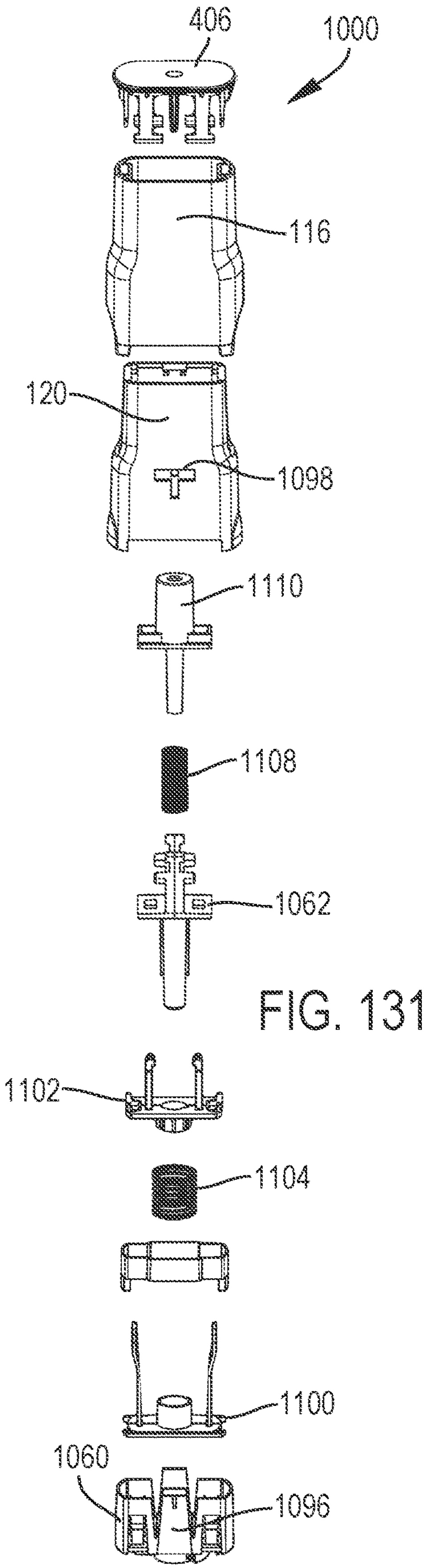
Figure 131B:
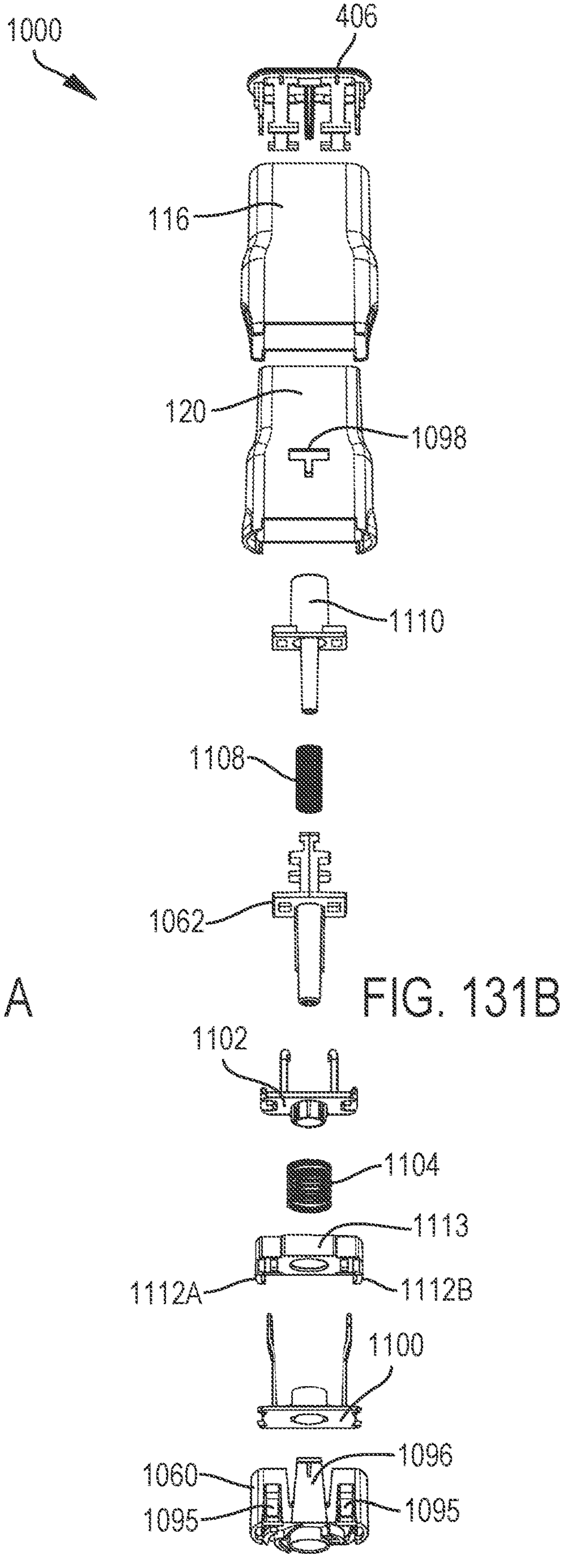
Figure 132:
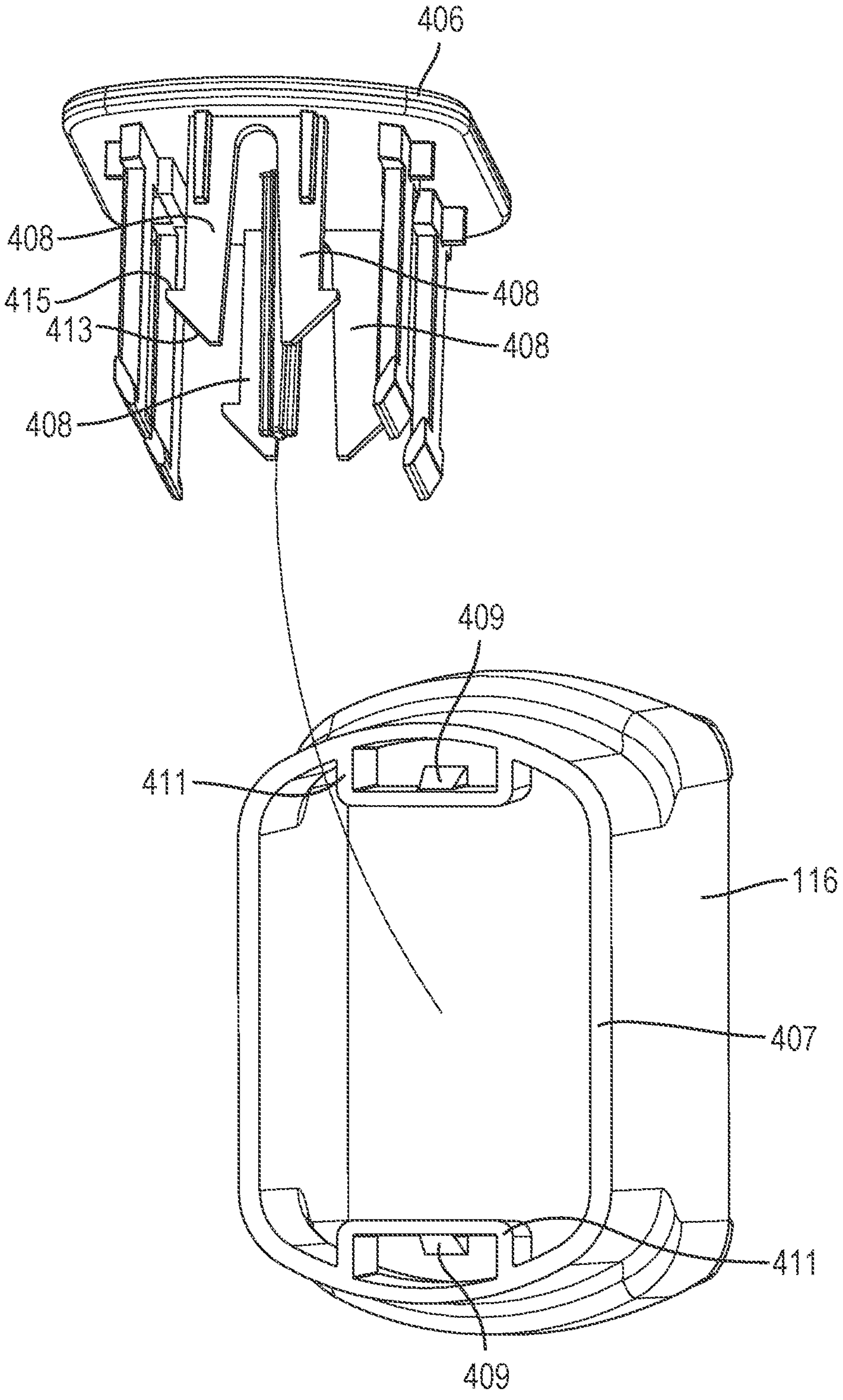
Figure 133:
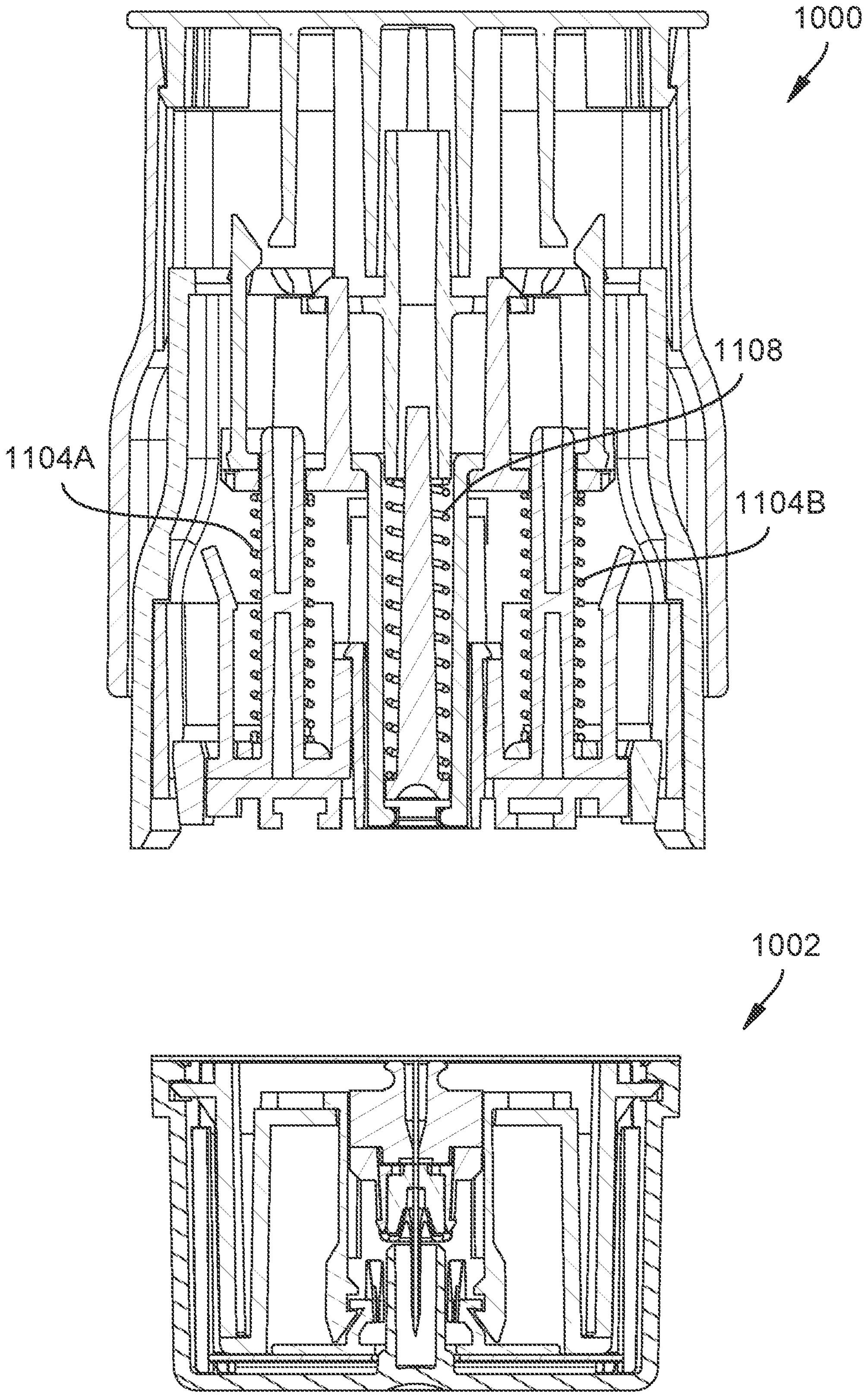
Figure 135:
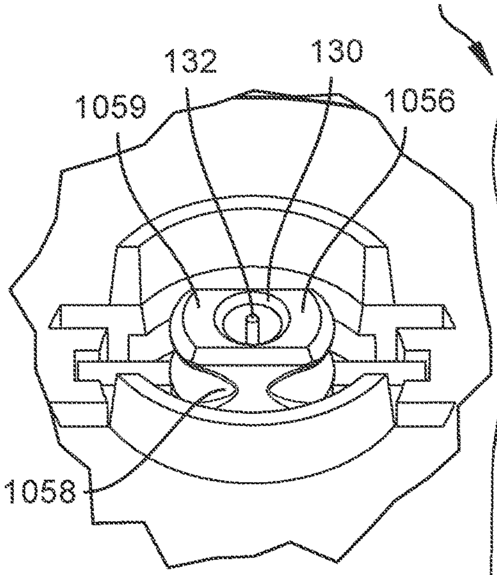
Figure 134:
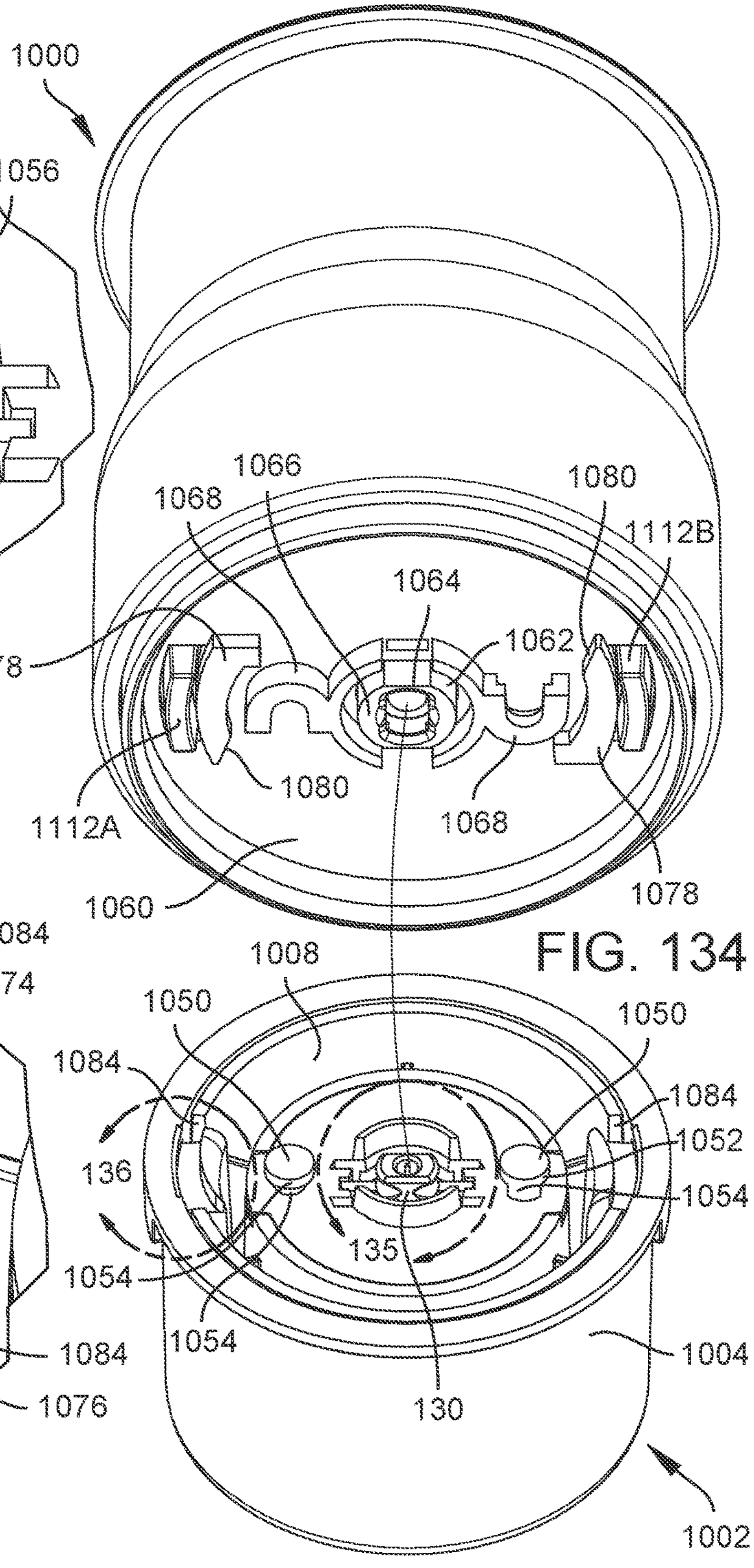
Figure 136:
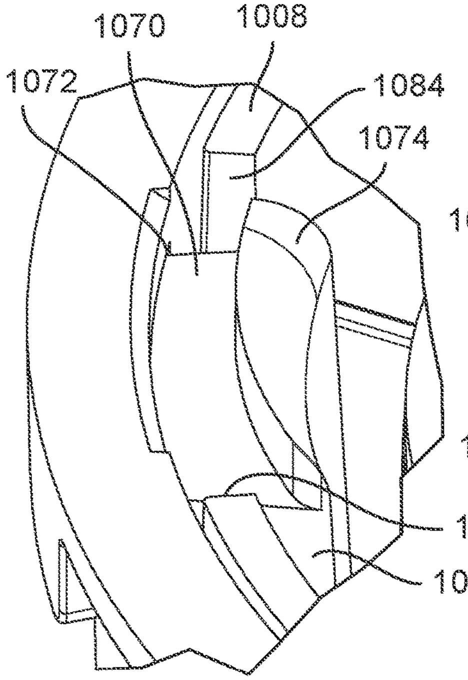
Figure 137A:
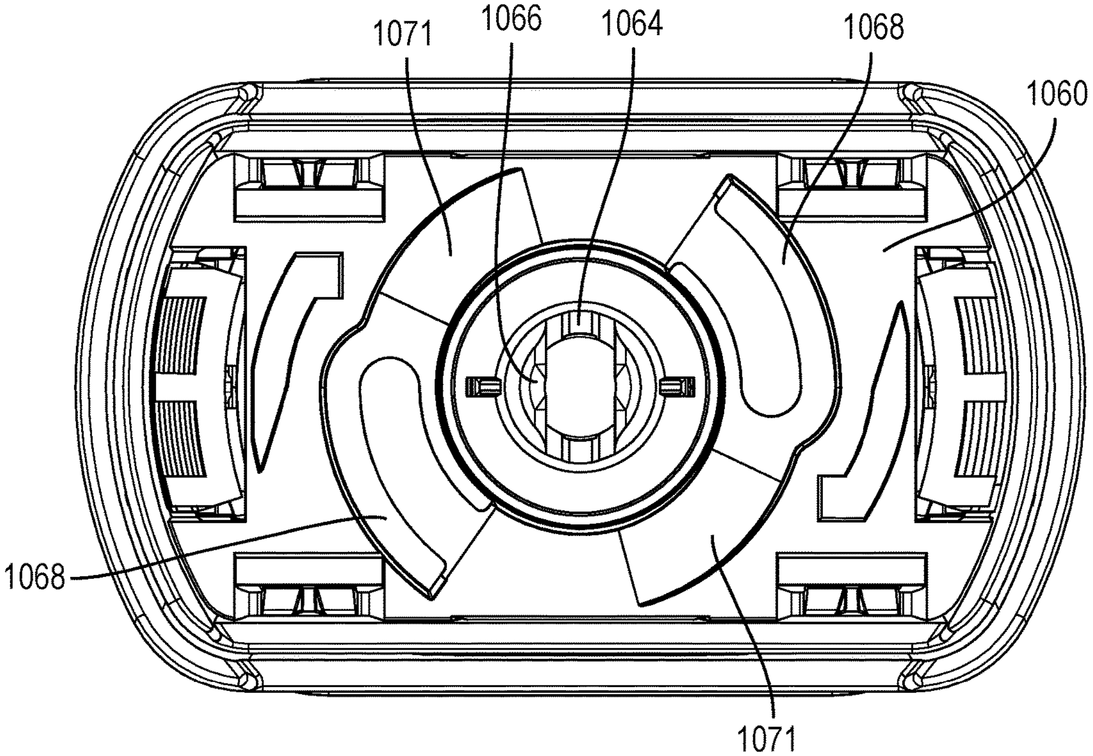
Figure 137B:
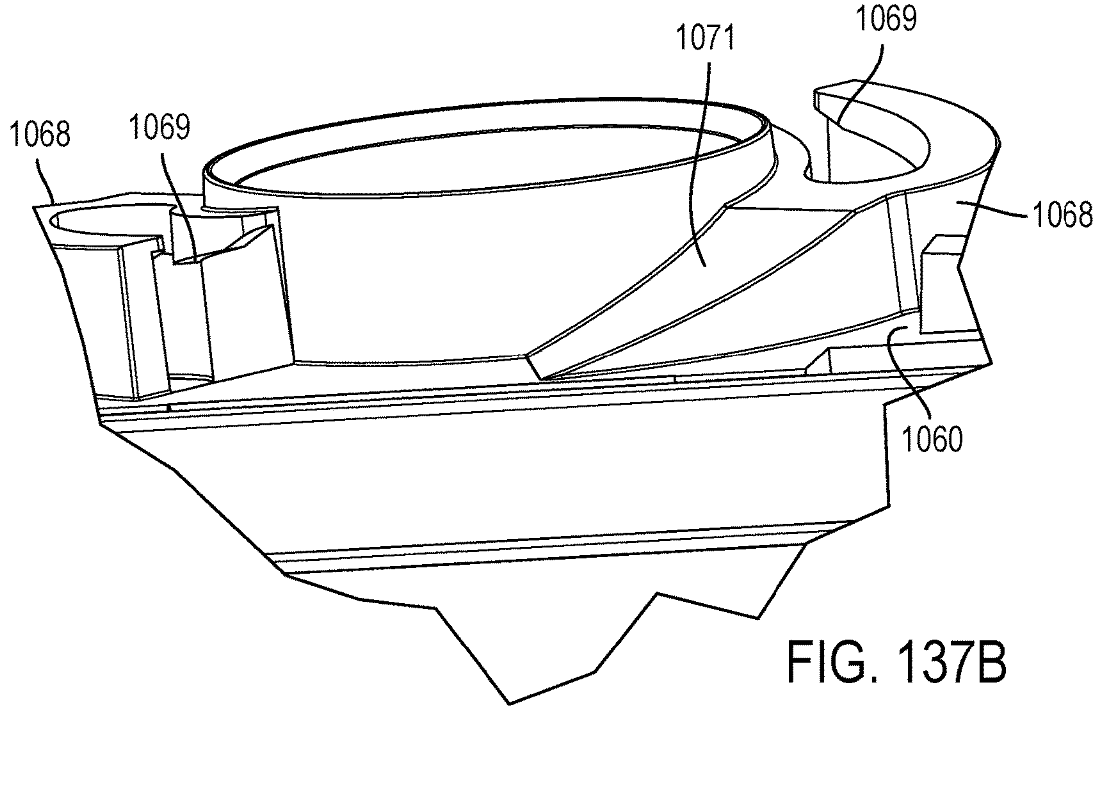
Figure 138A:
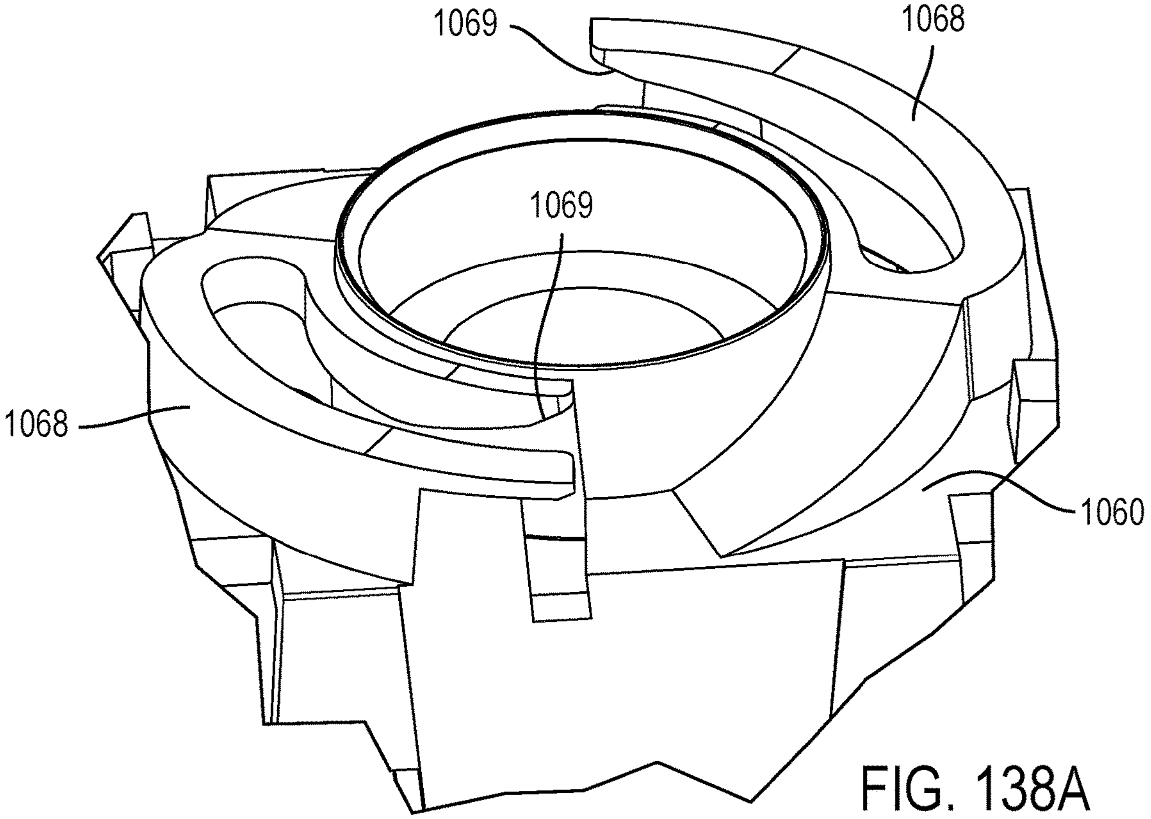
Figure 138B:
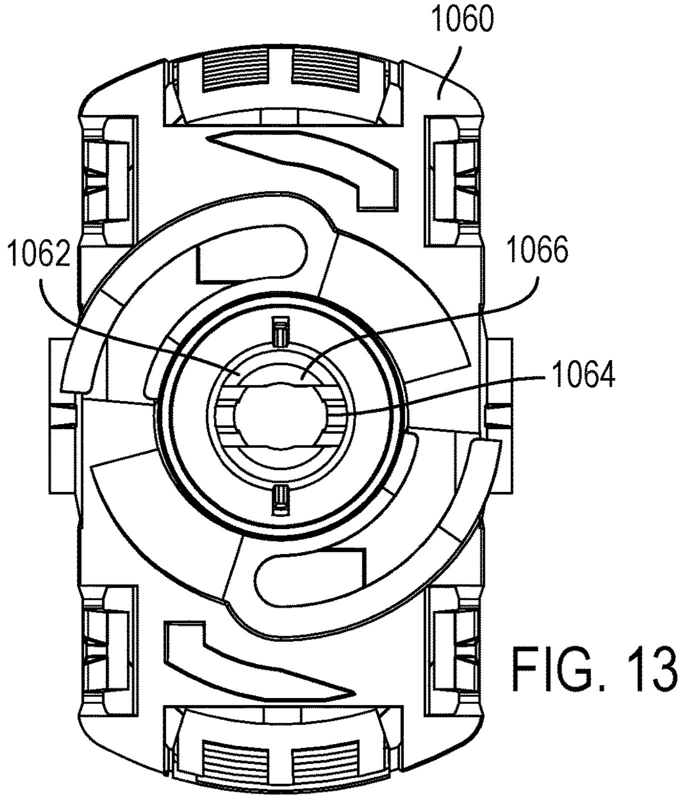
Figure 139:
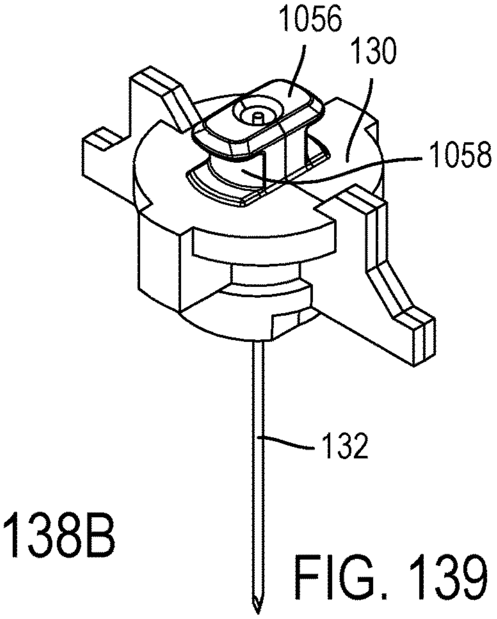
Figure 140A:
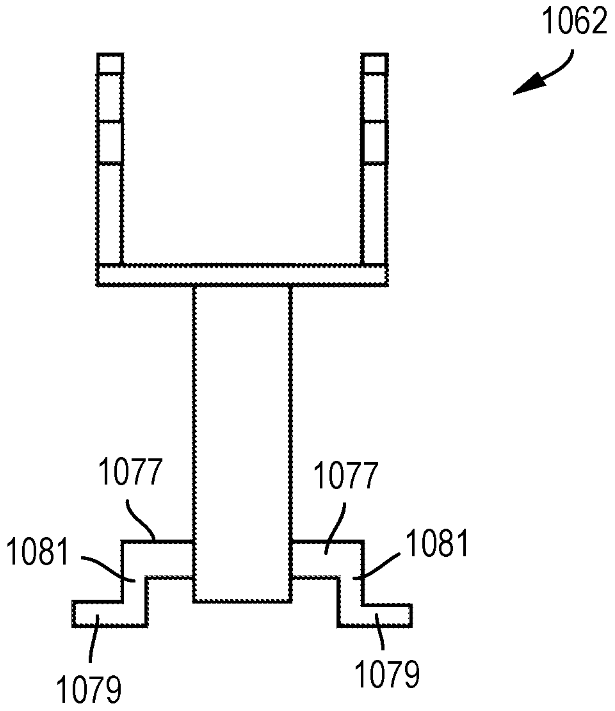
Figure 140B:
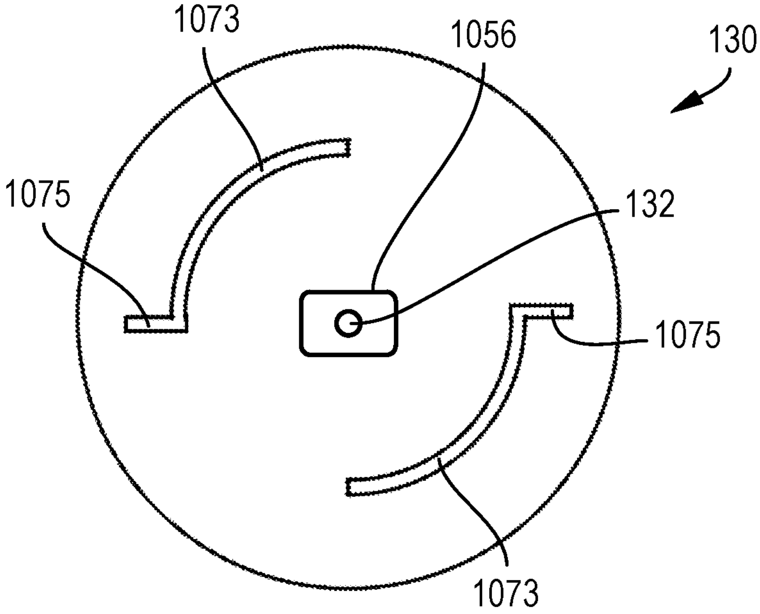
Figure 141:
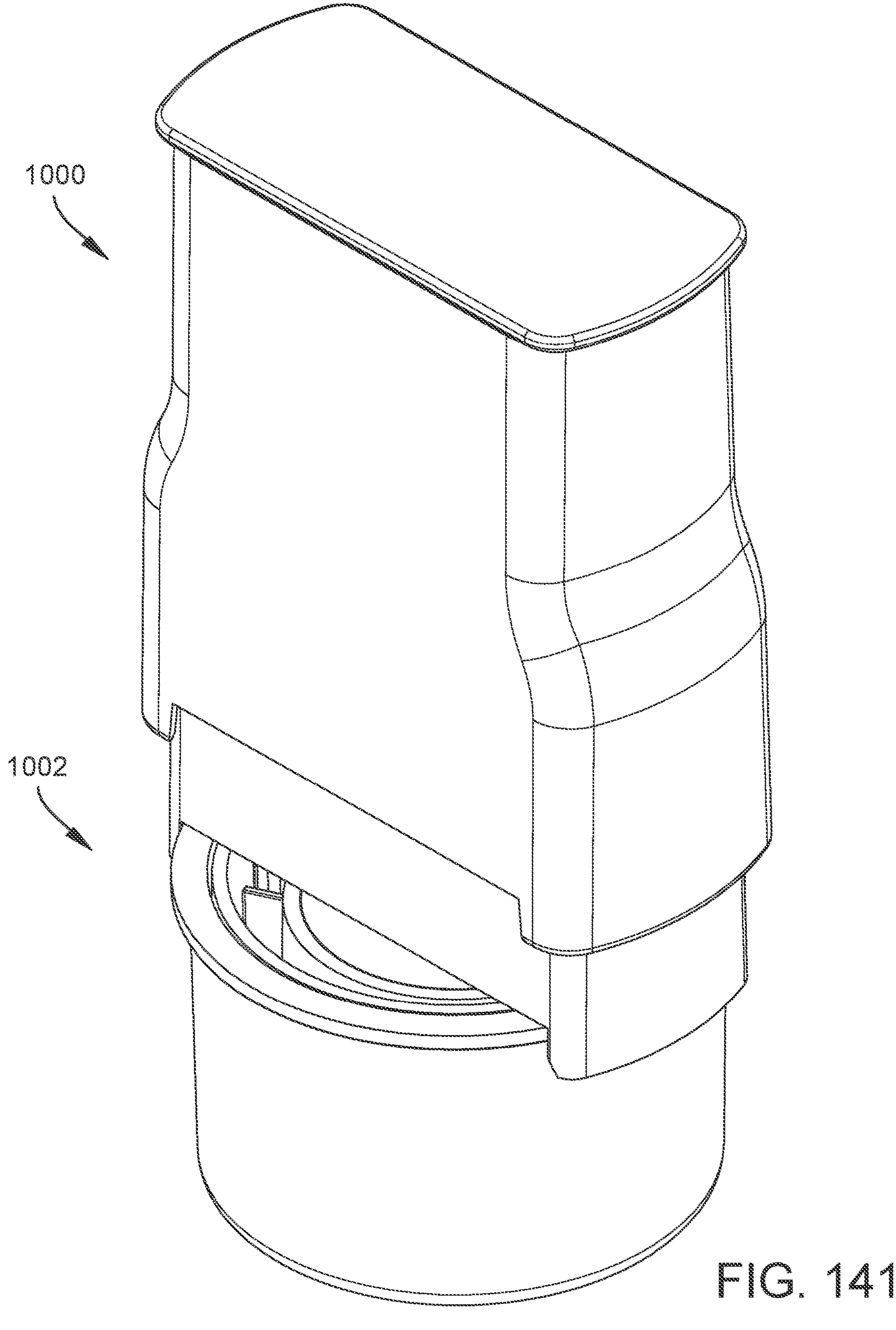
Figure 142:
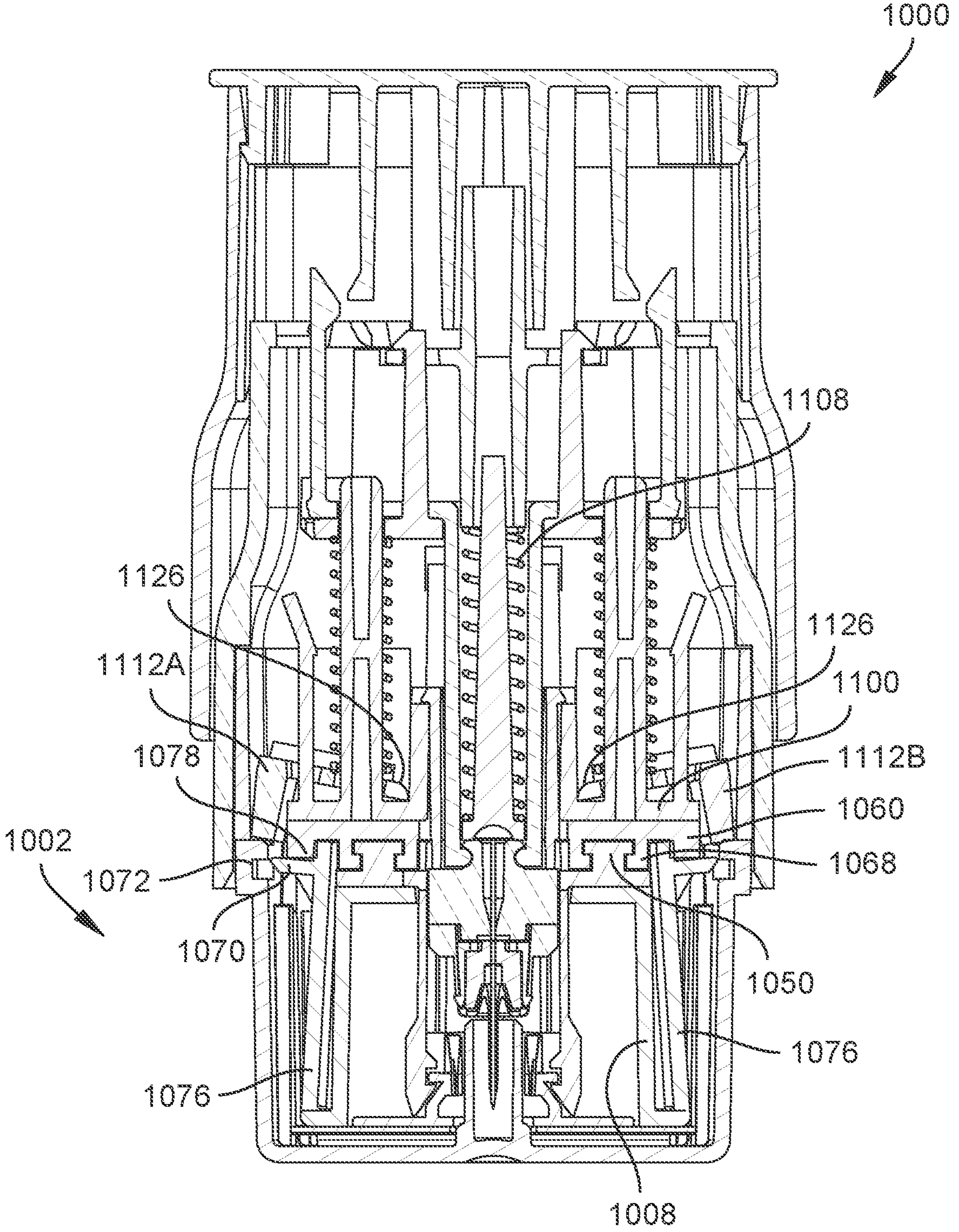
Figure 143:
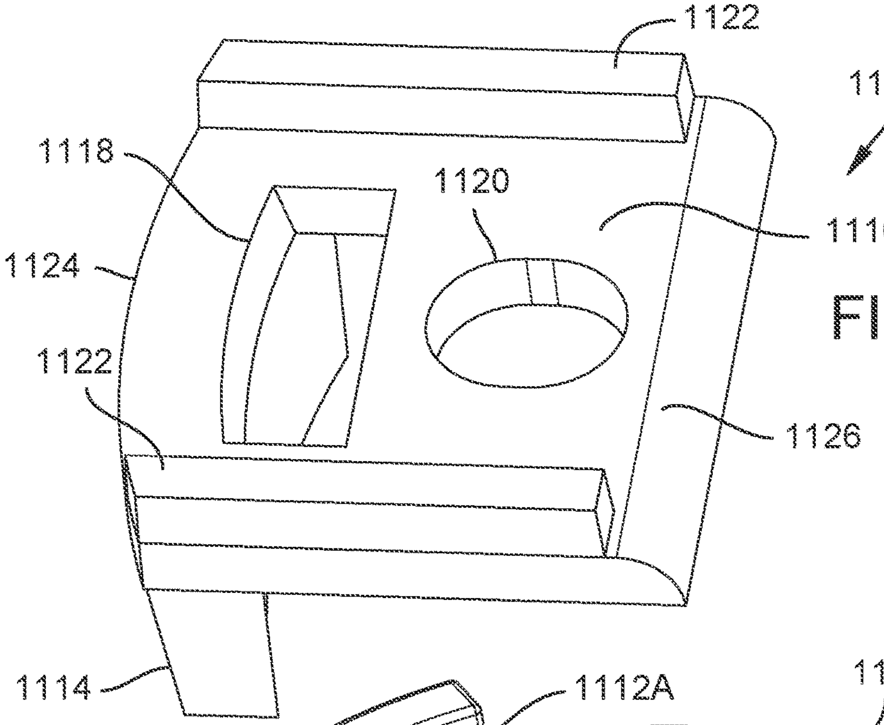
Figure 144:
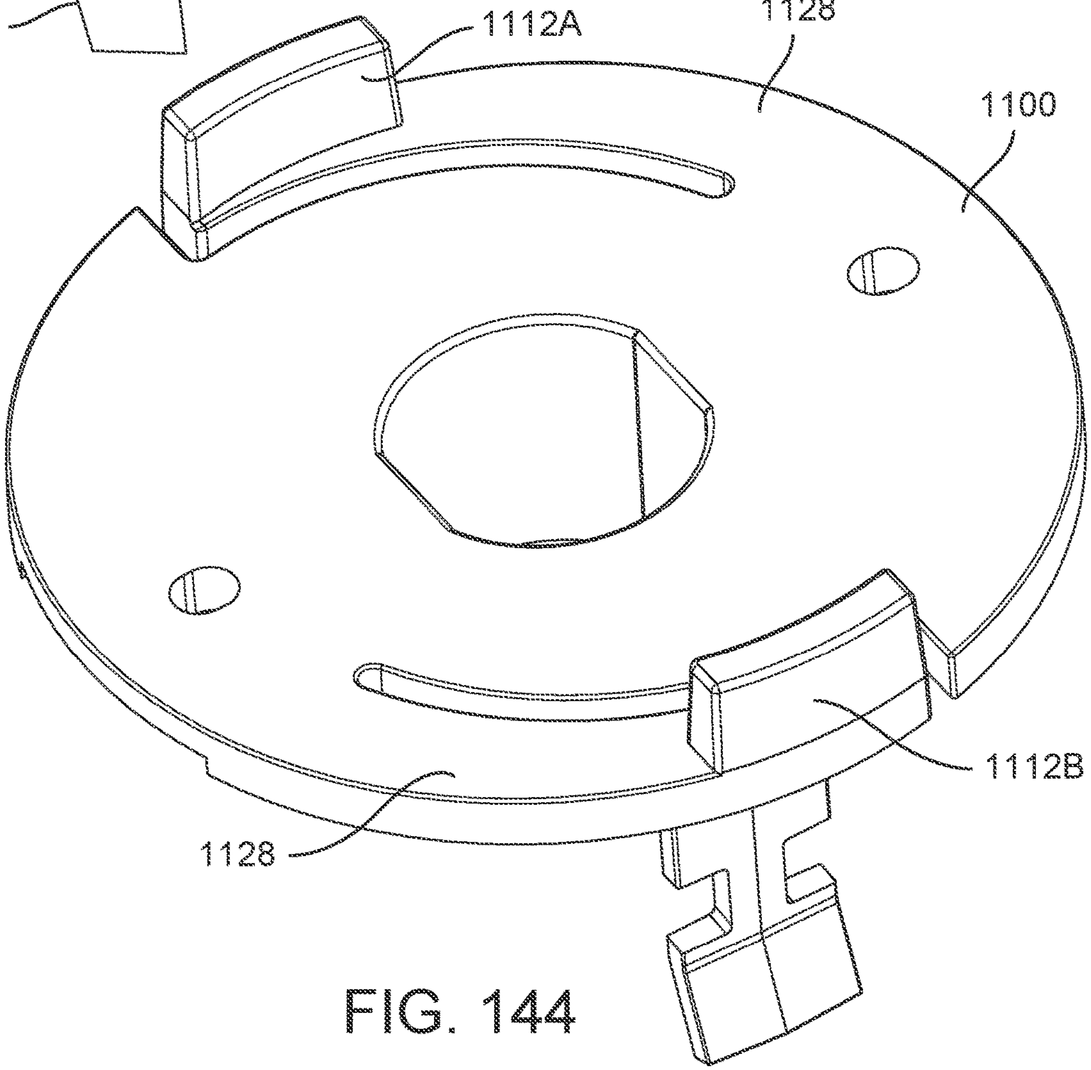
Figure 145:
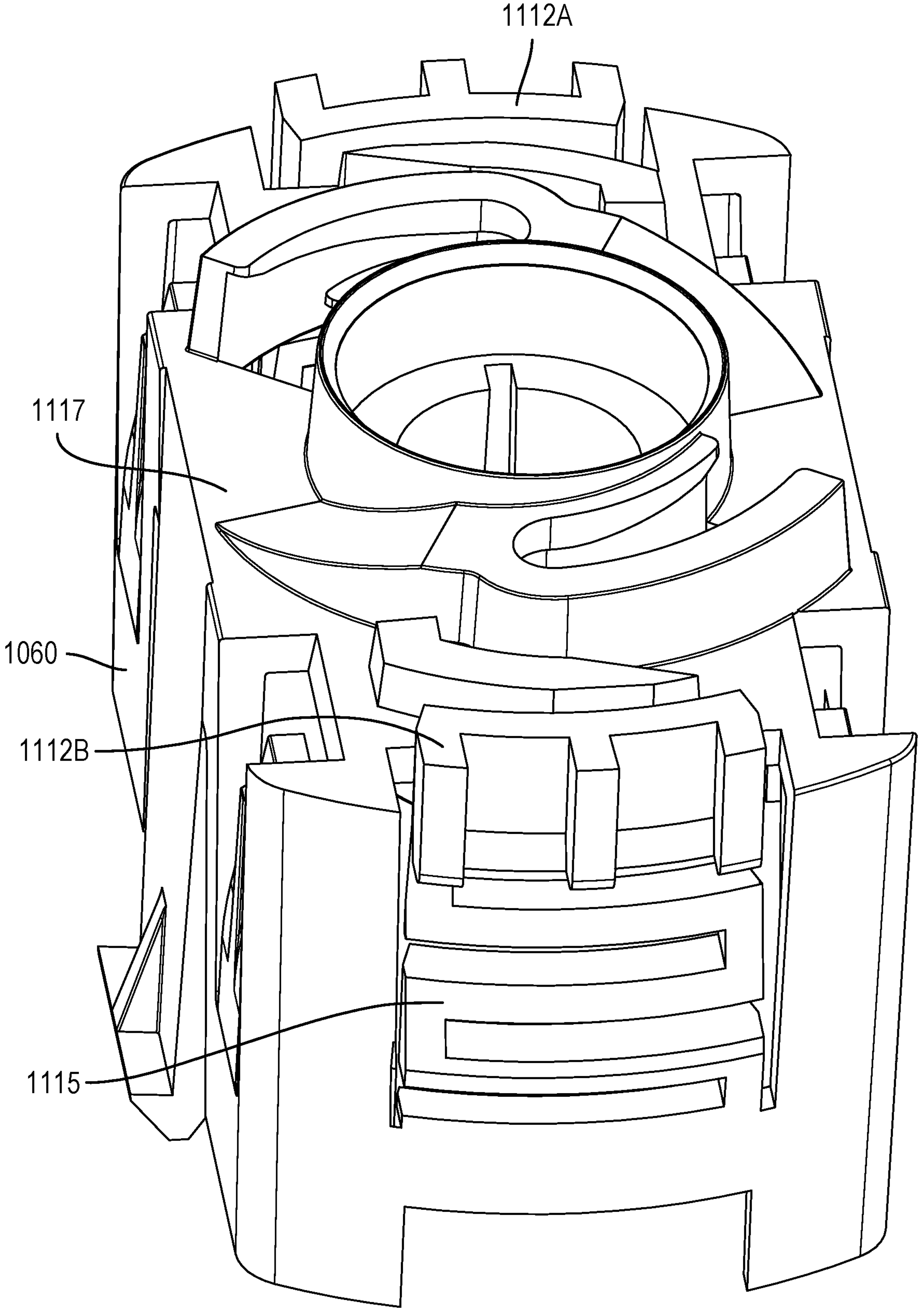
Figure 146:
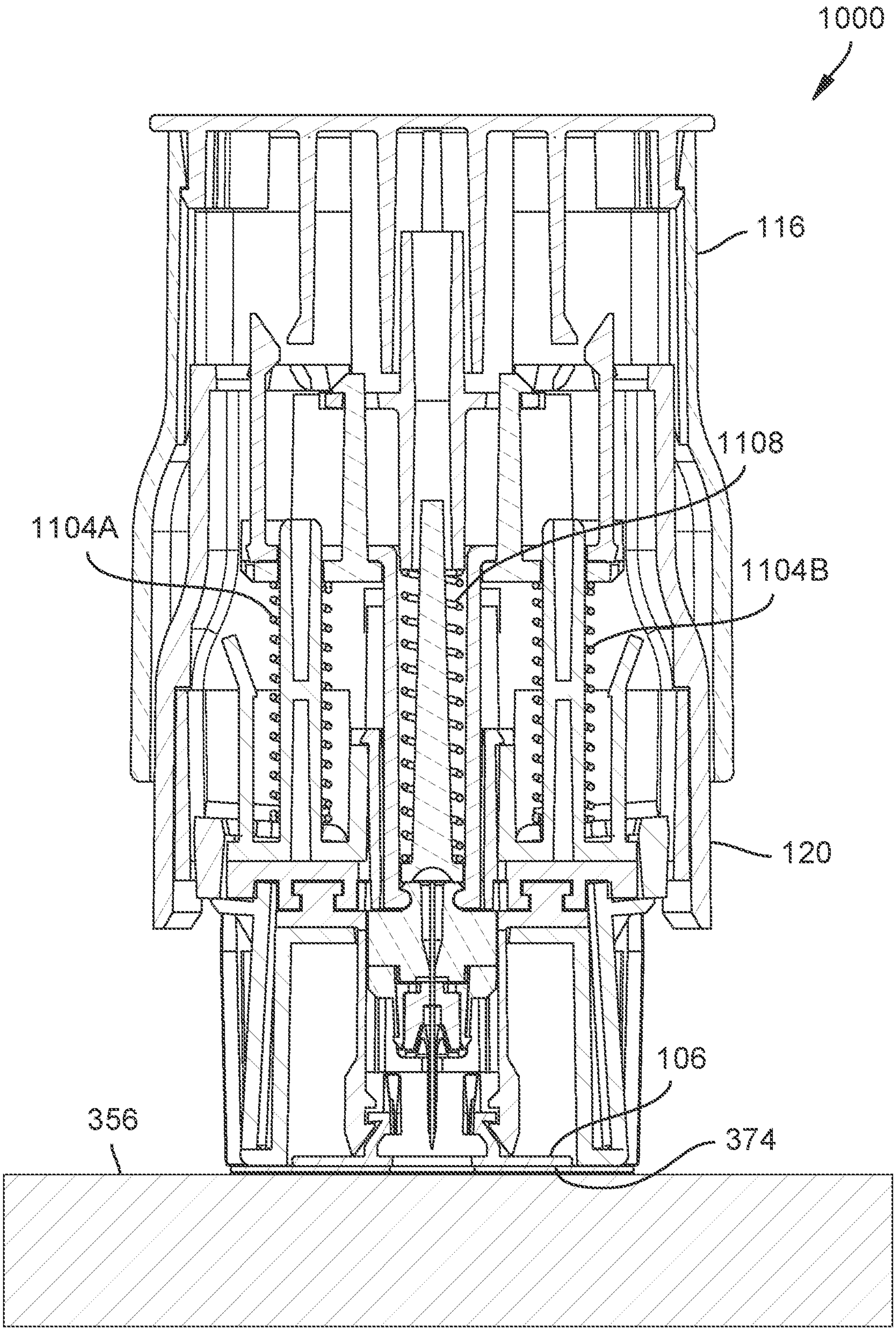
Figure 147:
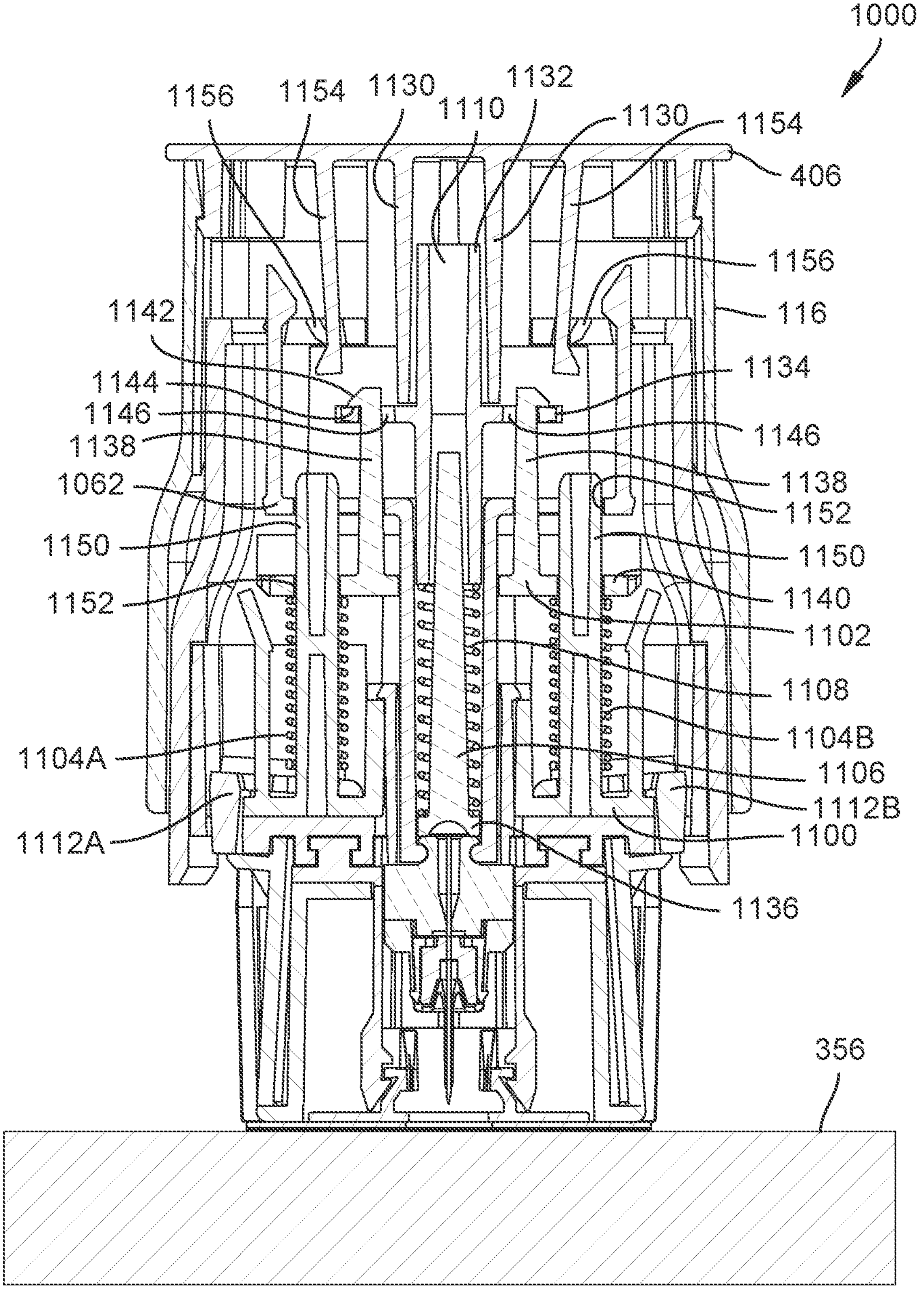
Figure 148:
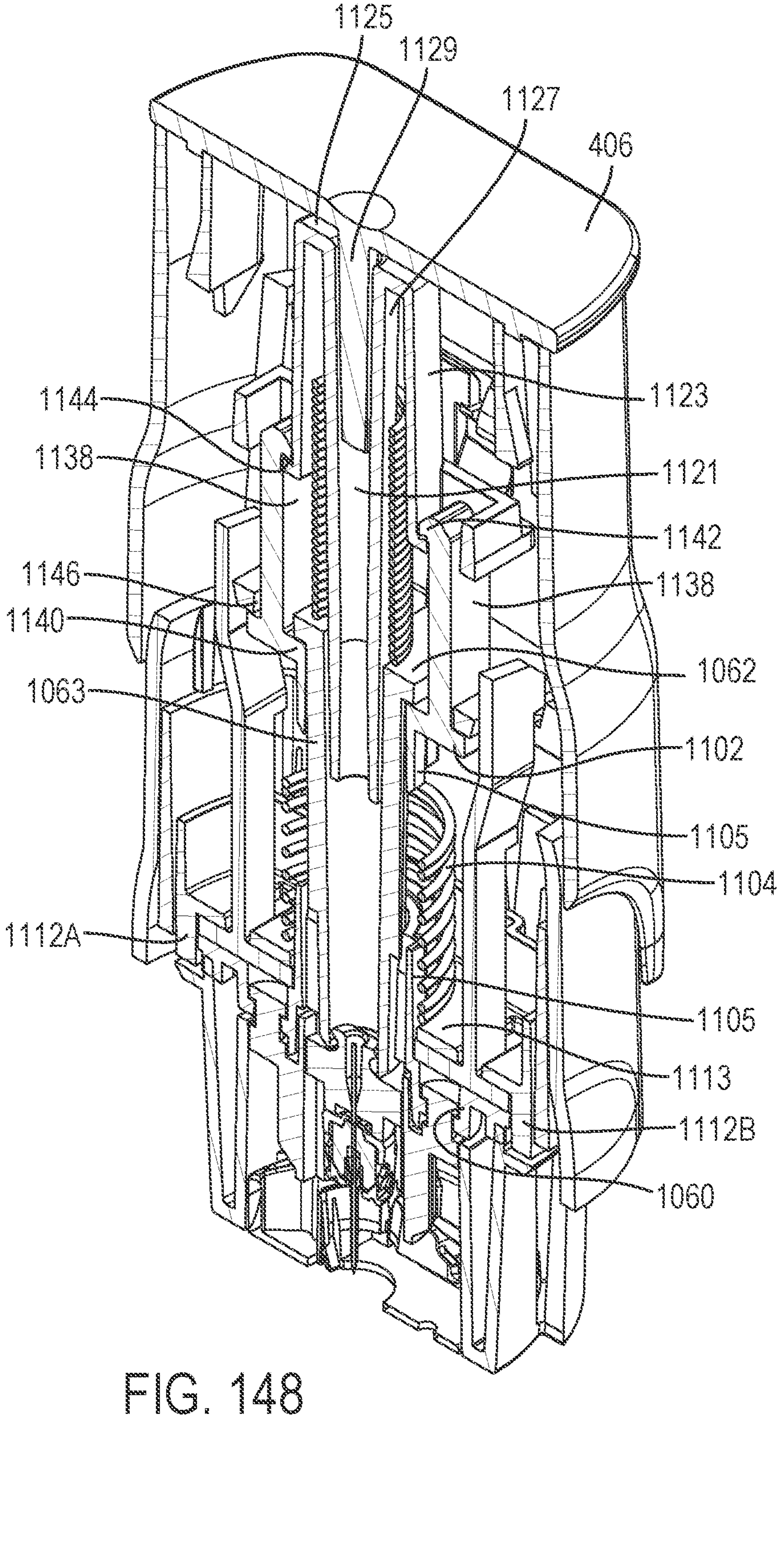
Figure 149:
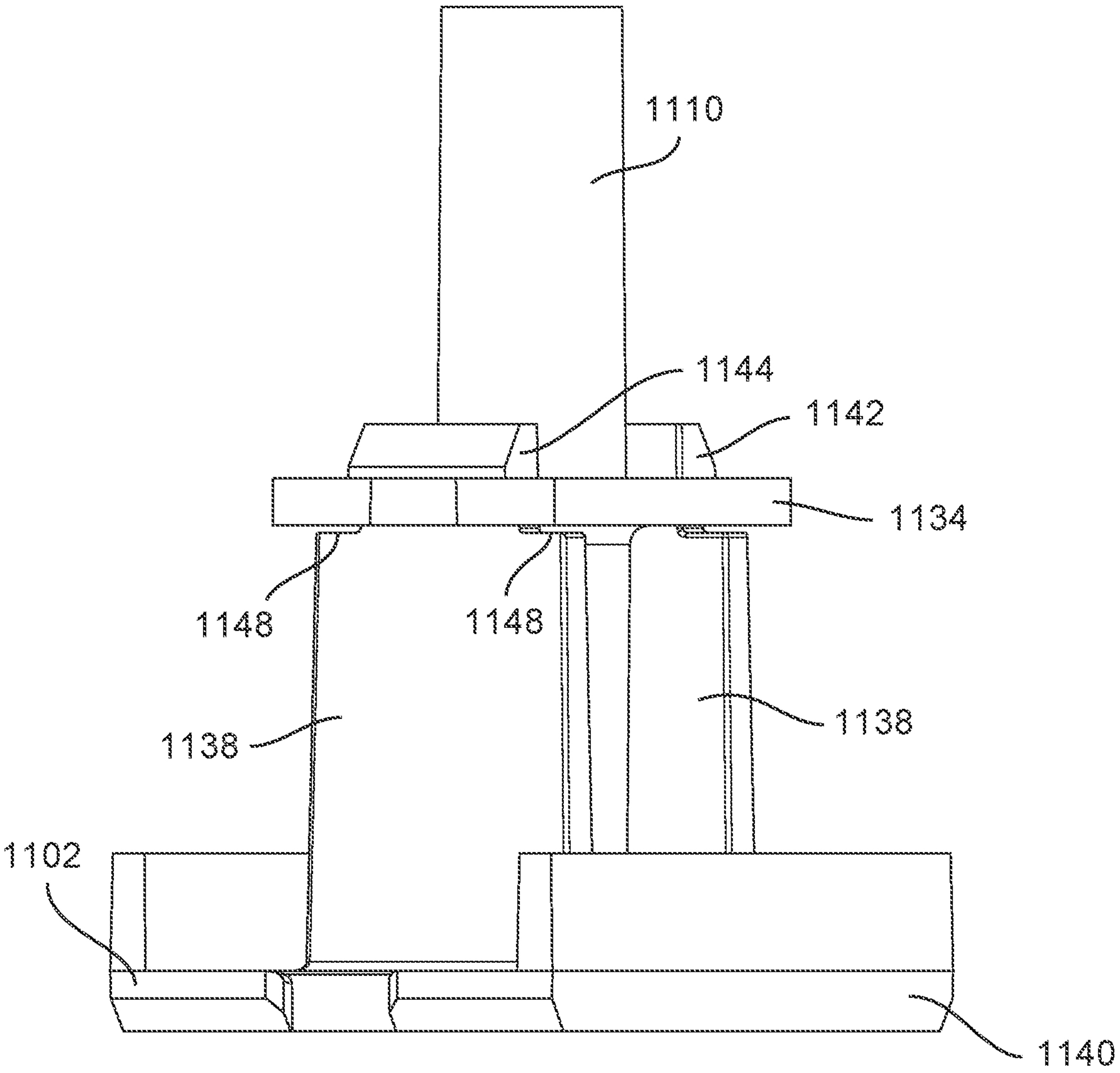
Figure 150:
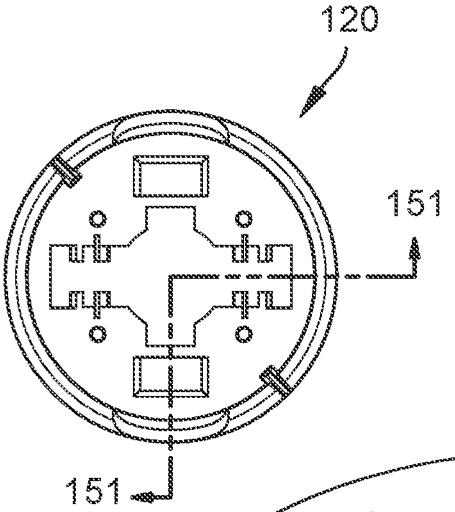
Figure 151:
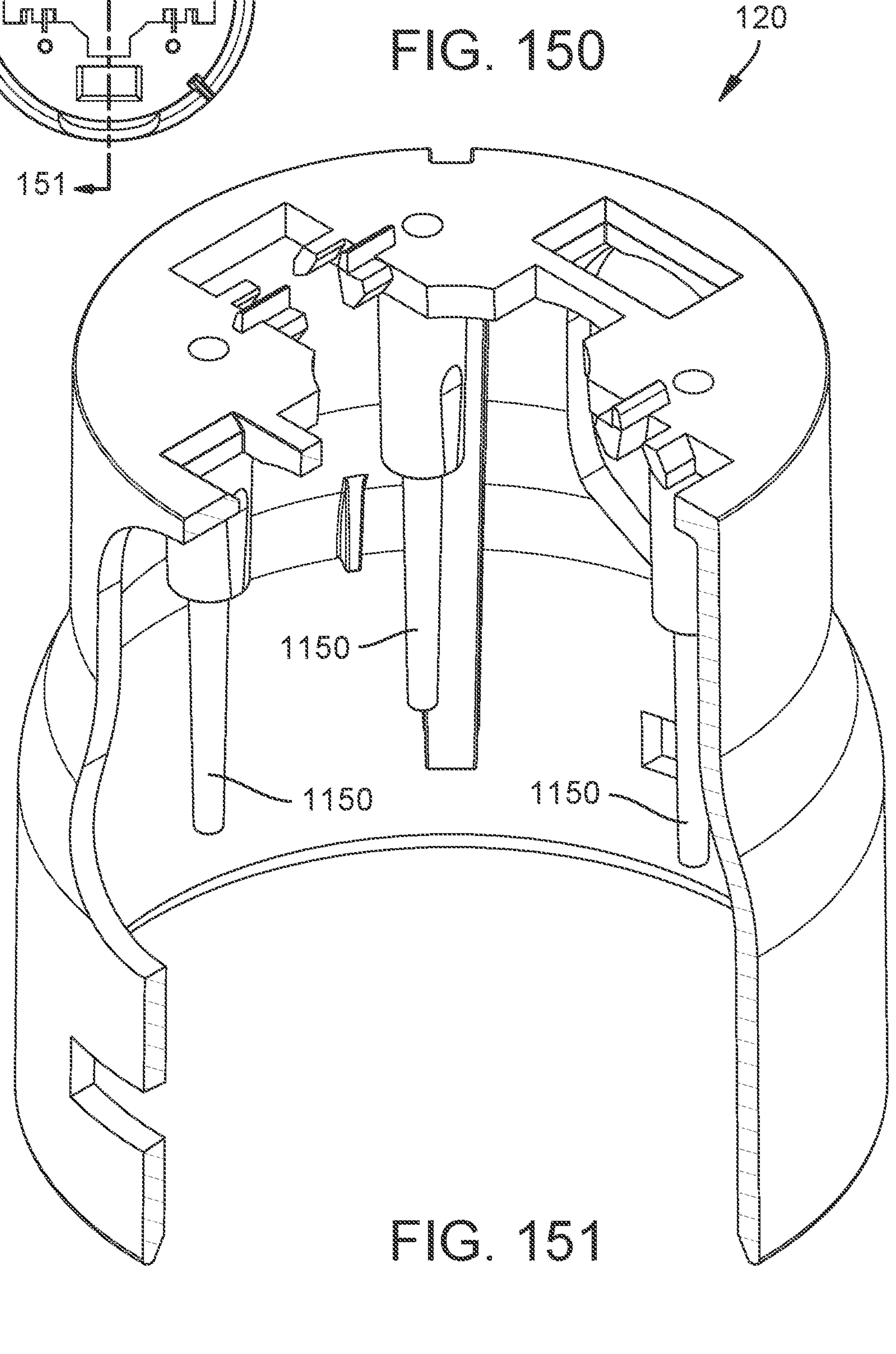
Figure 152:
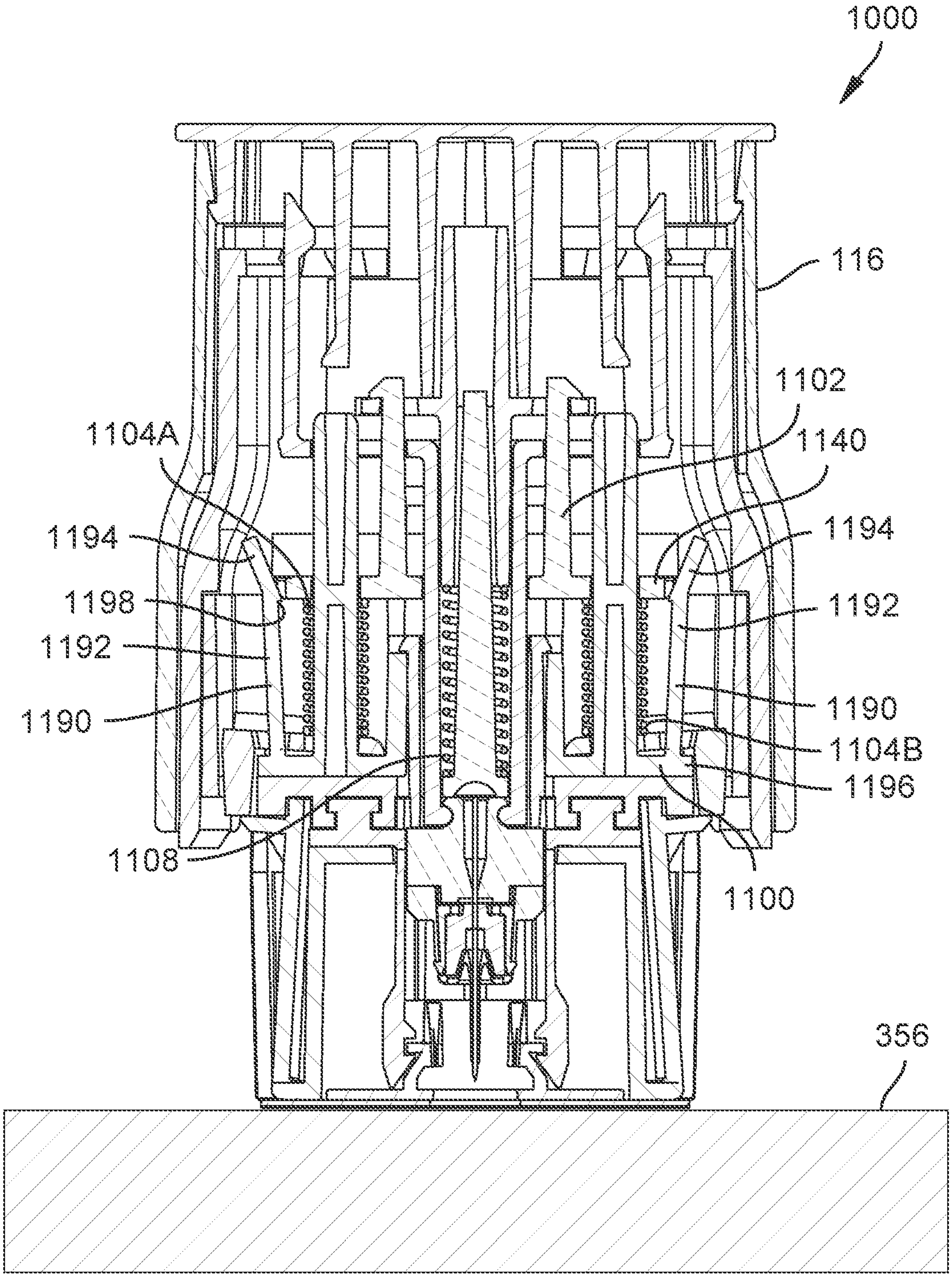
Figure 153:
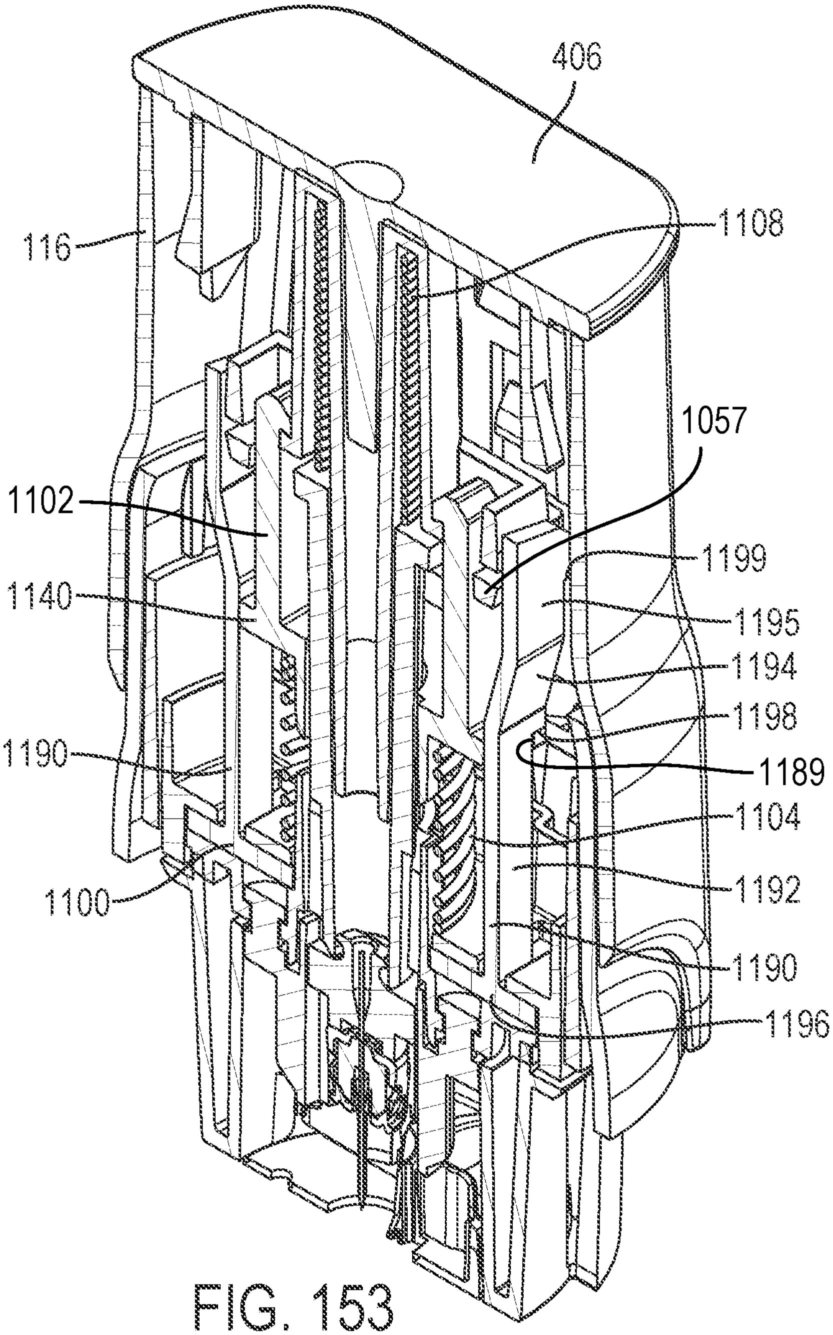
Figure 154:
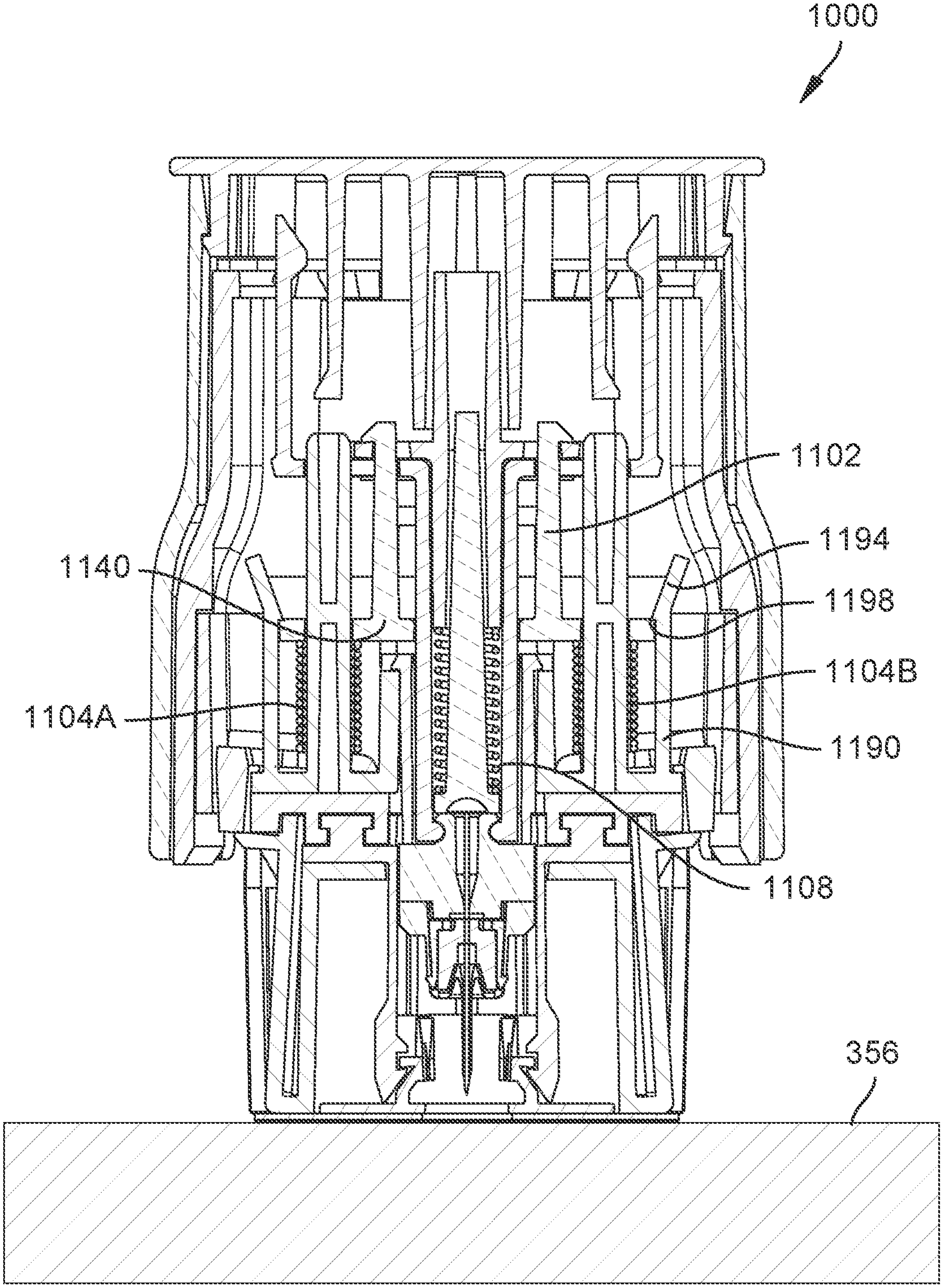
Figure 155:
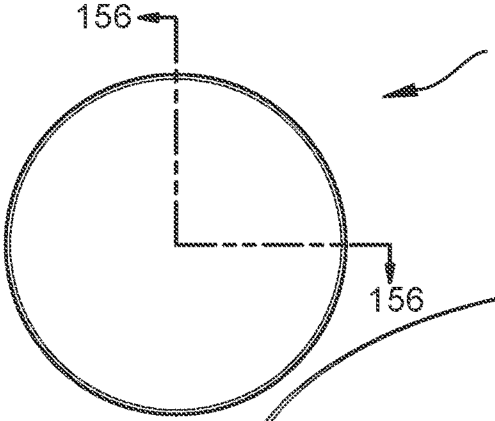
Figure 156:
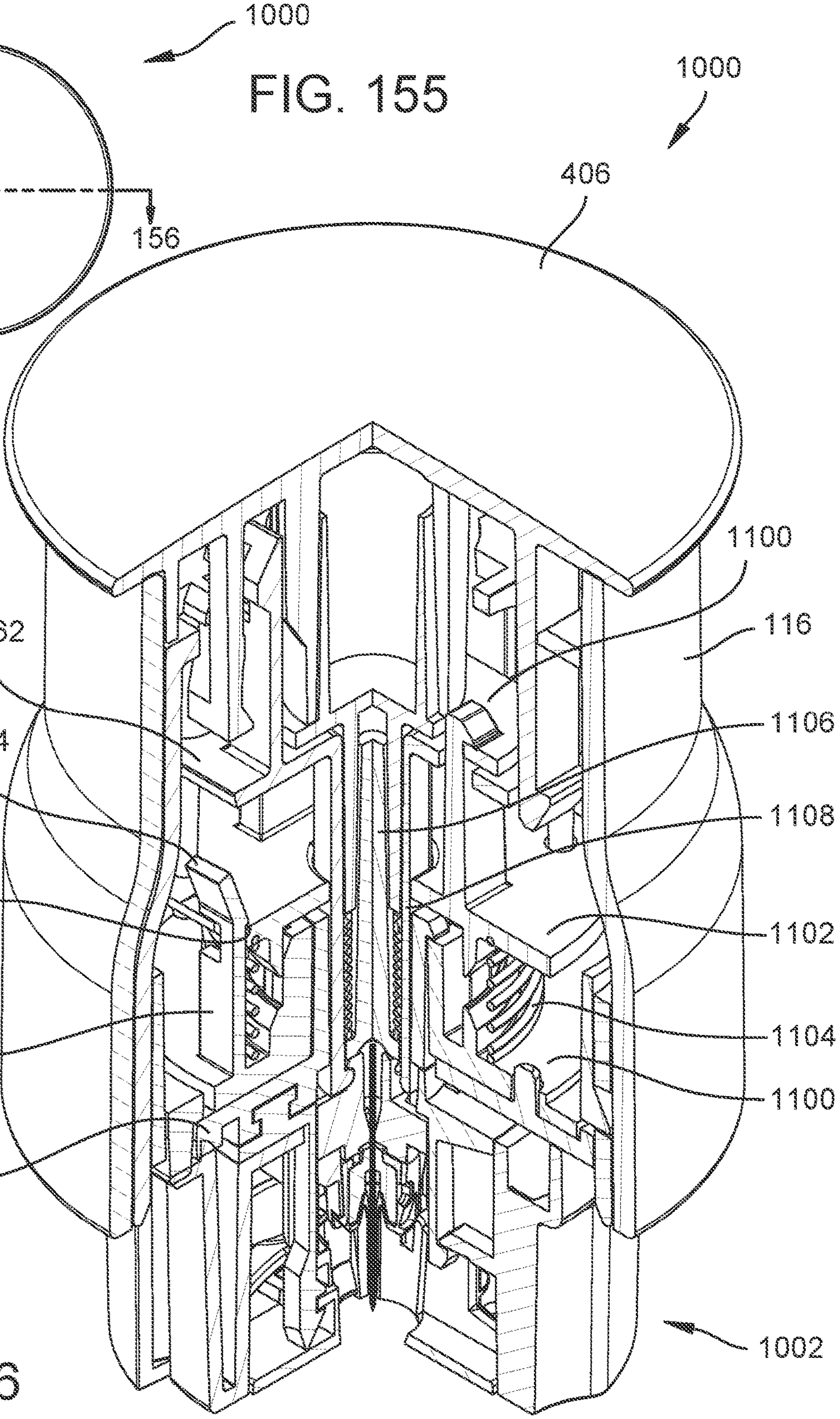
Figure 157A:
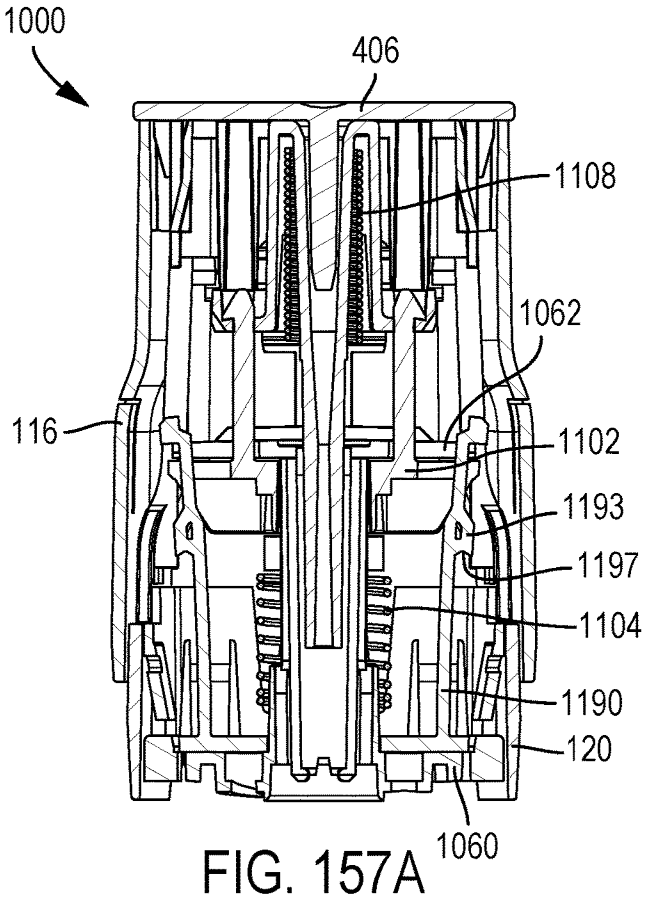
Figure 157B:
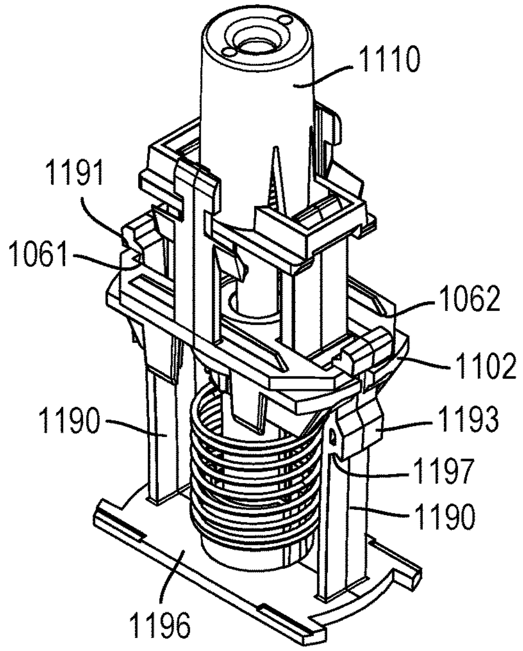
Figure 157C:
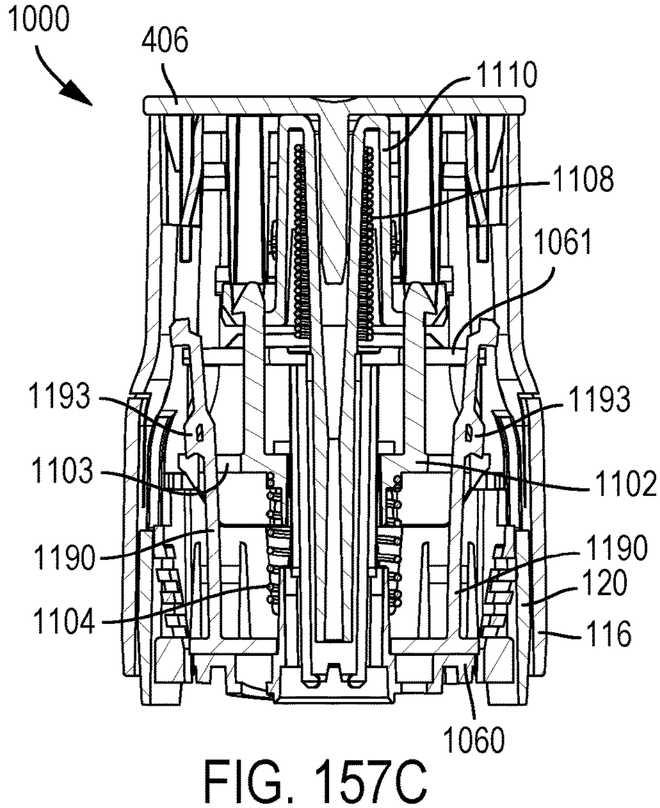
Figure 157D:
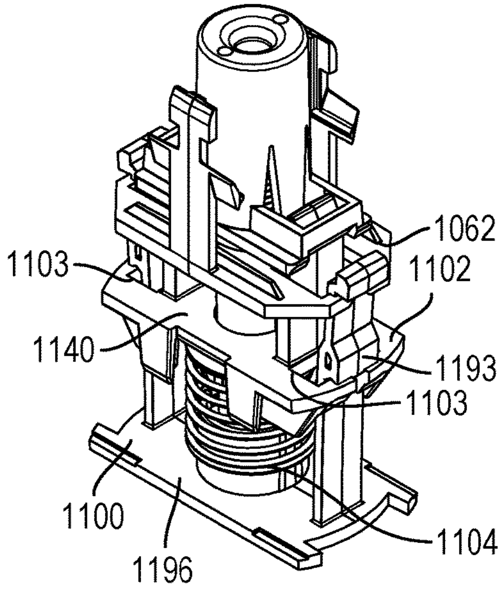
Figure 158:
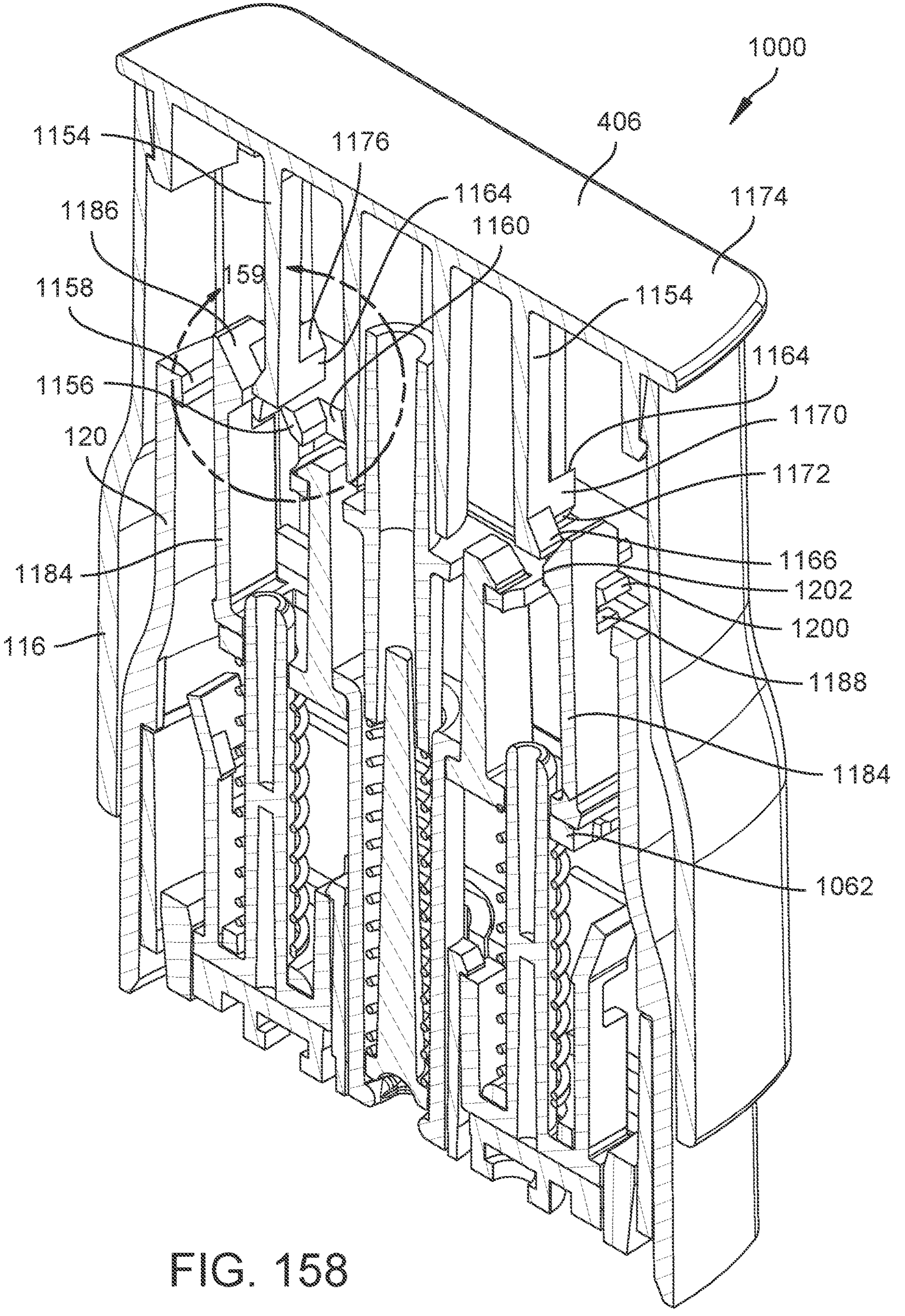
Figure 159:
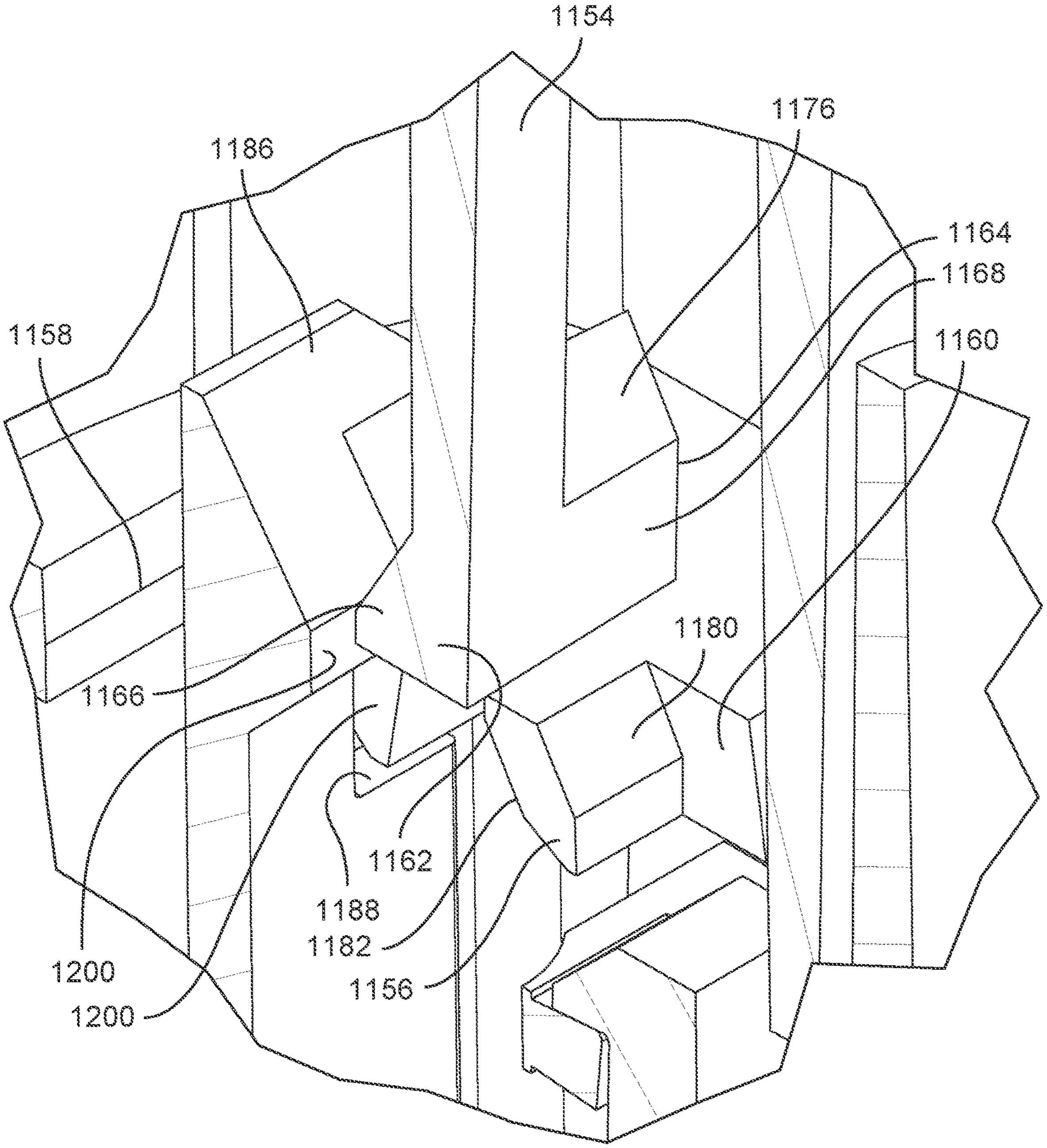
Figure 160:
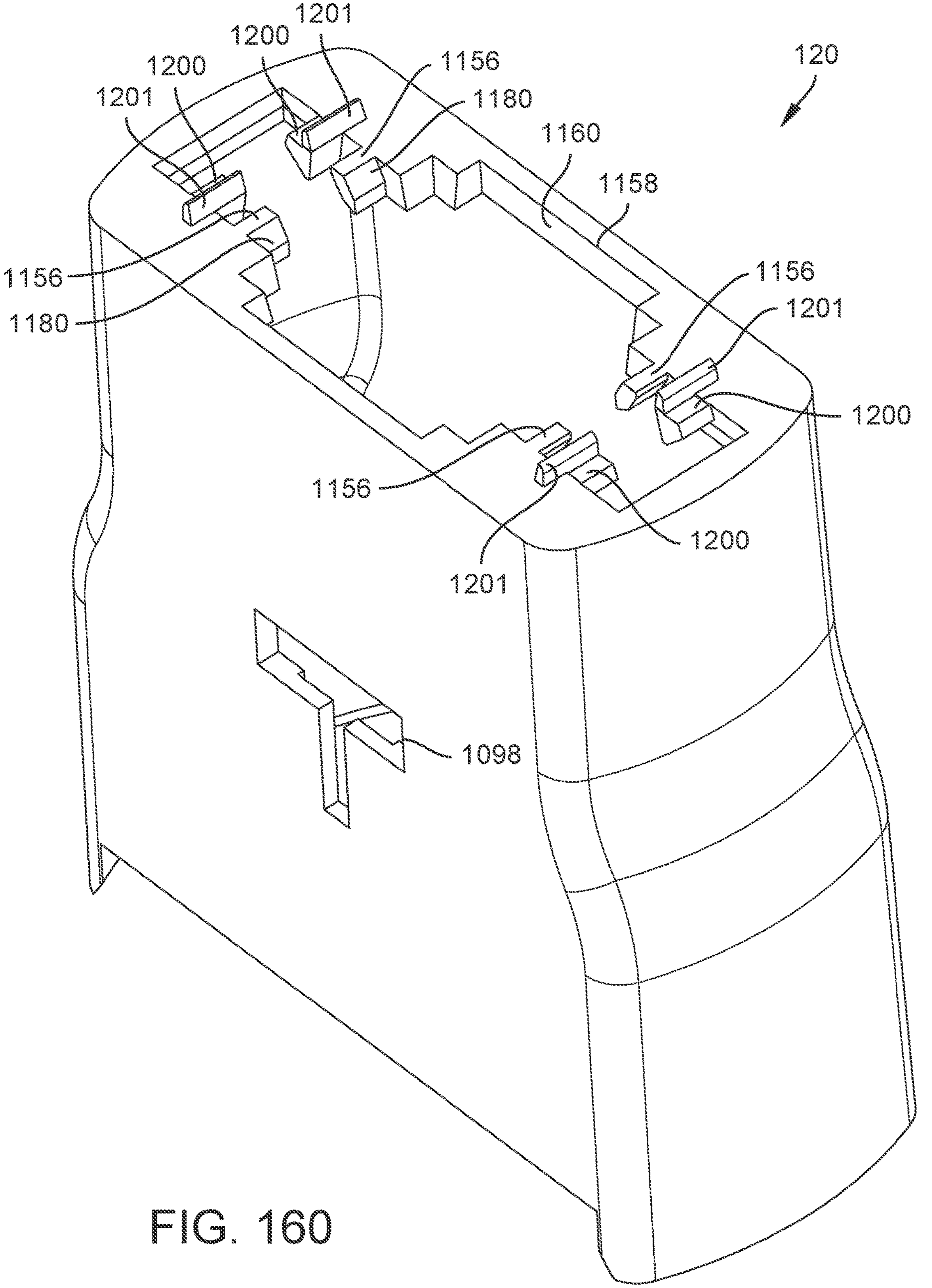
Figure 162A:
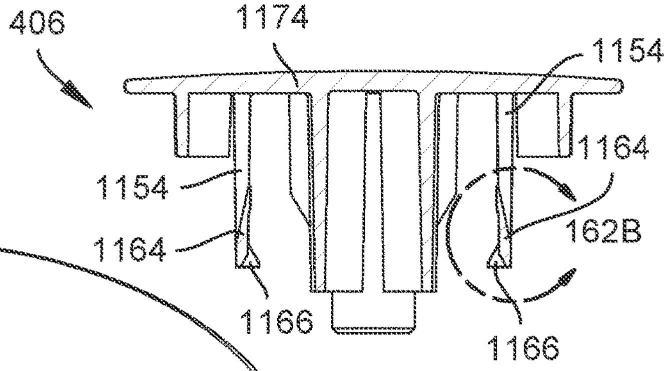
Figure 161:
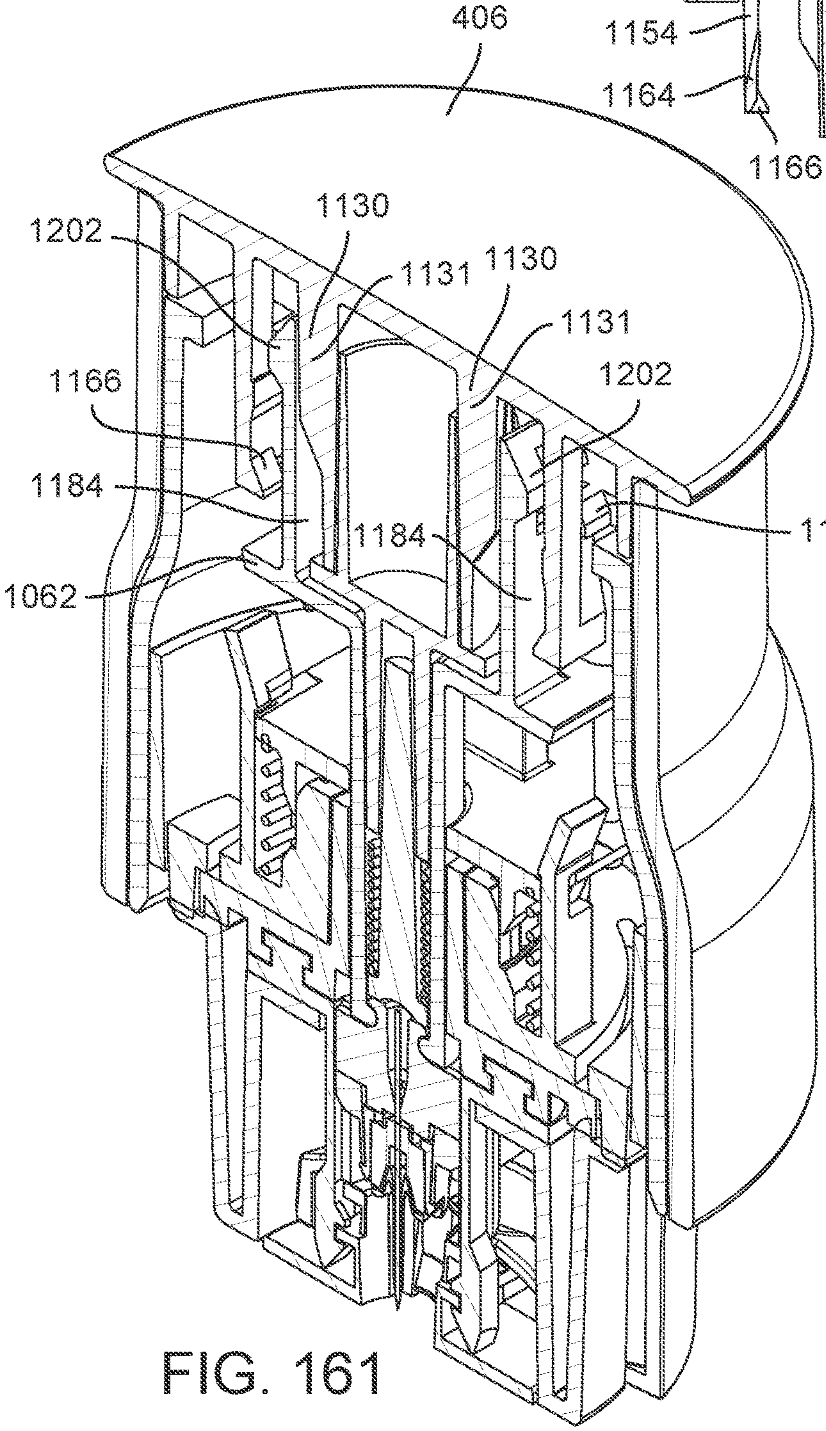
Figure 162B:
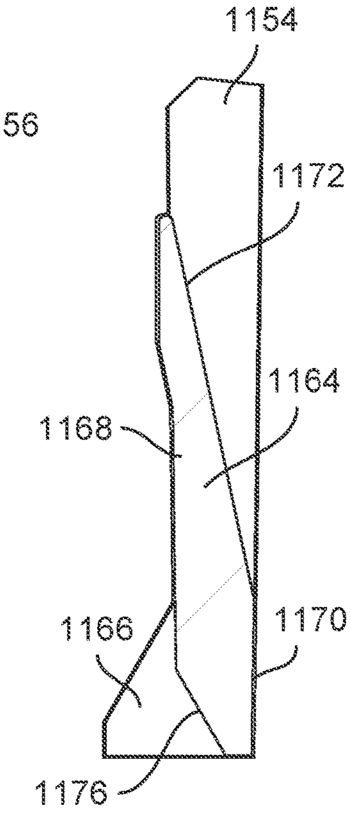
Figure 163:
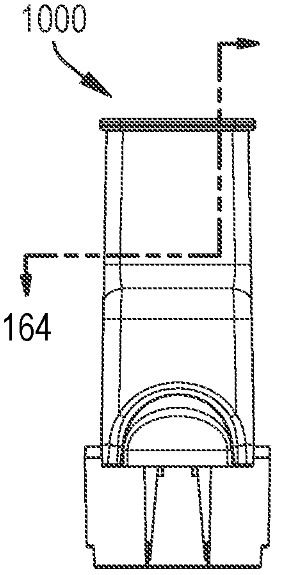
Figure 164:
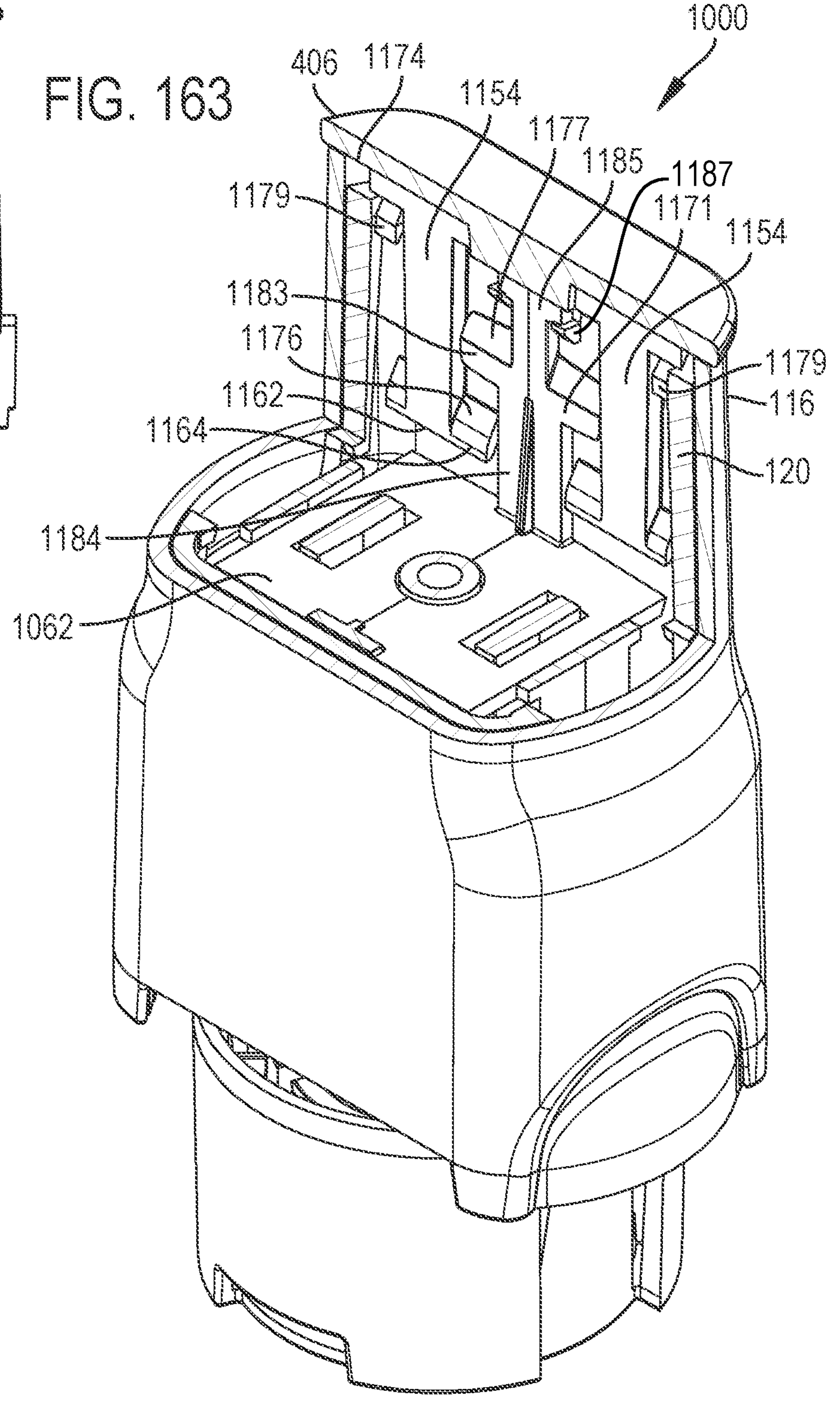
Figure 165:
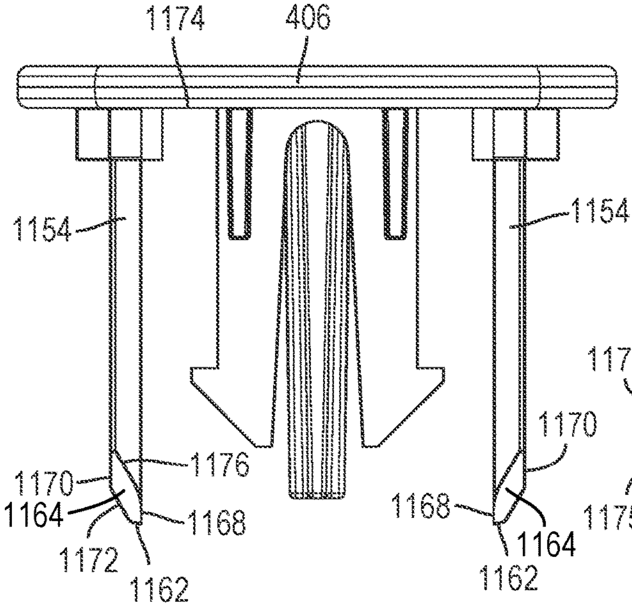
Figure 166:
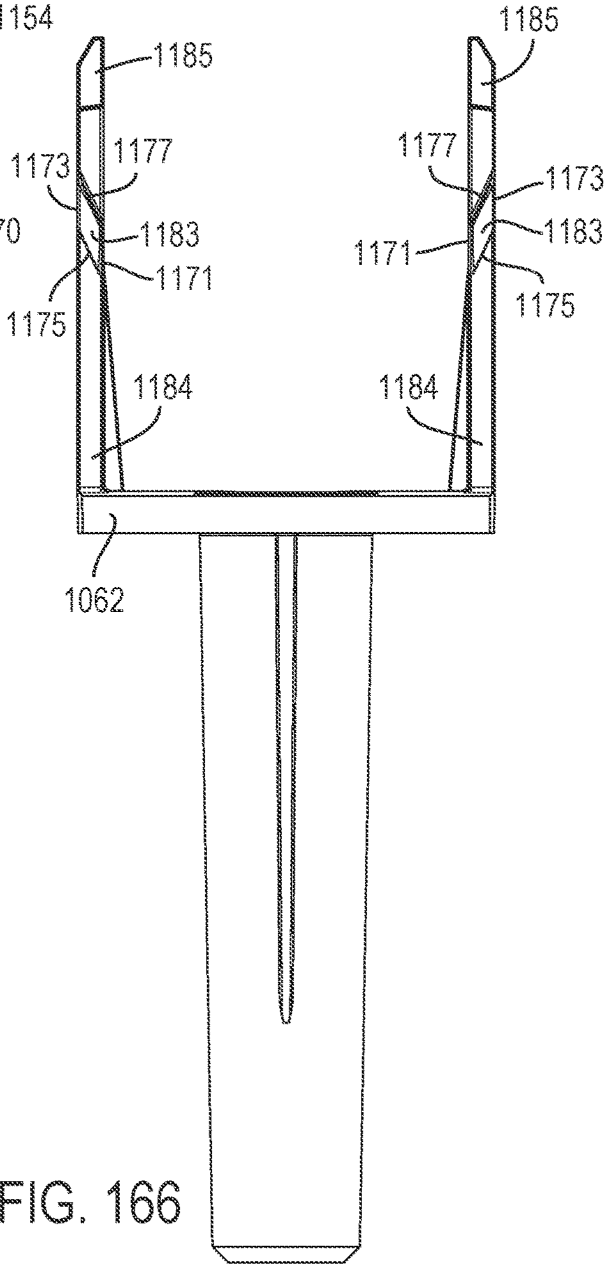
Figure 167:
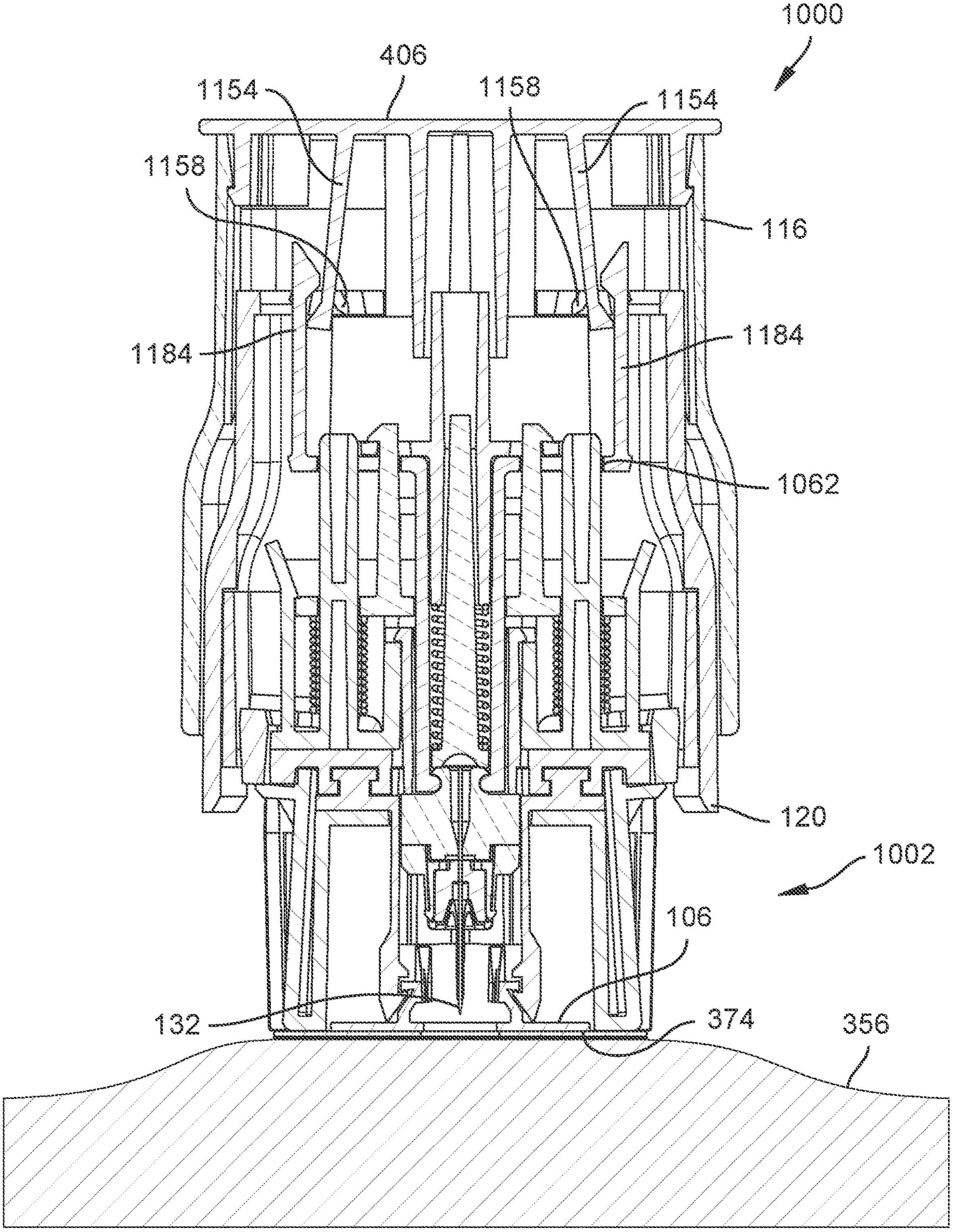
Figure 168:
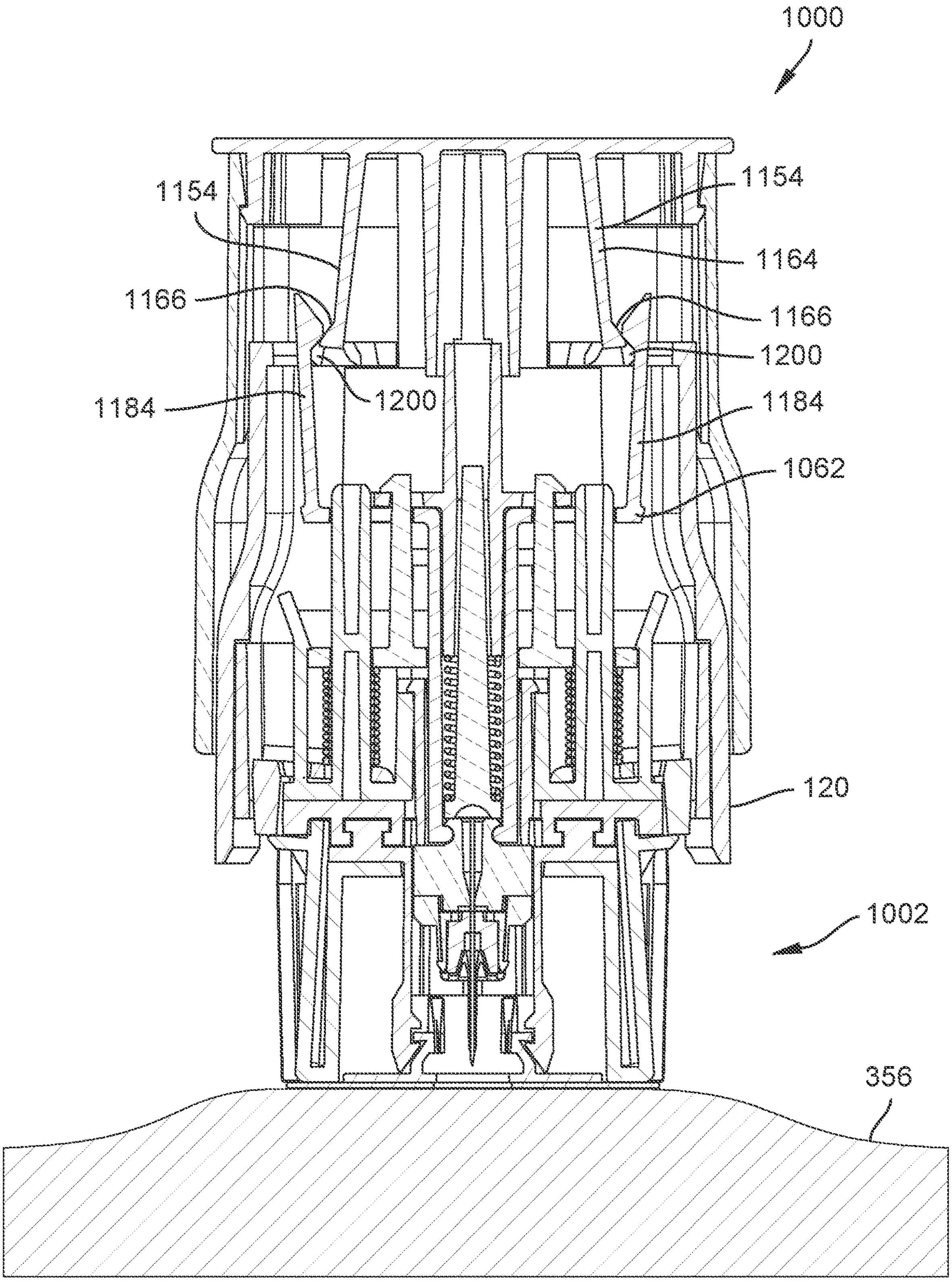
Figure 169:
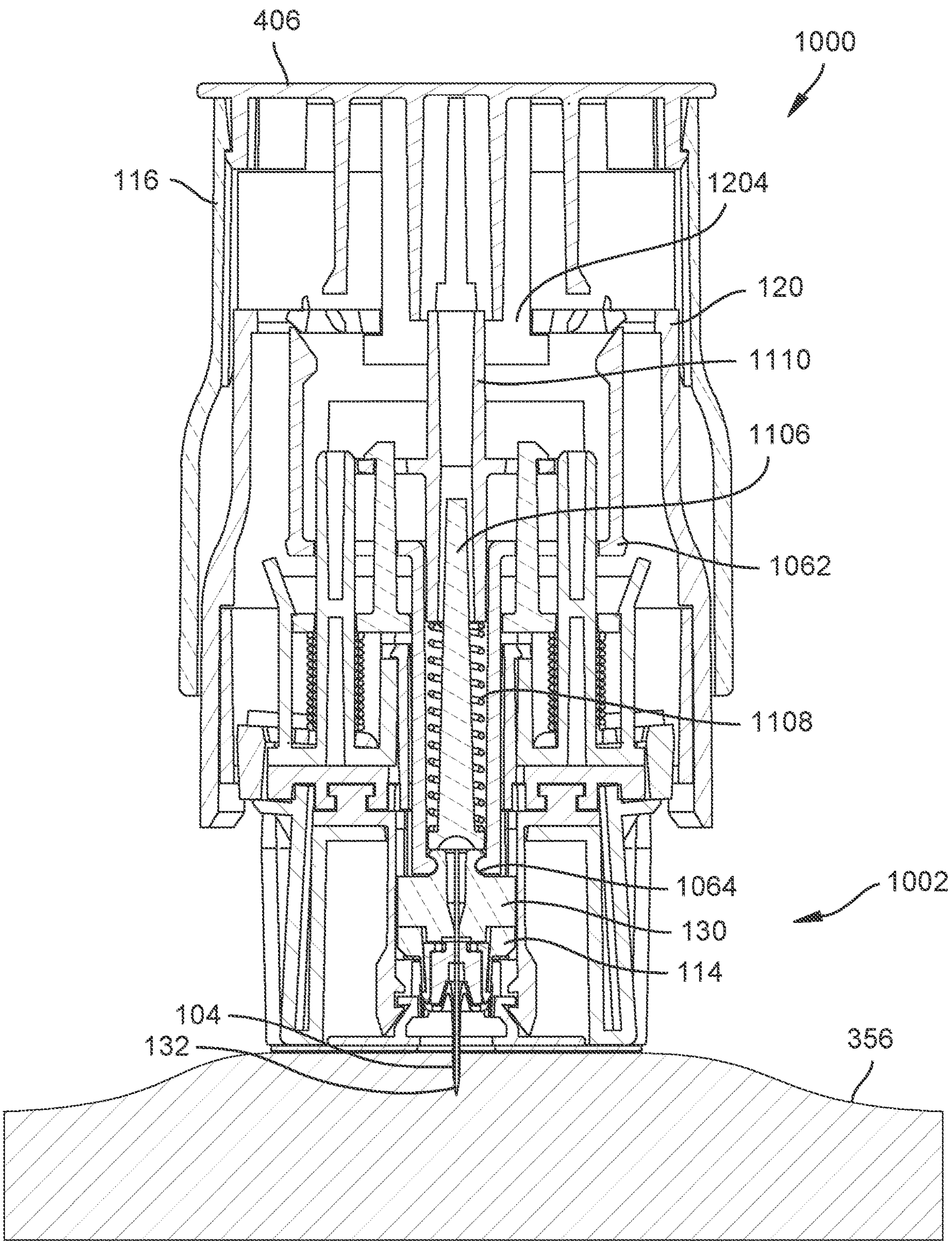
Figure 170:
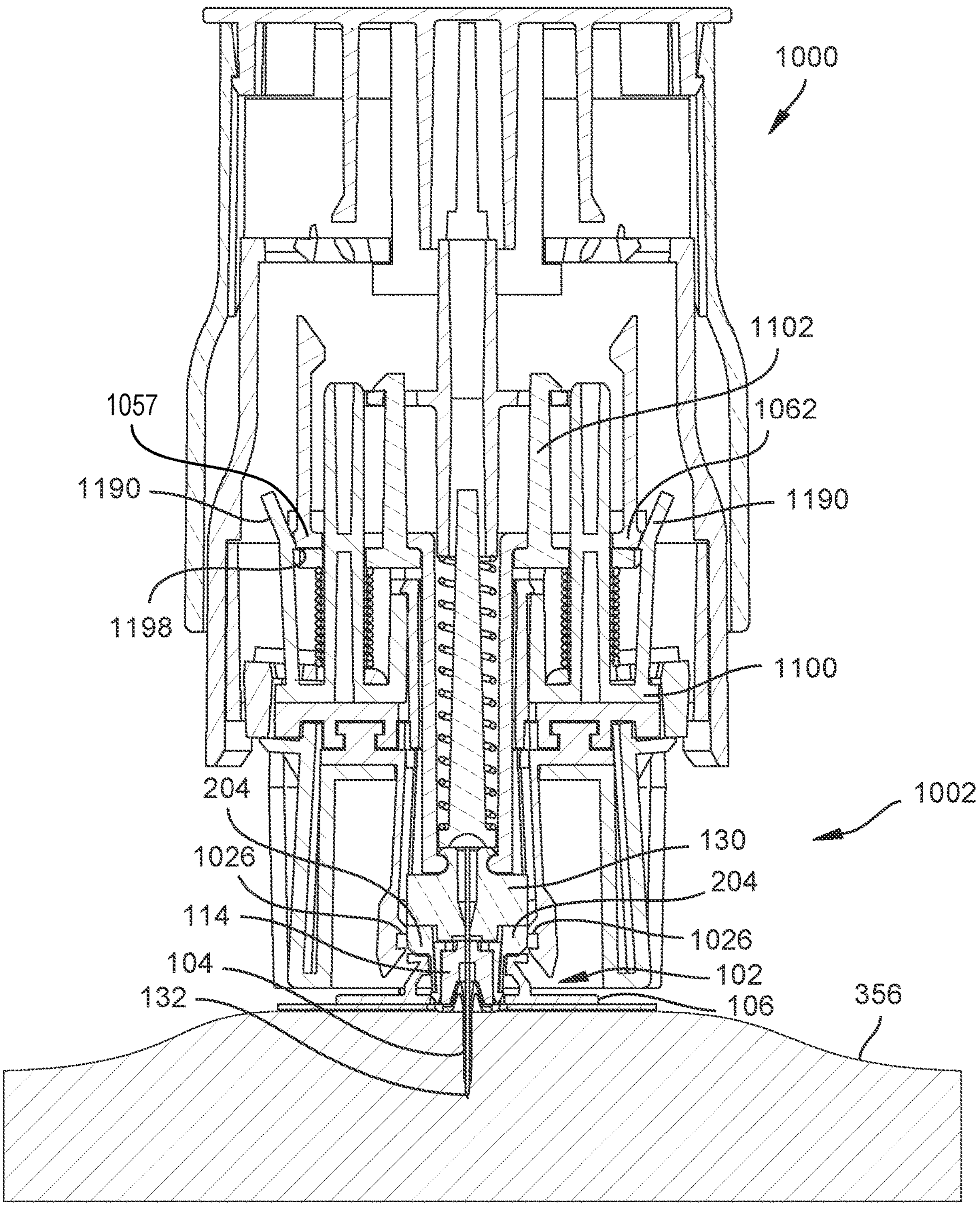
Figure 171A:
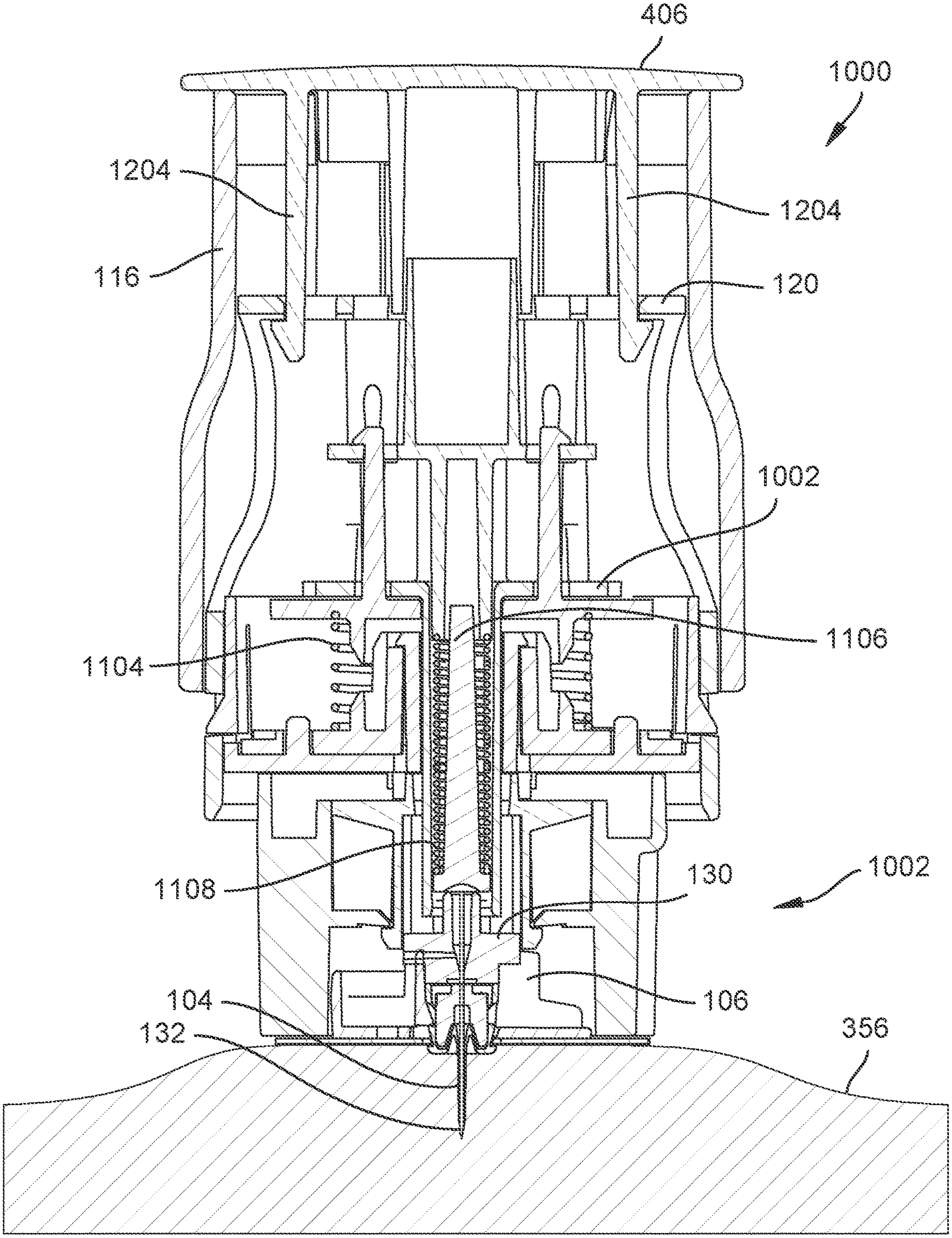
Figure 171B:
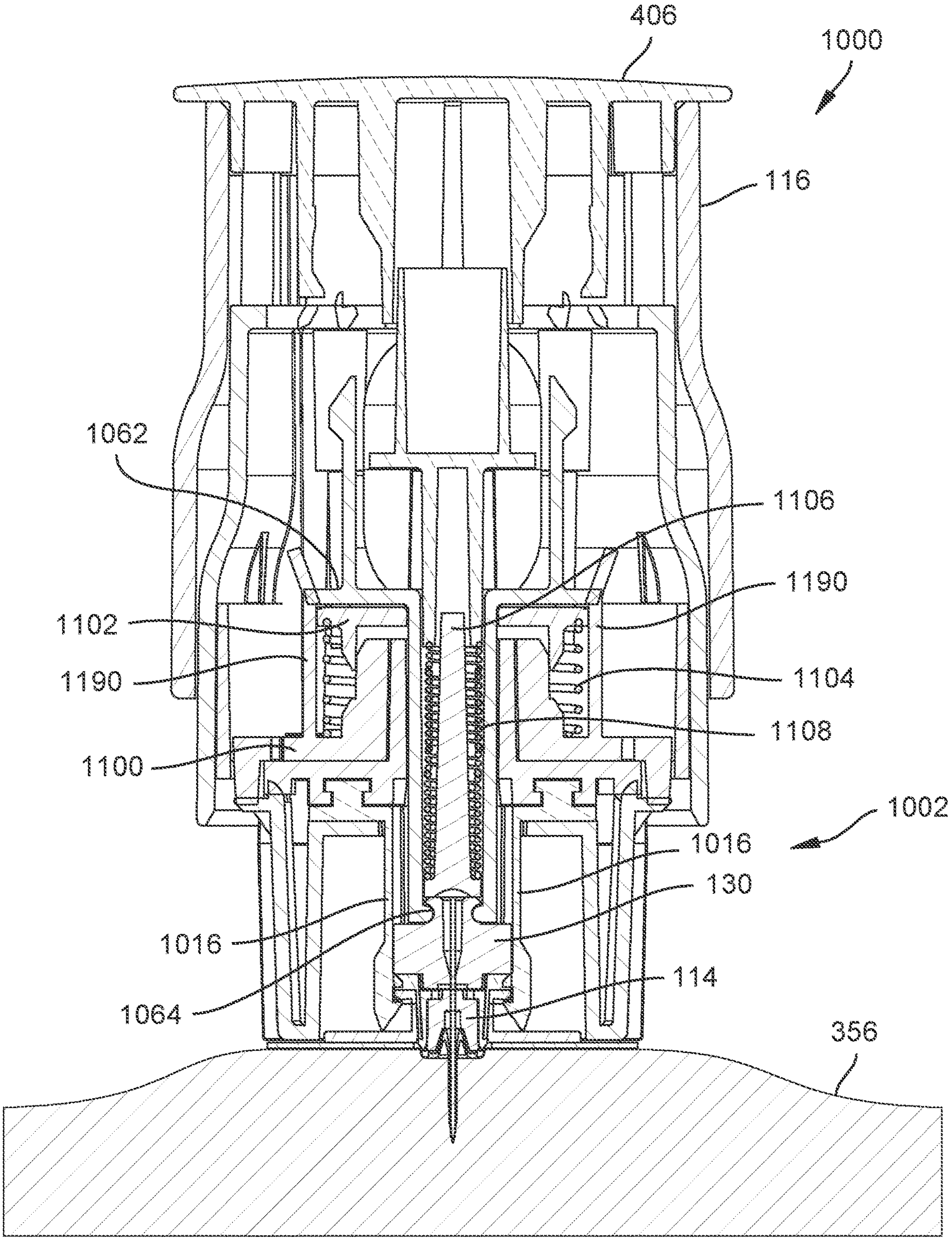
Figure 172:
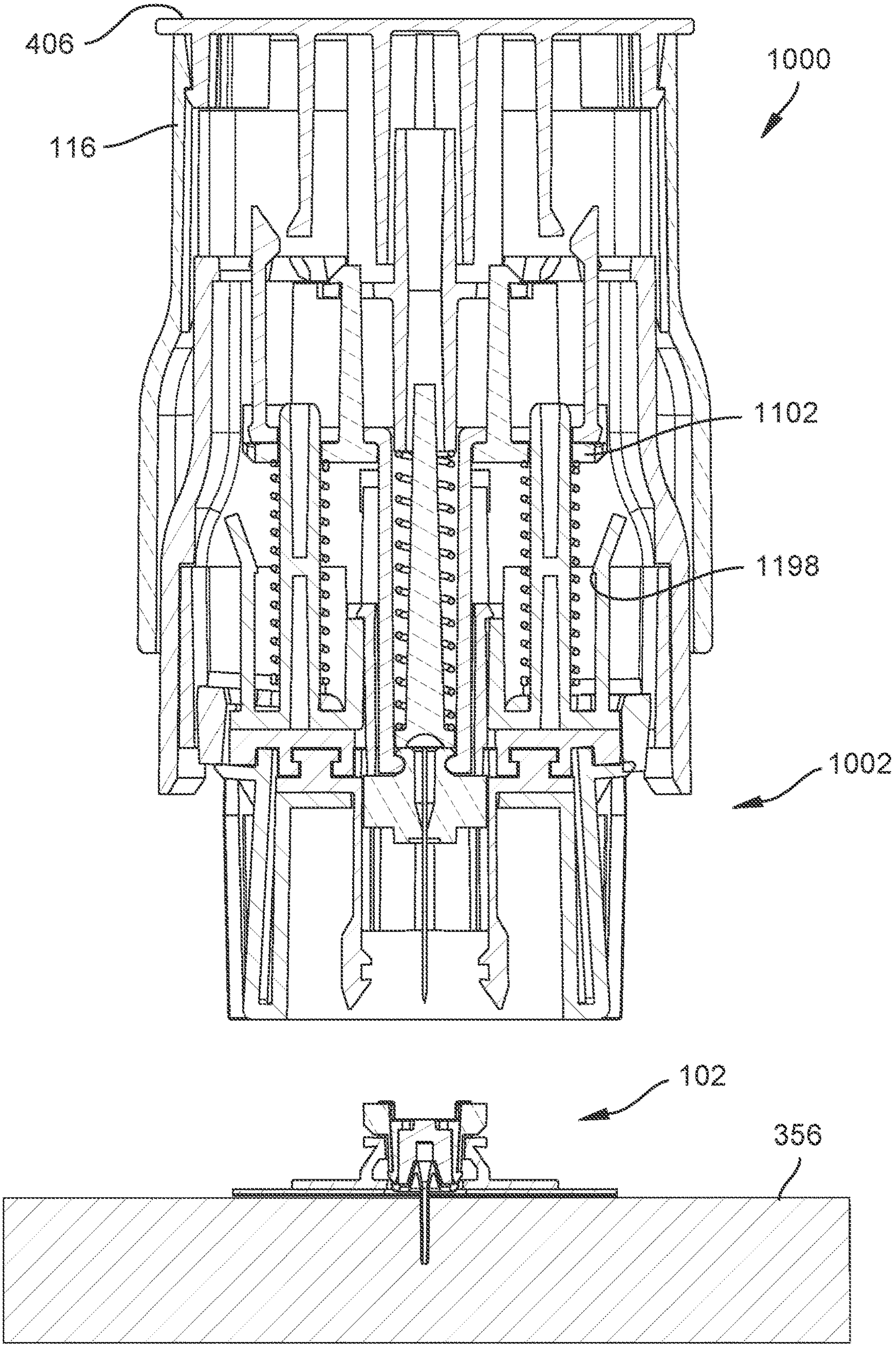
Figure 173:
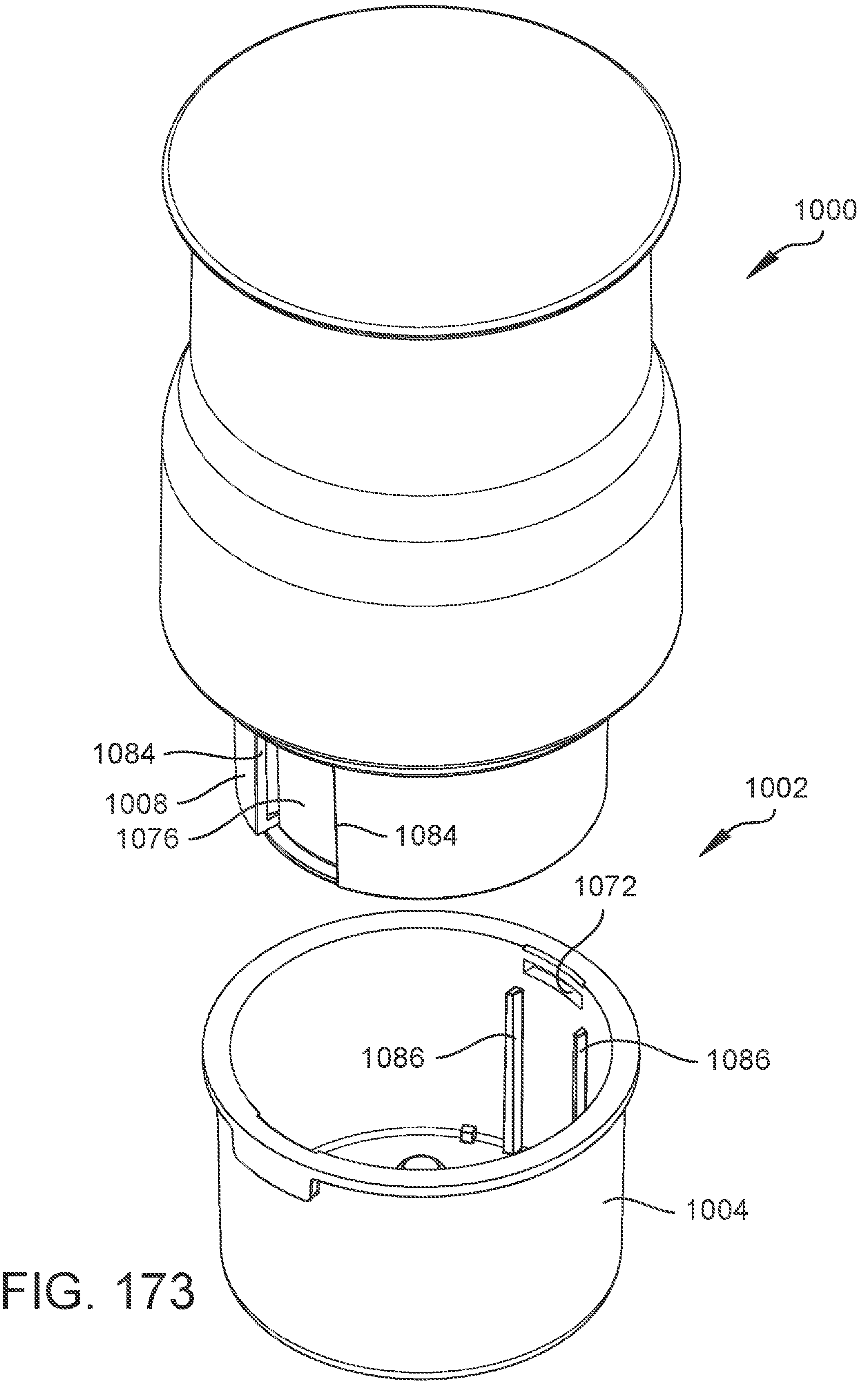
Figure 174A:
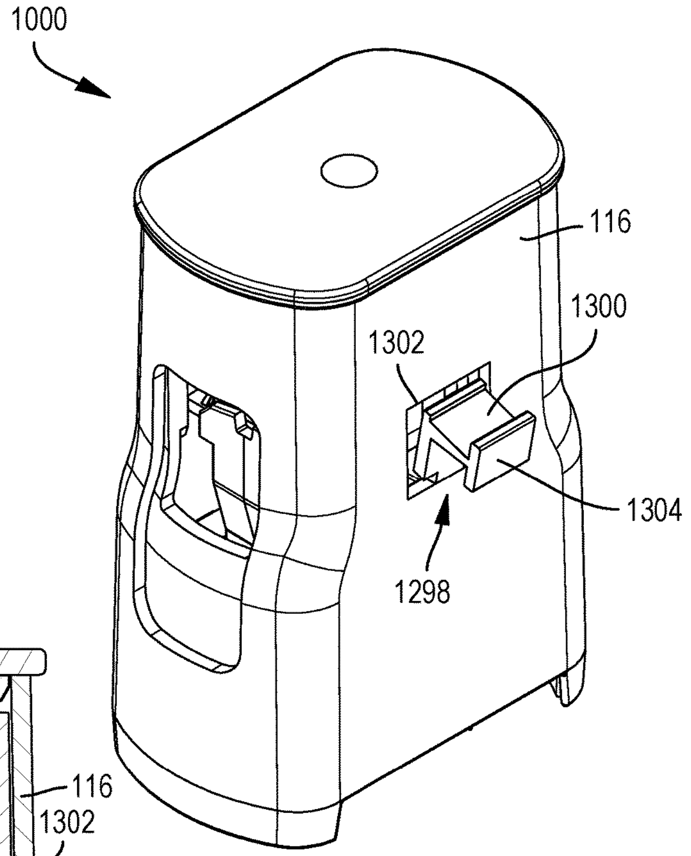
Figure 174B:
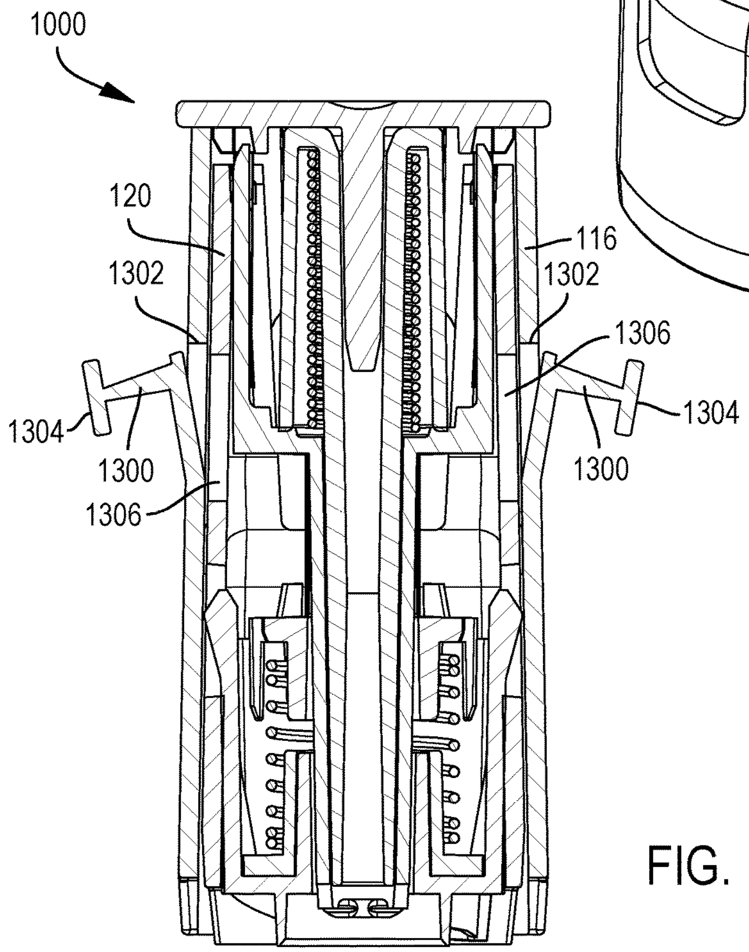
Figure 175A:
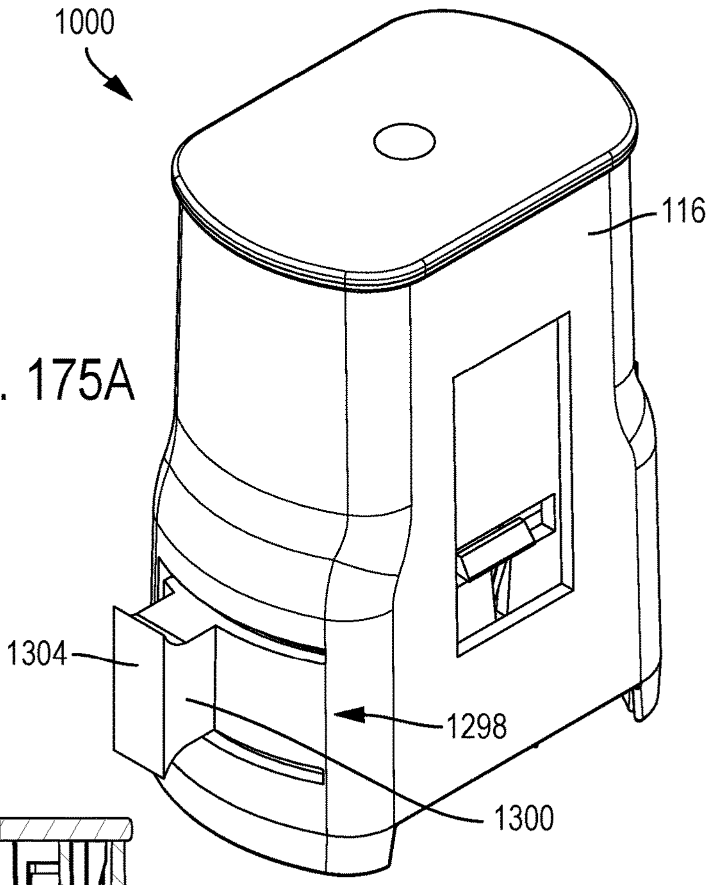
Figure 175B:
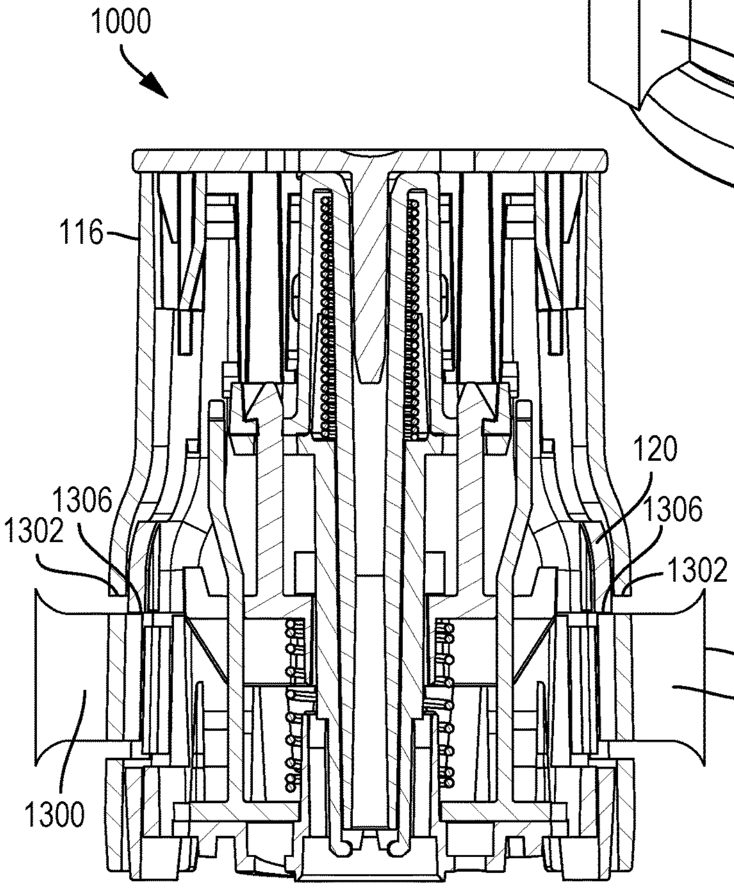
Figure 176A:
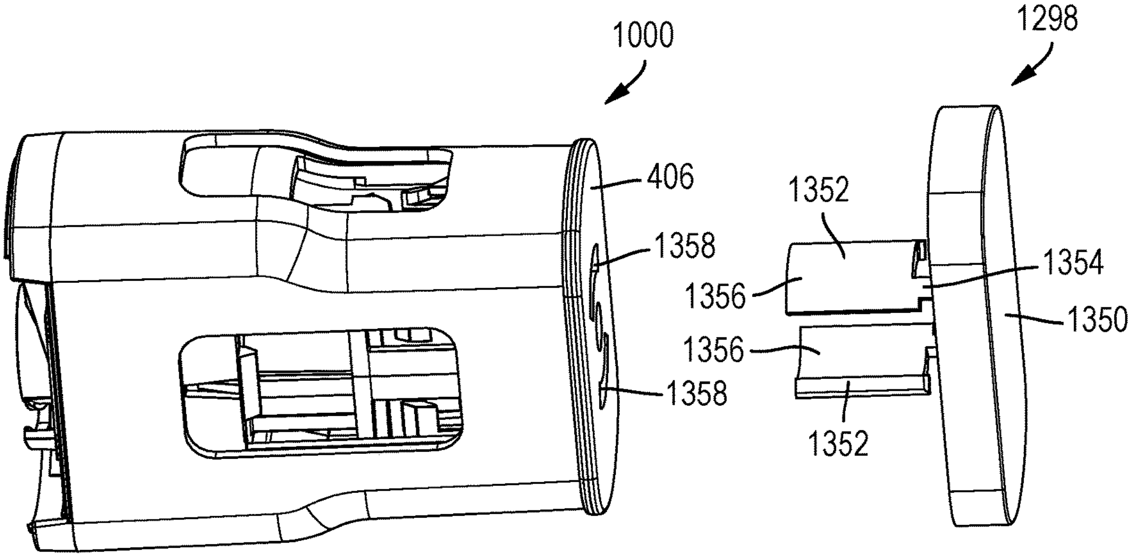
Figure 176B:
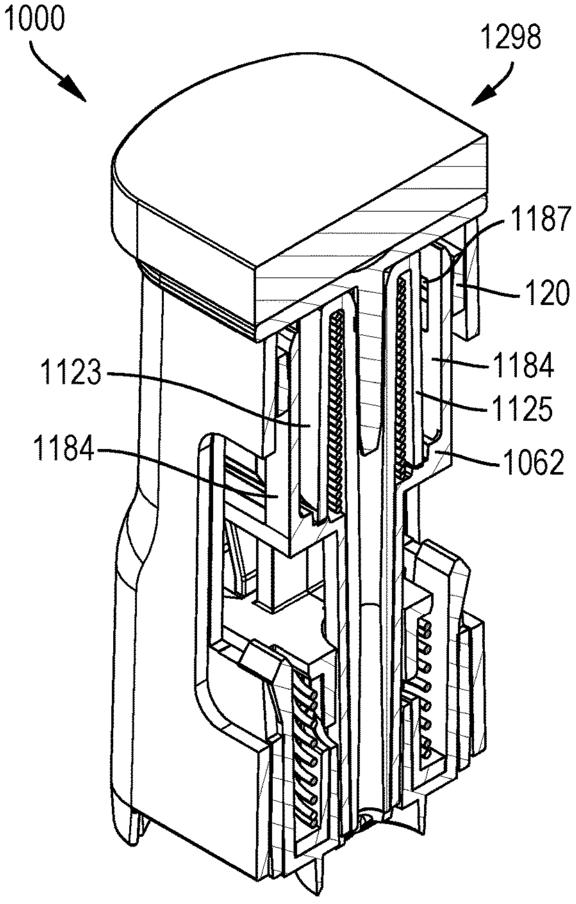
Figure 176C:
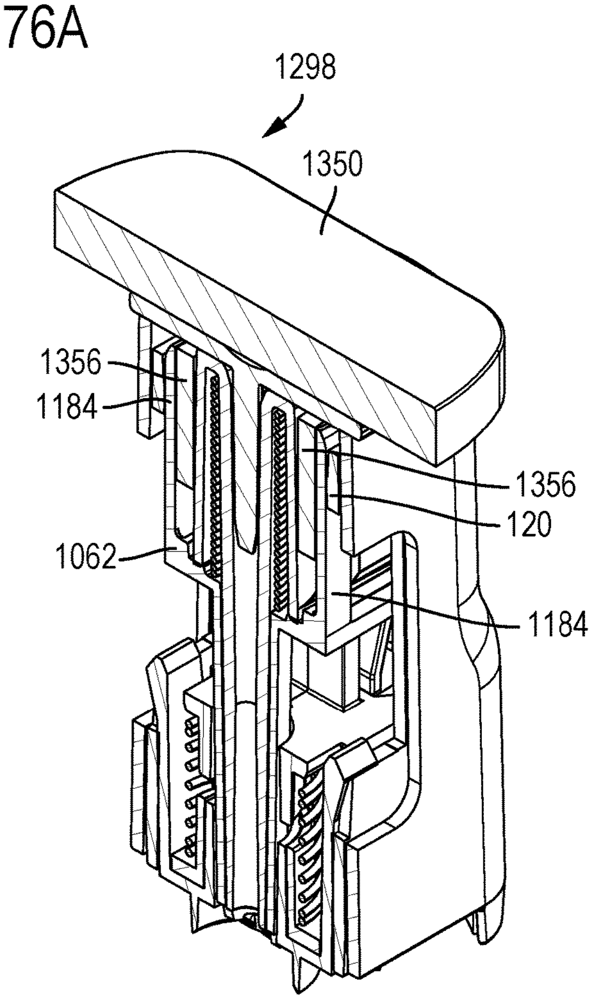
Figure 177A:
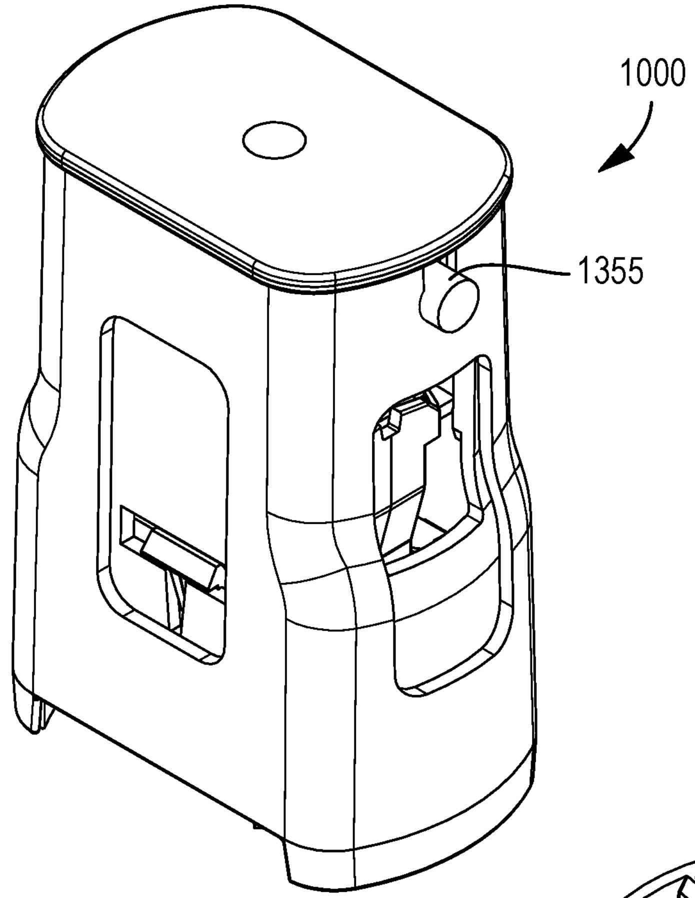
Figure 177B:
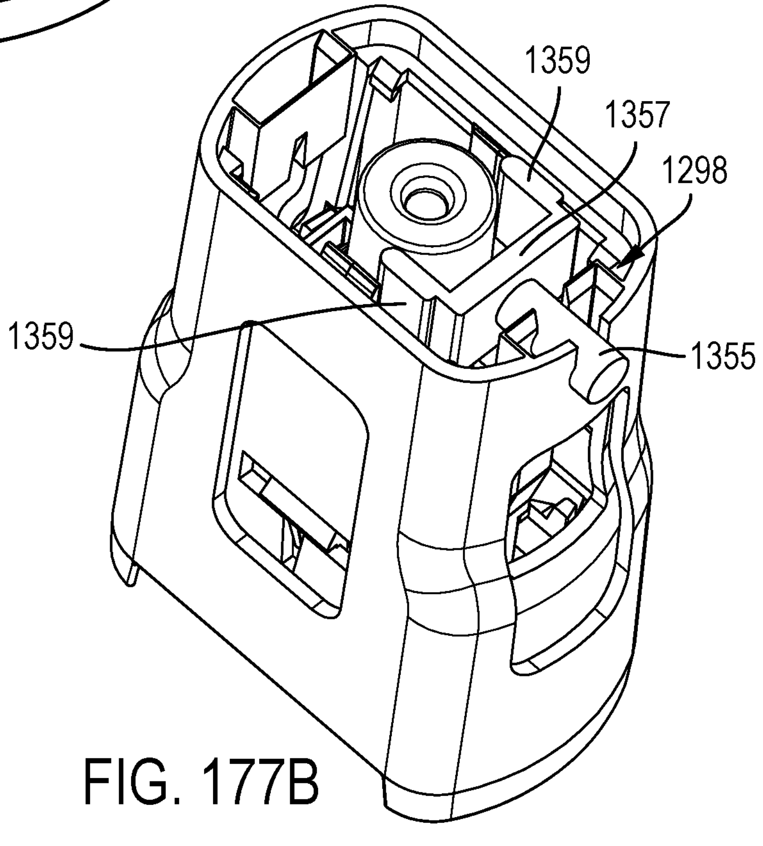
Figure 178A:
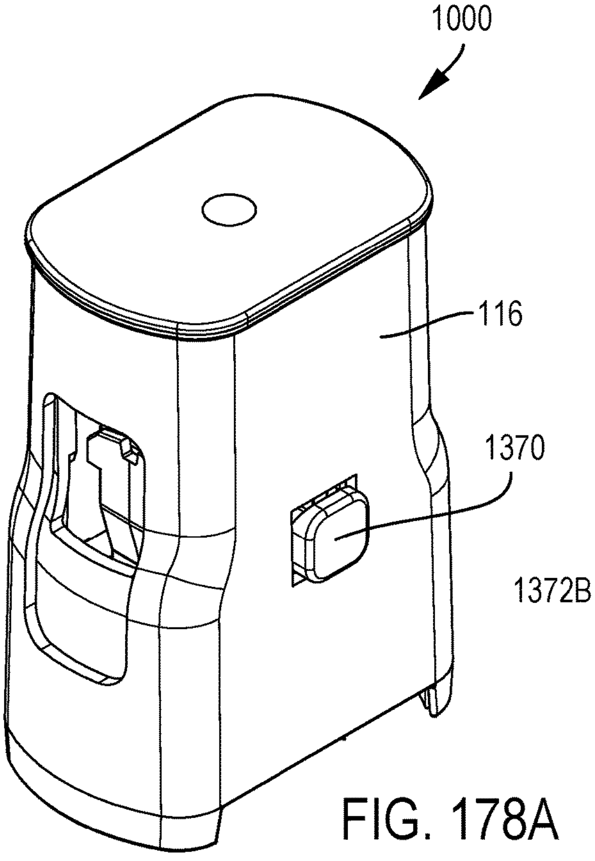
Figure 178B:
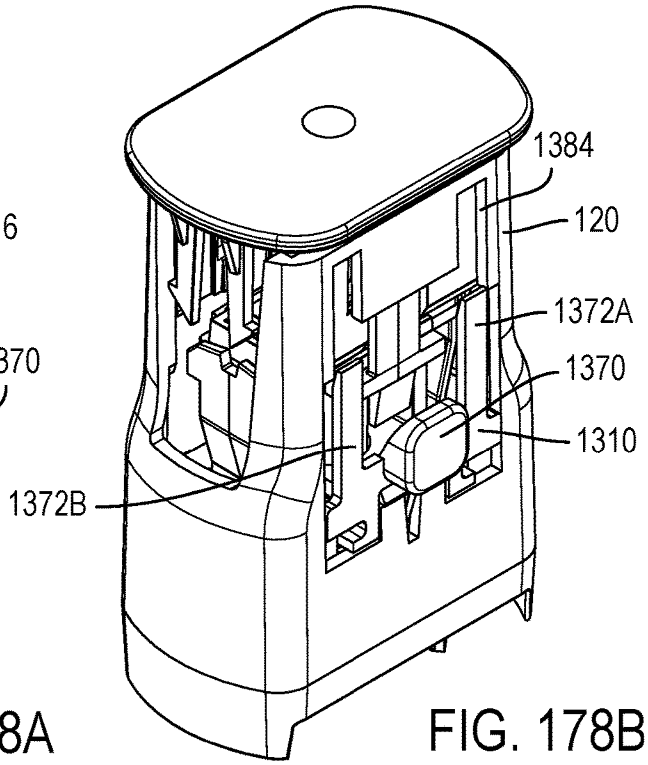
Figure 178C:
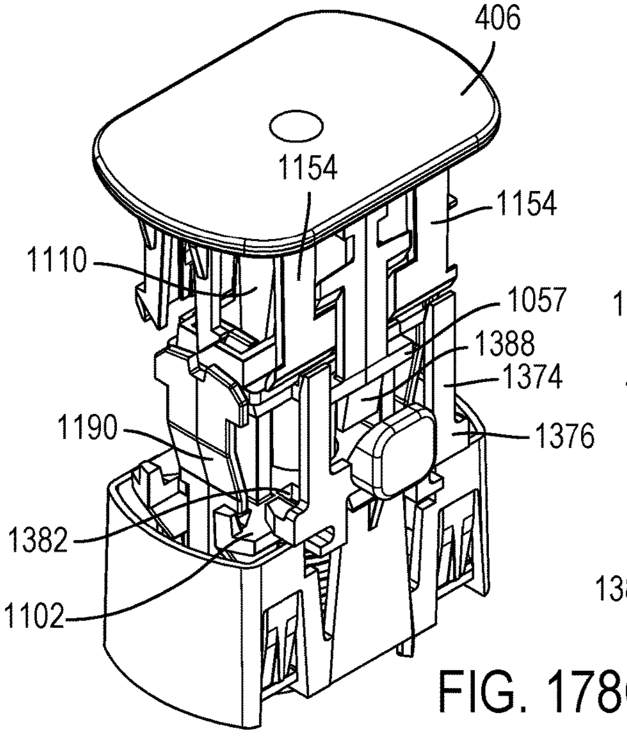
Figure 178D:
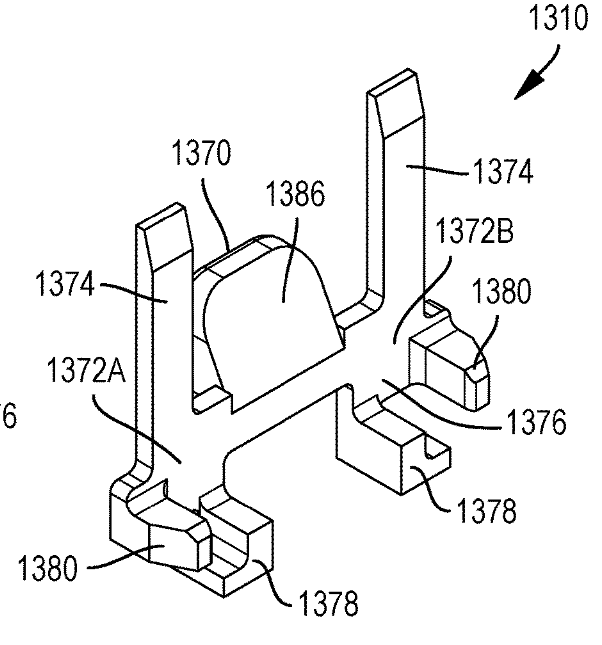
Figure 179A:
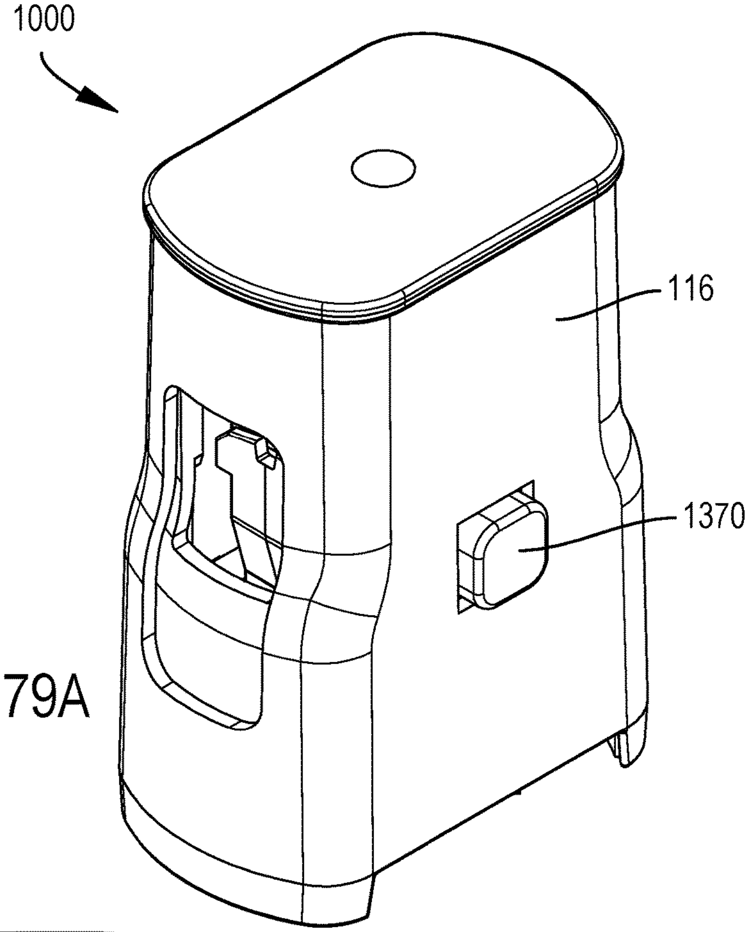
Figure 179B:
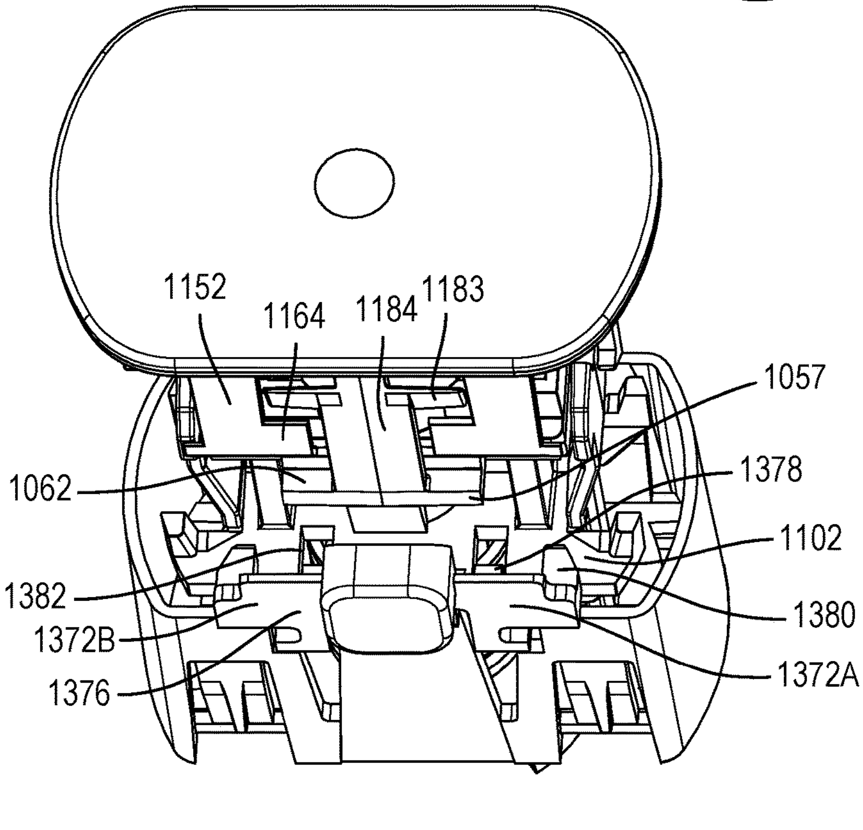
Figure 180A:
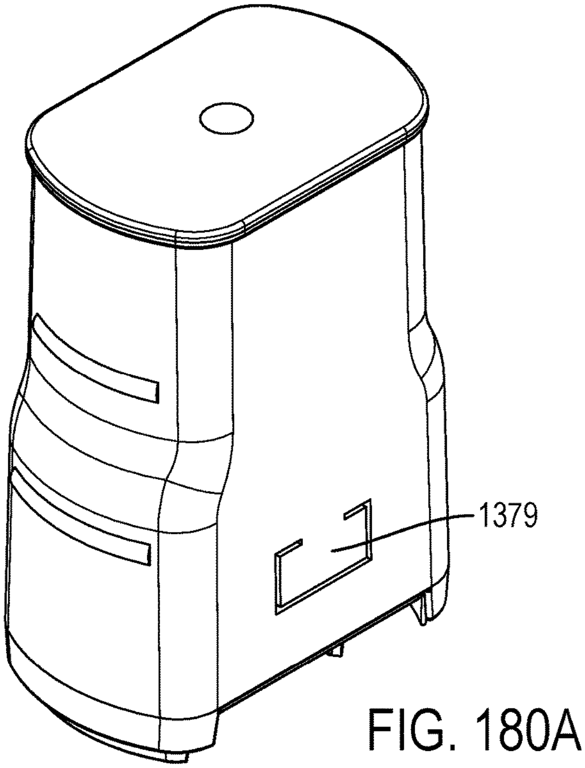
Figure 180B:
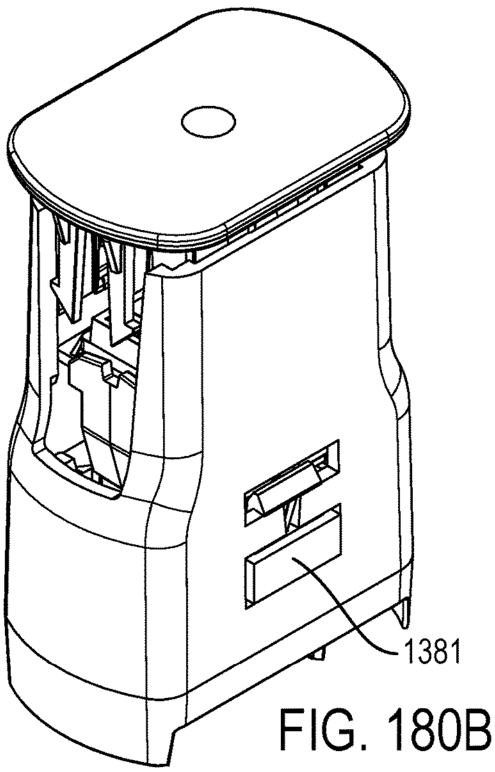
Figure 180C:
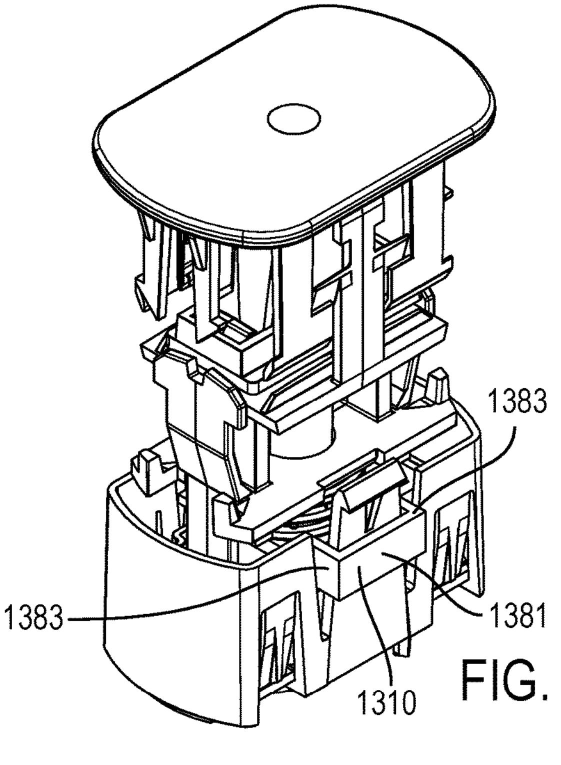
Figure 180D:
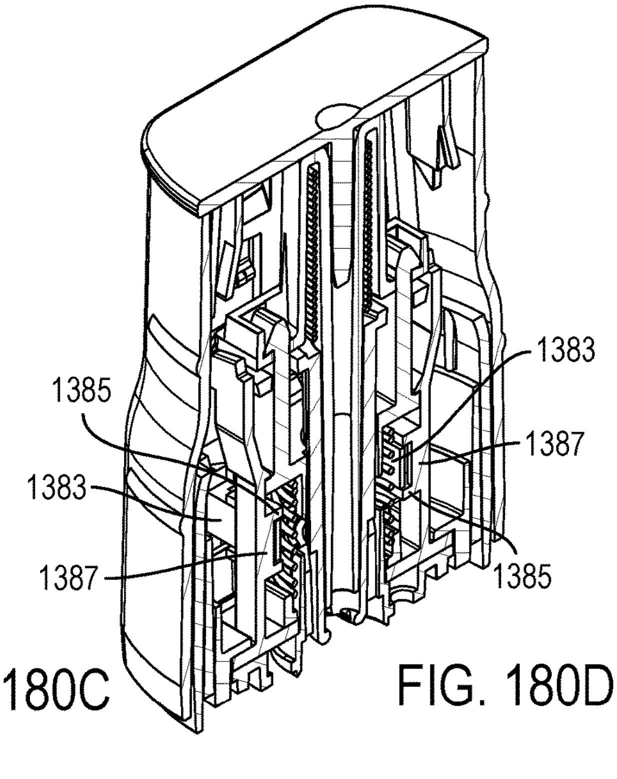
Figure 181A:
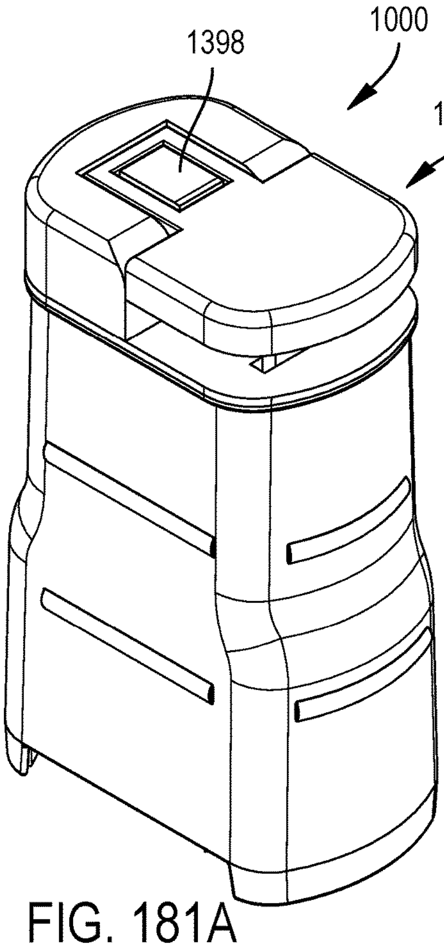
Figure 181B:
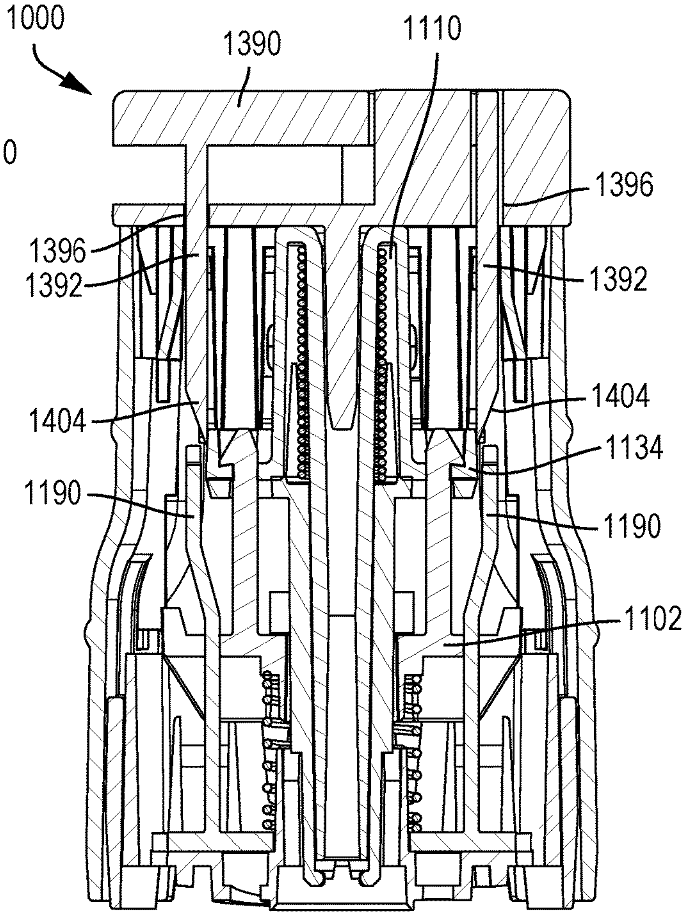
Figure 181C:
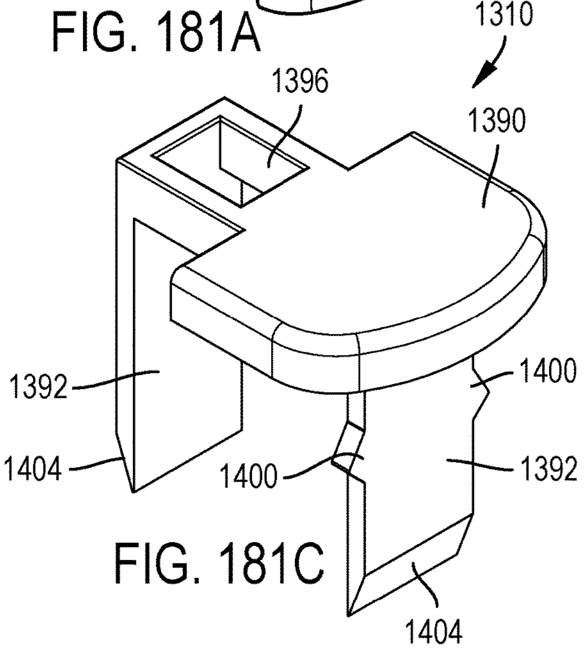
Figure 181D:
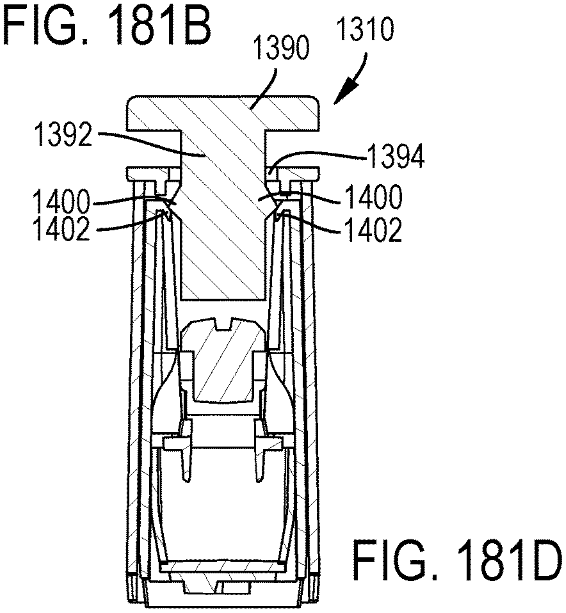
Figure 182A:
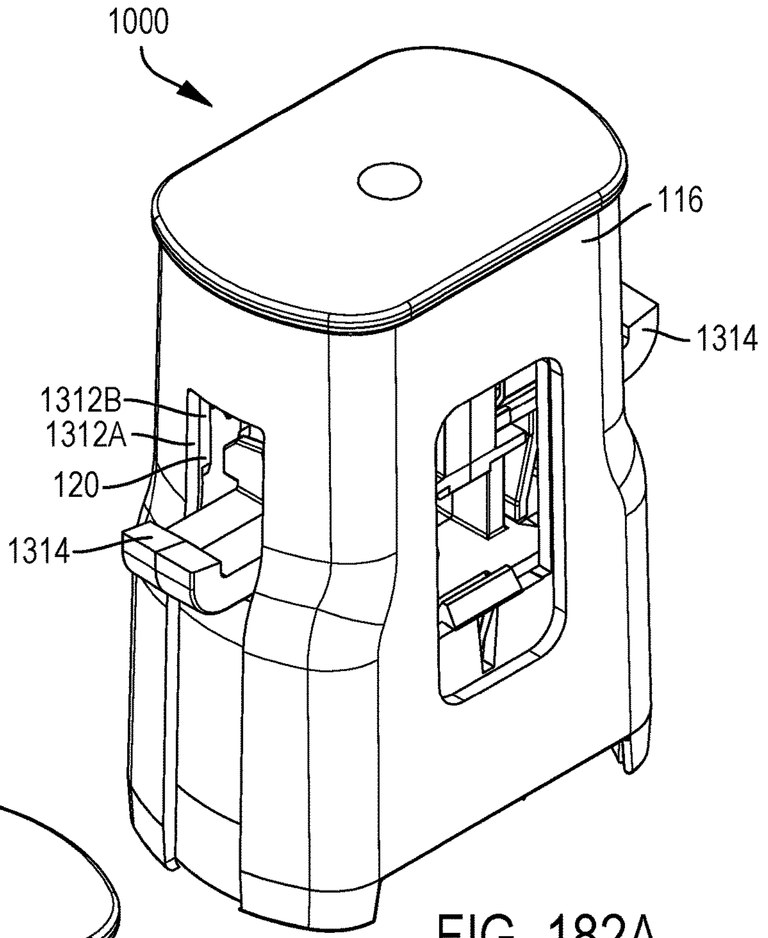
Figure 182B:
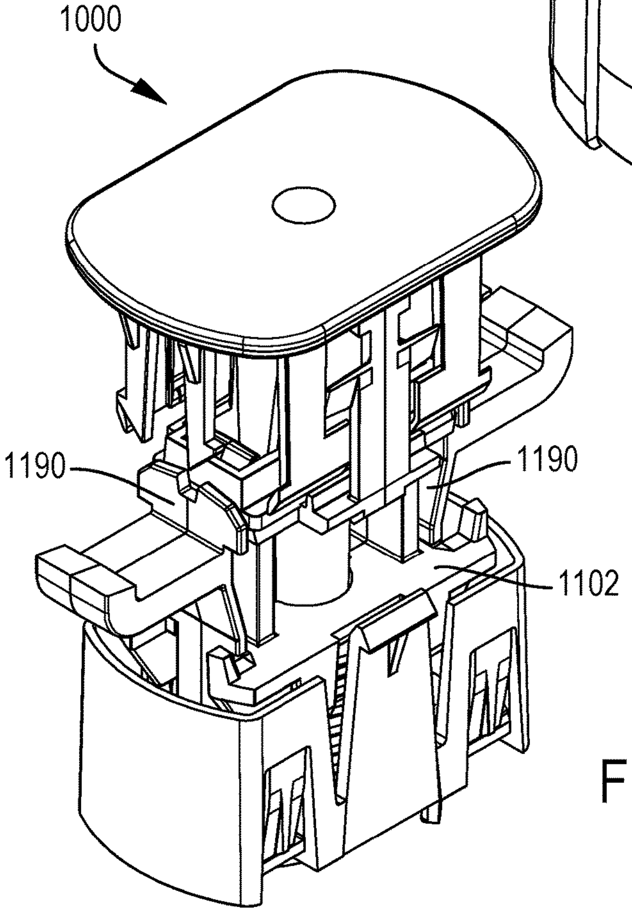
Figure 183A:
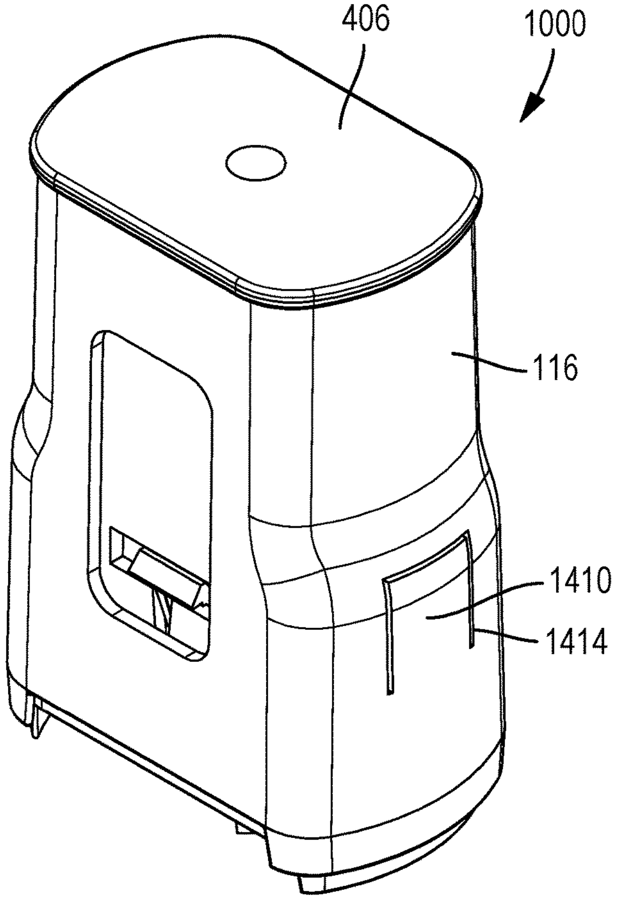
Figure 183B:
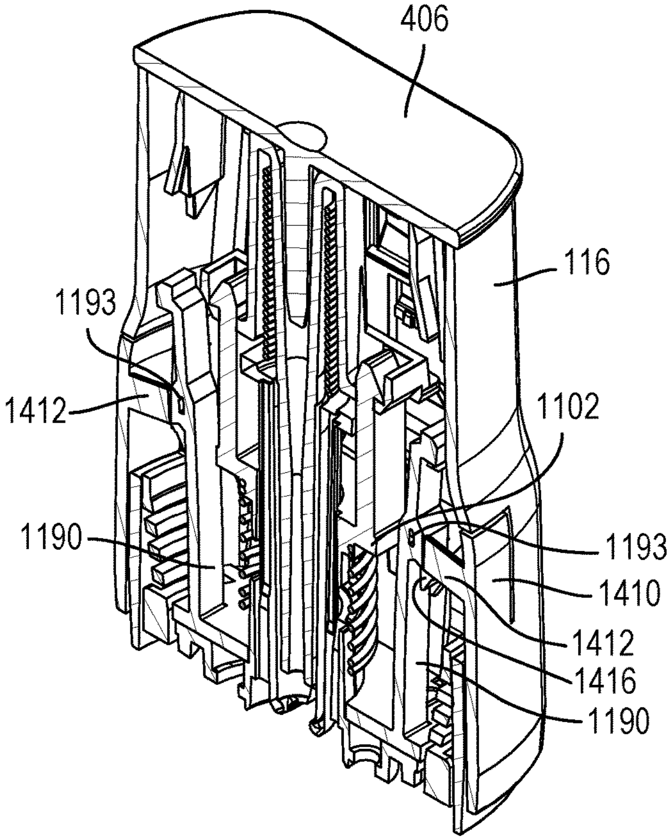
Figure 184:
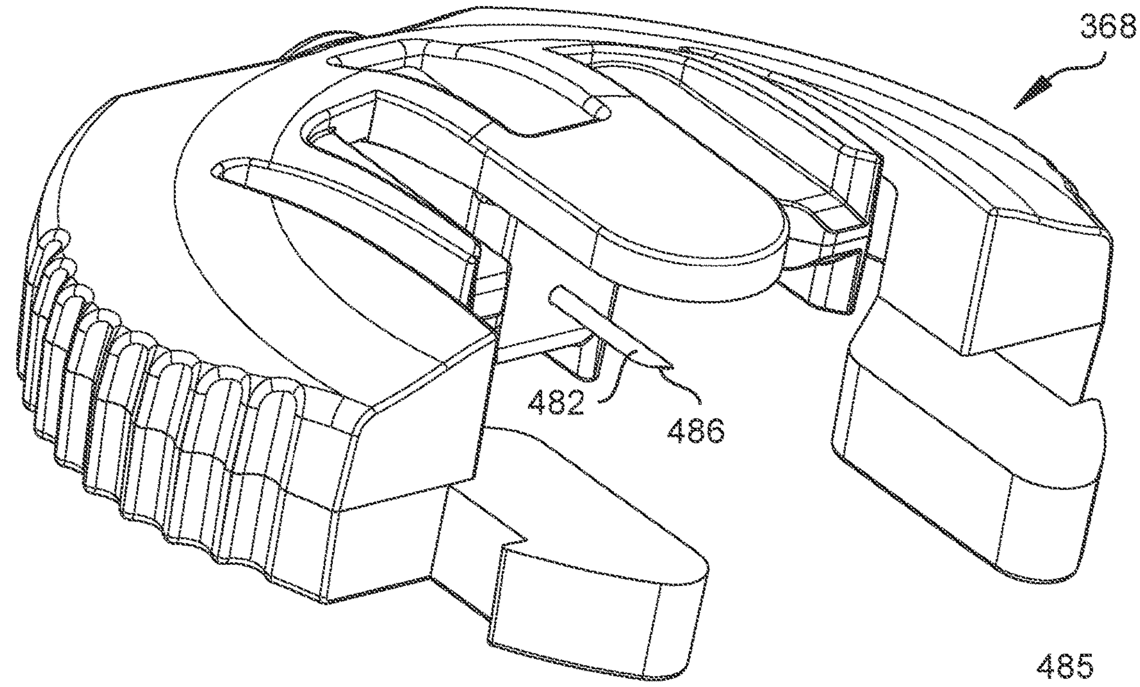
Figure 185B:
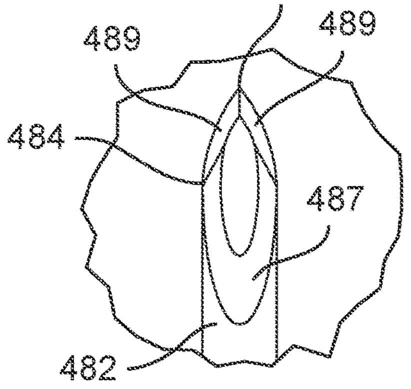
Figure 185A:
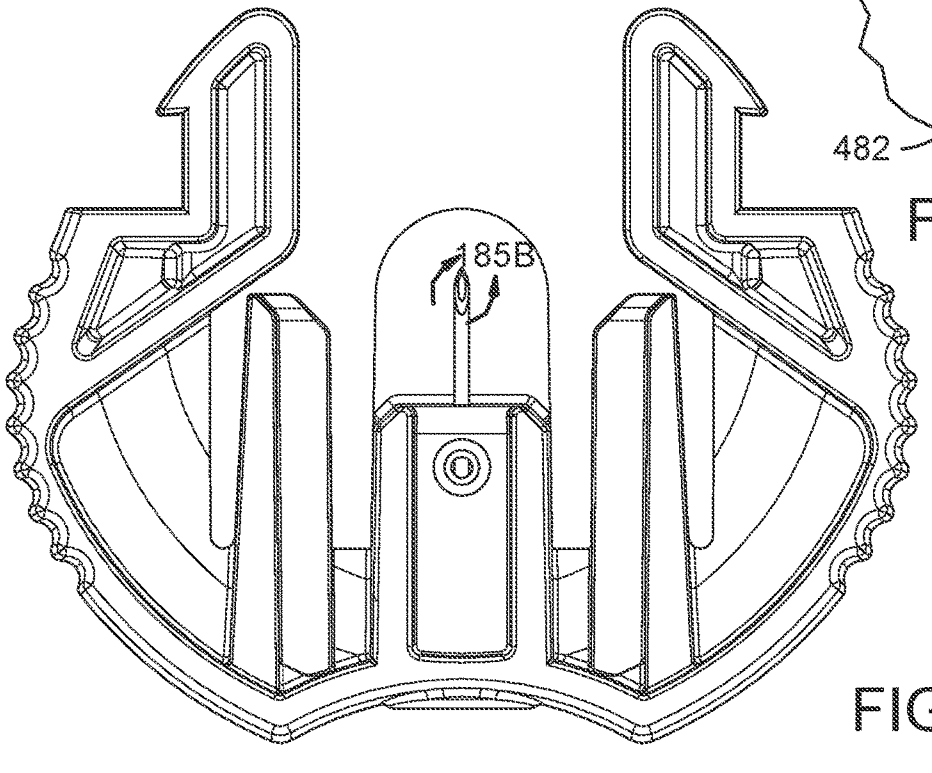
Figure 186:
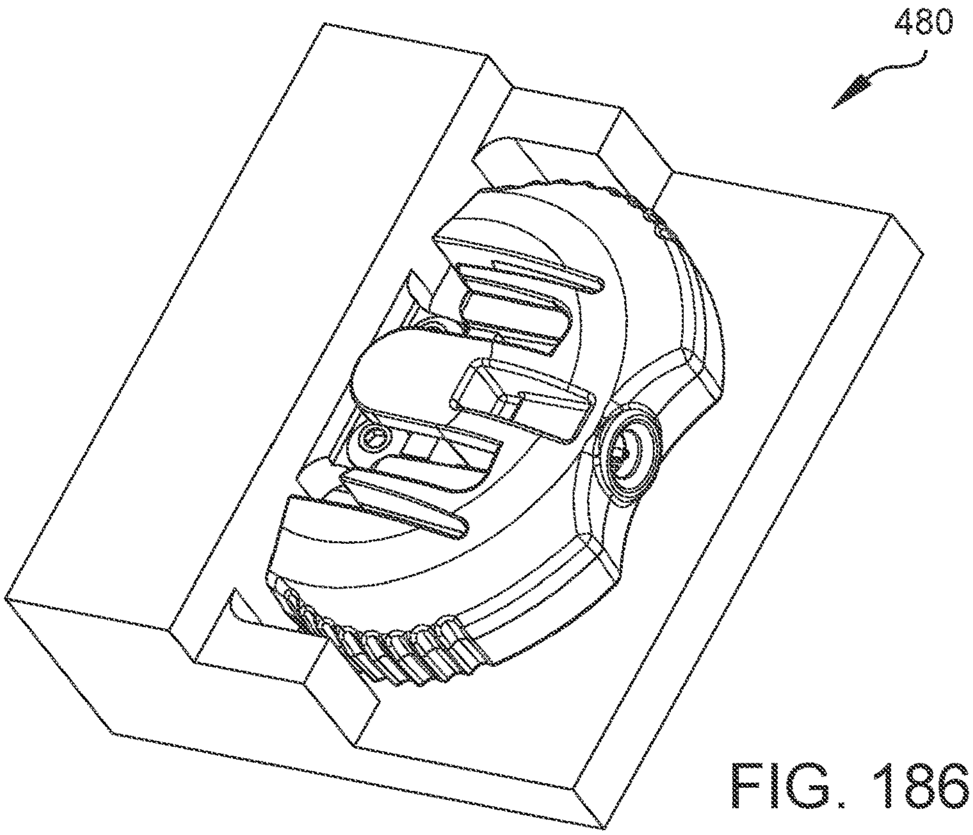
Figure 187:
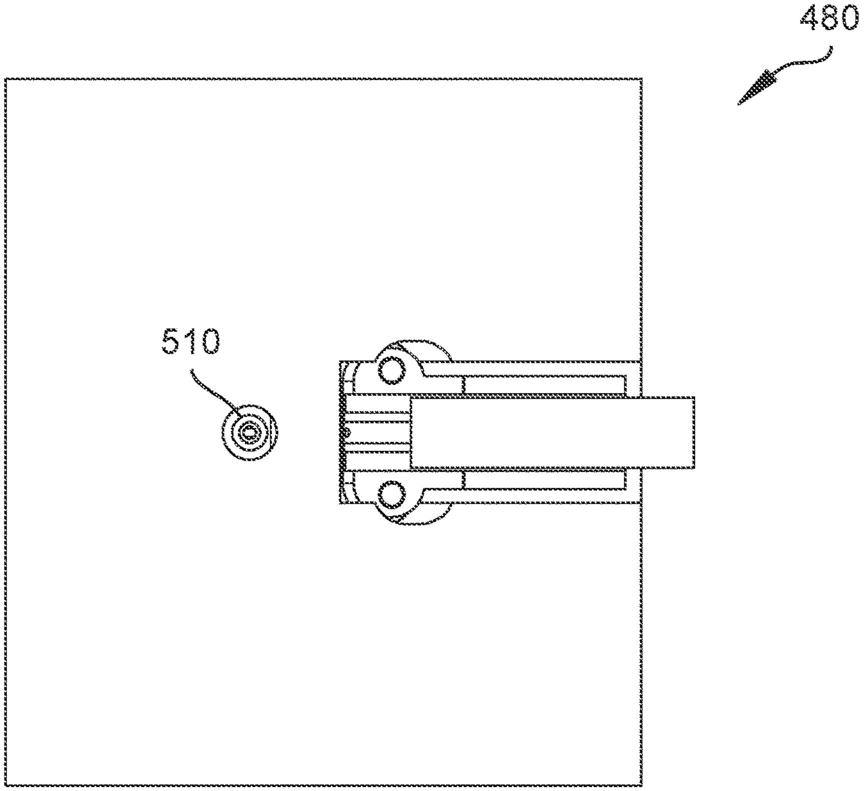
Figure 188:
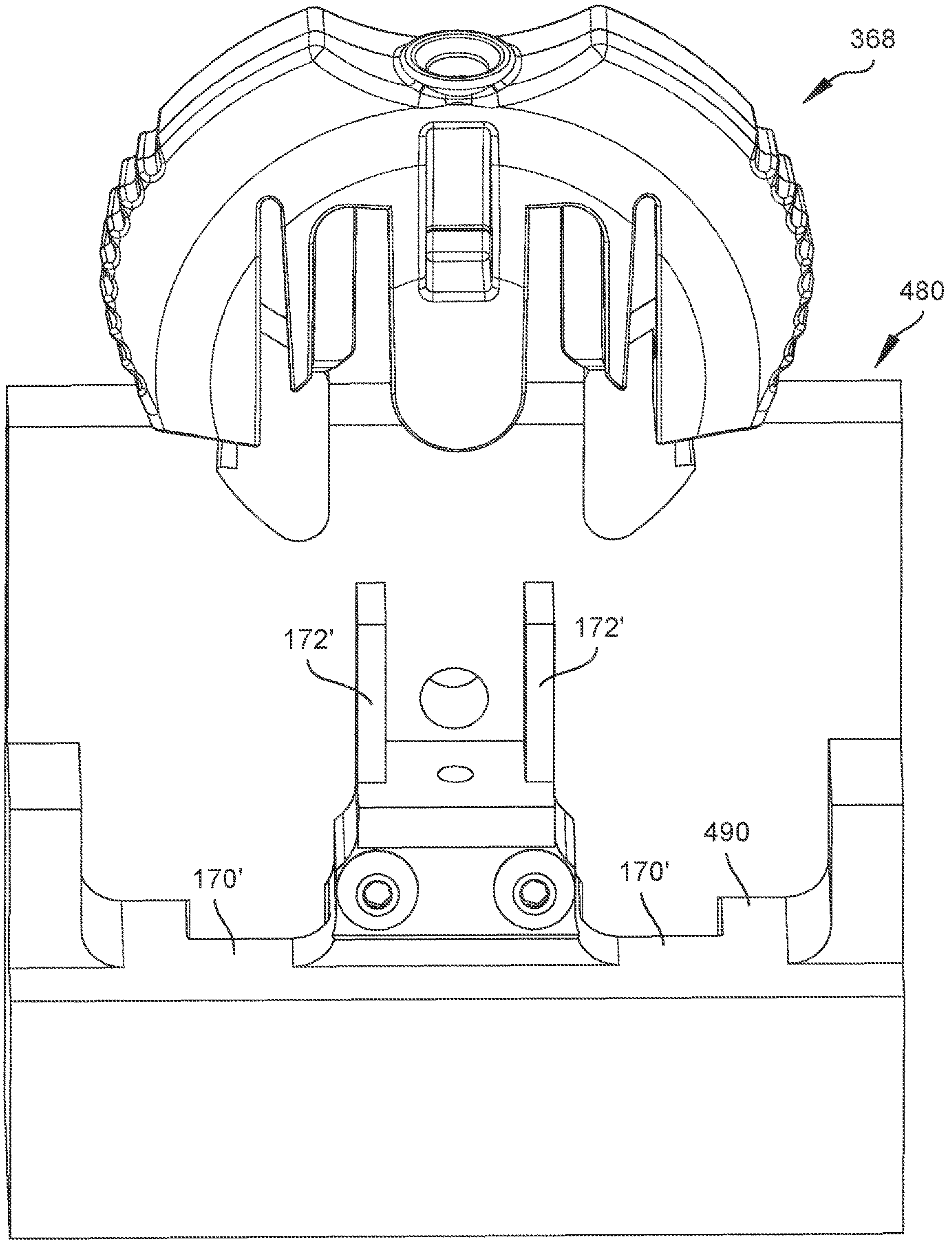
Figure 189:
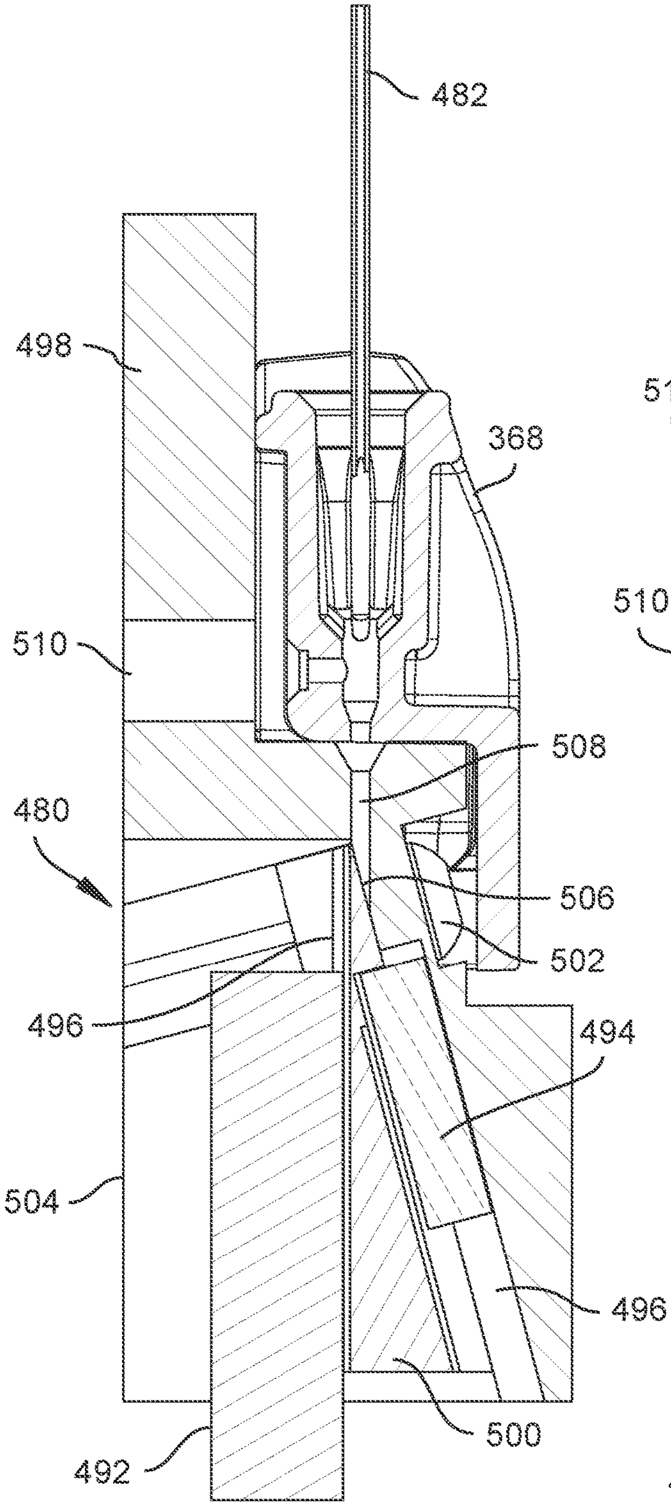
Figure 190:
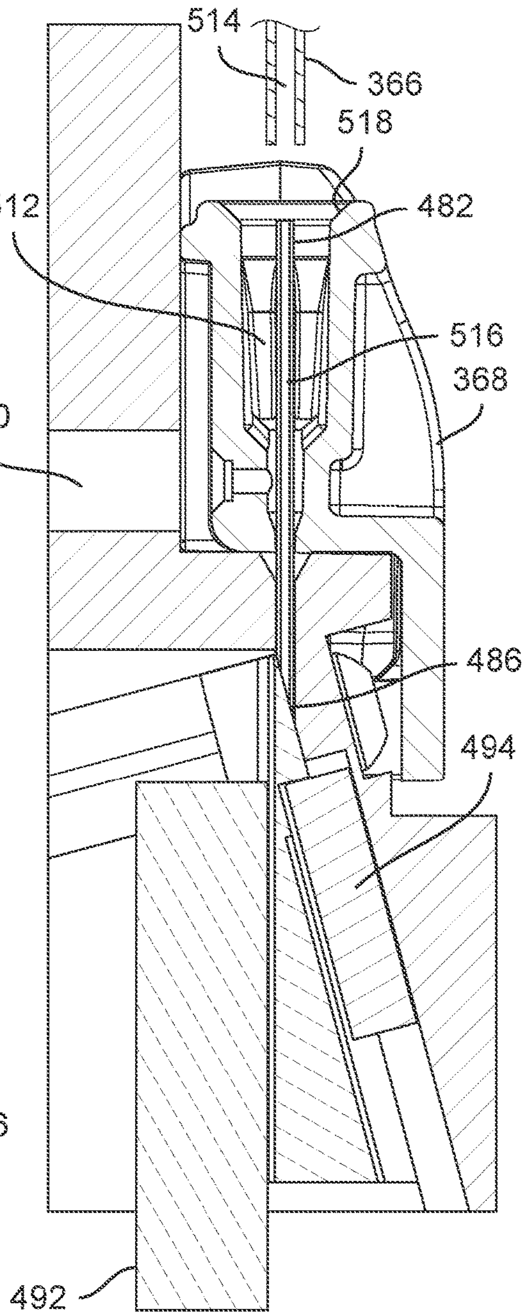
Figure 191:
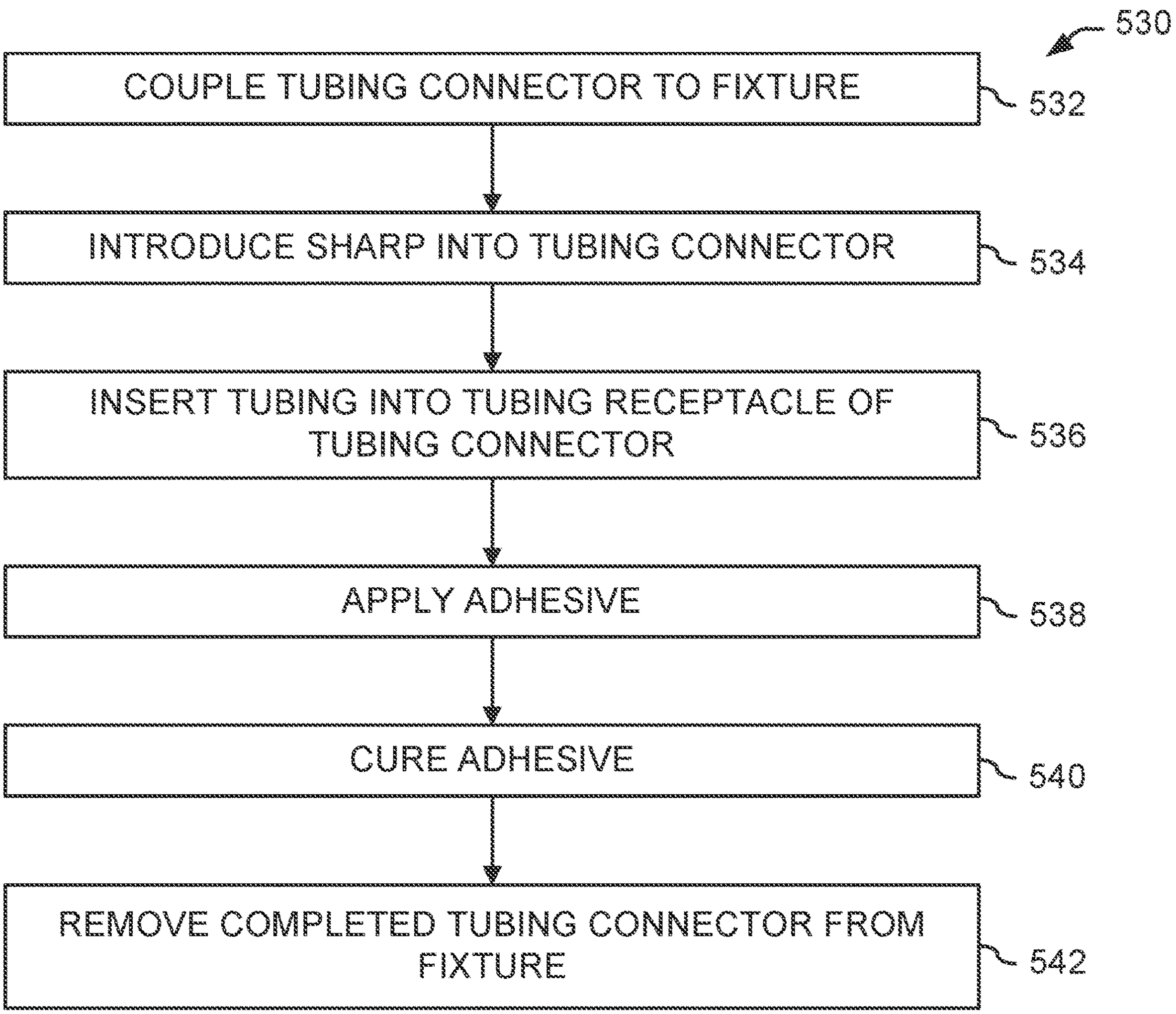

FIG. 95A depicts a top down view of the inserter assembly shown in FIG. 94;

FIG. 95B depicts a cross-sectional view taken at cut plane 89B-89B of FIG. 95A;

FIG. 95C depicts a perspective three-quarter section view taken along 95C-95C of FIG. 95A;

FIG. 96 depicts a perspective view of an example exterior housing of an inserter assembly including a button;

FIG. 97 depicts a perspective view of an example inserter assembly with an exterior housing of the inserter assembly removed;

FIG. 98 depicts a perspective view of an example inserter assembly with an exterior housing of the inserter assembly removed;

FIG. 99 depicts a detailed view of the indicated region of FIG. 98;

FIG. 100 depicts a perspective view of an exemplary sled which may be included in an inserter assembly;

FIG. 101 depicts a perspective view of an example exterior housing for an inserter assembly including a deformable region;

FIG. 102 depicts a perspective view of another example exterior housing for an inserter assembly including a protuberance on an interior face thereof;

FIG. 103 depicts a flowchart detailing a number of actions which may be used to assemble an inserter assembly;

FIG. 104 depicts a flowchart detailing a number of example actions which may be executed to place a patient care assembly with an example inserter assembly;

FIG. 105 depicts an exploded view of an example inserter assembly;

FIG. 106 depicts a cross-sectional view of an example inserter assembly;

FIG. 107 depicts a perspective view of an example lock member;

FIG. 108 depicts a top plan view of an example inserter assembly;

FIGS. 109A-109B depict cross-sectional view of an inserter assembly in a storage state;

FIG. 110, depicts a perspective view of an example sharp shuttle which may be included in certain example inserter assemblies;

FIGS. 111A-111B depict views of an example trigger body which may be included in certain example inserter assemblies;

FIG. 112 depicts a perspective view of an example bias member retainer which may be included in certain example inserter assemblies;

FIGS. 113A-113B depict views of an example care assembly base holder which may be included in certain example inserter assemblies;

FIGS. 114A-114B depict cross-sectional views of an example inserter assembly at a trigger state;

FIGS. 1115A-115B depict cross-sectional views of an example inserter assembly in a state where an example patient care assembly of the inserter assembly is released from the inserter assembly;

FIGS. 116A-116B depict cross-sectional views of an example inserter assembly in a retraction release state;

FIGS. 117A-117B depict cross-sectional views of an example inserter assembly in a retracted state;

FIG. 118 depicts a side view of an example inserter assembly and an example cartridge which may be coupled to the inserter assembly;

FIG. 119A depicts an exploded view of an example cartridge;

FIG. 119B depicts another exploded view of the example cartridge shown in FIG. 119A;

FIGS. 120A-120B depict exploded views of another example cartridge;

FIG. 121 depicts a perspective view of an exemplary infusion set base retainer;

FIG. 122 depicts a perspective view of an example interior housing of an example cartridge;

FIG. 123 depicts a perspective view of an example base retainer which may be included in certain example cartridges;

FIG. 124 depicts a perspective view of an example interior cartridge housing which may be included in certain example cartridges;

FIG. 125 depicts a bottom plan view of an example cartridge;

FIG. 126A depicts a cross sectional view taken at cut plane 126A-126A of FIG. 1125;

FIG. 126B depicts another cross sectional view taken at cut plane 126B-126B of FIG. 125;

FIG. 127 depicts a bottom plan view of an example cartridge;

FIG. 128A depicts a cross-sectional view taken at the indicated cut plane of FIG. 127;

FIG. 128B depicts a cross-sectional view taken at the indicated cut plane of FIG. 127;

FIG. 129A depicts an exploded view of an example inserter assembly which may be reusable;

FIG. 129B depicts another exploded view of the example inserter assembly in FIG. 129A;

FIG. 130A depicts an exploded view of another example inserter assembly which may be reusable;

FIG. 130B depicts another exploded view of the example inserter assembly in FIG. 130A;

FIGS. 131A-131B depict exploded view of another example inserter assembly which may be reusable;

FIG. 132 depicts an exploded view of an example casing which may be included in certain example inserter assemblies;

FIG. 133 depicts a cross sectional view of an example inserter assembly;

FIG. 134 depicts a view of an example inserter assembly exploded away from an example cartridge;

FIG. 135 depicts a detailed view of the indicated region of FIG. 134;

FIG. 136 depicts a detailed view of the indicated region of FIG. 134;

FIG. 137A depicts a bottom plan view of an example inserter assembly;

FIG. 137B depicts a detailed view of the exemplary receptacle body of the example inserter assembly shown in FIG. 137A;

FIG. 138A depicts a detailed view of a portion of an exemplary receptacle body which may be included in inserter assemblies described herein;

FIG. 138B depicts a plan view of an example receptacle body which may be included in inserter assemblies described herein;

FIG. 139 depicts a perspective view of an example sharp holder which may be included in example cartridges for inserter assemblies described herein;

FIG. 140A depicts an example insertion driver which may be included in example inserter assemblies described herein;

FIG. 140B depicts a view of a portion of an example sharp holder;

FIG. 141 depicts a perspective view of an example inserter assembly with a cartridge coupled thereto;

FIG. 142 depicts a cross sectional view of an example inserter assembly;

FIG. 143 depicts a perspective view of an example lock member;

FIG. 144 depicts a perspective view of a retraction latch body;

FIG. 145 depicts a perspective view of an example receptacle body for an inserter assembly which has integrally formed lock members;

FIG. 146 depicts a cross sectional view of an example inserter assembly;

FIG. 147 depicts a cross sectional view of an example inserter assembly;

FIG. 148 depicts a cross sectional view of an example inserter assembly in a storage state;

FIG. 149 depicts a view of an example resetting body coupled to an example retraction spring retainer;

FIG. 150 depicts a top plan view of an example interior housing of an example inserter assembly;

FIG. 151 depicts a cross sectional view taken along cut plane 151-151 of FIG. 150;

FIG. 152 depicts a cross sectional view of an example inserter assembly;

FIG. 153 depicts a cross sectional view of an example inserter assembly in a ready state;

FIG. 154 depicts a cross sectional view of an example inserter assembly;

FIG. 155 depicts a top plan view of an example inserter assembly;

FIG. 156 depicts a cross sectional view taken at 156-156 of FIG. 155;

FIG. 157A depicts a cross-sectional view of another exemplary inserter assembly in a storage state;

FIG. 157B depicts a perspective view of the inserter assembly of FIG. 157A with certain components removed;

FIG. 157C depicts a cross-sectional view of the inserter assembly of FIG. 157A in a ready state;

FIG. 157D depicts a perspective view of the inserter assembly of FIG. 157C with certain components removed;

FIG. 158 depicts a cross sectional perspective view of an example inserter assembly;

FIG. 159 depicts a detailed view of the indicated region of FIG. 158;

FIG. 160 depicts a perspective view of an example interior housing of an example inserter assembly;

FIG. 161 depicts a cross sectional perspective view of an example inserter assembly;

FIG. 162A depicts a cross sectional view of a retainer cap of an example inserter assembly;

FIG. 162B depicts a detailed view of the indicated region of FIG. 162A;

FIG. 163 depicts a side view of an example inserter assembly;

FIG. 164 depicts a sectional view of an example inserter assembly taken at the indicated cut plane of FIG. 163;

FIG. 165 depicts an example end cap which may be included as part of a casing for certain example inserter assemblies;

FIG. 166 depicts an example insertion driver which may be included in certain example inserter assemblies;

FIG. 167 depicts a cross sectional view of an example inserter assembly;

FIG. 168 depicts a cross sectional view of an example inserter assembly;

FIG. 169 depicts a cross sectional view of an example inserter assembly;

FIG. 170 depicts a cross sectional view of an example inserter assembly;

FIG. 171A depicts a cross sectional view of an example inserter assembly;

FIG. 171B depicts a cross sectional view of an example inserter assembly;

FIG. 172 depicts a cross sectional view of an example inserter assembly;

FIG. 173 depicts a perspective view of a cartridge coupled to an inserter assembly with an outer housing of the cartridge removed;

FIG. 174A depicts a perspective view of an example inserter assembly including a disarming lock;

FIG. 174B, depicts a cross-sectional view of the inserter assembly of FIG. 174A;

FIG. 175A depicts a perspective view of an example inserter assembly including an example disarming lock;

FIG. 175B, depicts a cross-sectional view of the inserter assembly of FIG. 175A;

FIGS. 176A-176C depict various views of another example inserter assembly including an example disarming lock;

FIGS. 177A-177B depict views of another example inserter assembly include an example disarming lock;

FIG. 178A depicts a perspective view of an example inserter assembly including an exemplary disarming actuator;

FIGS. 178B-178C depict views of the example inserter assembly of FIG. 178A which various components removed;

FIG. 178D depicts a perspective view of the example disarming actuator of the inserter assembly shown in FIG. 178A;

FIG. 179A depicts a perspective view of another example inserter assembly including an example disarming actuator;

FIG. 179B depicts a perspective view of the inserter assembly of FIG. 179A which certain components removed;

FIG. 180A depicts a perspective view of another example inserter assembly including an example disarming actuator;

FIG. 180B depicts a perspective view of the inserter assembly of FIG. 180A with a portion of the housing removed;

FIG. 180C depicts a perspective view of the inserter assembly of FIG. 180A with certain components removed;

FIG. 180D depicts a cross-sectional view of the inserter assembly of FIG. 181A;

FIG. 181A depicts a perspective view of another example inserter assembly including an example disarming actuator;

FIG. 181B depicts a cross-sectional view of the inserter assembly of FIG. 181A;

FIG. 181C depicts a perspective view of the disarming actuator of the inserter assembly depicted in FIG. 181A;

FIG. 181D depicts another cross-sectional view of the inserter assembly depicted in FIG. 181A;

FIG. 182A depicts a perspective view of another example embodiment of an inserter assembly including an example disarming actuator;

FIG. 182B depicts a perspective view of the example inserter assembly of FIG. 182A with certain components removed;

FIGS. 183A-183B depicts views of another example embodiment of an inserter assembly including an exemplary disarming actuator;

FIG. 184 depicts a perspective view of an example tubing connector;

FIG. 185A depicts a bottom up view of the tubing connector shown in FIG. 184;

FIG. 185B depicts a detailed view of a portion of FIG. 185A;

FIG. 186 depicts a perspective view of a tubing connector in place on a fixture;

FIG. 187 depicts a bottom up view of the fixture shown in FIG. 186;

FIG. 188 depicts a perspective view of a tubing connector aligned for installation into a fixture;

FIG. 189 depicts a cross-sectional view of a fixture with a tubing connector installed thereon and a sharp being introduced into the tubing connector;

FIG. 190 depicts a cross-sectional view of a fixture with a tubing connector installed thereon and a sharp in place and rotationally clocked to a prescribed position within the tubing connector; and FIG. 191 depicts a flowchart detailing a number of example actions which may be used to assembly of tubing connector.

DETAILED DESCRIPTION

In various embodiments, an infusion set may be used in conjunction with an infusion device, system, and related method as well as used in conjunction with an inserter assembly. In various embodiments, example infusion sets may be configured to be inserted into the subcutaneous layer of a user's skin and be fluidly connected to a fluid source. In various embodiments, example infusion sets may be fluidly connected to a length of tubing and/or to an infusion device. Infusion devices include any infusion pump and may include, but are not limited to, the various infusion devices described in U.S. patent application Ser. No. 15/434,906, Filed Feb. 16, 2017 and entitled Infusion Set and Inserter Assembly, now U.S. Pat. No. 10,792,419 issued Oct. 6, 2020, U.S. patent application Ser. No. 13/788,260, filed Mar. 7, 2013 and entitled Infusion Pump Assembly, now U.S. Publication No. US-2014-0107579, published Apr. 17, 2014; U.S. Pat. No. 8,491,570, issued Jul. 23, 2013 and entitled Infusion Pump Assembly; U.S. Pat. No. 8,414,522, issued Apr. 9, 2013 and entitled Fluid Delivery Systems and Methods; U.S. Pat. No. 8,262,616, issued Sep. 11, 2012 and entitled Infusion Pump Assembly; and U.S. Pat. No. 7,306,578, issued Dec. 11, 2007 and entitled Loading Mechanism for Infusion Pump; all of which are hereby incorporated herein by reference in their entireties.

Various embodiments are described and shown herein. Each embodiment of each element of each device may be used in any other device embodiment. Each embodiment of the inserter assembly may be used with any embodiment of an infusion set.

Figure 1A:
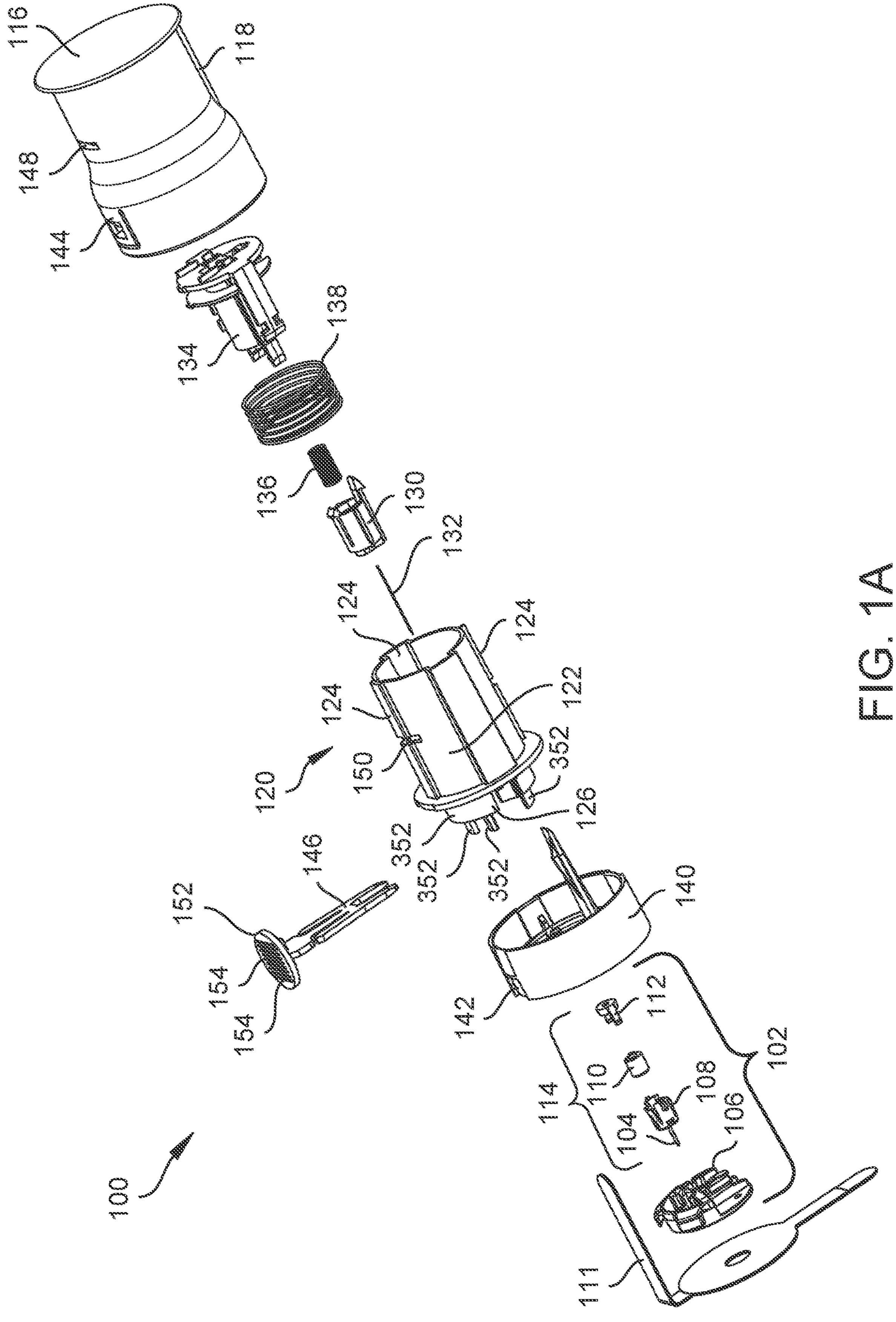
FIG. 1A depicts an exploded view of an exemplary inserter assembly.

FIG. 1A depicts an exploded view of an embodiment of an example inserter assembly 100. Inserter assemblies such as inserter assembly 100 may be used to place an infusion set 102 onto an infusion site of a patient and introduce a cannula 104 of an infusion set 102 into the patient's body. In some embodiments, inserter assemblies 100 may be used to place other patient care assemblies onto the body of a patient. For example, certain inserter assemblies 100 may be operated to place physiological monitors into working relationship with a patient's body. In certain examples, an analyte sensor may be placed onto a patient with an inserter assembly 100. Infusion sets 102 may be used to supply a drug from an infusion pump to a particular location (e.g. subcutaneously) within a patient's body.

Drugs or other agents supplied may include drugs or agents which are generally supplied as a continuous or substantially continuous infusion though other drugs or agents may also be used. This may include small molecules, biologicals, recombinantly produced pharmaceuticals, and analogs thereof. Hormones such as insulin or glucagon may be administered through an infusion set 102. Other drugs such as peptides (e.g. amylin) may be provided. Drugs affecting the cardiovascular system may also be provided via an infusion set 102. As another example, vasodilators such as treprostinil may be delivered to a patient with an infusion set 102. Chemotherapy drugs may additionally be used. Exemplary physiological monitors may include blood glucose monitors such as continuous glucose monitors. Any other type of body analyte monitor such as interstitial fluid analyte monitors may also be used.

In some embodiments, inserter assemblies 100 may place an infusion set 102 on a site as well as at least partially assemble the infusion set 102. For example, the infusion set 102 may be provided as a number of portions (e.g. separate components, subassemblies, or combinations thereof) within an inserter assembly 100. Actuation of the inserter assembly 100 may cause each portion of the infusion set 102 to be coupled together to complete the assembly of an infusion set 102. For example, assemblage of an infusion set 102 may occur as an initial stage of the actuation of the inserter assembly 100 or may occur as part of an insertion stage of inserter assembly 100 actuation which results in the cannula 104 being introduced into the patient.

As shown in the exploded view in FIG. 1A, the inserter assembly 100 contains components of an infusion set 102. The inserter assembly 100 may not be provided with an assembled infusion set 102 installed therein. The infusion set 102 may include a first portion and a second portion which are separate from one another, but coupled together during actuation of the inserter assembly 100 to form the infusion set 102. The first portion may include a base 106 which may be applied to the skin of a patient and may couple to a fluid pathway (e.g. via a terminal connector on the pathway) which is part of or extends from an infusion pump. Example infusion pumps may include any one or more disclosed in the various references incorporated by reference above, though in various embodiments, any infusion pump may be used. The base 106 may be provided with an adhesive (e.g. adhesive pad) which retains the infusion set 102 in place on the patient. The adhesive may be covered by an adhesive backing 111, liner, or film which is removed to expose the adhesive before use.

The second portion of the infusion set 102 may be a subassembly 114 of two or more components of the infusion set 102. The second portion may include a cannula 104, septum housing 108, septum 110, and septum retainer 112 for example. In some embodiments, though not all, one or more components of the second portion may be provided integrated to one another such that the components are manufactured as a single, monolithic part during, for example, a single molding operation. Any attachment, fastening, bonding, fitting together, or other assembly of these parts after manufacture may thus be avoided. The cannula 104 and the septum housing 108 are shown as such a single continuous unitary part in the example embodiment. This cannulated housing may be a molded part which is constructed of a single material such as, PTFE, Teflon, polypropylene, etc. for example. Certain components may also be joined to one another during manufacture. For example, the septum retainer 112 may be over molded onto the septum 110 or vice versa.

As shown in FIG. 1A, an insertion assembly 100 may include a number of additional components. For example, the insertion assembly 100 may include an exterior housing 116. The exterior housing 116 may enclose various components of the inserter assembly 100 and serve as the portion of the inserter assembly 100 which the user grips during operation. The exterior housing 116 in the example embodiment has a cross sectional shape which is round, though other embodiments may have different shapes such as any type of polygonal shape. In certain examples described elsewhere in the specification, a rectangular cross-sectional shape which easily fits within a pocket may be used. The cross sectional area in the example embodiment also varies with the bottom section (that most proximal the skin when in use) of the exterior housing 116 being wider than the top. The exterior housing 116 may include various ergonomic features which facilitate grasping of the inserter assembly 100 in which it is included. For example, texturing or a finger or thumb depression may be included on the outer surface of the exterior housing 116. Alternatively or additionally, a region of the external housing 116 may be thinner in width than the remaining portion of the external housing 116. This may make firm grasping of the inserter assembly 100 easier.

The exterior housing 116 may include a marking, tab, embossed section, recessed section, textured section, protuberance, color coding, appliqué, or other indicia which serves to indicate position and/or orientation of the infusion set 102 within the inserter assembly 100. For example, the exterior housing 116 in FIG. 1A includes a raised rib 118 on the outer surface of the exterior housing 116. The raised rib 118 in the example extends substantially parallel to a direction of elongation of the exterior housing 116, but may be disposed on any or partially on any exterior face(s) of the exterior housing 116 in alternative embodiments. The rib 118 is disposed to indicate the orientation of a portion of the infusion set 102 to which a fluid conduit from the infusion device may be connected. This may allow a user to position the inserter assembly 100 in a desired orientation so as to allow for a run of infusion tubing to be routed in a planned manner once the infusion set 102 is attached to the user.

An inserter assembly 100 may also include an interior housing 120. The interior housing 120 may be disposed inside of the external housing 116 when the inserter assembly 100 is assembled. Various interior housings 120 may have at least one segment which is asymmetrically designed. In the exemplary embodiment shown in FIG. 1A, the interior housing 120 includes a railed segment 122 which includes a number of rails 124. The rails 124 extend substantially parallel to one another and may be of at least two different widths. The interior face of the exterior housing 116 may include tracks or slots which cooperate with the rails 124. Due to the differing rail 124 widths, a keyed arrangement may be provided such that the interior housing 120 may only be nested within the exterior housing 116 in a prescribed orientation. The interaction of the rails 124 within the tracks may also inhibit rotation of the interior housing 120 and exterior housing 116 relative to the other. Though rails 124 are shown on the interior housing 120 in the example, the rails 124 may instead be present on the interior face of the exterior housing 116 in some embodiments. In such examples, the tracks may be located on the interior housing 120. Additionally, as shown, at least some of the rails 124 may also form channels or tracks in the interior face of the interior housing 120.

In other embodiments, a rail and track type arrangement may not be used. One of the interior housing 120 or exterior housing 116 may include at least one projection such as a tab which interfaces with a recess or guide in the other. This may similarly provide a keyed engagement and prevent relative rotation. In other embodiments, the cross sectional shape of the interior housing 120 and external housing 116 may only allow for the parts to be placed together in one orientation and may inhibit any relative rotation. For example, the cross section may be tear drop shaped or various asymmetric polygonal shapes.

The interior housing 120 may also include an infusion set base interfacing segment 126. This base interfacing segment 126 may include a number of projections 352 which may ensure that the base 106 may only be inserted into the inserter assembly 100 in a desired orientation. The projections 352 may also optionally aid in retention of the base 106 within the inserter assembly 100 and some friction between the projections 352 and surfaces of the base 106 may be present when the base 106 is installed in the inserter assembly 100. For example, the base 106 may be press fit into the projections 352. The tightness of the fit may be minimal so as to allow removal of the base 106 from the base interfacing segment 126 with little force. The projections 352 may also aid in maintaining the base 106 in a level orientation within the base interfacing segment 126.

An inserter assembly 100 may further include a sharp holder 130. The sharp holder 130 may retain an insertion sharp 132 thereon. The insertion sharp 132 may be glued or otherwise bonded into the sharp holder 130 so as to be fixedly located relative to the sharp holder 130. Any suitable type of sharp 132 may be used. For example, the sharp 132 may be a hollow or solid needle, stylet, or other pointed member which may be made of a metal material such as steel. A sharp retractor 134 and a number of springs 136, 138 may also be included in an inserter assembly 100. A retainer base 140 may serve to couple to a bottom portion of the inserter assembly 100 to hold the various components in place within the inserter assembly 100. In the example, the retainer base 140 includes retaining interfaces 142 which may snap into cantilevered retainer arms 144 included on the exterior housing 116. Other couplings are also possible such as a bayonet mount, interference fit, snap fit, adhesive, glue, threads, solvent bonding, welding, etc. When coupled together, the exterior housing 116 and retainer base 140 may form a casing of the inserter assembly 100.

As will be further described later in the specification, a latch arrangement may be included in the inserter assembly 100 and may hold the sharp holder 130 and sharp retractor 134 in place prior to and during portions of the inserter assembly 100 actuation. The latch arrangement may include a number of catches. When free to move, the springs 136, 138, may displace the sharp holder 130 and sharp retractor 134 as well as components retained thereon to complete the insertion of the cannula 104 into the patient and attach the infusion set 102 onto an infusion site. Retraction of the sharp 132 into the inserter assembly 100 may also occur as part of the actuation so as to displace the sharp 132 to a point where it is pulled out of the infusion set 102 and protected from contact with a user.

When unpacked by a user, an insertion assembly 100 may be provided with a lock member 146. The lock member 146 may be inserted through fenestrations 148, 150 in the exterior housing 116 and interior housing 120 respectively so as to span the width of at least a portion the interior housing 120. While present in the inserter assembly 100, the lock member 146 may prevent actuation of the inserter assembly 100. Example lock members 146 may mechanically prevent displacement of one or more component of the inserter assembly 100 which initiates the actuation action of the inserter assembly 100. In the example embodiment, the lock member 146 includes a flange 152 which may be grasped by a user during removal of the lock member 146.

As shown, a lock member 146 may include a number of raised sections 154 (e.g. ridges or bumps) thereon. These raised sections 154 may provide material which may help to bond to a portion of the adhesive backing 111 during a welding operation. As a result, the lock member 146 may be attached to the adhesive backing 111 such that a user would have a visual cue in the event that one of the lock member 146 or adhesive backing 111 is removed while the other is still in place. This may help to encourage removal of both components prior to an attempt to actuate the inserter assembly 100 making the device more intuitive.

Figure 1B:
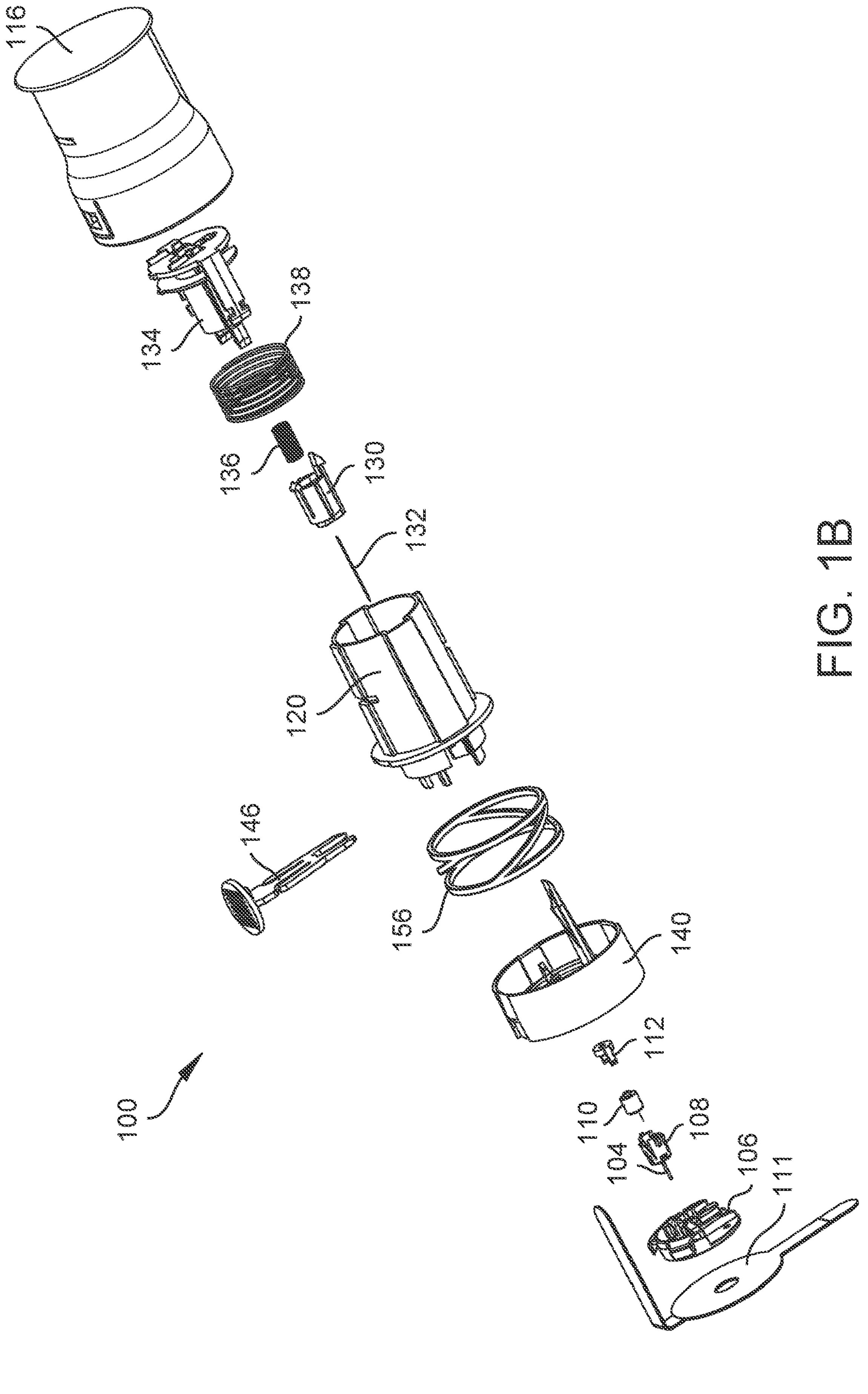
FIG. 1B depicts an exploded view of another exemplary inserter assembly.
Figure 1C:
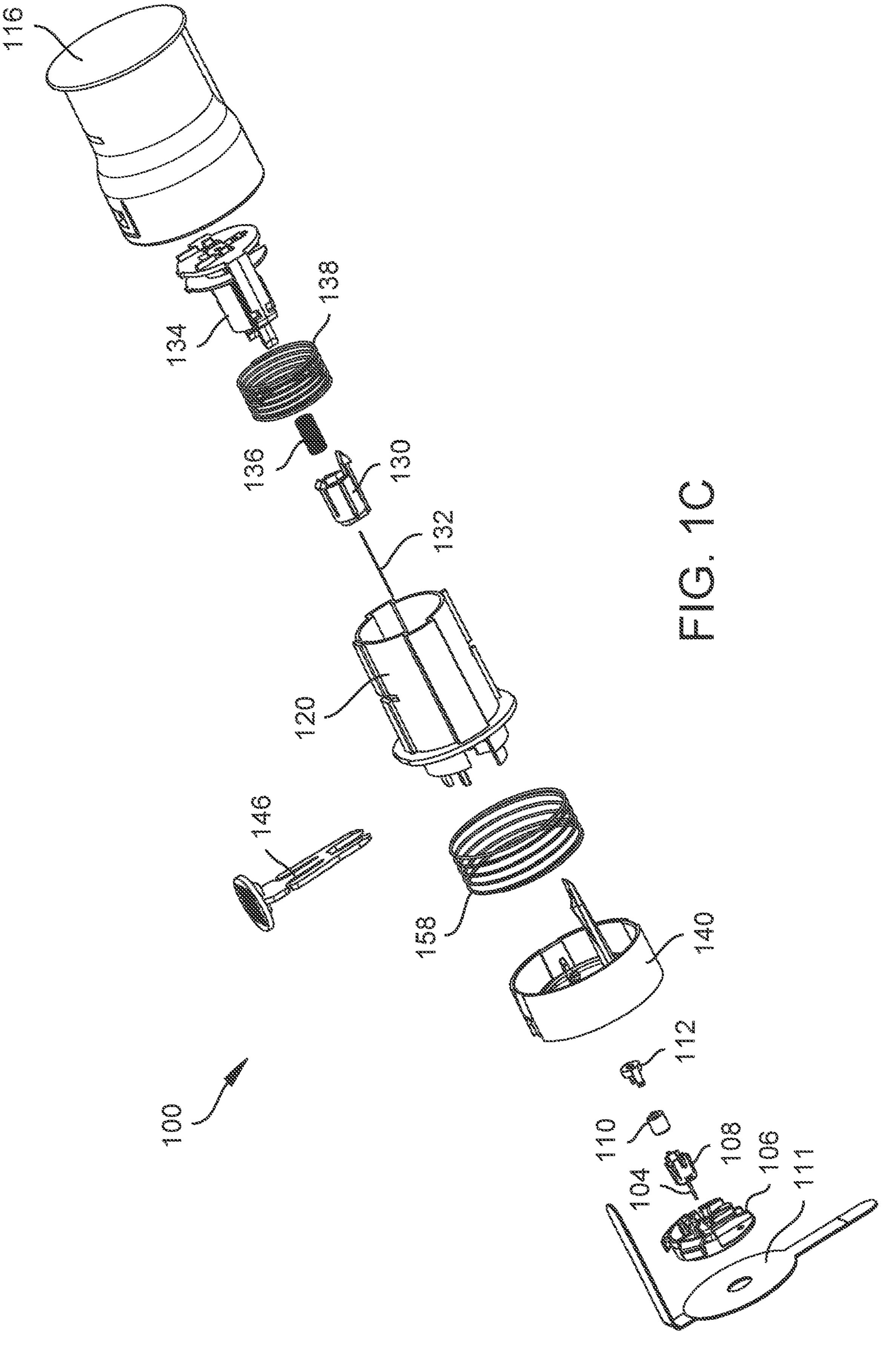
FIG. 1C depicts an exploded view of another exemplary inserter assembly.

Referring now also to FIG. 1B and FIG. 1C, in some examples, an inserter assembly 100 may include one or more additional springs 156, 158. As shown in FIG. 1C, the additional spring 158 may be a conventional metallic spring. Alternatively, and as depicted in FIG. 1B, a plastic spring 156 may be used. In certain embodiments, the plastic spring 156 may be injection molded, cut out of a tube of material (e.g. via laser cut), made via a material additive process, or any other suitable method. Such springs 156, 158 will be further described later in the specification.

Figure 2:
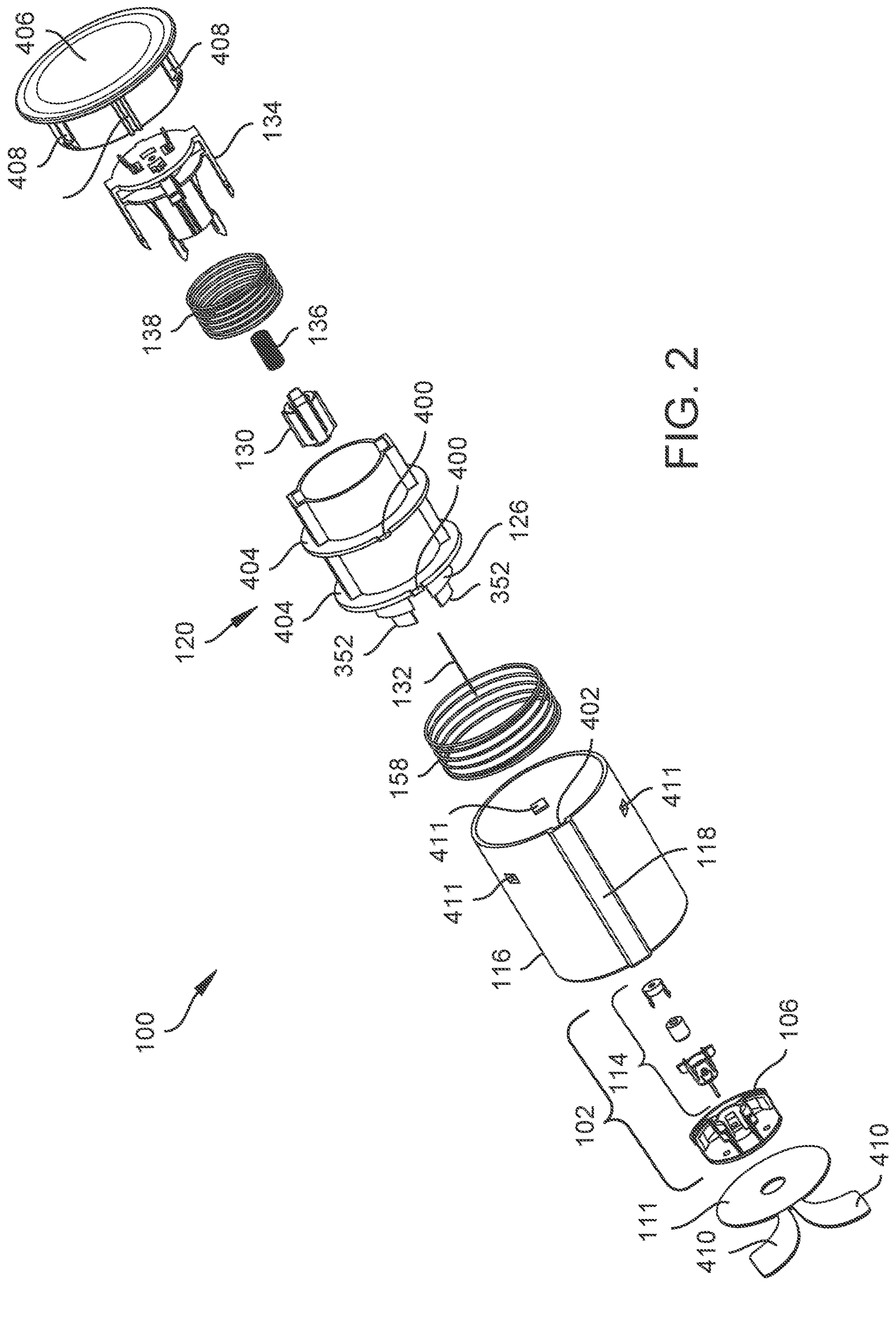
FIG. 2 depicts an exploded view of another exemplary inserter assembly.

Referring now also to FIG. 2, another inserter assembly 100 is depicted. The insertion assembly 100 in FIG. 2 includes an exterior housing 116 which may enclose various components of the inserter assembly 100 and serve as the portion of the inserter assembly 100 which the user grips during operation. Though depicted as round, the exterior housing 116 may have other cross-sectional shapes or various ergonomic features as described above. The exterior housing 116 includes a position indicium in the form of a raised rib 118 extending off the outer surface of the exterior housing 116. The rib 118 may be disposed to indicate the orientation a portion of an infusion set 102 contained within the inserter assembly 100.

An interior housing 120 is also included in FIG. 2 and may be keyed so as to ensure it is assembled into the inserter assembly 100 in a prescribed orientation and prevent relative rotation. As in FIG. 2, the interior housing 120 may be made asymmetric by the inclusion of at least one projection 400 such as a tab which interfaces with a recess or guide 402 in the exterior housing 116. In the example, the guide 402 is provided by a channel formed by the raised rib 118 on the interior face of the exterior housing 116. The projections 400 on the inserter assembly 100 in FIG. 2 are included on spacing plates 404 which ensure that the interior housing 120 fits snuggly within the exterior housing 116. An infusion set base interfacing segment 126 is also included on the example interior housing shown in FIG. 2.

A sharp holder 130 which may be affixed to an insertion sharp 132 is shown in the example embodiment. Additionally, a sharp retractor 134 and a number of springs 136, 138 may also be included. A retainer cap 406 may serve to couple to a top portion of the inserter assembly 100 to hold the various components in place within the inserter assembly 100. In the example, the retainer cap 406 includes cantilevered retainer arms 408 which may snap into retaining interfaces 411 included on the exterior housing 116. Other couplings are also possible such as a bayonet mount, interference fit, snap fit, adhesive, glue, threads, solvent bonding, welding, etc. When coupled together, the exterior housing 116 and retainer cap 406 may form a casing of the inserter assembly 100.

As described in detail elsewhere herein, a latch arrangement may be included in the inserter assembly 100 may hold the sharp holder 130 and sharp retractor 134 in place prior to and during portions of the inserter assembly 100 actuation. The latch arrangement may include a number of catches. When free to move, the springs 136, 138, may displace the sharp holder 130 and sharp retractor 134 as well as components retained thereon to complete the insertion of the cannula 104 into the patient and attach the infusion set 102 onto an infusion site. Retraction of the sharp 132 into the inserter assembly 100 may also occur as part of the actuation.

In the example embodiment depicted in FIG. 2, the inserter assembly 100 does not include a lock member 146. In various embodiments, however, fenestrations similar to fenestrations 148, 150 in FIGS. 1A-1C in the exterior housing 116 and interior housing 120 may be included to accommodate a lock member 146. In these embodiments, the adhesive backing 111 could be bonded onto the lock member 146. In the example embodiment, however, the adhesive backing 111 includes two pull tabs 410 (though any suitable number may be included). These pull tabs 410 may be grasped by a user to facilitate removal of the adhesive backing 111. The additional spring 158 depicted in FIG. 1C is also included in FIG. 2.

Figure 3:
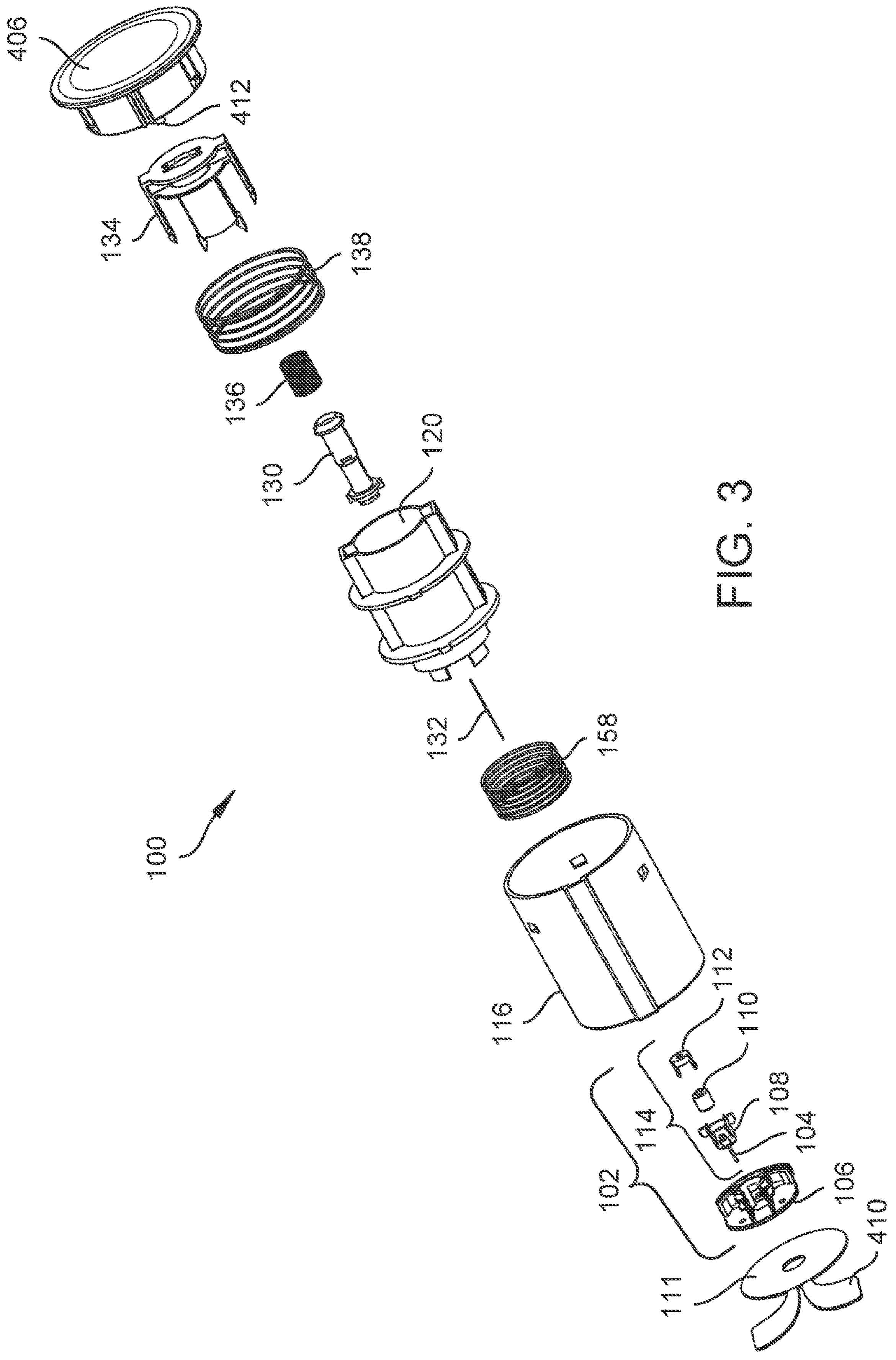
FIG. 3 depicts an exploded view of another exemplary inserter assembly.

Referring now to FIG. 3, another example embodiment of an inserter assembly 100 is depicted. As shown, the inserter assembly 100 in FIG. 3 includes an exterior housing 116 and interior housing 120 similar to those shown in the example depicted in FIG. 2. The sharp holder 130 and sharp retractor 134 differ from those depicted in FIGS. 1A-2. A retainer cap 406 may serve to couple to a top portion of the inserter assembly 100 to hold the various components in place within the inserter assembly 100 and form a casing of the inserter assembly 100. The retainer cap 406 couples to the exterior housing 116 in a similar manner to the embodiment described in relation to FIG. 2, however, any other type of coupling may be used in alternative embodiments. The retainer cap 406 also includes a projection 412 which may fit within a portion of the sharp holder 130 when the inserter assembly 100 is fully assembled and ready for actuation.

As described in detail elsewhere herein, a latch arrangement may be included in the inserter assembly 100 and may hold the sharp holder 130 and sharp retractor 134 in place prior to and during portions of the inserter assembly 100 actuation. The latch arrangement may include a number of catches. When free to move, the springs 136, 138, may displace the sharp holder 130 and sharp retractor 134 as well as components retained thereon to complete the insertion of the cannula 104 into the patient and attach the infusion set 102 onto an infusion site. Retraction of the sharp 132 into the inserter assembly 100 may also occur as part of the actuation.

In the example embodiment depicted in FIG. 3, the inserter assembly 100 does not include a lock member 146. However, in various embodiments, fenestrations similar to fenestrations 148, 150 in FIGS. 1A-1C may be included in the exterior housing 116 and interior housing 120 to accommodate a lock member 146. In these various embodiments, the adhesive backing 111 may be bonded onto the lock member 146. In the example embodiment, however, the adhesive backing 111 includes two pull tabs 410. These pull tabs 410 may be grasped by a user to facilitate removal of the adhesive backing 111. The additional spring 158 depicted in FIG. 1C is also included in FIG. 3

Figure 4A:
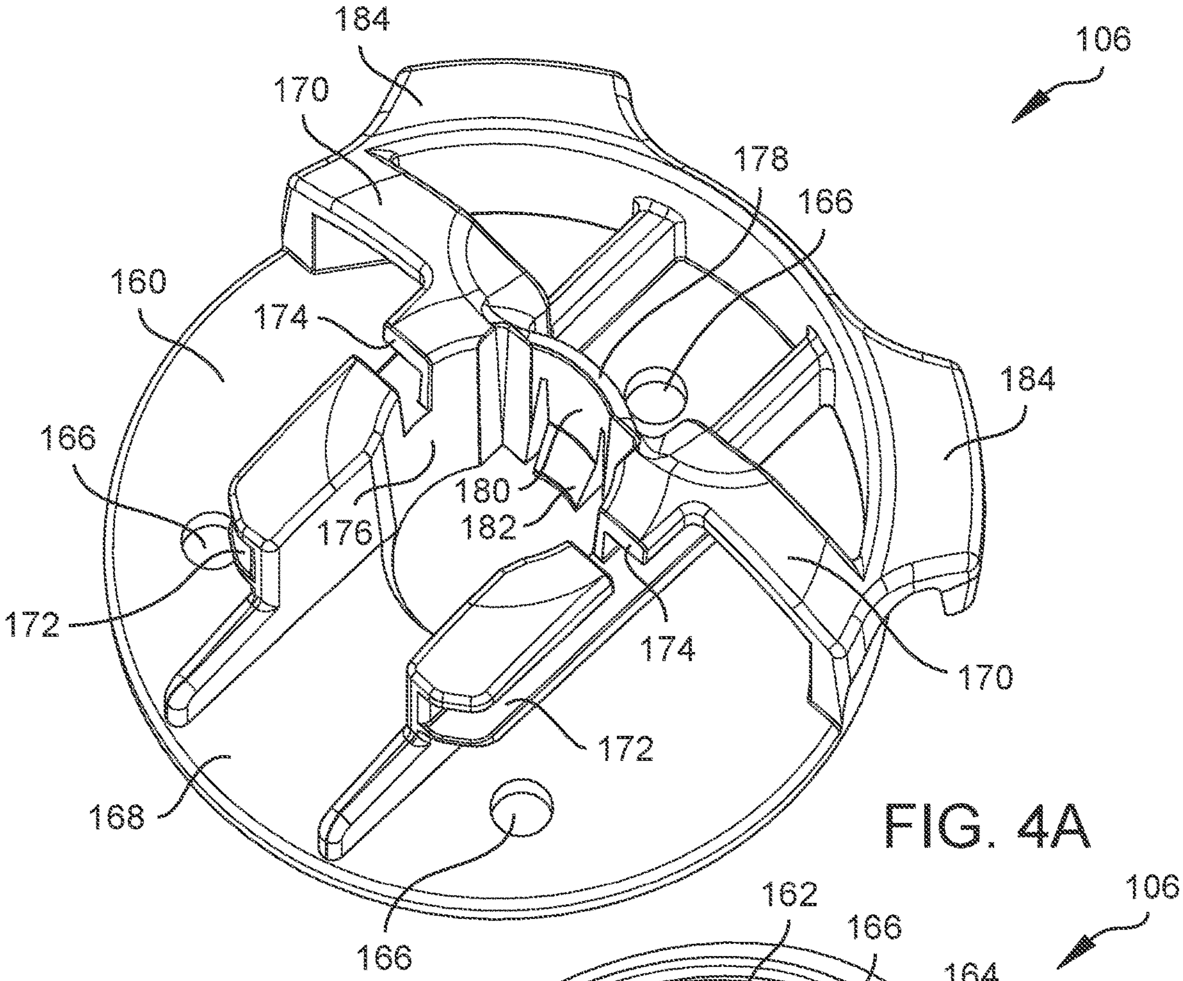
FIG. 4A depicts a perspective view of an exemplary infusion set base.
Figure 4B:
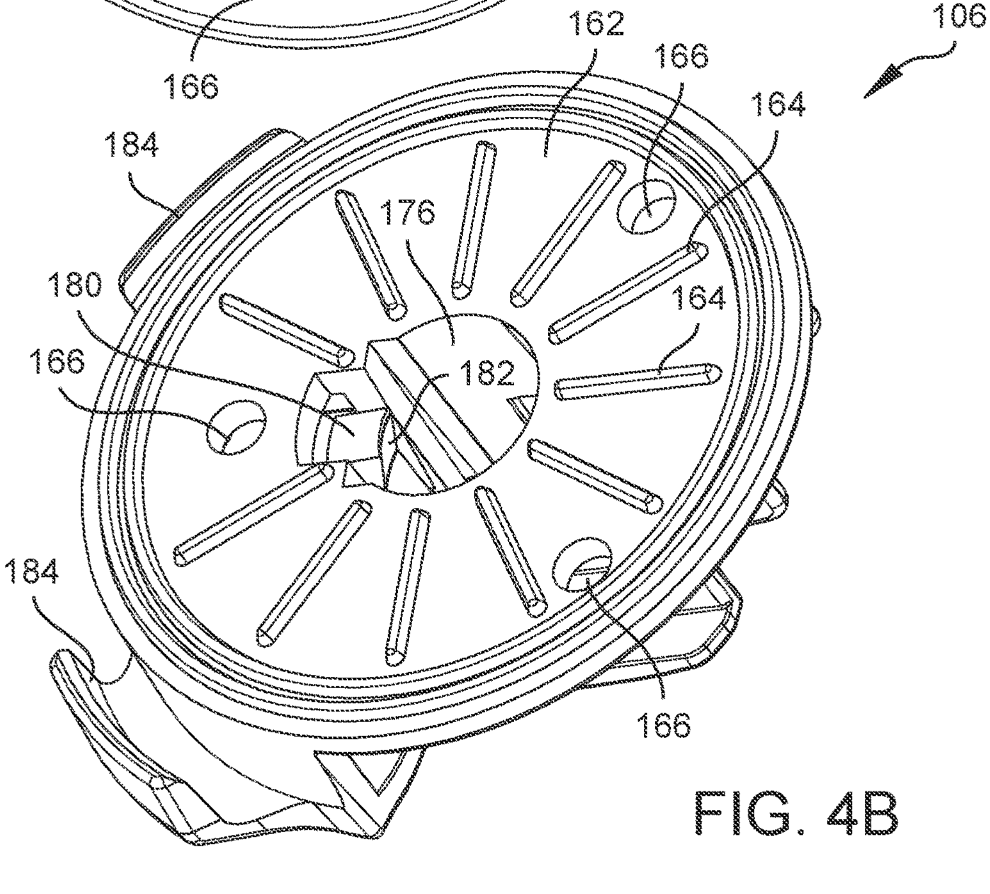
FIG. 4B depicts another perspective view of the example infusion set base of FIG. 4A.

Referring now to FIG. 4A and FIG. 4B, top and bottom perspective views of an infusion set base 106 are respectively shown. As shown, the base 106 may have a platform portion 160. The platform portion 160 may be positioned against the skin of a patient while the infusion set 102 is in place on an infusion site. In the example embodiment, the platform portion 160 has a substantially round, and in this case generally circular, disc-like foot print. In other embodiments, the platform portion 160 may be obround (see, e.g., FIGS. 21A-21F), egg shaped or ovate (see, e.g., FIGS. 22A-22C). The platform portion 160 is also substantially flat. This, however, need not be the case in all embodiments.

In various embodiments, adhesive may be applied to the bottom face 162 of a platform portion 160. An adhesive backing 111 (see, e.g. FIG. 1A) may overlay the adhesive. In the example embodiment, the bottom face 162 of the platform portion 160 includes a number of raised segments 164. The exemplary raised segments 164 are depicted as radially arrayed ridges which are spaced at substantially regular angular intervals over a portion of the bottom face 162. Two concentric raised rings are also present around the periphery of the bottom face 162. In other embodiments, raised segments other than ridges may be included and/or the raised features may not be radially arrayed or regularly spaced. In some embodiments the raised segments 164 may be dots or round regions spaced around the bottom face 162. Any suitable pattern may be used in various embodiments. The raised segments 164 may allow for the adhesive to be bonded (e.g. ultrasonically or High frequency welded) onto the bottom face 162. For example, the adhesive may be included on a substrate which may be a plastic such as polypropylene or any other plastic which would be amenable to a welding operation. The raised segments 164 and substrate may melt together during the welding operation creating a bond which keeps the adhesive on the bottom face 162 of the infusion set base 106. In alternative embodiments, a bonding agent such as double-sided tape may couple the substrate to the bottom face 162 and the bottom face 162 may be devoid of raised segments 164.

In various embodiments, a platform portion 160 may include a number of pass throughs 166. Three circular pass throughs 166 are shown in FIGS. 4A-B though any number may be included in other examples and their shape may differ. Pass throughs 166 may be provided for ease of manufacturing as they may allow for projections on a portion of an assembly line to interface therewith. This interface may aid in orienting or centering of the base 106 or any infusion set 102 subassemblies including the base 106 during manufacturing operations. Where the pass throughs 166 aid in orientation, it may be desirable that the pass throughs 166 be disposed in an asymmetric manner (though symmetric pass through 166 arrangements are also possible). In the example, the pass throughs 166 are disposed in a triangle type layout such that the base 106 would only mate into a set of corresponding projections in one orientation. Additionally, in some embodiments, any adhesive and adhesive liner 111 may include holes which align with the locations of pass throughs 166. Thus, even when the inserter assembly 100 is fully assembled and ready for triggering, the pass throughs 166 may be used to aid in the manufacturing process. The pass thoughs 166 may also be engaged by a portion of any packaging that the inserter assembly 100 is provided in to help hold the inserter assembly 100 in place.

Though the pass throughs 166 may be helpful during manufacturing, the pass throughs 166 may also provide other benefits. For example, the pass throughs 166 may provide a window to view skin around the infusion site. As a result, a user may be able to assess the skin for signs of irritation or inflammation (e.g. rubor or redness). Additionally, the pass throughs 166 may provide a pathway through which ambient air may be in communication with space between any raised segments 164 on the bottom face 162 of the infusion set base 106. This may help to allow the area under an infusion set 102 to breathe while the infusion set 102 is adhered against the skin.

Extending from the periphery of the platform portion 160 may be a number of tubing retainers 184. The tubing retainers 184 may allow for infusion tubing 366 (see, e.g., FIG. 6) to be wrapped around a portion of the infusion set 102 and held in place. This may aid in inhibiting kinking of the tubing 366 and help a user to conveniently route infusion tubing 366 as needed. Tubing retainers 184 may be omitted in alternative embodiments of infusion set bases 106 described herein (see, e.g., FIGS. 22A-22C).

Figure 6:
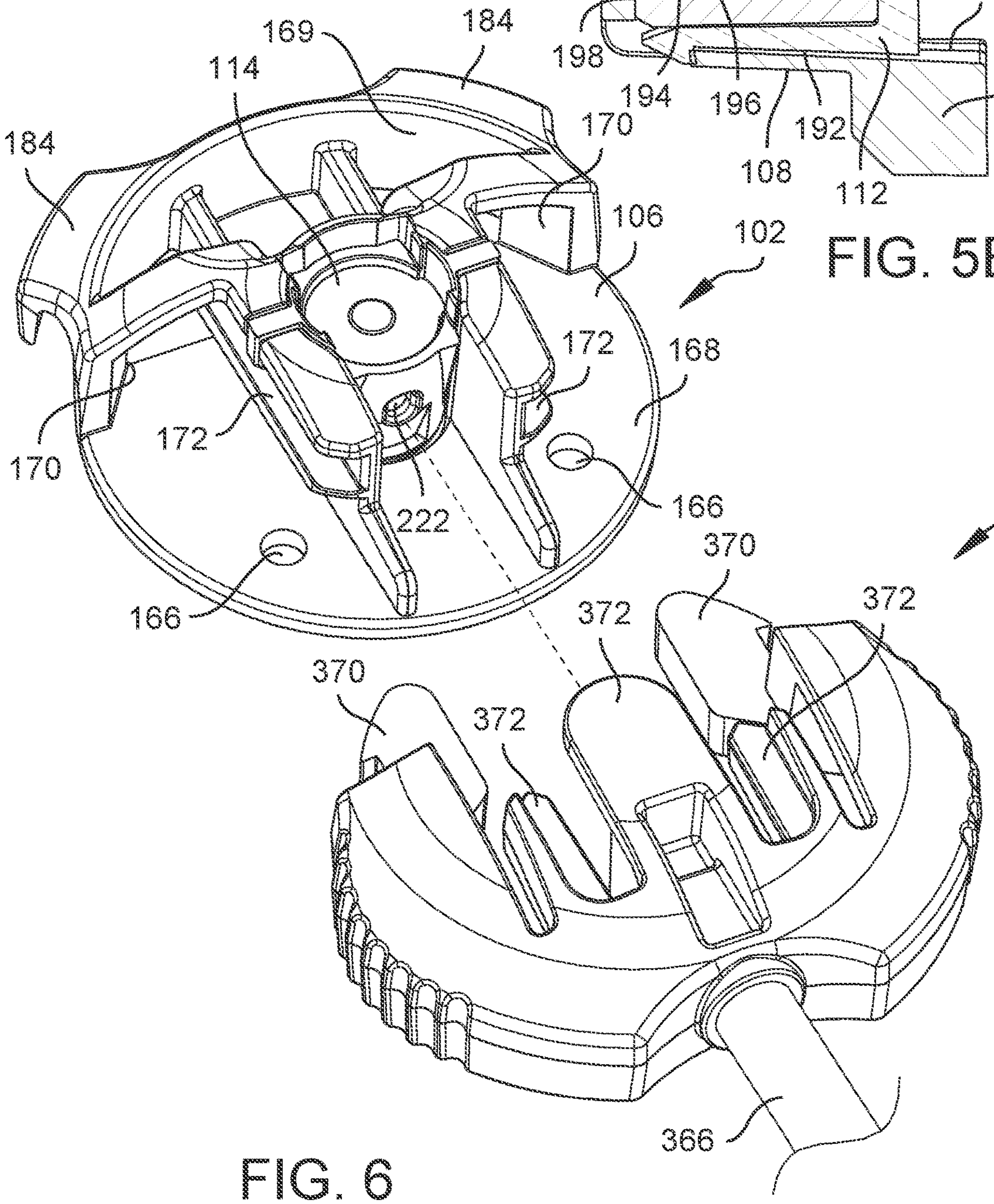
FIG. 6 depicts a perspective view of an example infusion set and tubing connector.
Figure 7A:
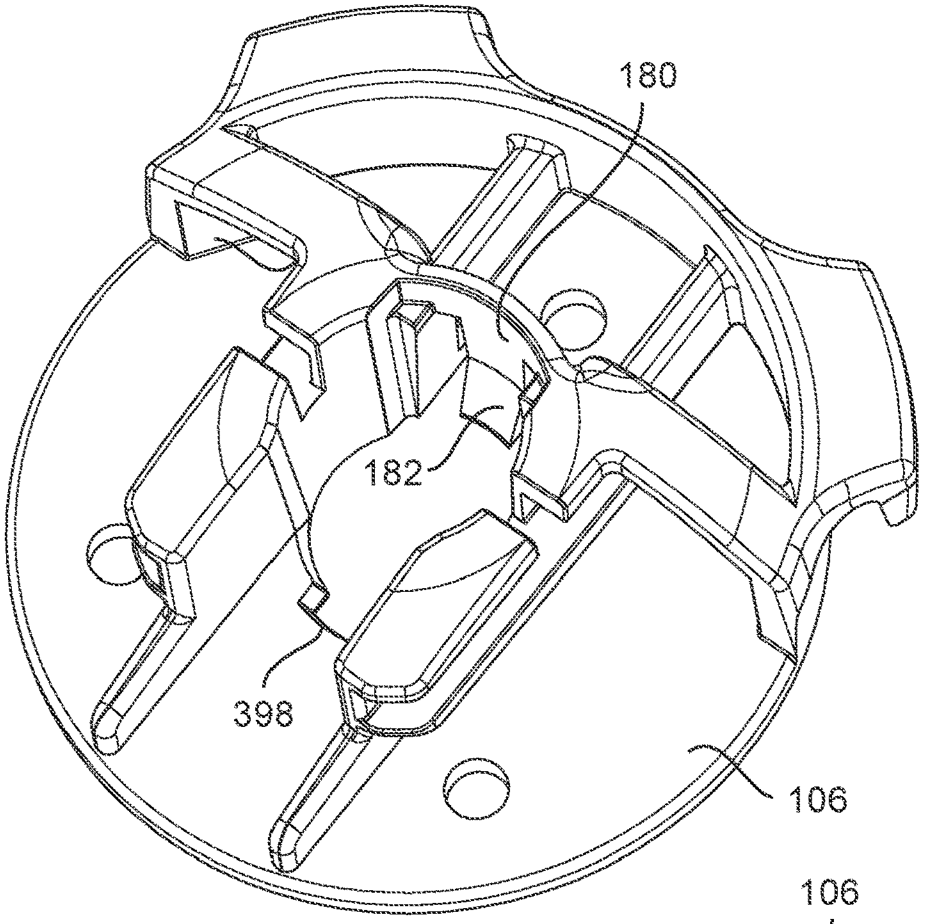
FIG. 7A depicts a perspective view of another exemplary infusion set base.
Figure 7B:
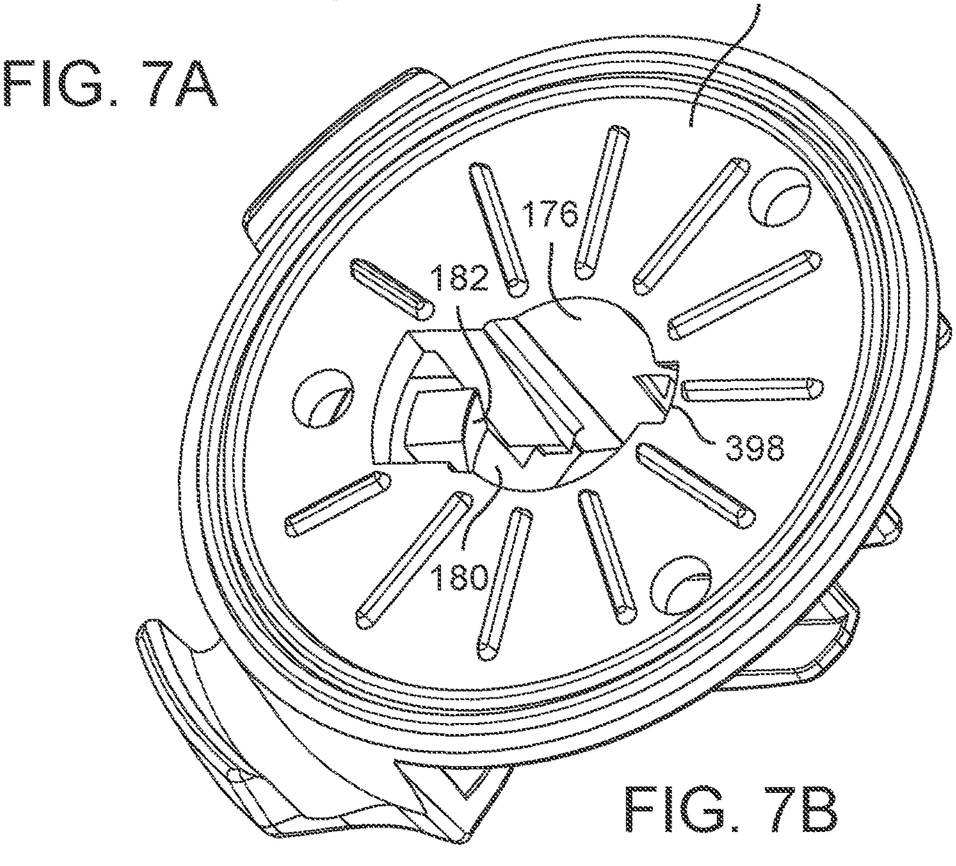
FIG. 7B depicts another perspective view of the example infusion set base of FIG. 7A.
Figure 8A:
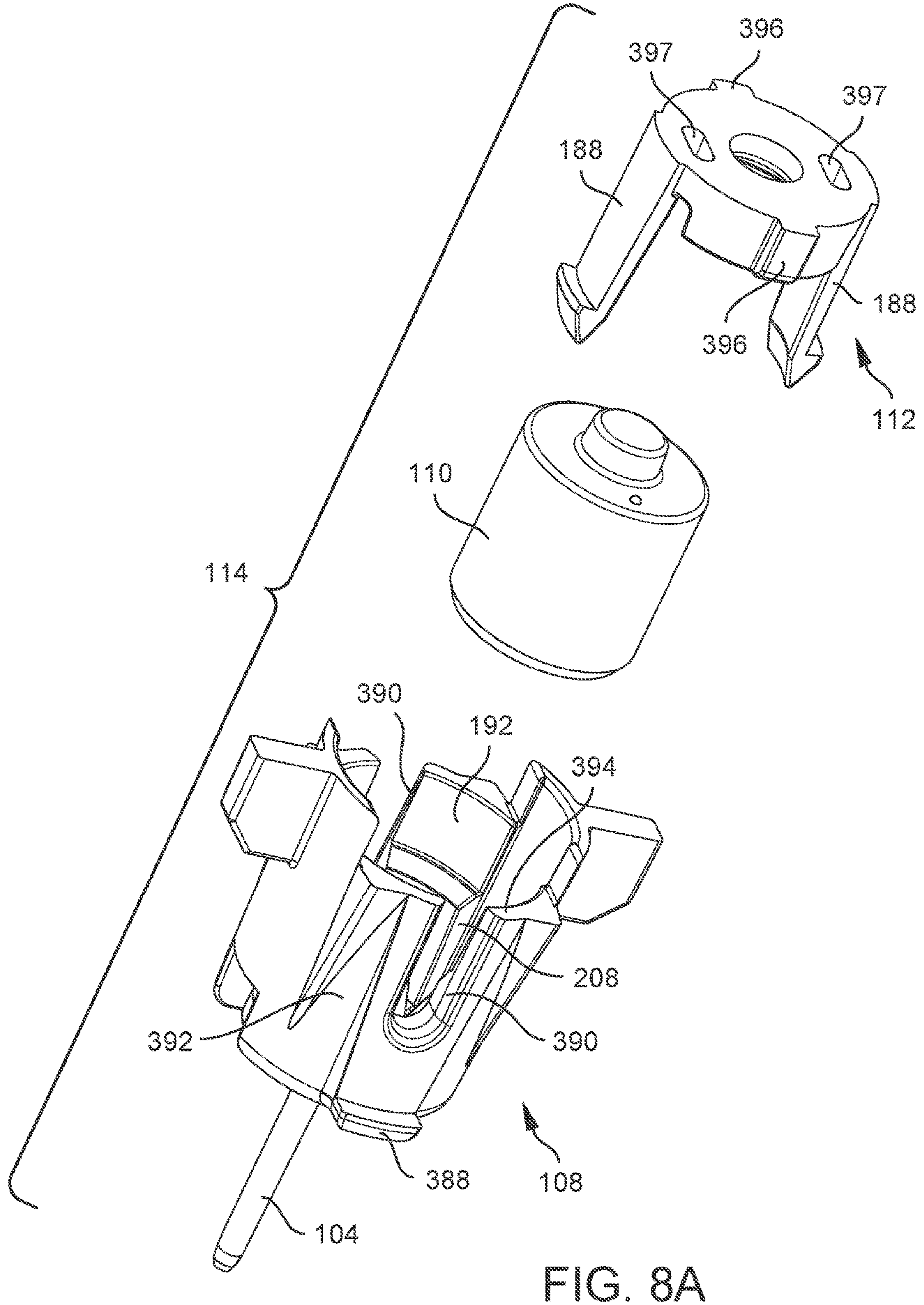
FIG. 8A depicts an exploded view of an exemplary cannula subassembly.
Figure 8B:
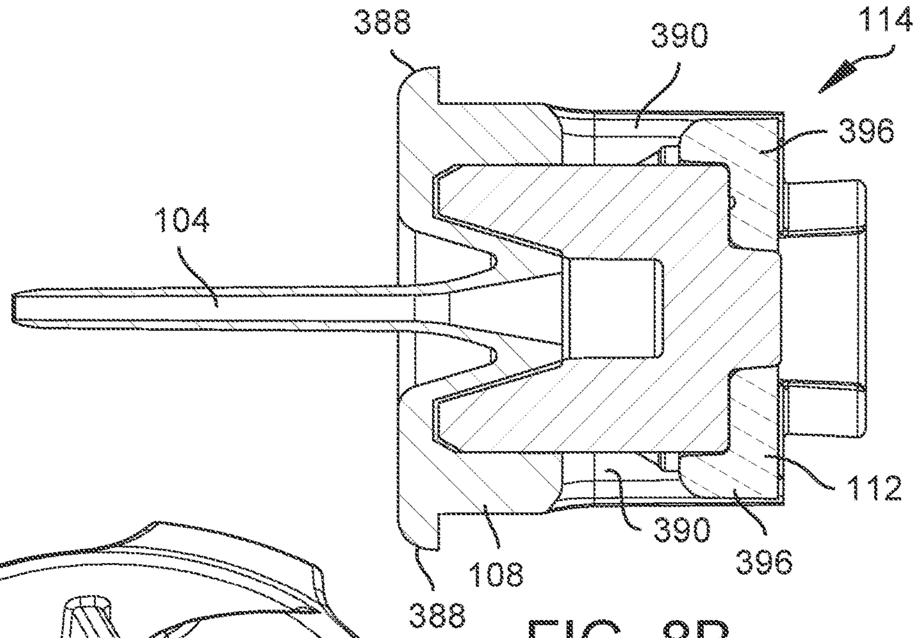
FIG. 8B depicts a cross-sectional view of the example cannula subassembly shown in FIG. 8A.
Figure 9:
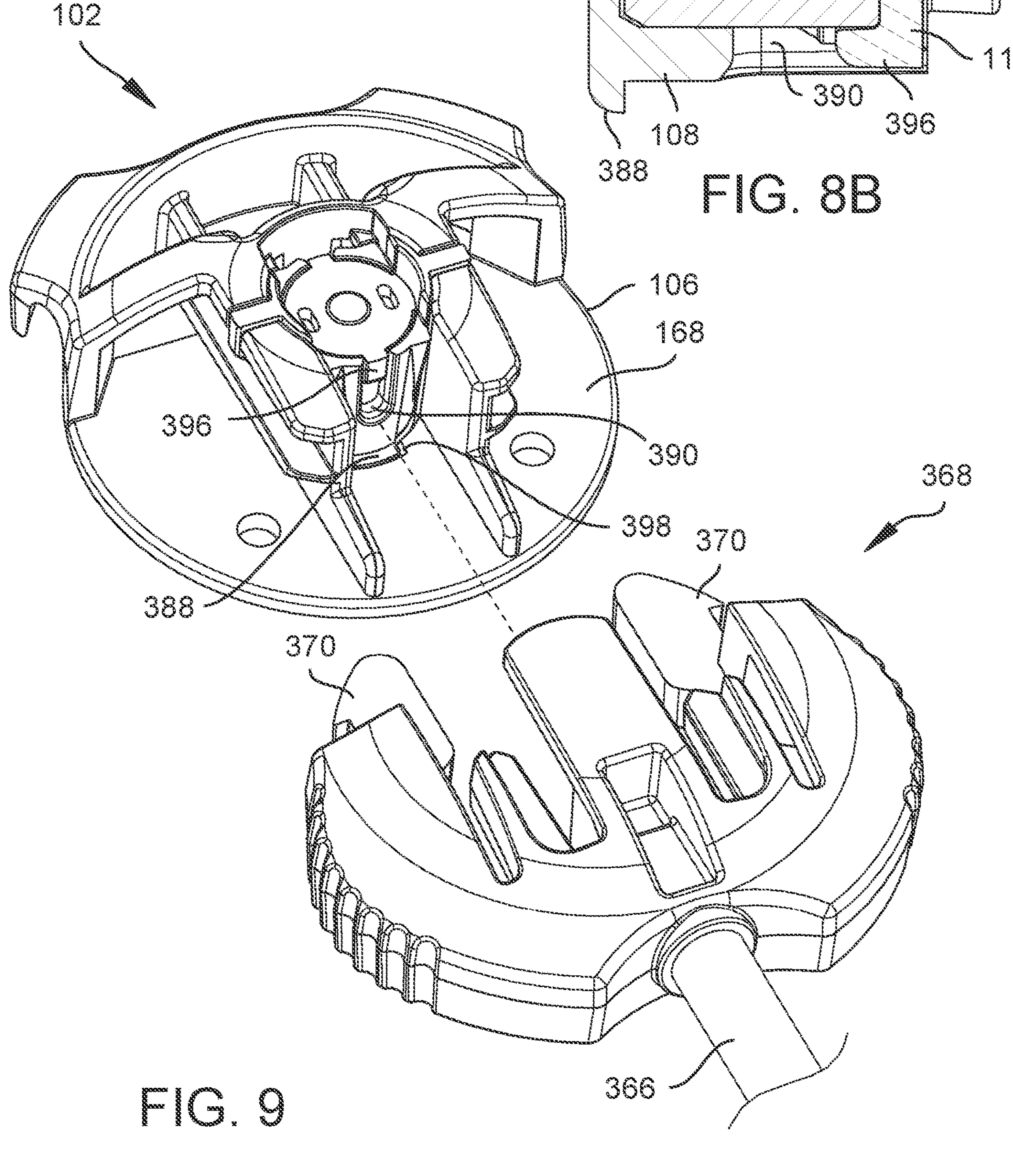
FIG. 9 depicts a perspective view of another example infusion set and tubing connector.
Figure 15A:
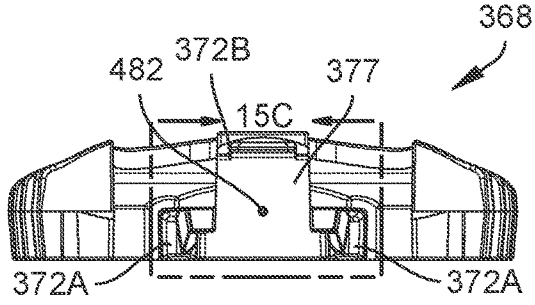
FIGS. 15A-15F depict various views of an exemplary tubing set connector.
Figure 15D:
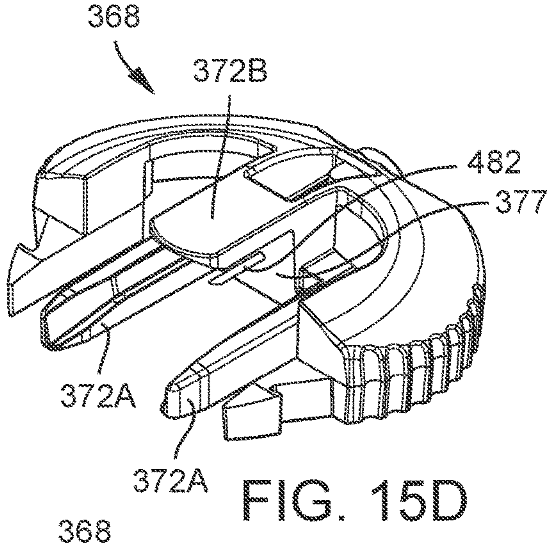
Figure 15B:
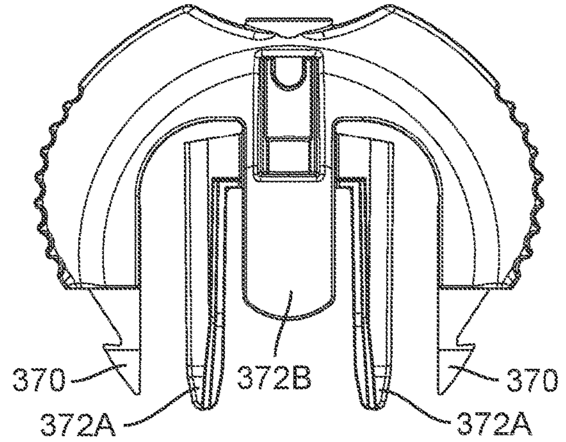
Figure 15E:
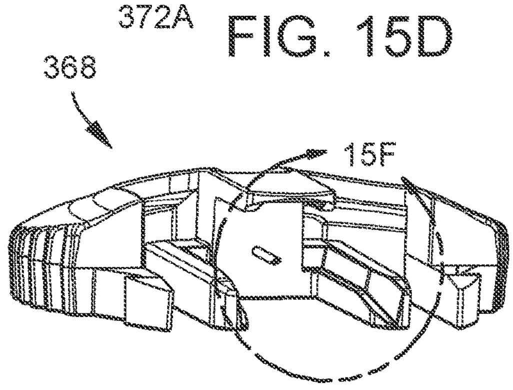
Figure 15C:
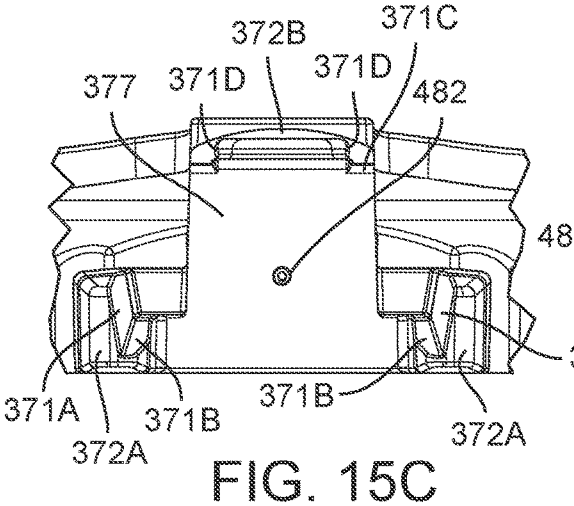
Figure 15F:
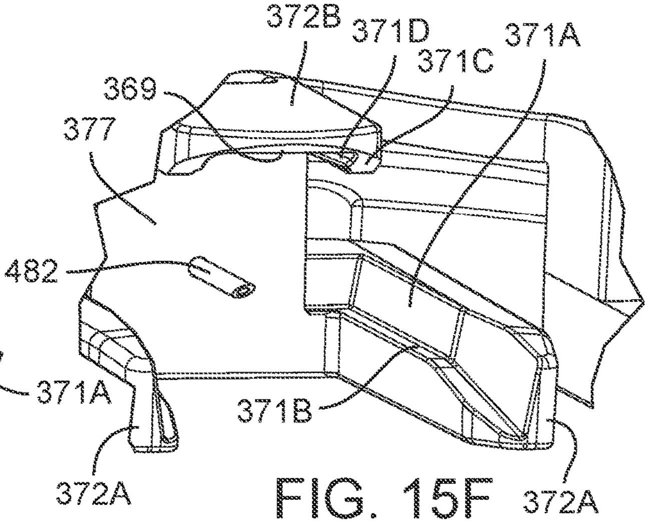

Referring now also to FIG. 6, the top face 168 of the platform portion 160 may include various receiving features extending therefrom which may mate or interface with a connector 368 included at a terminal end of infusion tubing 366 extending from an infusion pump. The infusion tubing 366 may be coupled to an infusion pump reservoir such as a syringe or an infusion pump outlet in various embodiments. Infusion tubing 366 may be coupled to an infusion pump via luer lock, or other mechanical coupling, adhesive, solvent boding, or in any other suitable fashion. The base 106 may include connector receivers 170 which cantilevered fingers 370 on the tubing set connector 368 may deflect around as the connector 368 is slid onto the base 106. Once past the connector receivers 170, the cantilevered fingers 370 may restore to their undeflected position and a bump or catch projection on the cantilevered fingers 370 may displace into latching engagement with a cooperating feature of the connector receivers 170. Sharp flanking projections 372 may also be present on the connector 368. These flanking projections 372 may extend substantially parallel to a sharp 482 (see, e.g., FIG. 15F) included on the connector 368 and may present an obstacle which helps block accidental contact between the sharp 482 and the user. A shielding wall 169 may be provided on the base 106 and may help to block fingers or objects from inadvertently dislodging the cantilevered fingers 370 out of engagement with the connector receivers 170. The shielding wall 169 may be continuous with the connector receivers 170.

Guides 172 for each of the connector fingers 370 and the flanking projections 372 may also be included and in the example embodiment define a number of slots along which the connector fingers 370 and flanking projections 372 may be slid as the connector 368 is displaced into engagement with the infusion set 102. The guides 172 may make it easier for a user to couple the infusion set 102 and connector 368 together. Additionally, the guides 172 may help to ensure that a sharp 482 (see, e.g. FIG. 15F) on the connector 368 is introduced into the infusion set 102 along or close to a desired insertion axis. In the example, the guides 172 include a notch 174. Each notch 174 may be sized to accept a projection on a component of the inserter assembly 100. Notches 174 may also be sized to accept at least a portion of a projection included on a cannula subassembly 114 (see, e.g. FIG. 5A). The flanking projections 372 may be sized so as to extend from the connector 368 a distance shorter than the location of the notches 174 when the connector 368 is attached to the infusion set 102. As described in further detail later in the specification, the notches 174 may aid in facilitating release of the base 106 from the inserter assembly 100 during actuation.

In various embodiments, the base 106 may also include a receptacle 176 for mating with a cannula subassembly 114 (see, e.g. FIG. 5A) of an infusion set 102. In the example, the receptacle 176 is generally centrally disposed on the base 106 and the receptacle 176 is flanked on each side by the guides 172. The receptacle 176 may be surrounded, at least partially, by a receptacle wall 178 which projects upwardly from the top face 168 of the platform portion 160. Thus the receptacle wall 178 and portions of the guides 172 including the notches 174 may define the receptacle 176. Part of the receptacle wall 178 may include a cantilevered section 180. The cantilevered section 180 may include a protuberance (e.g. barb or ramp) 182. In some embodiments, a portion of a receptacle wall 178 and/or guides 172 may include a tapered section (see, e.g. the embodiment depicted in FIGS. 10A-10B). The tapered section may be included at the portion of the receptacle wall 178 and/or guides 172 most distal to the platform 160. Such a tapered section may aid in guiding a cannula subassembly 114 into place as the infusion set 102 is assembled by funneling the cannula subassembly 114 into the receptacle 176. Additionally or alternatively, the notches 174 may be tapered (see, e.g., FIGS. 21A-21F) along at least a portion of their length. This may aid in guiding a cannula subassembly 114 into place as the infusion set 102 is assembled.

Figure 5A:
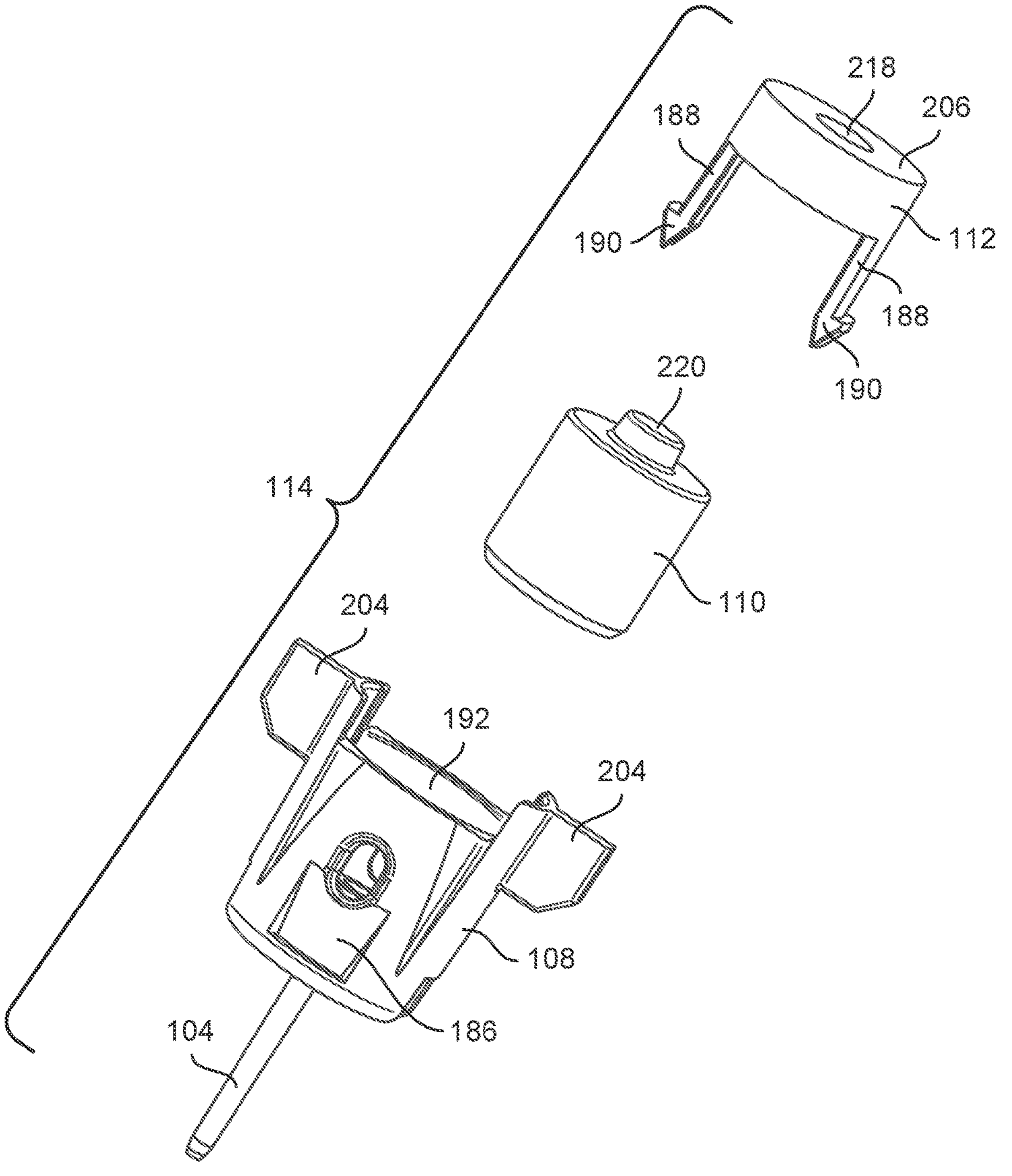
FIG. 5A depicts an exploded view of an exemplary cannula subassembly.

Referring now also to FIG. 5A, an example cannula subassembly 114 is depicted. As shown, the septum housing 108 may include a notch 186. The notch 186 may be recessed into an exterior face of the septum housing 108. During displacement of the cannula subassembly 114 into the receptacle 176 of the base 106, the cantilevered section 180 of the base 106 may deflect around the septum housing 108 until the protuberance 182 is free to spring into the notch 186. Once the cantilevered projection 180 has restored into its undeflected state and the protuberance 182 is disposed within the notch 186, the cannula subassembly 114 may be retained within the base 106. In the retained state, ears or nubs 204 of the septum housing 108 may at least partially reside within the notches 174 of the base 106 (shown in FIG. 6).

Figure 5B:
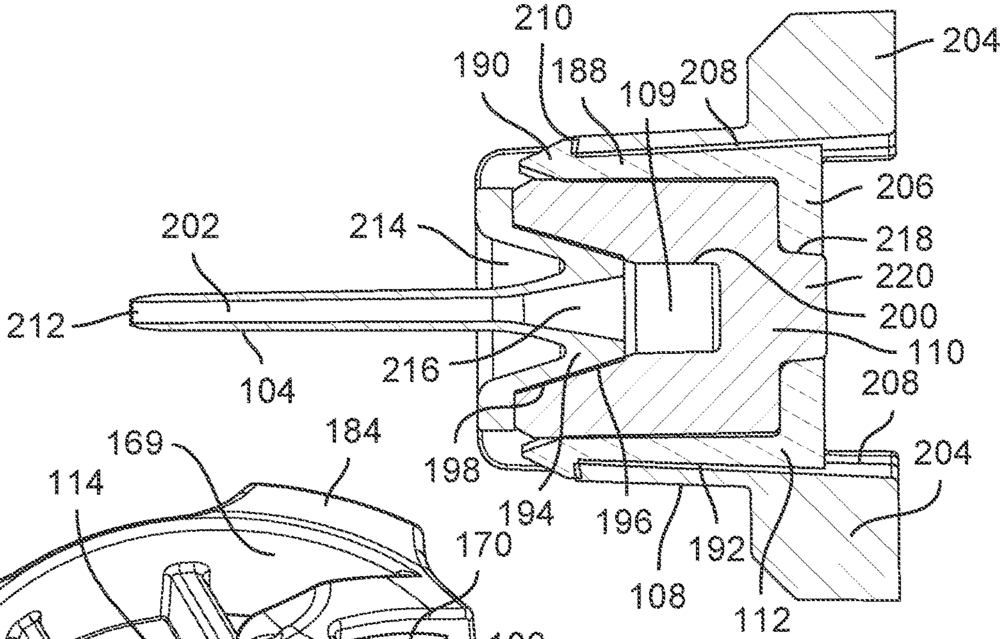
FIG. 5B depicts a cross-sectional view of the example cannula subassembly shown in FIG. 5A.

Referring now additionally to FIG. 5B, which depicts a cross sectional view of an assembled cannula subassembly 114, the cannula subassembly 114 may further include a septum 110 and a septum retainer 112 in certain embodiments. In alternative embodiments, and as described in relation to other examples herein, multiple septums 110 may be included in place of the single septum 110. The septum housing 108 may include a cup like receiving section or receptacle 192 into which the septum 110 may be introduced. The receiving section 192 may include a raised region 194 in a center thereof. In the example, the raised region 194 may have a conic frustum type shape though other shapes are also possible. Shapes such as those included on the septum interface regions 183 of cannulas 104 depicted in FIGS. 29A-31G could for example be used for alternative raised regions 194. The septum 110 may also have a cup like septum recess 196 included in the bottom face thereof. The septum recess 196 may include an enlarged or flared out section 198 (or section which otherwise corresponds to the shape of an example raised region 194) which is formed as a negative version of the raised region 194 in the receiving section 192 of the septum housing 108. Thus the enlarged section of the septum recess 196 may self-center the septum 110 as the septum 110 is introduced into the receiving section 192 and may be referred to herein as a centering wall of the septum recess 196. A second section 200 of the septum recess 196 most distal to the bottom face of the septum 110 may define, at least partially, a fluid introduction volume 109 into which a needle or sharp 482 (see, e.g., FIG. 15F) included on the tubing connector 368 may penetrate to deliver fluid into the infusion set 102. Fluid may pass from the fluid introduction volume 109 to the lumen 202 of the cannula 104 and into the patient. The second section 200 of the septum recess 196 may have any suitable cross section though in the example has a round, roughly circular cross section. The septum housing 108 may include a connector needle passage 222 in a sidewall thereof (as shown in FIG. 6) which may allow a needle or sharp 482 (see, e.g., FIG. 15D) of the connector 368 access to the fluid introduction volume 109. In the example embodiment, the connector needle passage 222 is depicted as a fenestration extending though the septum housing 108. A connector needle passage 222 and notch 186 may (though need not be) be present on opposing sides of the septum housing 108 so as to allow the cannula subassembly 114 to be capable of being installed into the base 106 in two orientations. This may make assembly of the inserter assembly 100 simpler.

The receiving section 192 of the septum housing 108 may also receive a portion of a septum retainer 112. The septum retainer 112 may be constructed with a body 206 from which extends at least one cantilevered projection 188 including a terminal protuberance or latch member 190. In the example, the body 206 is substantially planar. Additionally, two cantilevered projections 188 which are disposed opposite one another and extend generally perpendicular to the body 206 are present. These cantilevered projections 188 may fit within guides 208 included on the interior surface of the receiving section 192 of the septum housing 108. The guides 208 shown are recessed into the interior surface of the receiving section 192 and are substantially in the same plane as the ears 204. The guides 208 are ramped such that distance between the two guides 208 decreases as distance from the cannula 104 decreases. This may deflect the cantilevered projections 188 of the septum retainer 112 toward the axis of extension of the cannula 104 as the septum retainer 112 is advanced into the receiving section 192. Once the septum retainer 112 has been advanced into the septum housing 108 a certain distance, the cantilevered projections 188 may spring outward such that the protuberance 190 on each cantilevered projection 188 enters into latching engagement with a catch 210 on the septum housing 108 as shown in FIG. 5B. In some embodiments, a portion of the cantilevered projections 188 may extend into or through an aperture included in the bottom of the septum housing 108 and enter into latching engagement with a catch adjacent to the aperture or formed by a wall of that aperture. With the septum retainer 112 latched into place within the cannula subassembly 114, the septum 110 may be placed into sealing relationship with the septum housing 108. Fluid contained in the fluid introduction volume 109 of the septum 110 may thus be provided a sealed fluid flow path to the outlet 212 of the cannula 104.

As shown, the septum retainer 112 includes a channel 218 which extends therethrough. The example channel 218 is disposed in substantially the center of the body 206. When the septum retainer 112 is locked in place within the cannula subassembly 114, a nub or projection 220 of the septum 110 may extend into the channel 218. Thus the channel 218 may provide an access pathway for an insertion sharp 132 of the inserter assembly 100 to extend though the infusion set 102 and out of the outlet 212 of the cannula 212. In the example shown, the nub 220 is in the shape of a conic frustum and the channel 218 is shaped in a cooperative manner to receive the nub 220. Other nub 220 shapes may be used in alternative embodiments such as any of those described herein (see, e.g., FIGS. 32A-32D).

The cannula 104 may include an insertion sharp guide section 216 which may aid in directing the insertion sharp 132 into the lumen 202 of the cannula 104. The insertion sharp guide section 216 may have a funnel like shape though other shapes are also possible. In the example embodiment, the insertion sharp guide section 216 includes relatively steep sides and is encompassed by a flat (or perhaps chamfered or rounded) peripheral edge which forms a wall of the fluid introduction volume within the infusion set 102. This peripheral edge may be the uppermost face of the raised section 192 in some embodiments. The insertion sharp guide section 216 may be continuous with the walls of the lumen 202 of the cannula 104 and may be wetted by any fluid delivered through the infusion set 102. The insertion sharp guide section 216 may also be continuous with the raised region 194 in the receiving section 192 of the septum housing 108.

Referring primarily to FIG. 5B, a recess 214 may be included in the septum housing 108 which surrounds, or at least partially surrounds, the cannula 104. This recess 214 may not be covered by adhesive when the adhesive is placed onto the infusion set base 106. The recess 214 may provide room for the cannula 104 to move relative to the base 106 if the infusion set 102 or a portion of the patient's body causes a force to be applied to the cannula 104. This may minimize shearing action on the cannula 104. Additionally, the recess 214 may serve as a volume into which an agent may be placed. For instance, an antiseptic, disinfectant, anti-inflammatory, anesthetic, or other topical agent such as an ointment may be contained in the recess 214. This agent may be medicinal, nutritional, or some other type of agent. Thus upon application of the infusion set 102, the agent may be introduced to the skin of the patient and may be held in contact with therewith. In some examples, the agent may be kept in contact with the recess 214. This may be desirable or beneficial for a number of reasons including that it may aid in preventing infection, inflammation, or pain and may provide a way to apply the agent in a convenient manner. In the example embodiment, the recess 214 is shaped in the form of a conic section (e.g. hyperbola or parabola) revolved around the center axis of the cannula 104.

In various embodiments, the cannula 104 may be tapered or non-tapered. In some embodiments, the cannula 104 may include one or more tapered section and one or more untapered or straight section. Any tapered sections may extend at an angle to the long axis of the cannula 104. In some embodiments, instead of being at some constant angle to this axis, a curvature may be present. The angle or the degree of curvature over a tapered section may also vary over the extent of a tapered section.

In some embodiments, a first portion of the cannula 104 proximal the outlet 212 is tapered. The taper present at this section results in a reduced wall thickness as proximity toward the outlet 212 of the cannula 104 increases. Additionally, a second portion of the cannula 104 adjacent the point on the septum housing 108 from which it extends is also tapered. The angle of the taper of the second portion may be substantially equal to the angle of the insertion sharp guide section 216 in certain embodiments. The taper at the second portion decreases the width of the cannula 104 at this section without substantially decreasing the thickness of the wall of the cannula 104 surrounding the lumen 202. A straight section may be disposed intermediate the first and second portions of the cannula 104 in the example embodiment. Alternatively, a slightly tapered section may be used as the intermediate segment. This section may be tapered to a lesser degree than the first and second portion of the cannula and may or may not be tapered in a manner which maintains a constant wall thickness along the length of the intermediate segment.

Referring now to FIGS. 7A-9 another example infusion set 102 is depicted. As shown, the cannula subassembly 114 of the example infusion set 102 is designed to allow production via straight pull molding. Features which may require molds with side actions or other special characteristics are not present on the example cannula subassembly 114. For example, in some embodiments, undercut features may not be present. This may allow the cannula subassembly 114 or components thereof to be constructed of a wider array of different materials.

As shown, the cannula subassembly 114 includes a septum 110 similar to that shown in FIGS. 5A-5B. In alternative embodiments, a plurality of septums 110 may be included in place of the single septum 110 shown. The septum housing 108 does not include notches 186. In place of the notches 186, the septum housing 108 includes salients 388 which extend outward from the outer surface of the septum housing 108. During joining of the cannula assembly 104 to the infusion set base 106, one of the salients 388 may deflect the cantilevered section 180 of the base 106 until the protuberance 182 is free to spring back into a position overhanging the salient 388. Once the cantilevered projection 180 has restored into its undeflected state and the protuberance 182 is over the salient 388, the cannula subassembly 114 may be retained within the base 106. In the retained state (see, e.g. FIG. 9), ears or nubs 204 of the septum housing 108 may at least partially reside within the notches 174 of the base 106. The receptacle 176 portion of the infusion set base 106 is widened with respect to that shown in FIG. 4A-B so as to accommodate the greater footprint of the cannula subassembly 114. Additionally, the receptacle 176 includes a salient receiving region 398 opposite the cantilevered projection 180 so as to accept the salient 388 not engaged by the protuberance 182. This may allow the cannula subassembly 114 to be made symmetrically and allow for it to be installed into the infusion set base 106 in two orientations. This may aid in simplifying manufacturing and assembly. In other embodiments, a salient 388 may only be included on one side of the cannula subassembly 114 and the salient receiving region 398 of the base 106 may be omitted.

Additionally, in the exemplary embodiment, the septum housing 108 does not include fenestrations which form a connector needle passage 222 (see, e.g. FIG. 6) in a sidewall thereof. The septum housing 108 in FIGS. 8A-9 includes slots 390 in the side wall 392 of the septum housing 108 recessed into the top face 394 of the side wall 392. The septum retainer 112 may include projections 396 which align with the slots 390 when the cantilevered projections 188 are fitted within guides 208 included on the interior surface of the receiving section 192 of the septum housing 108. When the cannula subassembly 114 is coupled together (see, e.g. FIG. 8B), the projections 396 may occupy a portion of the slots 390. Thus an access hole for a sharp 482 (see, e.g., FIG. 15D) or needle included on a tubing connector 368 may be provided in the cannula subassembly 114. The septum retainer 112 also includes a number of pass throughs 397. The pass throughs 397 may aid in manufacture and assembly similar to pass throughs 166 in the infusion set base 106.

In some embodiments, the slots 390 in the side wall 392 of the septum housing 108 may be used in place of the salient 388 as a retention arrangement which cooperates with a protuberance included as part of the base 106. The protuberance may catch against or engage with a wall of one of the slots 390 inhibiting removal of the cannula subassembly 114. In such embodiments, the salients 388 may not be included on the septum housing 108. This may help to further simplify production of the cannula subassembly 114.

Figure 10A:
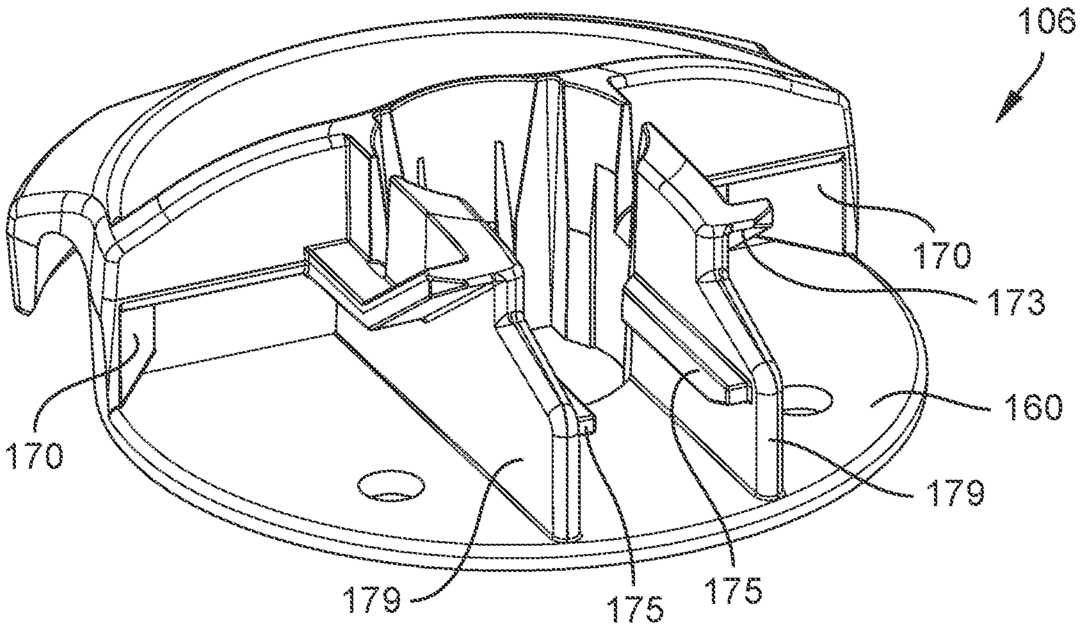
FIG. 10A depicts a perspective view of an example infusion set base.
Figure 10B:
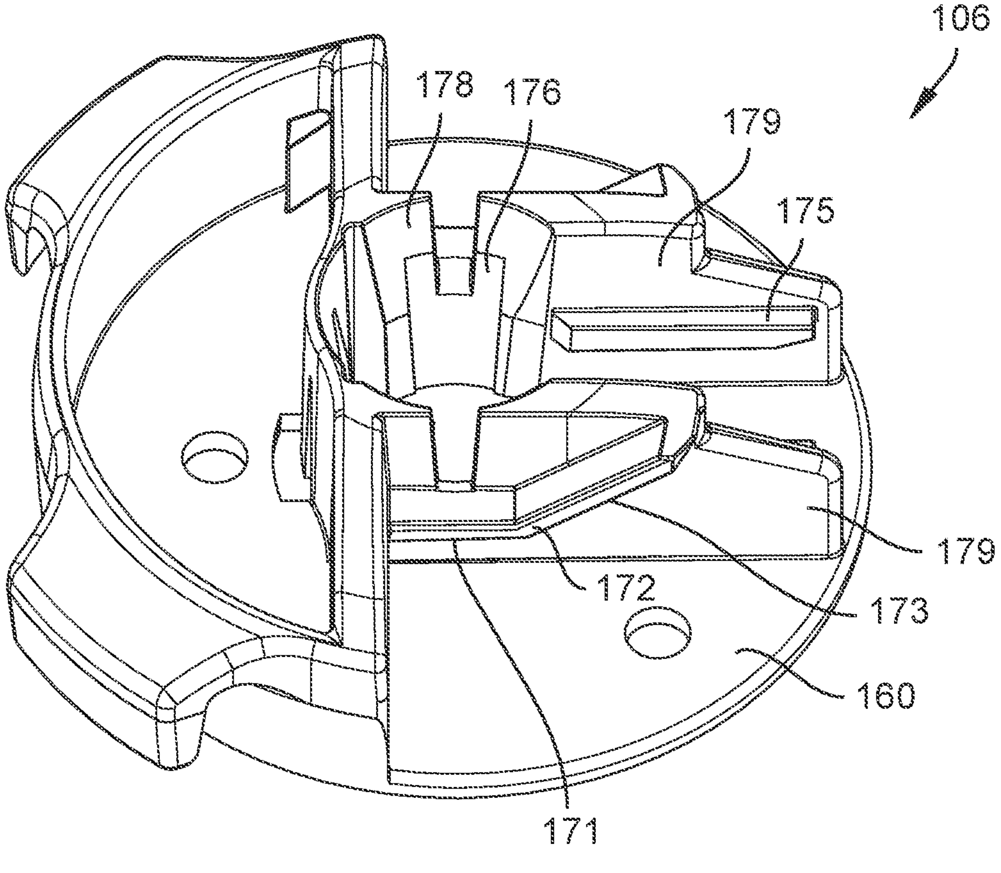
FIG. 10B depicts another perspective view of the infusion set base of FIG. 10A.

Referring now to FIG. 10A and FIG. 10B, another example base 106 is depicted. As in FIG. 6, the top face 168 of the platform portion 160 may include various receiving features extending therefrom which may mate or interface with a connector 368. The base 106 may include connector receivers 170 which may allow for coupling of the base 106 with cantilevered fingers 370 on the tubing set connector 368 as described above (see, e.g. description of FIG. 6). Guides 172 for each of the connector fingers 370 may also be included in the example embodiment. As shown, the exemplary guides 172 include a first section 171 and a second section 173. The first section 171 of each guide 172 may be disposed so as to have a portion which extends in a substantially parallel fashion to the plane of the platform 160 of the base 106. The second section 173 of each guide 172 may include a portion disposed at an angle with respect to the first section 171. In the example, each of the first and second portion 171, 173 include a ledge which projects from a main portion of that guide 172. The distance between the platform 160 and the proximal surface of the ledge of the second section 173 of the guide 172 may increase as the second section 173 extends distally from the ledge of the first portion 171 of the guide 172. This may allow the tubing set connector 368 to initially be introduced at a substantial angle to the plane of the platform 160 of the base 106. Further introduction may cause the connector fingers 370 to contact the platform 160 and be redirected to an appropriate displacement pathway for coupling of the tubing set connector 368 to the base 106. Thus, the guides 172 may aid in allowing a user to blindly insert the connector fingers 370 into the connector receivers 170 as coupling of a base 106 and tubing set connector 368 is performed. As shown, a second set of additional guide ledges 175 may be included on receptacle wall extensions 179. These additional guide ledges 175 may extend to the periphery of the base 106. In the example embodiments, the second set of guide ledges 175 extend substantially perpendicularly from the medial faces of the receptacle wall extensions 179 and toward the axis along which the sharp 482 (see, e.g., FIGS. 184-188) of the tubing set connector 368 is inserted into the cannula subassembly 114. A face of each of the second set of guide ledges 175 which is disposed near an end of each guide 172 most proximal to the periphery of the base 106 may include a ramped region.

Figure 11A:
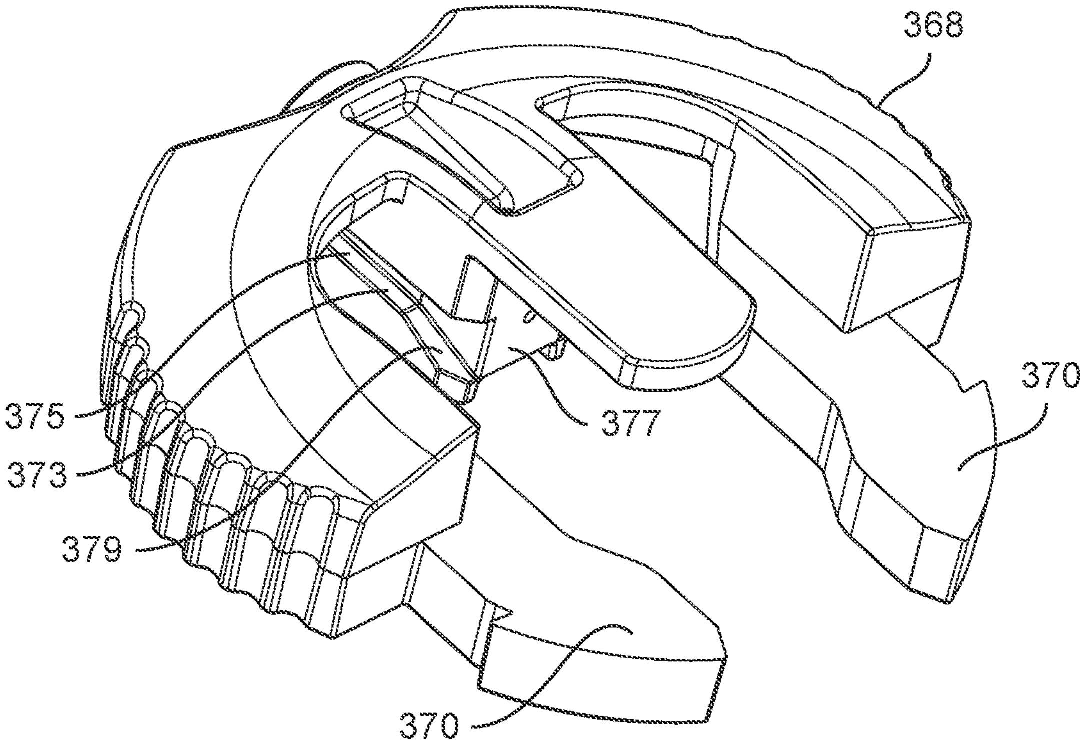
FIG. 11A depicts a perspective view of an example infusion set base.
Figure 11B:
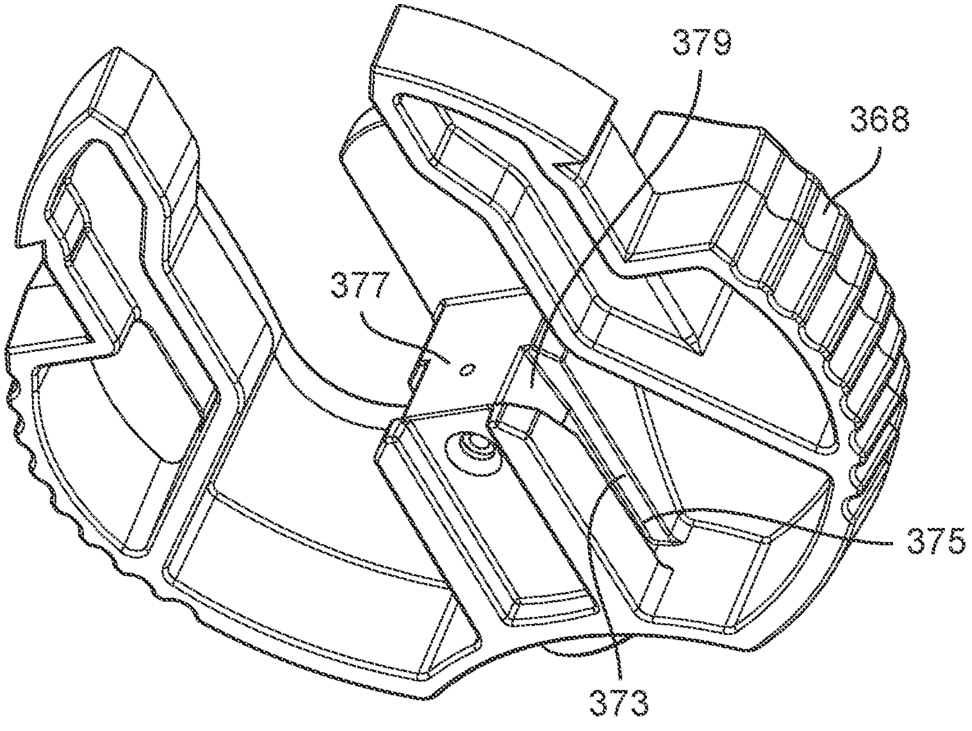
FIG. 11B depicts another perspective view of the infusion set base of FIG. 11A.
Figure 12A:
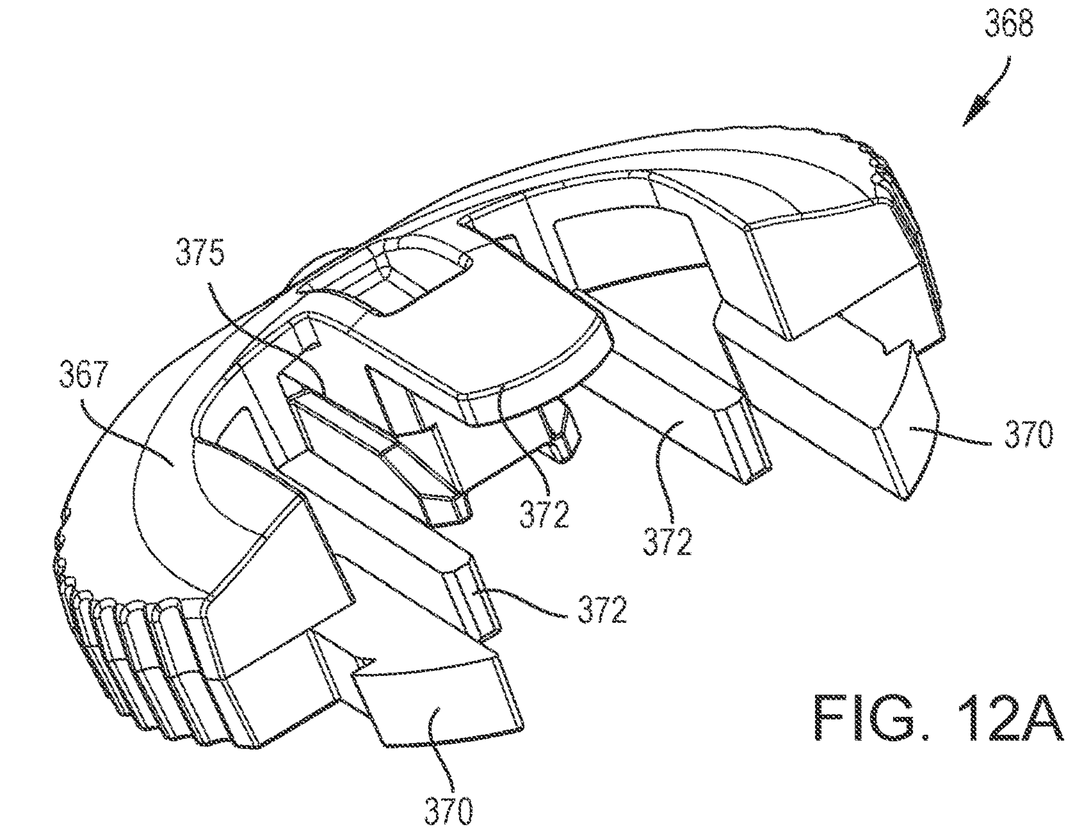
FIG. 12A depicts a perspective view of an example infusion set base.
Figure 12B:
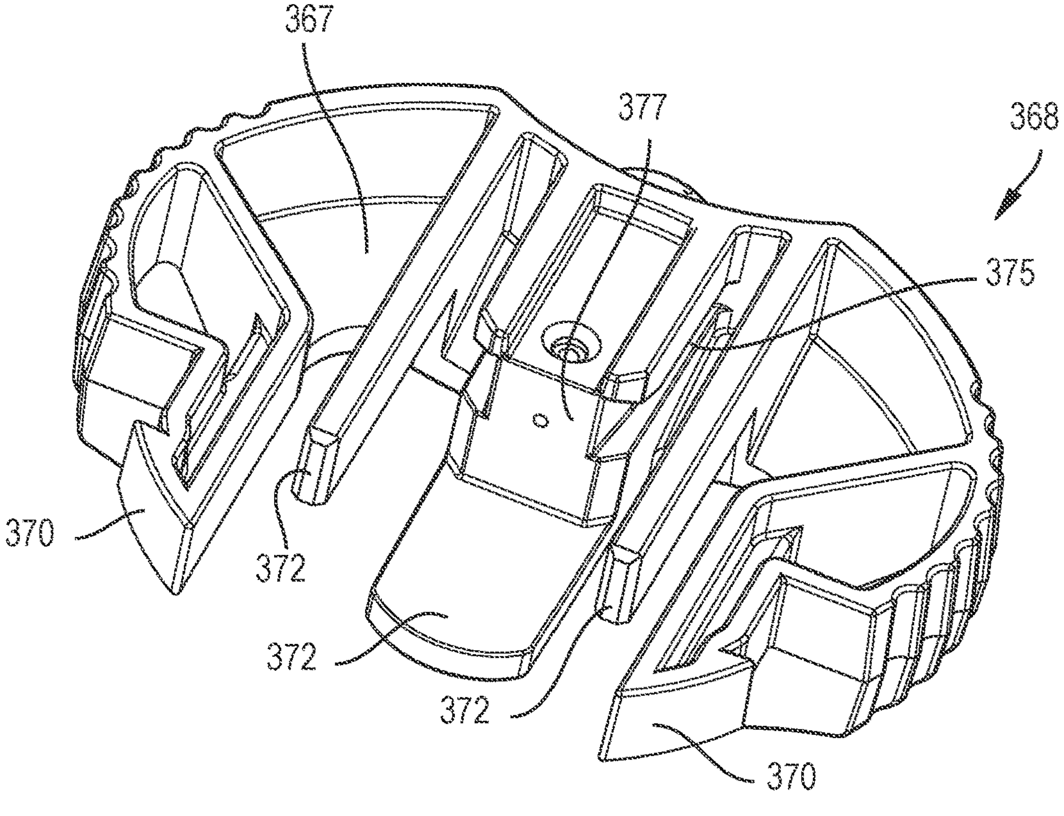
FIG. 12B depicts another perspective view of the infusion set base of FIG. 12A.

Referring now to also to FIGS. 11A-11B, the tubing set connector 368 may include a flow hub 377 to which tubing 366 and a sharp 482 (see, e.g., FIGS. 184-188) may be coupled. Fluid flowing through the connector 368 may pass through lumens 514 and 516 (see, e.g., FIGS. 184-188) of the tubing 366 and sharp 482 respectively within the flow hub 377. As shown in FIGS. 11A-11B, the flow hub 377 may include alignment channels 375 recessed therein. As shown, the alignment channels 375 include a constant width segment 373 and a variable width segment 379. Upon coupling of a tubing set connector 368 and infusion set 102, the alignment channels 375 may interact with the second set of guide ledges 175 of the base 106. The ramped section of each of the second set of guide ledges 175 and the variable width section 379 of the alignment channels 375 may allow the tubing sharp connector 368 to initially be introduced at a substantial angle to the plane of the platform 160 of the base 106. Further introduction may cause the second set of guide ledges 175 to contact the wall of their respective alignment channels 375 and redirect the tubing set connector 368 toward an appropriate displacement pathway for coupling of the tubing set connector 368 to the base 106. The second set of guide ledges 175 in conjunction with the alignment channels 375 may thus aid in allowing a user to blindly couple the base 106 and tubing set connector 368.

Referring now to FIGS. 12A-12B and FIGS. 13A-13B, in some embodiments, sharp flanking projections 372 may be included as part of the tubing set connector 368. As shown, the sharp flanking projections 372 may extend parallel to the axis of a sharp 482 (see, e.g., FIGS. 184-188) which may be included in the tubing set connector 368. The sharp flanking projections 372 may aid in preventing any user contact with the sharp 482 by providing an obstruction which inhibits a finger from reaching the sharp 482. The sharp flanking projections 372 may include a centrally disposed projection 372 which extends over the sharp 482 from a top face of the tubing set connector 368. The sharp flanking projections 372 may also include a set of projections which are in the same plane as the connector fingers 370 of the tubing set connector 368, but disposed more medially than the connector fingers 370. In the example embodiments, the connector fingers 370 and this set of projections 372 are in line with the bottom face of the tubing set connector 368. Each projection 372 of this set of projections 372 may be disposed so as to extend from a point on the body 367 of the tubing set connector 368 which is intermediate the flow hub 377 and the connector fingers 370. These projections 372 may be disposed so as to interact with guides 172 of a base 106 during coupling of the tubing set connector 368 to a corresponding base 106. In such embodiments, the connector fingers 370 may not interact with guides 172 on the base 106.

Figure 13A:
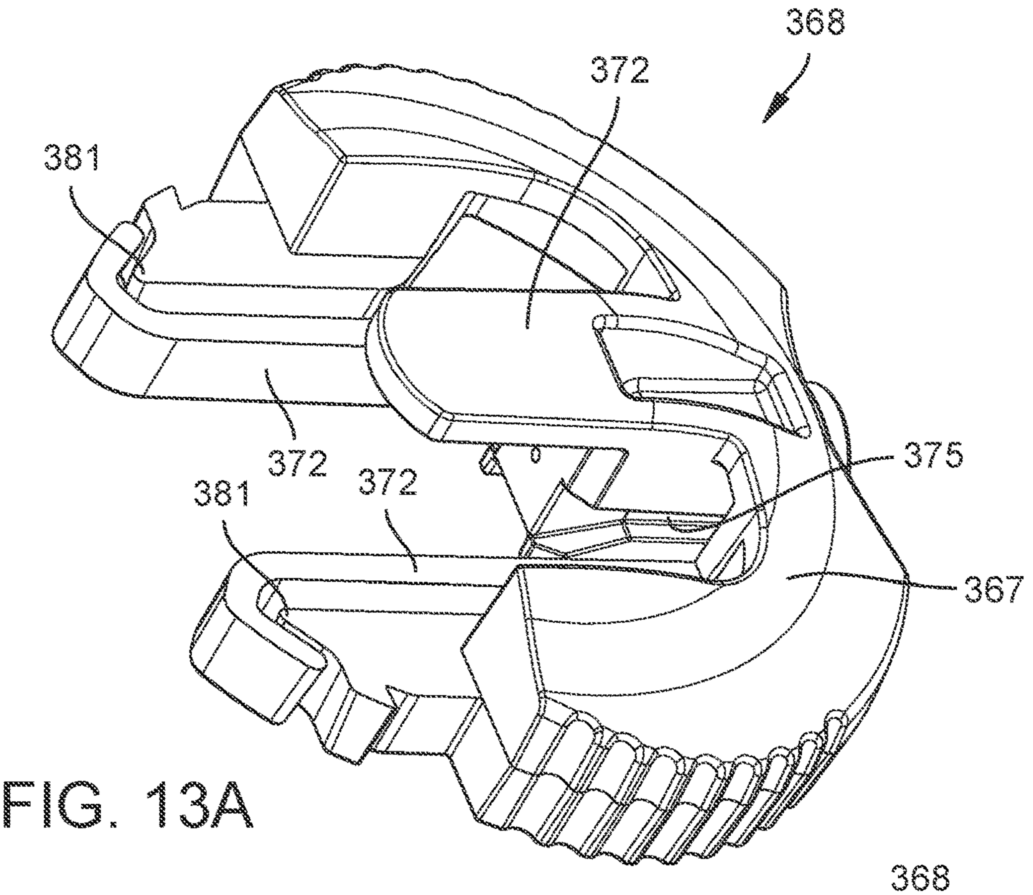
FIG. 13A depicts a perspective view of an example infusion set base.
Figure 13B:
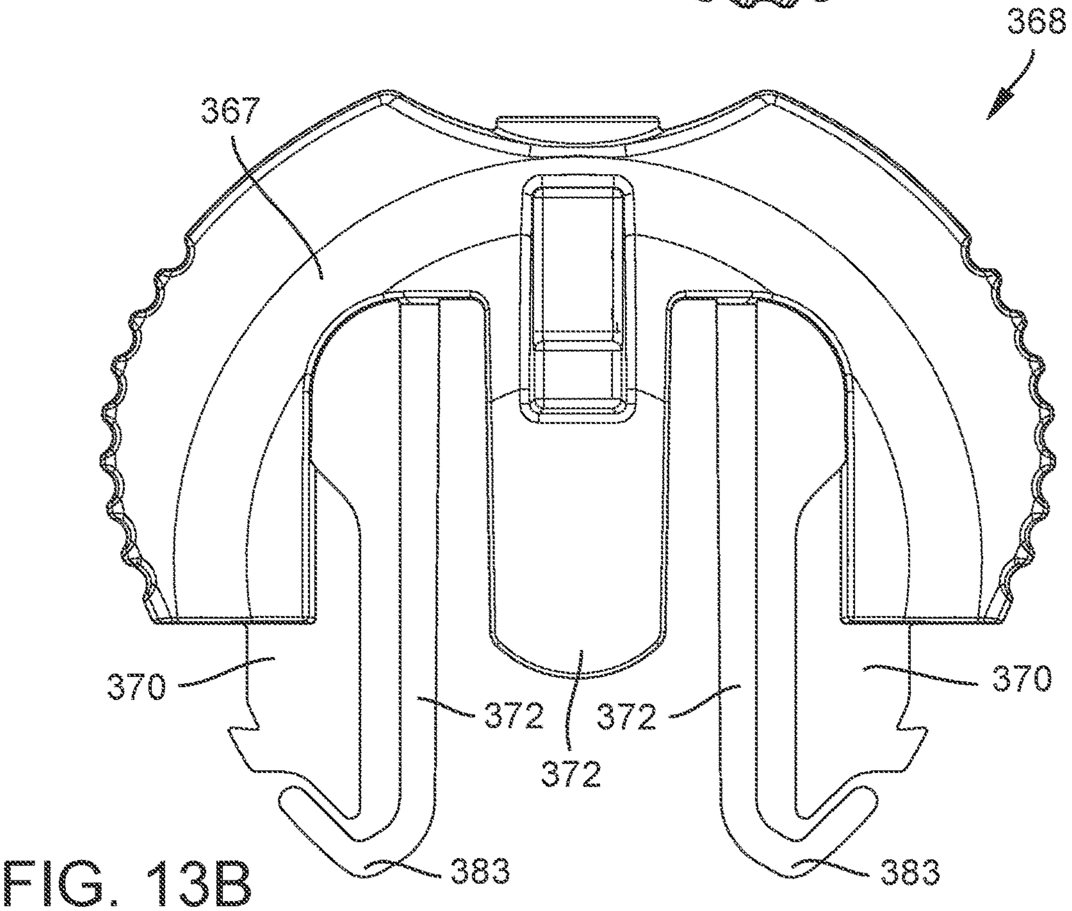
FIG. 13B depicts a bottom plan view of the infusion set base of FIG. 13A.

In some embodiments, and as shown in FIGS. 13A-13B, the pair of sharp flanking projections 372 which are in the plane of the connector fingers 370 may extend beyond the tips 381 of the connector fingers 370. These projections 372 may include a curved end region 383 at an end of the projections 372 opposite that attached to the body 367 of the tubing set connector 368. The curved end regions 383 may curve in a direction lateral to the axis of the sharp 482 (see, e.g., FIGS. 184-188) of the tubing set connector 368. In the example, the curved end regions 383 may have a curvature which swings an arc greater than 90°. In the example, the curved end regions 383 have a curvature such that the curved end regions 383 begin to extend back toward the body 367 of the tubing set connector 368. The radius of the curved end regions 383 may or may not be constant. Additionally, the curved end regions 383 may include one or more straight expanse. As shown best in FIG. 13B, the portion of the curved end region 383 leading to the terminus of the projection may be substantially straight. In the example, the curved end regions 383 curve around and in front of a portion of the respective connector fingers 370. The distance between the projections 372 may be slightly smaller than the spacing between the guides 172 of a corresponding base 106. The distance between the projections 372 at the curved end regions 383, however, may be slightly greater facilitating maneuvering of the projections 372 into their respective guides 172. Once the projections 372 are located within the guides 172, advancement of the tubing set connector 368 may cause the projections 372 to be resiliently splayed apart. Due to the resiliency of the projections 372, the projections 372 press against a surface of the guides 172 ensuring a tight and substantially wiggle free fit. This may help to further confine displacement of the tubing set connector 368 along a desired path as coupling of a tubing set connector 368 to a base 106 is completed.

Figure 14A:
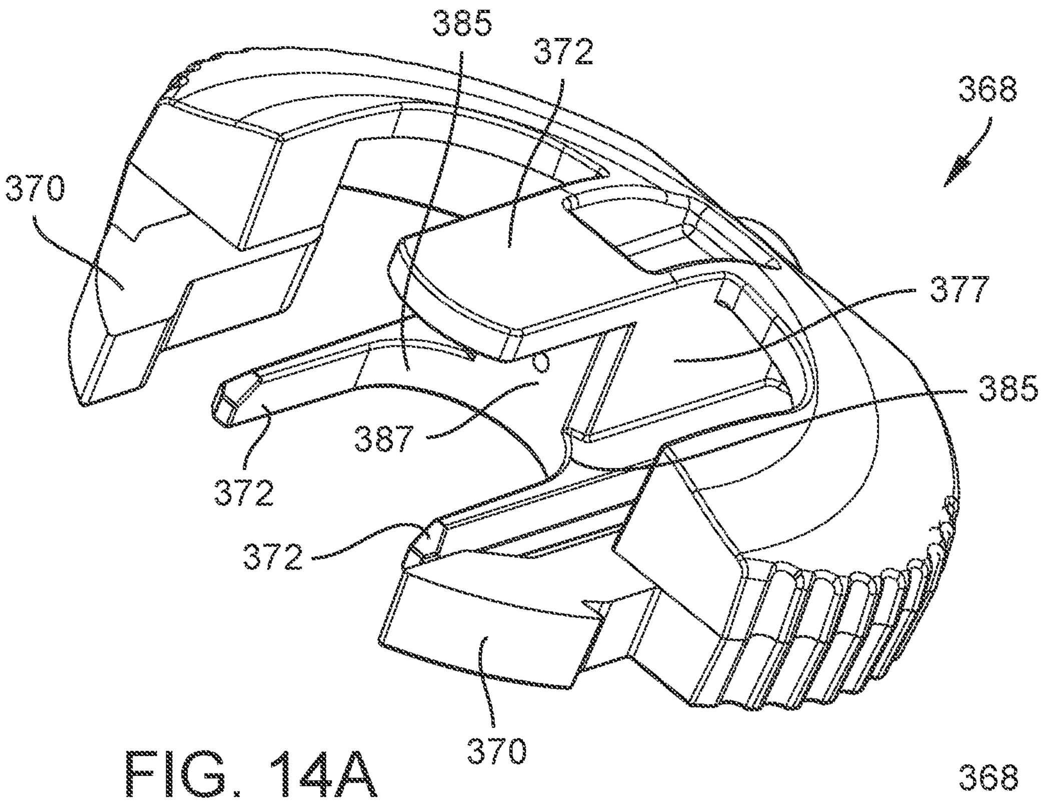
FIG. 14A depicts a perspective view of an example infusion set base.
Figure 14B:
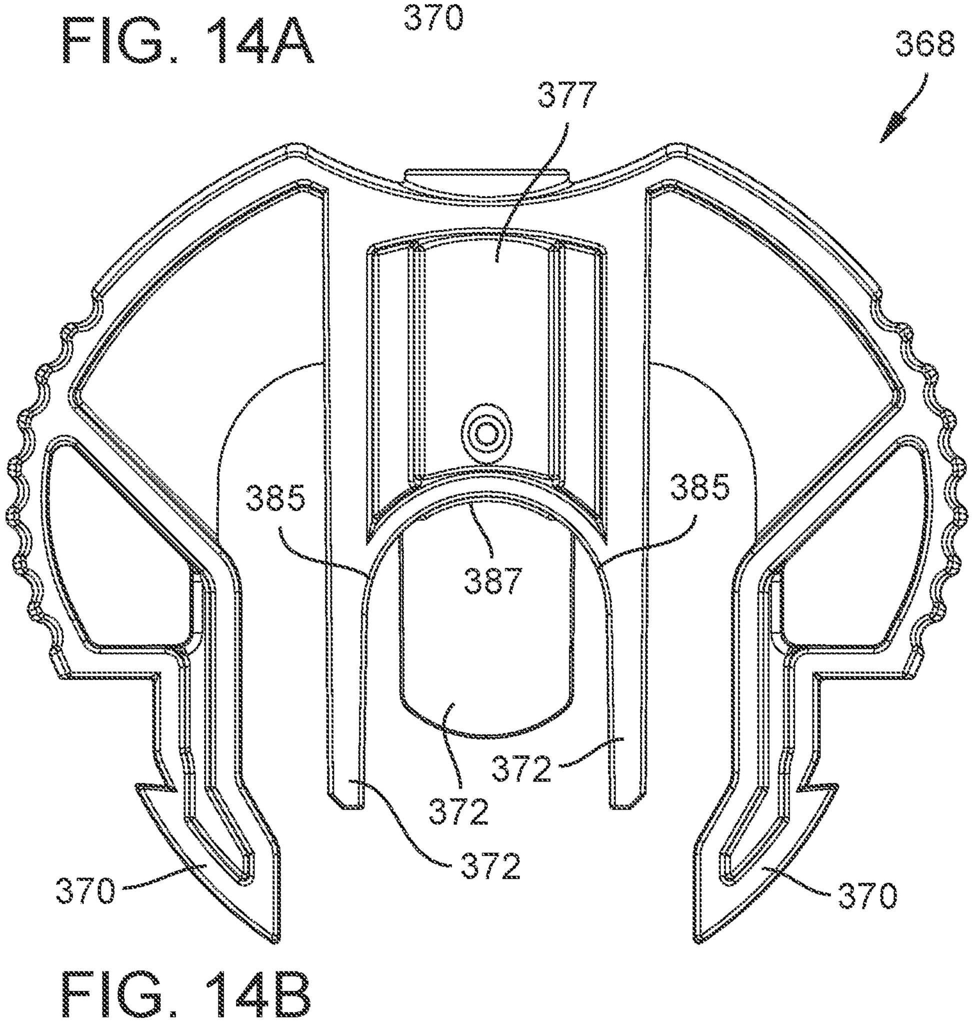
FIG. 14B depicts a bottom plan view of the infusion set base of FIG. 14A.

In certain examples, and referring now to FIGS. 14A-14B, a set of sharp flanking projections 372 in line with the connector fingers 370 may extend from the flow hub 377. This may decrease the gap between the sharp flanking projections 372 of the tubing set connector 368 and may help to further minimize the ability of the user to access space in the vicinity of the sharp 482 (see, e.g., FIGS. 184-188) with a finger. In the example embodiment depicted in FIGS. 14A-14B, a set of sharp flanking projections 372 which extend along and from opposing faces of the flow hub 377 lateral to the axis of the sharp 482 are included. These projections 372 may each include a support segment 385. These support segments 385 may be located in the region of the sharp flanking projections 372 which extends beyond the face 387 of the flow hub 377 from which the sharp 482 extends. As shown, the support segments 385 are disposed in the portion of this region most proximal to the flow hub 377. The support segments 385 in the example embodiment include an arched face which may lend additional robustness to the set of sharp flanking projections 372. The face 387 of the flow hub 377 from which the sharp 482 extends may also be arched which may further add robustness to the projections 372.

Referring now to FIGS. 15A-H, another exemplary tubing set connector 368 is depicted. As shown, a set of sharp flanking projections 372A which may be line with the connector fingers 370 may extend from the flow hub 377 similarly to FIGS. 14A-B. As in FIGS. 14A-B, this may aid in avoiding inadvertent contact with the sharp 482. A centrally disposed sharp flanking projection 372B which extends over the sharp 482 from a top face of the tubing set connector 368 may also be included.

The sharp flanking projections 372A, B may include at least one guide surface 371A-D. In some embodiments, each of the sharp flanking projections 372A, B may include at least one guide surface 371A-D. The sharp flanking projections 372A depicted in FIGS. 15A-H each include a lateral adjusting guide surface 371A and a height adjusting guide surface 371B. At least one of any lateral adjusting guide surface 371A and height adjusting guide surface 371B may include a sloped segment. As shown, the lateral guide surface 371A and height adjusting guide surface 371B may both include a first region proximal the flow hub 377 and a second region at the end of the sharp flanking projections 372A distal to the flow hub 377. The second regions may be sloped (ramped or curved) while the first regions may be substantially straight or sloped to a lesser degree.

The sharp flanking projection 372B may also include at least one height adjusting guide surface 371C and at least one lateral adjusting guide surface 371D. In the example, at least one of the height adjusting guide surface 371C and at least one lateral adjusting guide surface 371D may include a sloped section. In the example, the height adjusting guide surface 371C includes a first region proximal the flow hub 377 and a second region at the distal end of the sharp flanking projection 372B. The second region is sloped (ramped or curved) in the example embodiment. The sharp flanking projection 372B includes a centrally disposed trough 369 which runs along the underside (that closest to the sharp 482) of the sharp flanking projection 372B. The side walls of this trough 369 may form the two lateral guide surfaces 371D. A portion (e.g. that most distal the flow hub 377) of at least one of the lateral guide surfaces 371D may be sloped.

Figure 16A:
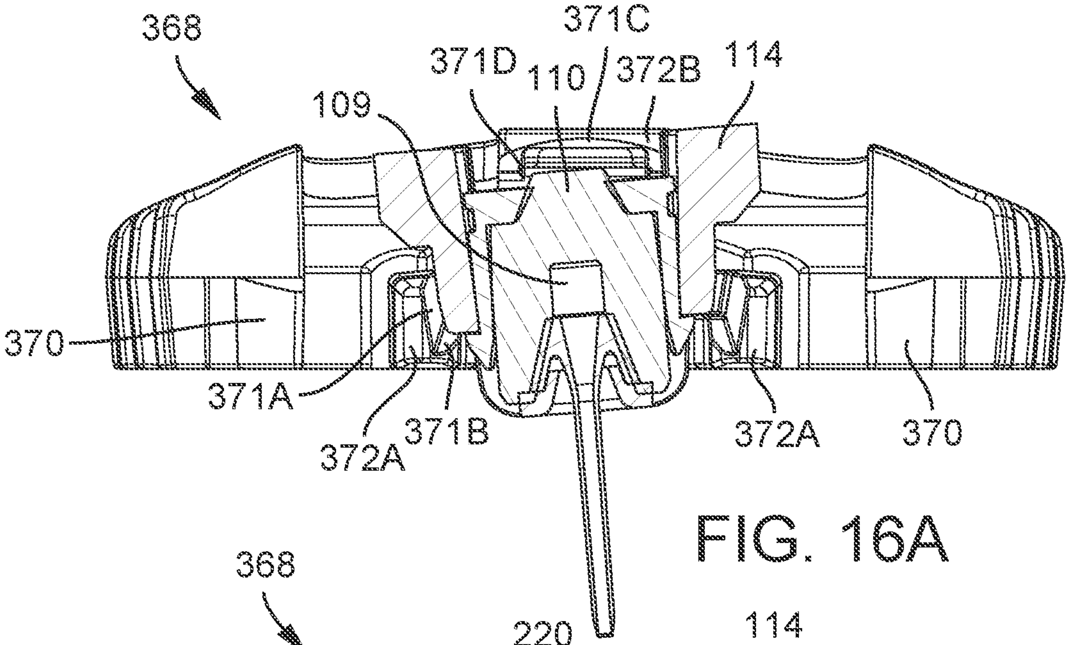
FIG. 16A depicts an example tubing set connector and an example cannula subassembly which is in an exaggerated askew position for illustrative purposes.
Figure 16B:
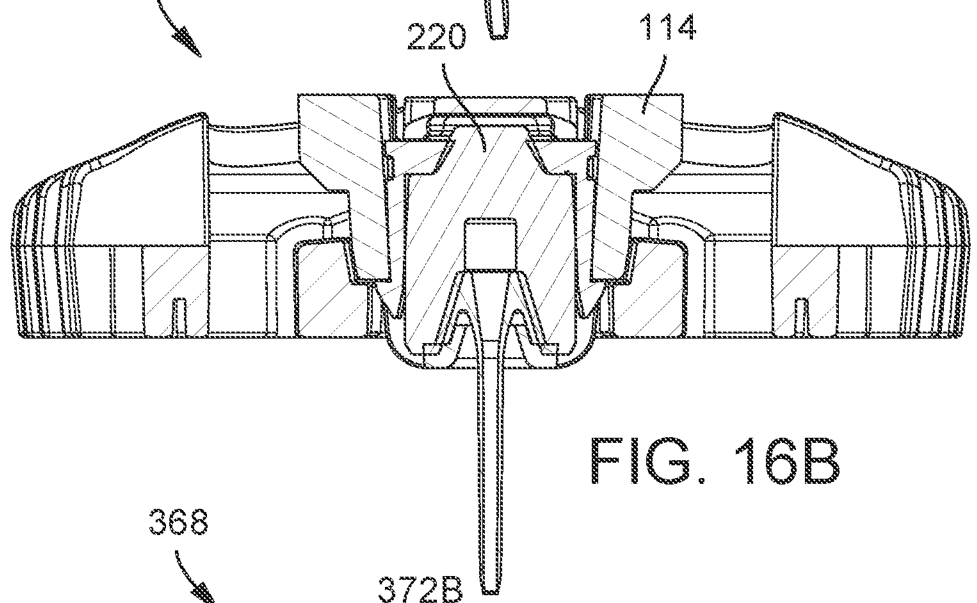
FIG. 16B depicts an example tubing set connector and an example cannula subassembly with the cannula subassembly being displaced by the tubing set connector to a home position.
Figure 16C:
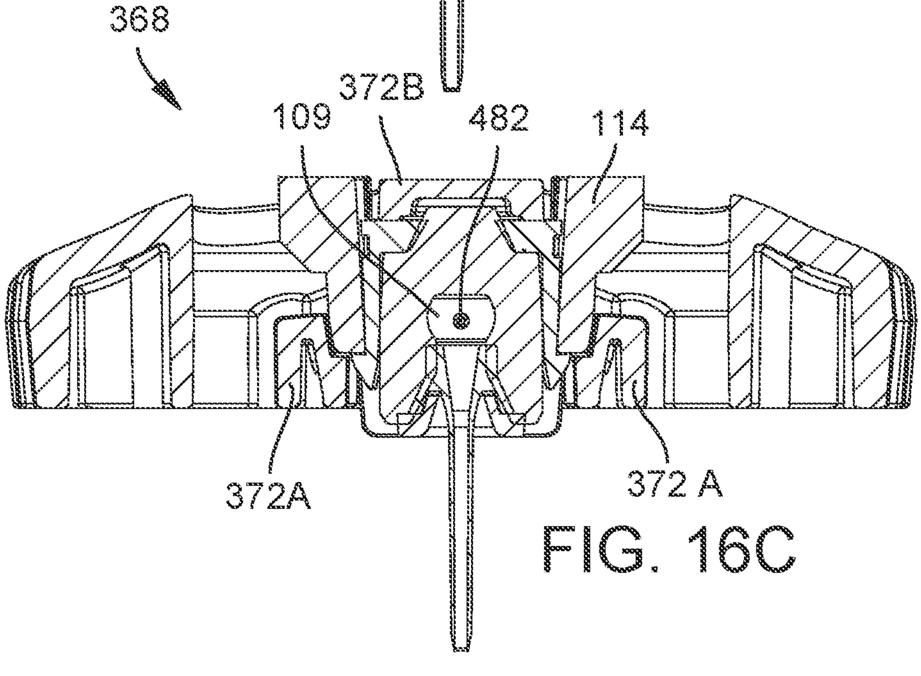
FIG. 16C depicts an example tubing set connector and an example cannula subassembly with the tubing set connector puncturing a septum of the cannula subassembly such that a delivery sharp of the tubing set connector is in fluid communication with a fluid introduction volume of the cannula subassembly.

Referring now also to FIGS. 16A-16C, it may be desirable that portions of the infusion set base 106 and/or cannula subassembly 114 have relatively loose tolerance to facilitate ease of manufacturing. Thus, in some embodiments, a cannula subassembly 114 may be slightly askew when retained in an infusion set base 106 (see, e.g., FIG. 9) due to the loose tolerancing. Additionally, the cannula subassembly

114 may alter position slightly with repeated connection and disconnection of the tubing set connector 368 to the infusion set base 106.

FIGS. 16A-16C depict cross-sectional view through an exemplary cannula subassembly 114 which is held stationary as a tubing set connector 368 is progressively advanced closer to the cannula subassembly 114. As the tubing set connector 368 is docked to the infusion set base 106 (see, e.g., FIG. 9), the exemplary tubing set connector 368 shown in FIGS. 15A-15F may be displaced from an initial position (see, e.g., FIG. 16A) to an intermediary position just prior to the sharp 482 puncturing septum 110 material of the cannula subassembly 114 (see, e.g. FIG. 16B). This range of displacement of the tubing set connector 368 may be referred to as a homing displacement range. As the tubing set connector 368 is displaced through the homing displacement range, any guide surfaces 371A-D of the tubing set connector 368 may contact various regions or surfaces of the cannula subassembly 114 in the event that the cannula subassembly 114 is askew. For illustrative purposes, a depiction of a cannula subassembly 114 in an exaggerated askew position is depicted in FIG. 16A. The infusion set base 106 to which the cannula subassembly 114 would be coupled is hidden for clarity.

As the tubing set connector 368 is further displaced though the homing displacement range, the guide surfaces 371A-D may push, direct, and/or adjust the cannula subassembly 114 into a home position. The sloped sections included on any of the guide surfaces 371A-D may facilitate this by helping to funnel the cannula subassembly 114 into or toward its home position. The cannula subassembly 114 is depicted adjusted into the home position in FIG. 16B (again infusion set base 106 hidden to show cannula subassembly 114 with greater clarity). The guide surfaces 371A-D may adjust the position of the cannula subassembly 114 along two axes which may be substantially perpendicular to one another and in a plane substantially perpendicular to the direction of elongation of the sharp 482 of the tubing set connector 368.

The tubing set connector 368 may then be displaced through a piercing displacement range in which the sharp 482 of the tubing set connector 368 pierces through the septum(s) 110 included in the cannula subassembly 114. At the end of the piercing displacement range and as shown in FIG. 16C, the tip of the sharp 482 may be disposed within the fluid introduction volume 109 of the septum 110 and the connector fingers 370 may enter into engagement with the connector receivers 170 on the infusion set base 106. During puncture of the septum(s) 110, the cannula subassembly 114 may be substantially inhibited from displacing by the guide surfaces 371A-D of the tubing set connector 368. The tubing set connector 368 may be considered to be in a fully docked position on the infusion set base 106 at the end of the piercing displacement range.

This two stage connection of the tubing set connector 368 to the infusion set base 106 may help to ensure that the cannula subassembly 114 septum(s) 110 are located in a consistent position prior to piercing of the septum(s) 110 by the sharp 482 of the tubing set connector 368. This may be true even in the event that loose tolerances are employed during manufacturing of certain components of the infusion set 102. The home position of the cannula subassembly 114 may place the septum(s) 110 in an appropriate position to allow the sharp 482 of the tubing set connector 368 to enter a fluid introduction volume 109 in the cannula subassembly 114. This may allow the fluid introduction volume 109 to be made smaller to minimize dead volume. Moreover, any connector needle passages 222 (see, e.g., FIG. 31B) or other openings in the septum housing 108 which allow the sharp 482 to pass through the septum housing 108 may be made smaller. Additionally, since the home position may be consistently achieved during each reconnection of the tubing set connector 368 to the infusion set base 106, the sharp 482 may puncture the septum(s) 110 in substantially the same location.

In certain examples, a mechanical interference may be present between at least one of the guide surfaces 371C-D on the sharp flanking projection 372B and the nub 220 of the septum 110. At least by the point that the tubing set connector 368 is displaced to the fully docked position, the mechanical interference may cause the nub 220 material to become compressed in a manner similar to the compression from projections 221 described in relation to FIGS. 32A-32D. Lateral adjusting guide surfaces 371D may, for example, cause the nub 220 material to compress toward the puncture pathway for the insertion sharp 132 (see, e.g., FIG. 74B). Height adjusting guide surfaces 371C may cause the nub 220 material to compress and seal against that guide surface 371C.

Figure 17:
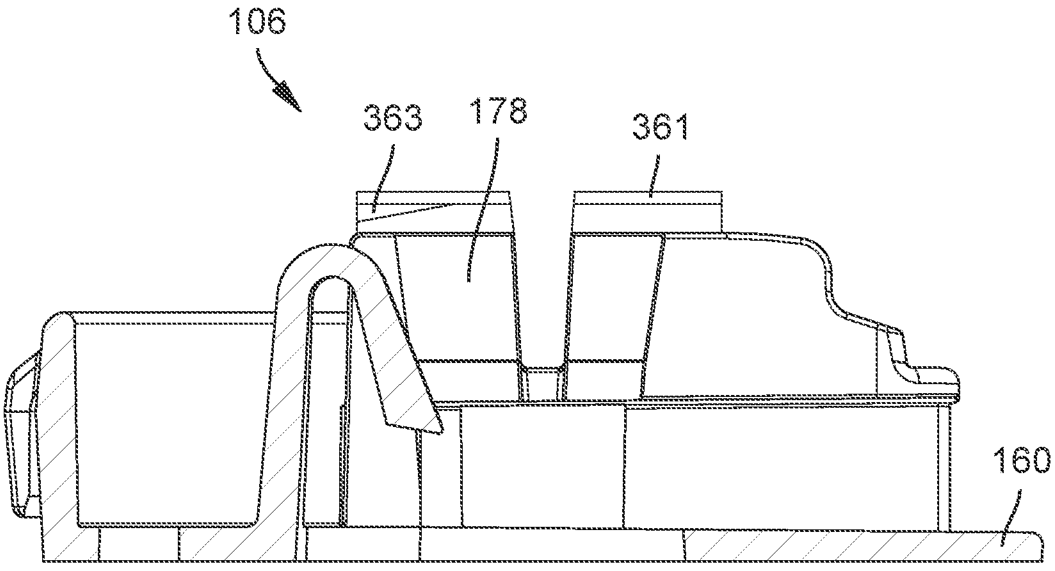
FIG. 17 depicts an example infusion set base with an example deflector.

In some examples, and referring now primarily to FIG. 17, an infusion set base 106 may include a track 361 which may engage with and guide a sharp flanking projection 372 as a tubing set connector 368 (see, e.g., FIGS. 15A-15F) is docked to the infusion set base 106. The track 361 may include a deflector body 363 which may cause a sharp flanking projection 372 to resiliently deflect as a tubing set connector 368 and infusion set base 106 are coupled to one another. In the example shown in FIG. 17, the track 361 is arranged to interface with sharp flanking projection 372B (see, e.g., FIG. 15D) though tracks 361 for other sharp flanking projections may include deflector bodies 363 as well. The example track 361 extends from the portion of the receptacle wall 178 most distal to the platform portion 160 of the base 106. As shown, the deflector body 363 may be a ramp in certain examples. Upon contacting the deflector body 363, the sharp flanking projection 372B may be deflected and pressed against the nub 220 (see, e.g., FIG. 5B) of the septum 110 of a cannula subassembly 114 installed in the infusion set base 106. Though the sharp flanking projection 372B may be deflected against the nub 220 in the example embodiment, sharp flanking projections 372A, B may be deflected against any exposed portion of a septum 110 of a cannula subassembly 114 in various embodiments.

Figure 18A:
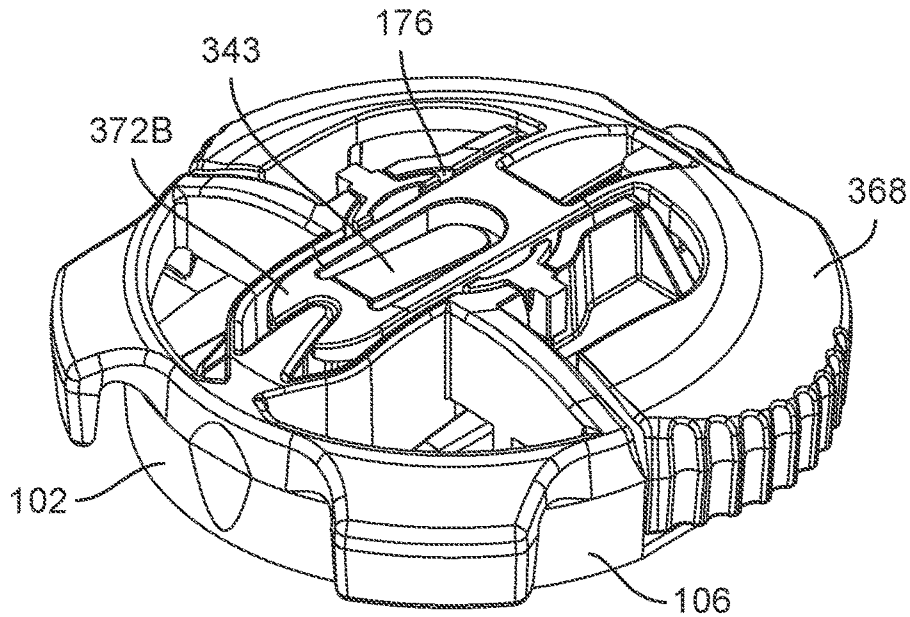
FIGS. 18A-18B depict views of an example tubing set connector and an example infusion set assembly, the tubing set connector including an example tine.
Figure 18B:
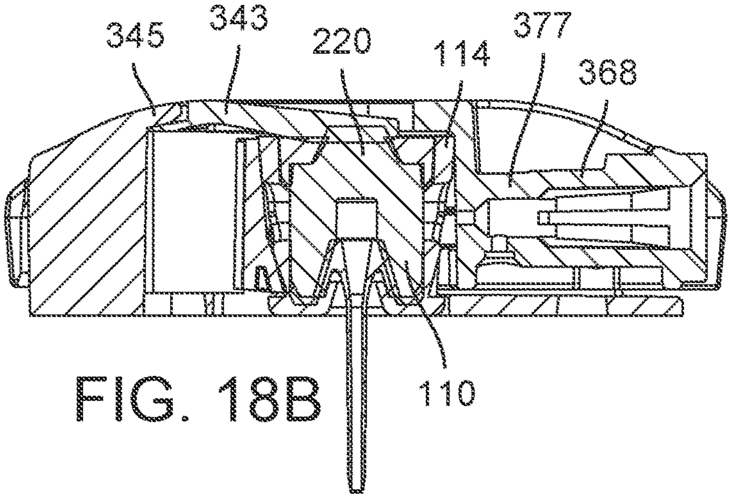
Figure 18C:
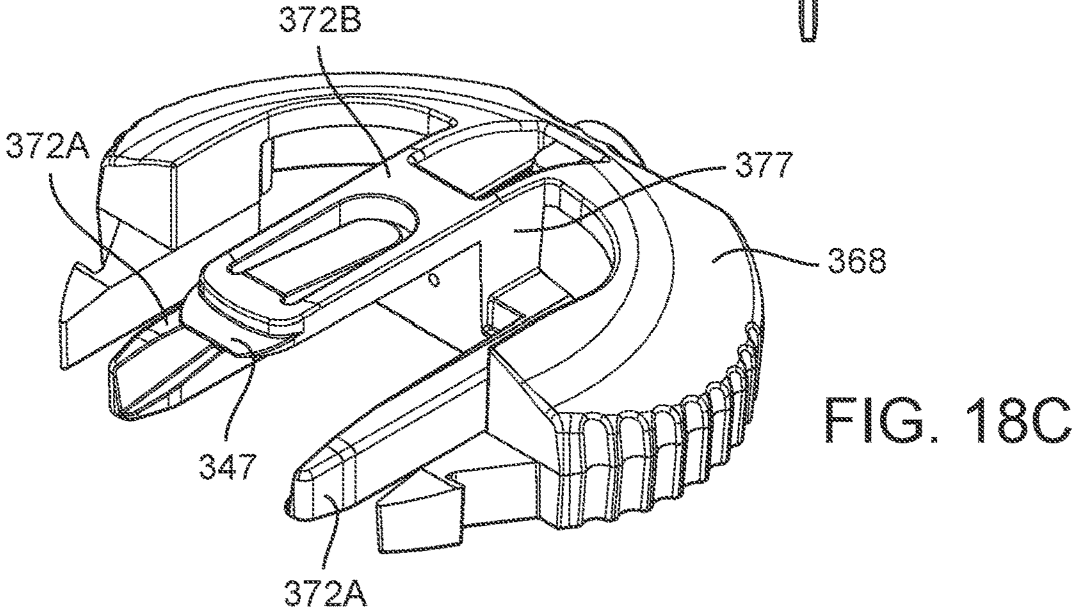
FIG. 18C depicts a perspective view of an exemplary tubing set connector including an example tine.

In some example embodiments, and referring now to FIGS. 18A-18C, a tubing set connector 368 may include a tine 343. The tine 343 may be included in a sharp flanking projection 372A, B of the tubing set connector 368. Such a tine 343 may be cantilevered with respect to the remainder of the sharp flanking projection 372A, B. The tine 343 may be constructed to have at least a sections which extends out of the plane of the remainder sharp flanking projection 372A, B. The tine 343 may be deflected toward the sharp flanking projection 372A, B, but may possess a degree of resiliently which urges the tine 343 to restore to its unstressed state when in a deflected state.

In the example embodiment, the tine 343 is included in sharp flanking projection 372B of the tubing set connector 368. The tine 343 is attached to the sharp flanking projection 372B in a region of the tine 343 which is most distal the flow hub 377 of the tubing set connector 368. The unsupported end of the tine 343 is included in a portion of the tine 343 which extends substantially parallel to the remainder of sharp flanking projection 372B. When the tubing set connector 368 is coupled to an infusion set 102, the tine 343 may be advanced over a cannula subassembly 114 coupled within a receptacle 176 of the infusion set base 106. The tine 343 may resiliently deflect as this occurs. When in the coupled state, tine 343 may be prevented from fully returning to the unstressed state by the cannula subassembly 114. Instead, the tine 343 may press against the nub 220 of the septum 110 of cannula subassembly 114.

In some embodiments, the end of the sharp flanking projection 372B most distal the flow hub 377 may include ramp 347. Such a ramp 347 may be included on a portion of the end (see, e.g., FIG. 18B) or may extend across the entirety of the end (see, e.g., FIG. 18C). The infusion set base 106 may include a deflector 345 into which the ramp 347 may be advanced when the tubing set connector 368 is coupled to the infusion set 102. The deflector 345 may be a projection extending from a portion of the infusion set base 106 in some embodiments. Alternatively, the deflector 345 may be a slot in the infusion set base 106 into which the ramp 347 is displaced during coupling of a tubing set connector 368 to an infusion set assembly 102. As the ramp 347 is displaced into the slot 345, the sharp flanking projection 372B may be deflected toward the platform portion 160 of the infusion set base 106. This may, in turn, cause the tine 343 to be further pressed against the nub 220.

Though shown in relation to FIGS. 18A-18C, tines 343 and ramps 347 may be included on any tubing set connectors 368 described herein. Deflectors 345 may be included on any infusion set base 106 described herein.

Figure 19A:
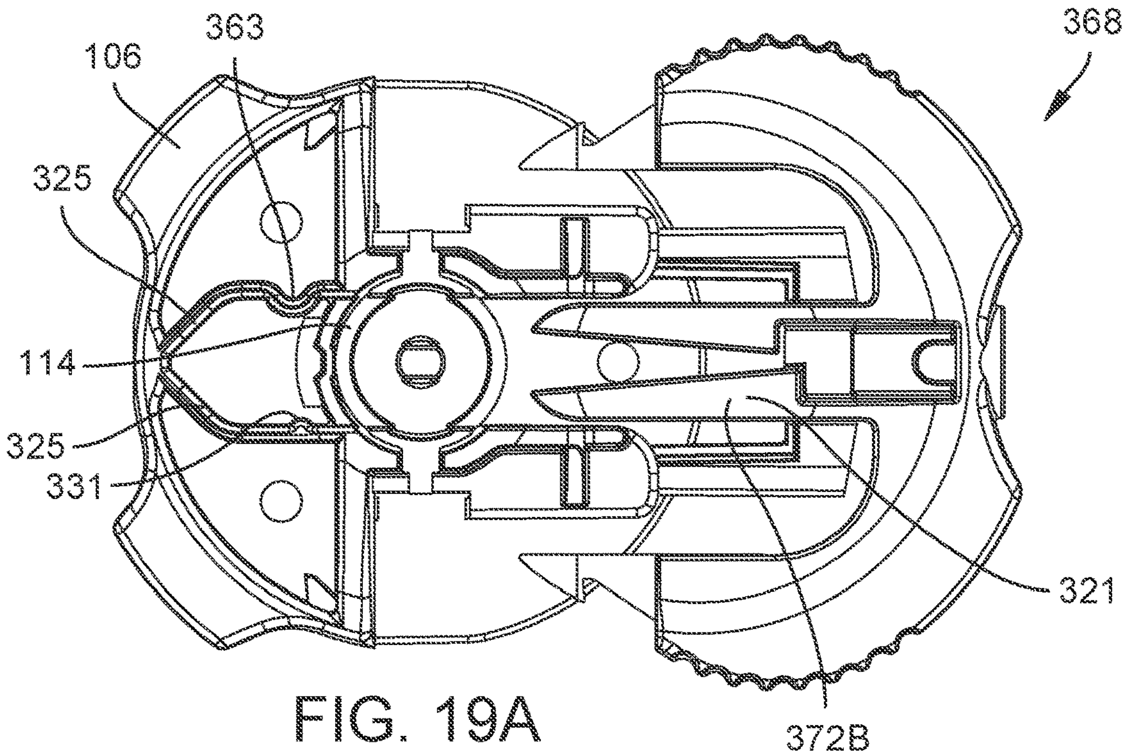
FIG. 19A depicts a top down view of an example infusion set assembly and an example tubing set connector including an example clamp, the tubing set connector being decoupled from the infusion set assembly.
Figure 19B:
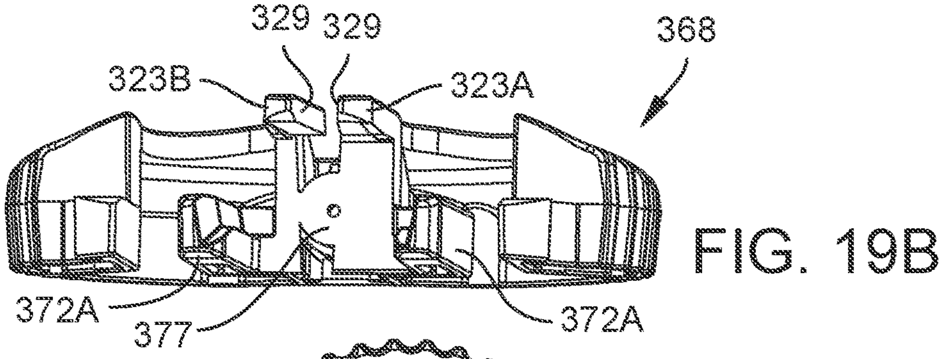
FIG. 19B depicts a view of an example tubing set connector having an example clamp.
Figure 19C:
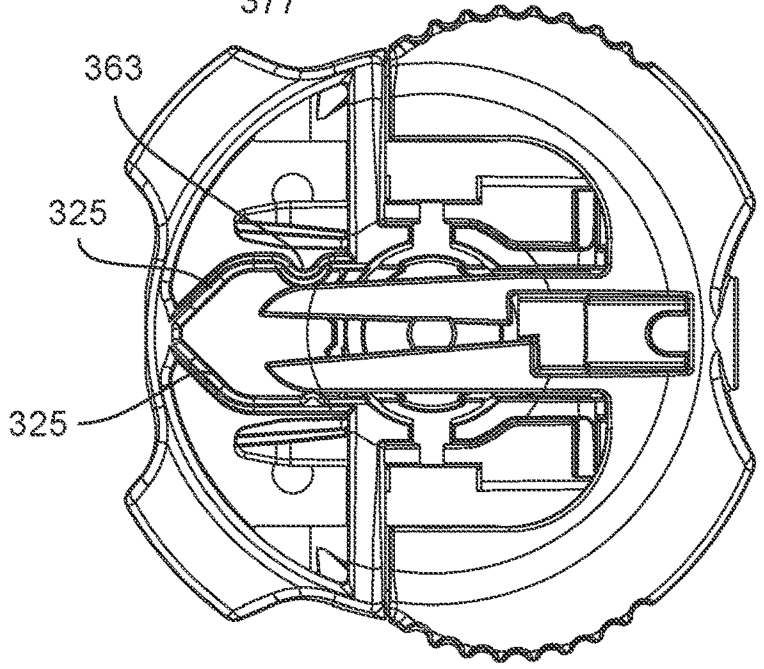
FIG. 19C depicts a view of an example tubing set connector with an example clamp coupled to an example infusion set assembly.

Referring now to FIGS. 19A-19C, in some embodiments a tubing set connector 368 may include a clamp 321. As a tubing set connector 368 including a clamp 321 is coupled into engagement with an infusion set assembly 102, the clamp 321 may act against an exposed portion of a septum 110 of a cannula subassembly 114 of the infusion set assembly 102. The clamp 321 may, for example, press into opposing sides of an exposed portion of a septum 110 (e.g. a nub 220) to compress the septum 110 material.

A clamp 321 may, in some examples, be defined in a sharp flanking projection 372 or may form a sharp flanking projection 372. As shown, sharp flanking projection 372B is formed as a clamp 321. The clamp 321 may include a first body 323A and a second body 323B which are spaced from one another by a gap. At least one of the first and second body 323A, B may be configured to displace toward the other of the first and second bodies 323A, B. Any suitable arrangement to facilitate such displacement may be used. In the exemplary embodiment and as best shown in FIG. 19B, the second body 323B is coupled to the flow hub 377 along a portion of an end of the second body 323B proximate the flow hub 377. This partial connection may allow the second body 323 to resiliently deflect or pivot toward the first body 323A. The first body 323A may be connected along the entirety of its second end to the flow hub 377. Thus, the example first body 323A may be resistant to deflection and may remain stationary.

The infusion set assembly 102 may include a deflector body 363. In the example embodiment, the infusion set base 106 includes a set of ribs 325. The deflector body 363 is defined as an outcrop or bump in one of the ribs 325. As the tubing set connector 368 is coupled into engagement with an infusion set assembly 102, a portion of the clamp 321 may be displaced into the deflector body 363. Further displacement of the tubing set connector 368 may cause deflector body 363 to deflect a part of the clamp 321. In the example embodiment, the second body 323B may be deflected toward the first body 323A as the second body 323B is driven into the deflector body 363. In turn, the clamp 321 may close about the nub 220 of the septum 110. Clamping surfaces 329 of the first and second bodies 323A, B may press against and compress the nub 220. To help inhibit turning or veering of the tubing set connector 368 as the clamp 321 contacts the deflector body 363, a stop member 331 may be included. The stop member 331 may present a mechanical interference to undesired movement of the tubing set connector 368 during coupling. In the example embodiment, the stop member 331 is a bulge on the rib 325 opposite the deflector body 363.

Referring to FIGS. 15A-19C, compression of the nub 220 of the septum 110 and ensuring a sharp 482 of a tubing set connector 368 punctures a septum 110 in substantially the same location as described above may be desirable for a variety of reasons. For example, these features may help extend a range over which a cannula subassembly 114 may resist leaks to pressures even further in excess of those expected during use. Compression of the nub 220 may allow for a wider variety of materials to be used for a septum 110 of a cannula assembly 114. Likewise, a greater range of material durometers may be used. Compression of the nub 220 via projections 221 (see, e.g., FIGS. 32A-32D) or lowering potential compressive stress relaxation of the material forming the nub 220 (see discussion in relation to FIGS. 32A-32D) may also aid in accomplishing the above.

Figure 20A:
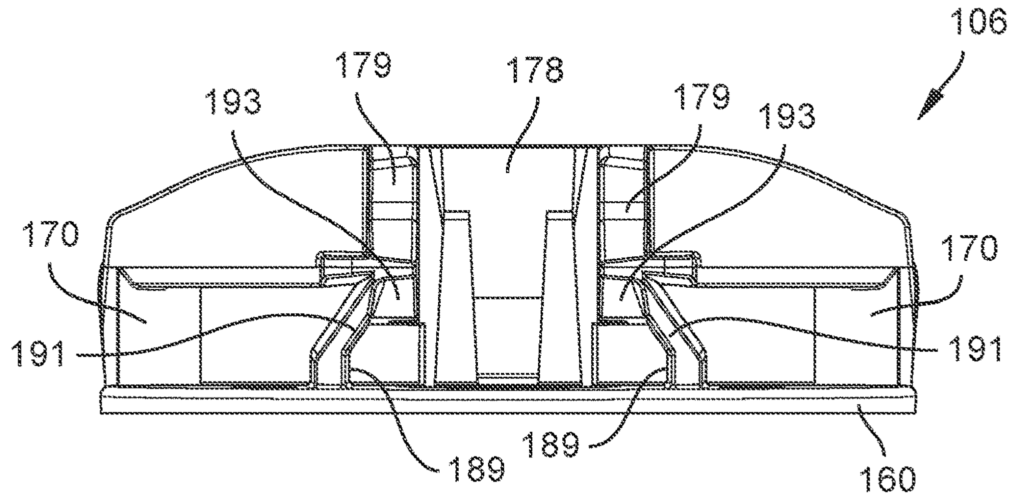
FIG. 20A depicts a side view of an example infusion set base.
Figure 20B:
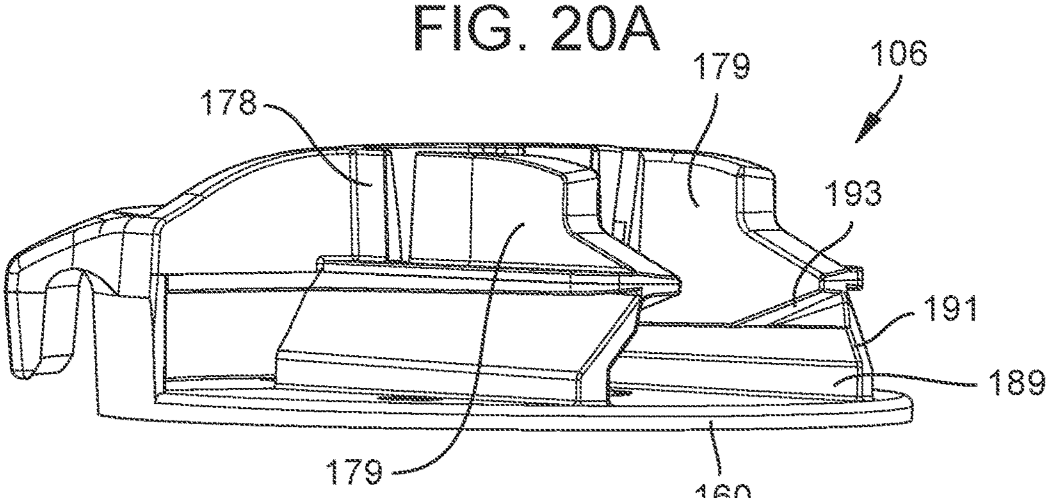
FIG. 20B depicts another side view of the example infusion set base of FIG. 20A.
Figure 20C:
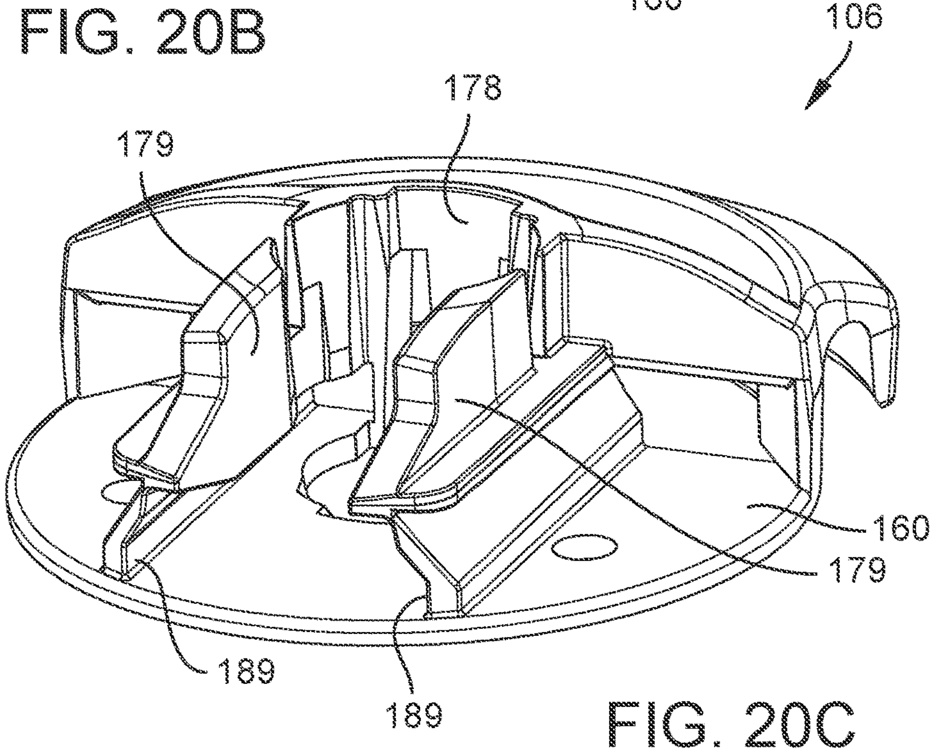
FIG. 20C depicts a perspective view of the example infusion set base of FIG. 20A.

Referring now also to FIGS. 20A-20C, another example base 106 is depicted. The example base 106 may couple to a tubing set connector 368 such as that shown in FIG. 14A and FIG. 14B. The base 106 may include connector receivers 170 which may allow for coupling of the base 106 with cantilevered fingers 370 on the tubing set connector 368 as described elsewhere herein. Though not shown in the example embodiment, guides 172 for each of the connector fingers 370 such as those shown in FIG. 6 and FIG. 10A may be included. Such guides 172 may also be included on any other infusion set base 106 shown or described herein. As shown, the base 106 may define receiver tracks 189 which may accept a set of sharp flanking projections 372 which are in the plane of the connector fingers 370. As shown, the receptacle wall extensions 179 and the portions of the receptacle wall 178 which extend parallel to one another may be separated from one another by a channel. The receiver tracks 189 are recessed into the receptacle wall extensions 179 and the portions of the receptacle wall 178 which extend parallel to one another adjacent the platform 160. Thus, the width of the channel between the receptacle wall extension 179 and portions of the receptacle wall 178 may be greatest adjacent the platform 160. The width of the channel may decrease as distance from the platform 160 increases. As shown, the receiver tracks 189 may each include a sloped wall 191. The sloped wall 191 may aid in locating of the sharp flanking projections 372 of a tubing set connector 368 in the receiver tracks 189. Additionally, the base 106 may include ramped sections 193 which are located at the open end of the receiver tracks 189. The ramped section 193 may, similarly to the second section 173 of the guides 172 in FIGS. 10A-10B, allow the tubing set connector 368 to initially be introduced at a substantial angle to the plane of the platform 160. Further introduction may cause the flanking projections 372 to be redirected into the receiver tracks 189. Thus, the sloped walls 191 and ramped section 193 may facilitate blind insertion of the tubing set connector 368 into coupled relationship with the base 106.

Referring now to FIGS. 21A-24C, additional example infusion set bases 106 are depicted. The bases 106 may include connector receivers 170 which may allow for coupling of the base 106 a tubing set connector 368. The example base 106 shown in FIGS. 21A-F may couple to a tubing set connector 368 such as that shown in FIGS. 15A-16C as described elsewhere herein. The example bases 106 shown in FIGS. 22A-24C may couple to a tubing set connector 368 such as those shown in FIGS. 25A-26C.

As shown, the receptacle wall extensions 179 may be separated from one another by a channel. The receptacle wall extensions 179 and the portions of the receptacle wall 178 forming each side of the channel may also include a segment 177 which is disposed substantially parallel to the platform portion 160 of the infusion set base 106. Thus, the channel may include a wide section adjacent the platform portion 160 and a narrow portion distal to the platform portion 160. The wide section of the channel may define receiver tracks 189 which may accept a set of sharp flanking projections 372A. Though not shown in FIGS. 21A-21F and FIGS. 22A-24C, ramped sections 193 (see, e.g., FIGS. 20A-20C) may be included in some embodiments. The receiver tracks 189 may guide sharp flanking projections 372A as a tubing set connector 368 is coupled to a base 106. The channel may thus be referred to as a guide channel.

Figure 21A:
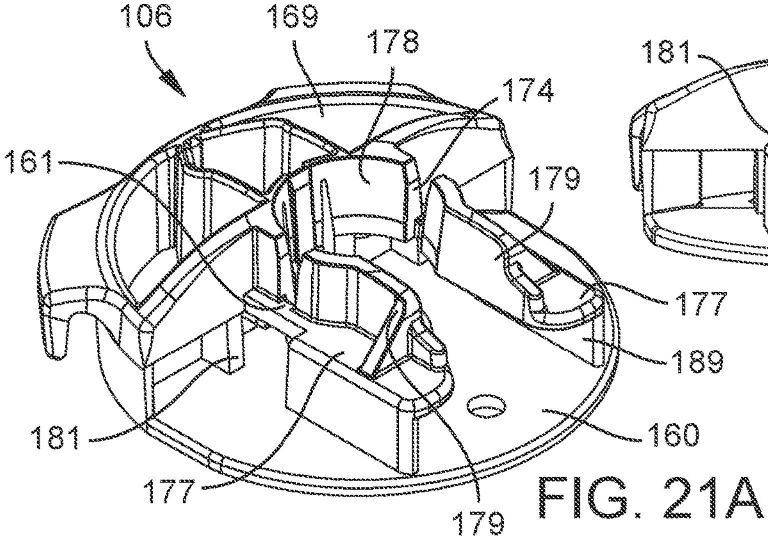
FIGS. 21A-21F depict various views of another example infusion set base.
Figure 21B:
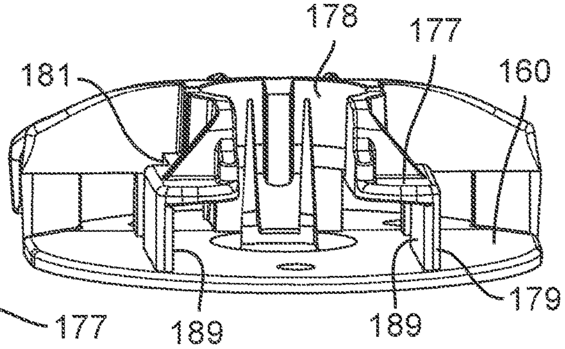
Figure 21C:
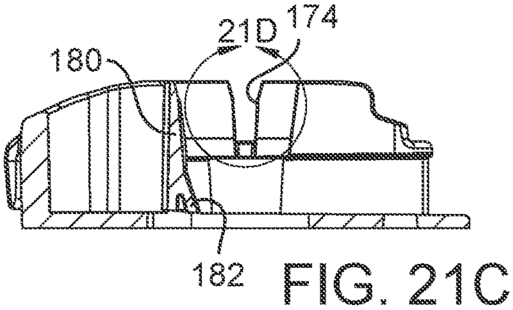
Figure 21D:
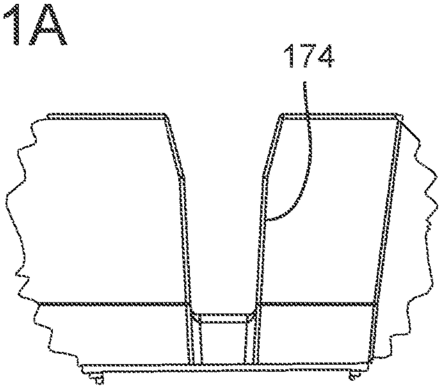
Figure 21E:
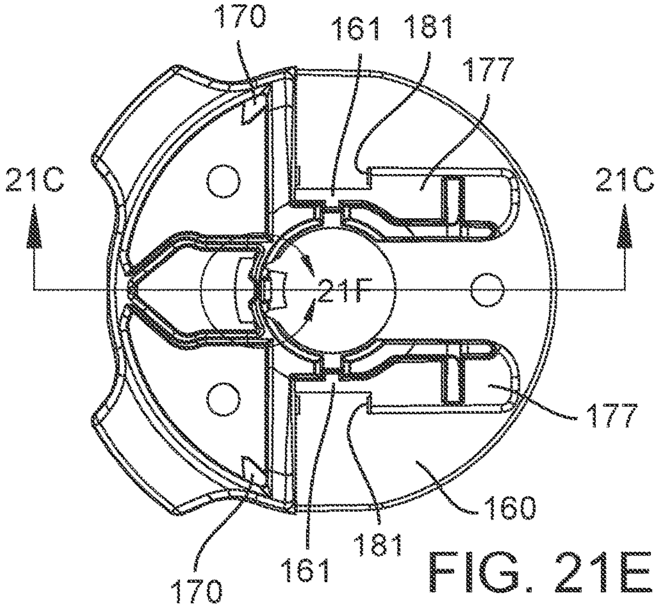
Figure 21F:
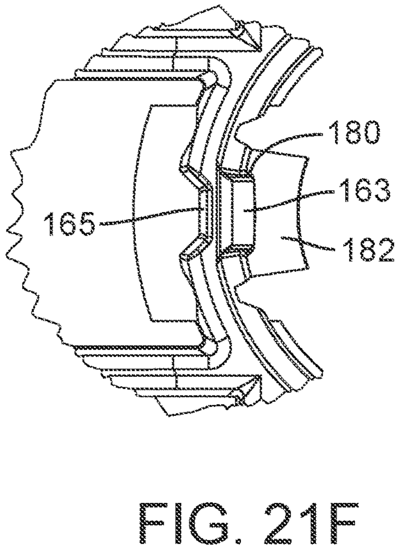

As shown, the receptacle walls 178 may include breaks 181 in the portion of the receptacle walls 178 defining the receiver tracks 189. The breaks 181 may be aligned with the notches 174 included in the receptacle walls 178. The breaks 181 may extend through a portion of the segments 177 of the receptacle wall 178 which is parallel to the platform portion 160. The more medial regions 161 of these segment 177 may be uninterrupted by the breaks 181. The breaks 181 may extend from the segments 177 to the platform portion 160. The breaks 181 may define receiving slots for a portion of a respective arm 332 (see, e.g., FIG. 59A) of part of an inserter assembly 100. These receiving slots may also be referred to as inserter interface slots. The medial regions 161 adjacent the breaks 181 may act as a catch for a ledge 348 defined on the arms 332 mentioned above (further described in relation to FIG. 59A). As best shown in FIG. 21D, the notches 174 in the receptacle wall 178 may be tapered along at least a portion of their length (e.g. portion most distal to the platform portion 160). Such tapered notches 174 may aid in guiding a cannula subassembly 114 into place as the infusion set 102 is assembled. In some embodiments, the entirety of each notch 174 may be tapered to varying degrees. For example, a portion of each notch 174 most distal the platform portion 160 may have a greater taper than a second portion of each notch 174 more proximal the platform portion 160. Such tapered notches 174 may be included on any of the infusion set bases 106 described or shown herein.

The example infusion set base 106 in FIGS. 21A-F also includes a receptacle wall 178 including a cantilevered section 180 with a protuberance 182. The cantilevered section 180 may be constructed so as to resiliently deflect out of the way as a cannula assembly 114 is introduced, but resist deflection when a force exerted along the long axis of the cantilevered section 180 is applied. The cantilevered section 180 may include one or more ribs 163. The rib(s) 163 may project from the cantilevered section 180 into the receptacle 176 and may extend along the length of the cantilevered section 180. Though ribs 163 are shown, other projecting bodies may be included in alternative embodiments. One or more recess 165 may be disposed on a side of the cantilevered section 180 opposite that from which the protuberance 182 extends. A recess 165 may be disposed opposite each of the ribs 163 or otherwise thickened regions. As a cannula assembly 114 is introduced, the rib(s) 163 may help to locate the cannula subassembly 114 within the receptacle 176. The rib(s) 163 may also inhibit wiggling of the cannula subassembly 114 when the cannula subassembly 114 is within the receptacle 176 and coupled to the base 106.

Figure 22A:
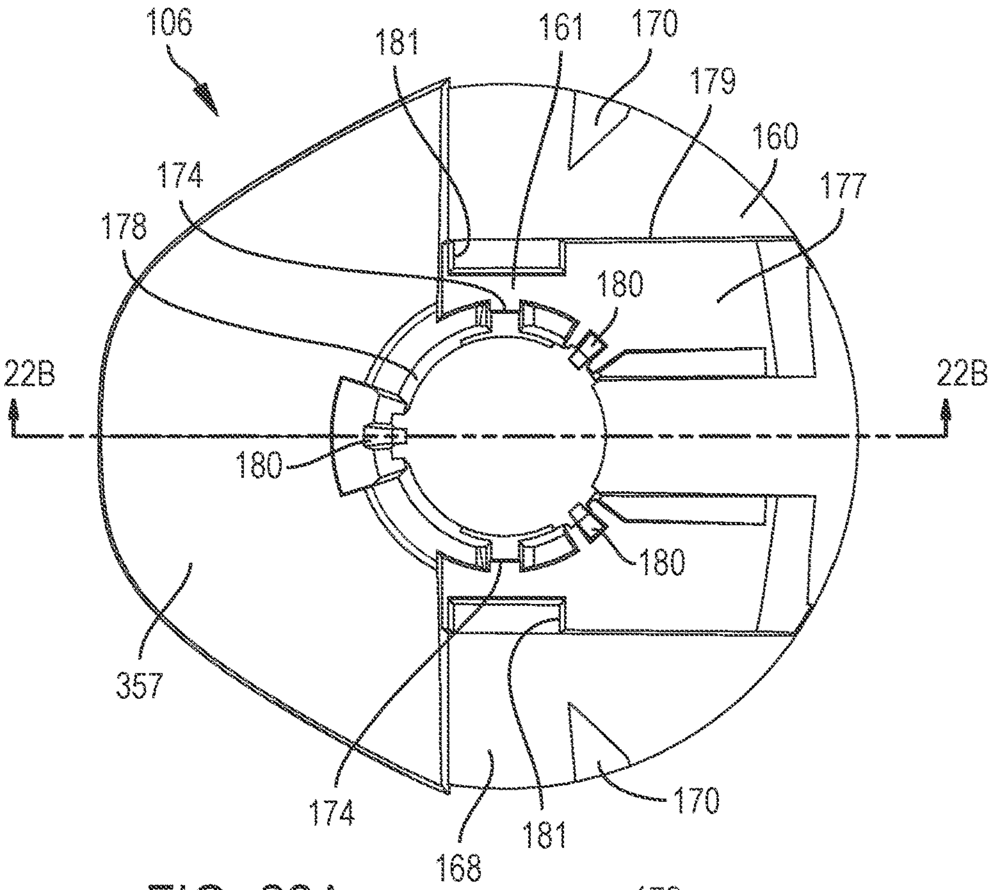
FIGS. 22A-22C depict various views of another example infusion set base.
Figure 22B:
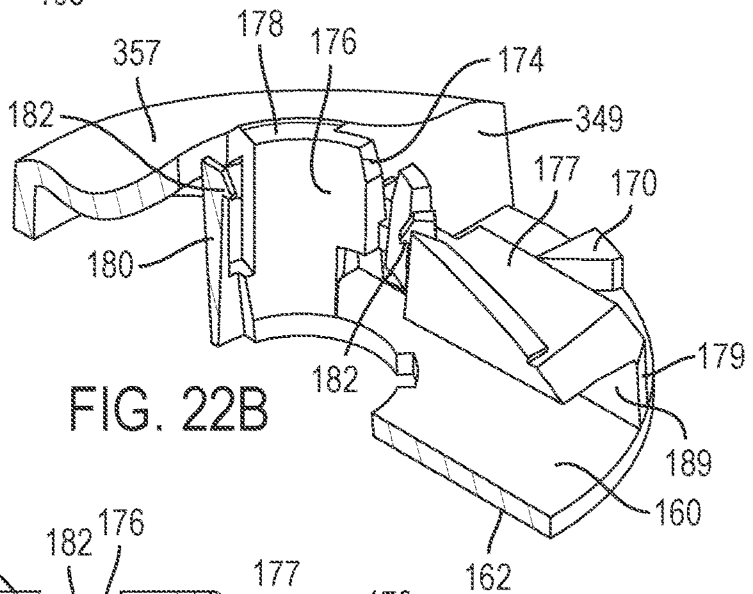
Figure 22C:
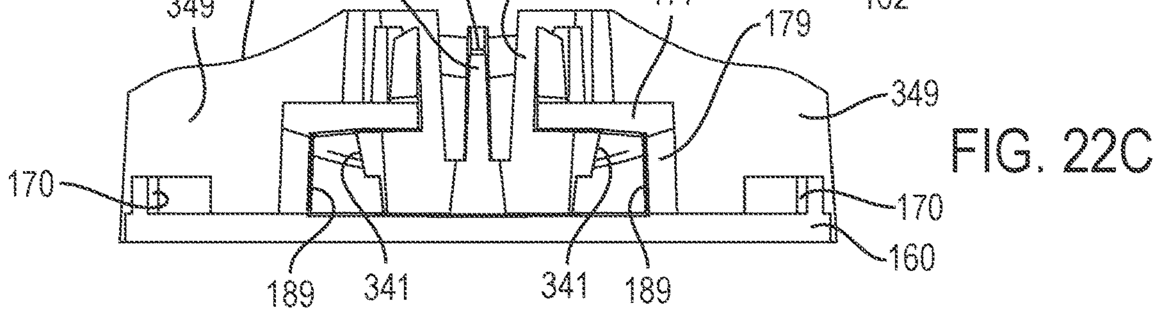

The example infusion set base 106 depicted in FIGS. 22A-22C includes a plurality of cantilevered sections 180 each including protuberances 182. The receptacle wall 178 includes a cantilevered section 180. This cantilevered section 180 projects from the receptacle wall 178 away from the platform portion 160 such that the unsupported end including the protuberance 182 is the portion of the cantilevered section 180 most distal to the platform portion 160. A pair of cantilevered sections 180 are also disposed opposite one another on the receptacle wall extensions 179 adjacent the receptacle wall 178. This pair of cantilevered sections 180 extend in a direction away from (e.g. substantially perpendicular to) the platform portion 160 such that the unsupported ends including the respective protuberances 182 are the portions of the cantilevered sections 180 most distal to the platform portion 160. As a cannula subassembly 114 is introduced, each of the cantilevered sections 180 may resiliently deflect out of the way to allow passage of the cannula subassembly 114 into the infusion set base 106. The ramped faces of the protuberances 182 may aid in facilitating this deflection. Once the cannula subassembly 114 has advanced beyond a threshold amount into the receptacle 176 of the infusion set base 106, the cannula subassembly 114 may be displaced clear of the protuberances 182. The cantilevered sections 180 may each restore to a less stressed or less deflected state and the protuberances 182 may each overhang a portion of the cannula subassembly 114 (e.g. the septum housing 108). Thus, a cannula subassembly 114 may be captured within the infusion set base 106. Though three cantilevered sections 180 are shown, differing numbers of cantilevered sections 180 may be included in alternative embodiments. The receptacle wall 178 may, for example, include a greater number of cantilevered sections 180. In alternative embodiments, at least some of the cantilevered sections 180 may project toward the platform portion 160 such that their unsupported, protuberance 182 bearing ends are the portions of the cantilevered sections 180 most proximal the platform portion 160 (see, e.g., cantilevered section 180 of FIGS. 21A-F). The height of each cantilevered sections 180 is substantially the same in FIGS. 22A-22C. In alternative embodiments, the height of at least one cantilevered section 180 may differ. The heights may be selected such that the protuberances 182 overhang and capture the cannula subassembly 114 to be installed in the receptacle 176. Cannula subassemblies 114 for use with infusion set base 106 embodiments such as that shown in FIGS. 22A-22C may not include notches 186 (see, e.g., FIG. 5A) or salient 388 (see, e.g., FIG. 8A). The top face 394 (see, e.g., FIG. 29C) of the side wall 392 of the septum housing 108 (see, e.g., FIG. 29C) may provide the engagement surface by which the protuberances 182 retain the cannula subassembly 114 in the base 106.

Referring now to FIGS. 23A-24C, two exemplary infusion set base 106 embodiments are depicted. As shown, in certain examples, an additional retainer member 261 may be included and may project from the platform portion 160 of the infusion set base 106. The example embodiments depict the retainer members 261 on an infusion set base 106 similar to that depicted in FIGS. 22A-22C, however, such retainer members 261 may be included on any infusion set base 106 described herein (e.g. that shown in FIGS. 21A-F). The retainer members 261 are disposed adjacent the receptacle 176 and nearest the open end of the guide channel. In the example embodiments, the retainer members 261 are positioned opposite cantilevered sections 180. Such an example retainer members 261 may be hooked or hook like in shape. As a tubing set connector 368 is coupled to the exemplary infusion set bases 106, a sharp 482 (see, e.g., FIG. 15F) may travel along an approach path within the respective guide channels. The height of the retainer members 261 may be selected so as to not project into the approach path of the sharp 482, thus the retainer members 261 may not obstruct the sharp 482 during coupling of a tubing set connector 368. As shown in various embodiments described herein, a cannula subassembly 114 may include a set of notches 186 (see, e.g., FIG. 5A or FIG. 24E). The notches 186 may be disposed on opposing sections of the exterior side wall of a portion of the cannula subassembly 114.

Figure 23A:
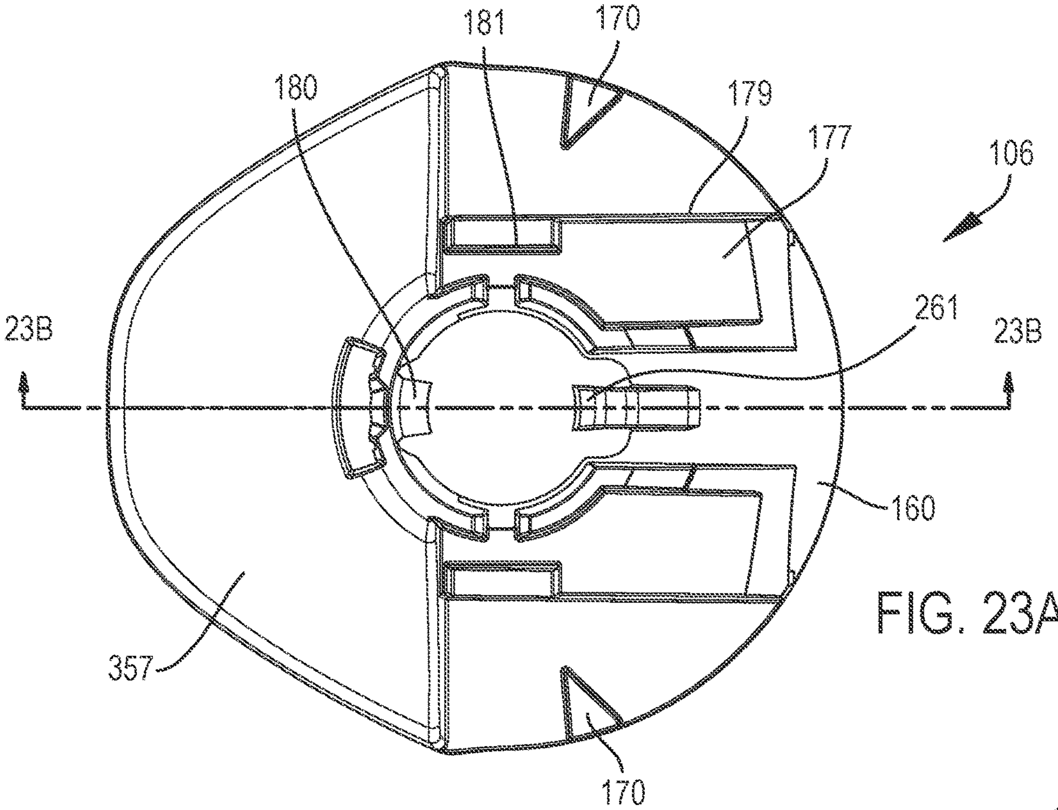
FIGS. 23A-23C depict various views of another example infusion set base.
Figure 23B:
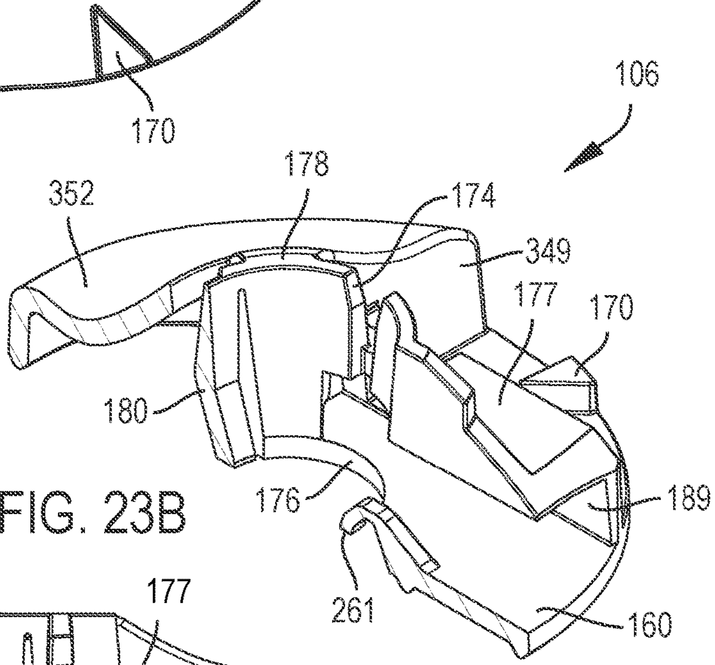
Figure 23C:
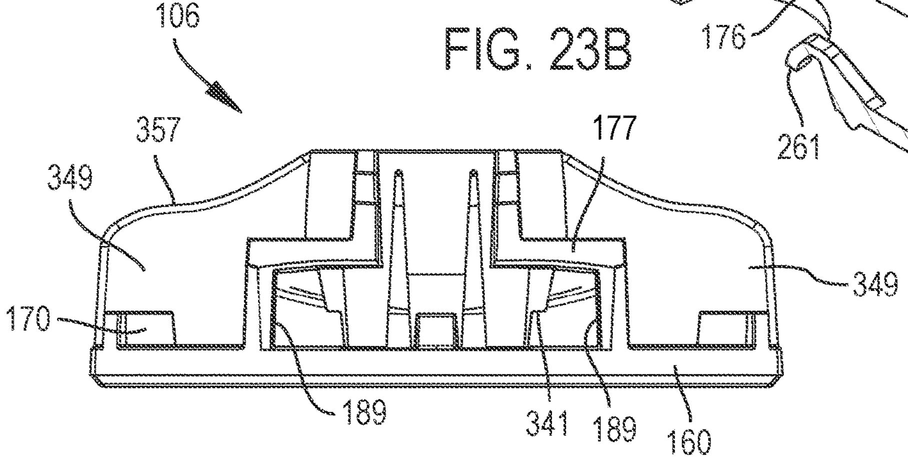
Figure 24A:
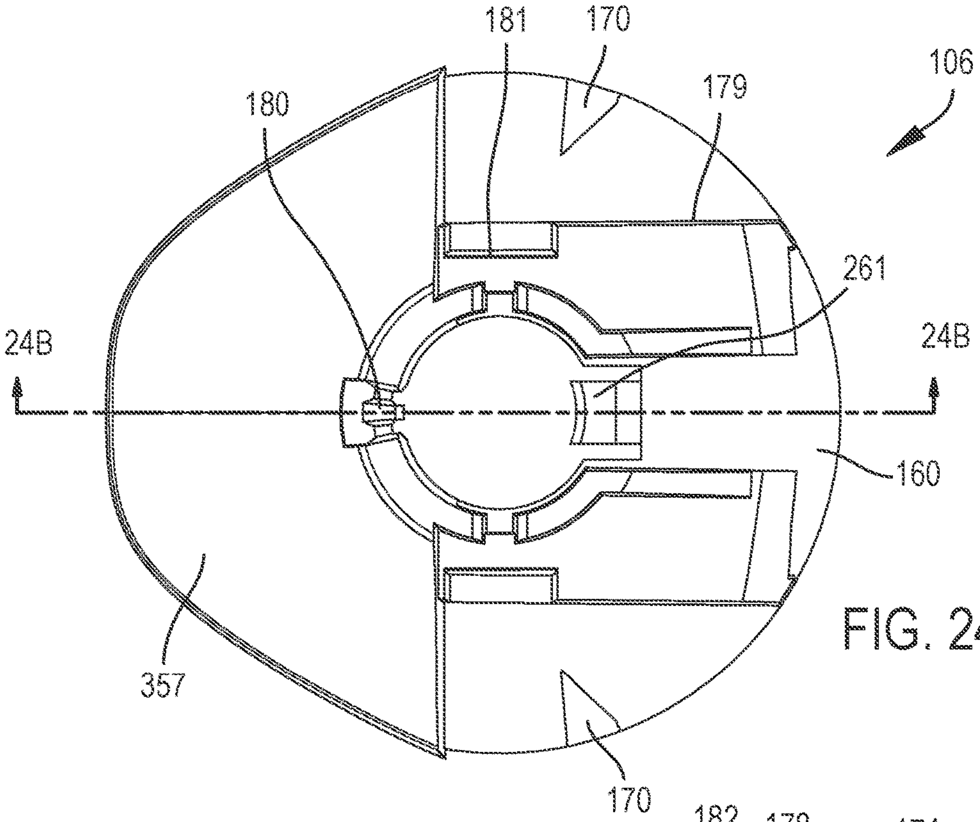
FIGS. 24A-24C depict various views of another example infusion set base.
Figure 24B:
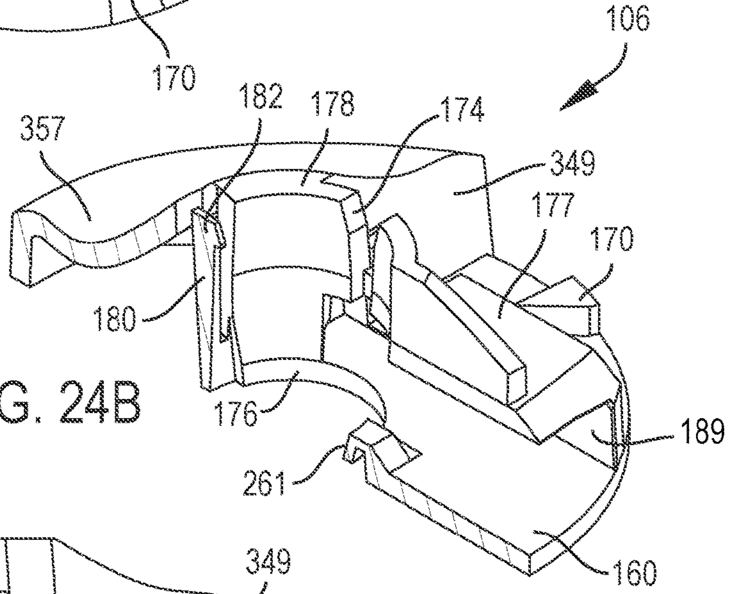
Figure 24C:
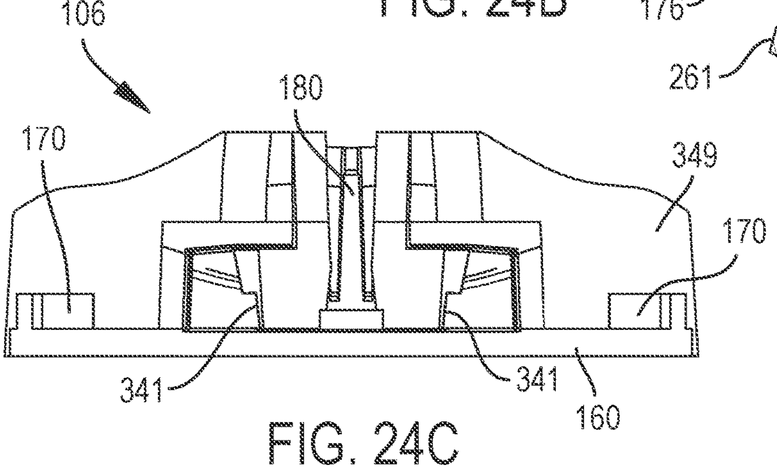

With reference to FIGS. 23A-23C, the cantilevered section 180 of the receptacle wall 178 may snap into a first of the notches 186 retaining the cannula subassembly 114 within the receptacle 176 after the cannula subassembly 114 has been advanced into the receptacle 176 beyond a certain distance. The retainer member 261 may deflect as the cannula subassembly 114 is advanced into the receptacle 176. The retainer member 261 may restore to an undeflected (or at least less deflected) state and snap into the second of the notches 186 when the cannula subassembly 114 has been advanced into the receptacle 176 beyond a certain distance. In various embodiments, the cantilevered section 180 and retainer member 261 may snap into the notches 186 at substantially the same time. In the example embodiment shown in FIGS. 24A-24C, the protuberance 182 of the cantilevered member 180 may clip in place against the top face 394 of the septum housing 108 of the cannula subassembly 114. The retainer member 261 may help to limit jostling of the cannula subassembly 114 within the receptacle 176 and potentially allow for looser tolerancing. Additionally, the retainer member 261 may assist in centering the cannula subassembly 114 within the receptacle 176.

Referring now to FIGS. 25A-26C, example tubing set connectors 368 which may be used, for example, with an infusion set base 106 such as those shown in FIGS. 22A-24C are depicted. The example tubing set connectors 368 include sharp flanking projections 372A, B, but do not include connector fingers 370. The example tubing set connectors 368 include a set of connector latches 365. Though shown in relation to FIGS. 25A-26C, connector latches 365 may be included in place of connector fingers 370 of other embodiments of tubing set connectors 368 described herein. The example connector latches 365 may be disposed on an undersurface of the body 367. As the tubing set connectors 368 are coupled to an infusion set 102, the connector latches 365 may engage the connector receivers 170 on the infusion set base 106. The body 367 of the tubing set connector 368 may double as a shield which may help to block fingers or objects from inadvertently disengaging the connector latches 365 from the connector receivers 170. To facilitate this, and referring now also to FIGS. 22A-24C, the connector receivers 170 may be on opposing portions of the base 106 intermediate the closed and open ends of the guide channel and lateral to the receptacle wall extensions 179. The portions of the body 367 including the connector latches 365 may attach to the flow hub 377 so as to be deflectable relative to the flow hub 377 and may be referred to herein as deflectable body segments. Squeezing force toward the axis of the sharp 482 exerted on these segments of body 367 may displace the connector latches 365 out of engagement with the connector receivers 170. The tubing set connector 368 may then be separated from the infusion set 102 if desired. These segments of the body 367 may include uneven, scalloped, ruffled, etc. gripping regions 475 to assist in grasping of the tubing set connector 368. In some examples (best shown in FIG. 26C), the connector latches 365 may include stop bodies 479. The stop bodies 479 may limit deflection of the deflectable body segments as they may abut against the receptacle wall extensions 179 when deflected beyond a certain amount. Additionally, as best shown in FIG. 26B, in certain example tubing set connectors 368, the tubing set connector 368 may have an angled face 477 on each deflectable body segment. When the deflectable body segments are squeezed toward one another, the angled faces 479 may be displaced against the connector receivers 170. The angled faces 479 may cause the tubing set connector 368 to push away from the engaged state as the angled faces 479 are driven into the connector receivers 170 on the infusion set base 106. Thus, the angled faces 479 may facilitate decoupling of a tubing set connector 368 from the infusion set base 106.

Still referring to FIGS. 22A-26C, as the example tubing set connectors 368 cover the couplings between the connector latches 365 and the connector receivers 170, a shielding wall 169 (see, e.g., FIG. 21A) is not included in the example infusion set base 106 of FIGS. 22A-24C. When coupled together, the example tubing set connector 368 and base 106 may form a low profile, contoured assembly which mitigates potential for snagging of, for example, clothing.

Still referring primarily to FIGS. 22A-24C, the portion of the example base 106 opposite the open end of the guide channel, may be formed by a contoured wall 357. The contoured wall 357 may extend from the top of the receptacle wall 178 to a portion of the periphery of the base 106 opposite the open end of the guide channel. The contoured wall 357 may trend toward dropping in the direction of the plane of the platform portion 160 as proximity to the periphery of the base 106 increases. The platform portion 160 may not continue under the contoured wall 357. Instead, a cavity may be present on the underside of the contoured wall 357 which may help facilitate molding. As shown in FIG. 22B for instance, a transition wall 349 may extend from the platform portion 160 to the edge of the contoured wall 357 most proximal the open end of the guide channel. The transition wall 349 may be disposed generally perpendicular to the axis of the guide channel in some embodiments.

Figure 25A:
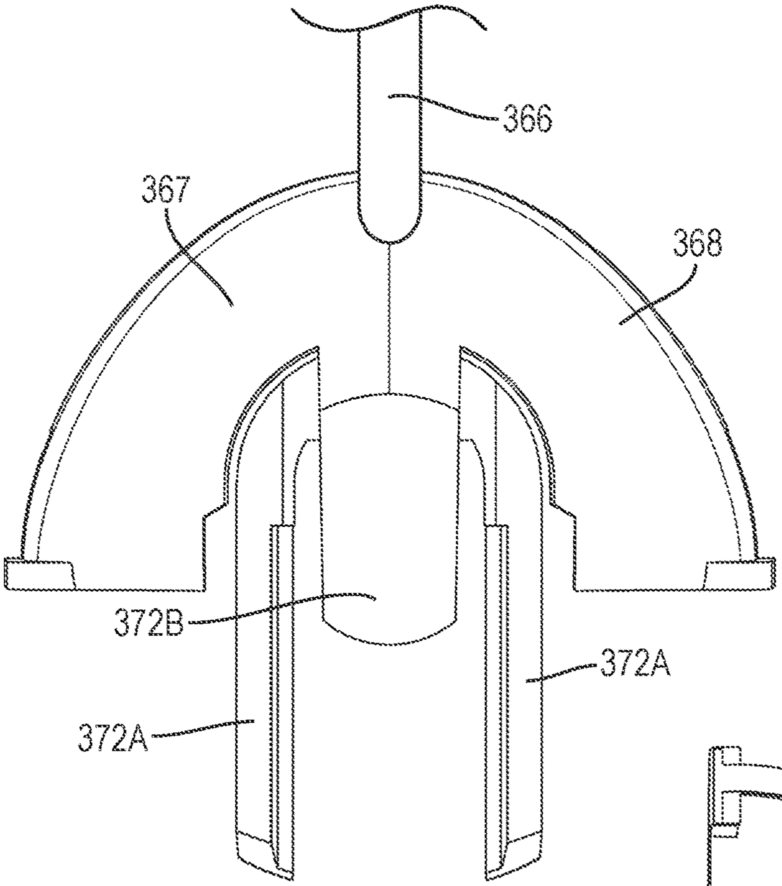
FIGS. 25A-25C depict various views of an exemplary tubing set connector.
Figure 25B:
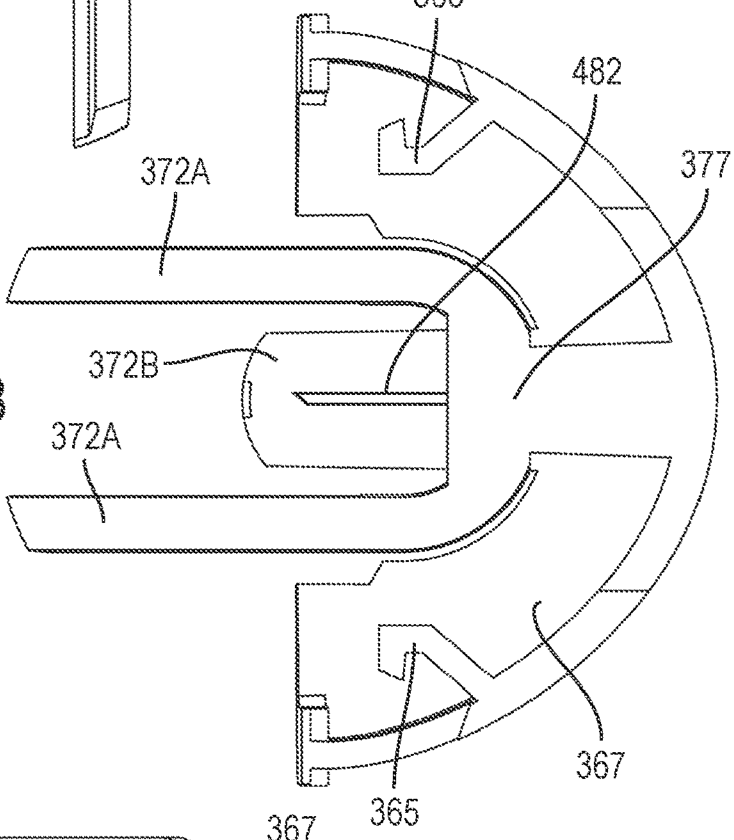
Figure 25C:
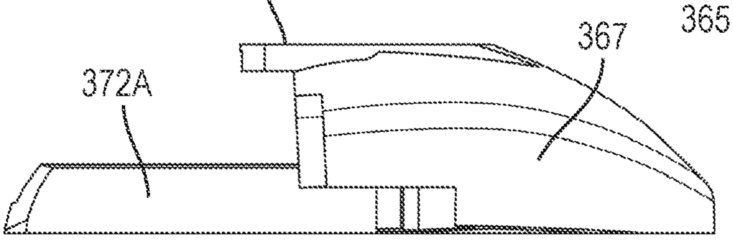

Referring now also to FIGS. 25A-25C, the transition wall 349 may include passages 341 which extend through the transition wall 349 and into the cavity on the underside of the contoured wall 357. When the tubing set connector 368 is coupled to the infusion set base 106, the sharp flanking projections 372A may extend through passages 341 in the transition wall 349. The unsupported ends of the sharp flanking projections 372A may project into the cavity. The contoured wall 357 of the infusion set base 106 may also be substantially even with the exterior surface of the body 367 of the tubing set connector 368. The deflectable body segments of the tubing set connector 368 body 367 may seat against the transition wall 349 of the infusions set base 106 such that no substantial gap is present between the transition wall 349 and the tubing set connector 368 when the base 106 and tubing set connector 368 are connected.

Figure 26A:
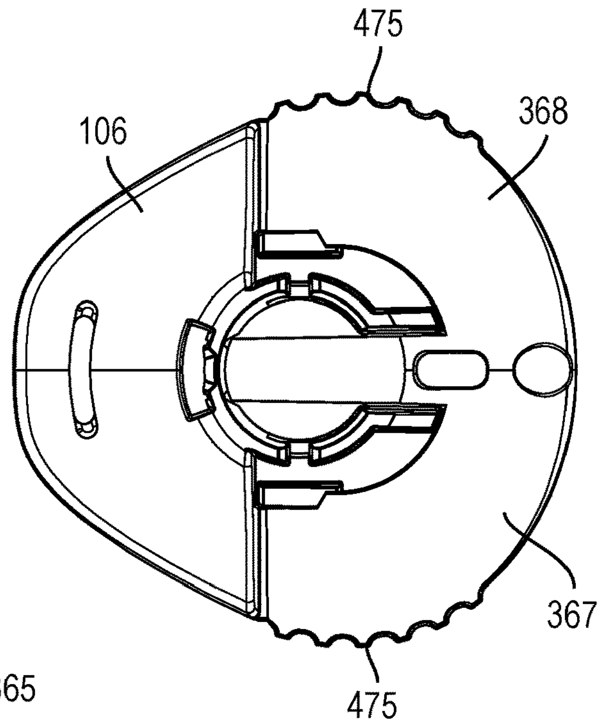
FIG. 26A depicts a view of an exemplary infusion set base and exemplary tubing set connector.
Figure 26B:
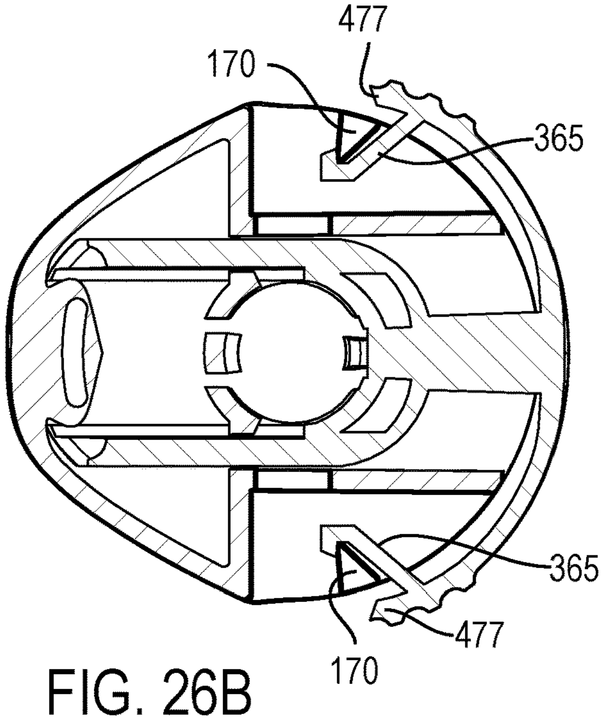
FIG. 26B depicts a cross-sectional view of the exemplary infusion set base and exemplary tubing set connector of FIG. 26A.
Figure 26C:
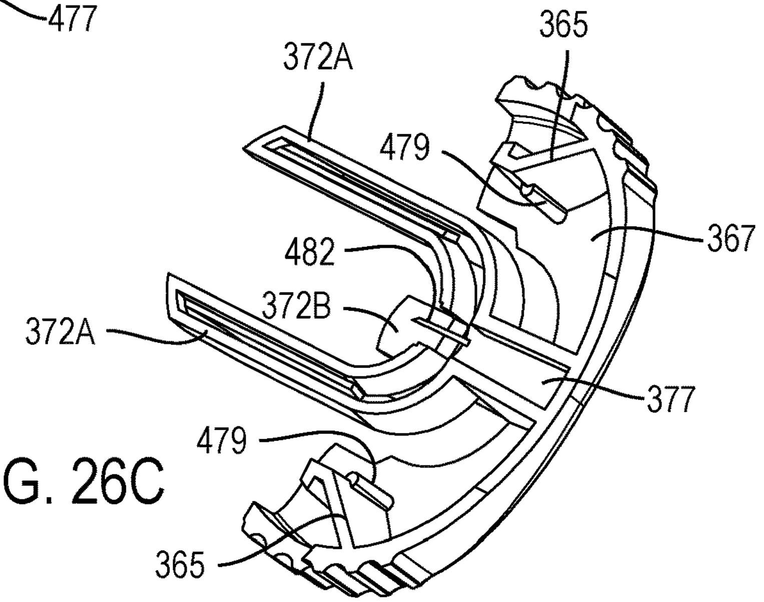
FIG. 26C depicts a perspective view of the exemplary tubing set connector of FIG. 26A.
Figure 27A:
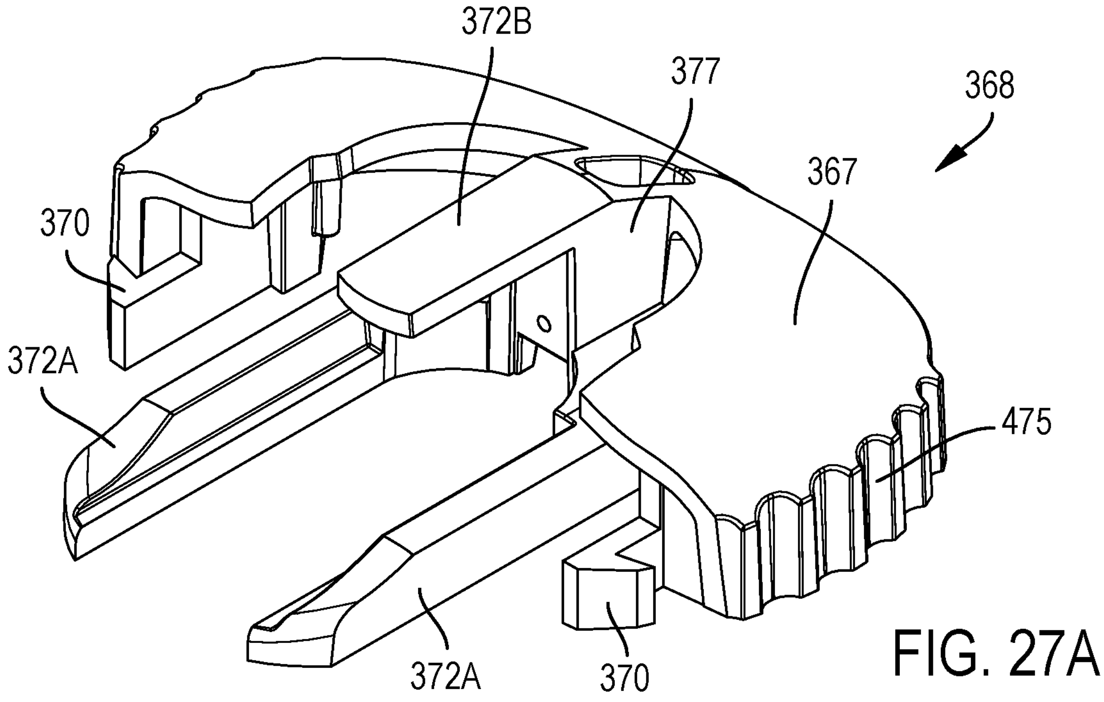
FIG. 27A depicts a perspective view of another example tubing set connector.
Figure 27B:
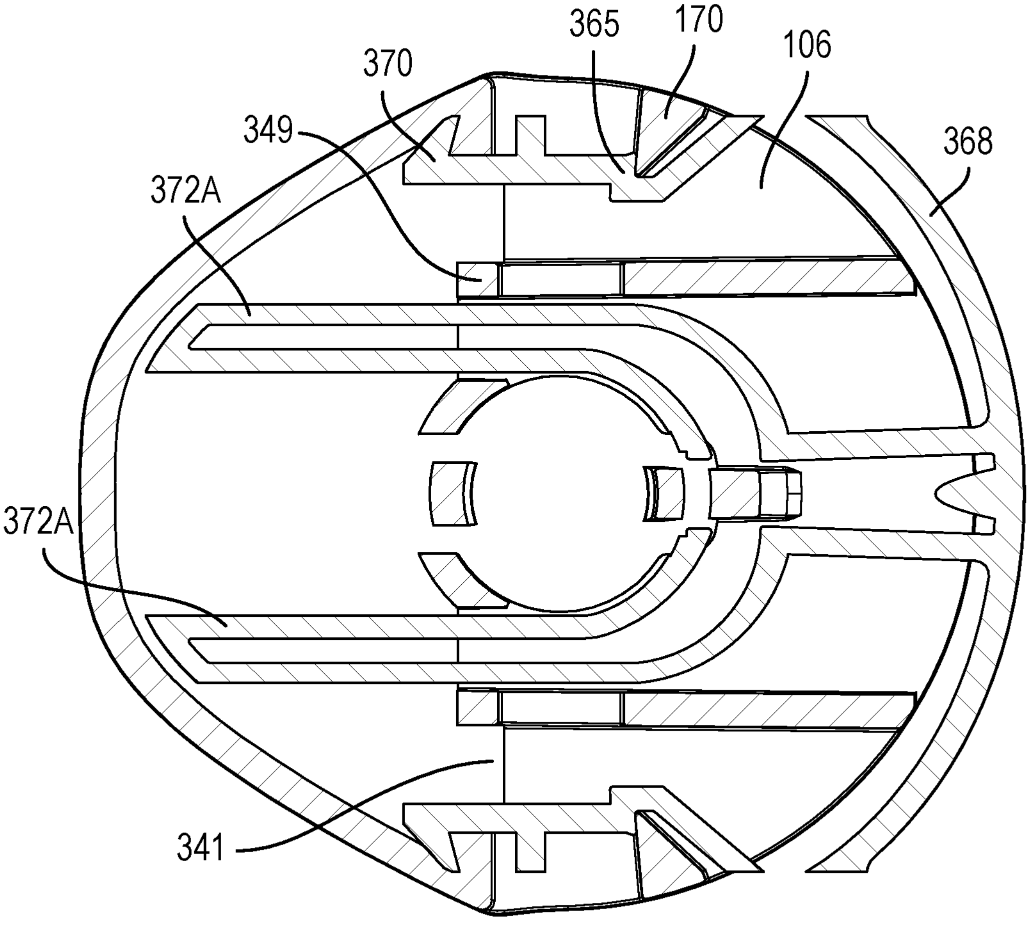
FIG. 27B depicts a cross-sectional view of the example tubing set connector of FIG. 27A coupled to an example infusion set base.

In an alternative embodiment shown in FIGS. 27A-27B, the tubing set connector 368 of FIGS. 26A-C may include connector fingers 370 in addition to the connector latches 365. The infusion set base 106 may include an additional set of passages 341 in the transition wall 349. When the tubing set connector 368 is displaced into engagement with the infusion set base 106, the connector fingers 370 may deflect around sidewalls of respective additional passages 341. The connector fingers 370 may clip into engagement with the backside of the transition wall 349 as shown in FIG. 27B when coupled to the infusion set base 106. The connector latches 365 may also engage the connector interfaces 170. Thus, the infusion set base 106 and the tubing set connector 370 may be coupled to one another by multiple sets of coupling arrangements.

Figure 28A:
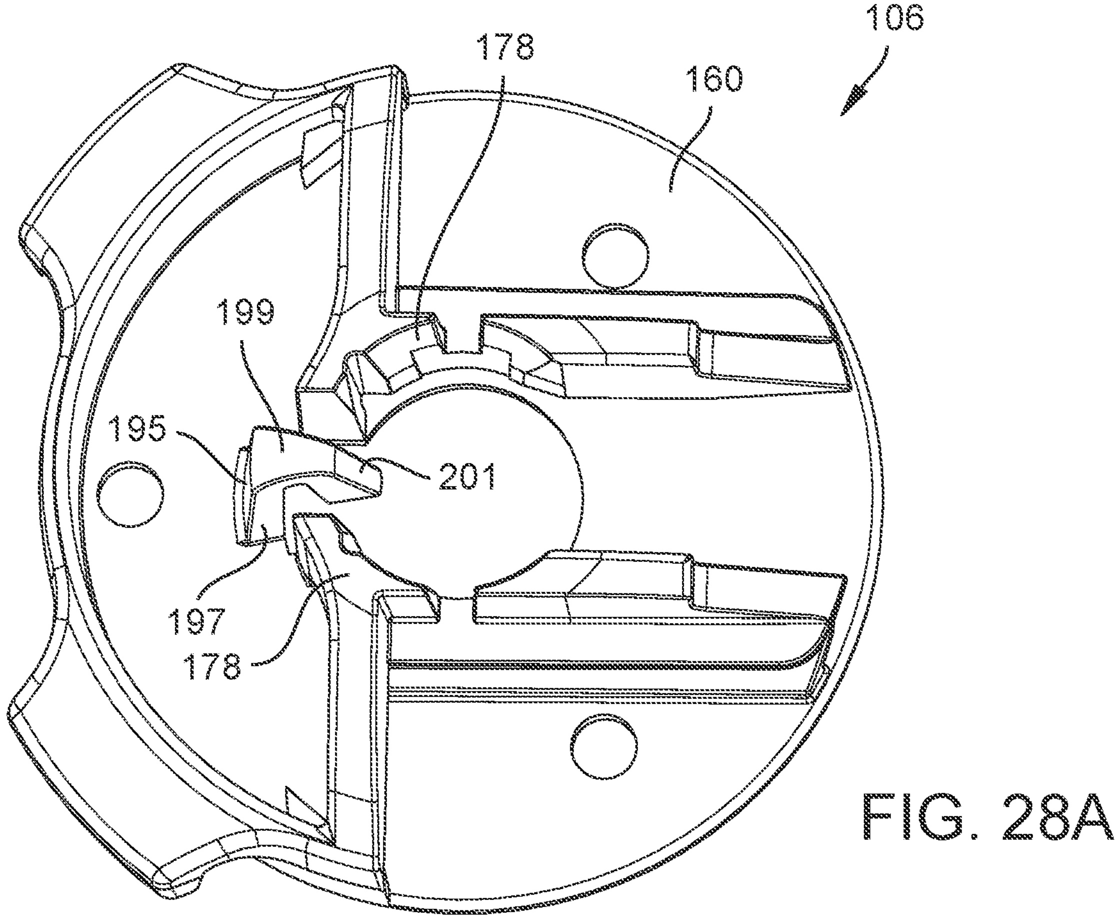
FIG. 28A depicts a perspective view of an example infusion set.
Figure 28B:
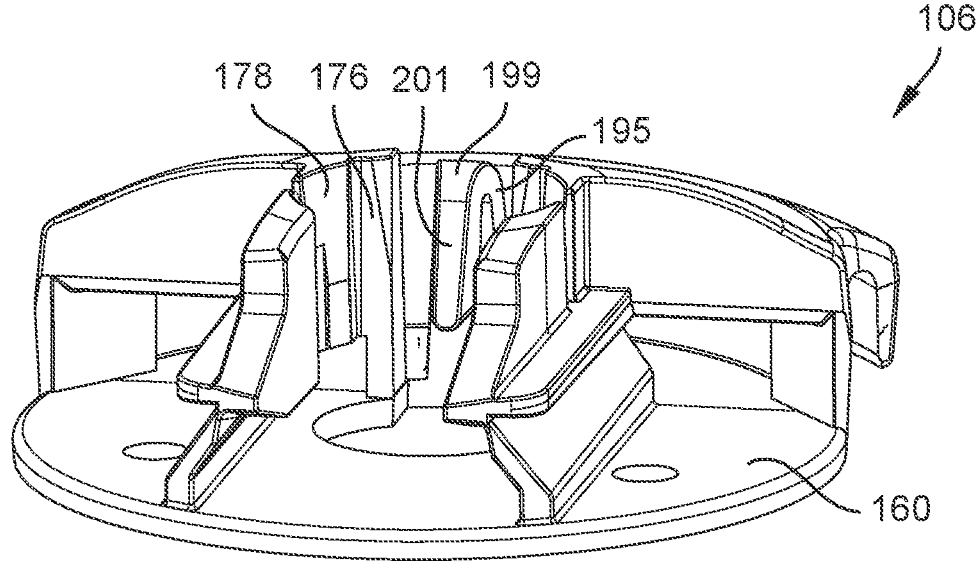
FIG. 28B depicts another perspective view of the example infusion set of FIG. 28A.
Figure 29A:
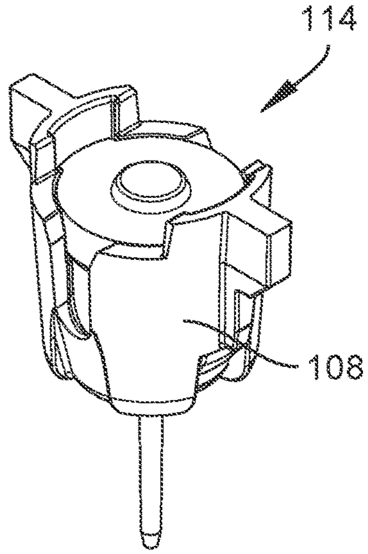
FIGS. 29A-29D depict a number of views of an exemplary cannula subassembly.
Figure 29B:
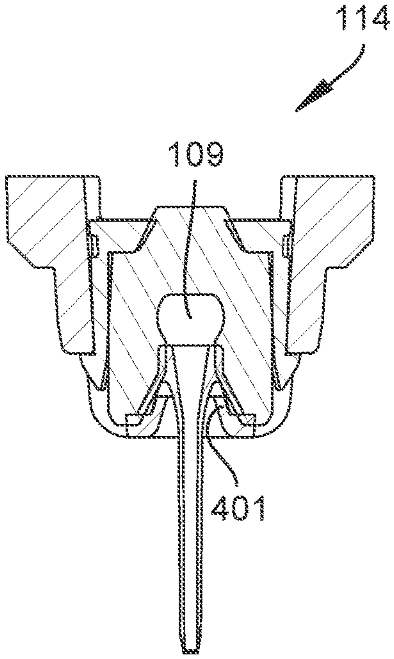
Figure 29C:
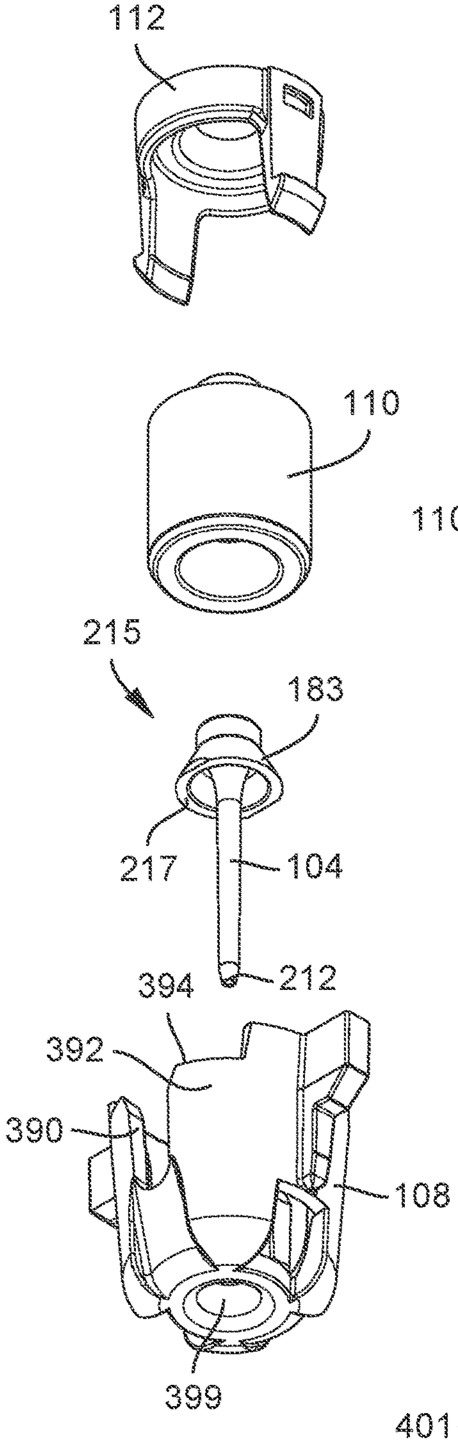
Figure 29D:
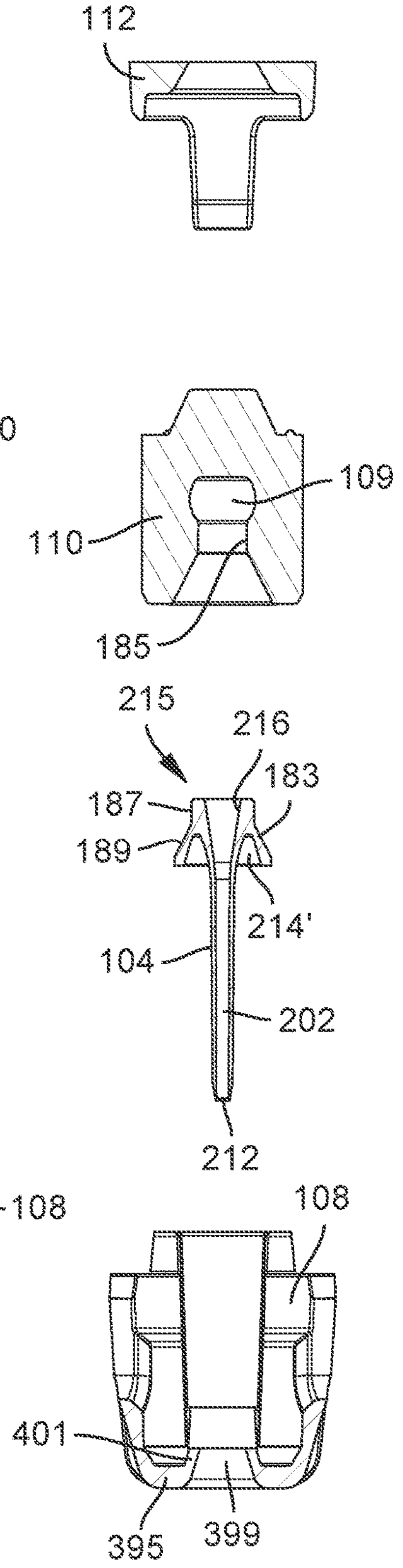

Referring now to FIGS. 28A and 28B, another example infusion set base 106 is shown. In certain embodiments, a base 106 may not include a receptacle wall 178 which has a cantilevered projection 180 (see, e.g., FIG. 4A) defined therein. As shown in FIG. 28A and FIG. 28B, in some examples, a base 106 may include a retainer member 195 which extends from the platform 160. The retainer member 195 may be freestanding and not supported by or continuous with the receptacle wall 178. In FIG. 28A and FIG. 28B, the retainer member 195 is depicted as a hooked body which extends from the platform and is located in an opening between the two sections of the receptacle wall 178. In other examples, a hooked body may not be used. Instead, a cantilevered member including a protuberance 182 such as a barb or ramp which engages a portion of a cannula subassembly 114 may be used. The hooked body may include a shank region 197 which is attached to and continuous with the platform 160. The shank region 197 may extend from the platform 160 to a bend region 199. The shank region 197 may be perpendicular to the platform 160 or may be angled so as to extend toward the receptacle 176. The hooked body may also include a catch segment 201 which extends from the bend region 199. The catch segment 201 may be disposed orthogonally to the shank region 197. In the example, the catch segment 201 extends at an acute angle with respect to the shank 197. For example, the catch segment 201 may be disposed at an angle of 35-40° with respect to the shank 197.

Upon introduction of a cannula subassembly 114 into the base 106, the septum housing 108 (see, e.g., FIG. 8A) may contact the catch segment 201 and resiliently deform the retainer member 195 such that the catch segment 201 is bent out of the way. After advancement of the cannula subassembly 114 into the receptacle 176 beyond a certain point, an engagement surface of the septum housing 108 may pass the end of the catch segment 201. At this point, the catch segment 201 may be free to spring back from its deflected position. The catch segment 201 may include a least a portion which overhangs the engagement surface of the septum housing 108 once sprung back to its unstressed state. Thus, the catch segment 201 may inhibit removal of the cannula subassembly 114 from the base 106. The engagement surface of the septum housing 108 may be any suitable engagement surface on any portion of the cannula subassembly 118. For example, the engagement surface may be a notch 186 (see, e.g. FIG. 5A) in the septum housing 108, a wall of a fenestration in the septum housing 108 (see, e.g. connector needle passage 222 of FIG. 6), a wall of a slot 390 included in the septum housing 108, or a salient 388 included as part of the septum housing 108.

Referring now to FIG. 29A-29D, various views of an example embodiment of a cannula subassembly 114 are depicted. The example cannula subassembly 114 includes a septum housing 108, cannula 104, septum 110, and a septum retainer 112. The septum housing 108 includes slots 390 in the side wall 392 of the septum housing 108 recessed into the top face 394 of the side wall 392. When installed into the cannula subassembly 114, the septum retainer 112 may block access to the sides of the septum 110 in a region proximal the top face 394 of the septum housing 108. A region of the septum 110 between the septum retainer 112 and the end of the slot 390 may be exposed to provide an access for a sharp 482 (see, e.g., FIG. 15D) included on a tubing connector 368. The terminal end of the slot 390 may provide an engagement surface for a cantilevered projection 180 (see, e.g., FIG. 4A) or retainer member 195 (see, e.g., FIG. 28A) which may capture the cannula subassembly 114 within an infusion set base 106.

As shown, the cannula 104 and the septum housing 108 are depicted as separate discrete components in FIGS. 29A-29D. Though shown as discrete components, the cannula 104 and septum housing 108 may be integral to one another as discussed elsewhere herein. The example cannula 104 may include an enlarged end region 215. The enlarged end region 215 may include an insertion sharp guide section 216 which may be continuous with the walls of the lumen 202 of the cannula 104. The insertion sharp guide section 216 may aid directing an insertion sharp 132 (see, e.g., FIG. 1A) into the lumen 202 of the cannula 104 during assembly. The enlarged end region 215 may also include a septum interface region 183 upon which a corresponding portion 185 of the septum 110 may be seated. The septum interface region 183 may surround the insertion sharp guide section 216. The septum interface region 183 may contact the corresponding portion 185 of the septum 110 and provide a sealing surface against which the septum 110 may be compressed to form a fluid tight seal when the cannula subassembly 114 is assembled.

The septum interface region 183 may have a number of different geometries depending on the embodiment. In the example, the septum interface region 183 may have a substantially straight walled portion 187 along a section most distal the outlet of the cannula 104. The straight walled portion 187 may extend substantially parallel to the long axis of the cannula 104. The straight walled portion 187 may transition to a conic frustum type shape section 189 which widens as the septum interface region 183 extends toward the cannula 104 outlet 212. In alternative embodiments, the entire septum interface region 183 may be straight walled (see, e.g., FIG. 31E) or may be in the shape of a conic frustum.

A recess 214' may be included in a face of the enlarged portion 215 which surrounds, or at least partially surrounds, the cannula 104. In the example embodiment, the recess 214' is approximately shaped in the form of a conic section (e.g. hyperbola or parabola) revolved around the center axis of the cannula 104. The septum housing 108 includes a passage 399 which extends through the bottom wall 395 of the septum housing 108. A cannula seat 401, which may be a raised wall or post surrounding the passage 399, may also be included in the septum housing 108. The recess 214' in the enlarged portion 215 of the cannula 104 may accept at least a portion of the cannula seat 401 and may aid in locating and retaining the cannula 104 in place within the cannula subassembly 114. The bottom face 217 (that most proximal the outlet 212 of the cannula 104) of the enlarged portion 215 may rest against the bottom wall 395. When the cannula assembly 114 is assembled, the cannula 104 may extend through the passage 399 such that the outlet 212 is external to the septum housing 108. A volume may be present between the exterior of the cannula 104 and the side walls of the passage 399. This volume may provide room for the cannula 104 to displace relative to the base 106 if the infusion set 102 or a portion of the patient's body causes a force to be applied to the cannula 104. This may minimize shearing action on the cannula 104. Additionally, this volume may serve as a volume into which an agent may be placed. Any agent(s) discussed in relation to FIG. 5B may, for example, be used.

As shown, the septum 110 may include a fluid introduction volume 109. The example fluid introduction volume 109 includes at least one rounded sidewall. In the example, the fluid introduction volume 109 is in the shape of a spherical slice in which opposing sphere caps have been removed. In other embodiments, a generally globe shaped or otherwise rounded volume with no straight side walls may be used. Such a shape may help to ensure a relatively large fluid introduction volume 109 exists even under distortion of the volume which may occur when the septum 110 becomes compressed during assembly of the cannula subassembly 114. Additionally, such a shape may allow for a larger fluid introduction volume 109 without any change in the size of the enlarged portion 215 of the cannula 104. This may result in the fluid introduction volume 109 being a larger target for a sharp 482 of a tubing set connector 368 (see, e.g., FIGS. 15A-16C). Consequently, it may be possible to construct components of the infusion set 102 or tubing set connector 368 with looser tolerancing thus simplifying manufacturing.

Figure 30A:
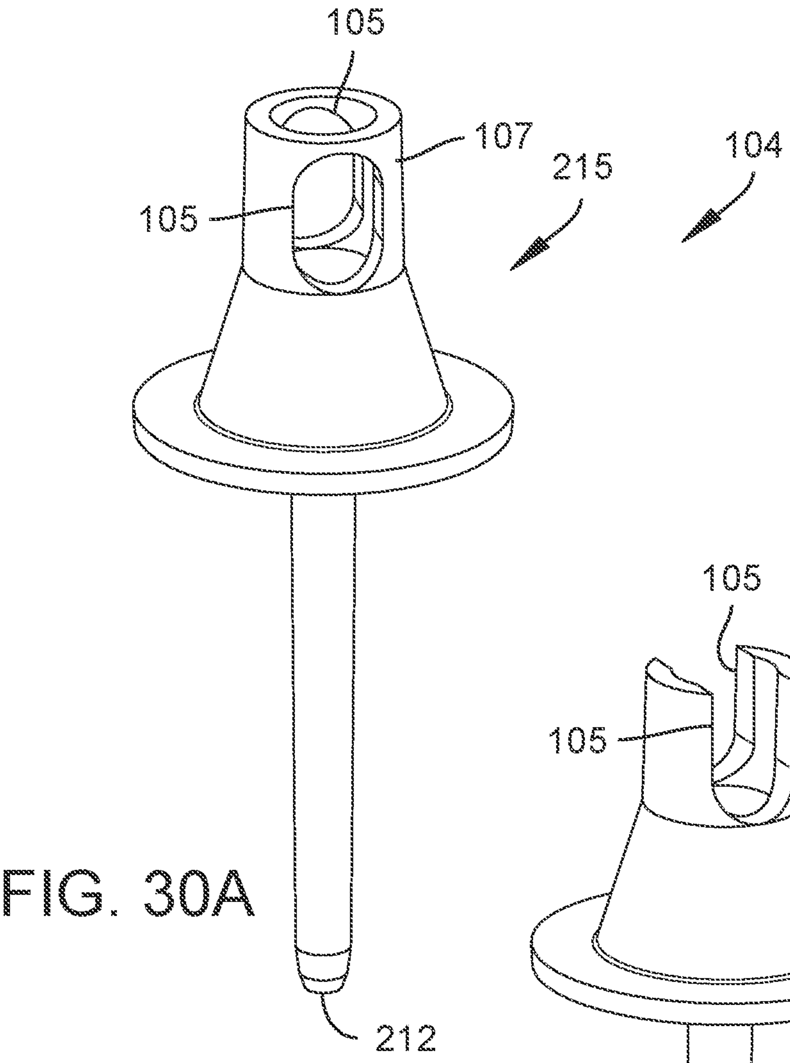
FIGS. 30A-30B depict embodiments of cannulas which may be used in a cannula subassembly.
Figure 30B:
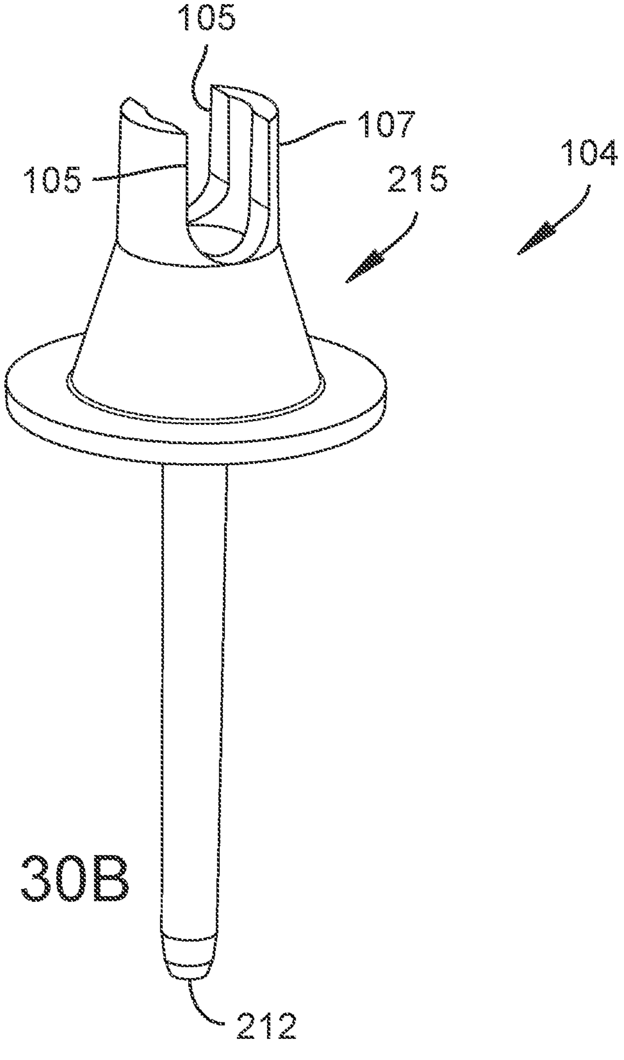

Referring now also to FIGS. 30A-30B, two example cannula embodiments are depicted. In some embodiments, there may be a fluid introduction volume reinforcing body 107 at an end of the enlarged region 215 most distal the outlet 212 of the cannula 104. The reinforcing body 107 may extend into the fluid introduction volume 109 and may abut walls sidewalls of the fluid introduction volume 109. The reinforcing body 107 may prevent distortion of the fluid introduction volume 109 when the septum 110 becomes compressed. The reinforcing body 107 may include passages 105 which may align with the slots 390 (see, e.g., FIG. 29C or connector needle passage (see, e.g., FIG. 6). This may allow for a sharp 482 (see, e.g., FIG. 15C) on a tubing set connector 368 (see, e.g., FIG. 15C) a path through the reinforcing body 107 and into the fluid introduction volume 109 during connection of the tubing set connector 368 to an infusion set base 106. As shown, the passages 105 may be fenestrations (obround in the example, but could be any suitable shape) or slots. Such reinforcing bodies 107 may be included on any of the cannulas 104 described and/or shown herein.

Figure 31A:
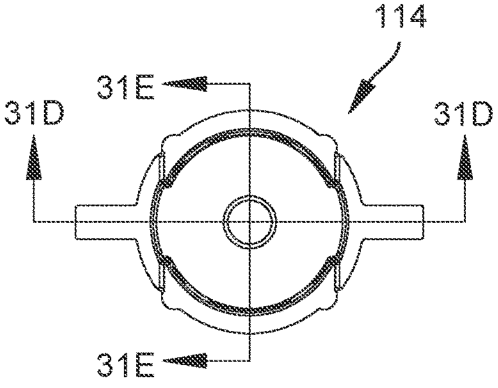
FIGS. 31A-31G depict a number of views of another example cannula subassembly.
Figure 31B:
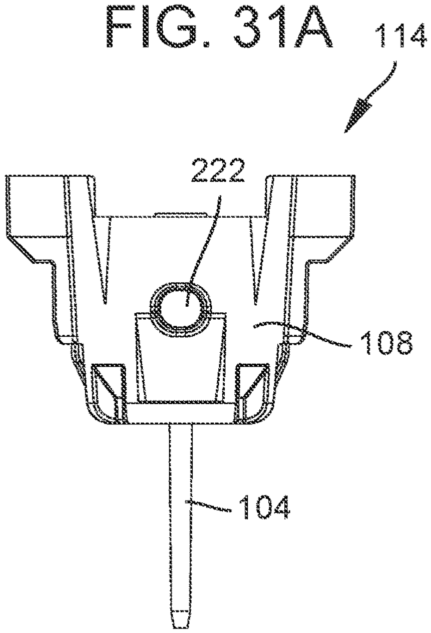
Figure 31C:
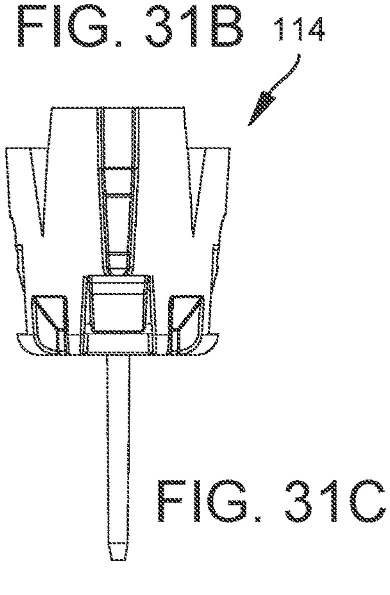
Figure 31D:
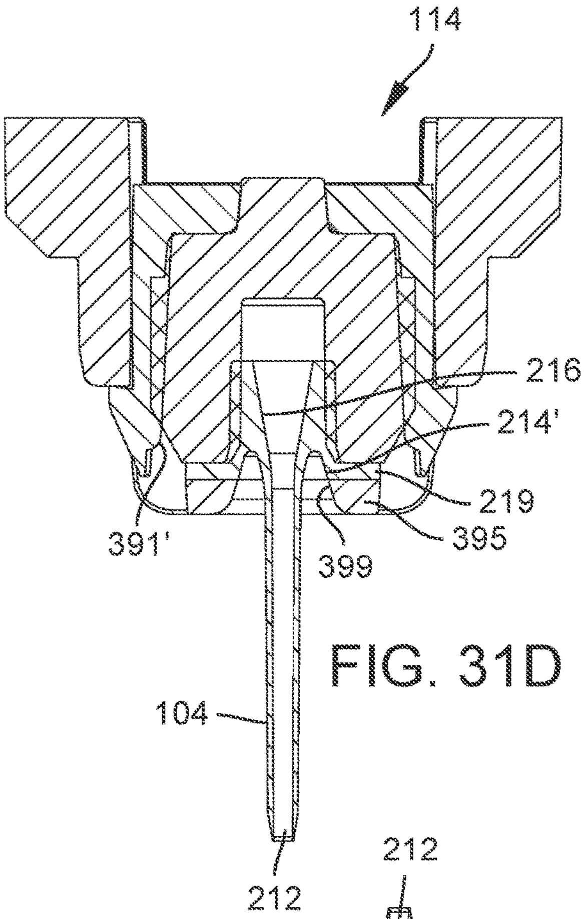
Figure 31E:
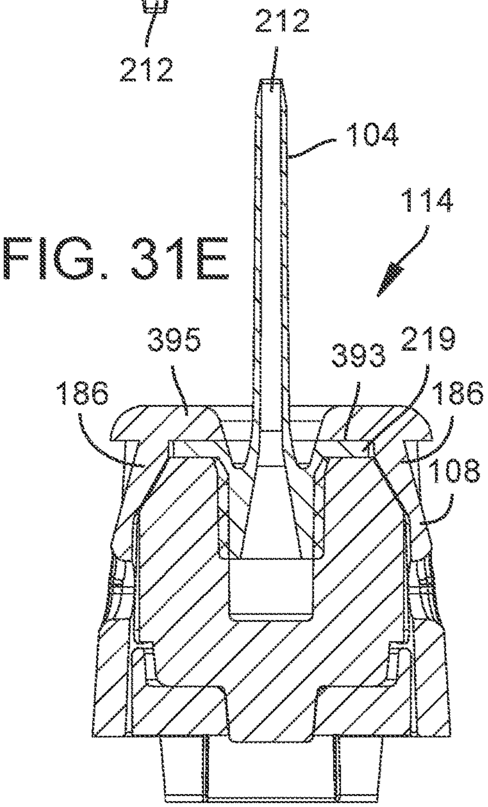
Figure 31F:
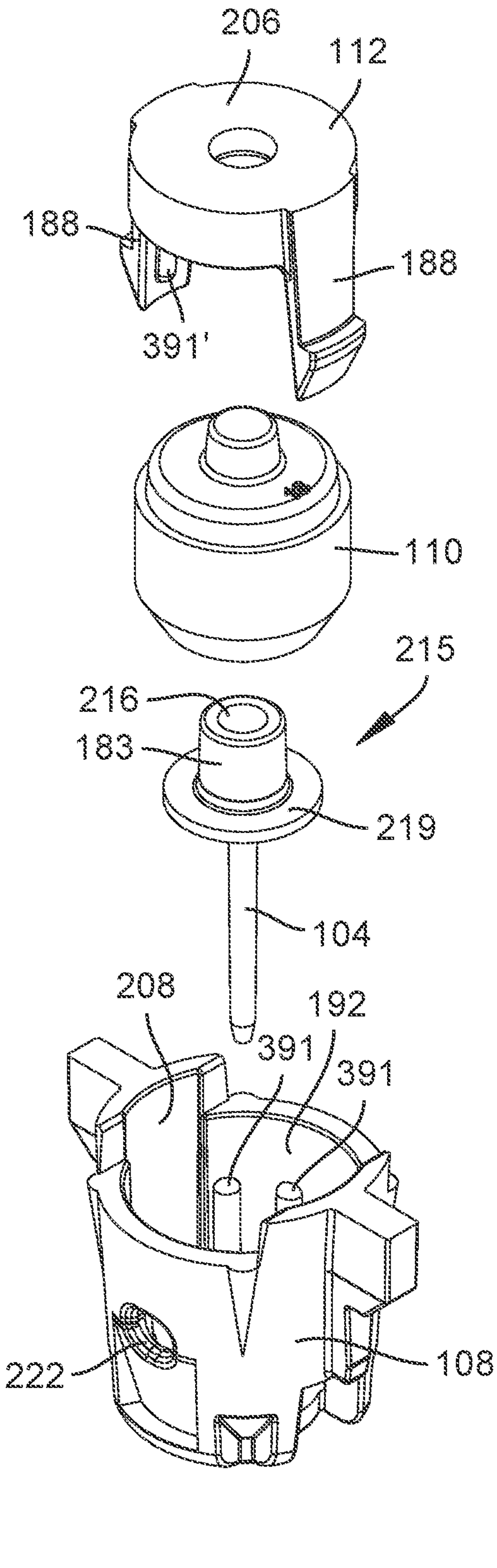
Figure 31G:
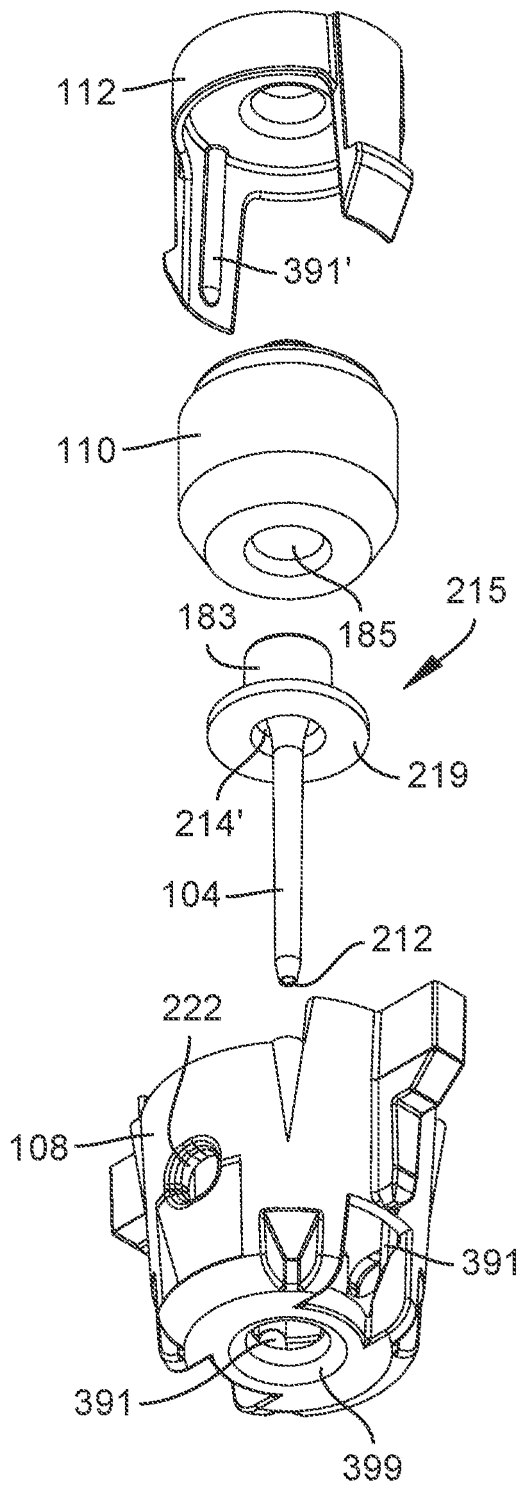
Figure 32A:
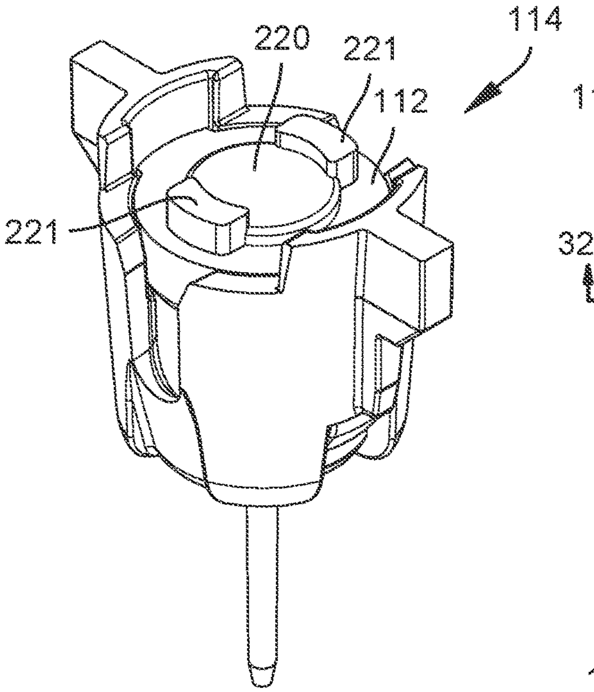
FIGS. 32A-32D depict a number of views of another example cannula subassembly.
Figure 32B:
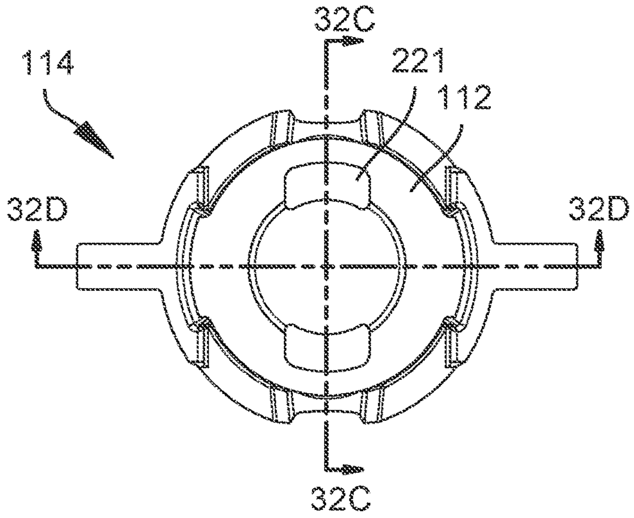
Figure 32C:
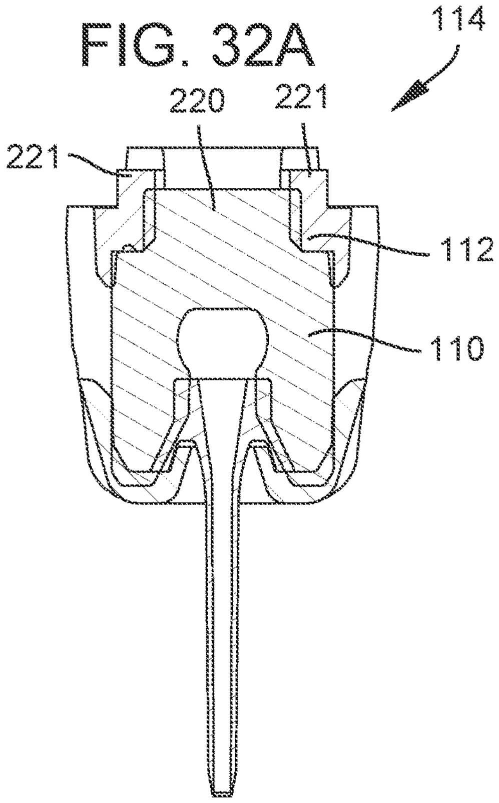
Figure 32D:
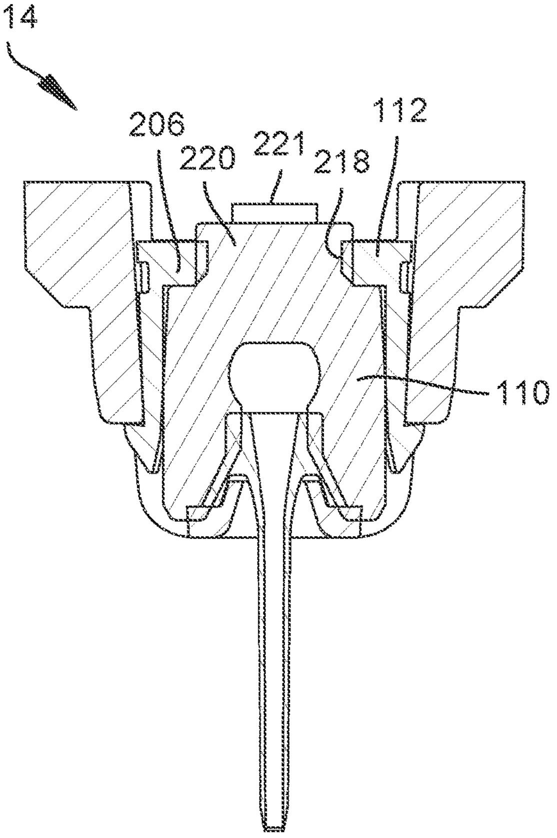
Figure 33A:
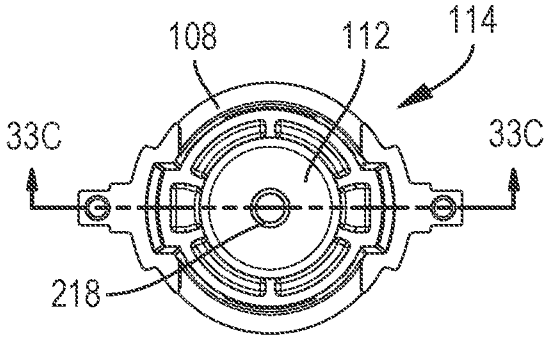
FIGS. 33A-33D depict a number of views of another example cannula subassembly.
Figure 33B:
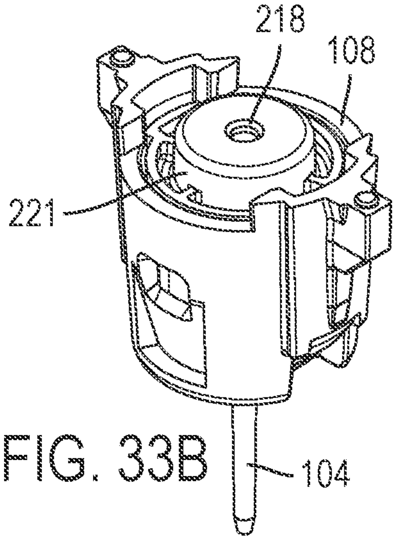
Figure 33C:
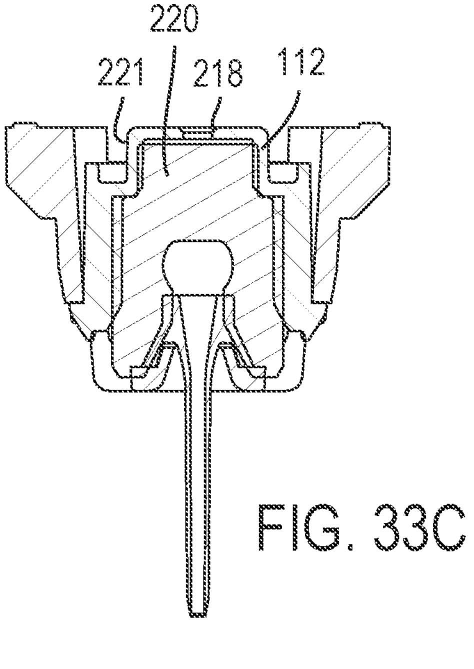
Figure 33D:
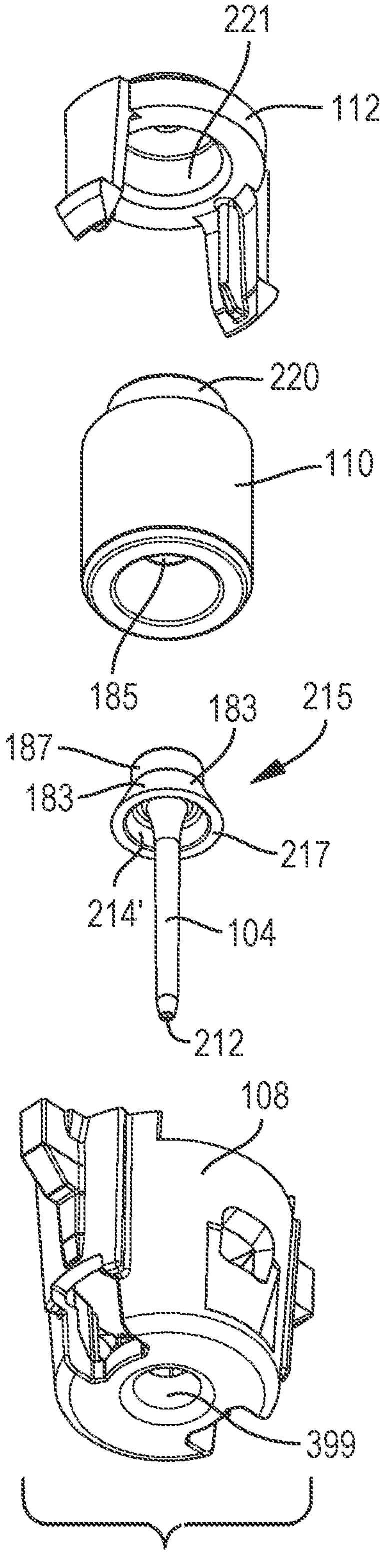
Figure 34A:
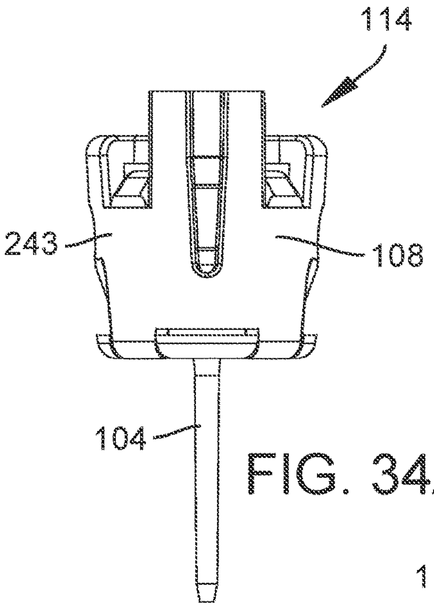
FIGS. 34A-34F depict a number of views of another exemplary cannula subassembly.
Figure 34B:
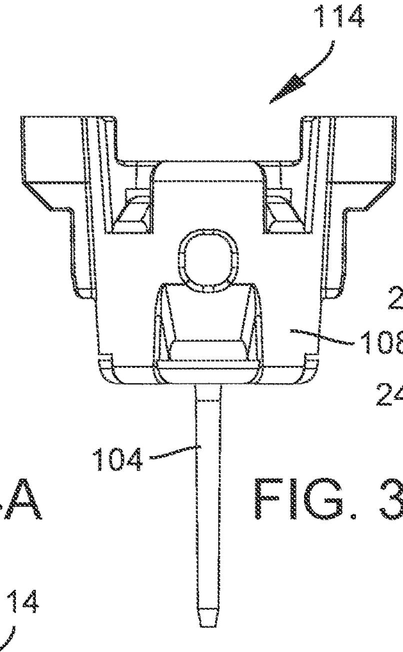
Figure 34C:
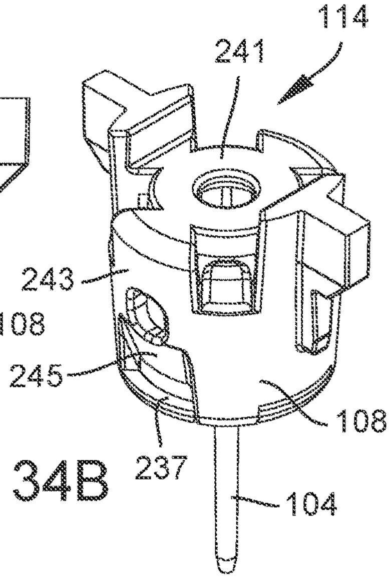
Figure 34D:
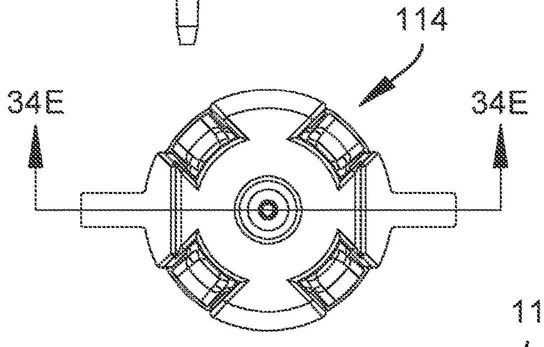
Figure 34E:
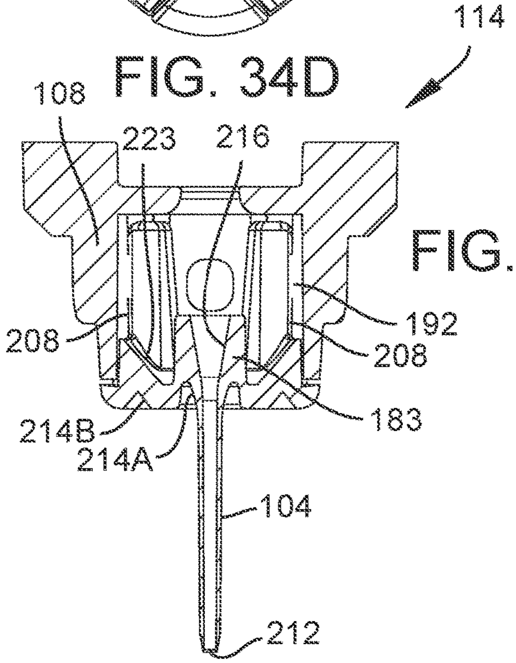
Figure 34F:
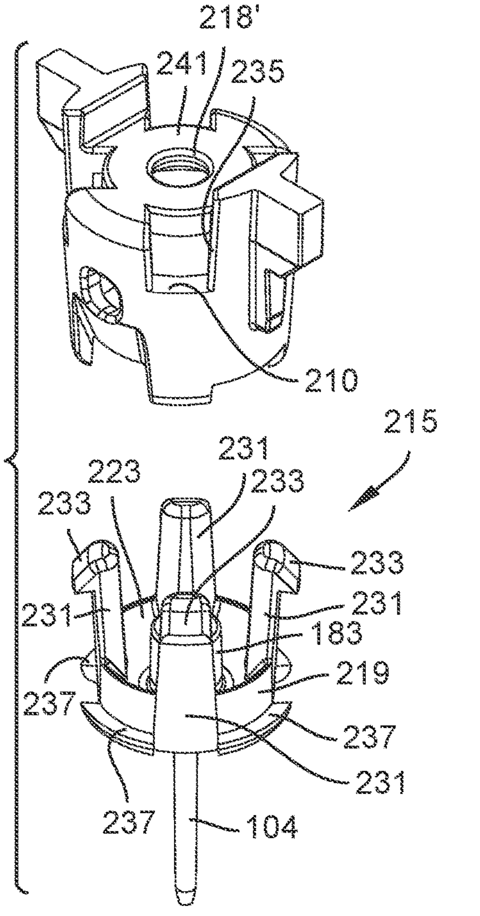
Figure 35A:
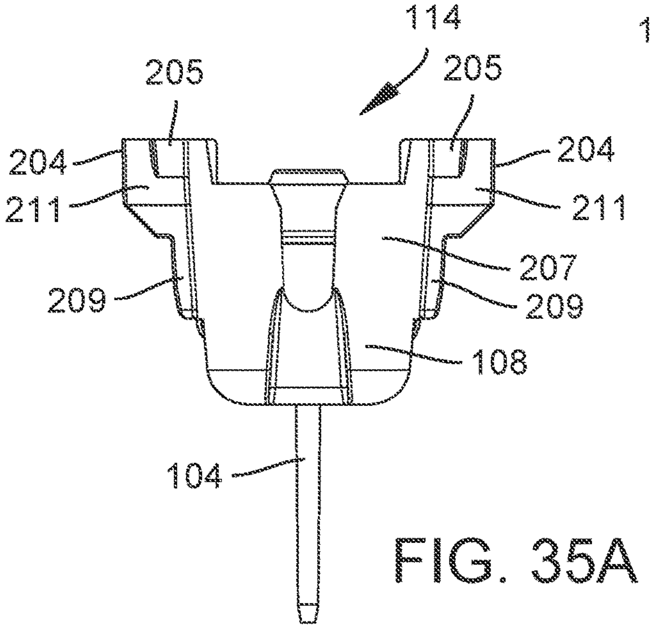
FIGS. 35A-35F depict a number of views of another example cannula subassembly.
Figure 35B:
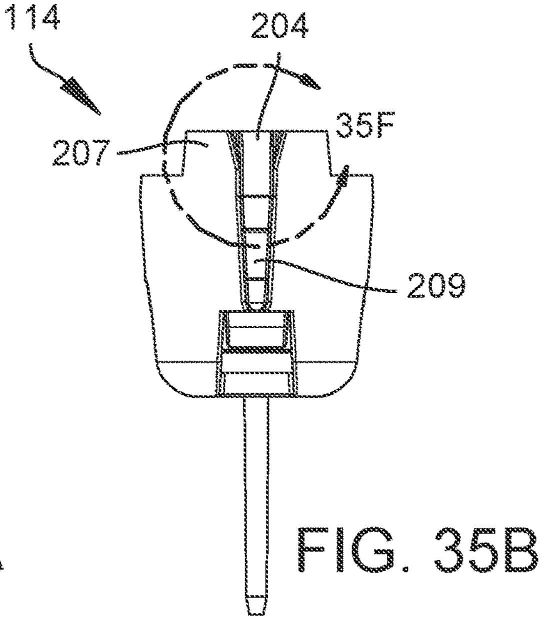
Figure 35C:
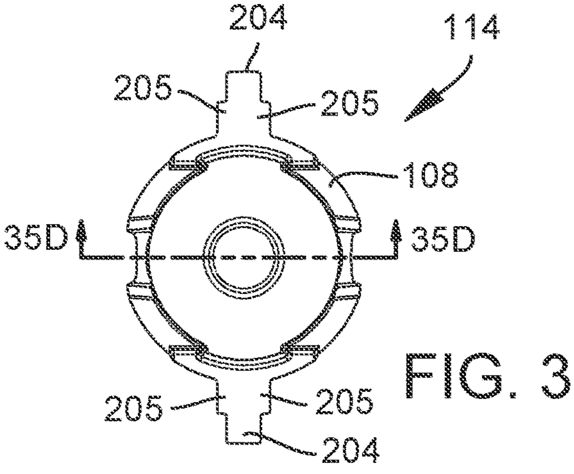
Figure 35D:
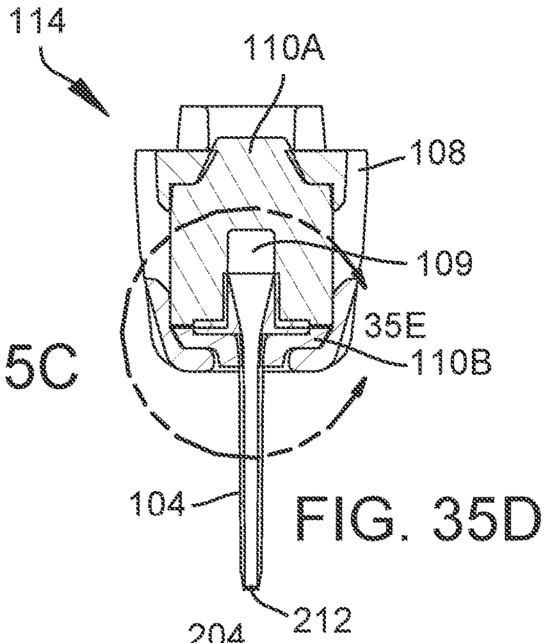
Figure 35E:
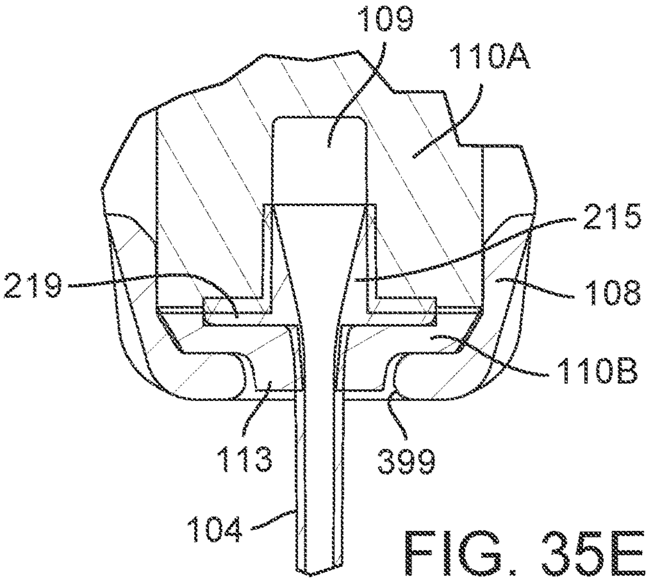
Figure 35F:
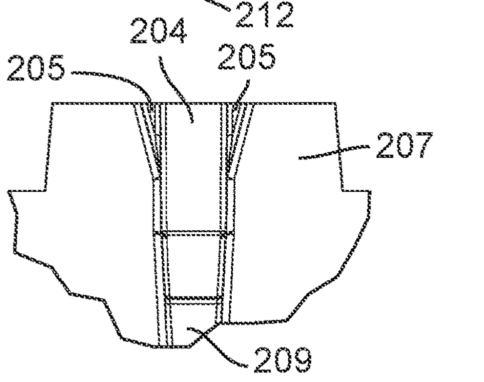
Figure 36A:
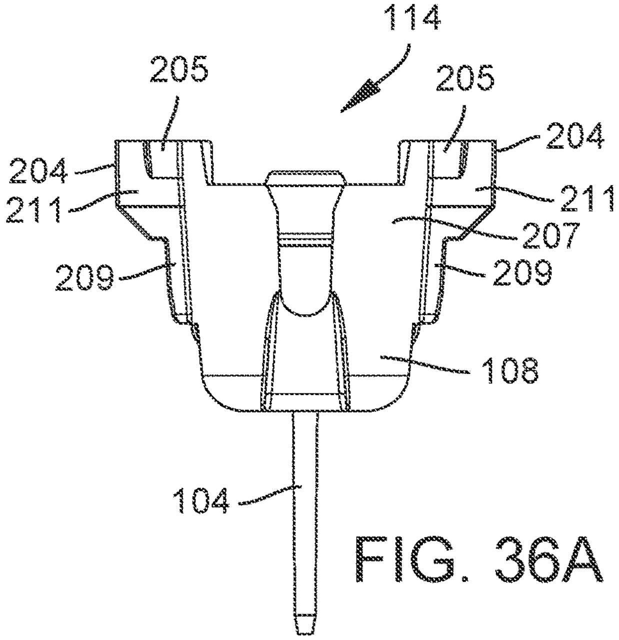
FIGS. 36A-36E depict a number of views of yet another example cannula subassembly.
Figure 36B:
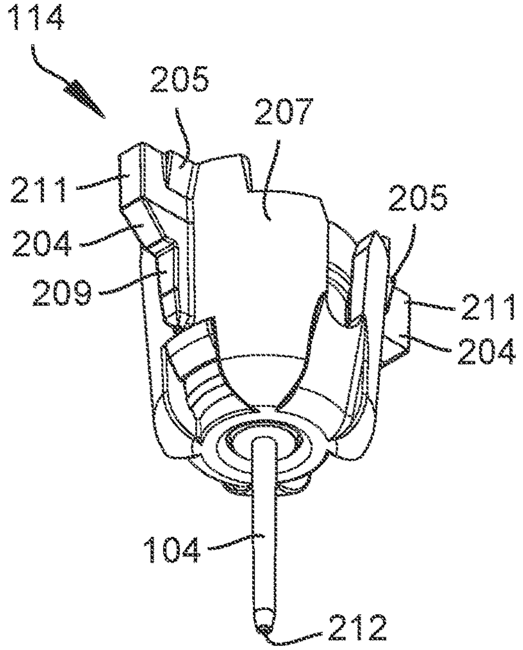
Figure 36C:
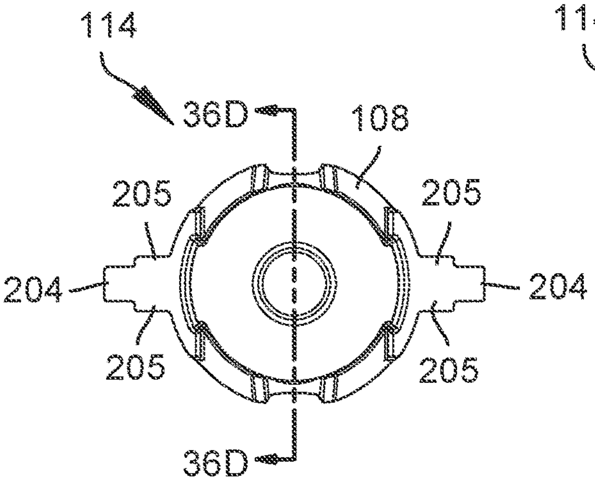
Figure 36D:
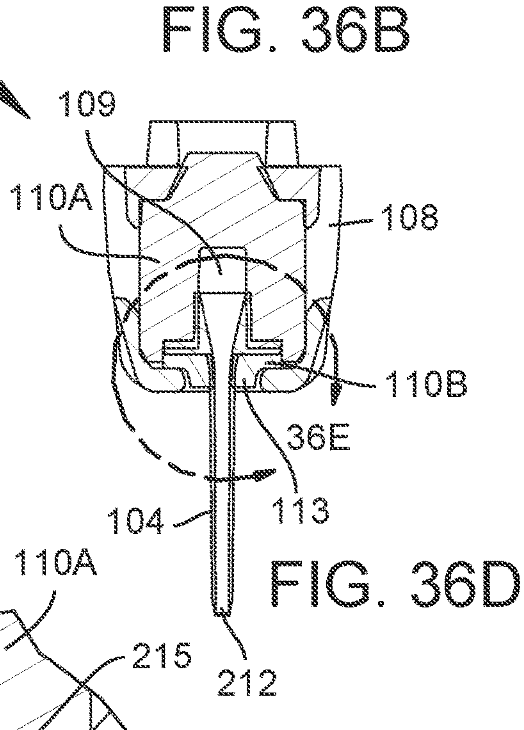
Figure 36E:
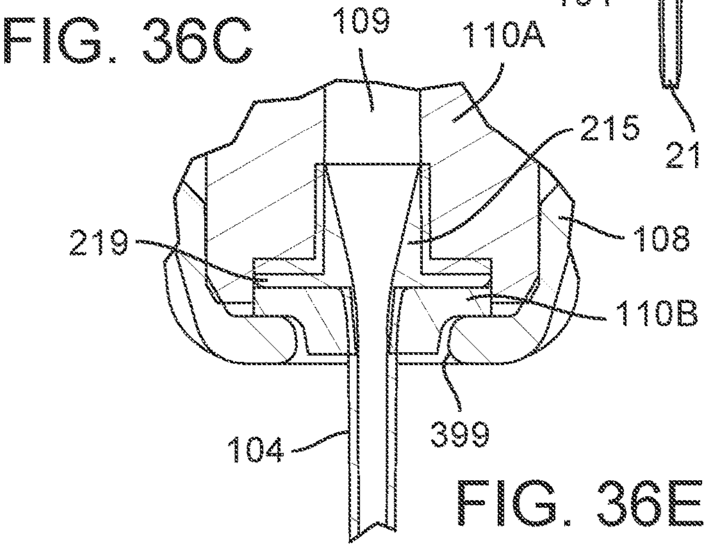

Referring now to FIGS. 31A-31G, another exemplary cannula assembly 114 is depicted. As in FIGS. 29A-29D, the example cannula subassembly 114 includes a cannula 104 and septum housing 108 which are separate discrete components (though they could be integral with one another in alternative embodiments). The cannula 104 may have an enlarged region 215 which includes a septum interface region 183 that surrounds the insertion sharp guide 216 of the cannula 104. When assembled, a corresponding portion 185 of the septum 110 may be seated against the septum interface region 183. The enlarged region 215 may also include a flange 219 which may be disposed at an end of the enlarged region 215 most proximal the outlet 212 of the cannula 104. As best shown in FIG. 31E, the bottom wall 395 of the septum housing 108 may include a seat for the cannula 104. In the example, the seat is shown as a receptacle 393 into which the flange 219 may be seated. The receptacle 393 may aid in centering the cannula 104 within the septum housing 108.

A recess 214' may be included in a face of the enlarged portion 215 which surrounds, or at least partially surrounds, the cannula 104. In the example embodiment, the recess 214' is approximately shaped in the form of a conic section (e.g. hyperbola or parabola) revolved around the center axis of the cannula 104. The septum housing 108 includes a passage 399 which extends through the bottom wall 395 of the septum housing 108. The walls of the passage 399 may be angled or contoured to match and form a continuation of the recess 214'. This may create a volume which may be filled with agent (described elsewhere herein) and/or allow for some movement of the cannula 104 with respect to the infusion set base 106. The receptacle 393 (or other seat) may surround the passage 399.

The septum housing 108 may include a number of protuberances 391 (best shown in FIG. 31F) which extend from the wall of the receiving section 192 of the septum housing 108 toward the axis of elongation of the cannula 104. In the example embodiment, these protuberances 391 are in the form of substantially straight ridges or ribs. Each of the protuberances 391 may be the same length or at least one of the protuberances 391 may have a length which differs from at least one of the other protuberances 391. In certain embodiments, ends of the protuberances 391 most distal the cannula 104 outlet 212 may be ramped or curved (shown in FIG. 31F). Each of the connector needle passages 222 (an aperture in the example shown but potentially slots 390 in alternative examples where slots 390 are present in the septum housing 108) may be flanked by protuberances 391 which may run directly adjacent each side of the connector needle passages 222. The protuberances 391 may contact the septum 110 (or at least one of the septums 110 in embodiments with a plurality of septums 110) when the septum 110 is installed in the septum housing 108. Spaces between the protuberances 391 may provide a volume into which material of the septum 110 may be squeezed when the cannula subassembly 114 is assembled and the septum 110 is under compression. The septum retainer 112 also includes a set of protuberances 391' included on the cantilevered projections 188 that extend from the body 206 of the septum retainer 112. When the cannula subassembly 114 is fully assembled, the protuberances 391, 391' may contact the septum 110 and provide additional compression of the septum 110 to further increase robustness of the fluid tight seals formed by the septum 110. Such protuberances 391, 391' may also allow for less stringent tolerancing to be used in order to help simplify manufacturing.

Referring now to FIGS. 32A-32D, another example cannula subassembly 114 is depicted. The example cannula subassembly 114 includes a septum retainer 112 which includes a channel 218 substantially centrally disposed in the body 206 of the septum retainer 112. A nub 220 of the septum 110 may project into and perhaps partially through the channel 218. The nub 220 of the septum 110 may have a diameter which is slightly larger than the diameter of the channel 218. Thus, the nub 220 may be compressed by the channel 218. Additionally, the channel 218 may have a diameter which extends across a large portion or a majority of the diameter of the body 206 of the septum retainer 112. This may spread compression exerted by the channel 218 walls over a relatively large amount of septum 110 material. As a result, compressive stress relaxation of the septum 110 material may be decreased over the shelf life of an inserter assembly 100.

The insertion sharp 132 of an inserter assembly 100 may extend through the nub 220 (see, e.g. FIG. 74B) before the inserter assembly 100 is used. The septum 110 may be completely self-sealing upon removal of the insertion sharp 132 and leak-proof thereafter. In certain examples, the average width or diameter of the nub 220 may be selected such that the diameter of the insertion sharp 132 is less than 10% the average width of the nub 220. This may further aid in reducing stress relaxation of the septum 110 material during storage while an inserter assembly 110 is awaiting use.

As shown, the channel 218 may include sidewalls which are primarily straight and extend parallel to the axis of elongation of the cannula 104. Thus, the compression exerted by the sidewalls of the channel 218 against the nub 220 may be directed primarily normal to the axis of elongation of the cannula 104. This may maximize compression exerted by the channel 218 toward the puncture path of the insertion sharp 132. Moreover, by decreasing compressive stress relaxation of the septum 110, a greater degree of resiliency may be maintained in the septum 110 material. Thus, the channel 218 of FIGS. 32A-32D may help may resist leaks at pressures even further in excess of those expected during use. Additional potential benefits are described above in relation to FIGS. 15A-16C and FIG. 17.

Example septum retainers 112 may also include one or more projection 221 raised from the exposed surface of the septum retainer 112 which may at least partially surround the channel 218. In some embodiments, the entirety of the channel 218 may be surrounded. In the example embodiment, the projections 221 are included as part of a crenellated wall surrounding the channel 218. In the example, only two merlons and associated crenels are shown. The merlons may be disposed in opposition to one another about the channel 218. In other embodiments, any suitable number of crenellations may be included and the crenellations may or may not be spaced at regular angular intervals. In the example, the at least one projection 221 extends substantially perpendicular to the main body 206 of the septum retainer 112. In other embodiments the at least one projection 221 may extend toward the axis of the channel 218 or have a portion which extends toward the axis of the channel 218.

Referring now also to FIGS. 33A-33D, in some examples, the channel 218 may be entirely surrounded by a projection 221 having at least a portion angled toward the axis of the channel 218. Thus, the projection 221 may block all but a small portion of the nub 220. The projection 221 in FIGS. 33A-33D forms a cap or cover over the nub 220 and may be referred to herein as a cap or cover portion of the septum retainer 112. The portion of the projection 221 most distal to the outlet 212 of the cannula 104 is substantially planar and oriented perpendicularly to the axis of the channel 218. In certain examples, the wall of projection 221 adjacent the nub 220 may include one or more protuberance similar to protuberances 391 described in relation to FIG. 31F.

As the nub 220 of the septum 110 is compressed during assembly of a cannula subassembly 114, the material may have a tendency to "mushroom" out as it projects through the channel 218. The projections 221 may aid in preventing this "mushrooming" and force septum 110 material toward the puncture pathway for the insertion sharp 132 (see, e.g., FIG. 74B). This may help the cannula subassembly 114 resist leaks at pressures even further in excess of those expected during use. Additional potential benefits are described above in relation to FIGS. 15A-16C and FIG. 17.

Referring now to FIGS. 34A-34F, another example cannula subassembly 114 is depicted. As shown, the cannula subassembly 114 includes a cannula 104 and a septum housing 108. No septum retainer 112 (see e.g. FIG. 32A) is included in the embodiment depicted in FIGS. 34A-34F. This may lower part count and may aid in simplifying manufacture of a cannula assembly 114.

The example cannula 104 includes an enlarged region 215 which includes a septum interface region 183 surrounding the insertion sharp guide 216 of the cannula 104. When assembled, a corresponding portion 185 of the septum 110 (no septum shown in FIGS. 34A-34F, see e.g., FIG. 32D) may be seated against the septum interface region 183. The enlarged region 215 may also include an outwardly extending flange 219. A surface of the flange 219 most distal the cannula outlet 212 may include a depression 223 which may receive an end of a septum 110. The depression 223 may also include contoured surfaces which may aid in centering or locating the septum 110 in the cannula subassembly 114. The opposing surface of the flange 219 may include a set of recesses 214A, B. Recess 214A may provide a space for the portion of the cannula 104 extending from this surface to move relative to an infusion set base 106 minimizing shearing action on the cannula 104. Agent may be provided in either recess 214A, B as described elsewhere herein.

At the periphery of the flange 219 a number of cantilevered arms 231 may be included. A terminal protuberance or latch member 233 may be included at the unsupported end of each of the cantilevered arms 231. Thus, the cantilevered arms 231 may be referred to as latch arms. During assembly, the latch member 233 of each cantilevered arm 231 may slide within a respective guide 208 for the arm 231 included on the interior surface of the receiving section 192 of the septum housing 108. The guides 208 shown are recessed into the interior surface of the receiving section 192 of the septum housing 108. The cantilevered arms 231 may be resiliently deflected toward the axis of elongation of the cannula 104 when the latch members 233 are within the guides 208. As the septum housing 108 and cannula 104 are displaced toward one another beyond a certain distance, the latch members 233 may exit the guides 208 and pass through apertures 235 included in the septum housing 108. This may allow the cantilevered arms 231 to resiliently restore and spring outward such that the latch member 233 on each cantilevered arm 231 enters into latching engagement with a catch surface 210 defined by each of the apertures 235. In the example embodiment, the cannula 104 includes a set of four cantilevered arms 231. The cantilevered arms 231 are also spaced from one another at substantially regular angular intervals though need not be in all example embodiments. In other embodiments, a greater or lesser number of cantilevered arms 231 may be included. The apertures 235 in the example are notches which are recessed into a first end wall 241 of the septum housing 108 and partially into the sidewall 243 of the septum housing 108. The first end wall 241 may close one end of the septum housing 108 and the flange 219 of the cannula 104 may close the second end of the septum housing 108 when the cannula 104 is coupled to the septum housing 108. The septum 110 (not shown) may be captured between the flange 219 and the first end wall 241 within the septum housing 108 when the cannula subassembly 114 is assembled. The first end wall 241 may include a channel 218' which extend therethrough and accepts a nub 220 of a septum 110 (see, e.g., FIG. 32D).

As shown, the flange 219 may also include a number of ledge members 237 which may extend outwardly from the periphery of the flange 219. When the cannula subassembly 114 is assembled, the ledge members 237 may provide a retention interface which may, for example, engage a protuberance 182 on a cantilevered projection 180 (see, e.g., FIG. 4A) of an infusion set base 106. Thus, the ledge members 237 may aid in coupling of a cannula subassembly 114 into an infusion set base 106. The septum housing 108 may include a recess 245 adjacent at least one of the ledge members 237.

Referring now to FIGS. 35A-35F and FIGS. 36A-36E, additional example cannula subassembly 114 embodiments are depicted. The ears 204 extending from the main portion of the example septum housing 108 may include wedge bodies 205. Such wedge bodies 205 may be included on the ears 204 of any other cannula subassemblies 114 shown and described herein. The wedge bodies 205 may be disposed on the portion of each of the ears 204 which is most distal to the outlet 212 of the cannula 104 and may be disposed in opposition to one another on opposing faces of the ears 204. The thickness of the wedge bodies 205 may decrease as distance to the outlet 212 of the cannula 104 decreases. The wedge bodies 205 may extend from the sidewall 207 of the septum housing 108.

Additionally, the ears 204 may include an expanse 209 which extends from the main portion 211 of the ears 204 toward the outlet 212 of the cannula 104. Such an expanse 209 may be included on other cannula subassemblies 114 shown and described herein. The expanse 209 may be tapered such that width of the expanse 209 decreases with increasing proximity to the outlet 212 of the cannula 104. As the cannula subassembly 114 is displaced into an infusion set base 106, the taper on the expanse 209 may aid in directing the cannula subassembly 114 into the notches 174 (see, e.g., FIG. 4A) of the infusion set base 106. In certain examples, an end of the expanse most distal the main portion 211 of the ears 204 may thinned so as to be potentially sacrificial. In the event that the expanse 209 is too long (e.g. due to tolerancing), this sacrificial portion of the expanse 209 may deform as it is displaced into an interfering structure of a base 106. Thus, the sacrificial portion of the expanse 209 may allow a cannula subassembly 114 to couple to the base 106 without issue even if relatively loose tolerances are used. The wedge bodies 205 may assist in ensuring that the cannula subassembly 114 is snuggly retained within the notches 174 (see, e.g., FIG. 4A) during assembly and may aid in centering the cannula subassembly 114 within the receptacle 176 (see, e.g., FIG. 4A). The wedge bodies 205 may allow the notches 174 and/or septum housing 108 to be made with less stringent tolerancing while minimizing potential for the cannula subassembly 114 to have room to wiggle when retained within the receptacle 176 (see, e.g., FIG. 4A). The wedge bodies 205 may also aid in guiding of the cannula subassembly 114 into place during assembly into a base 106.

Figure 37A:
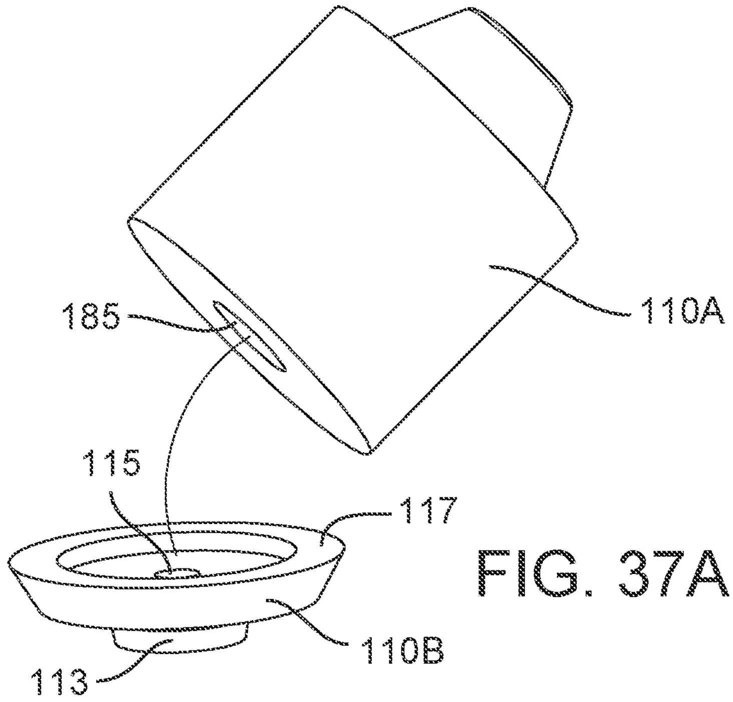
FIGS. 37A & 37B depict views of example septums which may be included in an example cannula subassembly.
Figure 37B:
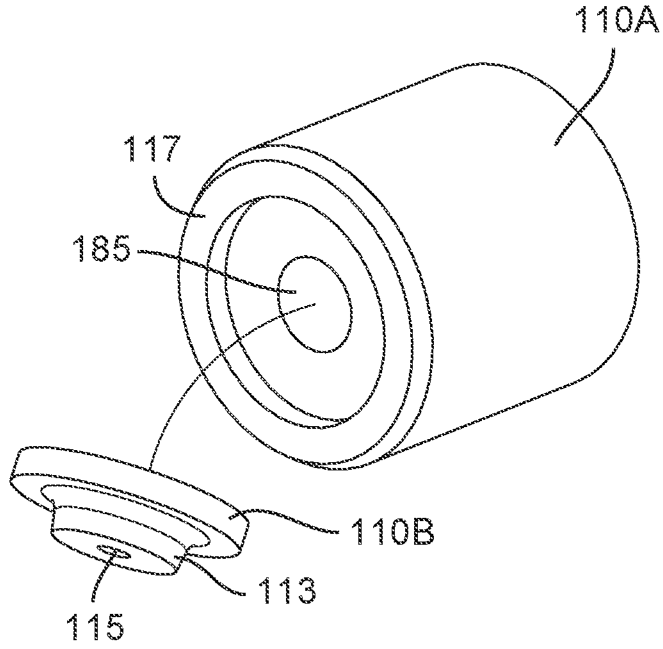
Figure 38A:
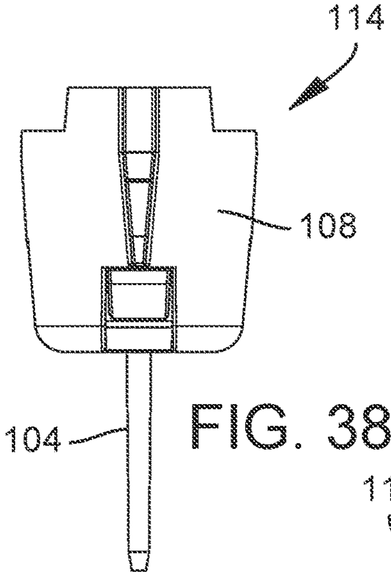
FIGS. 38A-38E depict views of another example cannula subassembly.
Figure 38B:
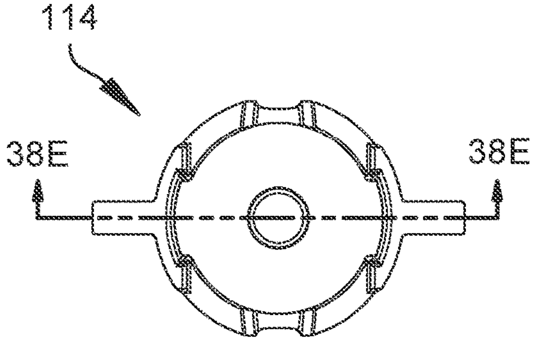
Figure 38C:
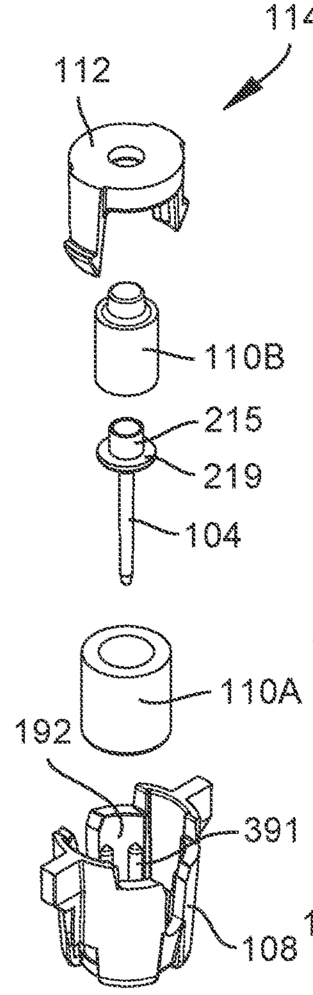
Figure 38D:
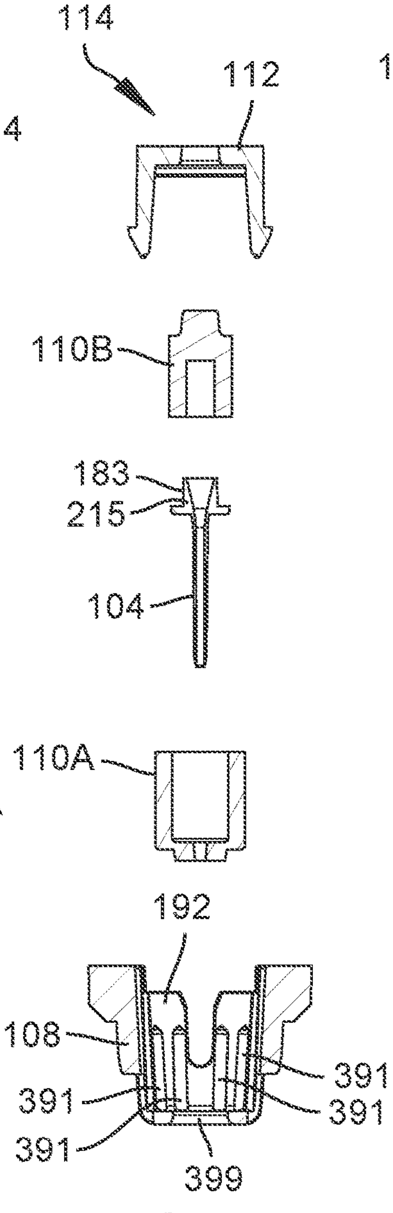
Figure 38E:
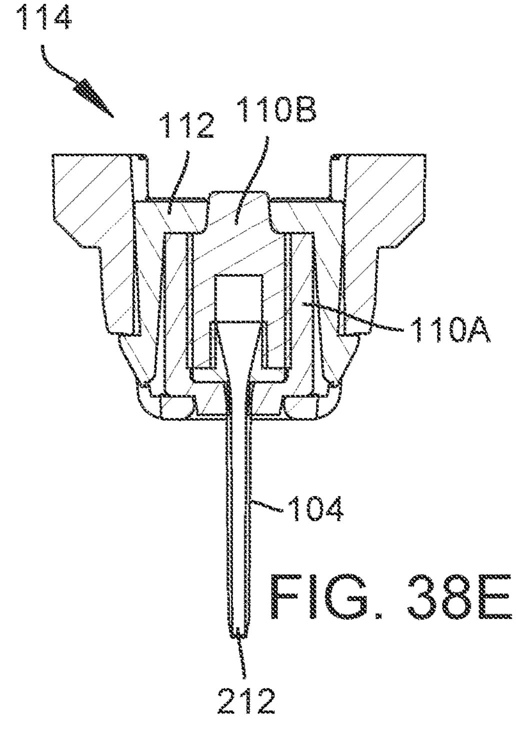
Figure 39A:
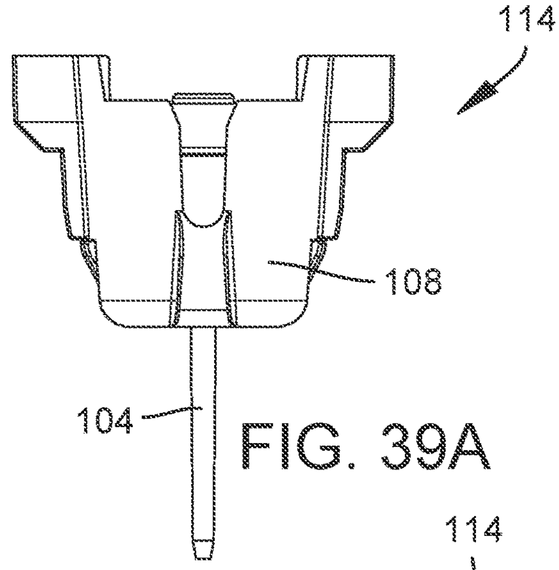
FIGS. 39A-39E depict views of another example cannula subassembly.
Figure 39B:
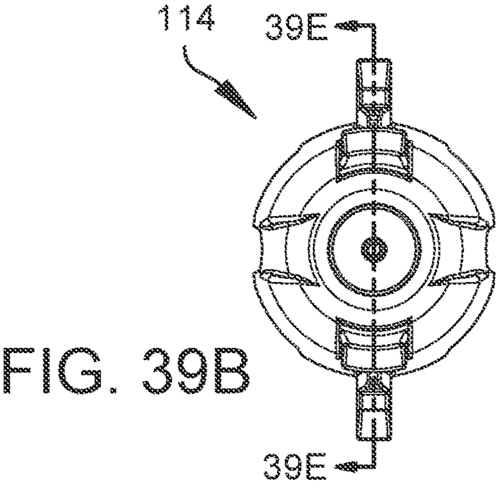
Figure 39C:
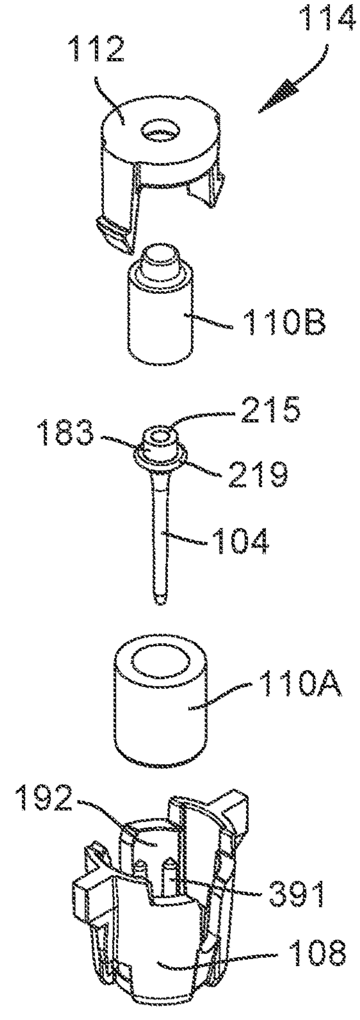
Figure 39D:
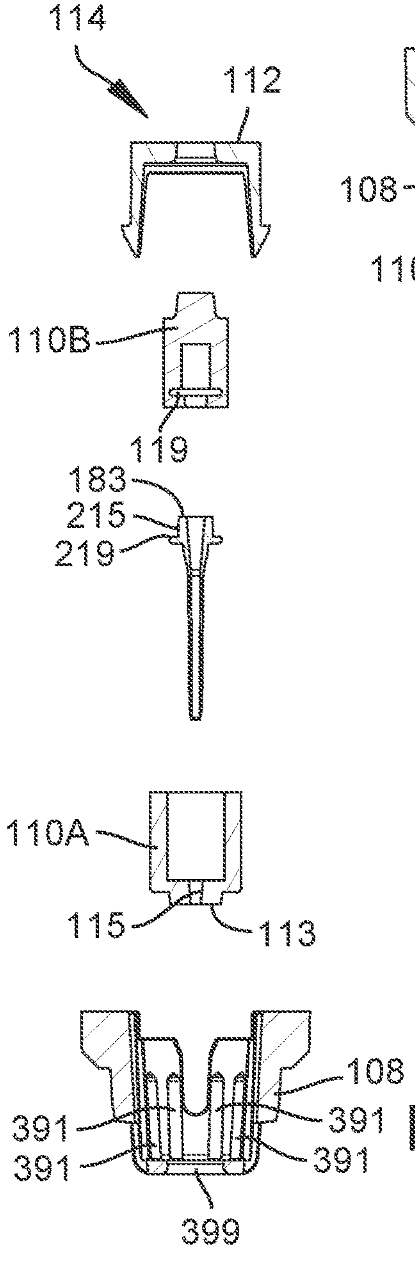
Figure 39E:
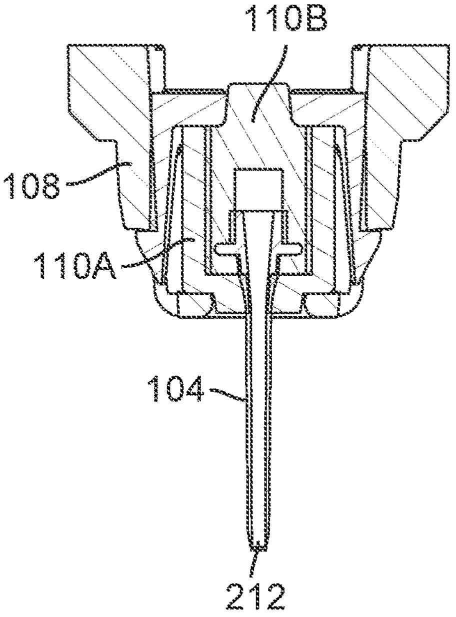

Still referring to FIGS. 35A-36E and additionally to FIGS. 37A-37B, in certain embodiments where the cannula 104 and septum housing 108 are discrete components, a plurality of septums 110A, 110B may be included. A multiplicity of septums 110 may be included in other embodiments as well. The exemplary septums 110A, B may each be made of the same or a different material and/or durometer material. The cannula 104 may include an enlarged region 215 and a flange 219 as described, for example, in relation to FIGS. 31A-31G. The flange 219 may be captured in fluid tight manner between each of the septums 110A, 110B. In the example embodiment, a first of the septums 110A may include a fluid introduction volume 109 and may include a corresponding portion 185 which seats against the septum interface region 183 of the cannula 104. A second of the septums 110B may be disposed in opposition to the first septum 110A. The second septum 110B may include a protruding section 113 which extends into a passage 399 of the septum housing 108. An orifice 115 may be included in a central region of the protruding section 113. The cannula 104 may extend through the orifice 115 (best shown in FIGS. 37A-37B) to the exterior of the cannula subassembly 114. The orifice 115 may also seal against the surface of the cannula 104. As the septum 110B material may be elastomeric, the septum 110B may allow for the cannula 104 to move in relation to relative to an infusion set base 106 minimizing shearing action on the cannula 104.

Referring primarily to FIGS. 37A-37B, views of the septums 110A, B from FIGS. 35A-35F and FIGS. 36A-36E are respectively shown. At least one of the septums 110A, B may include a peripheral rim 117 on a side of the septum 110A, B closest to the opposing septum 110A, B. The peripheral rim 117 may form a fluid tight seal and extend adjacent the edge of the flange 219 of the enlarged portion 215 of the cannula 104 when the cannula subassembly 114 is assembled. The peripheral rim 117 may also surround a receptacle region of the septum 110A, B in which it is included. During assembly, the receptacle region may accept the flange 219 of the cannula 104.

Referring now to FIGS. 38A-38E and FIGS. 39A-39E, further exemplary cannula subassembly 114 embodiments are depicted. As shown, the cannula subassemblies 114 include a plurality of septums 110A, B. In the example embodiment, the first septum 110A is cup-like. The second septum 110B is also cup like in shape, but inverted with respect to the first septum 110A when the septums 110A, B are installed into the receptacle 192 of the septum housing 108. As may be true of any other cannula assembly 114 shown and described herein, the receptacle 192 of the septum housing 108 may include protuberances 391 (further described above in relation to FIGS. 31A-31G)

In the examples shown in FIGS. 38A-39E, the second septum 110B is sized so as to nest within the cup or cavity formed by the first septum 110A. The interior walls of the cup of the first septum 110A may establish a fluid seal against the exterior sidewall of the second septum 110B. The second septum 110B may seal against the septum interface portion 183 of the enlarged region 215 of the cannula 104. The flange 219 of the cannula 104 may be captured in fluid tight sealing relationship between the two septums 110A, B (see FIGS. 38A-38E). Alternatively, the second septum 110B may include a recess 119 defined on the interior wall of the cup portion of that septum 110B (see FIGS. 39A-39E). The flange 219 of the cannula 104 may seat within this recess 119 when the cannula subassembly 114 is assembled and the recess 119 may establish a fluid tight seal against the flange 219. The first septum 110A may include a protruding section 113 which projects into a passage 399 defined in the septum housing 108. The cannula 104 may extend through an orifice 115 in the protruding section 113 and out of the septum housing 108. The elastomeric material of the septum 110A may allow for displacement of the cannula 104 relative to the infusion set base 106 and minimize any potential shearing on the cannula 104 during use.

Figure 40A:
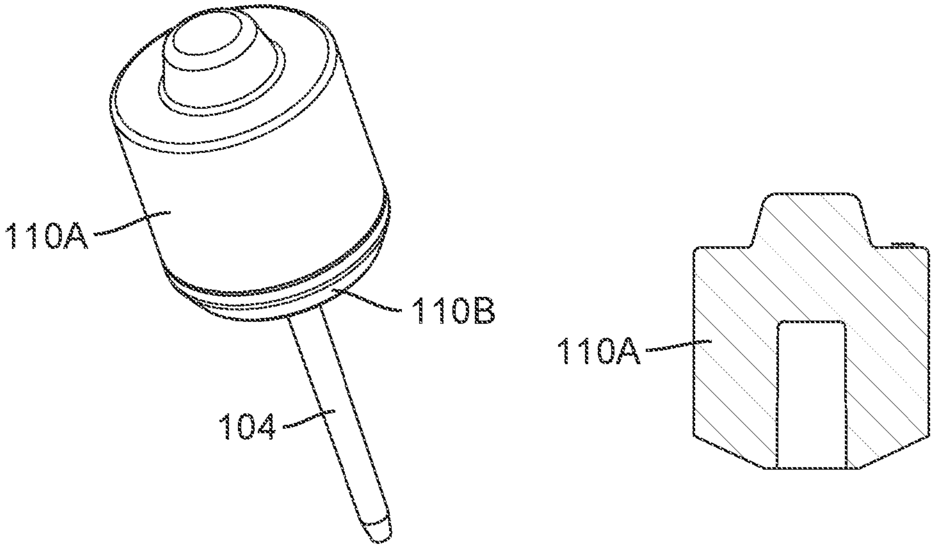
FIGS. 40A-40C depict views of an example cannula and set of exemplary septums which may be included in a cannula subassembly.
Figure 40B:
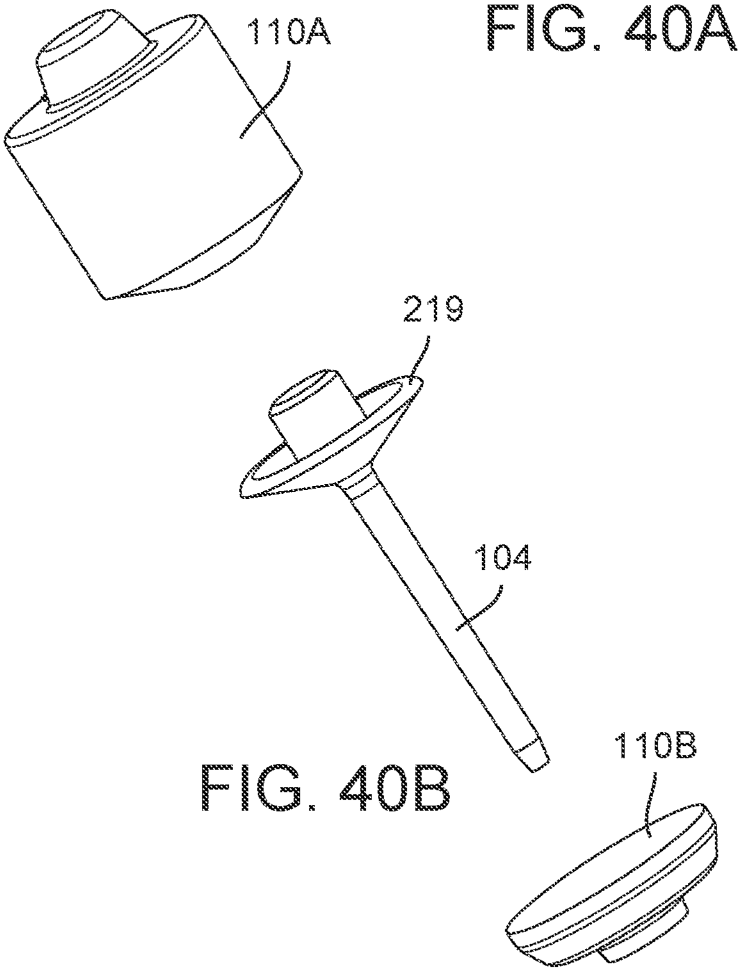
Figure 40C:
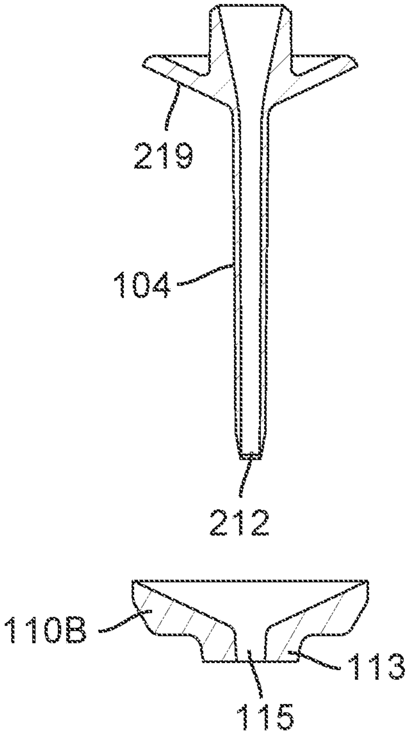

Referring now to FIGS. 40A-40C, in some embodiments, a flange 219 may extend from a cannula 104 in a non-radial manner and may not be substantially planar. The flange 219 may extend from the cannula 104 such that distance from the outlet 212 of the cannula 104 increases in a linear (or not linear in alternative examples) relationship as the flange 219 widens. Thus, the flange 219 may be in the shape of a frustum of a hollow cone. In other embodiments, the relationship between the distance from outlet 212 to the width of the flange 219 need not be linear and at least a portion of the flange 219 may have a curved contour when viewed in cross-section. The first and second septums 110A, B may include cooperatively angled or contoured surfaces which mate against opposing sides of the flange 219 to form a fluid tight seal. The second septum 110B may include a protruding portion 113 with an orifice 115 therein through which the cannula 104 may extend. The flange 219 may establish a ball and socket type relationship with the septums 110A, B allowing for greater motion of the cannula 104 relative to the rest of an infusion set 102 while maintaining a robust seal. Such a ball and socket type arrangement between the cannula 104 and septums 110A, B may be used in any embodiment where a cannula 104 is not monolithically formed together with the septum housing 108.

A variety of embodiments of infusion set bases 106, tubing set connectors 368, and cannula subassemblies 114 are described herein. Though certain features of these components may be described in the context of a particular example embodiment, the scope of the disclosure is not limited thereto. It is contemplated that features of any infusion set base 106, tubing set connector 368, or cannula subassembly 114 may be incorporated into other infusion set base 106, tubing set connector 368, or cannula subassembly 114 embodiments without departing from the scope of this disclosure. Additionally, any of the tubing set connectors 368 described herein may also be constructed as cap bodies which do not include sharps 482 (see, e.g., FIG. 15D), attached infusion tubing 366 (see, e.g., FIG. 6), and/or any flow passages, tubing receptacles 512 (see, e.g., FIG. 190), adhesive introduction apertures 520 (see, e.g., FIG. 190), etc. Such cap bodies may be placed on an infusion set assembly 102 when the infusion set assembly 102 is not connected to a tubing set connector 368 (e.g. when an infusion pump is disconnected during bathing).

Figure 41A:
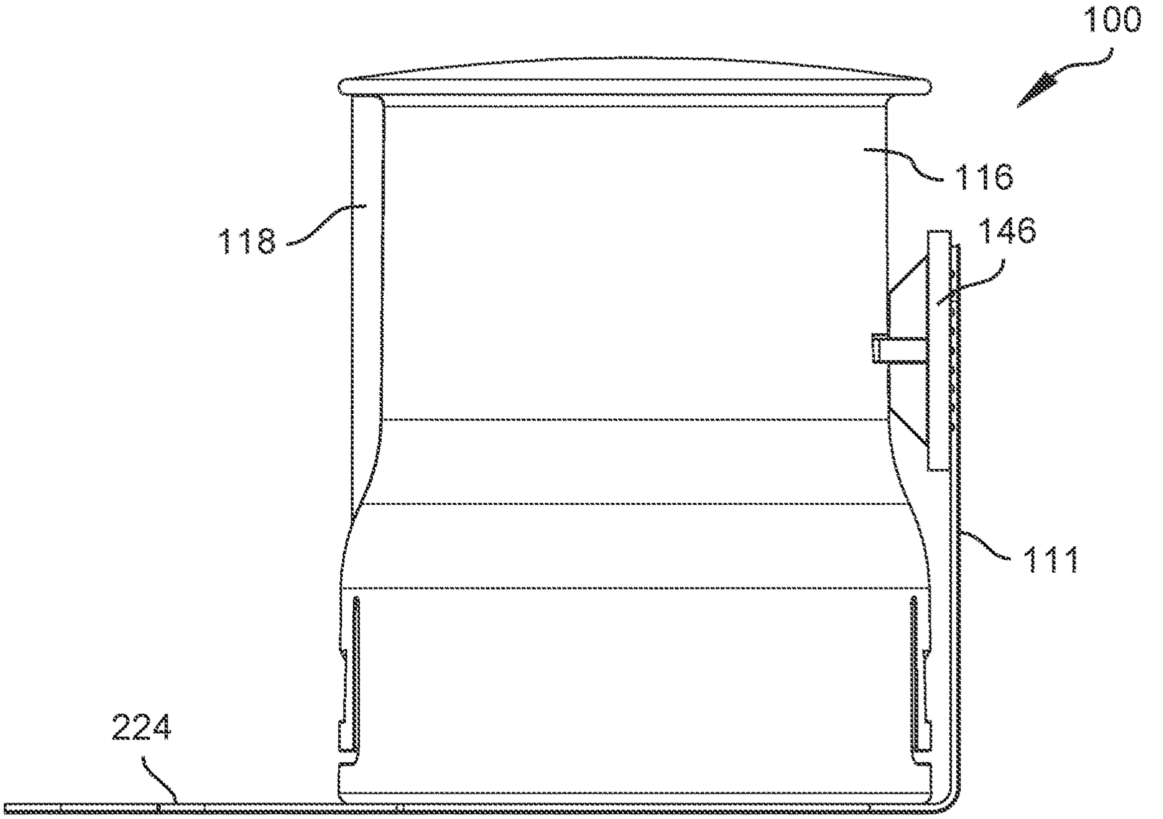
FIG. 41A depicts a side view of an example inserter assembly having an exemplary lock member installed therein.
Figure 41B:
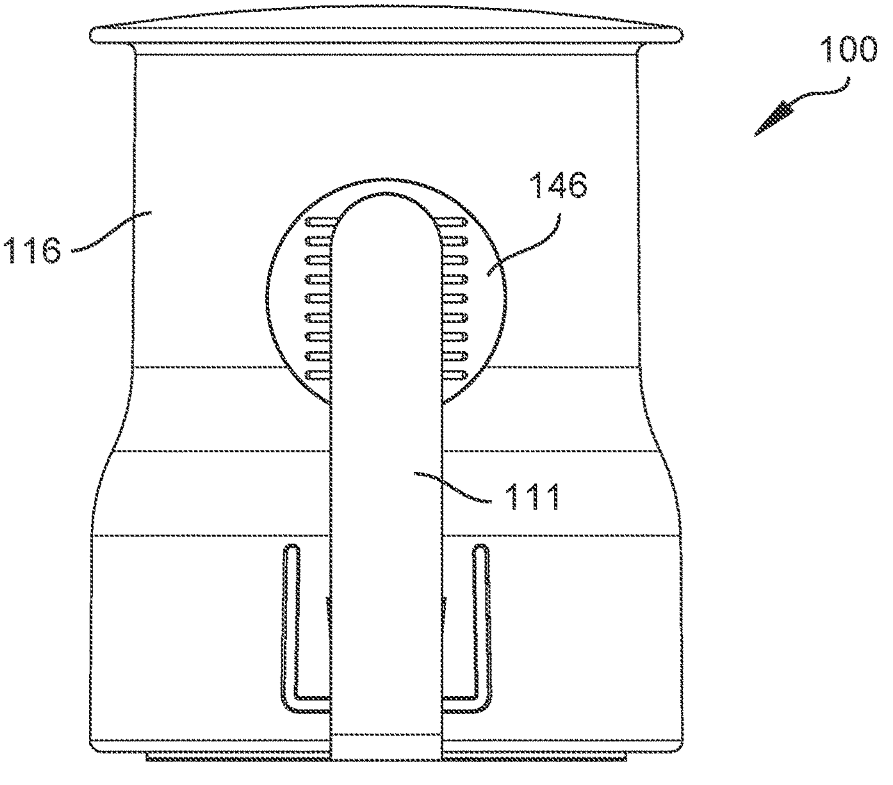
FIG. 41B depicts another side view of an example inserter assembly having an example lock member installed therein.

Referring now to FIG. 41A and FIG. 41B, two side views of an inserter assembly 100 are depicted. The inserter assembly 100 in FIG. 41B has been rotated clockwise 90° from its orientation in FIG. 41A. The example inserter assembly 100 is an assembled version of the exploded view depicted in FIG. 1A. The two views may be representative of the appearance of the inserter assembly 100 before use and after the inserter assembly 100 has been removed from its shipping/storage packaging. As shown, the exterior housing 116 of the inserter assembly 100 is visible and the lock member 146 is in place. Additionally, the adhesive backing 111 is present and covers an adhesive layer present on the bottom face 162 of the infusion set base 106. The adhesive backing 111 may include a gripping region 224 which may be in the form of a flange, tab, or other projection of backing material which extends beyond the footprint of the inserter assembly 100. This gripping region 224 may be grasped by a user and used to peel the adhesive backing 111 off of the infusion set 106. Once the backing 111 has been removed, the inserter assembly 100 may be placed against the desired infusion site using the raised rib 118 to aid in alignment. The lock member 146 may then be pulled out of the inserter assembly 100 to allow for the inserter assembly 100 to be actuated. As the example adhesive backing 111 is attached to the lock member 146, extraction of the lock member 146 may complete disassociation of the adhesive backing 111 from the inserter assembly 100. In the event that the user is unsatisfied with the location the inserter assembly 100 has been placed, the user may leave the lock member 146 in the inserter assembly 100 and pull the inserter assembly 100 off of the body. The presence of the lock member 146 may prevent actuation as this occurs and may allow the user to choose another infusion site.

Figure 42A:
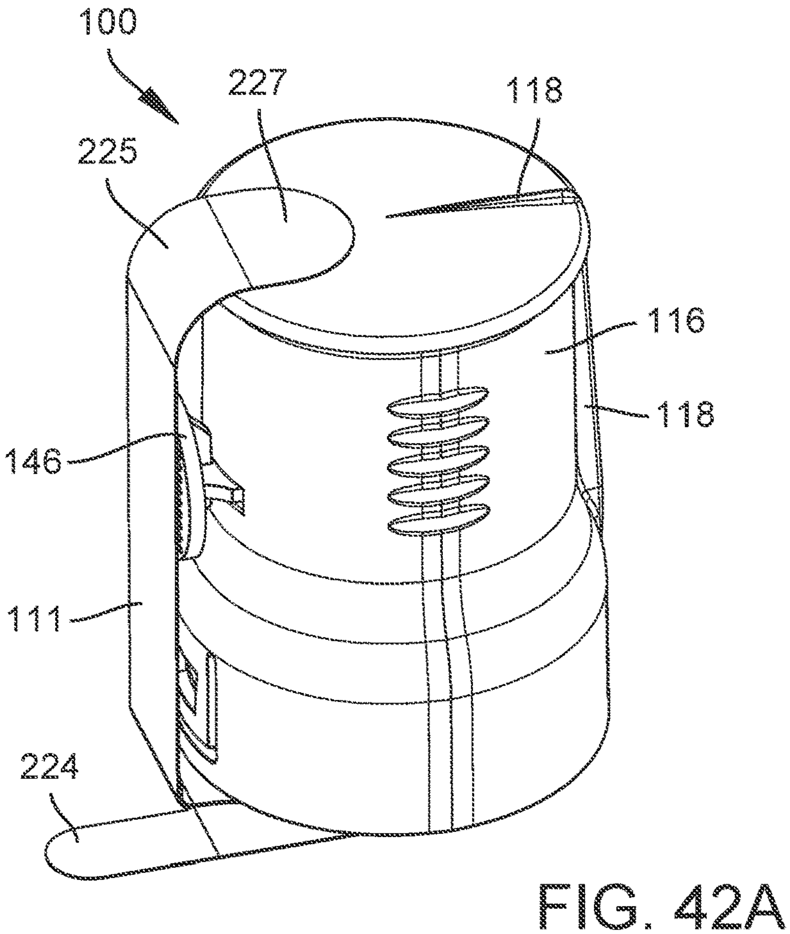
FIG. 42A depicts a perspective view of an example inserter assembly with a lock member and adhering assembly in place.
Figure 42B:
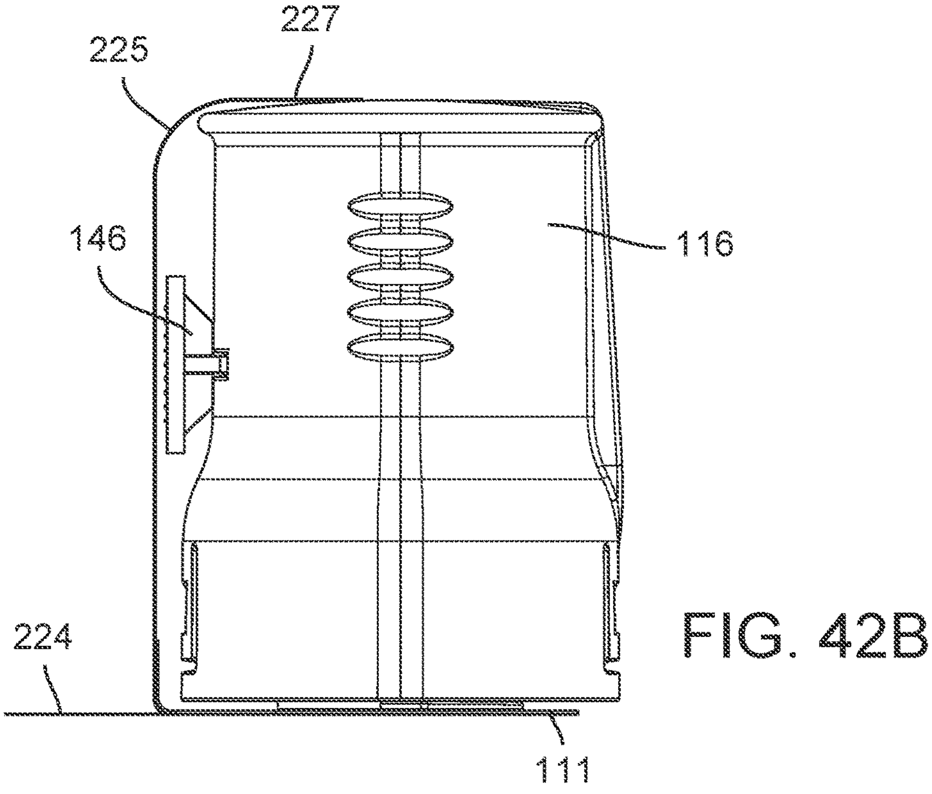
FIG. 42B depicts a side view of the inserter assembly of FIG. 42A.

Referring now also to FIG. 42A and FIG. 42B, two additional views of an inserter assembly 100 are depicted. The example adhesive backing 111 includes a strip 225 which extends from the portion of the adhesive backing 111 covering the adhesive layer present on the bottom face 162 of the infusion set base 106 (see, e.g., FIG. 43-45). The strip 225 may, in some embodiments, extend substantially parallel to and adjacent a gripping region 224 of the adhesive backing 111. In the example shown in FIG. 42A and FIG. 42B, the adhesive backing 111 is coupled to the exterior housing 116 of the inserter assembly 100 instead of the lock member 146. The strip 225 may have a length which is greater than the height of the inserter assembly 100. Thus, a terminal end region 227 of the strip 225 may be coupled to a top surface of the exterior housing 116. The terminal end region 227 may, for example, be attached via heat stake, weld (e.g. sonic weld), or adhesive (e.g. double sided tape or other sticking agent). The terminal end region 227 may be coupled to a spot which does not obstruct view of any raised alignment ribs 118 present on the top surface of the exterior housing 116. The strip 225 may be attached to other portions (e.g. side surface of exterior housing 116 and/or lock member 146) of the inserter assembly 100 as well in certain embodiments. In other embodiments, the length of the strip 225 may differ and the terminal end region 227 may be coupled to another portion of the inserter assembly 100 (e.g. a side surface of the exterior housing 116 or the lock member 146).

Figure 43:
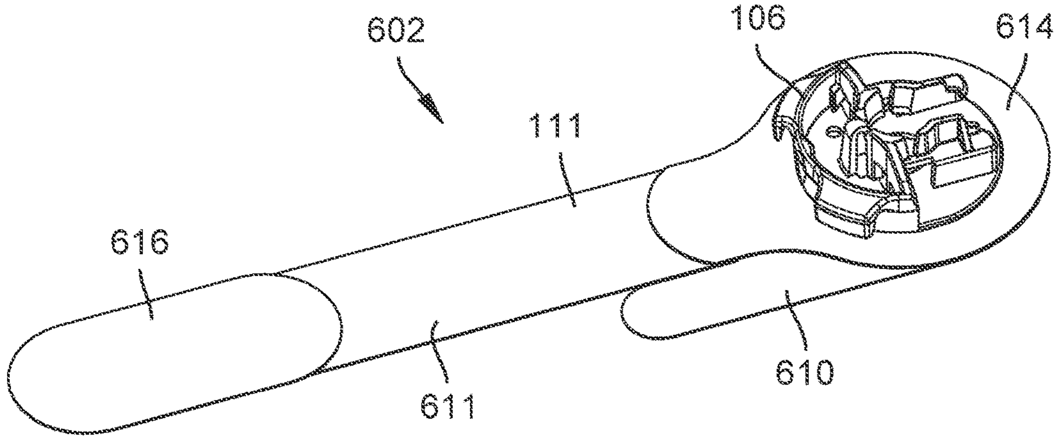
FIG. 43 depicts a perspective view of an example infusion set base and an example adhering assembly.
Figure 44:
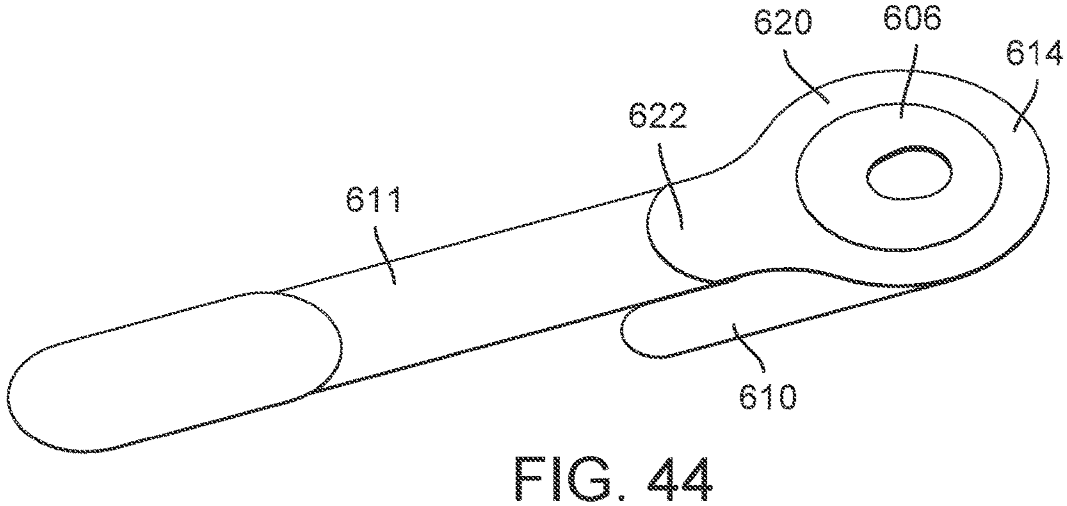
FIG. 44 depicts a perspective view of an exemplary adhering assembly for a portion of an infusion set assembly.
Figure 45:
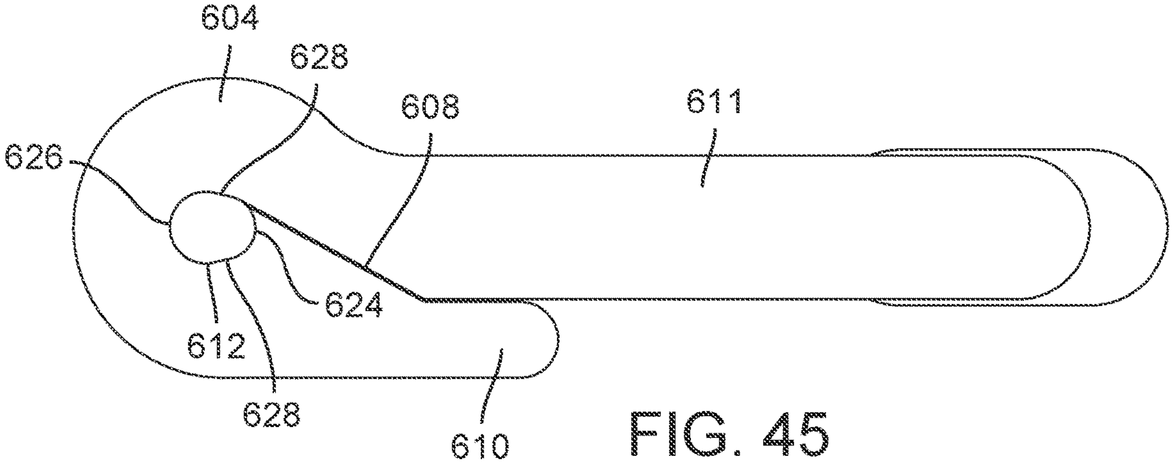
FIG. 45 depicts a bottom plan view of the adhering assembly of FIG. 44.

Referring now to FIGS. 43-45, an exemplary adhering assembly 602 is depicted. The example adhering assembly 602 shown in FIGS. 43-45 may be installed on an inserter assembly 100 in the manner depicted in relation to FIGS. 42A-42B. The exemplary adhering assembly 602 is depicted with an infusion set base 106 in FIG. 43. The infusion set base 106 is not depicted in FIGS. 44-45. In some examples, the infusion set base 106 may be installed into an inserter assembly 100 and the adhering assembly 602 may then be coupled to the base 106.

As shown, the adhering assembly 602 may include a liner 111 or backing. The liner 111 may cover and protect an adhesive patch 614 affixed to the infusion set base 106. The liner 111 may be constructed of any suitable material such as a polymer or waxed paper and may be removed from the infusion set base 106 prior to use of an inserter assembly 100 in which the base 106 is included. Optionally, adhering assemblies 602 may include an adhesive body 616 separate from the adhesive patch 614 on another region of the liner 111. This adhesive body 616 may be used to couple the liner 111 to a portion of an inserter assembly 100 such as an exterior housing 116 of an inserter assembly 100 or a flange 152 of a lock member 146.

As shown, the liner 111 may have substantially flat and elongate shape (e.g. die cut, laser cut, etc. from a larger sheet of material) though may be flexible and bent or folded so as to be routed as shown in FIGS. 42A-42B. One end of the liner 111 may include an enlarged region 604. The enlarged region 604 may be an adhesive patch covering section of the liner 111 which may cover adhesive of an adhesive patch 614 attached to the infusion set base 106. The enlarged region 604 and adhesive patch 614 may have an at least partially round footprint which may be aesthetically preferable. The liner 111 may also include an appendage or strip portion 611 which may extend from the enlarged region 604 to the opposing end of the liner 111. The strip portion 611 may, though need not, be substantially straight and may, though need not, have a generally uniform width. The end opposite the enlarged region 604 may be rounded. The strip portion 611 may have a width which is smaller than the enlarged region 604. The strip portion 611 may have a length which is greater than a height of an inserter assembly 100.

The liner 111 may also include a tab or flap 610. The flap 610 may be connected at a first end to the enlarged region

604. The flap 610 may extend to a second end opposite the first in a direction substantially parallel to the strip portion 611. The flap 610 may extend directly adjacent the section of the strip portion 611 most proximal the round region 604. This may give the liner 111 a compact look and help save material during manufacture.

Example adhesive patches 614 may be constructed of a substrate which bears a skin compatible adhesive on one side thereof. An adhesive patch 614 may include a main region 620 and a protruding region 622. The main region 620 may be flat and round and may have a foot print greater than that of the infusion set base 106 to which it is attached. The protruding region 622 may extend from the periphery of the main region 620 and partially along the strip portion 611 of the liner 111. A segment of the strip portion 611 closest to the enlarged region 604 may cover adhesive on the protruding region 622. When the infusion set base 106 is attached to an infusion site, the protruding region 622 may serve as a removal tab which may facilitate peeling of the adhesive patch 614 and infusion set base 106 off of the infusion site.

The adhesive patch 614 may be attached to a bottom face 162 (see, e.g., FIG. 4B) of the infusion set base 106 in any suitable manner. In certain examples and as best shown in FIG. 44, a double sided tape 606 or other adhesive may be used to couple the adhesive patch 614 to the base 106. In alternative embodiments, the adhesive patch 614 may include a substrate which may be heat staked or welded (e.g. sonically, RF) to the bottom face 162 of the base 106. The adhesive patch 614, liner 111 and any double sided tape 606 may include an aperture extending therethrough.

Referring primarily to FIG. 45, the liner 111 may include a partition which divides a portion of the liner 111. In the example embodiment, a slit 608 which extends through the liner 111 is included though perforations and/or scoring may alternatively be used in place of the slit 608. In the example embodiment, a single slit 608 is used and extends across a portion of the enlarged region 604. The slit 608 may be oriented to encourage the liner 111 to peel off the adhesive patch 614 in a single piece and limit the potential for regions of high stress to form in the liner 111 as the liner 111 is removed. The shape of the aperture 612 of the liner 111 may also be selected to encourage this.

The slit 608 orientation and aperture 612 shape may facilitate simple, quick, and unitary removal of the liner 111 from the adhesive patch 614. This may be so even if a user aggressively removes the liner 111 or only roughly/loosely follows a prescribed removal motion when peeling the liner 111 from the adhesive patch 614. Additionally, the slit 608 orientation and aperture 612 shape may facilitate use of a wider range of materials for the liner 111.

As shown, the slit 608 may extend from a point between the first end of the flap 610 and the strip portion 611 of the liner 111. The slit 608 may extend to the aperture 612 in the liner 111. The slit 608 may be angled so as to be tangent to the edge wall of the aperture 612. The slit 608 may extend in a straight line. The slit 608 may be angled such that the slit 608 is at a tangent to a far side of the aperture 612 with respect to the flap 610. The aperture 612 may be constructed so as to have a minimum number of corners or regions where the sidewall of the aperture 612 otherwise redirects from extending in one direction to another differing direction. As shown, the sidewall of the aperture 612 includes a first rounded span 624 and a second opposing rounded span 626. These spans 624, 626 may be the only spans of the aperture 612 wall where the wall redirects. The first rounded span 624 may have a tighter curvature (e.g. smaller radius) than the second rounded span 626. The aperture 612 may also include two substantially straight sidewall spans 628 which connect the first and second rounded spans 624, 626. Transitions between each of these spans 624, 626, 628 is gentle. The first rounded span 624 may be more proximal the flap 610 than the second rounded span 626. The slit 608 may end at a point of tangency to the first rounded span 624. In some embodiments, the slit 608 may be collinear with one of the straight sidewall spans 628 of the aperture 612.

As the liner 111 is unfurled from the adhesive patch 614, the example liner 111 may redirect around a portion of the aperture 612. In the example embodiment, the liner 111 may make a turn around the second rounded span 626 of the aperture 612 as the liner 111 is peeled from the adhesive patch 614. As the second rounded span 626 has a gentler curvature (e.g. wider radius), the turn made by the liner 111 may be relatively gentle. This may mitigate opportunity for the liner 111 to develop points of high stress during removal. Additionally, the shortest distance between a point on the second rounded span 626 and the periphery of the liner 111 may be shorter than the shortest distance between the peripheral edge of the liner 111 and any other portion of the aperture 612. As a result, a relatively small surface area of the liner 111 may be attached to the adhesive patch 614 in the region where the liner 111 makes a turn about the aperture 612 during removal of the liner 111. Due to the lower surface area, the liner 111 may be least firmly or relatively weakly adhered to the adhesive patch 614 in this region. This may further aid in limiting stress on the liner 111 material as the liner 111 is peeled off the adhesive patch 614 around the second rounded span 626.

As the liner 111 is unfurled around the aperture 612, the orientation of the slit 608 may help ensure that the only portions of the liner 111 adhered to the adhesive patch 614 are disposed ahead of the area where the liner 111 is disassociating with the adhesive patch 614. Thus, the direction of pulling by a user to remove the liner 111 would not need to differ significantly from the direction of the lagging portion of the liner 111. This may prevent the generation of points of high stress on the liner 111 material where regions lagging behind the area where the liner 111 is disassociating from the adhesive patch 614 are still attached to the adhesive patch 614.

As a user pulls on the flap 610 to peel the liner 111 from the adhesive patch 614, the tangent orientation of the slit 608 with respect to the far side of the aperture 612 may be preferred as it may aid in allowing the liner 111 to be removed easily and unitarily. The orientation of the slit 608 may encourage a user to naturally peel the liner 111 along the direction of extension of the slit 608. A straight pull of the liner 111 along this direction may substantially inhibit the formation of stress points at the edge of the liner 111 along the second rounded span 626. A situation where the liner 111 is being pulled by a user in a direction significantly different than the direction of adjacent downstream portions of the liner 111 may be avoided as the liner 111 is disassociated from the adhesive patch 614 around the second rounded span 626. Thus, the region of the liner 111 which redirects around the second rounded span 626 may be more easily peeled off the adhesive patch 614.

Figure 46A:
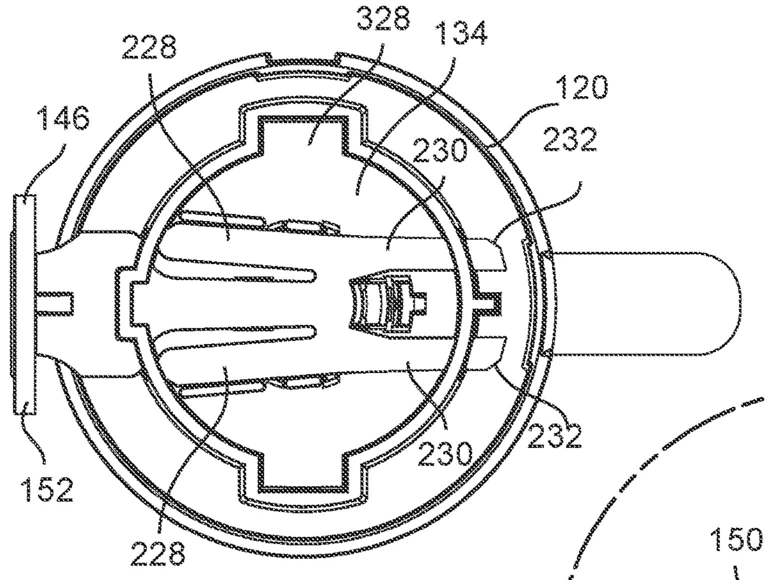
FIG. 46A depicts a top down view of an example inserter assembly with its exterior housing removed.
Figure 46B:
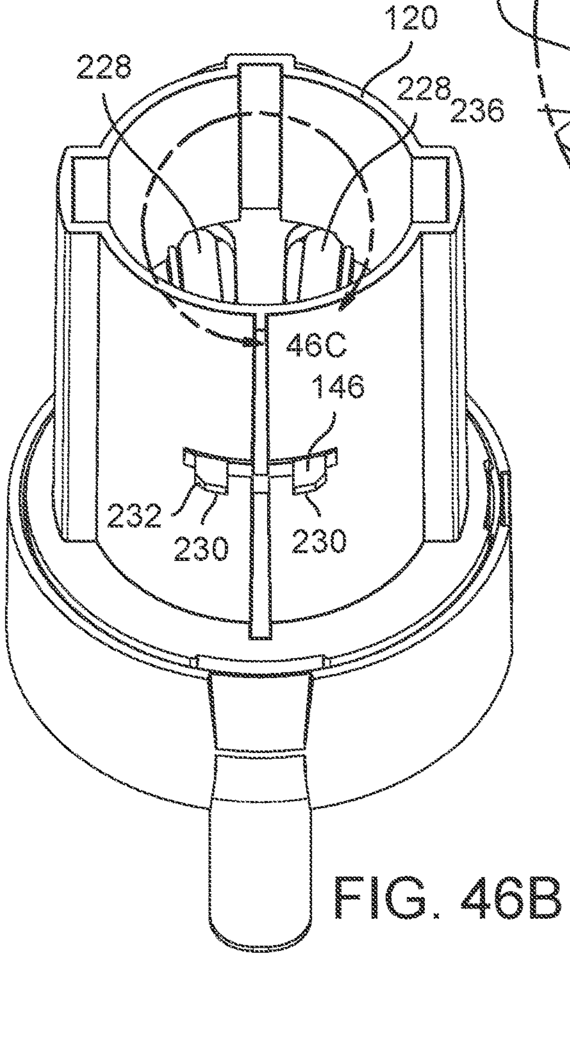
FIG. 46B depicts a perspective view of an example inserter assembly with its exterior housing removed.
Figure 46C:
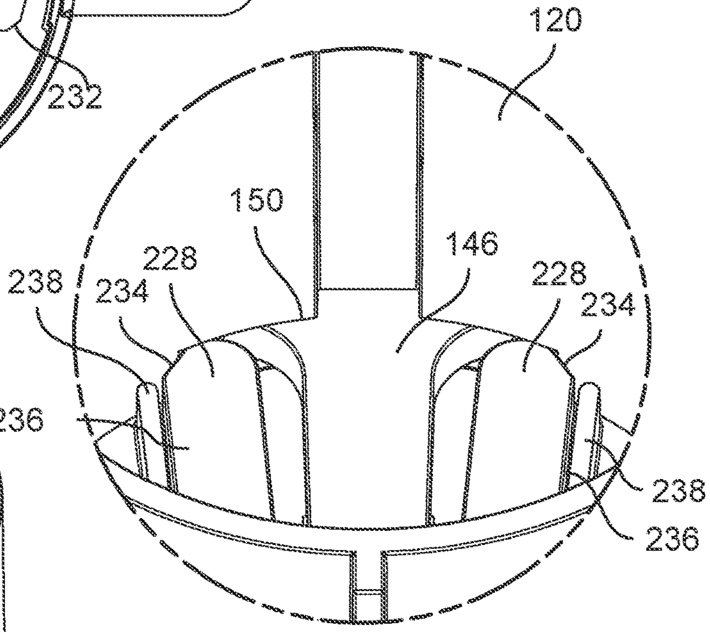
FIG. 46C depicts a detailed view of a portion of the FIG. 46B.
Figure 47:
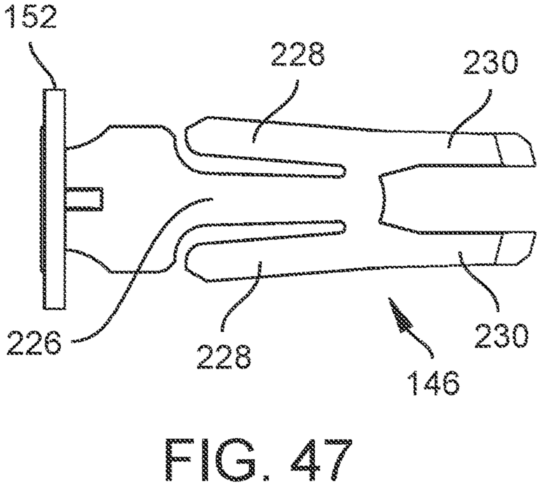
FIG. 47 depicts a top down view of an example lock member.

Referring now also to FIGS. 46A-47, various views of the inserter assembly 100 with the exterior housing 116 removed and a view of the lock member 146 in isolation (FIG. 47) are depicted. As shown, when in place within the inserter assembly 100, the lock member 146 may act as a safety. The inserter assembly 100 may be designed such that it cannot fire until the lock member 146 has been removed.

The lock member 146 may extend across the entire width of the interior housing 120 and be above other components of the inserter assembly 100. The lock member 146 may be directly adjacent to at least one of the other components so as to prevent its movement.

The lock member 146 may include a flange 152 which may be grasped to aid in extraction. The lock member 146 may also include a stem portion 226 or appendage which projects away from the flange 152. The stem portion 226 may support a number of arms 228, 230. In the example embodiment, the arms 228, 230 are arranged in an "H" like pattern and the stem portion 226 is connected to the arms 228, 230 via the cross piece of the "H". Arms 230 may reside in the fenestration 150 of the interior housing 120 most distal to the flange 152. Arms 230 may also include a chamfer feature 232 which may aid in guiding the lock member 146 during its installation into the inserter assembly 100.

As shown, arms 228 may be cantilevered so as to be able to deflect inward toward the stem portion 226. The distance between the outer edges of the arms 228 may be greater than the width of the fenestration 150 through which they pass when the lock member 146 is installed into the inserter assembly 100. During installation, the arms 228 may deflect toward the stem portion 226 to allow the arms 228 to pass through the fenestration 150. Once through the fenestration 150, the arms 228 may spring back outward to their unstressed state. Thus, as best shown in FIG. 46C, the width between the outer edges of the arms 228 may be wider than the width of the fenestration 150 when the lock member 146 is in place. This may ensure that some force may be required to remove the lock member 146 from the inserter assembly 100 and may inhibit the lock member 146 from being inadvertently dislodged. As shown, the arms 228 may include a chamfer region 234. The chamfer region 234 may abut a wall of the fenestration 150 of the interior housing 120 most proximal to the flange 152. The chamfer region 234 may aid in deflection of the arms 228 toward the stem portion 226 during extraction of the lock member 146 from the inserter assembly 100. Though an angled chamfer is shown, a rounded or curved region may be included in alternative embodiments.

In various examples, at least one component of the inserter assembly 100 may include at least one lock member constraining member such as raised bumpers 238. In the example embodiment, the bumpers 238 are included on the needle retractor 134 and extend from a top plate 328 thereof. The raised bumpers 238 may flank or be positioned aside or adjacent at least a portion of the lock member 146. The bumpers 238 may thus prevent any wobbling or pivoting of the lock member 146 within the inserter assembly 100. The bumpers 238 may also aid in redirecting the lock member 146 during installation if the lock member 146 is introduced into the inserter assembly 100 crookedly. A bumper 238 may also be provided to limit the depth which the lock member 146 may be pressed into the inserter assembly 100.

Figure 48:
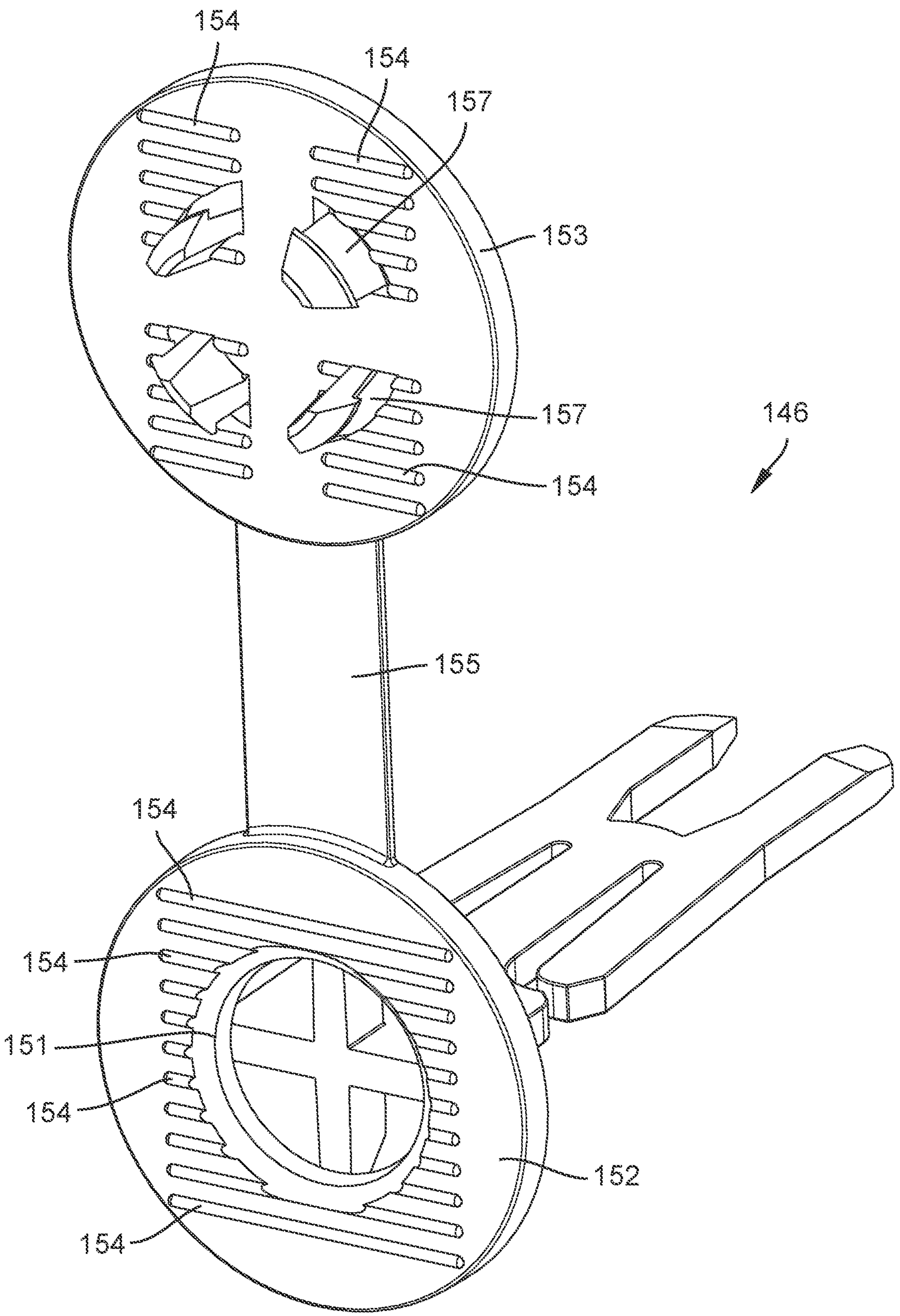
FIG. 48 depicts a perspective view of another example lock member.

Referring now to FIG. 48, an alternative embodiment of the lock member 146 shown in FIGS. 46A-47 is depicted. As shown, the flange 152 of the lock member 146 may include an aperture 151 which may extend through the flange 152. The aperture 151 may be centrally disposed within the flange 152. A cap body 153 may be coupled to the lock member 146 by a strand or strip 155 of flexible material. In the example embodiment, a strip 155 of material extending from the periphery of the flange 152 to the periphery of the cap body 153 is used. The flexible strand or strip 155 may allow the cap body 153 to be displaced relative to the flange 152 while being leashed to the flange 152. In other embodiments, the cap body 153 may be a separate component. The cap body 153 includes a number of latch fingers 157 which project from the cap body 153. The latch fingers 157 may be arranged to deflect as they are introduced into the aperture 151 via a first side of the flange 152. After being displaced into the aperture 151 beyond a certain distance, the latch fingers 157 may resiliently restore and catch against the opposing face of the flange 152. In certain examples, and adhesive liner 111 (see, e.g., FIG. 41A-B) may be captured between the cap body 153 and the flange 152 when the cap body 153 is engaged with the flange 152. Thus, no tape, adhesive, heat staking, RF welding, ultrasonic welding, etc. may need to be used to attach the liner 111 to the flange 152. In some embodiments, the liner 111 may include passages therein through which the latch fingers 157 may project. In other embodiments, the passages may not be included and the liner 111 may be crushed into the aperture 151 when the cap body 153 is coupled to the flange 152. Additionally, cap body 153 and flange 152 may include raised sections 154. The raised sections 154 may be spaced so as to interdigitate with one another when the cap body 153 is coupled to the flange 152. This may aid in firmly retaining a liner 111 between the cap body 153 and flange 153. Though sets of straight ridges are shown for the raised sections 154, other embodiments may include round raised sections (e.g. concentric circles) which may similarly capture the liner 111 therebetween when the cap body 153 and flange 152 are coupled. Cap bodies 153 and optionally the strand or strip 155 may be included for any other lock member shown or described herein. Any lock member 146 embodiments described herein may be modified to include a leashed or separate cap body 153.

Figure 49A:
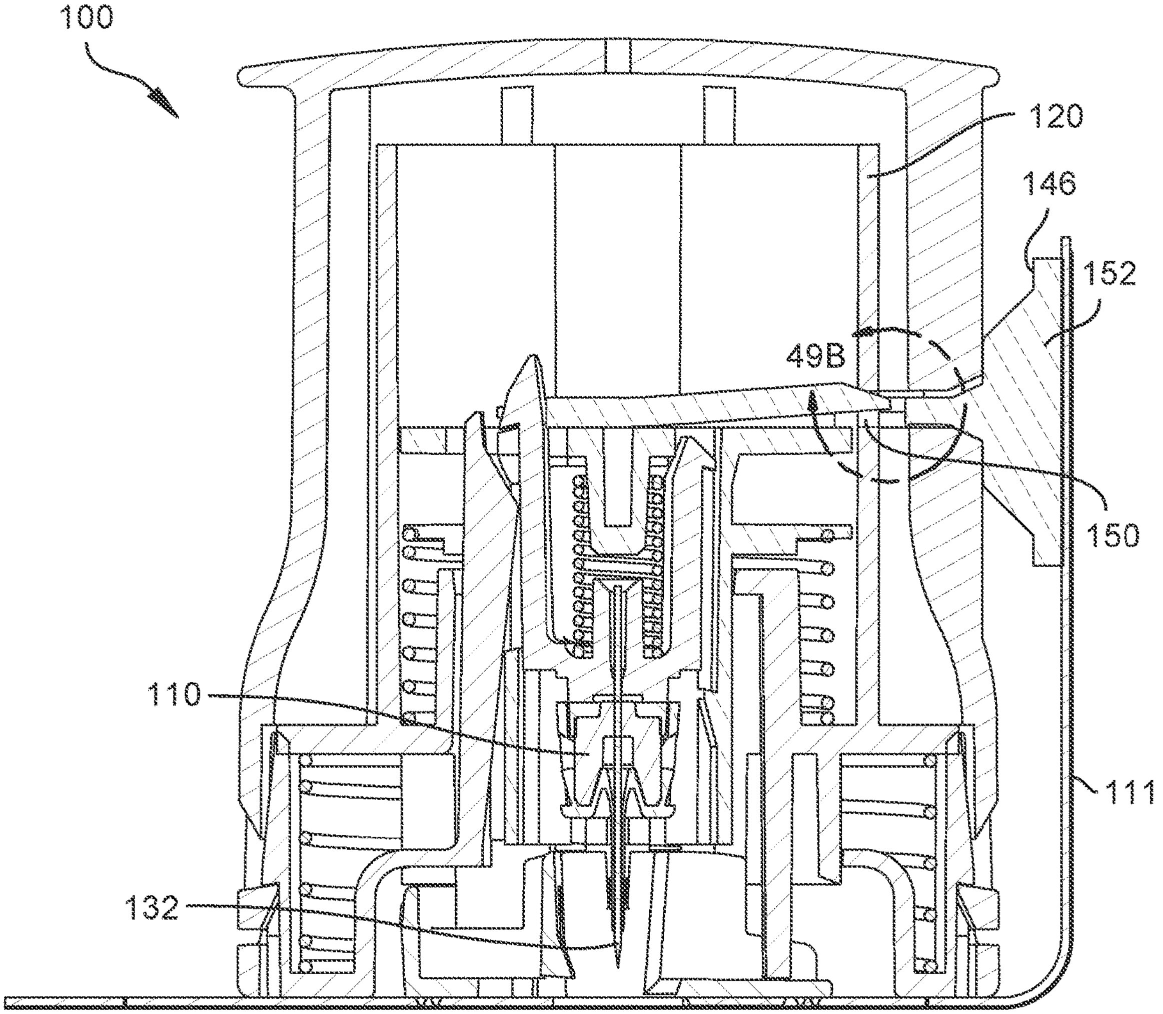
FIG. 49A depicts a cross sectional view of an example inserter assembly having an example lock member installed therein.
Figure 49B:
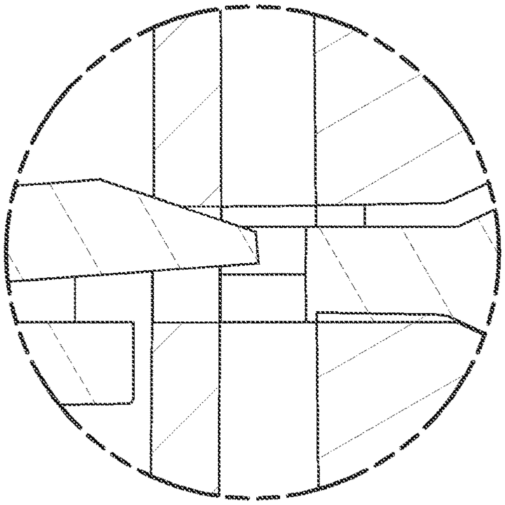
FIG. 49B depicts a detailed view of a portion of FIG. 49A.
Figure 50:
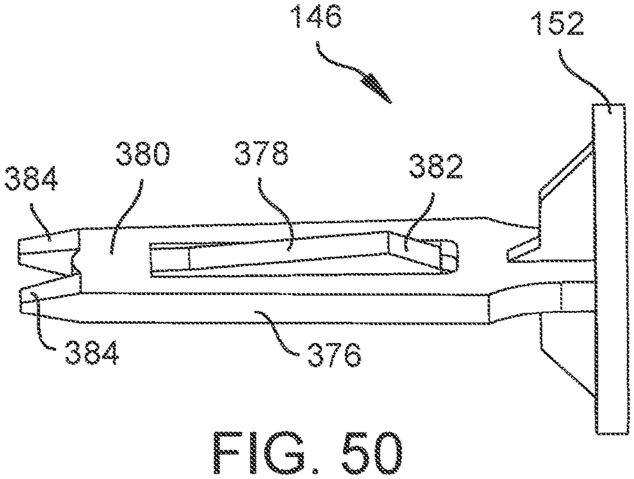
FIG. 50 depicts a perspective view of an example lock member.

Referring now also to FIG. 49A-50, various views of an inserter assembly 100 with an alternative lock member 146 and a view of the alternative lock member 146 in isolation (FIG. 50) are depicted. As above, when in place within the inserter assembly 100, the lock member 146 may act as a safety, preventing firing until the lock member 146 has been removed. The example lock member 146 extends across a portion, but not the entirety of the width of the interior housing 120 and is located above other components of the inserter assembly 100 to prevent movement. As shown best in FIG. 49A, the example lock member 146 is also directly adjacent an arm 296 of the sharp holder 130 and presents a mechanical interference to displacement of the arm 296 in the general direction of the flange 152. The interior housing 120 may only include one fenestration 150 instead of a set of opposing fenestrations 150.

The lock member 146 may include a flange 152 which may be grasped to aid in extraction. The lock member 146 may also include an appendage 376 which projects away from the flange 152. A tine 378 may be included within the appendage 376. The tine 378 is cantilevered to the appendage 376 at a portion of the tine 378 most distal to the flange. The tine 378 is also constructed to as to naturally project above a face 380 of the appendage 376 but be flexible when force is applied to the unsupported end of the tine 378. As shown, the unsupported end of the tine 378 includes a ramped region 382. The end of the appendage 376 most distal to the flange 152 may also include a chamfer feature 384 which may aid in guiding the lock member 146 during its installation into the inserter assembly 100. As the lock member 146 is installed into the inserter assembly 100, the top wall of the fenestration 150 may deflect the tine 378 toward the surface of the appendage 376 such that the tine 378 may pass through the fenestration 150. After completing introduction of the lock member 146, the tine 378 may spring back toward its initial unstressed state. Thus, as best shown in FIG. 49B, a portion of the tine 378 may be disposed above the top wall of the fenestration 150 when the lock member 146 is in place. This may ensure that some force may be required to remove the lock member 146 from the inserter assembly 100 and may inhibit the lock member 146 from being inadvertently dislodged. As shown, the ramped section 382 may abut the top wall of the fenestration 150. The ramped section 382 may aid in deflection of the tine 378 toward the surface 380 of the appendage 376 during extraction of the lock member 146 from the inserter assembly 100. Though an angled section 382 is shown, a rounded or curved region may be included in alternative embodiments. Lock member constraining features similar to the raised bumpers 238 shown in FIGS. 46A-47 may be included as well.

Figure 51:
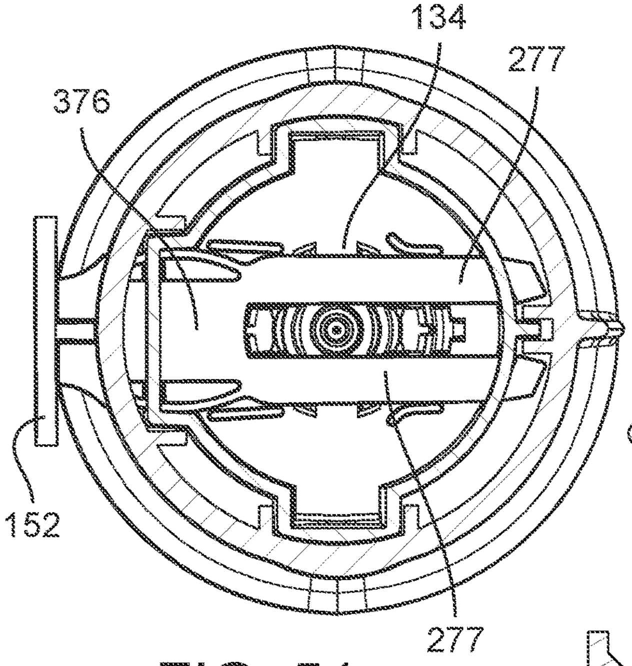
FIG. 51 depicts a view of an example inserter assembly which has been sectioned to reveal an exemplary lock member disposed partially within the inserter assembly.
Figure 52:
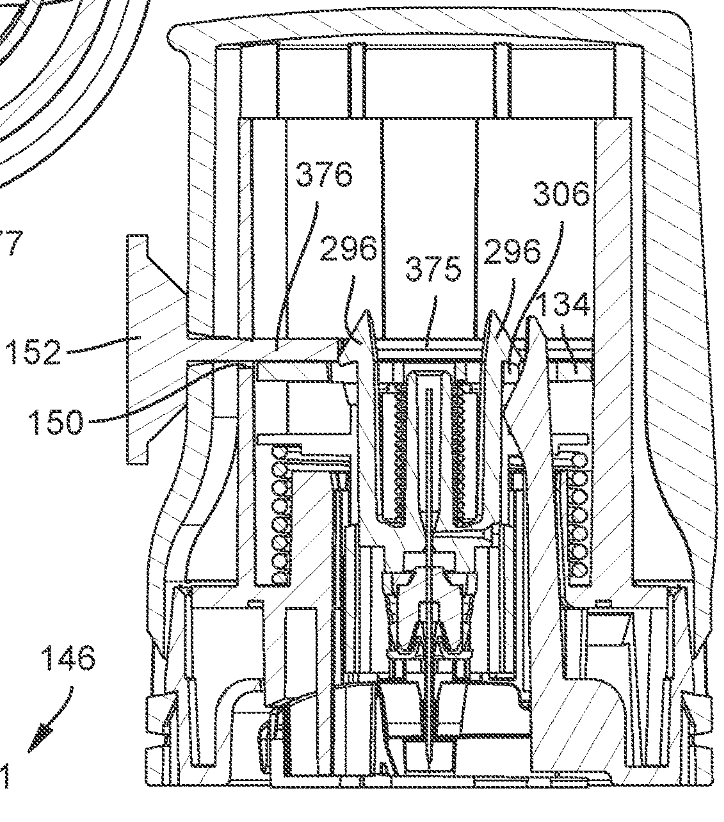
FIG. 52 depicts a sectional view of an example inserter assembly with an example lock member installed.
Figure 53:
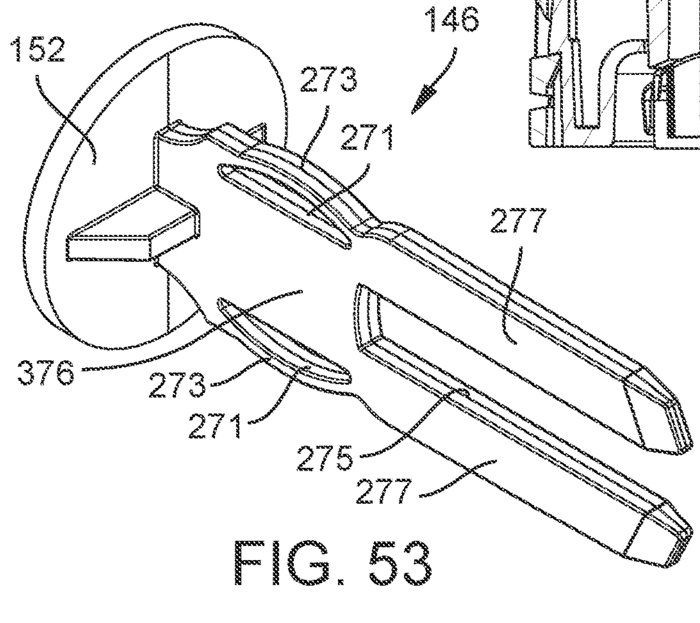
FIG. 53 depicts a perspective view of an example lock member.

Referring now also to FIG. 51-53, various views of an inserter assembly 100 with another alternative lock member 146 and a view of the alternative lock member 146 in isolation (FIG. 53) are depicted. As above, when in place within the inserter assembly 100, the lock member 146 may act as a safety, preventing firing until the lock member 146 has been removed. The example lock member 146 may include a flange 152 which may be grasped to aid in extraction. The lock member 146 may also include an appendage 376 which projects away from the flange 152. The appendage 376 may include a set of prongs 277 spaced apart by a slot 275 at a region of the appendage 376 most distal to the flange 152. As best shown in FIG. 52, the sharp holder 130 (further described in relation to FIGS. 60-68) may be symmetric and include two cantilevered arms 296 of substantially equal height. The slot 275 may accommodate these arms 296.

The portion of the appendage 376 most proximal to the flange 152 may include a set of arcuate members 273. The arcuate members 273 may be disposed on opposing sides of the appendage 376. An opening 271 between each arcuate member 273 and a main body 279 of the appendage 376 may be present. The distance between the outer sides of the arcuate members 273 may be greater than the width of the fenestration 150 through which they pass when the lock member 146 is installed into the inserter assembly 100. During installation, openings 271 may allow the arcuate members 273 may resiliently deflect toward the main body 279 of the appendage 279 such that the lock member 146 may fit through the fenestration 150. The arcuate members 273 may restore to their unstressed state once through the fenestration 150. This may ensure that some force may be required to deflect the arcuate members 273 to remove the lock member 146 from the inserter assembly 100 and may inhibit the lock member 146 from being inadvertently dislodged. Alternatively, when fully installed, the arcuate members 273 may not be advanced fully through the fenestration 150 and the arcuate members 273 may be in a deflected state pressing against the side wall of the fenestration 150. This may again help to ensure some force may be required to remove the lock member 146 and aid in preventing inadvertent dislodgement. When installed in the inserter assembly 100 the edge of the slot 275 most proximal the flange 152 may be directly adjacent an arm 296 of the sharp holder 130. This may help ensure that a cantilevered arm 296 of the sharp holder 130 is firmly held in place on a catch 306 of the sharp retractor 134 while the lock member 146 is in place.

Figure 54A:
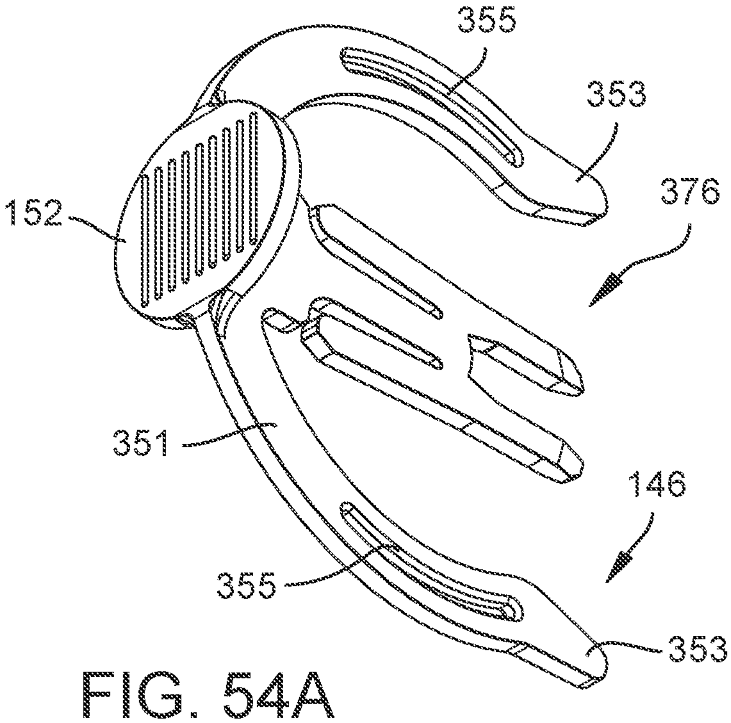
FIGS. 54A-54B depict views of yet another example lock member which may be used to prevent triggering of an example inserter assembly.
Figure 54B:
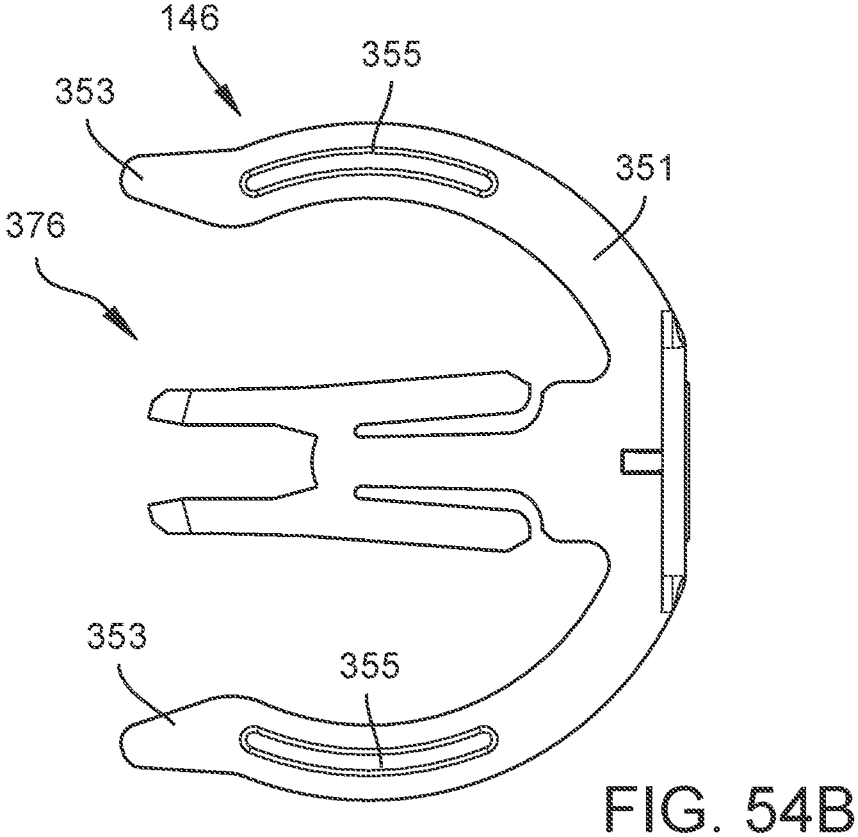

Referring now to FIGS. 54A-54B, yet another example lock member 146 is depicted. The exemplary lock member 146 includes an arcuate body 351. An appendage 376 may extend from the arcuate body 351. As shown, the appendage 376 extends from a midpoint of the arcuate body 351. In the example embodiment, the appendage 376 is that shown in FIGS. 46A-47 though any appendage 376 shown in embodiments herein may be used. When the lock member 146 is in place on an inserter assembly 100, the appendage 376 may extend into the inserter assembly 100 and prevent triggering of the inserter assembly 100. The arcuate body 351 may at least partially wrap around the exterior housing 116 of the inserter assembly 100. The end regions 353 of the crescent shaped body 351 may be ramped so as to aid in installation of the lock member 146 into the inserter assembly 100. As the lock member 146 is advanced toward an inserter assembly, the ramped end regions 353 may aid in centering the inserter assembly 100 with respect to the appendage 376. The arcuate body 351 may deflect such that the end regions 353 are spread apart from on another during a portion of the installation of the lock member 146 into the inserter assembly 100. The lock member 146 includes a flange 152 which may be grasped to aid in extraction.

The arcuate body 351 may include one or more slots 355. In the example embodiment two slots are included. The slots 355 may be disposed adjacent the end regions 353 of the arcuate body 351. The slots 355 may be sized such that a portion of a liner 111 may be fed through one of the slots 355. The liner 111 may then be coupled to a portion of the inserter assembly 100 (see, e.g., FIG. 42A). In the event that a user attempts to remove the lock member 146 prior to removal of the liner 111, the portion of the liner 111 passing through the slot 355 may inhibit extraction of the lock member 146. This may present a cue to a user which encourages a user to remove the liner 111 from an inserter assembly 100 prior to removal of the lock member 146.

Figure 55:
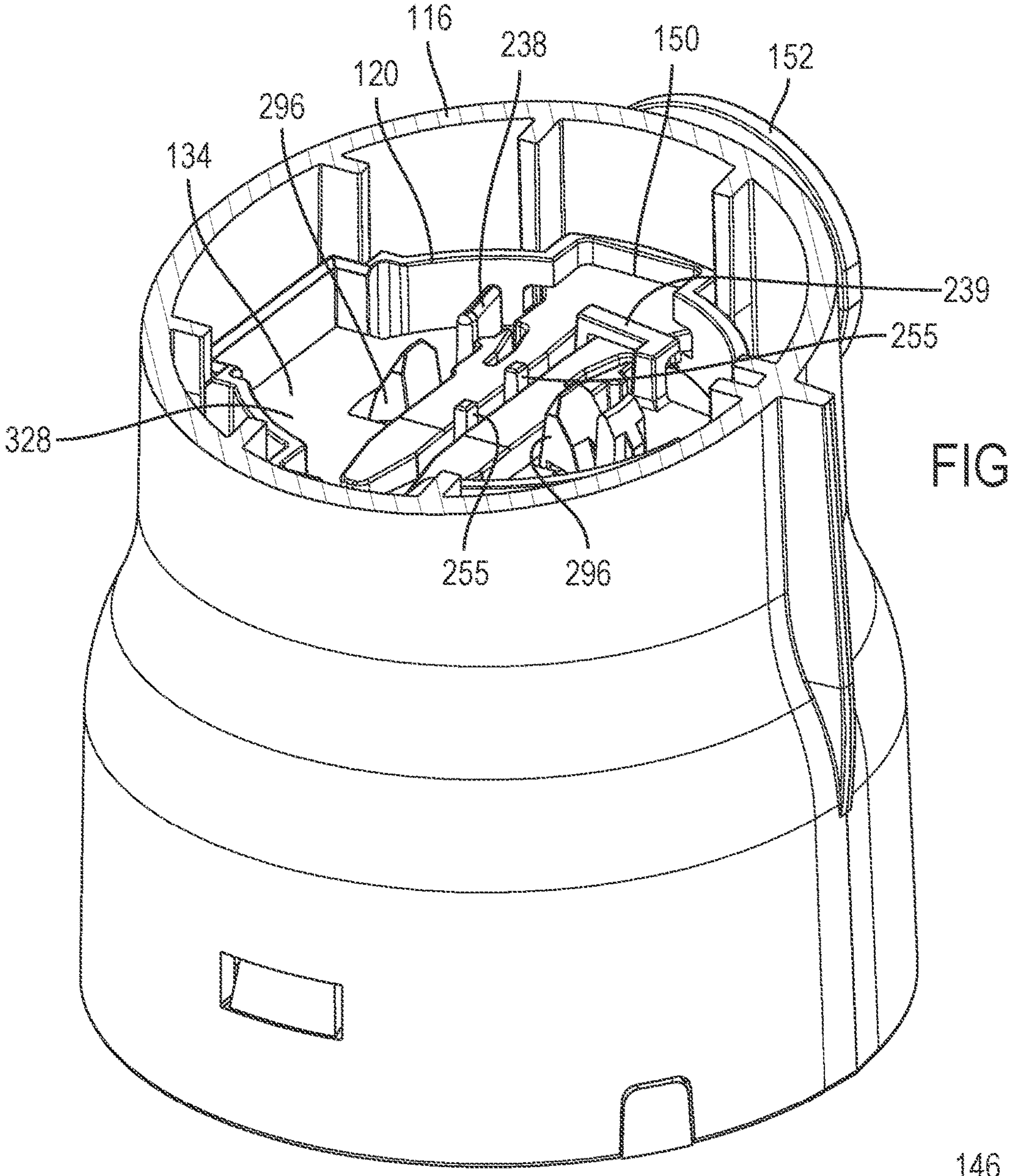
FIG. 55 depicts a cross-sectional view of an example inserter assembly with an example lock member installed.
Figure 56A:
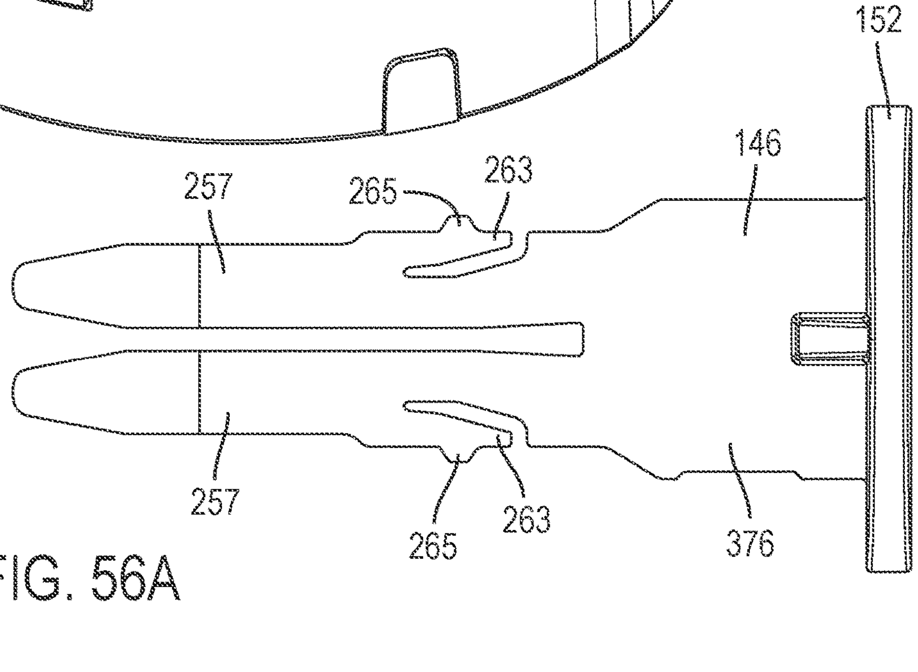
FIGS. 56A-56E depict views of a variety of exemplary embodiments of lock members.
Figure 56B:
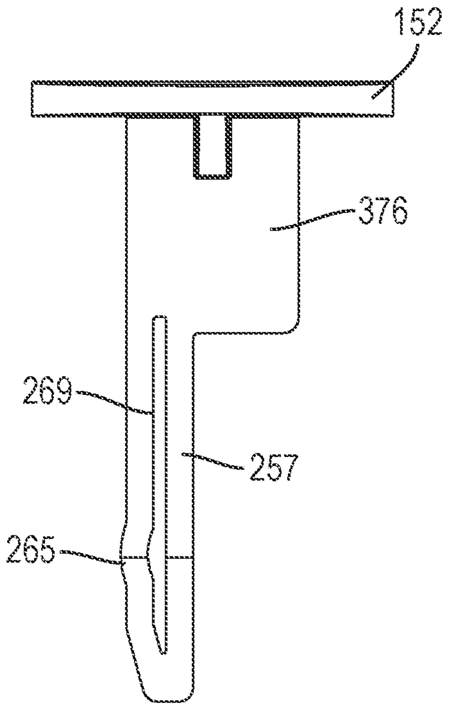
Figure 56C:
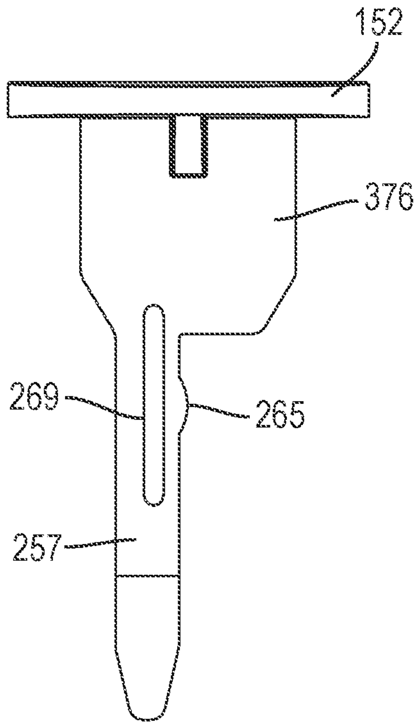
Figure 56D:
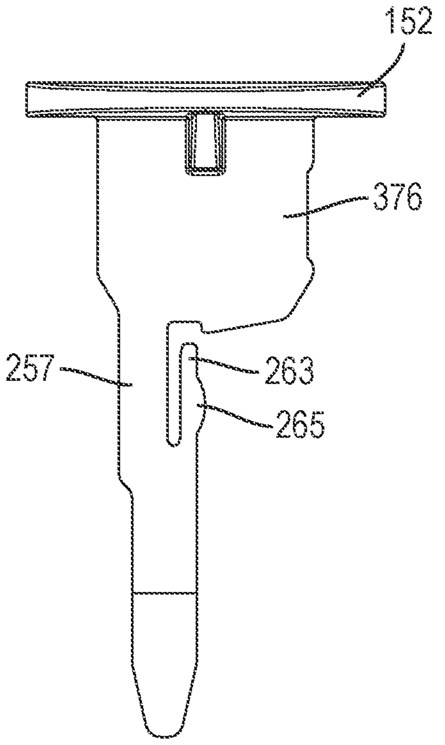
Figure 56E:
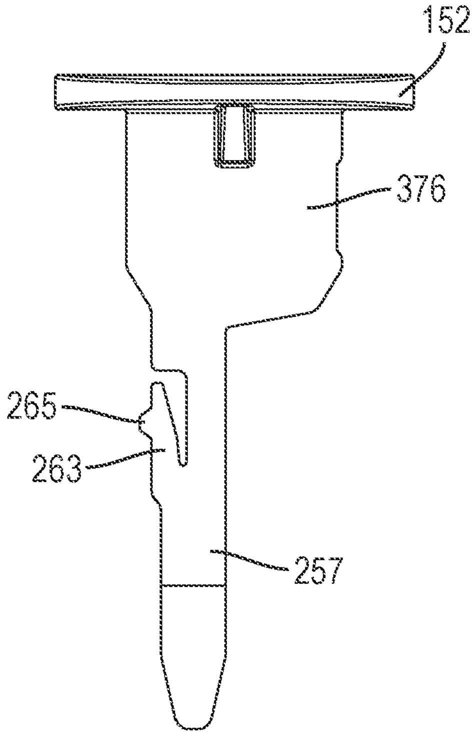

Referring now to FIGS. 55-56A, another example inserter assembly 100 and lock member 146 are depicted. As shown, the fenestrations 148, 150 in the exterior housing 116 and interior housing 120 respectively may be disposed to provide an introduction path for the lock member 146 which extends between arms 296 of the sharp holder 130. The lock member 146 may include a flange 152 from which an appendage 376 projects. At a portion of the appendage 376 opposite the flange at least one spreader projection 257 may be included (see, e.g., FIGS. 56B-56E for example embodiments with a single spreader projection 257). In the example embodiment, two spreader projections 257 are included and extend generally parallel to one another such that the exemplary lock member 146 is substantially symmetrical. The symmetrical nature of the lock member 146 may allow the lock member 146 to be installed in multiple orientations facilitating assembly. When installed in example inserter assemblies 100, the lateral faces of the spreader projections 257 may block deflection of the arms 296 of the sharp holder 130 toward a midplane of the inserter assembly 100. Thus, the example lock member 146 may keep the arms 296 spread apart from one another. In some embodiments, the spreader projections 257 may contact and press the arms 296 outward from the midplane when the lock member 146 installed in the inserter assembly 100. This may help to ensure that the arm 296 of the sharp holder 130 is retained in place on a catch 306 of the sharp retractor 134 while the lock member 146 is in place.

In the example embodiment, the sharp retractor 134 includes at least one interference body 255. In the example embodiment a set of interference bodies 255 is included. The interference bodies 255 may reside in a gap between the spreader projections 257 when the lock member 146 is installed. The interference bodies 255 may block displacement of the spreader projections 257 toward one another. In some embodiments, the interference bodies 255 may cause the spreader projections 257 to splay apart. The interference bodies 255 may aid in robustly retaining the arm 296 in engagement with the catch 306 (see, e.g., FIG. 52).

In the example embodiment, the top plate 328 of the sharp retractor 134 includes a bumper 238 (further described in relation to FIG. 46C) and passage through which a portion of the lock member 146 extends. In the example, the passage is defined by a bridge 239. At least one of the spreader projections 257 may extend under the bridge 239 when installed in the inserter assembly 100. This may inhibit movement of the sharp retractor 134 along the axis of the inserter assembly 100 when the lock member 146 is installed and may assist in preventing relative displacement of components within the inserter assembly 100. A portion of the bridge 239 may be received between the spreader projections 257 and double as an interference body 255 in some examples.

In various examples, the spreader projections 257 may each include a deflectable region. In the example embodiment, the spreader projections 257 each include a deflectable arm 263. As the lock member 146 is installed into the inserter assembly 100, one of the deflectable arms 263 may contact a surface of the bridge 239. The deflectable arms 263 may include nubs 265 such that further advancement of the lock member 146 toward the installed position may cause the deflectable arm 263 to bend toward the spreader projection 257 from which it extends. Upon the lock member 146 reaching the fully installed position, the nub 265 may be displaced clear of the bridge 239 and the deflectable arm 263 may restored to an undeflected state. Audible feedback (e.g. a click or slapping sound) may be generated as the deflectable arm 263 restores to the undeflected state. Tactile feedback may also be perceptible by the use as the arm 263 restores to the non-deflected state. The nub 265 may also inhibit inadvertent removal of the lock member 146.

Referring now also to FIGS. 56B-56E, a number of additional lock members 146 are depicted. Each of the lock members 146 includes a flange 152 from which an appendage 376 extends. A single spreader projection 257 which projects from a portion of the appendage 276 opposite the flange 152 is included in each example lock member 146. Each example lock member 146 could alternatively be symmetrical with two substantially parallel spreader projections 257. The spreader projections 257 of the lock members 146 each include deflectable regions. The examples shown in FIGS. 56D-56E include deflectable arms 263 with nubs 265 as described above in relation to FIGS. 55-56A. The spreader projections 257 in the example embodiments depicted in FIGS. 56B-56C include slots 269. The slots 269 may allow for regions of the spreader projections 257 adjacent the slots 269 to be deflected in the direction of the slot 269. With respect to FIG. 56C, as the lock member 146 is installed into an inserter assembly 100, a nub 265 on the spreader projection 257 may contact a surface of the bridge 239. Further advancement toward the installed position may cause a portion of the spreader projection 257 adjacent the slot 269 to bow or deflect inward. The nub 265 may be clear of the bridge 239 when the lock member 146 is in the fully installed position and the deflected portion of the spreader projection 257 may be free to restore to an undeflected state. With respect to FIG. 56B, the nub 265 may abut an arm 296 of the sharp holder 130 in engagement with the catch 306 (see, e.g., FIG. 52). When in the fully installed position, a portion of the spreader projection 257 adjacent the slot 269 to bow or deflect inward and the nub may press against the arm 296 holding the arm 296 in engagement with the catch 306.

Figure 57:
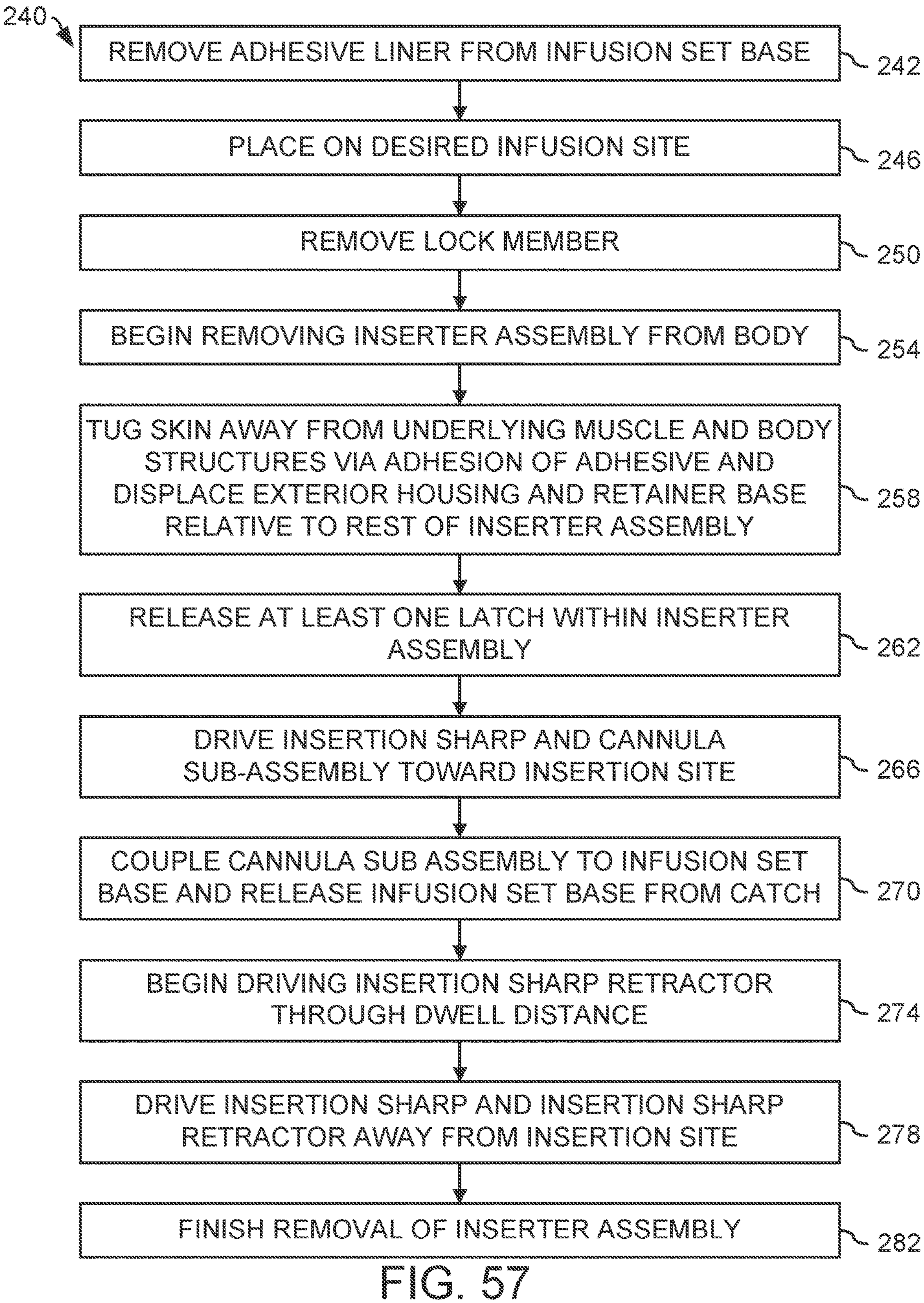
FIG. 57 depicts a flowchart detailing a number of actions which may be used to actuate an inserter assembly.

Referring now to FIG. 57, a flowchart 240 depicting a number of example actions which may be executed to place an infusion set 102 on a patient with an inserter assembly 100 is shown. Certain inserter assemblies 100, such as that shown in FIG. 1A, may be placed on the skin and be designed to prevent actuation until the skin has been displaced from its normal, resting position on the body. To this end, an inserter assembly 100 may include an actuation restricting arrangement (described elsewhere herein). Actuation of an inserter assembly 100 may be precluded until some degree of displacement of the skin has occurred. Actuation of an inserter assembly 100 may be prohibited until a certain amount of relative displacement between components of an inserter assembly 100 has occurred. This relative displacement may be effected as the skin is lifted and the inserter assembly 100 is withdrawn away from the body. The adhesion of the base 106 of the infusion set 102 to the skin may cause certain components (e.g. at least one component coupled to the base 106) to be restricted in their displacement as the user withdraws the inserter assembly 100. As the inserter assembly 100 is withdrawn, the elasticity of the skin may exert a force on the base 106 (and any coupled component) pulling it toward or holding it closer to the body. At least one other component of the inserter assembly 100 may be free to displace or have greater freedom to displace as the inserter assembly 100 is removed. Thus the inserter assembly 100 may be broken into a first unit and a second unit which is more constrained in its ability to displace as the inserter assembly 100 is pulled away from the body than the first unit. Relative movement may, in certain examples, be inhibited until a certain force is exerted against the base 106 by the skin. The user may need to pull the inserter assembly 100 away from the body with enough force to stretch the skin to a degree that relative movement of the different portions of the inserter assembly 100 is initiated. With the user pulling the inserter assembly 100 away from the infusion site and the elasticity of the skin pulling the second unit toward the infusion site in an opposing direction, a threshold force compelling separation of the first and second unit may be supplied. Once the threshold force is supplied, relative motion may begin.

A trigger for the inserter assembly 100 may be kept from actuation until the skin has been tugged away from the rest of the body a distance sufficient to generate the force required to begin relative movement. Triggering may not be possible until a requisite amount of relative displacement has occurred. Once triggered, an inserter actuation assembly (exemplary embodiments described below) of the inserter assembly 100 may be freed to complete placement of an infusion set 102 at the desired infusion site. The actuation assembly may include a trigger arrangement which, once released, causes an insertion sharp 132 to be driven into an infusion site. The actuation assembly may also retract the insertion sharp 132 back into the inserter assembly 100. The actuation assembly may couple a cannula subassembly 114 to an infusion set base 106. The actuation assembly may also uncouple the infusion set 102 from the inserter assembly 100 once the infusion set 102 has been installed at a desired infusion site.

In some embodiments, inserter assemblies 100 may be placed on the skin and trigger actuation as the inserter assembly 100 is lifted up so as to be removed. No other depression, twisting, squeezing, etc. of a trigger, button, housing sleeve or other portion of an inserter assembly 100 by a user may be needed to provoke the actuation, however, the actuation may still be under the control of the user. The relative movement of the free component(s) of the inserter assembly 100 with respect to the restricted component(s) may trigger actuation, by, for example, displacing or dislodging a latch and freeing one or more bias members to begin driving actuation. Thus, a trigger internal to the inserter assembly 100 may be actuated as a result of the removal action of the inserter assembly 100 from the body. The trigger may be automatically actuated, for example, when skin at the infusion site has been lifted at least a certain distance from underlying anatomy. From the perspective of a user, such an inserter assembly 100 may simply be placed on the skin and then withdrawn to execute placement of the infusion set 102.

In alternative embodiments, a discrete manual triggering action may be employed to trigger actuation of an inserter assembly 100. Any arrangement which would be apparent to one skilled in the art may be used to facilitate manual triggering. An inserter assembly 100 may include, for example, one or more button which when displaced may trigger actuation by dislodging a latch within the inserter assembly 100. Alternatively, a portion of the inserter assembly 100 may be deformable and squeezing the inserter assembly 100 may press a projection which displaces with the deformable section into a latch to dislodge the latch. The button or deformable section may, for instance, be included on exterior housing 116 in certain examples. A twisting action may be employed to trigger actuation of an inserter assembly 100. Such a twisting action of one portion of the inserter assembly 100 (e.g. the casing) relative to another (e.g. the remainder the inserter assembly 100) may sweep a projection of the inserter assembly 100 into a latch to dislodge the latch. In other embodiments, a pin or similar member may be pulled out of the inserter assembly 100 after the inserter assembly has been pulled away from the skin to trigger actuation. In embodiments including a lock member 146 (see, e.g., FIG. 47), the lock member 146 may be kept in place until the user has begun withdrawing the inserter assembly 100 from the skin. Actuation may be triggered when removal of the lock member 146 allows components of the inserter assembly 100 to displace relative to one another such that, for example, a latch may be released. Various combinations of manual triggering arrangements may also be used. A button press or squeeze followed by a twist or vice versa may trigger actuation for instance. The manual triggering action may not be possible until after the skin has been displaced from a resting position and/or until a certain degree of relative movement between the free and restricted components of the inserter assembly 100 has occurred. Any arrangement which would be apparent to one skilled in the art may be used to facilitate such a lockout. An interlock, for example, may prevent button displacement, twisting, squeezing, etc. until the skin has been displaced or until relative movement beyond a threshold magnitude has occurred. Alternatively, an interlock may block access to a latch within the inserter assembly 100 preventing it from being dislodged until the skin has been displaced or until relative movement beyond a threshold magnitude has occurred. In some embodiments, button displacement, twisting, squeezing, etc. may be possible but rendered impotent by the interlock until the skin has been displaced or until relative movement beyond a threshold magnitude has occurred. As one skilled in the art would appreciate, the inserter assembly 100 embodiments described herein could be otherwise modified to allow for various types of additional manual actuation schemes.

While such designs may make triggering actuation simple, intuitive, and more foolproof, other advantages may also be realized. For example, as the inserter assembly 100 is lifted, the inserter assembly 100 may be designed so as to tug the skin to which the base 106 of the infusion set 102 is attached away from the underlying muscle and other body structures or anatomy. Thus, when inserted, the cannula 104 of the infusion set 102 may be more reliably placed within a subcutaneous layer of adipose tissue. This may reduce pain upon insertion, help minimize bruising, increase the potential body area over which infusion sites may be chosen, and may lead to more predictable absorption of agents such as insulin. The skin may also be pulled taut facilitating easy penetration of the insertion sharp 132 through the skin. As the skin is passively lifted along with the inserter assembly 100, no pneumatic vacuum is required to be generated. This may allow an inserter assembly 100 to be less complicated and made with fewer parts. Additionally, pneumatic seals either against the skin or within the inserter assembly 100 may be omitted. Lifting of the skin may be more reliably accomplished as the contour of the body at the infusion site (which could present a sealing challenge) may be largely irrelevant. Furthermore, no pinching of the skin may be needed to pull the skin away from the underlying structures. This may help to make the insertion more comfortable, may limit bruising, and may more reliably pull the skin away from underlying structures. The inserter assembly 100 may also ensure that insertion of the cannula 104 into the skin occurs at a prescribed orientation. The skin may be held in place so as to be parallel or perpendicular to a reference plane or axis (e.g. parallel to the bottom face 162 of the base 106 of the infusion set 102 or perpendicular to the axis of the insertion sharp 132 or insertion sharp displacement path) which moves with the inserter assembly 100. Thus, the angle of the inserter assembly 100 or path along which the inserter assembly 100 is pulled away with respect to the body may not alter insertion angle. Example embodiments shown herein depict an insertion angle which is substantially perpendicular to the skin, however, insertion at any angle (just over 0° to 90°, e.g. 30°, 45°, 60° etc.) may be similarly ensured by fixing the skin relative to a reference plane or axis which moves with the inserter assembly 100. Another potential benefit is that there may be less psychological concern associated with the triggering of the actuation. As depression, twisting, squeezing, etc. of some actuator by the user may not be necessary, there may be less anxiety built up in anticipation of triggering the actuation. The exact moment of actuation as the inserter assembly 100 is withdrawn may not be known to the user. This may help to limit psychological concerns and may lower perceived pain.

As shown in FIG. 57, in block 242, an adhesive liner or backing 111 may be removed from an infusion set base 102 retained within the inserter assembly 100. The inserter assembly 100 may then be placed on a desired infusion site in block 246. This may cause the adhesive on the infusion set base 102 to stick to the skin of the patient. It may be desirable to press the inserter assembly 100 against the skin to ensure a robust attachment of the adhesive to the skin. A lock member 146 may be removed from the inserter assembly 100 in block 250. The inserter assembly 100 may begin to be removed from the body in block 254. In block 258, the skin may be tugged away from underlying muscle and body structures via the adhesion of the adhesive. The exterior housing 116 and retainer base 140 may also be displaced relative to the rest of the inserter assembly 100 in block 258. As mentioned above, relative displacement may not occur until the skin has been lifted from underlying anatomy and the elasticity of the skin exerts enough force to overcome built in resistance to the relative displacement. In block 262, at least one latch within the inserter assembly 100 may be released. As discussed above, this may occur automatically, or as a result of some manual triggering action. An insertion sharp 132 and cannula subassembly 114 may be driven towards the insertion site in block 266. The cannula subassembly 114 may couple into the infusion set base 106 in block 270. Additionally, a catch may be released from the infusion set base 106 in block 270. The act of coupling the cannula subassembly 114 into the set base 106 may cause release of the catch from the infusion set base 106. This may free the infusion set base 106 from the rest of the inserter assembly 100. The catch may hold an insertion sharp retractor 134 in place when the catch is engaged with the infusion set base 106. With the catch released, the insertion sharp retractor 134 may be driven through a dwell distance in block 274 (described in further detail later in the specification). The insertion sharp retractor 134 and insertion sharp 132 may be driven away from the infusion site in block 278. The removal of the inserter assembly 100 may be completed in block 282. With the removal of the inserter assembly 100 completed, the infusion set 102 may be fully assembled and in place on the infusion site. Additionally, the cannula 104 may be in place in the subcutaneous layer of skin.

Figure 58:
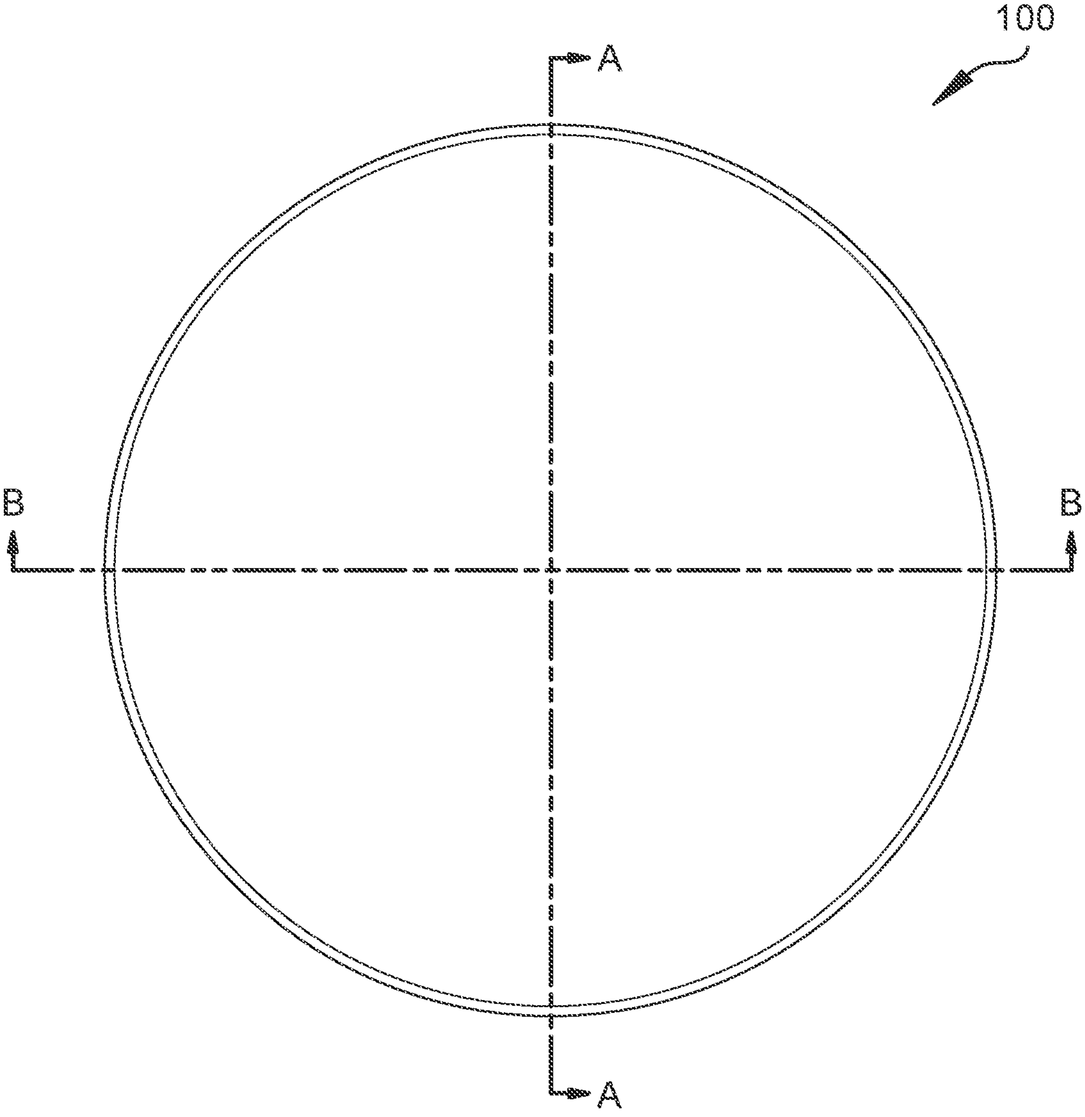
FIG. 58 depicts a top down view of an example inserter assembly.

Referring now to FIG. 58, a top down view of an inserter assembly 100 with a first and second cut plane superimposed thereon is depicted. The first cut plane is labeled A-A. The second cut plane is labeled B-B. This figure is provided for reference purposes in relation to a number of the forthcoming figures. Several of these figures are cross-sectional views of the inserter assembly 100 taken at the location of one or the other of these planes and depict the inserter assembly 100 in various stages of operation. Unless described otherwise, where one of the following inserter assembly 100 cross-sections is given with a figure numeral followed with the letter A, the figure is depicting a cross-section of the inserter assembly 100 at the location of plane A-A. Where one of the following inserter assembly 100 cross-sections is given with a figure numeral followed with the letter B, the figure is depicting a cross-section of the inserter assembly 100 at the location of plane B-B.

Figure 59A:
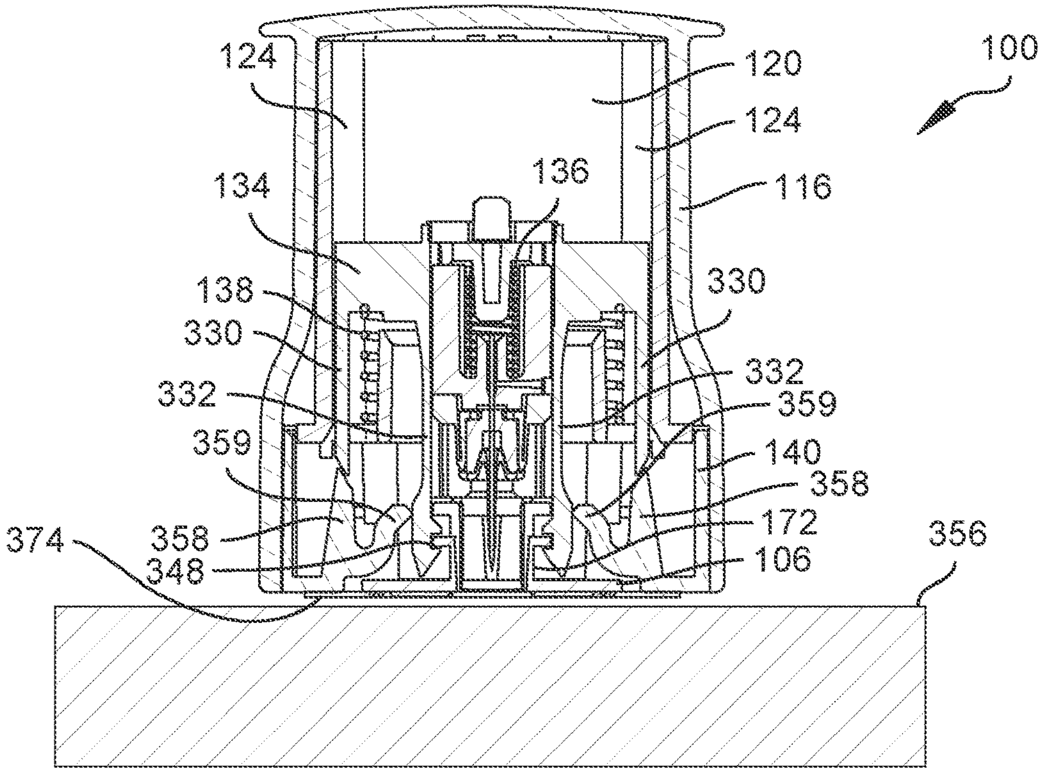
FIGS. 59A-59B depict cross-sectional views of an exemplary inserter assembly about to be applied to a user's skin.
Figure 59B:
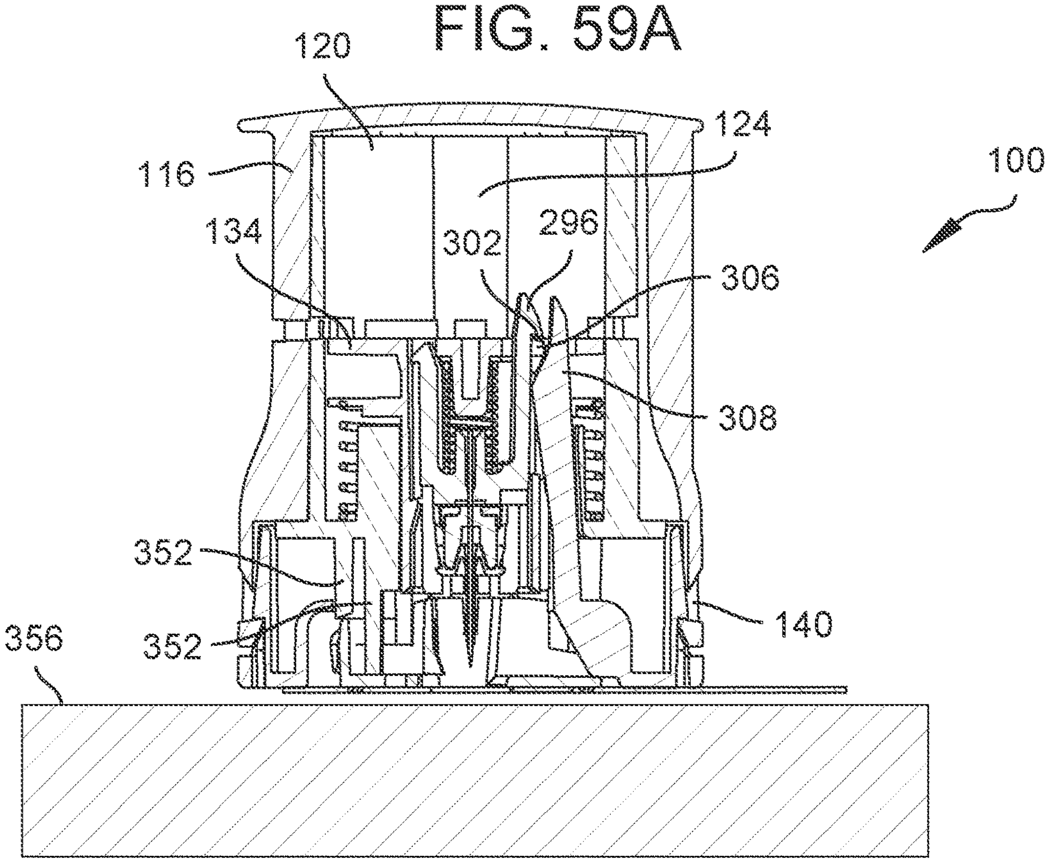
Figure 60:
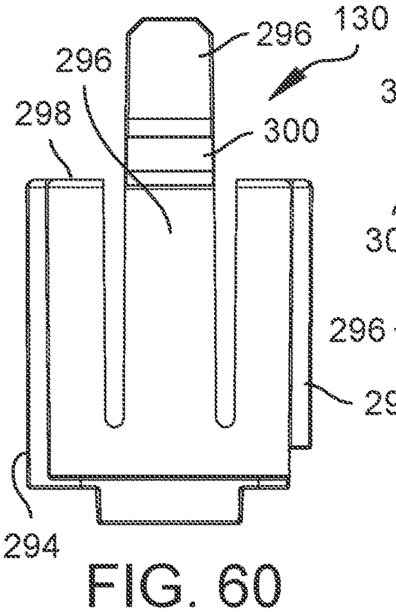
FIG. 60 depicts a side view of an exemplary sharp holder.
Figure 61:
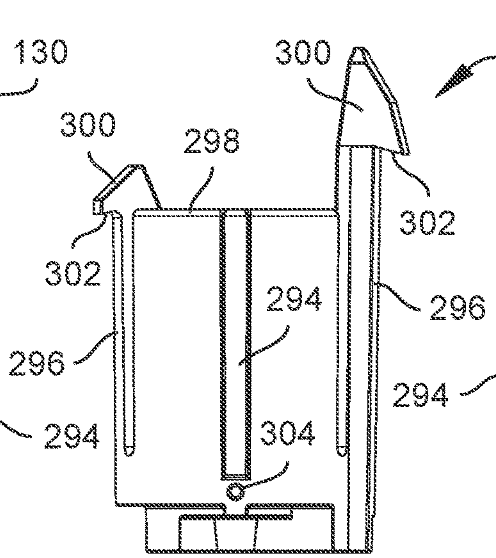
FIG. 61 depicts another side view of the exemplary sharp holder shown in FIG. 60.
Figure 62:
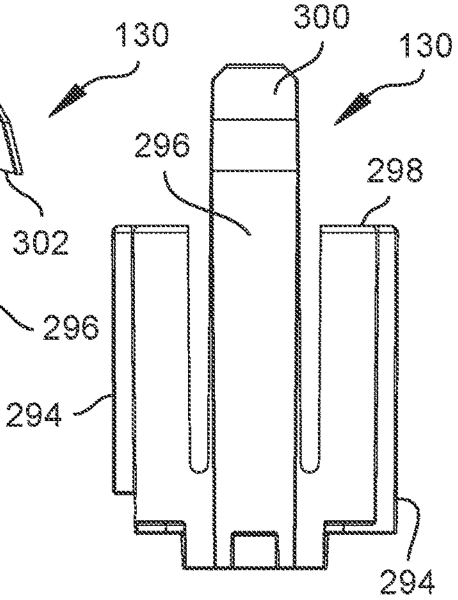
FIG. 62 depicts yet another side view of the example sharp holder shown in FIG. 59.
Figure 63:
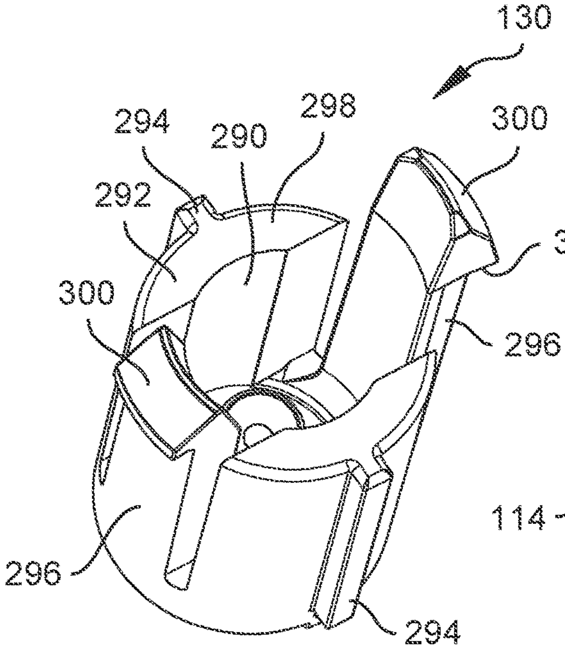
FIG. 63 depicts a perspective view of the example sharp holder shown in FIG. 60.
Figure 64:
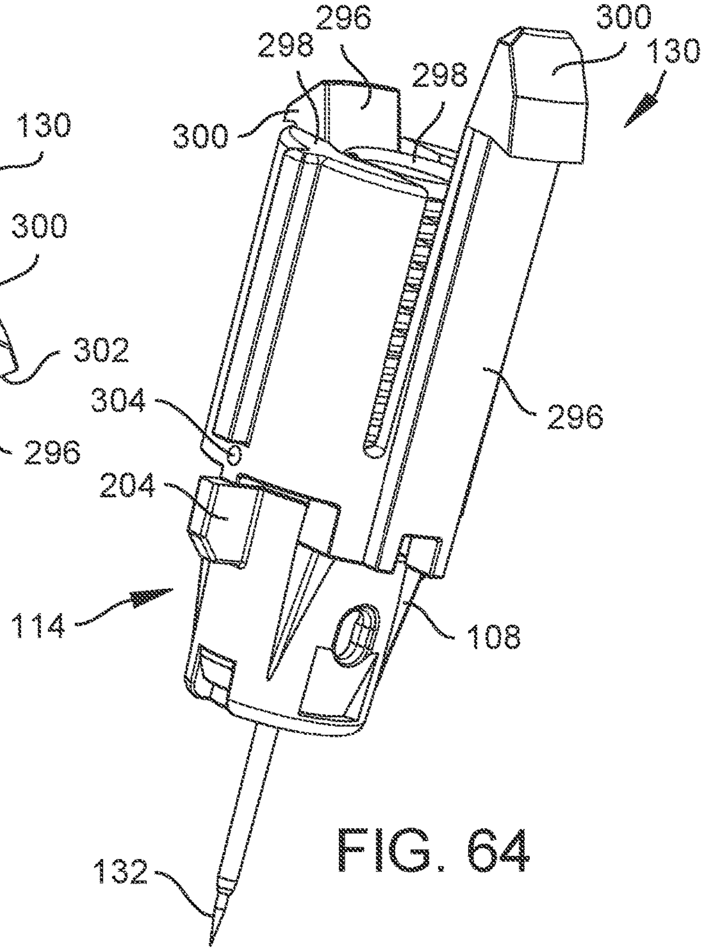
FIG. 64 depicts a perspective view of a sharp holder, sharp, and cannula assembly.
Figure 65:
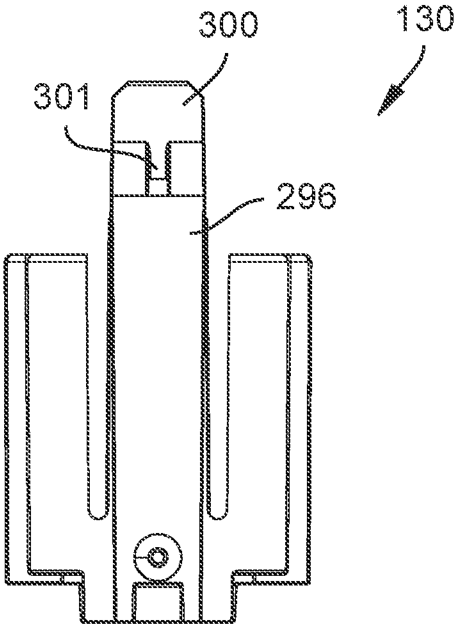
FIG. 65 depicts a side view of an example sharp holder.
Figure 66:
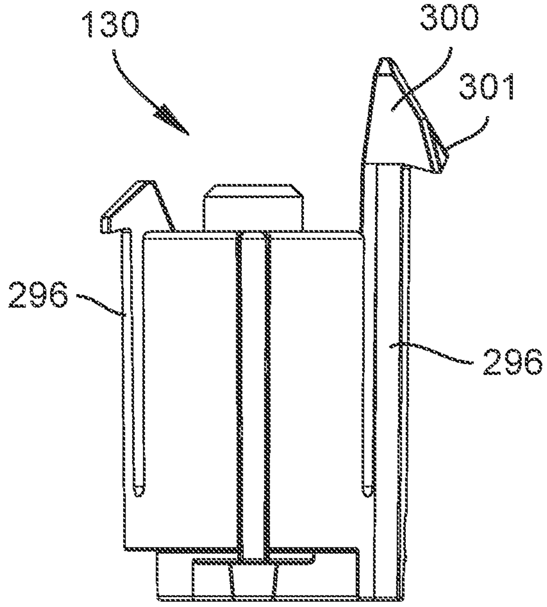
FIG. 66 depicts another side view of the example sharp holder of FIG. 65.
Figure 67:
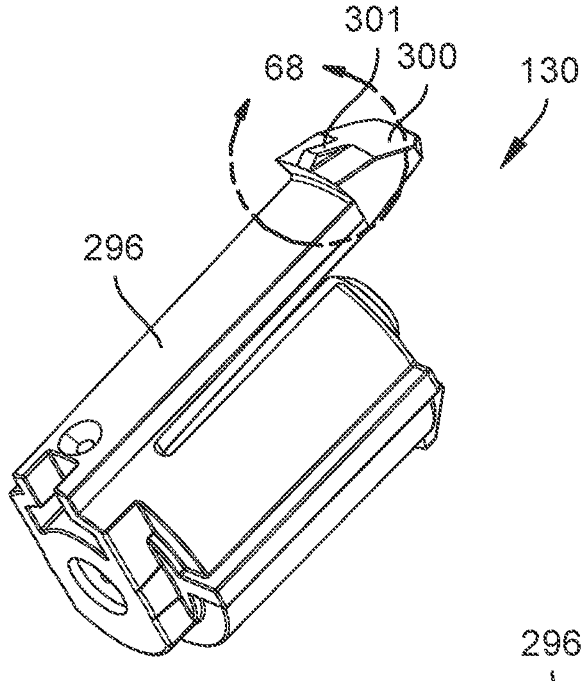
FIG. 67 depicts a perspective view of the example sharp holder of FIG. 65.
Figure 68:
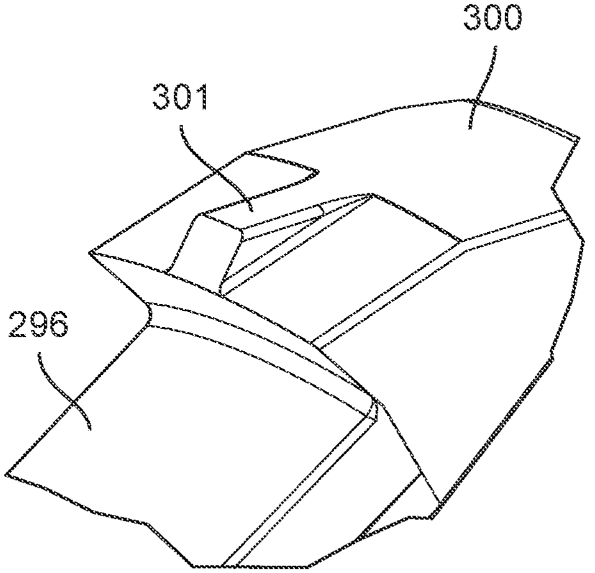
FIG. 68 depicts a detailed view of the indicated region of FIG. 67.

Referring now to FIGS. 59A-B, two cross-sectional views of an inserter assembly 100 are depicted. The inserter assembly 100 is depicted just as it is about to be applied to the skin 356. The lock member 146 (see, e.g., FIG. 50) and adhesive backing 111 (see, e.g., FIG. 1A) have been removed in FIGS. 59A-B. The adhesive 374 is depicted on the bottom face 162 of the infusion set base 106. As shown, both springs 136, 138 may be in an energy storing state, which in this particular embodiment is a compressed state. In the example, spring 136 serves as an insertion driving bias member while spring 138 serves as an insertion sharp retraction driving bias member. Spring 136 is held in compression between the insertion sharp holder 130 and the insertion sharp retractor 134 and when released drives the sharp holder 130 and components carried there on from a raised state to a forward state. Spring 138 is held in compression between the interior housing 120 and the sharp retractor 134. Upon release, spring 138 drives the sharp retractor 134 and sharp holder 130 from a post insertion state to a retracted state.

Referring now also to FIGS. 60-64, a number of views of a sharp holder 130 are depicted. The sharp holder 130 may include a bias member receiving bay 290 in which the spring 136 may be disposed. The sharp holder 130 may also include a wall 292 which surrounds the bias member receiving bay 290. The wall 292 may include two projections 294 on an exterior face thereof. The two projections 294 in the example embodiment are rails which are disposed opposite one another on the sharp holder 130. These rails may ride along guides 354 (see, e.g., FIGS. 70A-70B) on a portion of the sharp retractor 134. The projections 294 may extend from the sharp holder 130 so as to match the width of the cannula subassembly 114 at a plane of the cannula subassembly 114 including the ears 204 of the septum housing 108.

In various embodiments, the wall 292 may also include interrupted regions which create one or more cantilevered arms 296. In the example embodiment, the cantilevered arms 296 are disposed opposite one another on the sharp holder 130. One of the cantilevered arms 296 may have a greater length than the other of the cantilevered arms 296. In other embodiments, both cantilevered arms 296 may be identical mirror images (see, e.g., FIG. 78C) to allow for easier assembly of the inserter assembly 100. Both of the cantilevered arms 296 may extend above a top face 298 of the remainder of the wall 292. Each of the cantilevered arms 296 may include a protuberance 300 disposed at an unsupported or terminal end thereof. A ledge section 302 may be defined by a portion of each of the protuberances 300. At least one of the ledges 302 may extend substantially perpendicular to the cantilevered arms 296. At least one of the ledges 302 may be angled with respect to the cantilevered arm 296 on which it is included such that the undercut region has a triangular cross section. In the example embodiment, the ledge 302 on the longer of the two cantilevered arms 296 is so undercut. A sharp holder 130 may also include a port 304. The port 304 may be used to supply glue or adhesive into the sharp holder 130 to fixedly retain the insertion sharp 132 into the sharp holder 130.

An alternate embodiment of a sharp holder 130 is shown in FIGS. 65-68. As shown, the longer of the two cantilevered arms 296 of the sharp holder 130 includes a protuberance 300 with a ridge 301. The ridge 301 may be medially located on the protuberance 300 though may be located in other positions in alternative embodiments. As shown, the protuberance 300 may be double beveled. The portion of the protuberance 300 adjacent the ledge section 302 may have a steeper bevel than the portion of the protuberance 300 distal to the ledge section 302. The ridge 301 may be formed on the portion of the protuberance adjacent the ledge section 302. In the example, the ridge 301 is formed as an extension of the bevel angle from the portion of the protuberance 300 distal to the ledge section 302 which extends to the portion of the protuberance 300 adjacent the ledge section 302. Such a ridge 301 may be included on any of the sharp holder 130 embodiments depicted herein.

As best shown in FIG. 59B, the ledge 302 on the longer of the cantilevered arms 296 may rest on a catch 306. The catch 306 in the example embodiment is included on the sharp retractor 134. This may inhibit the release of energy stored in spring 136 and hold the spring 136 under compression in the example embodiment. The catch 306 may have an angle which cooperates with any angle of the ledge 302 to firmly retain the ledge 302 on the catch 306. A finger 308 extending from the base retainer 140 of the insertion assembly 100 may extend through a void 322 (see, e.g., FIG. 70C) adjacent the catch 306. Displacement of the finger 308 relative to the catch 306 may cause disengagement of the ledge 302 with the catch 306. This may trigger release of the sharp holder 130 and freeing of the spring 136 from its energy storing state. Though depicted as an upstanding finger 308, other types of actuation projections may be used. Additionally, in some embodiments, the finger 308 or other actuation projection may be included on another part of the inserter assembly 100. For example, a finger 308 may project from the interior surface of the top face of the exterior housing 116. The engagement of the catch 306 and ledge 302 is an example of a trigger (see, e.g., description of FIG. 57) which may be operated to begin actuation of an inserter assembly 100.

Figure 69:
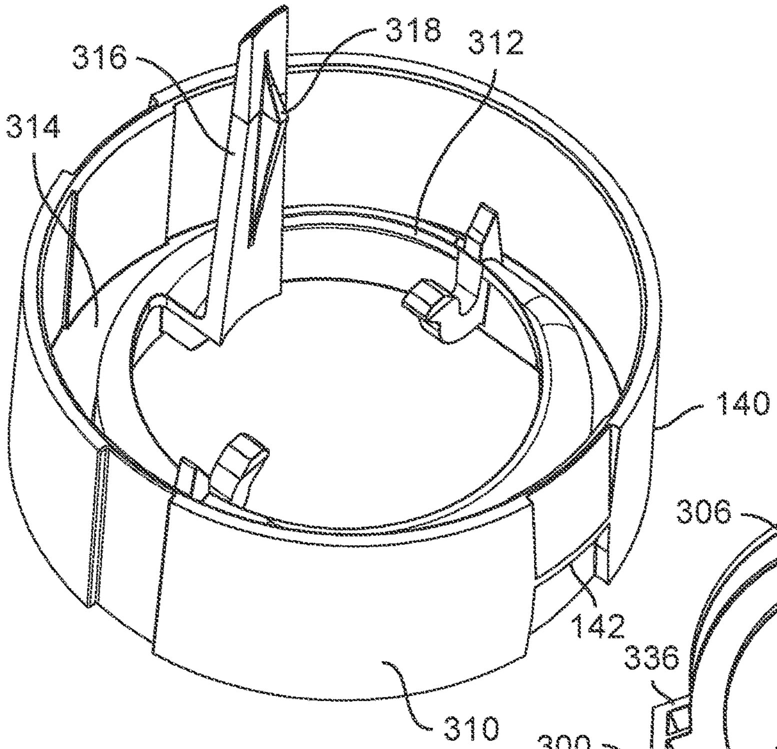
FIG. 69 depicts a perspective view of an example retainer base.
Figure 70B:
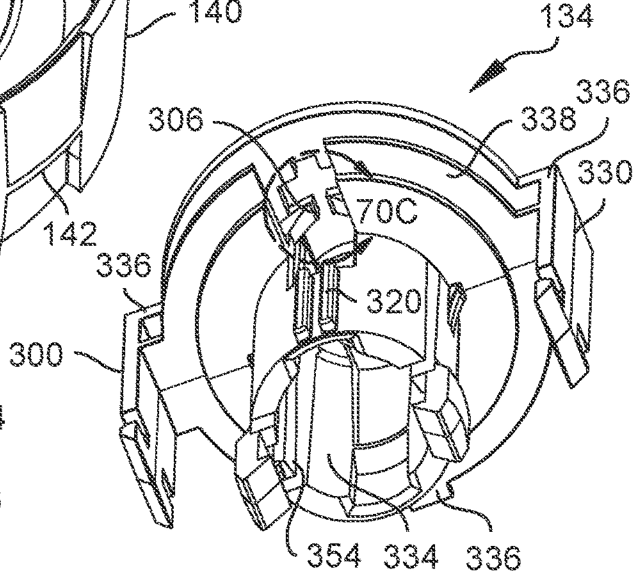
FIG. 70B depicts another perspective view of the exemplary sharp retractor shown in FIG. 70A.
Figure 70A:
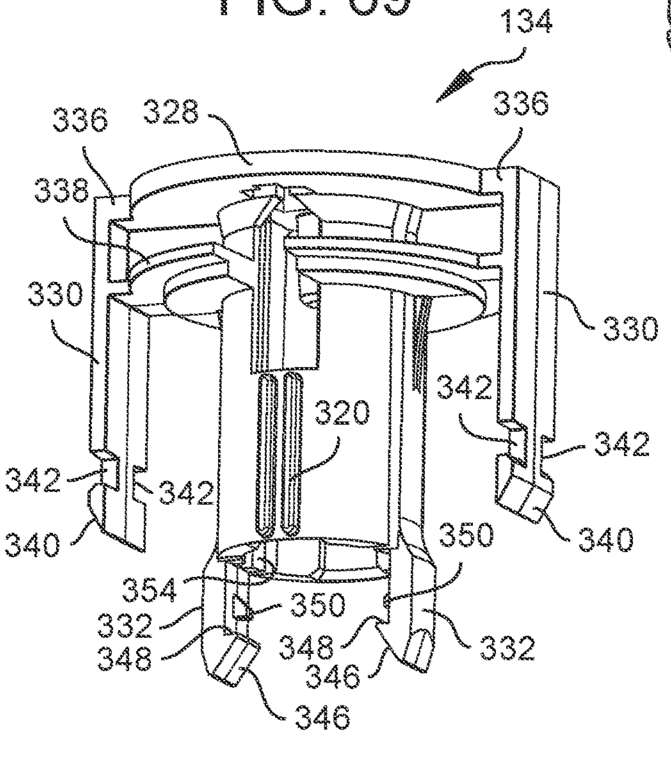
FIG. 70A depicts a perspective view of an example sharp retractor.
Figure 70C:
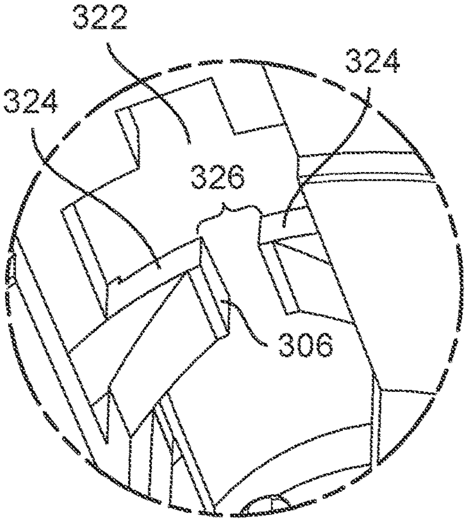
FIG. 70C depicts a detailed view of a portion of FIG. 70B.

Referring now also to FIGS. 69-70C, a number of views of a retainer base 140 and sharp retractor 134 are depicted. As shown, the finger 308 of the retainer base 140 (FIG. 69) is formed as a continuous part of the retainer base 140. The example retainer base 140 includes a first ring portion 310 and a second ring portion 312. The first ring portion 310 and second ring portion 312 are connected by an intermediary region 314 and may be concentric with one another. The intermediary region 314 may be generally flat and may serve as a skin contacting portion of the inserter assembly 100 which is substantially level with the bottom face 162 of the infusion set base 106. The finger 308 extends from the second ring portion 312. As shown, the finger 308 includes an upstanding segment 316 and a fin 318.

In various embodiments, the sharp retractor 134 may include a guide 320 along which the fin 318 may slide during assembly. The guide 320 may also, in certain embodiments, ride along the fin 318 during at least a portion of the retraction of the sharp retractor 134. The example guide 320 is formed as two raised parallel ribs. The catch 306 includes two supports 324 which the ledge 302 of the cantilevered arm 296 may engage with. The supports 324 may include a gap 326 therebetween. The gap 326 may have a width equal to or wider than the width of the fin 318. The fin 318 may be advanced through the gap 326 during lifting of the inserter assembly 100 from the skin 356. This may cause the fin 318 to come into abutment with the protuberance 300 on the cantilevered arm 296 and force the cantilevered arm 296 to bend inward. Once the fin 318 has progressed a certain distance, the cantilevered arm 296 may be deflected to the point that the ledge 302 no longer engages the catch 306 and the spring 136 may be released and actuation may be triggered. The location of the fin 318 on the finger 308 and/or the height of the finger 308 may be adjusted to alter the displacement distance at which release of the ledge 302 from the catch 306 occurs. In embodiments where the protuberance 300 includes a ridge 301 (see, e.g., FIGS. 65-68), the ridge 301 may be sized so as to fit through the gap 326. Thus, the ridge 301 may increase the total amount that the cantilevered arm 296 may be deflected by the fin 318 and provide extra assurance that ledge 302 is fully displaced off of the catch 306. As a result, the range of acceptable tolerances on various features related to the catch 306 and sharp holder 130 may be greater.

Still referring to FIGS. 59A-59B in conjunction with FIGS. 69-70B, spring 138 may be held in an energy storing state by at least one latching engagement as well. As shown, the sharp retractor 134 may include a first set of arms 330 and a second set of arms 332. The first set of arms 330 may extend from a top plate 328 of the sharp retractor 134. These arms 330 may extend substantially parallel to one another and may be disposed in opposing fashion on the sharp retractor 134. Additionally, the first set of arms 330 may extend laterally to a central cavity 334 of the sharp retractor 134. In some embodiments, the first set of arms 330 may be attached to the top plate 328 of the sharp retractor 134 at outcropped regions 336 of the top plate 328. The arms 330 may thus fit within channels formed by rails 124 of the interior housing 120 to prevent rotation and guide any displacement of the sharp retractor 134 during actuation. Additionally, outcropped regions 336 may be included in an asymmetric fashion on the sharp retractor 134 to ensure that the sharp retractor 134 is assembled into the inserter assembly 100 in a prescribed orientation. The first set of arms 330 may be cantilevered and attached to the sharp retractor 134 at the top plate and a second plate 338 which may extend parallel to the top plate 328 and below the top plate 328. Thus, the arms 330 may form resilient projections or members which may deflect if sufficient force is exerted against them. The unsupported end of the arms 330 may include a curved or ramped section 340. This section 340 may abut against a complimentarily contoured face of deflector members 358 to facilitate and or direct such deflection. A notch or pair of notches 342 may also be present on each of the first set of arms 330. In the example, each arm 330 includes a pair of notches 342 located near the unsupported ends of the arms 330.

Figure 71:
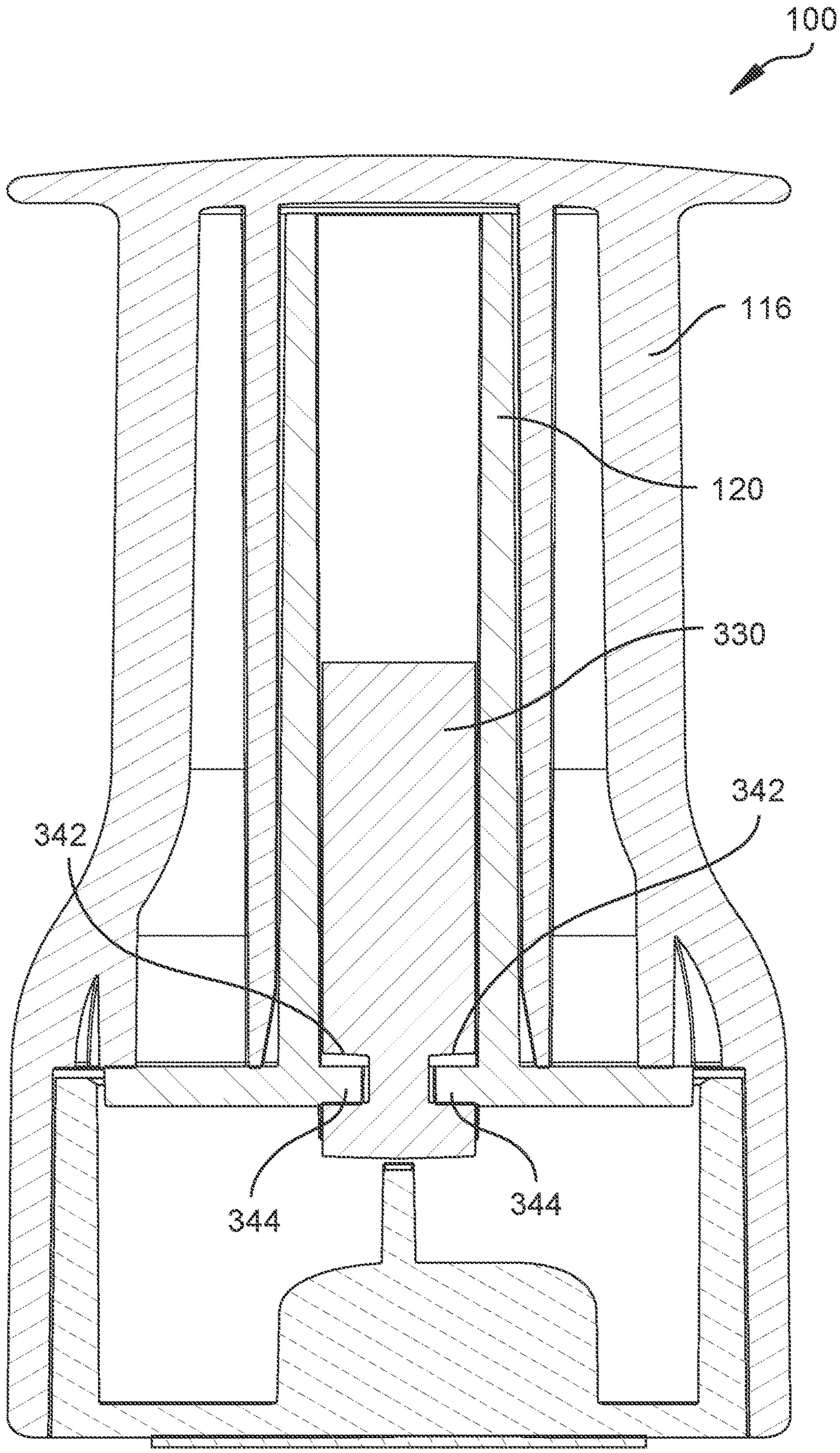
FIG. 71 depicts a cross-sectional view of an example inserter assembly taken through an arm included on a sharp retractor of the inserter assembly.

FIG. 71 depicts a cross-section of an inserter assembly 100 taken through a plane in one of the arms 330 which extends along the length of the arm 330. As shown, each of the one or more notches 342 may engage with a cooperating projection 344. The cooperating projection 344 may be included on the interior housing 120. Thus, the interaction of the notch(es) 342 and cooperating projection(s) 344 may maintain the spring 138 under compression and serve as a retraction prevention latch. This may be particularly helpful during assembly as the infusion set base 106 may not be in place and the spring 138 may otherwise be free to relax. Additionally, this engagement may ensure that the top plate 328 of the sharp retractor 134 is disposed slightly below the fenestrations 148, 150 to allow for introduction of a lock member 146. Though notches 342 are shown, the arms 330 and interior housing 120 may engage in other ways. For example, the arms 330 or interior housing 120 may include a projection which forms a ledge. The ledge may engage with a catching recess in the other of the arms 330 or interior housing 120.

Again referring now primarily to FIGS. 59A-59B in conjunction with FIGS. 69-70B, in some embodiments additional latches may be included in an inserter assembly 100 which aid in maintaining one of the springs 136, 138 in an energy storing state. In the example embodiment, spring 138 is held in an energy storing state by an additional latch arrangement. As shown, the second set of arms 332 of the sharp retractor 134 extend from a bottom portion of the wall defining the central cavity 334. The second set of arms 332 may be disposed in opposing relationship to one another and may be cantilevered. Each of the second set of arms 332 may include a protuberance 346 disposed at an unsupported end thereof. Each protuberance 346 may form a ledge 348 on the arm 332 on which it is included. Additionally, the arms 332 may include a nub 350 or raised ramp which increases in thickness as distance from the cavity 334 increases. The nub 350 may be disposed intermediate the unsupported end of the arm 332 and its attachment point to the remainder of the sharp retractor 134.

As best shown in FIG. 59A the ledge 348 may capture a portion of the infusion set base 106. Specifically, the ledges 348 may catch on an outcropped portion of the infusion set base 106. The base 106 may include rails, step features, nubs or any other suitable protrusions to provide a complimentary catch surface for the ledges 348. In certain embodiments, the ledges 348 may catch on guides 172 (see, e.g., FIG. 4A) of the infusion set base 106. Thus the infusion set base 106 may be retained within the inserter assembly 100. In alternative embodiments, such as those in which an infusion set base 106 of the type depicted in FIGS. 21A-21F is used, a portion of each arm 332 may extend at least partially into a respective receiving slot defined in the base 106. The ledges 348 may engage a catch present at an end of the respective receiving slots so as to retain the base 106 within the inserter assembly 100.

Ledges 348 may be angled with respect to the cantilevered arm 332 on which it is included such that the undercut has a triangular cross section. The portion of, for example, the guides 172 (or any other catch feature) on which each ledge 348 catches may be angled in a cooperating manner to help ensure a robust engagement. The retainer base 140 (or the exterior housing 116 in embodiments like that shown in FIG. 73A-73B) may include retaining projections 359 which may abut or nearly abut arms 332 and hold the arms 332 from displacement out of engagement with the infusion set base 106 prior to inserter assembly 100 actuation. This may help prevent any accidental firing of the inserter assembly 100.

In certain embodiments, only one arm 332 may be included. In some embodiments, the arms 332 on the sharp retractor 134 may not engage the infusion set base 106. The arms 332 may engage a portion of the interior housing 120 so as to prevent premature retraction of the sharp retractor 134. The interior housing 120 may also include latch which may interface with the guide 172 or another cooperative portion of the infusion set base 106 to retain the infusion set base 106 in place.

A number of standoffs or alignment projections 352 may be included in the inserter assembly 100 to aid in ensuring that the infusion set base 106 is assembled into the inserter assembly 100 in a desired orientation. The standoffs 352 may be disposed on an interior housing 120 of the inserter assembly 100 as shown. While retained by the arms 332 of the sharp retractor 134, the infusion set base 106 may be held such that surfaces of the infusion set base 106 are adjacent to the standoffs 352. This may prevent infusion set base 106 and the sharp retractor 134 on which it is retained from displacing into the inserter assembly 100 due to the presentation of a mechanical interference by the standoffs 352. As a consequence, the catching of the ledges 348 of the arms 332 on the infusion set base 106 may also aid in holding the spring 138 in an energy storing state. The standoffs 352 may also ensure that the infusion set base 106 is positioned within the inserter assembly 100 such that the adhesive 374 may be pressed against the skin 356. In the example, the standoffs 352 ensure that the infusion set base 106 is substantially even with the skin contact face on the retaining base 140.

With the infusion set base 106 so positioned, the infusion set base 106 may also act as a protective barrier. As the cannula subassembly 114 and insertion sharp 132 may be internal to the inserter assembly 100, when the infusion set base 106 in the initial retained position, the user may be protected from accidental contact with the insertion sharp 132. This may additionally help to keep the cannula 104 or insertion sharp 132 from coming into contact with contaminants. Though a void for receipt of the cannula subassembly 114 may extend through the entirety of the infusion set base 106, the void may be sized to prevent finger ingress (e.g. have a cross-section smaller than that of a finger). Thus the infusion set base 106 may present an obstacle which blocks unintentional access to the insertion sharp 132 and cannula 104. Additionally, as the cannula subassembly 114 is internal to the inserter assembly 100, any adhesive backing 111 provided on the infusion set base 106 need not include an interruption to allow for passage of the cannula 104 therethrough. Thus, the void in the infusion set base 106 for the cannula subassembly 114 may be blocked by the adhesive backing 111 until just prior to use. This may further prevent finger ingress and may mitigate potential for detritus to enter the inserter assembly 100. In some examples, the adhesive 374 may also extend over this opening and may be punctured through during insertion of the cannula 104 into the skin 356.

Figure 72:
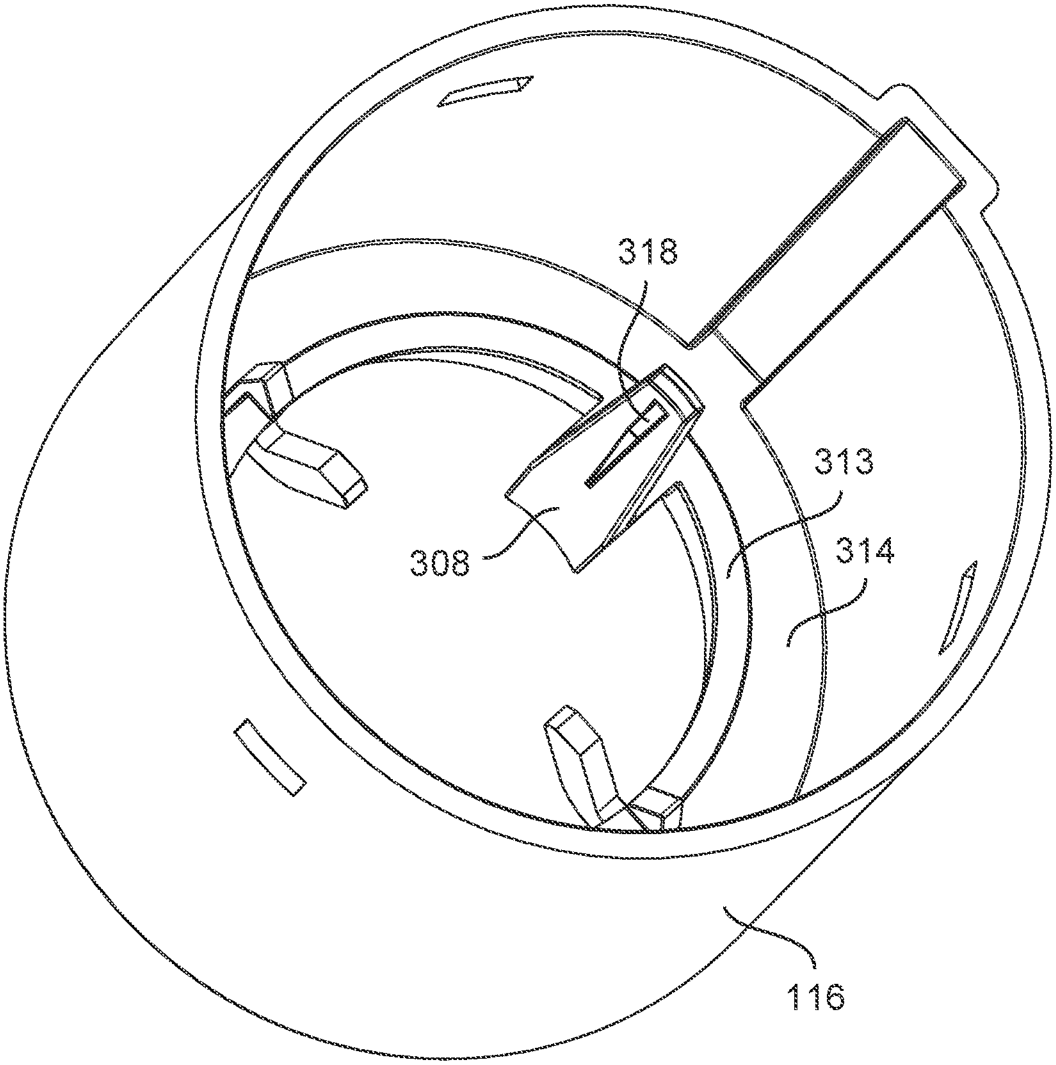
FIG. 72 depicts a perspective view of an example exterior housing.

Referring now to FIG. 72, an isolated view of the alternative exterior housing 116 depicted in the inserter assembly 100 embodiment of FIG. 2 is shown. As shown, instead of a retainer base 140, various features of the retainer base 140 may be included in the exterior housing 116. These features may all be formed unitarily and integral to one another as a single monolithic component during a molding operation for example. As shown, the finger 308 and fin 318 are included as part of the exterior housing 116. The finger 308 may extend from a central ring portion 313 connected by an intermediary region 314 to the rest of the exterior housing 116. The deflector members 358 are similarly included as part of the exterior housing 116.

Figure 73A:
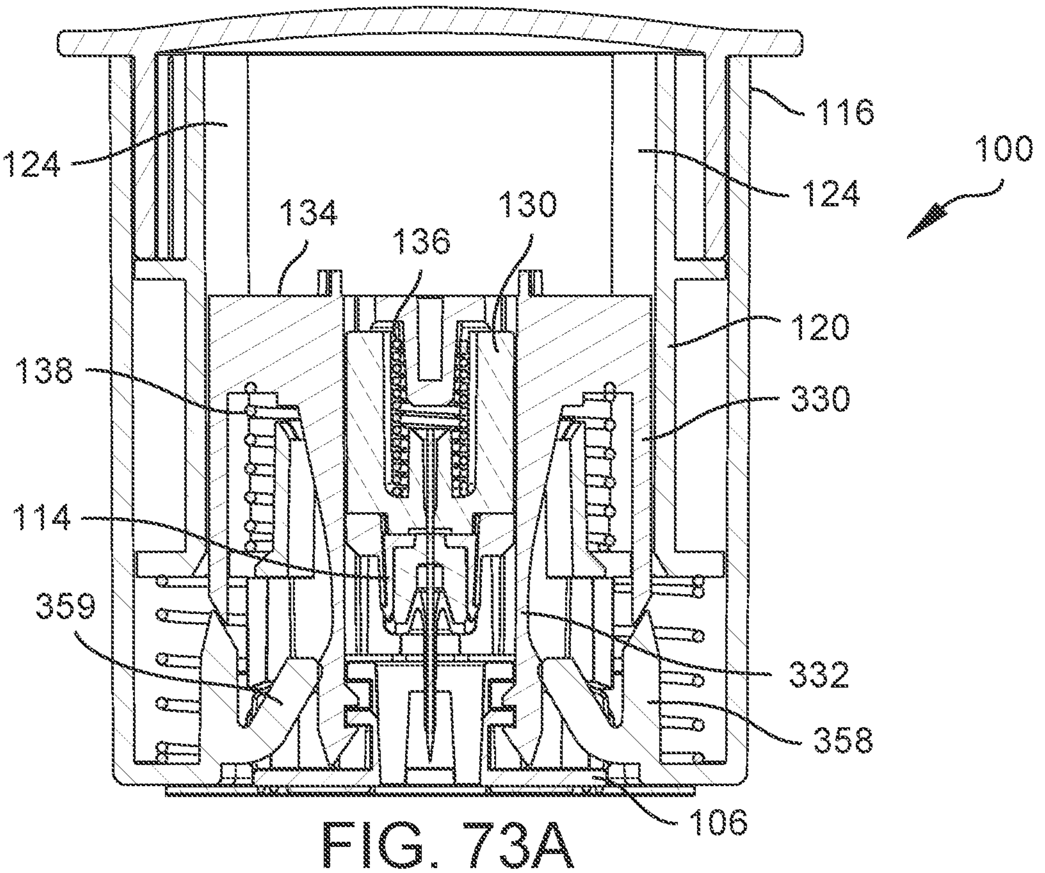
FIGS. 73A-73B depict cross-sectional views of an example inserter assembly including the exterior housing depicted in FIG. 72.
Figure 73B:
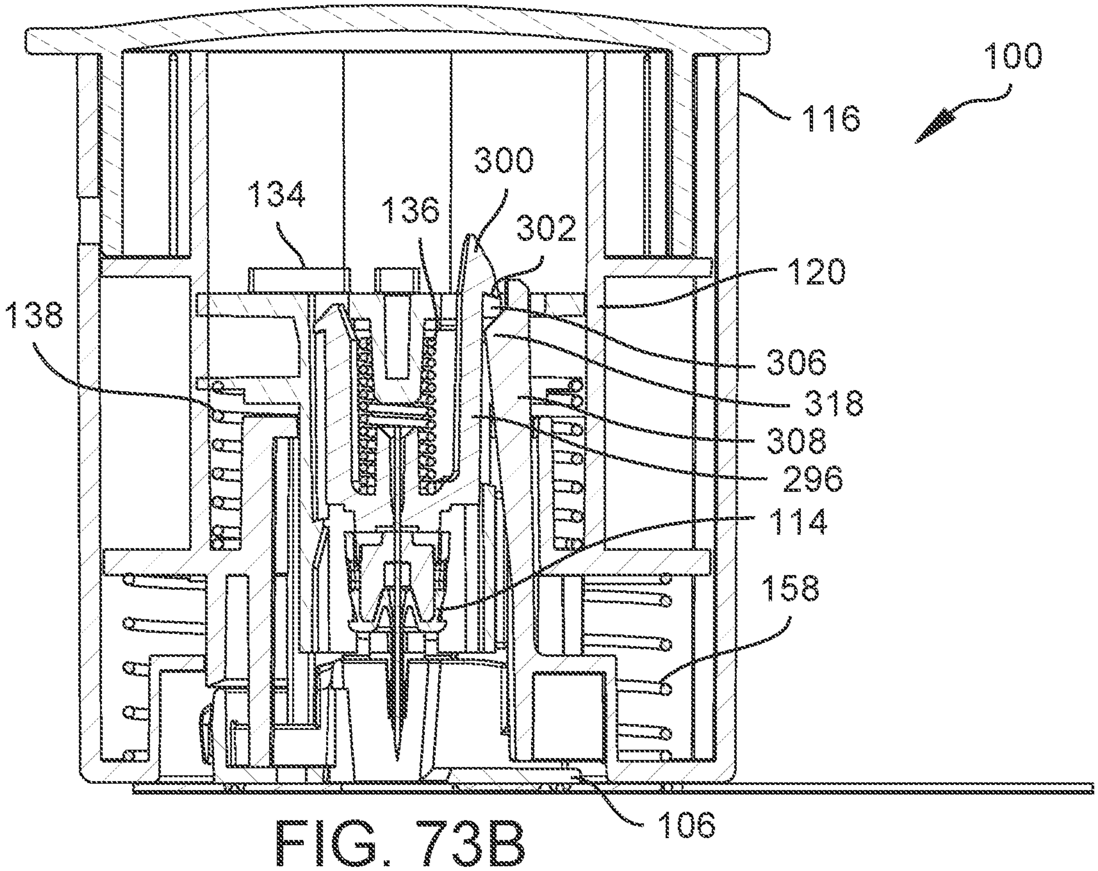

Cross sectional views of the example embodiment of the inserter assembly 100 in FIG. 2 are shown in FIGS. 73A-73B. This inserter assembly 100 includes the exterior housing 116 depicted in FIG. 72. The views in FIGS. 73A-73B show this alternate embodiment of the inserter assembly 100 in the same state as the inserter assembly 100 depicted in FIGS. 59A-B and FIG. 71. The inserter assembly 100 shown in FIGS. 73A-73B may operate similarly to the inserter assembly 100 depicted in FIGS. 59A-B and FIG. 71. For sake of brevity, the following describes various operational states of the inserter assembly 100 shown in FIGS. 59A-B and FIG. 71.

Figure 74A:
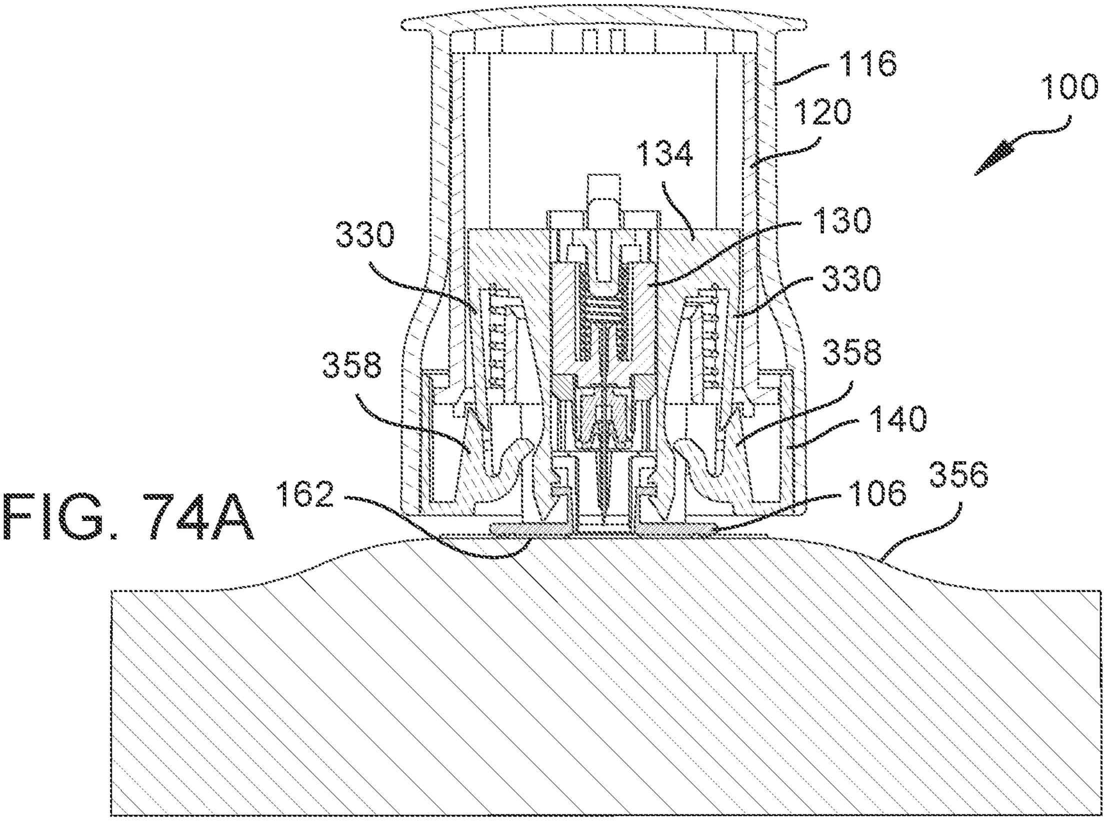
FIGS. 74A-74B depict cross-sectional views of an example inserter assembly being withdrawn away from a user after application to the skin.
Figure 74B:
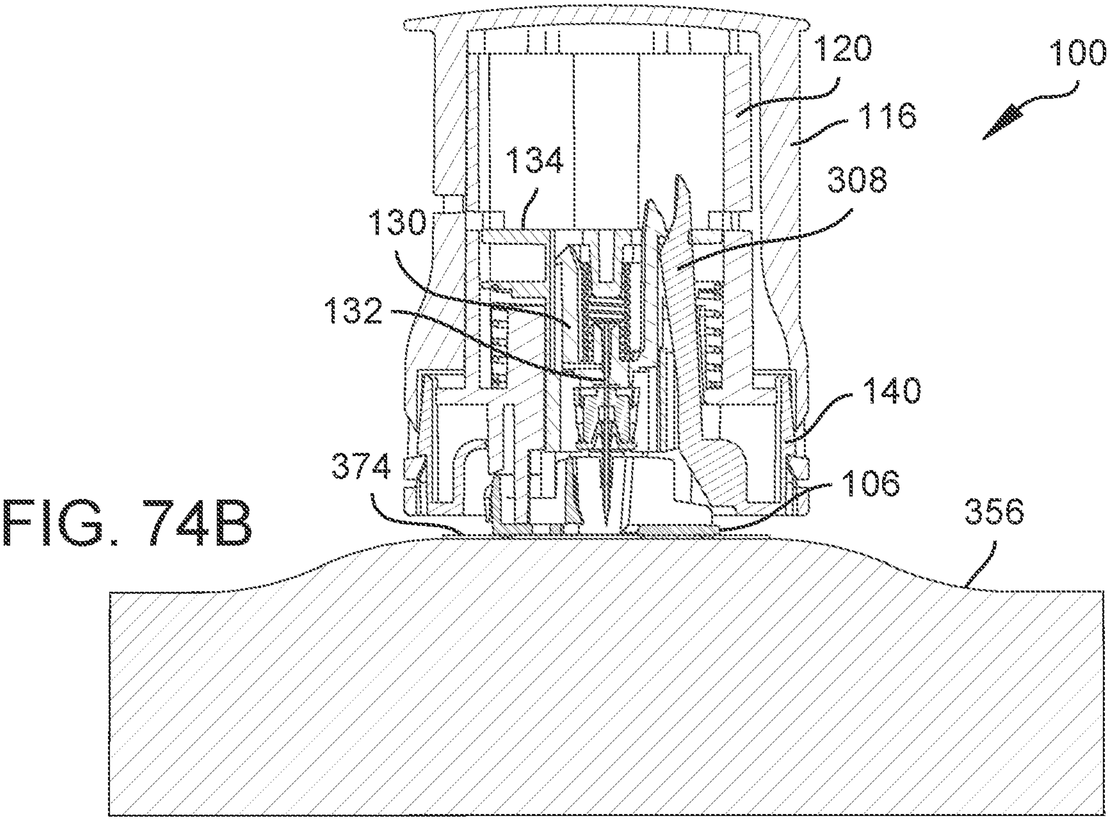

Referring now to FIGS. 74A-74B, two cross sectional views of an inserter assembly 100 are shown. In FIGS. 74A-74B, the example inserter assembly 100 has been placed against the skin 356 at a desired infusion site and is beginning to be withdrawn by a user. As shown, the adhesive 374 on the bottom face 162 of the infusion set base 106 may adhere to the skin 356 resulting in the skin 356 being tugged upward with the inserter assembly 100 as the inserter assembly 100 is pulled away from the body by the user. The adhesive 374 may be selected to be aggressive enough to maintain adhesion to the skin 356 while the skin 356 is lifted from the underlying anatomy. The exterior housing 116 and retainer base 140 which may form a casing for the inserter assembly 100 may displace together with the hand of the user as the user removes the inserter assembly 100 from their body. The other components of the inserter assembly 100 may not be constrained to displace as a unit with the exterior housing 116 and retainer base 140 (at least during a portion of the inserter assembly 100 removal action). As the infusion set base 106 is in latching engagement with the sharp retractor 134 and the sharp retractor 134 is in latching engagement with the interior housing 120 and sharp holder 130, these components may be held behind. Thus, these components may form a first unit of the inserter assembly 100 which is more constrained in its ability to displace than a second casing unit of the inserter assembly 100. As mentioned elsewhere herein, these components may move in tandem with the casing for at least an initial part of the inserter assembly 100 removal motion. The first and second unit may be releasably engaged with one another for this portion of the removal motion. For example, an interference or interfering relationship may be present between the first and second units. This interference may prevent relative motion of the first and second units until more than a threshold force is applied. When more than the threshold force is applied, the interference may be overcome and the first and second unit may begin to displace relative to one another.

Still referring to FIGS. 74A-74B, during removal, the exterior housing 116 and retainer base 140 may displace away from the skin 356 relative to the components of the second unit substantially along the axis of the insertion sharp 132. This may cause deflector members 358 included on the retainer base 140 to bend resilient members or arms 330 inward. It may also cause the finger 308 on the retainer base 140 to advance into the void 322 (see, e.g. FIG. 70C). Thus, the finger 308 may eventually displace a distance sufficient to trigger actuation of the inserter assembly 100. The resiliency of the arms 330 and the interference presented by the deflector members 358 may cause the entire inserter assembly 100 to move as a unit for at least a portion of the inserter assembly 100 withdrawal motion from the body. The deflector members 358 may bend or deflect the arms 330 out of the interfering relationship with the deflector members 358. Portions of the inserter assembly 100 may displace relative to one another once the force exerted by the elasticity of the skin exceeds a force threshold. Thus, the interference between the first and second unit preventing relative displacement of the first and second unit may be overcome by deflecting at least a part of one of the units out of an interfering relationship with the other of the units. This may occur after a threshold hold force is applied to pull the first and second unit apart. Separating force may be generated by a user displacing the casing away from the body and the elasticity of the tugged or lifted skin 356 pulling the first unit in the opposite direction.

In various embodiments, the resiliency of the resilient members or arms 330 may control, at least in part, a distance which a given user's skin 356 is tugged away from the body before actuation of the inserter assembly 100 occurs. As the skin 356 is tugged away from the body, the elasticity of the skin 356 may exert a pulling force which presses the arms 330 against the deflector members 358. The type, amount, and/or arrangement of adhesive 374 on the infusion set base 106 may be selected so as to withstand this force while maintaining adherence to the skin 356 and compatibility with the skin 356. Once this force overcomes the resiliency of the arms 330 and the components of the inserter assembly 100 described above begin to move relative to one another, the finger 308 may begin to advance into the void 322. Prior to this, triggering of actuation may be prohibited. Thus, the releasable engagement between the first and second units and the trigger may form an actuation restricting arrangement which may ensure that the skin is lifted prior to the inserter assembly being triggered. The resiliency may be chosen such that an inserter assembly 100 may be used on a wide range of individuals having different skin 356 properties (e.g. elasticity) while still ensuring the skin 356 is tugged at least some minimum distance before actuation is triggered. In some embodiments, inserter assemblies 100 may be produced with differing arm 330 resiliencies which may be suitable for different user groups. For example, arms 330 with less resiliency (e.g. an elderly resiliency) may be available for use for older user groups whose skin 356 has a tendency to be less elastic.

The steepness of the ramped section 340 on each arm 330 may be modified to alter the amount of force applied before relative movement occurs. Shallower angles on the ramped section 340 may be employed where more force before relative movement occurs is desired. Sharper angles on the ramped section 340 may be used where a lower force may be desirable. There may be a high (e.g. juvenile), medium (e.g. adult), and low (e.g. elderly) skin elasticity ramp angle in certain implementations. Additionally, the thickness of the arms 330 may be altered to change their resiliency. Thinner arms may be used where less force is desired and thicker arms may be used where more force is desired. Various supporting features such as buttresses may also be included and may support the arms 330 against deflection at a point near the supported end of the arms 330. The location of the second plate 338 may also be modified in certain examples to alter the length of the deflectable portion of the arms 330 making them more or less resilient. The material used to form the arms may also be selected based on its resiliency properties.

The length of the finger 308 and location of the fin 318 on the finger 308 may play a role in controlling, at least in part, the distance a user's skin 356 is tugged away from the body. These parameters may be modified to alter this distance.

Figure 74C:
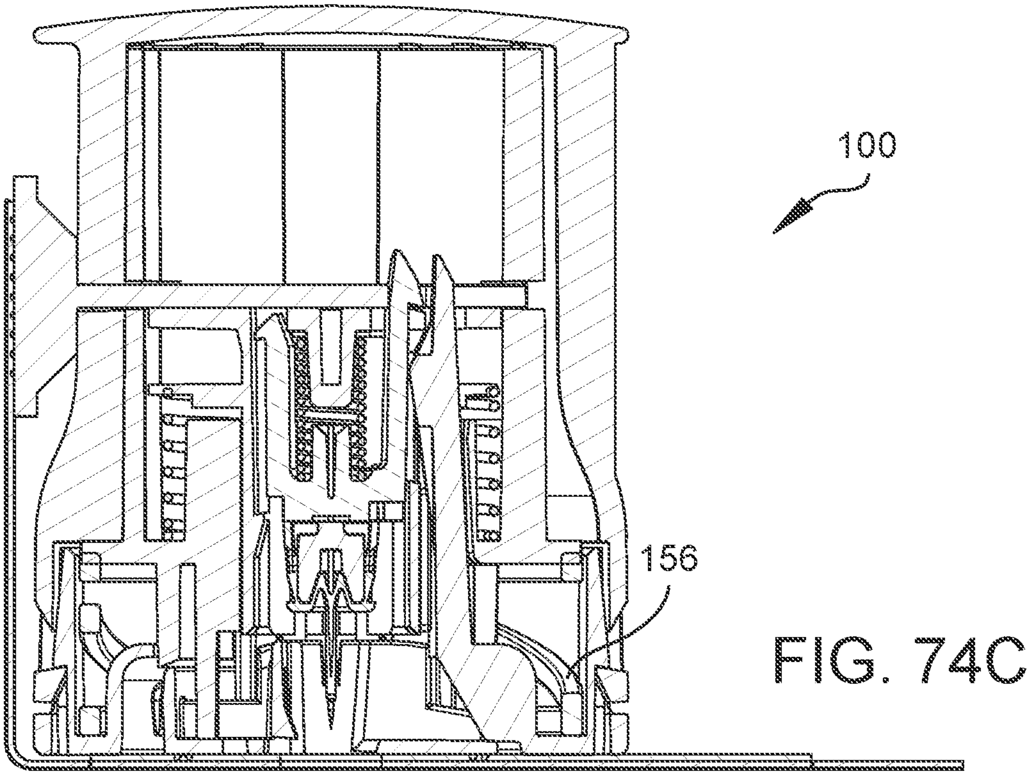
FIGS. 74C-74D depict cross-sectional views of exemplary inserter assemblies including additional springs.
Figure 74D:
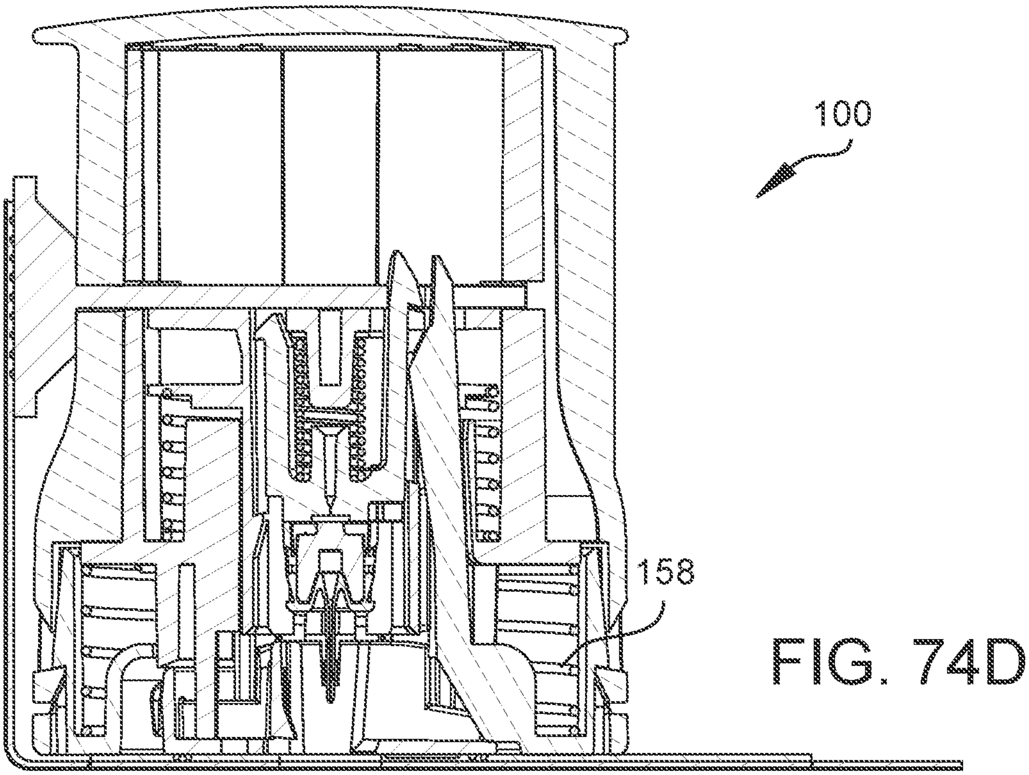

Referring now to FIGS. 74C-D two additional cross-sections of an example inserter assembly 100 are shown. Each of the example inserter assemblies 100 includes an additional spring 156, 158. These springs 156, 158, are described above in relation to FIGS. 1A-1C. An additional spring 156, 158 may be used to adjust the amount of force build up before the fin 318 triggers the beginning of inserter assembly 100 actuation (e.g. via disengagement of a catch 306 and ledge 302, see, e.g., FIG. 59B). Springs 156, 158 may also help to remove any mechanical slop which may be present due to tolerancing of various components of the inserter assembly 100. Varying the characteristics described in the above paragraphs may allow one to empirically determine appropriate designs for various patient populations (e.g. juvenile, adult, elderly or high skin elasticity, medium skin elasticity, low skin elasticity). A skin turgor test, elastomer, or other testing may be used to match an appropriate inserter assembly 100 type to a particular patient.

Figure 75A:
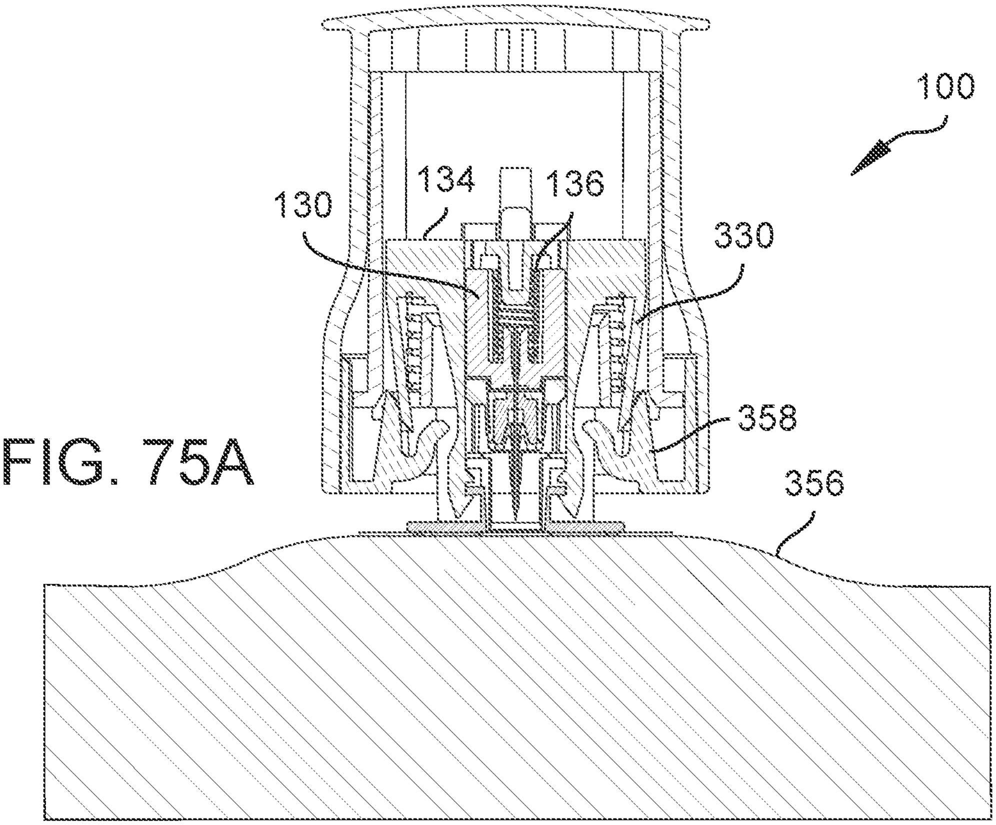
FIGS. 75A-75B depict cross-sectional views of an example inserter assembly being withdrawn away from a user after application to the skin.
Figure 75B:
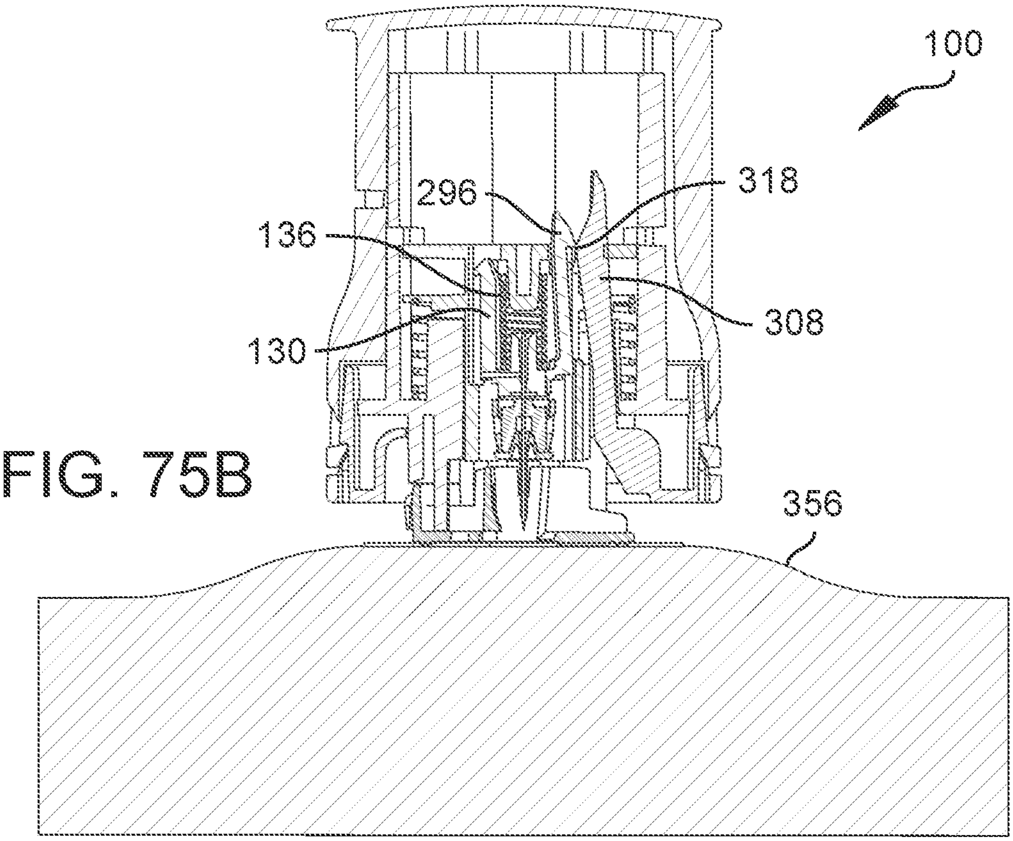

Referring now to FIGS. 75A-75B two cross sectional views of an inserter assembly 100 are shown. In FIGS. 75A-75B, the example inserter assembly 100 has been further withdrawn from the skin 356. The exterior housing 116 and retainer base 140 have continued to displace away from the skin 356 relative to the rest of the inserter assembly 100. The deflector members 358 included on the retainer base 140 have continued to flex or deflect the arms 330 inward. The finger 308 on the retainer base 140 has advanced into the void 322 (see, e.g. FIG. 70C) such that the fin 318 of the finger 308 has dislodged the cantilevered arm 296 of the sharp holder 130 from the catch 306 (see, e.g., FIG. 70C). Thus the movement of the exterior housing 116 and retainer base 140 has advanced the inserter assembly 100 to an insertion release point in FIGS. 75A-75B. With disengagement of the cantilevered arm 296 from the catch 306, the spring 136 is free to release its stored energy and begin driving actuation of the inserter assembly 100.

Prior to the magnitude of relative displacement between the portions of the inserter assembly 100 increasing to this insertion release point threshold, the inserter assembly 100 may be precluded from triggering actuation. This may ensure that the skin is lifted some distance before actuation of the trigger arrangement (e.g. disengagement of a catch 306 and ledge 302, see, e.g., FIG. 59B) for the inserter assembly 100 can occur.

Figure 76A:
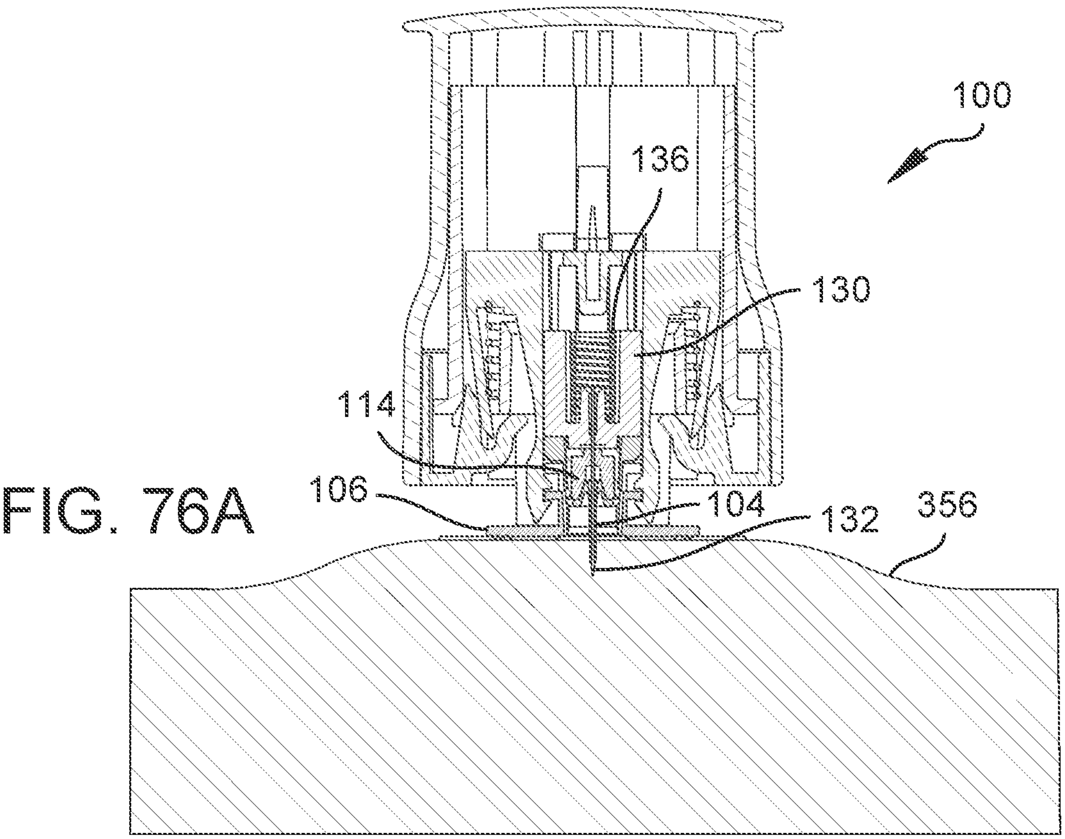
FIGS. 76A-76B depict cross-sectional views of an example inserter assembly after the sharp of the inserter assembly has pierced the skin of the user.
Figure 76B:
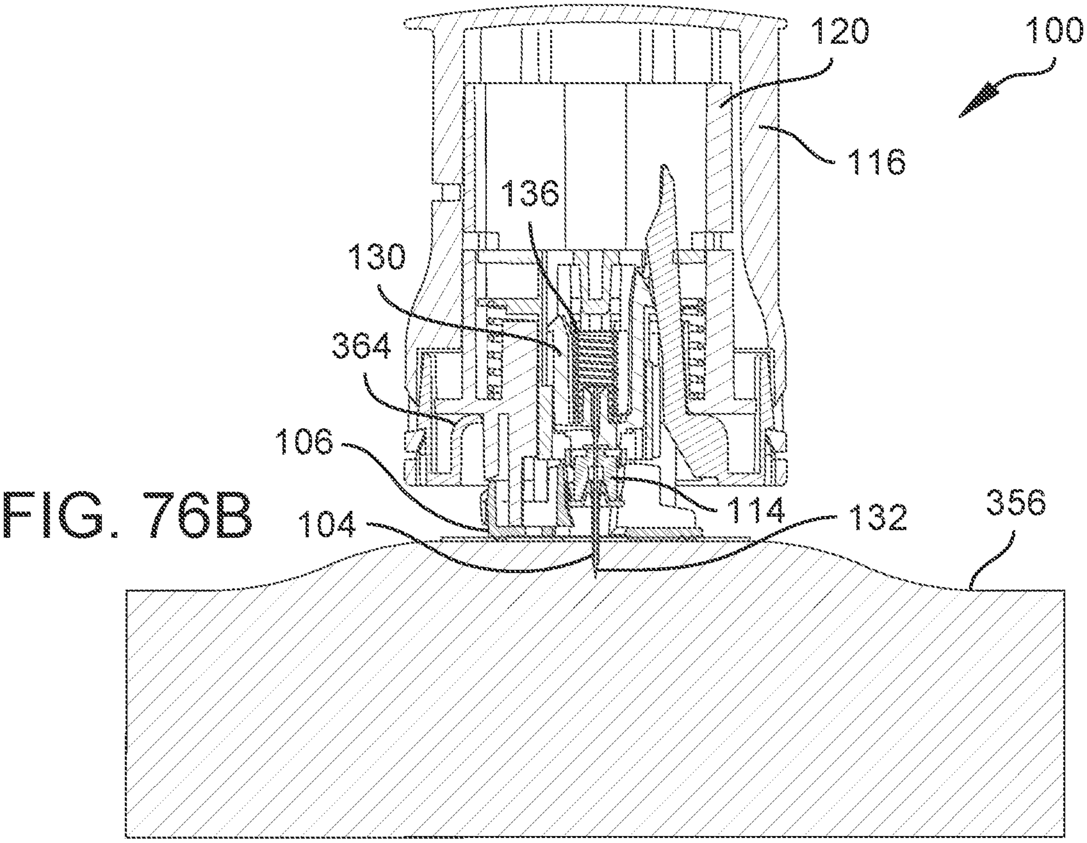

Referring now to FIGS. 76A-76B two cross sectional views of an inserter assembly 100 are shown. In FIGS. 76A-76B, the example inserter assembly 100 has been further withdrawn from the skin 356. As shown, the restoring action of the spring 136 may drive the sharp holder 130, insertion sharp 132, and cannula subassembly 114 toward the skin 356 along an insertion path. In the example embodiment, the sharp holder 130 at least partially extends out of the cavity 334 of the sharp retractor 130. As shown, the insertion sharp 132 and cannula 104 have just punctured through the skin 356. During puncture, the skin 356 may still be in a state in which it is tugged up away from muscle and other underlying body structures. The cannula subassembly 114 has also begun to be advanced toward the infusion set base 106. It should be noted that the spring 136 is still depicted in a compressed state in the forthcoming figures. This is for ease of illustration. As would be understood by one of skill in the art, the example spring 136 would expand over the course of the insertion movement. Also as shown, the retainer base 140 of the inserter assembly 100 may include a stop 364 which prevents relative movement beyond a certain point between the interior housing 120 and the casing formed by the exterior housing 116 and retainer base 140 (which may be connected to one another). This stop 364 may be included as a portion of the second ring 312 of the retainer base 140.

Figure 77A:
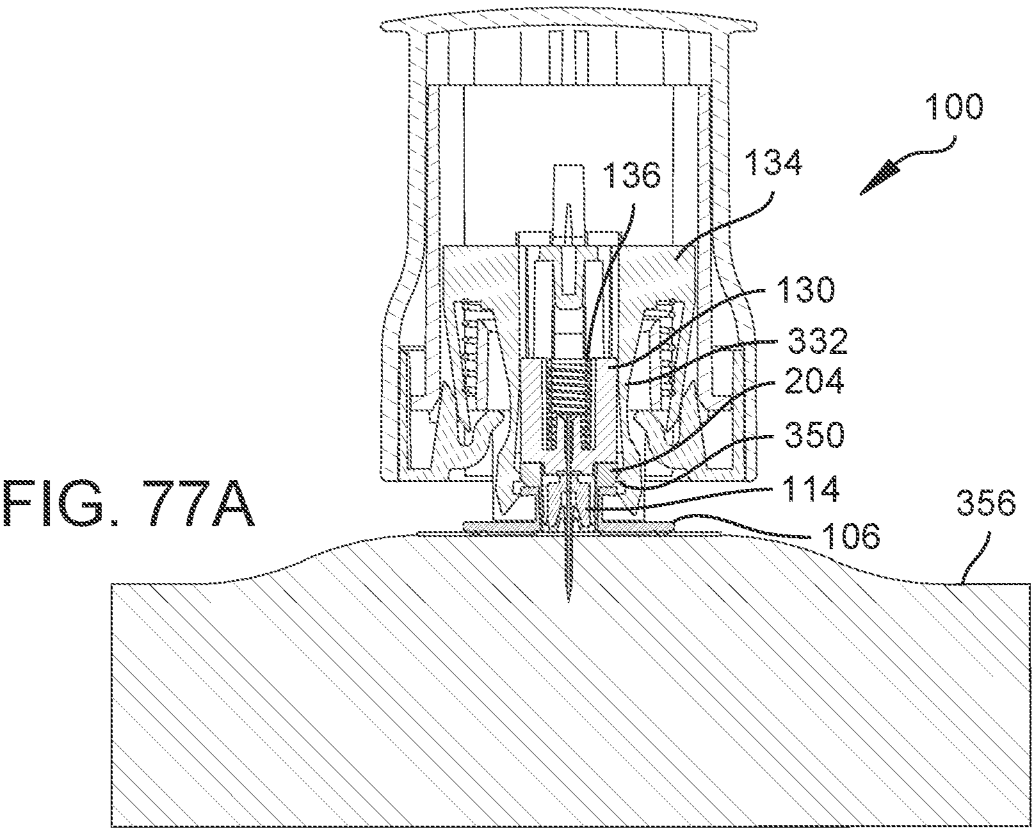
FIGS. 77A-77B depict cross-sectional views of an example inserter assembly after the sharp retractor has been freed to retract.
Figure 77B:
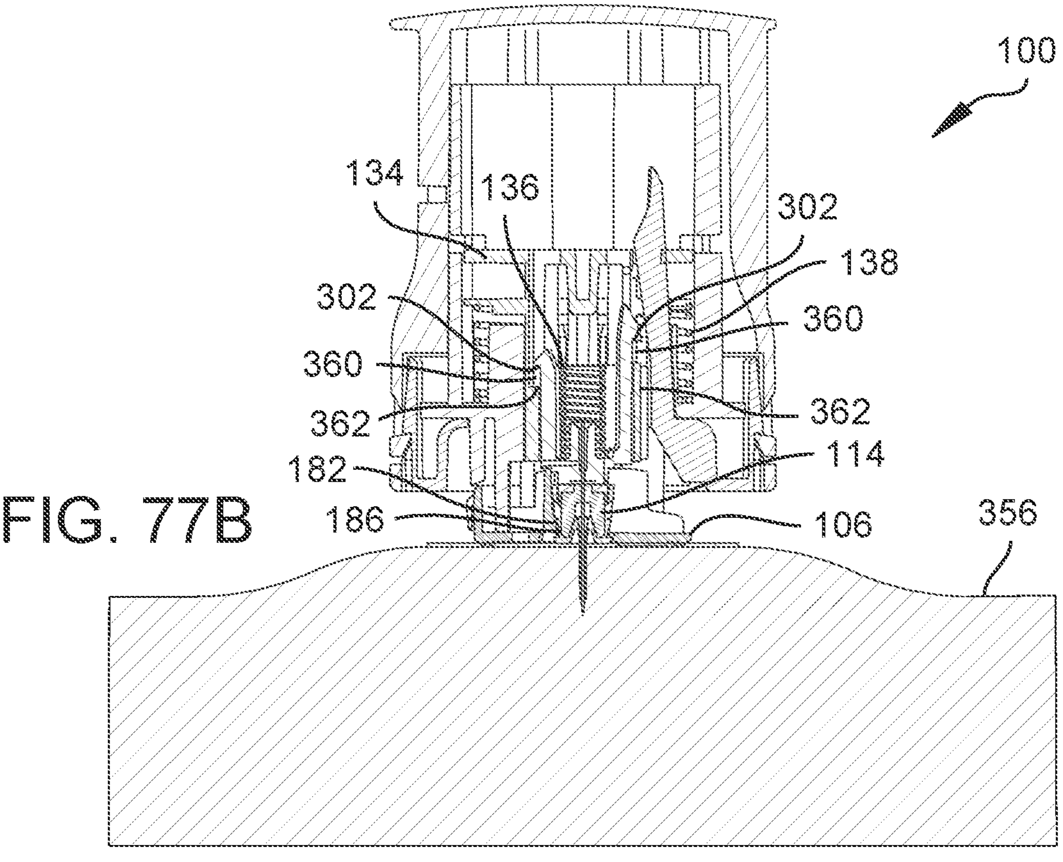

Referring now to FIGS. 77A-77B, two cross sectional views of an inserter assembly 100 are shown. As shown, the spring 136 has restored to a relaxed state and completed the insertion movement of the sharp holder 130, insertion sharp 132, and cannula subassembly 114 toward the skin 356. The relaxed state may be a completely relaxed state or a comparatively relaxed state where the spring 136 is still exerting some pressure against the sharp holder 130 to prevent it from jostling about. The notch 186 of the cannula subassembly 114 is shown in engagement with the protuberance 182 of the infusion set base 106 locking the cannula subassembly 114 in place and completing assembly of the infusion set 102. As shown, when the cannula subassembly 114 latches into the base 106, the ears 204 on the cannula subassembly 114 may press against the nubs 350 included on the arms 332. This may cause the arms 332 to be splayed apart resulting in disengagement of the arms 332 from the infusion set base 106. In turn, this may free spring 138 to begin releasing stored energy. Thus, FIGS. 77A-77B depict the insertion assembly 100 at a retraction release state and the arms 332 may serve as a retraction prevention latch.

Figure 78A:
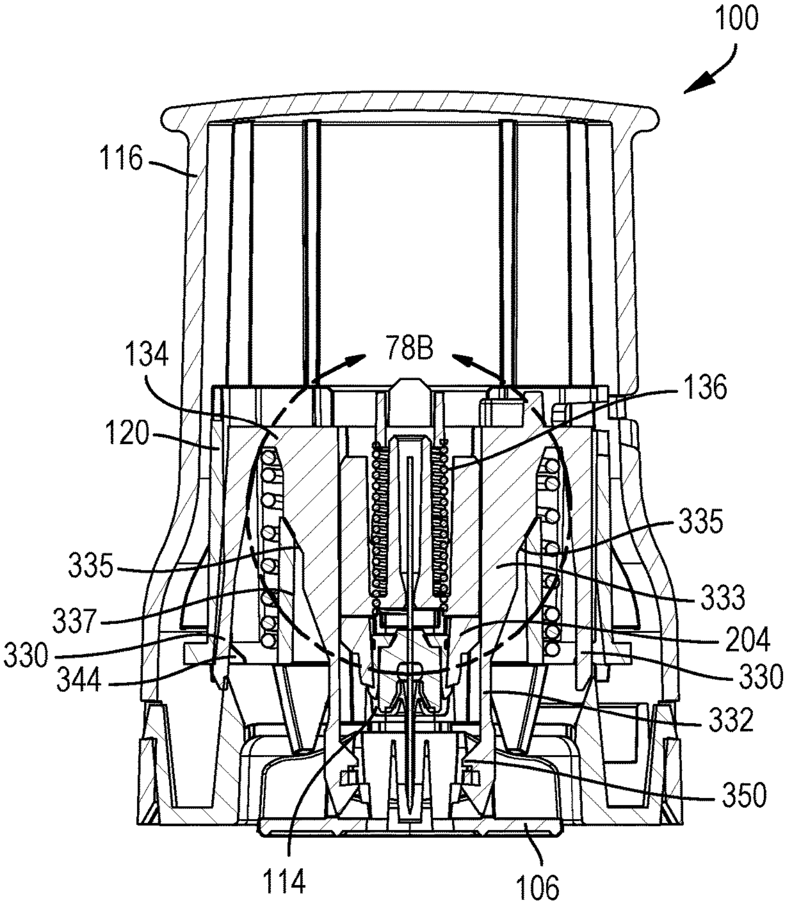
FIG. 78A depicts a cross-sectional view of an alternative example inserter assembly.
Figure 78B:
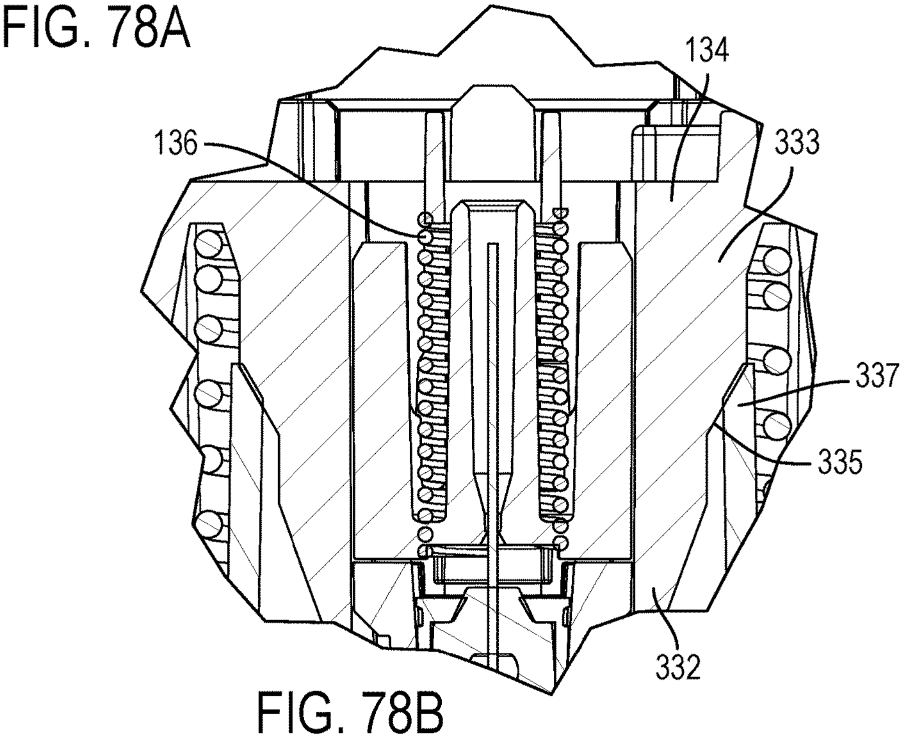
FIG. 78B depicts a detailed view of the indicated portion of FIG. 78A.

Referring now to FIGS. 78A-78B, in some examples, arms 332 of the needle retractor 134 may be provided with ribs 333. The ribs 333 may strengthen the arms 332 while still allowing for deflection of the arms 332 as the ears 204 of the cannula subassembly 114 are driven into the nubs 350 by the spring 136. The ribs 333 may help prevent and/or direct deflection of the arms 332 when the inserter assembly 100 is improperly handled (e.g. in the event that the inserter assembly 100 is dropped or subjected to other violent impact). This may assist in helping ensure the base 106 is not inadvertently dislodged. The ribs 333 may include ramped faces 335 which may collide with an end of a wall 337 of the interior housing 120 in the event that the sharp retractor 134 displaces slightly towards the open end of the inserter assembly 100 in such situations. The wall 337 end is ramped, the ribs 333 may cause the arms 332 to cinch up on the base 106 as this displacement occurs further helping to ensure that the base 106 is retained in place within the inserter assembly 100. Additionally, as shown, at least one of the first set of arms 330 of the sharp retractor 134 may be molded in an outwardly deflected state. Though depicted in its molded state in FIG. 78A, the arm 330 may be in an inwardly deflected state when in engagement with the projection 344 on the interior housing 120 (further described in relation to FIG. 71). Thus, the arm 330 may be biased into engagement with the projection 344. This may further increase resistance of the inserter assembly 100 to improper handling.

In certain other embodiments, and referring now to FIGS. 79A-82C, a set retention support such as a yoke 311 may be included in an inserter assembly 100. Exemplary supports may assist in robustly retaining the infusion set base 106 in place within the inserter assembly 100 even in the event that an inserter assembly 100 is improperly handled. Though the following embodiments are described in relation to infusion set bases 106, supports may be included to assist in retaining other patient care assembly bases in alternative examples. Supports may contact the arms 332 and increase the amount of force needed to distort the arms 332 in order to release the infusion set base 106. Various support embodiments, may abut against or be disposed adjacent to the arms 332, limiting the ability of the arms 332 to displace at least until the inserter assembly 100 is fired.

Figure 79A:
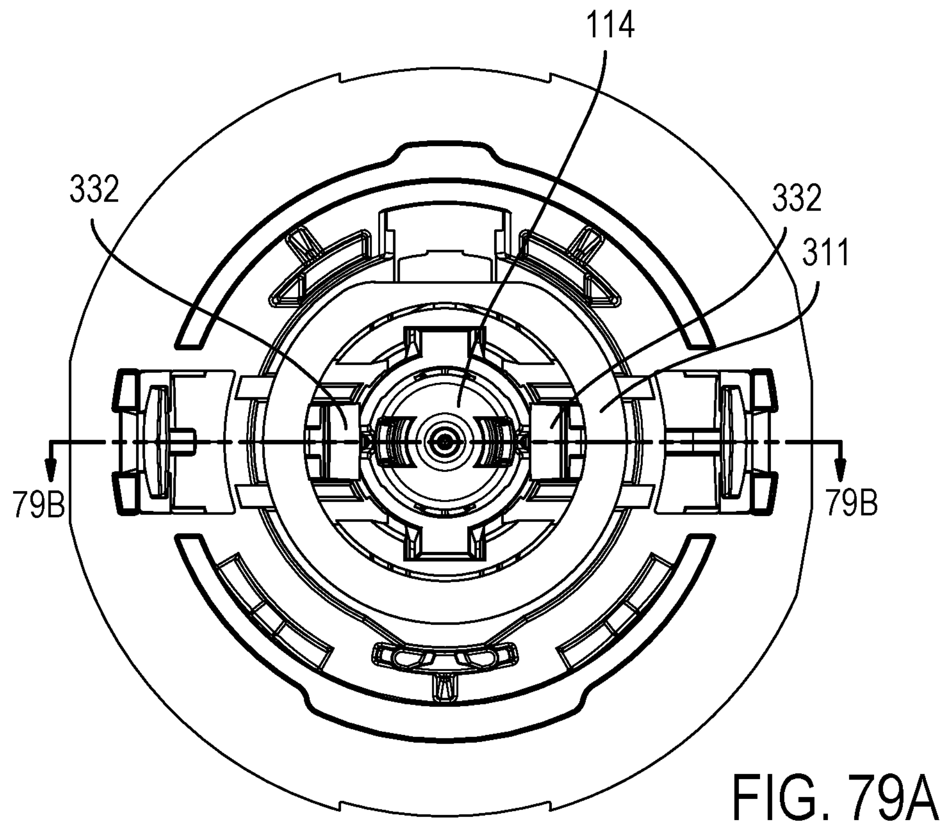
FIGS. 79A-82C depict example inserter assemblies including a variety of exemplary set retention supports.
Figure 79B:
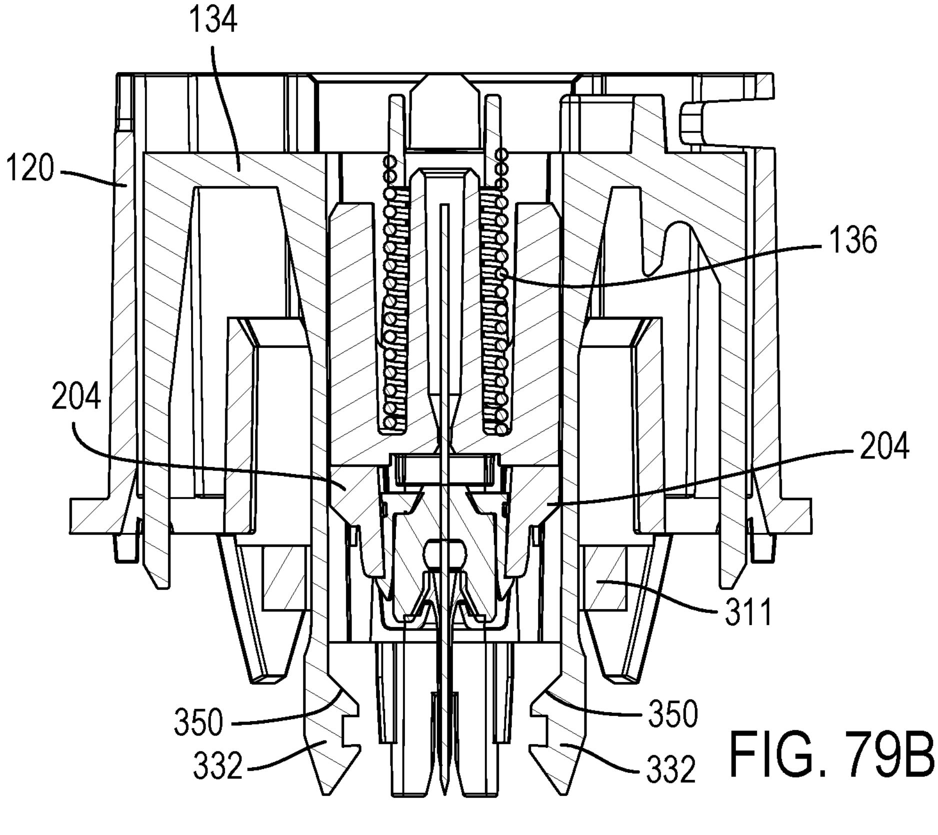

With reference primarily to FIGS. 79A-79B, a yoke 311 may, for example, be disposed encircling the arms 332. The arms 332 may be created (e.g. molded) such that there is a preload exerted against the yoke 311 to assist in holding the yoke 311 in place. Though the yoke 311 is depicted as a discrete component, in alternative embodiments the yoke 311 may be integrated into another component of the inserter assembly 100 (e.g. the interior housing 120). The yoke 311 may divide the each of the arms 332 into a restrained portion which may be inhibited from deflecting and a deflectable portion. The deflectable portion may be disposed more proximal the open end of the inserter assembly 100 than the yoke 311 with the remainder of each arm 332 forming the restrained portion. As described in relation to FIGS. 77A-B, the ears 204 on the cannula subassembly 114 may press against the nubs 350 included on the arms 332 when spring 136 restores toward a relaxed state. As this occurs, force provided by the spring 136 may be sufficient to deflect the deflectable portions of the arms 332 to release the infusion set base 106 (see, e.g., FIG. 77A, B) and free spring 138 (see, e.g., FIGS. 77A, B). The yoke 311 may, however, help ensure that the infusion set base 106 is robustly held when the inserter assembly 100 is improperly handled.

Figure 80A:
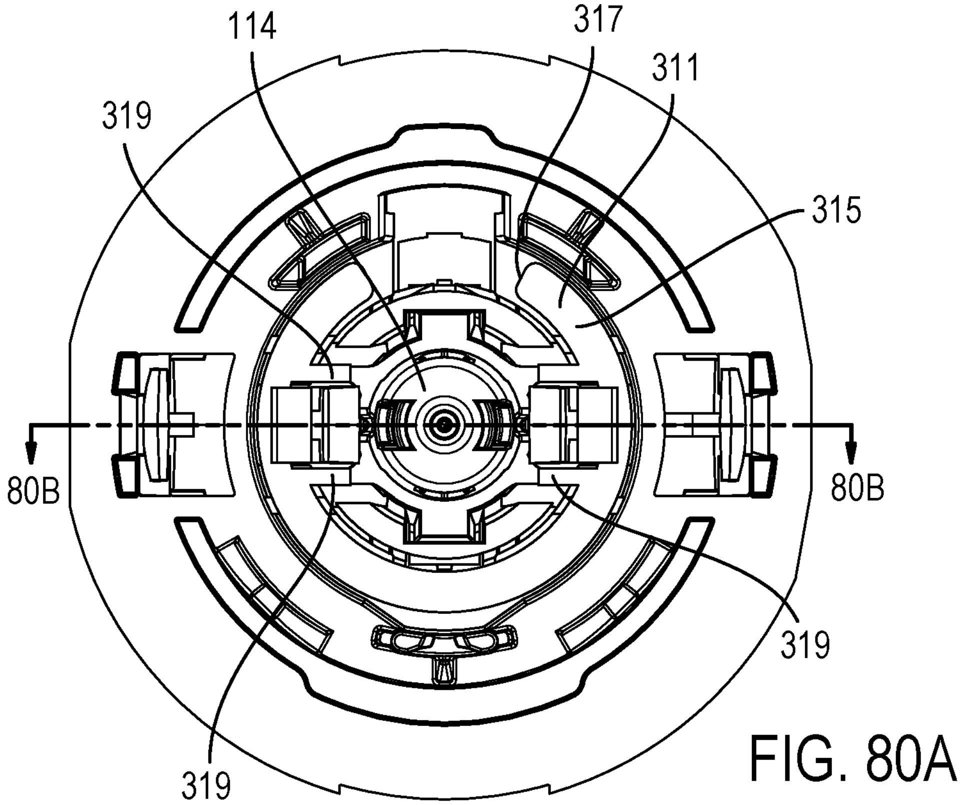
Figure 80B:
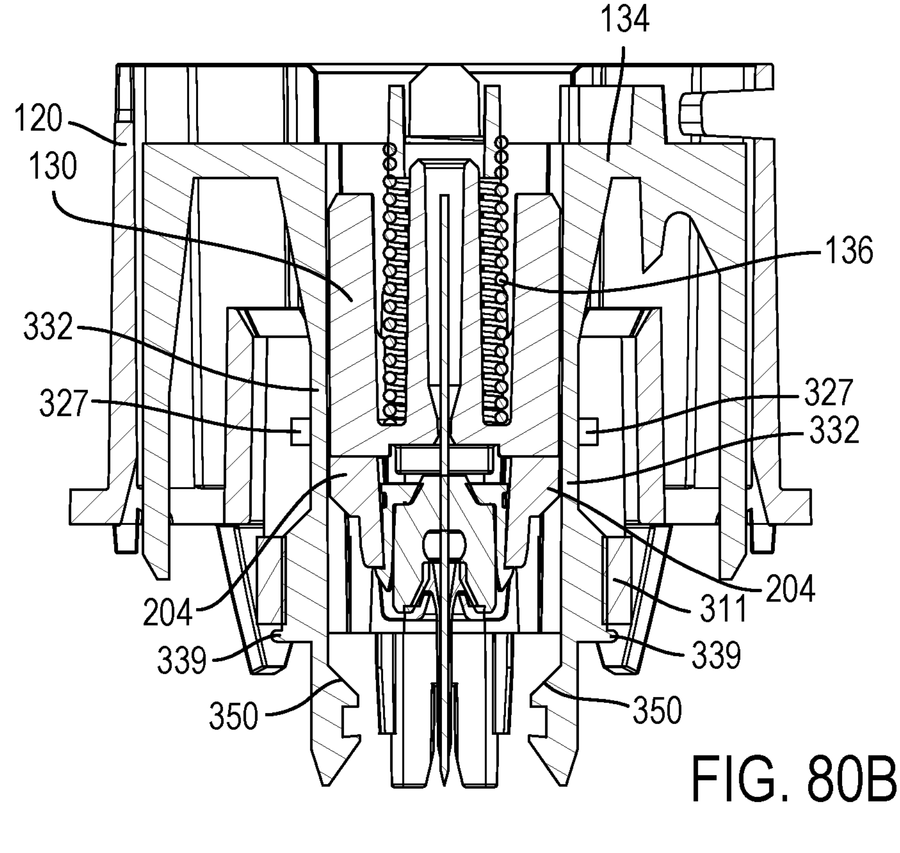

In alternative embodiments including a yoke 311 and referring now to FIGS. 80A-80B, the yoke 311 may transition between a restraining state and a disengaged state when the inserter assembly 100 is fired. The yoke 311 may, for example, be disengaged from the arms 332 as the cannula subassembly 114 is advanced toward the infusion set base 106. As shown, in some such embodiments the yoke 311 may be defined as a ring 315 having a split 317. The ring inner periphery may include protuberances 319. In the example shown, each of the arms 332 is flanked by a protuberances 319. The protuberances 319 may be disposed in the displacement path of portions of the sharp holder 130 as the sharp holder 130 is propelled toward the open end of the inserter assembly 100. In the example shown, the sharp holder 130 includes wings 327 which collide with the protuberances 319 as the sharp holder 130 is driven by spring 136.

The arms 332 may include a sill 339 on which the yoke 311 may rest when the inserter assembly 100 is in a storage state. Additionally, the inner sidewall of the yoke 311 may be against the lateral surfaces of the arms 332. In some embodiments, the yoke 311 may be held in place by a slight interference fit type engagement with the arms 332. Thus, the yoke 311 may restrain the arms 332 when the inserter assembly 100 is in the storage state and inhibit release of the infusion set base 106 in the event of improper handling. When the sharp holder 130 collides with the yoke 311, the yoke 311 may be driven into the sill 339. The split 317 may facilitate distortion of the yoke 311 such that the yoke 311 may be advanced past the sill 339 toward the open end of the inserter assembly 100 and into a disengaged state. With the yoke 311 in the released state, the ears 204 on the cannula subassembly 114 may press against the nubs 350 included on the arms 332 during operation to release the infusion set base 106 as described above (see, e.g., FIGS. 77A, B). As shown, the arms 332 may be thickened adjacent the sill 339. This may allow a wider yoke 311 to be utilized. When in the disengaged state, the large aperture of the yoke 311 may provide sufficient clearance for the arms 332 to splay apart in order to release the infusion set base 106. Though not shown, in certain examples, a stop may be included (e.g. on a retainer base 140) which may hold the yoke 311 in the disengaged state preventing the yoke 311 from falling out of the inserter assembly 100.

Figure 81A:
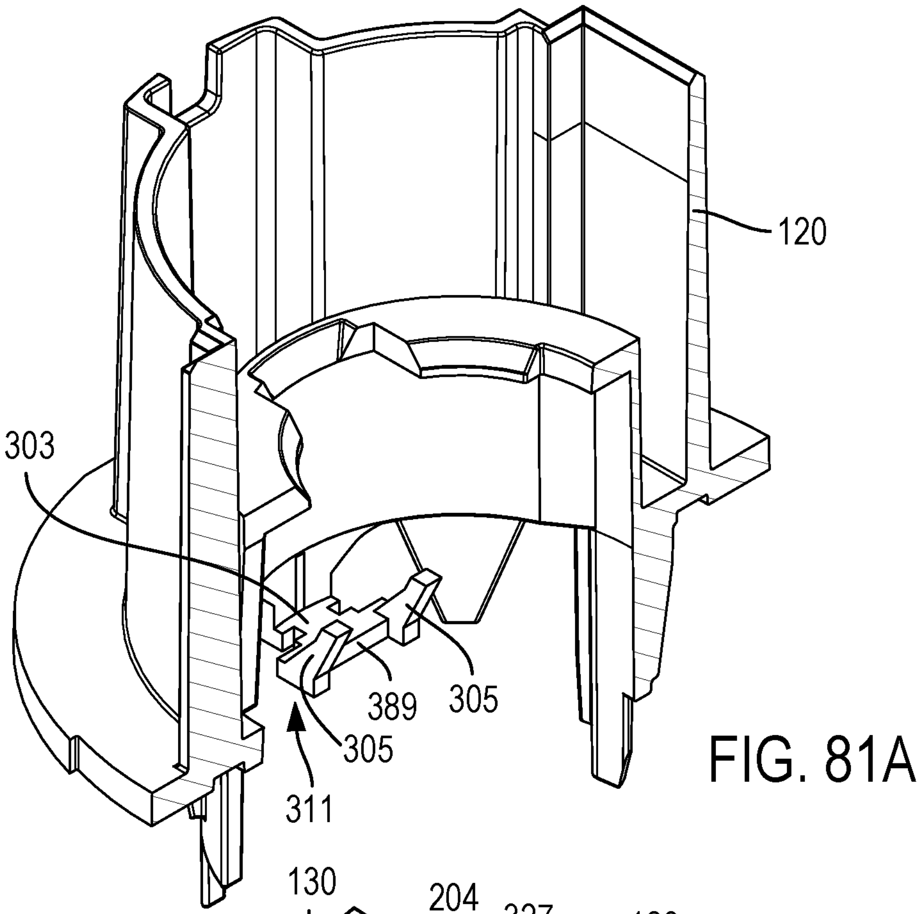
Figure 81B:
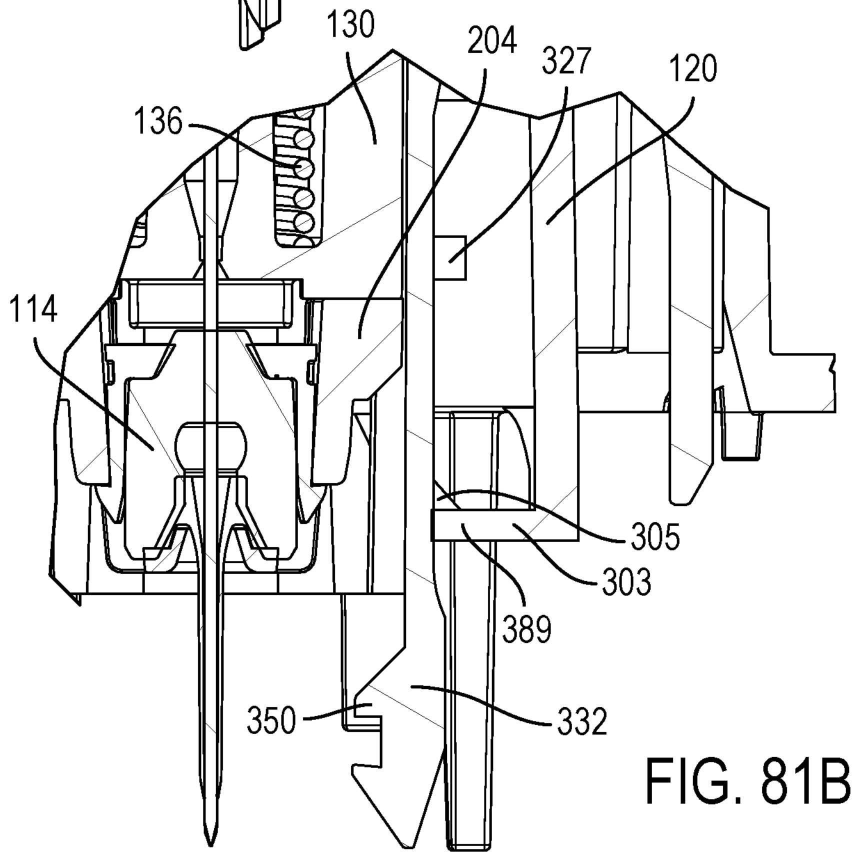

Referring now to FIGS. 81A-81B, in alternative embodiments, a yoke 311 may be included as a set of pads 389 which may be coupled to another component of an inserter assembly 100 via respective flexures 303. As best shown in FIG. 81A, pads 389 may be coupled to an example interior housing 120 via flexures 303. Though half of the interior housing 120 is removed in the cross-sectional view depicted in FIG. 81A, the opposing side of the interior housing 120 would mirror that shown and also include a pad 389. As best shown in the enlarged view of FIG. 81B, each pad 389 may be in abutment with a respective arm 332 of the sharp retractor 134. The pad 389 may inhibit displacement of the arm 332 and assist in retaining the infusion set base 106 in engagement with the arms 332 during improper handling.

When the inserter assembly 100 is fired, the yoke 311 may transition between a restraining state and a disengaged state via a deformation of the flexures 303 coupling each pad 389 to the interior housing 120. Portions of the sharp holder 130 may collide with the pads 389 as the sharp holder 130 is propelled toward the open end of the inserter assembly 100 as spring 136 relaxes. As shown, each of the pads 389 include legs 305 which may extend into the displacement path of a sharp holder 130. As shown in FIGS. 81A-81B, the legs 305 may, for instance, be positioned to be hit by wings 327 extending from the exemplary sharp holder 130. The flexures 303 may yield as the sharp holder 130 collides with the pads 389 causing the pads 389 to displace out of contact with the arms 332. The pads 389 may be displaced to a position in which the arms 332 are free to splay apart to release the infusion set base 106 as the ears 204 of the cannula subassembly 114 are driven into the nubs 350 of the arms 332. In preferred embodiments, as the sharp holder 130 drives the yoke 311 to the disengaged state, the pads 389 remain attached to the interior housing 120. The flexures 303 may be permanently deformed, but the flexures 303 may not be strained to the point of failure. In alternative embodiments, the flexures 303 may break and the pads 389 may disassociate from the inserter assembly 100.

Though the example yokes 311 in FIGS. 80A-81B are disengaged via a collision with a portion of the sharp holder 130, in other embodiments another portion of the spring biased unit formed by the sharp holder 130, insertion sharp 132, and cannula subassembly 114 may collide with the yokes 311 in alternative embodiments. The cannula subassembly 114 could include wings similar to the wings 327 included on the sharp holders 130 in certain alternatives. These wings could hit and disengage the yoke 311 when the inserter assembly 100 is fired.

Figure 82A:
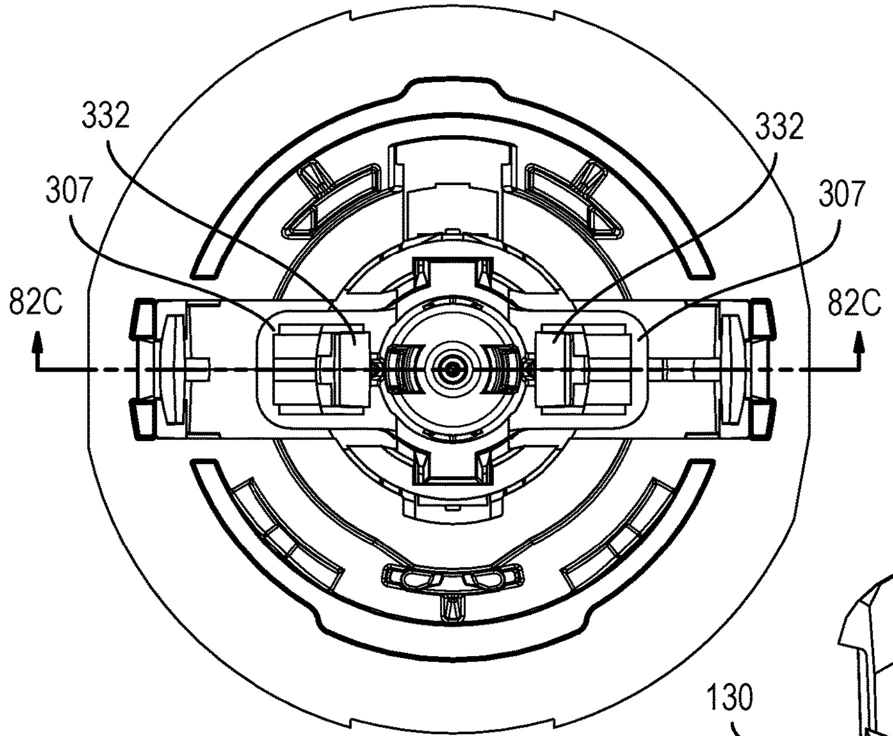
Figure 82B:
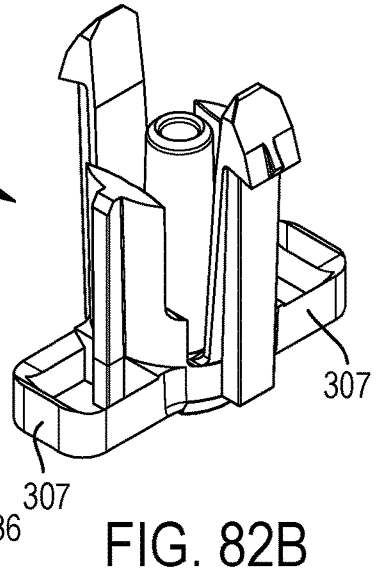
Figure 82C:
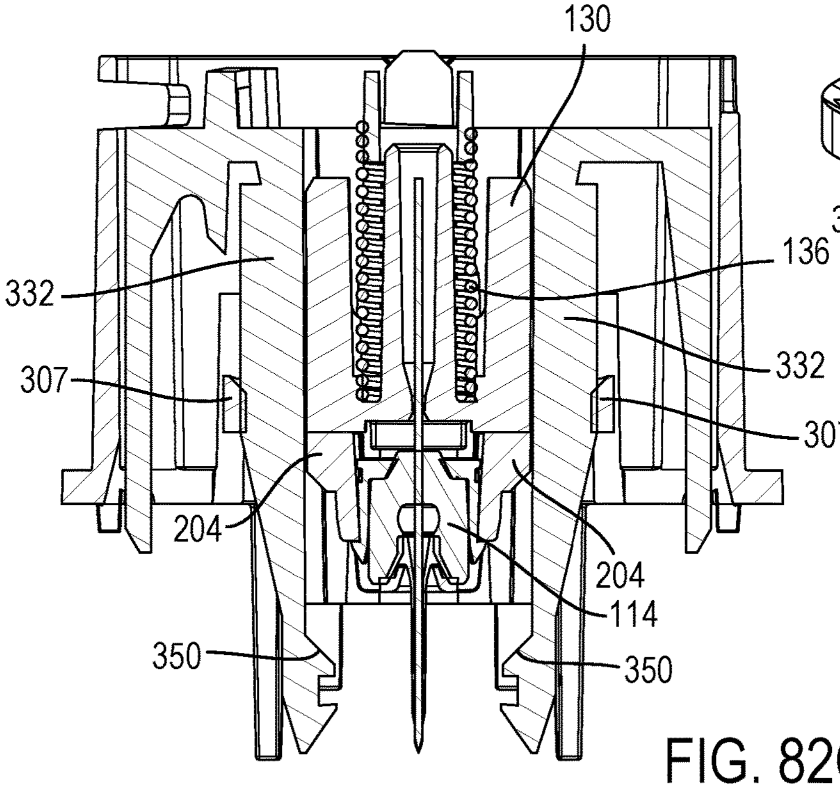

Referring now to FIGS. 82A-82C, in some embodiments, a yoke 311 may be incorporated into the sharp holder 130. As best shown in FIG. 82B, an example sharp holder 130 may include a set of lobes 307 which include an open central region or passage. The lobes 307 may be disposed on opposing sides of the sharp holder 130 and may be slide over the arms 332 during assembly of an inserter assembly 100. At least a portion of the arms 332 may be tapered such that the thickness of the arms 332 decreases as proximity toward the unsupported ends of the respective arms 332 increases. Though shown tapered, the thickness of the arms 332 could also alter in stepwise fashion depending on the embodiment. The lobes 307 may be sized to snuggly accept the thickest portion of each arm 332 in the storage state. In some examples, there may be a slight interference between the arms 332 and the lobes 307 when the lobes 307 are positioned around the thick regions of the arms 332. When in the storage state the lobes 307 may be positioned over the thick segments of the arms 332 limiting the ability of the arms 332 to deflect. As the sharp holder 130 is propelled toward the open end of the inserter assembly 100 when the inserter assembly 100 is fired, the lobes 307 may reach a thin segment of the respective arms 307. The apertures defined by the lobes 307 may be sized to permit the arms 332 to splay apart releasing the infusion set base 106 as the ears 204 of the cannula subassembly 114 collide with the nubs 350 of the arms 332. Thus, the yoke 311 provided by the lobes 307 may transition between a restraining state and a disengaged state as the sharp holder 130 displaces during the insertion stroke of the inserter assembly 100.

Referring again primarily to FIGS. 77A-77B, in certain embodiments, retraction may not be automatic and/or may not be spring biased. For example, the insertion sharp 132 may remain in the advanced position and the removal action of the user may manually pull the insertion sharp 132 out of the cannula 104. In such embodiments, spring 138 may be omitted. In some embodiments, disengagement of the arms 332 from the infusion set base 106 may not be automatic. Any arrangement which would be apparent to one skilled in the art may be used to facilitate manual decoupling of the arms 332 from the infusion set base 106. A twisting action may be employed to free the arms 332 from the infusion set base 106 allowing the insertion sharp 132 to then automatically retract or be manually pulled out. One or more button may be included in alternative embodiments. Displacement of the one or more button may uncouple the arms 332 from the infusion set base 106 allowing the insertion sharp 132 to then be manually or automatically retracted out of the cannula 104. Squeezing of a deformable portion of the inserter assembly 100 may similarly cause uncoupling of the arms 332 from the infusion set base 106. As would be appreciated by one skilled in the art, the inserter assembly 100 embodiments described herein could be otherwise modified to allow for various types of other manual arm 332 release schemes.

In alternative embodiments where the infusion set base 106 is retained by a portion of the interior housing 120 and the arms 332 engage a portion of the interior housing 120, displacement of the sharp holder 130 may similarly cause release of the infusion set 102 and trigger retraction. For example, the ears 204 may collide with and cause displacement of catch features (e.g. spread them away from the infusion set 102) on the interior housing 120 resulting in them decoupling from the infusion set 102. Additional ears 204 or other projections on the cannula subassembly 114 may be included to cause disengagement of the arms 332 (e.g. via spreading of the arms 332) from the interior housing 120 to permit retraction.

In certain embodiments, there may be a dwell period during inserter assembly 100 actuation where retraction of the insertion sharp 132 has been triggered and the sharp retractor 134 is displacing, however, the insertion sharp 132 remains substantially static. During this dwell period, spring 136 may continue to exert pressure on the cannula subassembly 114 through the sharp holder 130. This may block any possible tendency of the cannula subassembly 114 to bounce or rebound as it is propelled into the infusion set base 106 and ensure it is firmly retained in the base 106. As shown, once the insertion movement is complete, a dwell gap 360 may be present between a stop 362 on the sharp retractor 134 and the ledge 302 on each cantilevered arm 296 of the sharp holder 130. Spring 136 may still have energy stored therein and continue to press against the sharp holder 130. The dwell gap 360 on each side may be equal in size.

Figure 83A:
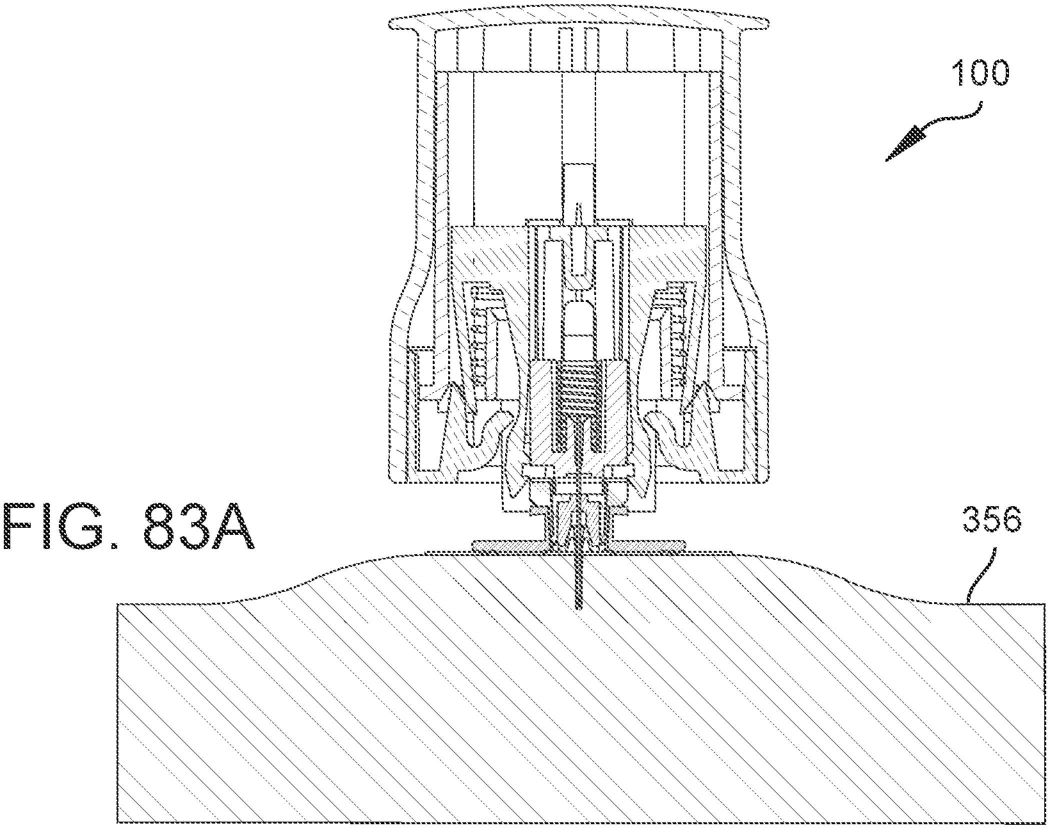
FIGS. 83A-83B depict cross-section views of an example inserter assembly during retraction of the sharp retractor.
Figure 83B:
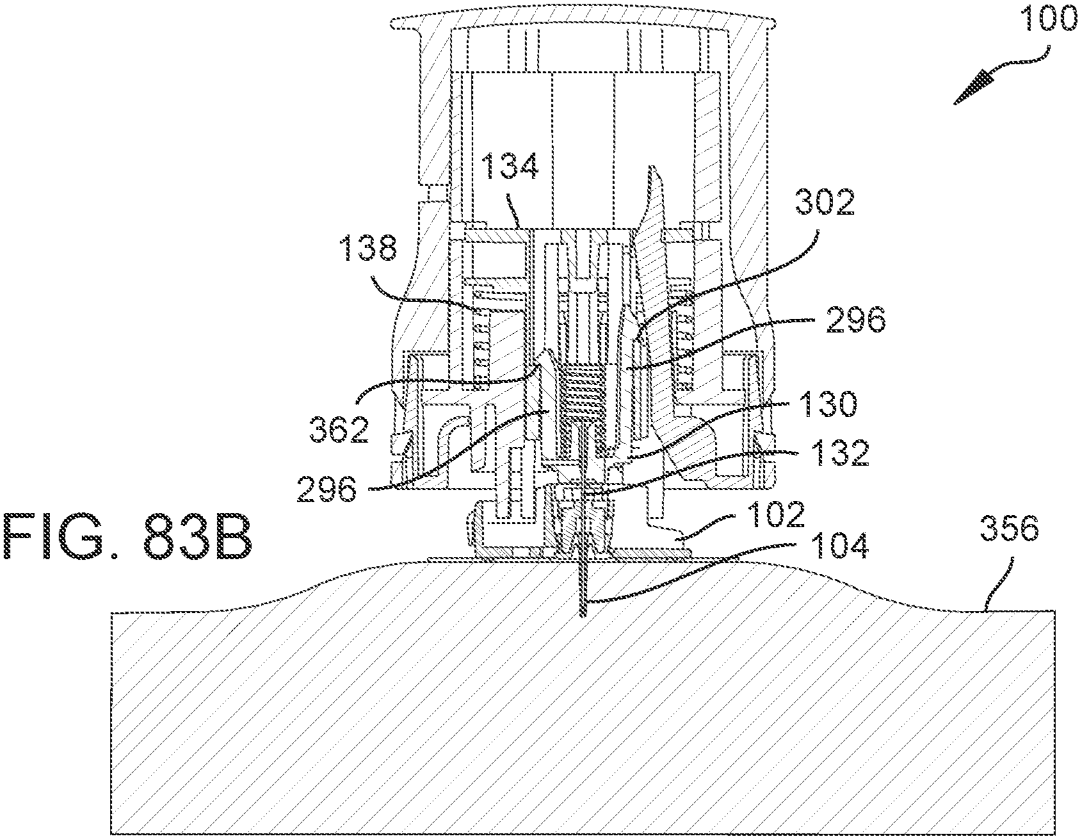
Figure 83C:
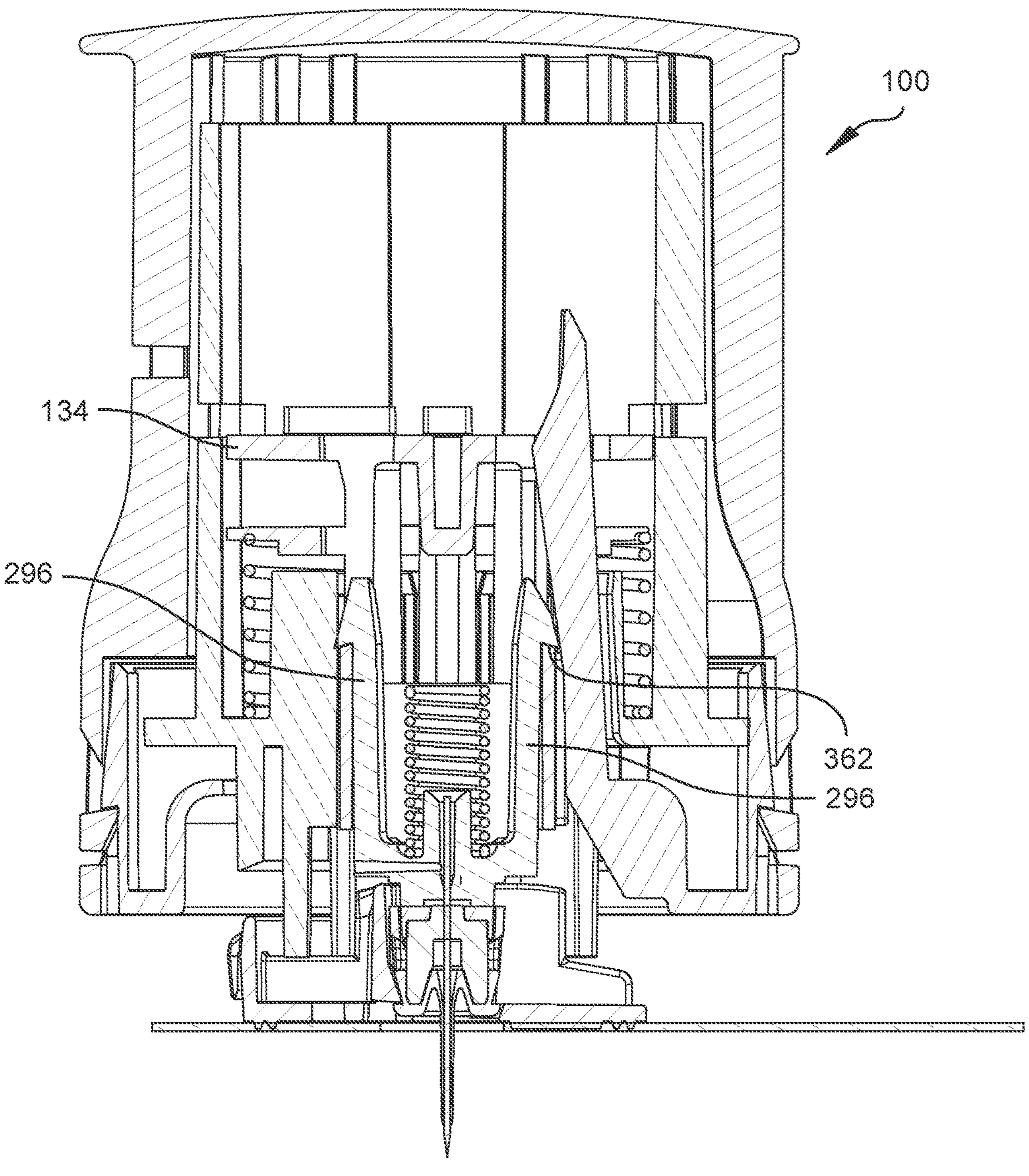
FIG. 83C depicts a cross sectional view of an alternative embodiment of an inserter assembly.

Referring now additionally to FIGS. 83A-83B, which depict two cross sectional views of an inserter assembly 100, the dwell gap 360 may decrease until the stops 362 on the sharp retractor 134 contact the ledges 302 of the cantilevered arms 296 on the sharp holder 130. Once this occurs, the restoring action of spring 138 may begin to displace the sharp holder 130 and insertion sharp 132 affixed thereon along with the sharp retractor 134. This displacement may retract the insertion sharp 132 out of the cannula 104 and the infusion set 102. An alternative embodiment of an inserter assembly 100 at this stage of actuation is shown in FIG. 83C. In FIG. 83C the cantilevered arms 296 are equal length mirror images of one another. The stops 362 on the sharp retractor 134 may be at even height with one another in such embodiments.

Figure 84A:
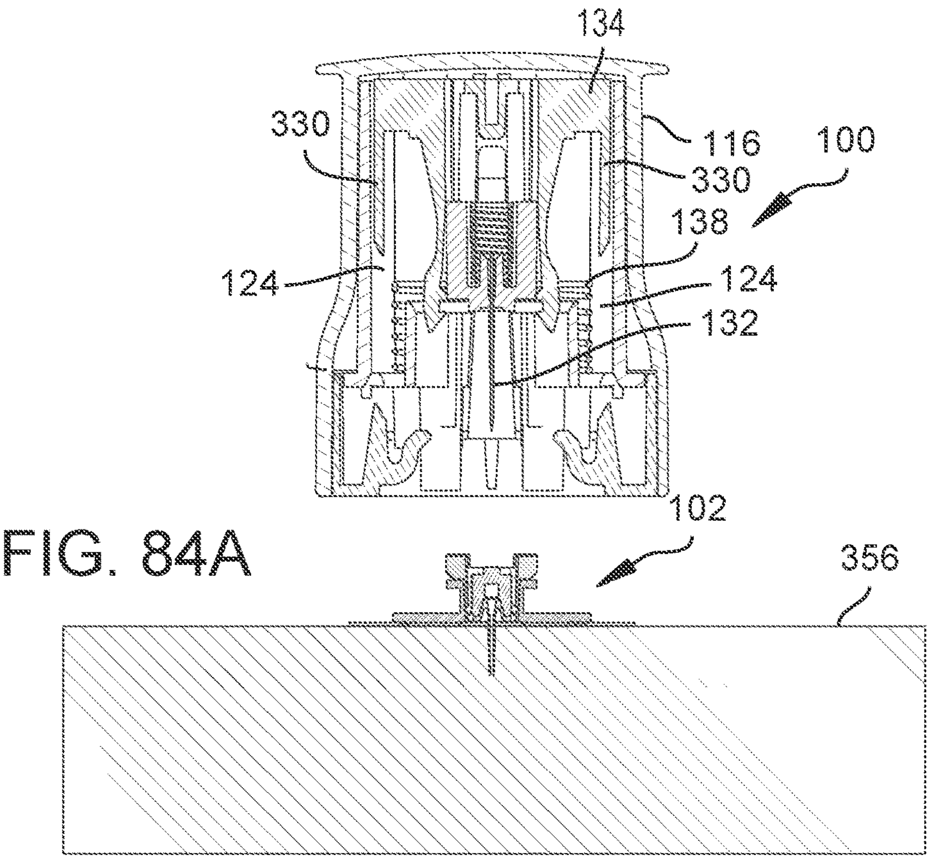
FIGS. 84A-84B depict cross-sectional views of an inserter assembly after inserter assembly actuation has completed.
Figure 84B:
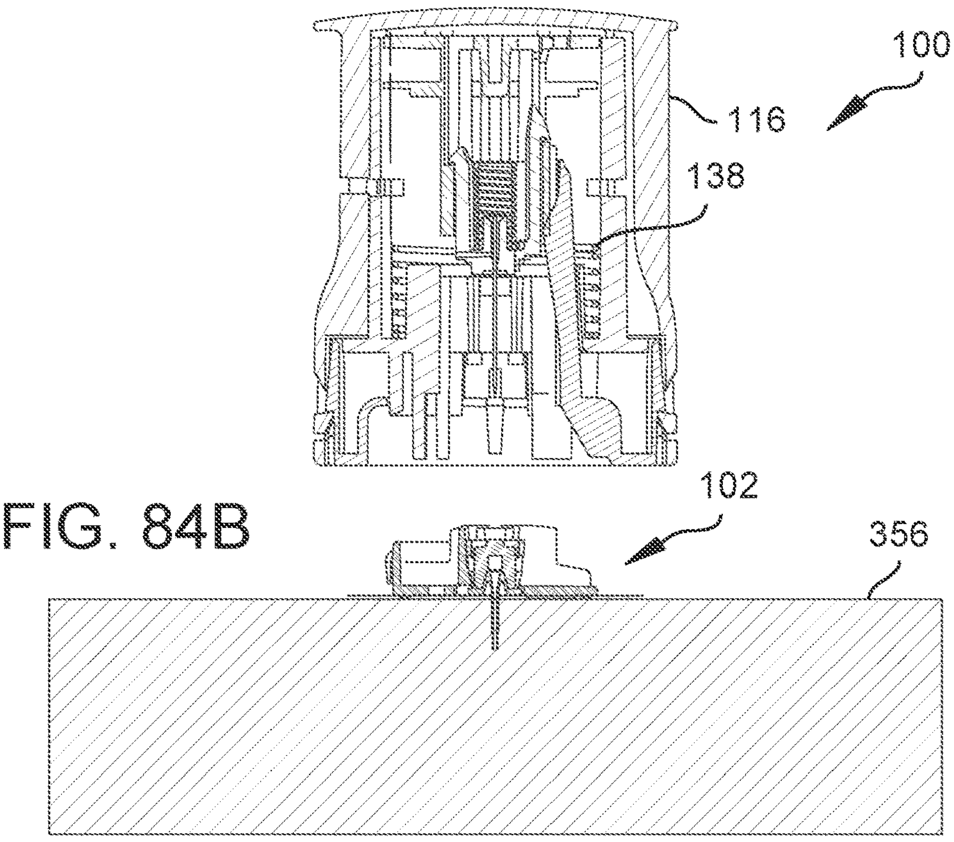

As shown in FIGS. 84A-84B, once retraction has completed the sharp retractor 134 may be pressed against the exterior housing 116 by spring 138. For ease of illustration the spring 138 is still depicted in the compressed state, but would decompress to a relaxed state over the progression of the retraction as would be understood by one skilled in the art. As with spring 136, the relaxed state may be a completely relaxed state or a comparatively relaxed state where the spring 138 is still exerting some pressure against the sharp retractor 134 to prevent it from jostling about. After retraction, the insertion sharp 132 may be housed within the inserter assembly 100 to aid in protecting against unintentional finger sticks or the like. In the example embodiment, the insertion sharp 132 is housed further within the inserter assembly 100 after retraction when compared to its starting position. In other embodiments, the retracted location of the insertion sharp 132 may differ but may be at least housed as deep within the inserter assembly 100 as its initial starting location. The infusion set 102 may be held in place on the skin 356 with the cannula 104 indwelling in the patient.

Figure 84C:
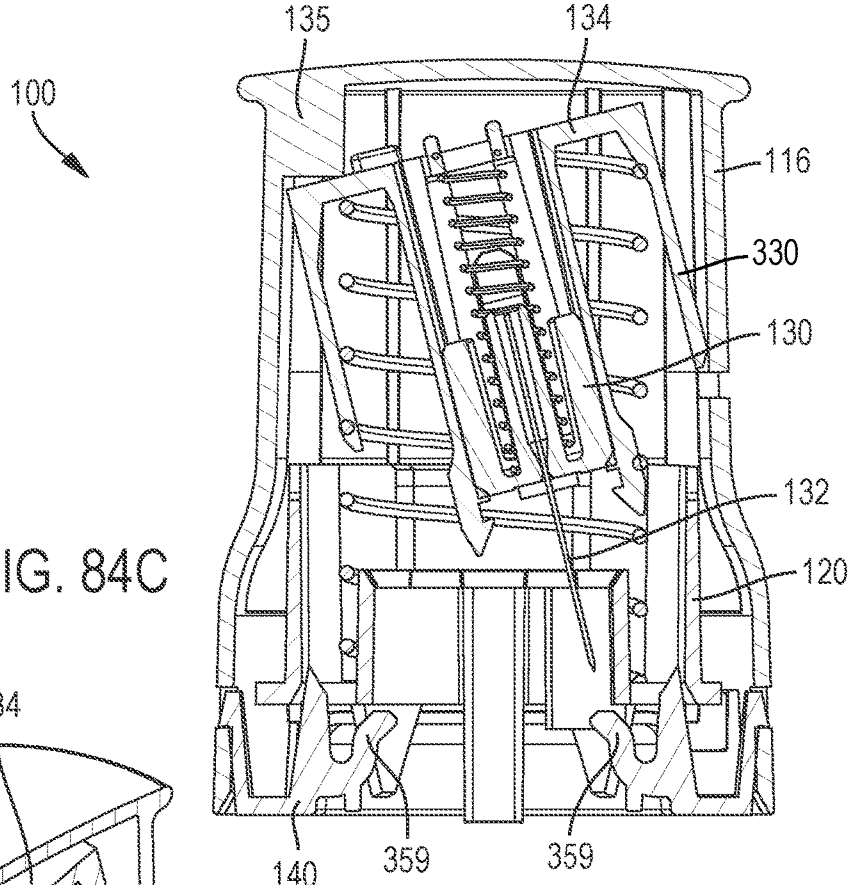
FIGS. 84C-84D depict cross-sectional views of an example inserter assembly after an inserter assembly actuation has completed.
Figure 84D:
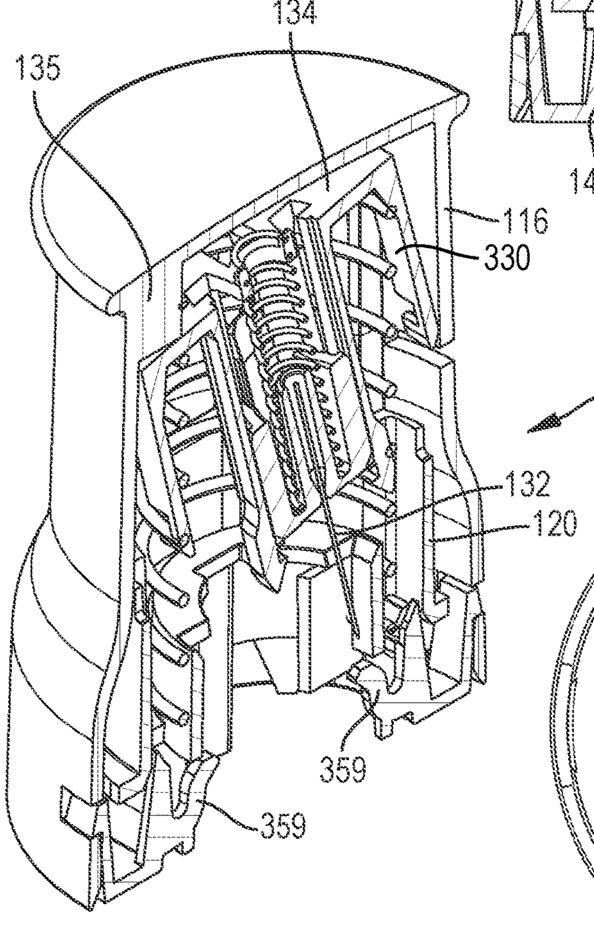
Figure 84E:
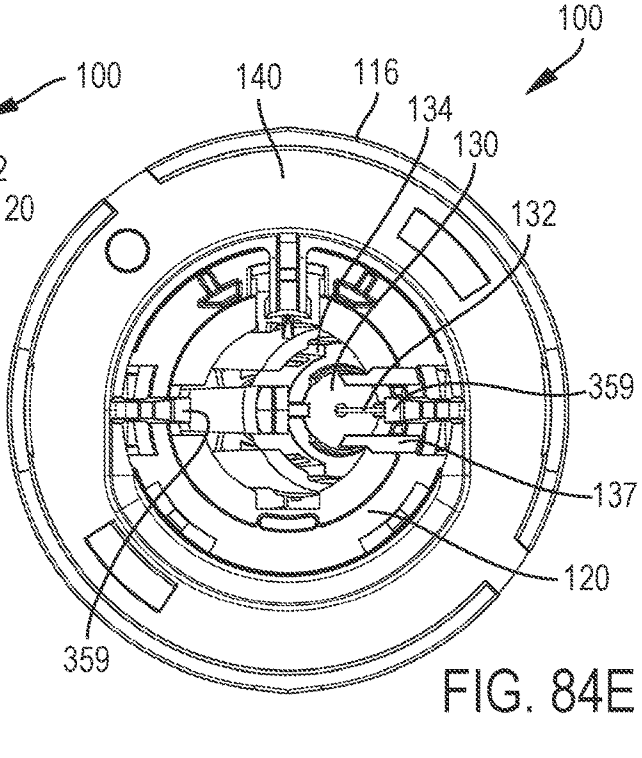
FIG. 84E depicts a bottom plan view of an example inserter assembly after an inserter assembly actuation has completed.

Referring now also to FIGS. 84C-E, an alternative embodiment of an inserter assembly 100 is depicted. As shown in FIGS. 84C-D, the interior housing 120 of the inserter assembly 100 is shortened compared to, for example, that shown in FIG. 84B. In the exemplary embodiment shown in FIGS. 84A-B, the arms 330 of the sharp retractor 134 may ride within the rails 124 defined in the interior housing 120 as the sharp retractor 134 is retracted. Thus, the interior housing 120 may act as a guide body and the sharp retractor 134 may be guided to the retracted state by the interior housing 120. In the example shown in FIGS. 84C-D, the height of the interior housing 120 is such that the sharp retractor 134 is guided for a first portion of the retraction stroke and unguided for the remainder of the stroke. The at least partially unguided retraction displacement of the sharp retractor 134 may allow for some movement of the sharp retractor 134 within the exterior housing 116 as the retraction stroke transpires.

In certain embodiments, the exterior housing 116 may include at least one tipping projection 135 which obstructs retraction of a portion of the sharp retractor 134. This portion of the sharp retractor 134 may collide with the tipping projection 135 during the unguided portion of the retraction stroke. The tipping projection(s) 135 may have an end surface which is spaced a distance from an interior surface of the closed end of the exterior housing 116. An example tipping projection 135 may extend from the interior surface of the closed end of the exterior housing 116. The tipping projection(s) 135 may be disposed in an off-center position and, as shown, may be connected to both the interior surface of the closed end and side wall of the exterior housing 116. In some examples, the tipping projection(s) 135 may have a cross-section in the shape of the Latin character "T". Example tipping projections 135 may include at least one nub body extending from the interior surface of the closed end of the exterior housing 116 to the open end of the exterior housing 116. In other embodiments, at least one ramped body may extend at an angle from the interior surface of the closed end of the exterior housing 116 to a point on the side wall of the interior of the exterior housing 116. In still other embodiments, the tipping projection(s) 135 may include at least one projection extending from a portion of interior side wall of the exterior housing 116 (e.g. near the closed end) into the interior volume of the exterior housing 116. Though such a tipping projection 135 may not directly connect with or contact the interior surface of the closed end of the exterior housing 116 such a tipping projection 135 may still be referred to as being disposed at the closed end of the exterior housing 116.

Thus, the sharp retractor 134 may be free to move all the way into contact with the interior surface of the exterior housing 116 on one side, but stopped shy on the other by the tipping projection 135. As the sharp retractor 134 displaces toward the closed end of the exterior housing 116, a portion of the sharp retractor 134 may contact the tipping projection 135. The tipping projection 135 may inhibit further displacement of that portion of the sharp retractor 134. Since the sharp retractor 134 may be unguided in a second stage of the retraction stroke, as the retraction displacement continues (e.g. as the retraction spring 138 continues to relax), the sharp retractor 134 may begin to tilt at an angle to the axis of the rest of the inserter assembly 100. As a result, the insertion sharp 132 on the sharp holder 130 would be tilted out of alignment with the axis of the inserter assembly 100. In alternative examples, the surface of the sharp retractor 134 most proximal the interior surface of the closed end of the interior housing 116 may be uneven so as to cause the sharp retractor 134 to tilt as described above. For example, tipping projection(s) 135 (e.g. ramped protrusions, nubs, "T" shaped projections, etc.) may be included on the sharp retractor 134 to engender tilting as the retraction stroke progresses.

When the retraction stroke completes, the insertion sharp 132 may be in a tilted state. This could further assist in stowing the insertion sharp 132 within the inserter assembly 100 after retraction. At the conclusion of the retraction stroke, the retraction spring 138 may not be fully relaxed. Thus, the retraction spring 138 may press the sharp retractor 130 against the closed end of the exterior housing 116 holding the insertion sharp 132 in the tilted state. This may also help prevent wiggling of the sharp retractor 134 when in the retracted state such that substantially no rattling occurs when the inserter assembly 100 is handled after use.

The location of the tipping projection(s) 135 may be selected to adjust the direction which the sharp retractor 134 tilts. In some examples including a tipping projection 135, the tipping projection 135 may be disposed such that the insertion sharp 132 is directed into a guard defined in another component of the inserter assembly 100. As shown best in FIG. 84D and FIG. 84E, the example tipping projection 135 is disposed such that tilting of the sharp retractor 134 displaces the insertion sharp 132 into a guide channel 137 of the interior housing 120 when the sharp retractor 134 is in the fully retracted state. Multiple tipping projections 135 arranged in a line or at least one tipping projection 135 with an elongate segment (e.g. cross-piece 135X of a "T" shaped tipping projection 135 shown in FIG. 84G) may assist in encouraging tilting of the insertion sharp 132 along a desired plane (e.g. perpendicular to the elongate segment or line of tipping projections 135). The guide channel 137 may assist in guiding an arm 332 of the sharp retractor 134 during a portion of the retraction stroke of the sharp retractor 134. The guide channel 137 may then serve as a guard into which the tip of the insertion sharp 132 is displaced as the sharp retractor 134 is tilted. In some embodiments, a retaining projection 359 of the retainer base 140 may further obstruct access to the tip of the insertion sharp 132 when the sharp retractor 134 is in the fully retracted state.

Figure 84F:
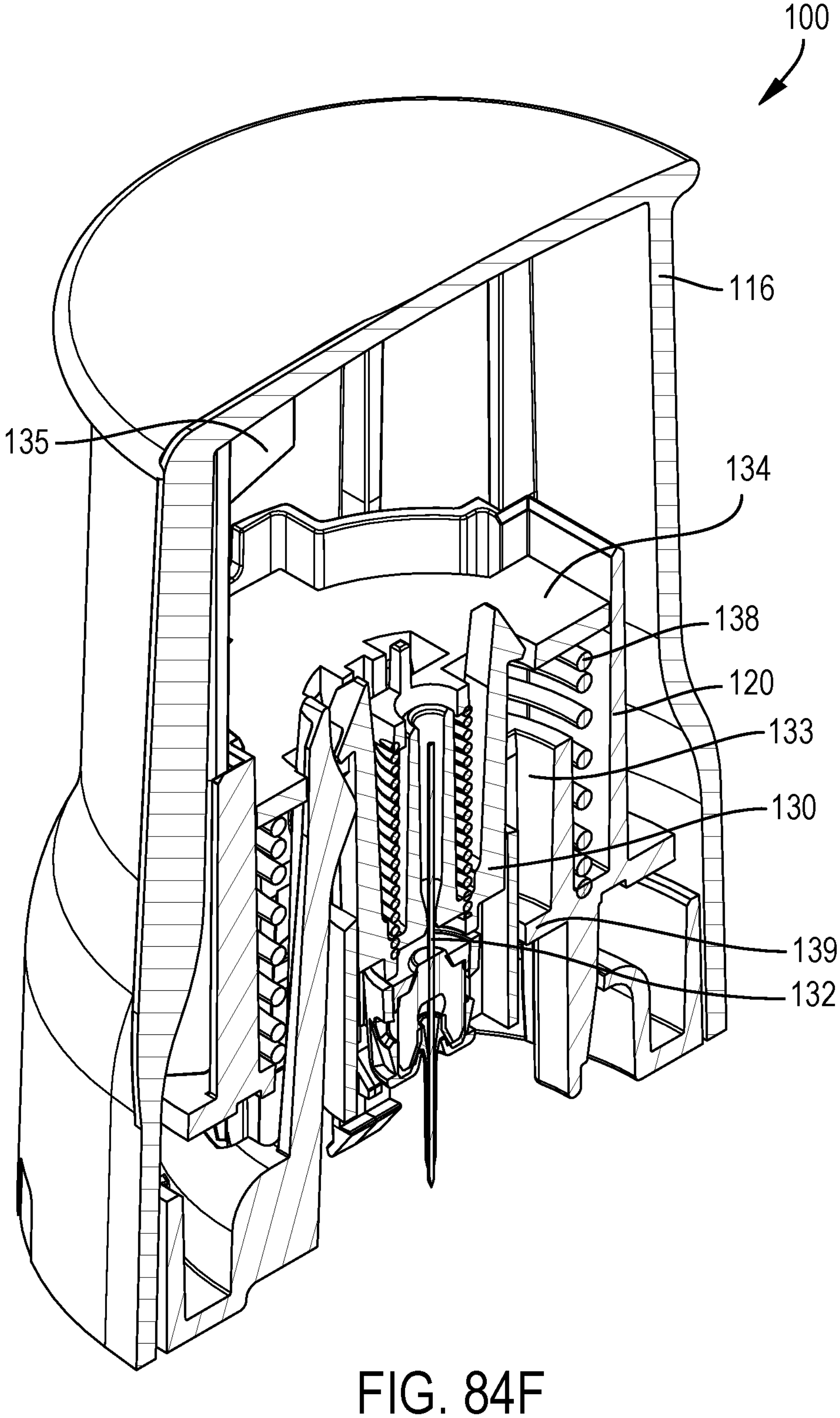
FIG. 84F depicts a cross-sectional view of an example inserter assembly.

Referring now to FIG. 84F, in certain examples, the guard may be a pocket 133 which is defined in the interior housing 116. As the sharp retractor 134 tilts during the retraction stroke, the tip of the insertion sharp 132 may be directed into the pocket 133. In certain examples pockets 133 may include a ledge or shelf 139 at an end thereof which is closest to the open end of the inserter assembly 100. The shelf 139 may obstruct an access pathway to the insertion sharp 132 after the retraction stroke transpires.

Figure 84G:
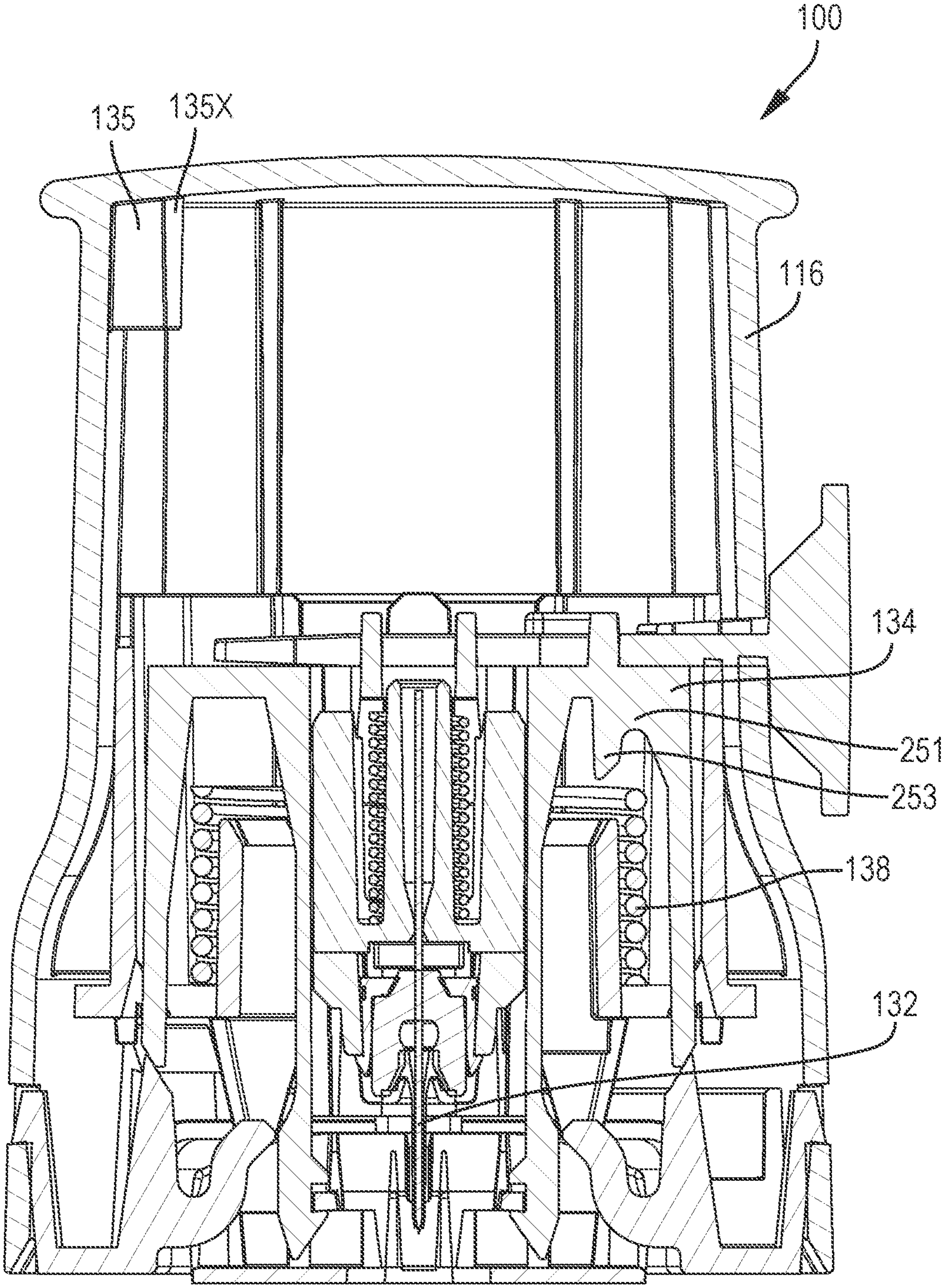
FIG. 84G depicts a cross-sectional view of an example inserter assembly.

In still other embodiments, and referring now also to FIG. 84G, the sharp retractor 134 may include at least one standoff 251. When an inserter assembly 100 with such a standoff 251 is assembled, bias member 138 may be held within the inserter assembly 100 under greater deformation on the portion of the bias member 138 which abuts the standoff 251. The standoff 251 may also include an arm or hook body 253 which may help to retain the bias member 138 in contact with the standoff(s) 251. As the retraction stroke of the sharp retractor 134 occurs, the uneven compression of the bias member 138 (a compression spring in certain examples) afforded by the standoff(s) 251 may assist in tilting the sharp retractor 134 and insertion sharp 132 as further described above. The position of the standoff(s) 251 may further be selected to encourage tilting in a specific direction (e.g. into a guard such as guide channel 137). In the example embodiment shown in FIG. 784G, the standoff(s) 251 may be positioned substantially opposite any tipping projection(s) 135 on the exterior housing 116.

Figure 85:
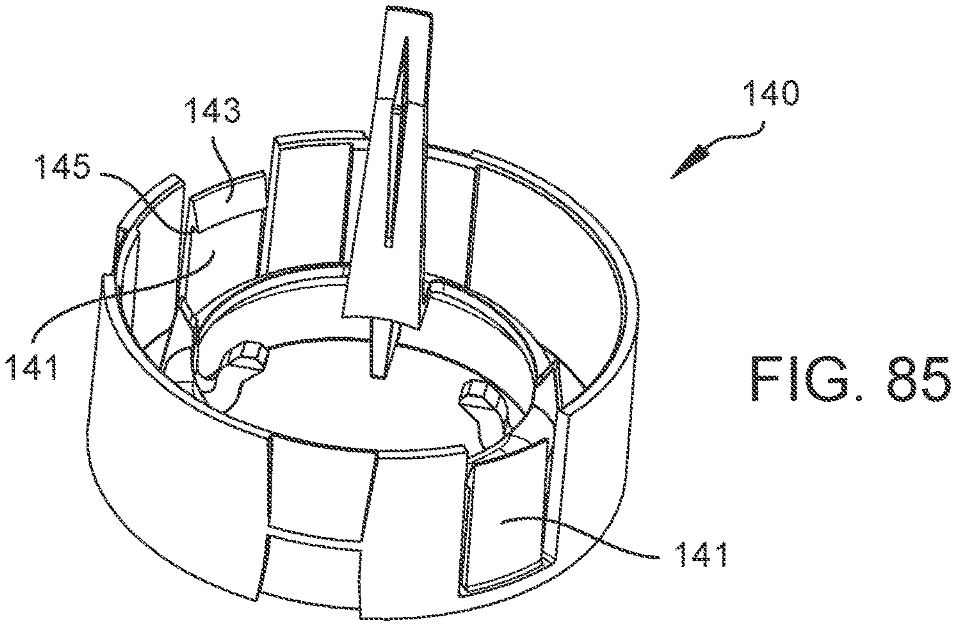
FIG. 85 depicts a perspective view of an example retainer base.
Figure 86:
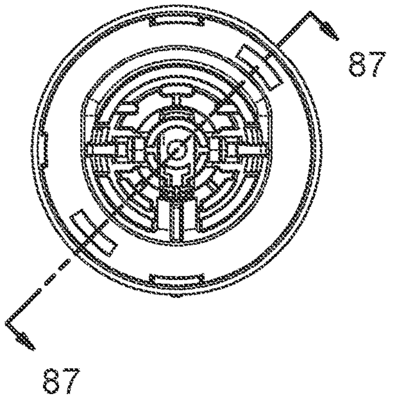
Figure 87:
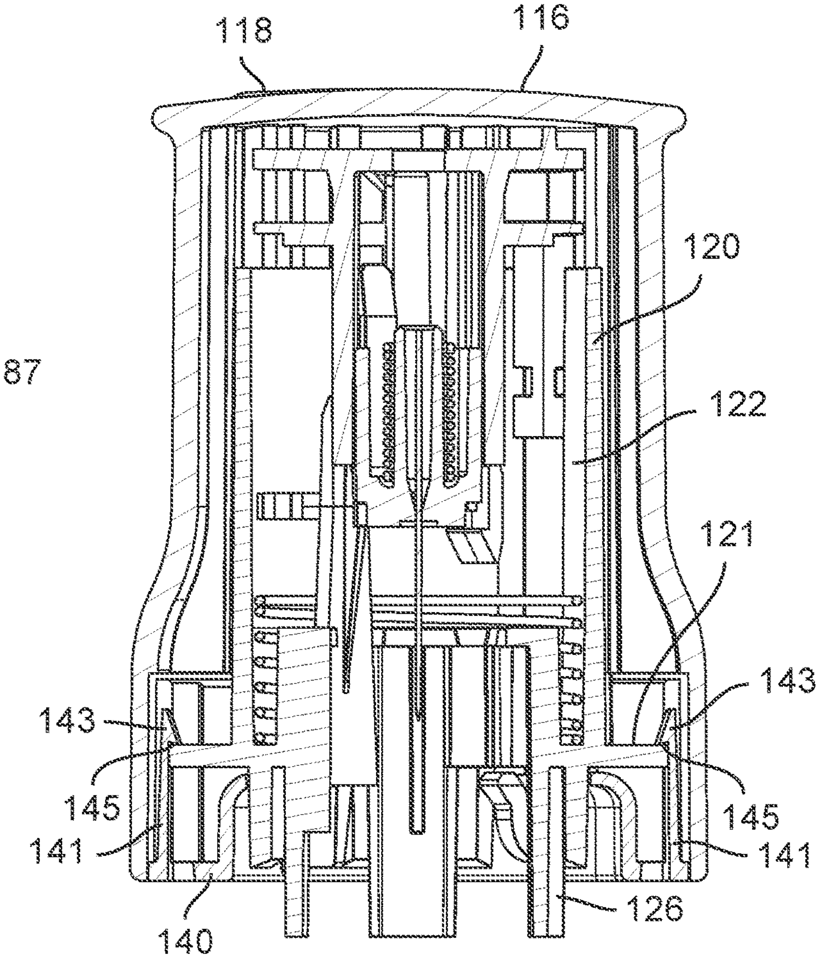

Referring now to FIGS. 85-87, in certain embodiments, after actuation certain components of the inserter assembly 100 may be locked in place. Alternatively, certain components may be prevented from displacement in particular directions or prevented from displacement beyond a predefined distance in particular directions. This may inhibit reuse of the inserter assembly 100 and may aid in protecting a user from unintended finger sticks. Some embodiments of retainer bases 140 may include one or more lock members 141. As shown, two lock members 141 are included though other embodiments, may include a greater or lesser number (e.g. three or four). The lock members 141 in the example embodiment are disposed opposite one another on the retainer base 140.

The exemplary lock members 141 in the example embodiment are depicted as cantilevered lock tabs. Each cantilevered tab includes a protuberance 143 which is disposed on a portion of that lock member 141 most distal to the skin contacting intermediary region 314 (see, e.g., FIG. 69) of the retainer base 140. The protuberance 143 be ramped and may define a ledge region 145. As the exterior housing 116 and the retainer base 140 displace relative to the interior housing 120 during withdrawal of the inserter assembly 100 from the skin 356, a portion of the interior housing 120 may contact ramped portion of the protuberance 143. As shown, the interior housing 120 includes a radial flange 121 which separates the infusion set base interfacing segment 126 of the interior housing 120 from the railed segment 122 (see FIG. 1A) of the interior housing 120. This radial flange 121 may be the portion of the interior housing 120 which contacts the protuberances 143 of the lock members 141. Further relative displacement may cause deflection of the lock members 141 to allow for passage of radial flange 121 of the interior housing 120 passed the protuberance 143. As shown, in FIG. 87, once the radial flange 121 has displaced beyond the protuberances 143, the lock members 141 may resiliently restore back to their unstressed state. In the event that a user presses against the interior housing 120 after actuation, the radial flange 121 may abut against the ledges 145 of the lock members 141 may be unable to further displace into the exterior housing 116. Thus, the interior housing 120 may be constrained after actuation such a portion of the interior housing 120 is held a predefined distance from the tip of the insertion sharp 132. This portion may present an obstruction which may aid in blocking inadvertent contact of the insertion sharp 132 with a user after actuation.

Figure 88A:
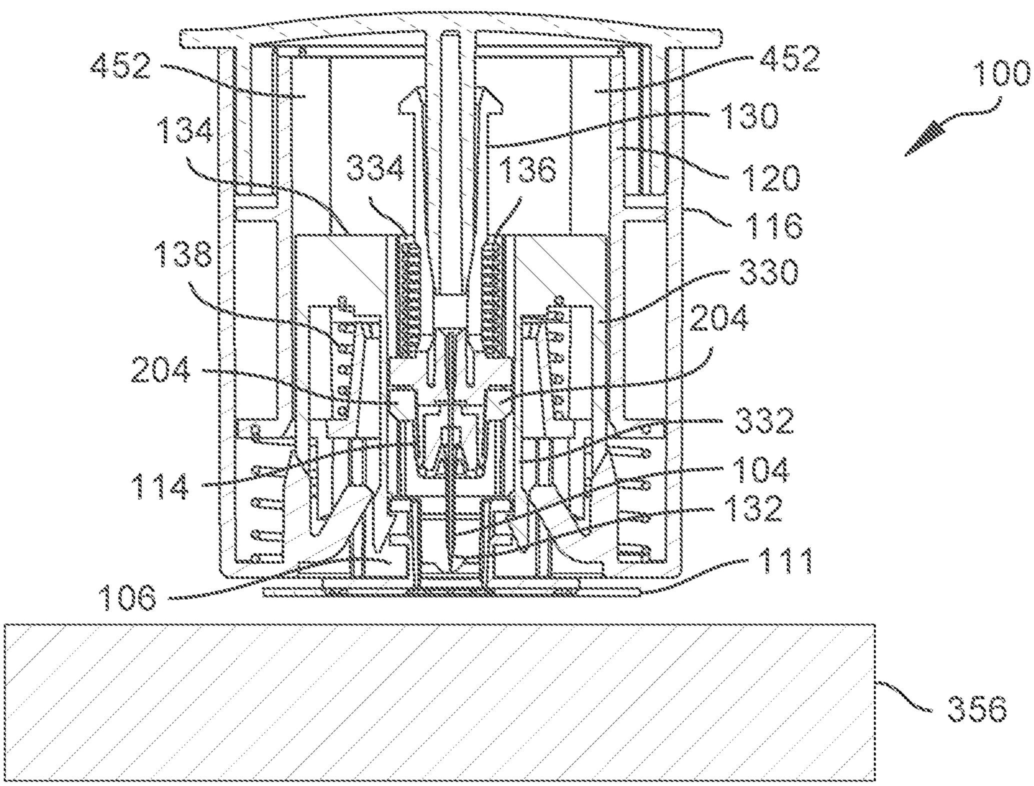
Figure 88B:
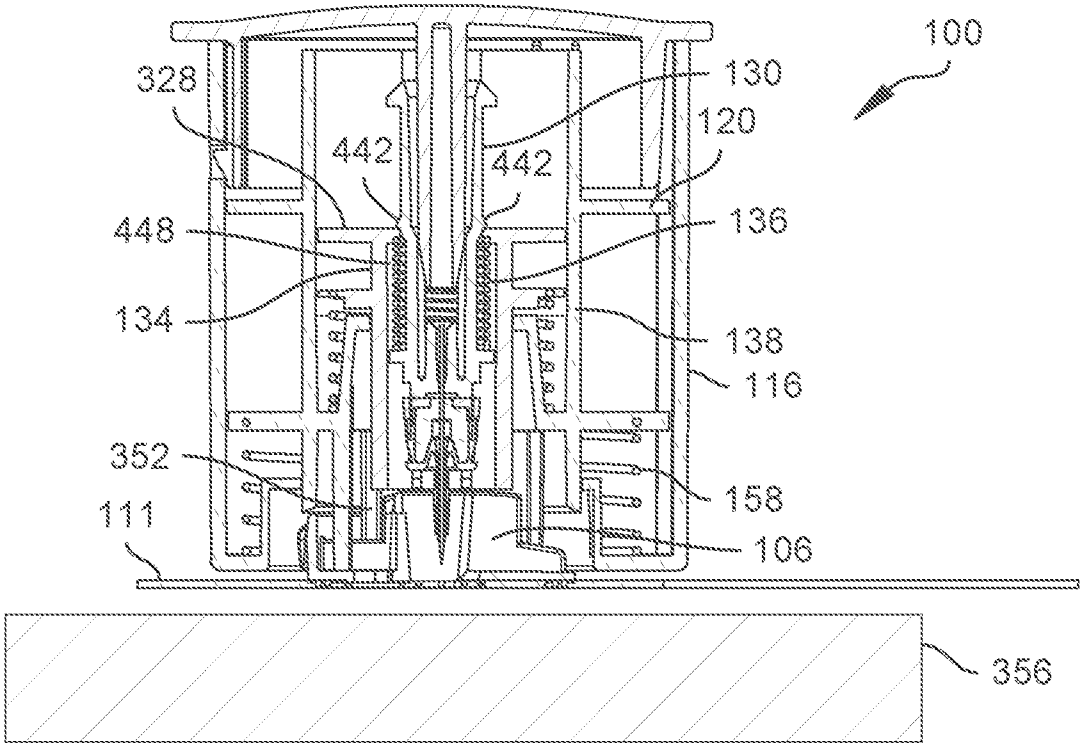

Referring now to FIGS. 88A-88B, two cross-sectional views of the example inserter assembly 100 depicted in FIG. 3 are shown. The inserter assembly 100 is depicted just as it is about to be applied to the skin 356. The adhesive backing 111 may be removed to expose the adhesive on the infusion set base 106. As shown, both springs 136, 138 may be in an energy storing state, which in this particular embodiment is a compressed state. In the example, spring 136 serves as an insertion driving bias member while spring 138 serves as an insertion sharp 132 retraction driving bias member. Spring 136 is held in compression between the insertion sharp holder 130 and the insertion sharp retractor 134 and, when released, drives the sharp holder 130 and components carried there on from a raised state to a forward state. Spring 138 is held in compression between the interior housing 120 and the sharp retractor 134. Upon release, spring 138 drives the sharp retractor 134 and sharp holder 130 from a post insertion state to a retracted state. An additional spring 158 is included in the example embodiment, though is optional. The additional spring 158 may alter the amount of force build up before actuation of the inserter assembly 100 is triggered and may help to remove any mechanical slop which may be present due to tolerancing of various components of the inserter assembly 100.

Referring now also to FIGS. 89A-92, a number of views of a sharp holder 130 and a retainer cap 406 are depicted. The sharp holder 130 may include a bias member receiving shelf 420 against which the spring 136 is held. The shelf 420 may include two projections 422 on a side thereof. The two projections 422 in the example embodiment are rails which are disposed opposite one another on the sharp holder 130.

These rails may ride along guides 354 (see, e.g., FIGS. 93A-93B) on a portion of the sharp retractor 134. The projections 422 may extend from the sharp holder 130 so as to match the width of the cannula subassembly 114 at a plane of the cannula subassembly 114 including the ears 204 of the septum housing 108.

A wall 426 may extend upward from the shelf 420. The exemplary wall 426 shown in FIGS. 89A-C includes interrupted regions which create one or more wall sections 428. The wall sections 428 may be crescent shaped as shown and are separated by an interrupt region formed by a U-shape recess which extends from the top face 430 of the sharp holder 130 nearly to the shelf 420. The recess may extend at least 90-95% or more of a distance extending from the top face 430 to the shelf 420. The recesses may allow deflection of the wall sections 428. The wall sections 428 may be disposed opposite one another on the sharp holder 130 and may be of equal length. In other embodiments, both wall sections 428 may not be identical mirror images. Each of the wall sections 428 may include a protuberance 432 at the end of the wall section 428 opposite the shelf 420. The protuberance 432 has a pileus type shape which generally widens as distance from the shelf 420 decreases. During assembly, this may facilitate installation of the sharp holder 130 into the insertion assembly 100 through the side of the sharp retractor 134 from which the arms 330, 332 (see, e.g. FIG. 88A) extend. A ledge section 434 may be defined by a portion of each of the protuberances 432. At least one of the ledges 434 may extend substantially perpendicular to the wall sections 428. At least one of the ledges 434 may be angled with respect to the wall section 428 on which it is included such that the undercut region has a triangular cross section.

Additionally, each wall section 428 may include a first section 436 and a second section 438. The first section 436 may have a smaller width than the second section 438 and may be the more proximal of the regions to the shelf 420. The first section 436 and second section 438 may be connected by an intermediary region 440. The intermediary region 440 may be angled or curved so as to transition between the differing widths of the first section 436 and second section 438. A nub 442 may be included projecting from the intermediary section 440 or a portion one of the first section 436 and second section 438 adjacent to the intermediary section 440. Though not shown a glue or adhesive supply port similar to port 304 of FIG. 61 may be included.

Figure 90:
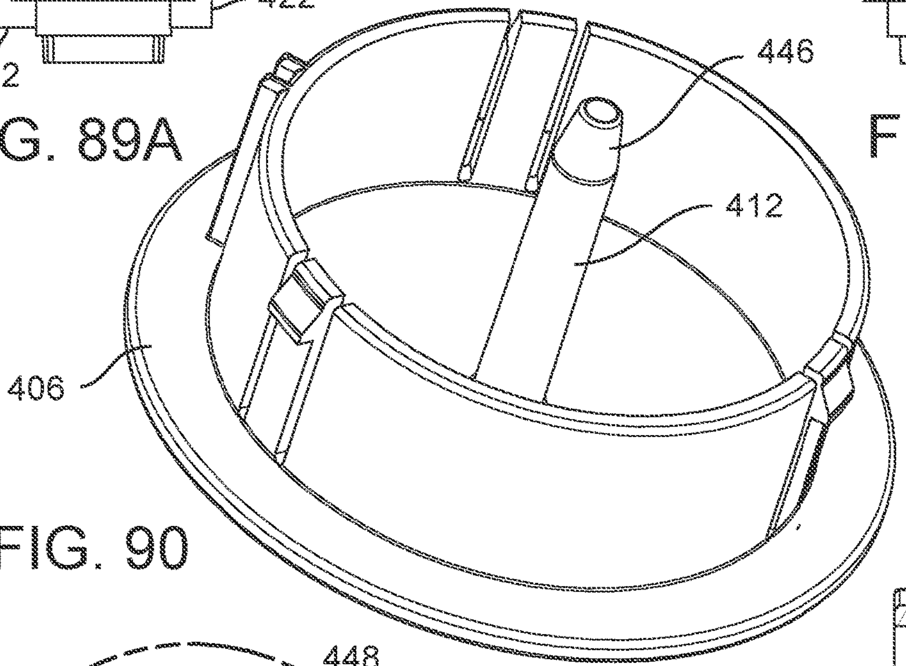
Figure 91:
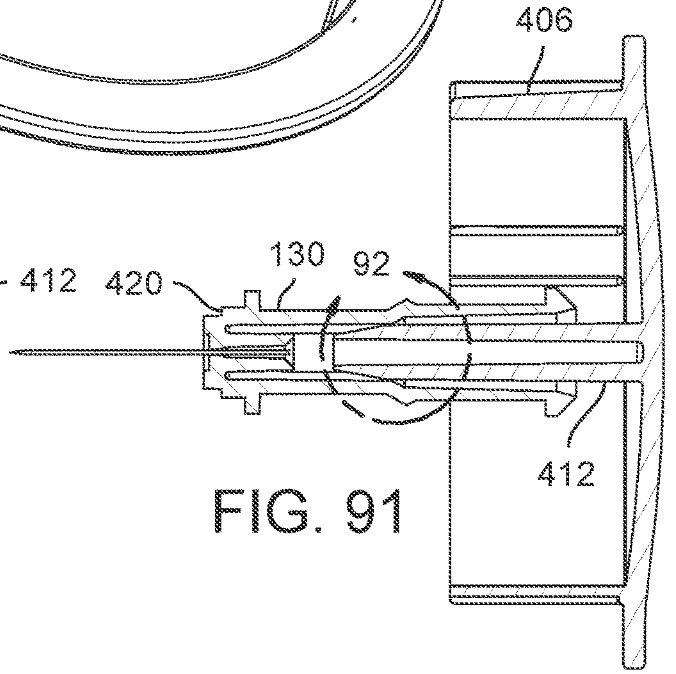
Figure 92:
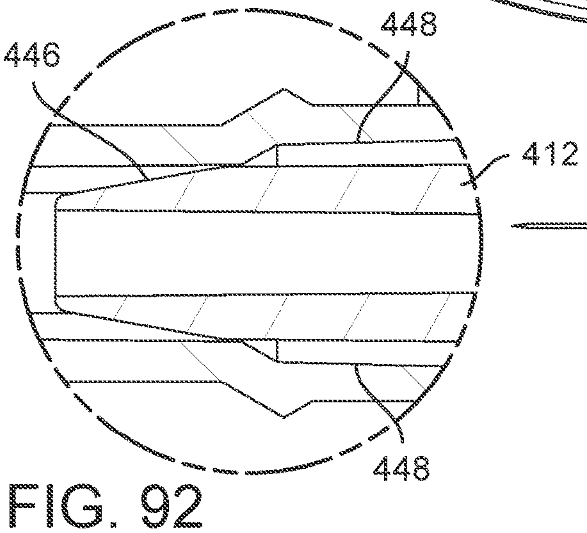

Referring now primarily to FIGS. 90-92, a projection 412, which may be referred to herein as a spreader pin 412, extending from the cap retainer 406 of the insertion assembly 100 may project into a receiving void 444 between the wall sections 428. The spreader pin 412 may include a tapered region 446 on an end thereof and may or may not be hollow. The tapered region 446 may abut into the interior faces 448 of the wall sections 428 as the spreader pin 412 is advanced into the sharp holder 130 beyond a certain distance and may help guide the spreader pin 412 as it is displaced into the sharp holder 130. Further displacement of the spreader pin 412 into the sharp holder 130 may cause the wall sections 428 to be resiliently deflected apart or spread apart from one another thus widening the sharp holder 130 in order to accommodate the spreader pin 412 therein. This may also cause the distance between outward facing surfaces of the nubs 442 to increase when the spreader pin 412 is present.

Figure 93A:
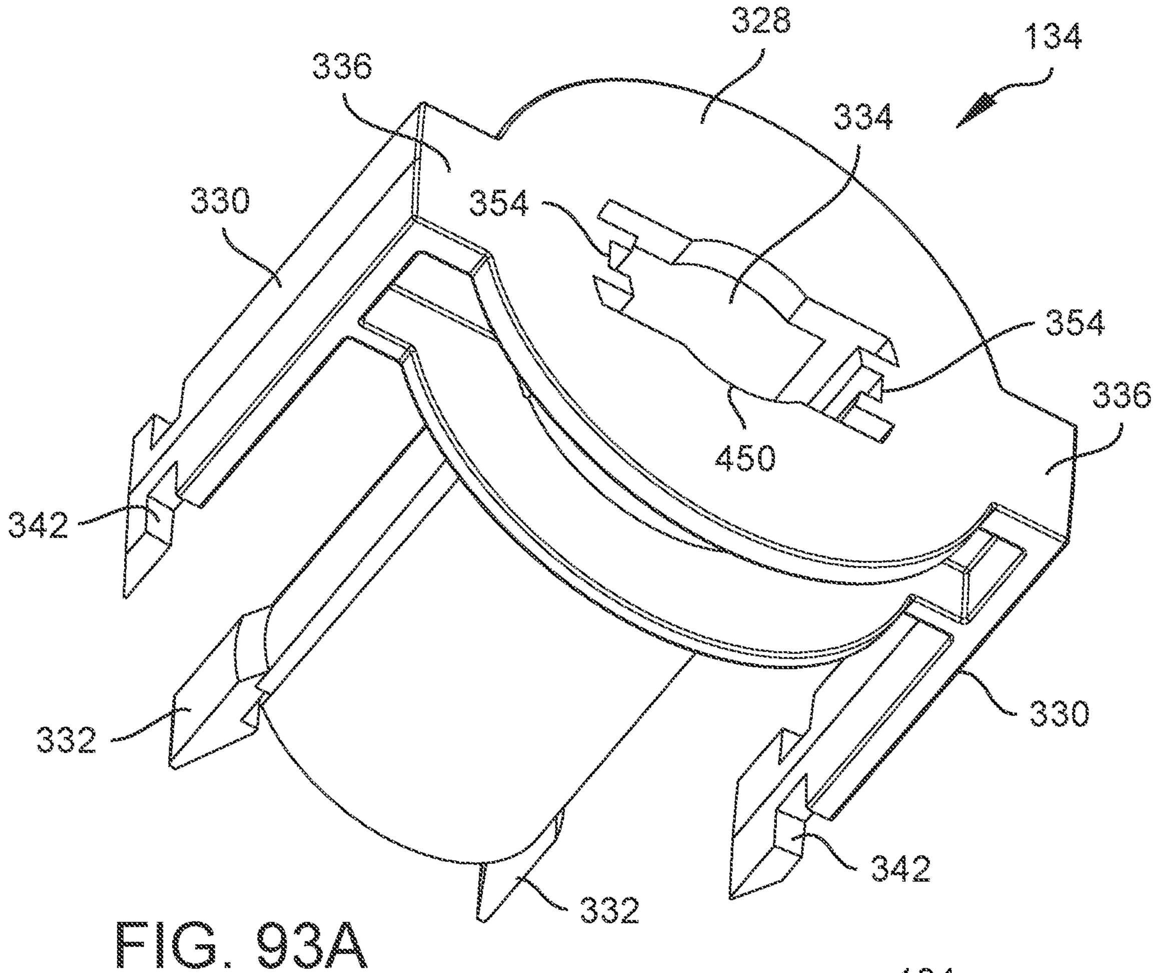
Figure 93B:
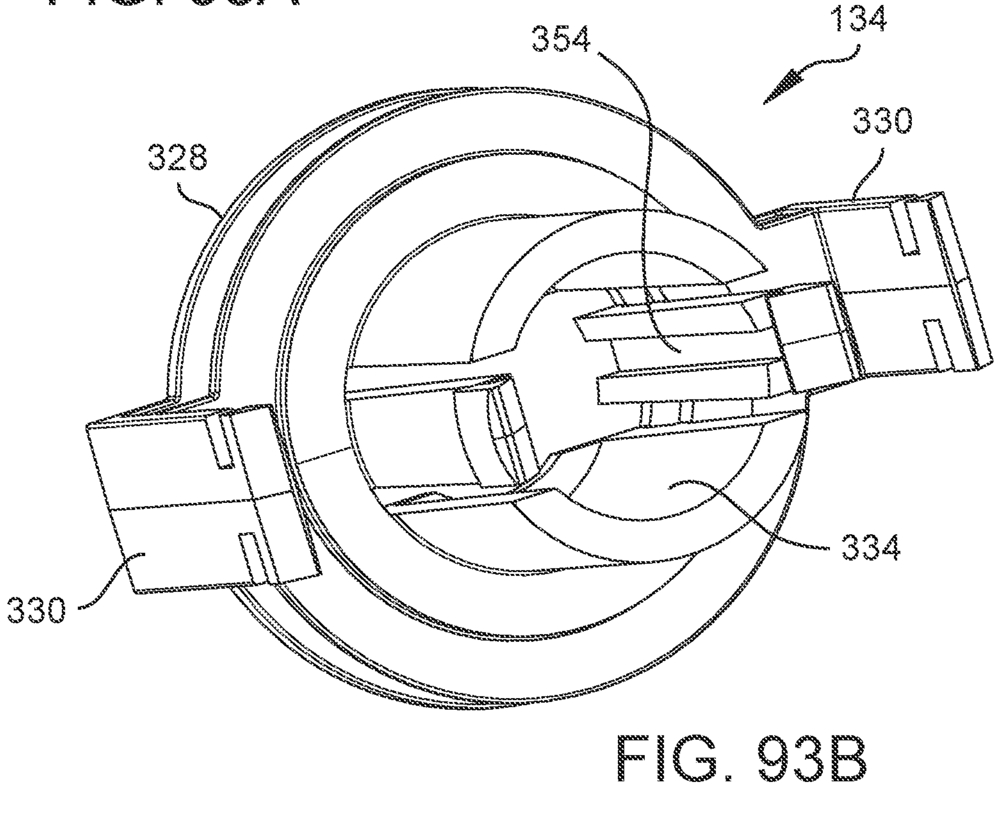

Referring now primarily to FIG. 88B and FIGS. 93A-B, the nubs 442 may interact with another component of the inserter assembly 100 and prevent the force exerted by spring 136 against the shelf 420 from displacing the sharp holder 130 to a forward position. In the example shown, the nubs 442 are sized such that they may not fit into a cavity 334 included in the sharp retractor 134 when the spreader pin 412 is in place within the sharp holder 130. As spring 136 is captured between the shelf 420 of the sharp holder 130 and an interior face of the top plate 328 of the sharp retractor 134, the nubs 442 may inhibit release of energy stored in spring 136.

Still referring to FIGS. 88A-88B in conjunction with FIGS. 93A-93B, spring 138 may be held in an energy storing state by at least one latching engagement as well. As shown, the sharp retractor 134 may include a first set of arms 330 and a second set of arms 332. These arms 330, 332 may be substantially as described above in relation to FIGS. 70A-B. The sharp retractor 134 in this embodiment is depicted as having a symmetric design so as to allow the sharp retractor 134 to be assembled into an inserter assembly 100 in multiple orientations. This may help to simplify assembly. The sharp retractor 134 of FIGS. 70A-70B may also be constructed symmetrically by including voids 322 (see, e.g., FIG. 70C) on opposing sides of the cavity 334.

Each of the one or more notches 342 or the arms 330 may engage with a cooperating projection 344 (see, e.g. FIG. 71) on the interior housing 120. Thus, the interaction of the notch(es) 342 and cooperating projection(s) 344 may maintain the spring 138 under compression and serve as a retraction prevention latch. This may be particularly helpful during assembly. Though notches 342 are shown, the arms 330 and interior housing 120 may engage in other ways as described elsewhere herein.

Again referring now primarily to FIGS. 88A-88B in conjunction with FIGS. 93A-93B, in some embodiments additional latches may be included in an inserter assembly 100 which aid in maintaining one or more of the springs 136, 138 in an energy storing state. In the example embodiment, spring 138 is held in an energy storing state by an additional latch engagement provided by features of the arms 332 interacting with features of the infusion set base 106. This latch arrangement may be similar to as described above in relation to FIGS. 59A-59B. While retained by the arms 332 of the sharp retractor 134, the infusion set base 106 may be held such that surfaces of the infusion set base 106 are adjacent to the standoffs 352. This may prevent the infusion set base 106 and the needle retractor 134 on which it is retained from displacing into the inserter assembly 100 due to the presentation of a mechanical interference by the standoffs 352. As a consequence, the engagement of the arms 332 with the infusion set base 106 may also aid in holding the spring 138 in an energy storing state. The standoffs 352 may also ensure that the infusion set base 106 is positioned within the inserter assembly 100 such that the adhesive 374 may be pressed against the skin 356. In the example, the standoffs 352 ensure that the infusion set base 106 is substantially even with the skin contact face on the retaining base 140. As described elsewhere herein, with the infusion set base 106 so positioned, the infusion set base 106 and/or adhesive liner 111 may also act as a protective barrier.

Still referring primarily to FIGS. 88A-88B, as the retainer pin 412 is withdrawn from the sharp holder 130, the wall sections 428 may restore back to a non-deflected state. This may decrease the distance between the nubs 442 so as to allow passage of the nubs 442 into the cavity 334 in the sharp retractor 134. In turn, this may allow the spring 136 to begin releasing energy and displace the sharp holder 130 toward a forward position. As shown, in FIGS. 88A-88B, the example inserter assembly 100 is configured such that the entire inserter assembly 100 may move as a unit for at least a portion of the inserter assembly 100 withdrawal motion from the body. This may cause the skin 356 to be lifted a certain distance before the retainer pin 412 begins to be withdrawn and actuation is triggered. The amount the skin 356 is lifted or the force applied before portions of the inserter assembly 100 displace relative to one another may be modified as described in relation to the discussion of FIGS. 74A-74B.

In various embodiments, the ledge section 434 of the sharp holder 130 may prevent displacement of the sharp holder 130 beyond a certain amount. Alternatively, the ledge section 434 may be disposed on the sharp holder 130 such that a dwell gap 360 (see, e.g., FIG. 77B) is present after the sharp holder 130 is propelled to the forward position. As described elsewhere herein, a dwell gap 360 may help to ensure the cannula subassembly 114 is firmly retained in the base 106.

In various embodiments, as the sharp holder 130 displaces, the cannula subassembly 114 may be coupled into the infusion set 106 as described elsewhere herein. Additionally, ears 204 of the cannula subassembly 114 may cause the arms 332 to spread apart as the sharp holder 130 is displaced leading to release of the infusion set base 106 from the arms 332. This may release spring 138 and begin retraction of the insertion sharp 132. During retraction, the dwell gap 360 may decrease (if present) until top plate 328 of the sharp retractor 134 contacts the ledges 434 on the sharp holder 130. Once this occurs, the restoring action of spring 138 may begin to displace the sharp holder 130 and insertion sharp 132 affixed thereon along with the sharp retractor 134. This displacement may retract the insertion sharp 132 out of the cannula 104 and the infusion set 102. Once retraction has completed the sharp retractor 134 may be pressed against the exterior housing 116 by spring 138 and the insertion sharp 132 may be housed within the inserter assembly 100 to aid in protecting against unintentional finger sticks or the like. The infusion set 102 may be held in place on the skin 356 with the cannula 104 indwelling in the patient.

Referring now to FIG. 94, another embodiment of an inserter assembly 100 including a manual trigger is depicted. The example inserter assembly 100 includes a button 550 which when displaced may trigger actuation. The button 550 may be included as a separate part which is assembled into the inserter assembly 100. Alternatively, and as shown, the button 550 may be formed monolithically with another portion of the inserter assembly 100. In the example embodiment, the button 550 is formed as a continuous part of the exterior housing 116. In the example embodiment, the button 550 includes an enlarged region that may include a depression 552 which may be substantially centrally located therein. The depression 552 may facilitate interaction with a user's finger. The button 550 may also include a cantilevered beam portion 554 which connects the button 550 to the rest of the exterior housing 116. In the example embodiment, the enlarged portion of the button 550 is disposed at a terminal unsupported end of the cantilevered beam portion 554, though may be located anywhere along the length of the cantilevered beam portion 554 in other embodiments. The cantilevered beam 554 extends in a direction substantially parallel to the longitudinal axis of the inserter assembly 100 and toward the top of the inserter assembly 100 in the example embodiment. In other embodiments, the cantilevered beam section 554 may extend in any direction. The cantilevered beam portion 554 may include a curvature which matches that of the exterior housing 116. A gap 556 surrounding the button 550 may be included to provide clearance for displacement or deflection of the button 550 during use. During actuation, the button 550 may be displaced at least partially into the inserter assembly 100 to trigger the insertion.

In some embodiments, the button 550 may not include a cantilevered beam section 554 and may instead be formed as a strip of material defined by cutouts flanking both sides of the strip. The enlarged section may be placed at or near the center of the strip. The strip may be deflected inward toward the inside of the inserter assembly 100 with application of pressure to trigger the insertion.

Figure 89A:
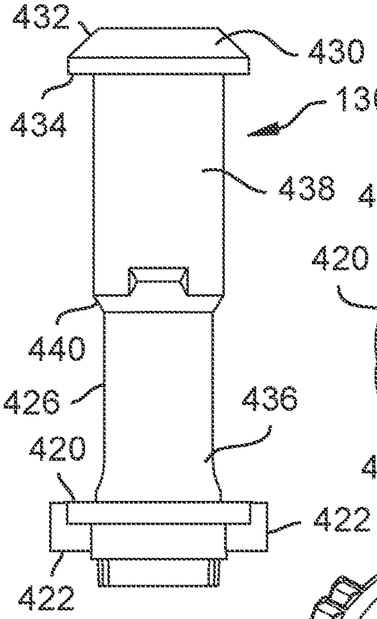
Figure 89B:
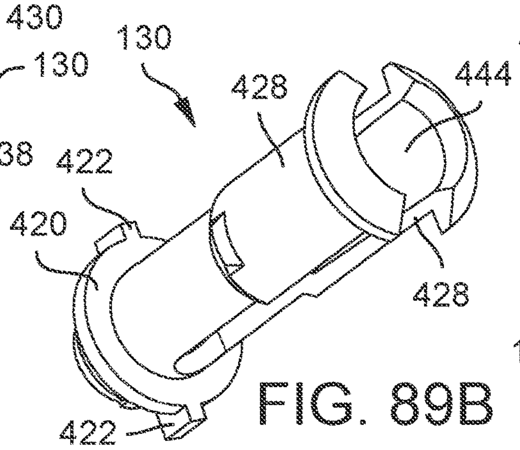
Figure 89C:
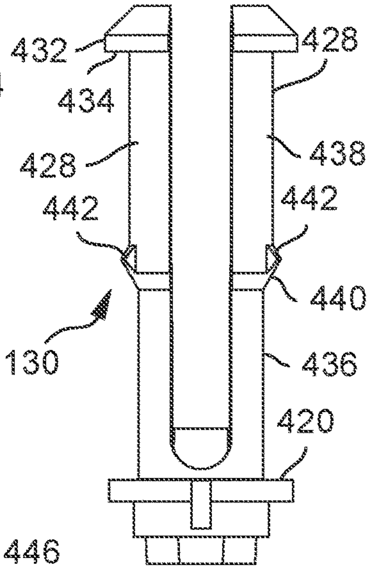

Referring now also to FIGS. 95A-95C and FIG. 96, an interlock may be included which prevents the button 550 from actuating the inserter assembly 100 until the skin has been displaced or until relative movement beyond a threshold magnitude has occurred. As shown, the button 550 may include a protuberance 558 (best shown in FIG. 96) on an inward face thereof. The protuberance 558 may be disposed opposite the depression 552 of the enlarged region of the button 550 as shown. In an initial state, the protuberance 558 may be out of alignment with a sled member 560 as shown in FIG. 89B for example. As the inserter assembly 100 is withdrawn from the body, the skin is lifted, and relative displacement of portions of the inserter assembly 100 occurs, the protuberance 558 may be brought into alignment with the sled 560. At this point, portions of the inserter assembly 100 may be disposed similarly to as shown in FIG. 75B. Once in the aligned state, the button 550 may be displaced so as to come into contact with the sled 560. Button 550 displacement may then drive the sled 560 into the protuberance 300 disposed at the terminal end of a cantilevered arm 296 on the sharp holder 130. As the sled 560 continues to advance, the protuberance 300 may be displaced off the catch 306 freeing bias member 136.

Referring primarily to FIGS. 96-99, in the initial state, the sled 560 may be may be disposed within a receiving void 564 included in the interior housing 120. The sled 560 may have a curved wall 566 which is substantially flush with the exterior face of the interior housing 120 in the initial state. As shown, the receiving void 564 is shaped so as to receive the protuberance 558 of the button 550. In the example embodiment, the protuberance 558 is cruciform in shape and the receiving void 564 mimics this shape. Until the inserter assembly 100 is in the aligned state, the wall of the interior housing 120 presents a mechanical interference which prevents the button 550 from being depressed. Once in the aligned state, the protuberance 558 may pass into the receiving void 564 and into the sled 560. Though a cruciform shape is used, any other type of shape may be used. For example, a star or asterisk type shape may be used in alternative embodiments. As shown best in FIG. 96, the shape chosen may include a ramped portion or portions which extend substantially parallel to the longitudinal axis of the inserter assembly 100. This may allow for increased tolerancing on the sled 560 and protuberance 558 and aid in ensuring smooth operation as the inserter assembly 100 is withdrawn from the body.

Referring primarily to FIGS. 99-100, the sled 560 may include a cantilevered member 568 including a sled protuberance 570 at a terminal unsupported end thereof. The cantilevered member 568 may be included within an actuation projection 576 of the sled 560. The sled protuberance 570 may form a ledge 572 which may catch on a component of the inserter assembly 100 to retain the sled 560 within the inserter assembly 100. As shown, the top plate 328 of the sharp retractor 134 includes a bridge 574. The bridge 574 forms an underpass which is in line with the receiving void 564 of the interior housing 120 when the inserter assembly 100 is assembled. During assembly, the sled 560 may be passed through the receiving void 564 and an actuating projection 576 of may travel through the underpass formed by the bridge 574. The ledge 572 of the cantilevered member 568 may catch on a surface of the bridge 574 retaining the sled 560 within the inserter assembly 100. The sled protuberance 570 on the cantilevered member 568 may be ramped so as to facilitate deflection of the cantilevered member 568 around the bridge 574 during installation of the sled 560. The bridge 574 may also act as a guide providing a displacement channel for the sled 560 as the sled 560 is driven into the protuberance 300 of the cantilevered arm 296.

Referring now also to FIG. 101, in some embodiments, a button 550 may not be included, however, a section of the exterior housing 116 may be deformable. In the example shown in FIG. 101, the exterior housing 116 includes a deformable region 580 including a protuberance 558 thereon. The deformable region 580 may be coupled to (e.g. over molded onto or otherwise adhered) the exterior housing 116 in certain examples. In embodiments including a deformable region, once the inserter assembly 100 is in an aligned state, a user may squeeze the exterior housing 116 at the deformable region 580 to drive the protuberance 558 into the sled 560 (see, e.g., FIG. 99) to trigger actuation.

In some embodiments, and referring now to FIG. 102, the interior face of the exterior housing 116 may include a protuberance 558. No button 550 or deformable region 580 may be included. During the withdrawal action of the inserter assembly 100 from the body, relative displacement of components of the inserter assembly 100 may automatically trigger the inserter assembly 100. The relative displacement may bring the protuberance 558 into contact with the sled 560 (see, e.g., FIG. 99) and drive the sled into 560 the protuberance 300 (see, e.g. FIG. 95B) on the cantilevered arm 296 (see, e.g. FIG. 95B) which may then be displaced off the catch 306 (see, e.g. FIG. 95B) freeing bias member 136 (see, e.g. FIG. 95B). The interior housing 120 may include an appropriately sized channel which accommodates the protuberance 558.

Referring now to FIG. 103, a flowchart 450 depicting a number of exemplary actions which may be executed to assemble an inserter assembly 100 such as that depicted in FIG. 59A-59B is shown. In block 452, a first bias member such as spring 136 may be placed into a cavity 334 in a sharp retractor 134. A cannula subassembly 114 may be placed on a sharp 132 attached to a sharp holder 130 in block 454. The sharp holder 130 may be placed into a sharp retractor 134 cavity 334 in block 456. In block 458, the sharp holder 130 may be latched into a position where the first bias member is in an energy storing state. This may be a compressed state in various examples. A second bias member such as spring 138 may be sandwiched between the sharp retractor 134 and an interior housing 120 in block 460. The sharp retractor 134 may be latched in a position in which the second bias member is in an energy storing state in block 462. This may be a compressed state in various embodiments. In block 464, a casing (which may be formed of an exterior housing 116 and retainer base 140) may be coupled together around the interior housing 120. An infusion set base 106 may be releasably coupled to the sharp retractor 134 in block 466. A lock member 146 may be installed into the inserter assembly 100 in block 468. As mentioned elsewhere herein the lock member 146 may be welded to the adhesive liner 111 coving adhesive on the infusion set base 106 in certain embodiments. During assembly of the components, any rails, guides, keyed features, fingers etc. included on a component may be aligned with cooperating features of the components in which they are being placed. Latching together of the various components of the inserter assembly 100 may simplify assembly of the inserter assembly 100 as the components may hold themselves in the proper orientation or position against any spring bias. Thus an assembler (human or robotic) may simply bring components into latching engagement with one another and be able to release the components thereafter. This may allow partially assembled portions of inserter assemblies 100 to be moved about a production facility or shipped to other facilities and may simplify any fixturing used during assembly.

Referring now to FIG. 104, a flowchart 600 depicting a number of example actions which may be executed to place a patient care assembly on a biological barrier with an example inserter assembly 100 (further described in relation to FIG. 105) is shown. As shown in FIG. 104, in block 602, an adhesive liner or backing 111 may be removed from a care assembly base (e.g. infusion set base 102 of FIG. 4A) retained within the inserter assembly 100. The inserter assembly 100 may then be placed on a desired site on a biological barrier (e.g. skin 356 shown in FIG. 109A for example) in block 604. This may cause the adhesive on the base to stick to the biological barrier. A lock member 146 (see, e.g., FIG. 56A) may be removed from the inserter assembly 100 in block 606. The inserter assembly 100 may begin to be removed from the body in block 608. Actuation of the inserter assembly 100 may be triggered as the inserter assembly 100 is removed and may not occur until the barrier has been lifted some distance from its normal, resting state. This may provide a number of benefits further described elsewhere herein (see, e.g., discussion of FIG. 57).

In block 610, the biological barrier may be lifted from a resting or relaxed state via the adhesion of the adhesive. A casing of the inserter assembly 100 may also be displaced from an initial position to a triggered position in block 610. In various examples, the adhesion of the base to the barrier may cause certain components (e.g. at least one component coupled to the base) to be restricted in their displacement as the user withdraws the inserter assembly 100. Such components may be anchored to the barrier via the adhesive and unable to move relative to the barrier. Thus, the barrier may be lifted as the user pulls the inserter assembly 100 away from the barrier. In some embodiments, all components aside from the casing may be anchored to the barrier via the adhesive. The casing may be displaced from the initial position to the trigger position relative to the anchored components.

An insertion latch arrangement may preclude actuation of the inserter assembly 100 when the insertion latch arrangement is in an engaged state. The insertion latch arrangement may be restricted in its displacement relative to the barrier and may block movement of the casing from the initial position to the triggered position. For example, at least one portion of the insertion latch arrangement (see, e.g., flared end regions 2242 of cantilevered arms 2240 described in relation to FIG. 114A) may be disposed in the path of a section of the casing (see, e.g., trigger protrusions 2241 described in relation to FIG. 114A) as the casing is displaced to the triggered position. As the removal of the inserter assembly 100 from the barrier proceeds, the lifted barrier may have an elasticity which pulls the components coupled to the base toward the resting position of the barrier. The user may pull the casing in a direction away from the barrier. Thus, force may be exerted on the insertion latch arrangement as the inserter assembly 100 is removed from the barrier. Once this force reaches a threshold disengagement force, the insertion latch arrangement may be transitioned to a disengaged state as noted in block 612. In certain examples, the insertion latch arrangement may be disengaged when one or more deflectable members (see, e.g., cantilevered arms 2240 described in relation to FIG. 114A) are deflected by the casing such that a ledge defined on each member is displaced off of a catch.

Still referring to FIG. 104, in block 614, an insertion unit of the inserter assembly 100 may be displaced in an insertion direction. The insertion unit may be associated with a bias member such that the insertion unit is spring biased to displace in the insertion direction once the insertion latch arrangement is transitioned to the disengaged state. The insertion latch arrangement may maintain the bias member in a distorted state and the insertion unit may be advanced in the insertion direction when the bias member is freed to restore to a less distorted state. An access assembly which may couple to the base (see block 620) may be displaced in the insertion direction with the insertion unit.

A retraction latch arrangement may be released in block 616 and a retraction unit may be displaced in a retraction direction in block 618. The retraction direction in which the retraction unit is displaced in block 618 may be opposite the insertion direction. The retraction unit may be associated with a bias member such that the retraction unit is spring biased to displace in the retraction direction once the retraction latch arrangement is transitioned to the released state. The retraction unit may, for example, include an insertion sharp 132 and a sharp shuttle 2130 such as those described in relation to FIG. 116B. The insertion sharp 132 may extend through the access assembly prior to displacement of the retraction unit in the retraction direction.

In certain embodiments, the retraction unit may displace in the insertion direction as the insertion unit is displaced in the insertion direction in block 614. Thus, the retraction unit may be referred to as a portion of the insertion unit herein. The retraction unit may be coupled to a body (see, e.g., trigger body 2002 of FIG. 115B) of the insertion unit by the retraction latch arrangement. As the insertion unit is advanced in the insertion direction, the retraction latch arrangement may be driven into a release trigger (see, e.g., trigger protrusion 2283 described in relation to FIG. 116B) which may cause disengagement of the retraction latch arrangement noted in block 616. The retraction latch arrangement may, in some embodiments, be disengaged when the insertion unit reaches a retraction release position as the insertion unit displaces along a displacement path in the insertion direction. In some embodiments, the insertion unit (or a portion of the insertion unit not including the retraction unit if the retraction unit is considered part of the insertion unit) may continue to displace in the insertion direction while the retraction unit is displaced in the retraction direction. Thus the access assembly may be displaced in the insertion direction simultaneously with an insertion sharp 132 being displaced in a retraction direction (further described in relation to FIG. 115A).

Still referring to FIG. 104, an access assembly may be coupled to the care assembly base and the base may be released from a retainer (see, e.g., retainer arms 2282 described in relation to FIG. 115A) of the inserter assembly 100 in block 620. Removal of the inserter assembly 100 from the barrier may be completed in block 622. With the removal of the inserter assembly 100 completed, the care assembly may be fully assembled and in place on the barrier. In examples where the patient care assembly is an infusion set 102, a cannula 104 may be in place in the subcutaneous layer of a patient's skin.

Referring now to FIG. 105, an exploded view of an embodiment of an example inserter assembly 100 is depicted. As with other inserter assemblies 100 described herein, the example inserter assembly 100 shown in FIG. 105 may be used to place an infusion set 102 onto the body of a patient. Inserter assemblies 100 such as that shown in FIG. 105 may be used to place other patient care assemblies onto a patient. Various transcutaneous access assemblies including delivery devices, physiological monitors, analyte sensor, interstitial fluid monitors, blood sugar monitors, continuous glucose monitors, etc. may be placed with an inserter assembly 100. In the example shown in FIG. 105, the inserter assembly 100 includes an infusion set 102 for purposes of example. The infusion set 102 is shown in a partially disassembled state with an infusion set base 106 (e.g. any of those shown or described herein) and cannula subassembly 114 (e.g. any of those shown or described herein) which may be coupled together during actuation of the inserter assembly 100. An adhering assembly (see, e.g. FIGS. 43-45) may also be included.

Exemplary inserter assemblies 100 such as that shown in FIG. 105 may include an exterior housing 2116. The exterior housing 2116 may enclose various components of the inserter assembly 100 and serve as the portion of the inserter assembly 100 which the user grips during operation. Inserter assemblies 100 may also include a bias member retainer 2000. The bias member retainer 2000 may be disposed within and adjacent the closed end of the exterior housing 2116 when the inserter assembly 100 is assembled. A first bias member 2136 (e.g. compression spring) may seat into a portion of the bias member retainer 2000 during assembly.

Various example inserter assemblies 100 may further include a sharp shuttle 2130 to which an insertion sharp 132 may be coupled. The insertion sharp 132 may be glued or otherwise bonded or affixed into the sharp shuttle 2130 so as to be fixedly located relative to the sharp shuttle 2130. Any suitable type of sharp 132 may be used. A trigger body 2002 and a second bias member 2138 may also be included in example inserter assemblies 100. When assembled and in a storage state, the second bias member 2138 may be captured between the sharp shuttle 2130 and the trigger body 2002. The insertion sharp 132 may extend through the trigger body 2002 and the cannula subassembly 114 may be carried on a portion of the insertion sharp 132 which projects through the trigger body 2002. A care assembly base holder 2004 may also be included in various inserter assemblies 100. In various examples the care assembly base holder 2004 is an infusion set base holder and may be referred to as a set base holder.

A retainer base 2140 may serve to couple to a bottom portion of the inserter assembly 100 to hold various components within the inserter assembly 100. In the example, the retainer base 2140 includes retaining interfaces 2142 which may snap into engagement with retention ledges 2144 defined in the exterior housing 2116. Other couplings are also possible such as a bayonet mount, interference fit, snap fit, adhesive, glue, threads, solvent bonding, welding, etc. When coupled together, the exterior housing 2116 and retainer base 2140 may form a casing of the inserter assembly 100. The retainer base 2140 may also include a number of projections 352 (further described in relation to FIG. 1A) which may assist in retention of an infusion set base 106 within the inserter assembly 100. The interior sidewalls of the retainer base 2140 may also include a number of ribs, bumpers, or the like which may assist in maintaining an infusion set base 106 in a prescribed position within the inserter assembly 100. The retainer base 2140 may define a portion of a trigger arrangement for the inserter assembly 100. The retainer base 2140 may, for example, include trigger protrusions 2241 which are disposed in opposition to one another on the interior sidewalls of the retainer base 2140.

As will be further described later in the specification, various latch arrangements may be included in the inserter assembly 100 and may maintain bias members 2136, 2138 in a distorted state prior to actuation. When free to move, bias member 2136 may displace the trigger body 2002 and sharp shuttle 2130 as well as components retained thereon to complete the insertion of the cannula 104 into the patient and install the infusion set 102 onto an infusion site. Retraction of the insertion sharp 132 into the inserter assembly 100 may also occur as part of the actuation due to disengagement of a latch arrangement. Bias member 2138 may urge the sharp shuttle 2130 and insertion sharp 132 to a retracted, and optionally tilted state, where the sharp 132 is pulled out of the infusion set 102 and blocked from inadvertent contact with a user.

Upon removal of an inserter assembly 100 from a package by a user, example inserter assemblies 100 may be provided with a lock member 146. Portions of the lock member 146 may be inserted through fenestrations 2148 in the exterior housing 2116 to prevent actuation of the inserter assembly 100. In various examples, actuation may be triggered by movement of the casing of the inserter assembly 100 relative to other components of the inserter assembly 100. Example lock members 146 may mechanically inhibit displacement of the casing relative to the rest of the inserter assembly 100 and thus prevent actuation of the inserter assembly 100.

Referring now to FIG. 106 and FIG. 107, an example lock member 146 and cross-sectional view of the inserter assembly 100 of FIG. 105 are respectively shown. The example inserter assembly 100 is depicted locked in the storage state. As shown, the lock member 146 may include a main body 2006 from which a set of arms 2008 project. The main body 2006 may be disposed external to the exterior housing 2116 and the arms 2008 may project through the fenestrations 2148 (see, e.g., FIG. 105) of the exterior housing 2116. The arms 2008 may include a slot 2010 extending along the axis of each arm 2008. The slots 2010 may allow adjacent portions of the arms to deflect when the lock member 146 is installed in the inserter assembly 100. When deflected, the arms 2008 may exert pressure against the walls of the fenestrations 2148 and may aid in frictionally retaining the lock member 146 in place within the inserter assembly 100.

The trigger body 2002 may include an elongate section such as a barrel 2226 which may include a shelf 2014. The shelf 2014 may be formed by a stepwise change in the width of the barrel 2226. When the inserter assembly 100 is in the storage state, the shelf 2014 may be aligned with the fenestrations 2148 in the exterior housing 2116. When the lock member 146 is installed, the arms 2008 of the lock member 146 may project between the shelf 2014 and a flange 2220 extending radially from the barrel 2226. Thus, movement of the trigger body 2002 in either direction along the axis of the inserter assembly 100 may be blocked by the arms 2008. The inserter assembly 100 may thus, be locked together such that the entire inserter assembly 100 may displace in unison. This may preclude actuation of the inserter assembly 100.

Referring now to FIG. 108, a top down view of the inserter assembly 100 of FIG. 105 is shown with a first and second cut plane superimposed thereon. The first cut plane is labeled A-A. The second cut plane is labeled B-B. This figure is provided for reference purposes in relation to a number of the forthcoming figures. Several of these figures are cross-sectional views of the inserter assembly 100 taken at the location of one or the other of these planes and depict the inserter assembly 100 in various stages of operation. Unless described otherwise, where one of the following inserter assembly 100 cross-sections is given with a figure numeral followed with the letter A, the figure is depicting a cross-section of the FIG. 105 inserter assembly 100 at the location of plane A-A. Where one of the following inserter assembly 100 cross-sections is given with a figure numeral followed with the letter B, the figure is depicting a cross-section of the FIG. 105 inserter assembly 100 at the location of plane B-B.

Referring now to FIGS. 109A-109B, cross-sectional views of an example inserter assembly 100 of FIG. 105 depicted in a ready state with the lock member 146 (see, e.g., FIG. 106) removed are shown. The inserter assembly 100 has been placed on a biological barrier in the depiction shown in FIGS. 109A-109B. In the example shown, the inserter assembly 100 has been placed on skin 356 at an infusion site such that an adhesive patch 614 affixed to the infusion set base 106 is in adhering relationship with the skin 356. Each of bias members 2136, 2138 are depicted in an energy storing state, which in this particular embodiment is a compressed state. In the example, bias member 2136 serves as an insertion driving bias member while bias member 2138 serves as an insertion sharp retraction driving bias member. Bias member 2136 is held in a distorted state between the bias member retainer 2000 and the trigger body 2002. Upon release of bias member 2136 from the energy storing state, the bias member 2136 may relax and urge the trigger body 2002 and components carried thereon from a raised state toward a forward state. Bias member 2138 is held in a distorted state between the sharp shuttle 2130 and the trigger body 2002. When freed, bias member 2138 may propel the sharp shuttle 2130 to a retracted, and in the example embodiment, tilted state.

Referring now to FIG. 110, a perspective view of the example sharp shuttle 2130 of the example inserter assembly 100 of FIG. 105 is depicted. As shown, the sharp shuttle 2130 includes a flange 2200. The flange 2200 includes a set (only one visible in FIG. 110) of guide passages 2202 which extend therethrough. A wall 2204 raised from a first face of the flange 2200 is present around the periphery of the flange 2200. The wall 2204 includes an extended section 2206 which extends a greater distance from the first face of the flange 2200 than other portions of the wall 2204. The extended section 2206 may act as a tipping projection as will be described later in the specification. A stem body 2208 may extend from a central region of a second face of the flange 2200 opposite the first face. The stem body 2208 may be hollow in various examples. As shown in the example embodiment, the insertion sharp 132 may extend from an end of the stem 2208 opposite the flange 2200. The insertion sharp 132 and sharp shuttle 2130 may be coupled together in any suitable manner (e.g. via adhesive). A set of arms 2210 which flank the stem body 2208 may also project from the second face of the flange 2200 of certain sharp shuttles 2130. The arms 2210 may be cantilevered and include protuberances 2212 on their unsupported ends. Each protuberance 2212 may define a ledge 2214 at an end thereof.

Referring now to FIGS. 111A-111B, views of the exemplary trigger body 2002 of the inserter assembly 100 of FIG. 105 are depicted. Example trigger bodies 2002 may include a trigger body flange 2220. Trigger body flanges 2220 may include a set of apertures 2222 which may extend through the trigger body flange 2220. A set of guide projections 2224 which may extend from a first face of the trigger body flange 2220 may also be included. A wall 2218 surrounding a central portion of the first face of the trigger body flange 2220 may extend from the first face. A barrel 2226 may project from a central region of a second face of the trigger body flange 2220 opposite the first face. The barrel 2226 may include a set of vane members 2228 which extend along the length of the barrel 2226. The vane members 2228 may alter in width in stepwise fashion to provide the shelf 2014 which cooperates with the lock member 146 (see, e.g., FIG. 107) to inhibit actuation of the inserter assembly 100. A number of outcropped regions 2230 may also be included on the exterior side wall of the barrel 2226. The outcropped regions 2230 in the example embodiment are ramped bodies which include a catch ledge 2232 on a portion thereof most distal to the trigger body flange 2220. The terminal end 2234 of the barrel 2226 opposite the trigger body flange 2220 may be closed with the exception of a small orifice 2236 sized to allow passage of the insertion sharp 132. The barrel 2226 may be hollow and the interior face of the terminal end 2234 of the barrel 2226 may include a locating projection 2238.

A set of cantilevered trigger arms 2240 may flank the barrel 2226 and may be positioned abreast of the vane members 2228. The cantilevered arms 2240 may include flared end regions 2242 at their unsupported ends which are angled so as to increase in distance from the barrel 2226 as distance from the trigger body flange 2220 increases. An intermediary region of the cantilevered arms 2240 may include a protrusion 2244 defining a ledge 2246.

Referring now also to FIGS. 109A-109B, when the inserter assembly 100 is assembled, the stem body 2208 of the sharp shuttle 2130 may extend into the barrel 2226 of the trigger body 2002. The insertion sharp 132 may project through the orifice 2236 in the barrel 2226 such that a terminal end of the insertion sharp 132 is disposed outside of the barrel 2226. The guide projections 2224 of the trigger body 2002 may project through the guide passages 2202 of the sharp shuttle 2130. The arms 2210 of the sharp shuttle 2130 may extend through apertures 2222 of the trigger body flange 2220. Bias member 2138 may be seated within the barrel 2226 around the locating projection 2238. The stem body 2208 may extend through the bias member 2138 (a compression spring in the example embodiment) so as to be surrounded by the bias member 2138. The ledges 2214 on the arms 2210 of the sharp shuttle 2130 may engage with the catch ledges 2232 of the outcropped regions of the barrel 2226 to hold the sharp shuttle 2130 and trigger body 2002 together. This may form a retraction latch arrangement which inhibits retraction of the sharp shuttle 2130 when engaged. The bias member 2138 may be held in a distorted state via engagement of the arms 2210 with the ledges 2232 defined on the barrel 2226. When the retraction latch arrangement is disengaged, the bias member 2138 may be free to relax and drive the sharp shuttle 2130 and sharp 132 to a retracted position.

Referring now also to FIG. 112, a perspective view of the example bias member retainer 2000 of FIG. 9105 is depicted. As shown, the bias member retainer 2000 may include a first end 2250 which may define a stop or seat 2252. As shown in FIG. 109A, for example, the seat 2252 may assist in locating the bias member 2136 within the bias member retainer 2000 when the inserter assembly 100 is assembled. The wall 2218 of the trigger body 2002 (see, e.g., FIG. 111B) may also assist in locating the bias member 2136 and may thus be referred to as a locating wall. The wall 2218 may be substantially the same size and shape as the seat 2252 and align with the seat 2252 when the inserter assembly 100 is assembled. The seat 2252 may also block displacement of the trigger body 2002 toward the closed end of the exterior housing 2116 as the seat 2252 may obstruct displacement of the wall 2218 in that direction.

An opening 2254 may be present in the central region of the first end 2250. The opening 2254 may be sized such that the sharp shuttle 2130 may displace through the first end 2250 of the bias member retainer 2000. A second end 2256 of the bias member retainer 2000 opposite the first end 2250 may include a number of notches 2258. The notches 2258 may define a set of opposing cantilevered arms 2260 which include a protuberance 2262 at their unsupported ends. Each protuberance 2262 may define a ledge 2264. The notches 2258 may also define canted panels 2266. The canted panels 2266 may be canted toward the longitudinal axis of the bias member retainer 2000 (best shown in FIG. 109B). The notches 2258 may further define standoffs 2268. At least one standoff 2268 may be present between each cantilevered arm 2260 and canted panel 2266 in various examples.

Referring now to FIGS. 113A-113B, views of the exemplary care assembly base holder 2004 of the inserter assembly 100 of FIG. 105 are depicted. The example care assembly base holder 2004 includes a latch plate 2270. The latch plate 2270 includes a set of first apertures 2272 and a set of second apertures 2274. The first apertures 2272 may be associated with recessed tracks 2278 which extend from the apertures 2272 to the peripheral edge of the latch plate 2270. The peripheral edge of the latch plate 2270 also includes a set of grooves 2276. The grooves 2276 may interface with rails 2280 (see, e.g., FIG. 109B) included on the interior surface of the exterior housing 2116 to inhibit rotation of the care assembly base holder 2004 within the inserter assembly 100 (and components coupled thereto). The interaction of the grooves 2276 with the rails 2280 may also assist in assuring that the care assembly base holder 2004 is installed in the inserter assembly 100 in a prescribed orientation. The latch plate 2270 also include a central passage 2284.

The care assembly base holder 2004 may include a set of retainer arms 2282. As shown, the set of retainer arms 2282 extend from a bottom face of the latch plate 2270. The retainer arms 2282 may be disposed in opposing relationship to one another and may be cantilevered. Each of the retainer arms 2282 may include a protuberance 2286 disposed at an unsupported end thereof. Each protuberance 2286 may form a ledge 2288 on the arm 2282 on which it is included. Additionally, the retainer arms 2282 may include a nub 2290 or raised ramp which increases in thickness as distance from the latch plate 2270 increases. The nub 2290 may be disposed intermediate the unsupported end of the retainer arm 2282 and its attachment point to the remainder of the care assembly base holder 2004.

As best shown in FIG. 109B the ledge 2288 may capture a portion of the infusion set base 106. The ledges 2288 may catch on rails, step features, nubs or any other suitable protrusions. In certain embodiments, the ledges 2288 may catch on guides 172 (see, e.g., FIG. 4A) of the infusion set base 106. Thus the infusion set base 106 may be retained within the inserter assembly 100. In alternative embodiments, such as those in which an infusion set base 106 of the type depicted in FIGS. 21A-21F is used, a portion of each arm 2288 may extend at least partially into a respective receiving slot defined in the base 106. The ledges 2288 may engage a catch present at an end of the respective receiving slots so as to retain the base 106 within the inserter assembly 100.

Ledges 2288 may be angled with respect to the cantilevered arm 2282 on which it is included such that the undercut has a triangular cross section. The portion of, for example, the guides 172 (or any other catch feature) on which each ledge 2288 catches may be angled in a cooperating manner to help ensure a robust engagement. Though not shown, in certain embodiments, the retainer base 2140 (see, e.g., FIG. 109A) may include retaining projections 359 (see, e.g., FIG. 59A) which may abut or nearly abut retainer arms 2282 and hold the retainer arms 2282 from displacement out of engagement with the infusion set base 106 prior to inserter assembly 100 actuation. This may help prevent any accidental firing of the inserter assembly 100 or inadvertent release of the infusion set base 106.

Referring now primarily to FIGS. 109A-109B, when the inserter assembly 100 is assembled, the cantilevered arms 2260 of the bias member retainer 2000 may project through the second apertures 2274 of the latch plate 2270. The arms 2260 may be deflected such that they may pass through the second apertures 2274 and then restore to a state in which the ledges 2264 of the arms 2260 rest against the surface of the bottom face of the latch plate 2270. This may inhibit separation of the bias member retainer 2000 and the care assembly base holder 2004. The protuberances 2262 at the unsupported ends of the arms 2260 may facilitate deflection of the arms 2260 as they are advanced through the second apertures 2274 during assembly.

The flared end regions 2242 of the cantilevered arms 2240 of the trigger body 2002 may be fed through the first apertures 2272 such that the ledges 2246 of the cantilevered arms 2240 abut the latch plate 2270. The ledges 2246 may seat within the recessed tracks 2278 associated with the first apertures 2272. The latch plate 2270 may thus provide a catch which block displacement of the trigger body 2002 toward the open end of the inserter assembly 100. The bias member 2136 may be captured between the first end 2250 of the bias member retainer 2000 and the trigger body flange 2220. When the ledges 2246 are caught on the latch plate 2270, the bias member 2136 may be held in a distorted state. Deflection of the cantilevered arms 2240 of the trigger body 2002 may displace the ledges 2246 into alignment with the first apertures 2272 such that the bias member 2136 may be freed to restore to a less stressed state. Thus, engagement of the cantilevered arms 2240 with the latch plate 2270 may form an insertion latch arrangement which may inhibit the insertion movement until being disengaged. Disengagement of the insertion latch arrangement may trigger actuation of the inserter assembly 100 and the trigger body 2002 and sharp shuttle 2130 may be driven toward a forward state.

Referring now to FIGS. 114A-114B, two cross sectional views of the example inserter assembly 100 of FIG. 105 are shown. In FIGS. 114A-114B, an example inserter assembly 100 which has been placed against a desired infusion site is being pulled away from the skin 356. The skin 356 at the infusion site is in an adhering relationship with an adhesive patch 614 coupled to the bottom face 162 of the infusion set base 106. Thus, as the example inserter assembly 100 is withdrawn from the skin 356, the skin 356 at the infusion site may be lifted along with the inserter assembly 100. The casing of the inserter assembly 100 formed by the exterior housing 2116 and retainer base 2140 may displace together with the hand of the user as the user withdraws the inserter assembly 100 from their body. The other components of the inserter assembly 100 may be anchored to the skin 356 via the adhesive patch 614. For example, as the infusion set base 106 is coupled to the care assembly base holder 2004 via the retainer arms 2282, care assembly base holder 2004 may be anchored to the skin 356. In turn, the bias member retainer 2000 may be coupled to the care assembly base holder 2004 and thus also be held behind. The trigger body 2002 and sharp shuttle 2130 coupled thereto (via the example retraction latch arrangement) may also be inhibited from displacing in tandem with the casing. Movement of the trigger body 2002 away from the patch of skin 356 adhered to the adhesive patch 614 may be blocked the by seat 2252.

Thus, the care assembly base holder 2004, bias member retainer 2000, trigger body 2002, sharp shuttle 2130, and insertion sharp 132 may form a first anchored unit of the inserter assembly 100 which is more constrained in its ability to displace than a second casing unit of the inserter assembly 100. In the example embodiment, a trigger arrangement for the inserter assembly 100 may establish a temporary engagement between the first unit and second unit such that the first and second unit are restricted from moving independently of one another for an initial portion of the inserter assembly 100 withdrawal motion. This may, in some embodiments, be the only interaction within the inserter assembly 100 which restricts independent motion of the units of the insertion assembly 100. Thus, the trigger arrangement may be responsible for lifting the skin 356 and controlling initiation of inserter assembly 100 actuation.

In the example embodiment, the trigger arrangement may provide the temporary engagement in the form of an interfering relationship between the first and second units. This interference may link motion of the first and second units until more than a triggering force is applied to separate the first and second units. This may result in the skin 356 being lifted as the inserter assembly 100 is withdrawn. When more than the triggering force is present, the interference may be overcome and actuation of the inserter assembly 100 may begin. In certain example embodiments, the trigger arrangement may include the trigger protrusions 2241 of the retainer base 2140 and the flared end regions 2242 of the cantilevered arms 2240 of the trigger body 2002. The trigger arrangement may be referred to herein as part of the insertion latch arrangement.

Still referring to FIGS. 114A-114B, during removal, the exterior housing 2116 and retainer base 2140 may be displaced in a direction away from the skin 356. The flared end regions 2242 of the cantilevered arms 2240 of the trigger body 2002 may abut against the trigger protrusion 2241. As the cantilevered arms 2240 may be resiliently deflected when more than a threshold amount of force is applied, the inserter assembly 100 may initially move substantially as a unit and the skin 356 may be lifted. As the inserter assembly 100 is further pulled by the user in a direction away from the skin 356, the elasticity of the skin 356 may tug the first anchored unit of the inserter assembly 100 in a direction toward the infusion site. When the force compelling separation of the first and second units reaches a triggering threshold, the cantilevered arms 2240 may be deflected to a triggering point (see, e.g., FIG. 114A) where the ledges 2246 are displaced into alignment with the first apertures 2272 in the latch plate 2270. Actuation of the inserter assembly 100 may then be triggered. When deflected to the triggering point, the flared end regions 2242 of the arms 2240 may be deflected clear of the trigger protrusions 2241 of the retainer base 2140.

In various embodiments, the amount of force require to deflect the cantilevered arms 2240 of the trigger body 2002 may be selected to adjust a distance which a given user's skin 356 is tugged away from the body before actuation of the inserter assembly 100 occurs. The cantilevered arms 2240 may be constructed such that an inserter assembly 100 may be used on a wide range of individuals having different skin 356 properties (e.g. elasticity) while still ensuring the skin 356 is tugged at least some minimum distance before actuation is triggered. In some embodiments, a variety of inserter assemblies 100 may be produced with differing cantilevered arm 2240 deflection thresholds (e.g. via material selection, thickness adjustments, presence/absence of supporting buttresses for the arms 2240, etc.) which may be suitable for different user groups. As shown, the terminal unsupported ends of the cantilevered arms 2240 and the triggering protrusions 2241 of the retainer base 2140 may be angled. These angles may be adjusted to alter the ease with which the cantilevered arms 2240 are deflected and may help ensure the skin 356 is lifted a desired amount.

Referring now to FIGS. 115A-115B, two cross-sectional views of the example inserter assembly 100 of FIG. 105 are shown. The example inserter assembly 100 depicted in FIGS. 115A-115B has been triggered and bias member 2136 has begun to restore to a less distorted state. As the bias member 2136 restores, the trigger body 2002 may be propelled toward the open end of the casing of the inserter assembly 100. The barrel 2226 of the trigger body 2002 may displace along the central passage 2284 of the care assembly base holder 2004. The vane members 2228 may be guided by tracks 2281 (see, e.g., FIG. 113B) in the retainer arms 2282 of the care assembly base holder 2004 as the trigger body 2002 is displaced. The canted panels 2266 of the bias member retainer 2000 may extend into the displacement path of the trigger body flange 2220 and may be deflected outward as the trigger body 2002 is advanced. Since the trigger body 2002 and the sharp shuttle 2130 are coupled together via the retraction latch arrangement, the sharp shuttle 2130 may displace along with the trigger body 2002. Bias member 2138 may also be urged toward the open end of the casing in its distorted state as bias member 2136 relaxes. As these components are displaced the insertion sharp 132 may be advanced into the skin 356 trailed by the cannula 104 of the cannula subassembly 114. As the skin 356 is penetrated by the insertion sharp 132 and cannula 104, the skin 356 may still be in a state in which it is tugged up away from underlying anatomy. In addition, the cannula subassembly 114 may be displaced into the receptacle 176 (see, e.g., FIG. 4A) of the infusion set base 106. The cannula subassembly 114 may engage a retention feature (e.g. protuberance 182 may engage notch 186 of the cannula subassembly 114) of the infusion set base 106. Thus, the infusion set 102 may be assembled as the insertion stroke of inserter assembly 100 proceeds.

As best shown in FIG. 115A, while the cannula subassembly 114 is advanced into latched engagement with the infusion set base 106, the ears 204 on the cannula subassembly 114 may press against the nubs 2290 included on the retainer arms 2282. This may cause the retainer arms 2282 to be splayed apart resulting in disengagement of the retainer arms 2282 from the infusion set base 106. Thus, the now assembled infusion set 102 may be released. Optionally, and as shown, the trigger body 2002 may be at an intermediate point in the insertion stroke when the infusion set 102 is released. The trigger body 2002 may continue to displace toward the open end of the casing after release of the infusion set 102 until the flange 2220 of the trigger body 2002 is against the latch plate 2270. This additional displacement may lead the trigger body 2002 to press against the cannula subassembly 114 for a short period of time after it has been deposited and engaged into the receptacle 176 (see, e.g., FIG. 4A) of the infusion set base 106. This may ensure that any tendency of the cannula subassembly 114 to rebound as it is propelled into the receptacle 176 is blocked.

Referring primarily to FIG. 115B, various inserter assemblies 100 may be arranged such that the point of disengagement of the retraction latch arrangement is adjustable. The retraction latch arrangement may be disengaged when the sharp shuttle 2130 and trigger body 2002 are displaced to a retraction release position by the first bias member 2136. For example, the retraction latch arrangement may be disengaged at an intermediate point in the displacement range of the trigger body 2002 or at a terminal portion (e.g. the end) of the displacement range of the trigger body 2002. The retraction latch arrangement may be disengaged before or after the cannula subassembly 114 is coupled into the infusion set base 106. Thus, depending on the release point of the retraction latch arrangement, the insertion sharp 132 may begin retraction prior to the cannula 104 completing its displacement into the skin 356. Bias member 2136 may drive the cannula subassembly 114 through the trigger body 2002 during a final portion of the insertion displacement of the cannula assembly 114. The cannula 104 may be displacing in a first insertion direction and the insertion sharp 132 may be displacing in a second, opposite, retraction direction for a portion of the actuation. Retraction of the insertion sharp 132 may partially overlap with the insertion displacement of the cannula 104.

In such examples, initial progress of the cannula 104 into the skin 356 may be assisted by the insertion sharp 132. A final distance the cannula 104 advances into the skin 356 may be unassisted by the insertion sharp 132. Similarly, where the inserter assembly 100 is for use with another patient care assembly such as a sensor assembly, a sensor assembly component, for example, may advance into the skin 356 unassisted by the insertion sharp 132 during a final portion of the insertion. Alternatively, as the insertion sharp 132 may typically have a lead length which extends beyond the end of the cannula 104 (or other transcutaneous access portion of a patient care assembly), the release point may be selected such that the cannula subassembly 114 travels a distance at least equal to the lead length after retraction is triggered. Where the distance and the lead length are equal, the furthest penetration distances of the insertion sharp 132 and the cannula 104 into the skin 356 may be substantially the same. The final, unassisted distance traveled by the cannula 104 or sensor assembly component (if any) may be varied by altering the release point of the retraction latch arrangement. In the example embodiment, the retraction latch arrangement is disengaged at the conclusion of the insertion stroke and after the cannula subassembly 114 is coupled into the infusion set base 106.

As shown in FIG. 115B, the care assembly base holder 2004 may include a set of retraction triggering protrusions 2283. As the trigger body 2002 is urged toward the forward state by the bias member 2136 during the insertion stroke, the protuberances 2212 on the arms 2210 of the sharp shuttle 2130 may be advanced into the triggering protrusions 2283. This may cause the arms 2210 to splay apart and out of engagement with the catch ledges 2232 on the outcropped regions 2230 of the trigger body 2002 barrel 2226. The protuberances 2212 may be ramped to facilitate spreading of the arms 2210 as the trigger body 2002 is advanced.

The height of the triggering protrusions 2283 may be selected to determine when the retraction latch arrangement is released. Taller triggering protrusions 2283 may engender an earlier release of the retraction latch arrangement (given constant arm 2210 length and outcropped region 2230 positions). Likewise, the position of the outcropped regions 2230 and correspondingly the length of the arms 2210 may be adjusted to alter the point during actuation at which the retraction latch arrangement is disengaged. Keeping the height of the triggering protrusions 2283 constant, longer arms 2210 with cooperating outcropped regions 2230 disposed more distal the flange 2220 of the trigger body 2002 result in an earlier disengagement of the retraction latch arrangement. Thus, the unassisted distance (if any) traveled by the cannula 104 (or portion of another patient care assembly) may be adjusted.

Referring now to FIG. 116A-116B, two cross-sectional views of the example inserter assembly 100 of FIG. 105 are shown. The example inserter assembly 100 is depicted in a retraction release state. As best shown in FIG. 116B, the arms 2210 of the sharp shuttle 2130 have been spread out of engagement with the catch ledges 2232 on the barrel 2226 of the trigger body 2002. Thus, the retraction latch engagement has been disengaged, freeing bias member 2138 to restore to a less stressed state. Additionally, the trigger body 2002 has been advanced such that the flange 2220 is in contact with the care assembly base holder 2004. Thus the care assembly base holder 2004 may provide a stop which limits the displacement range of the trigger body 2002 during actuation of the inserter assembly 100. As best shown in FIG. 116A, as the trigger body 2002 reaches the end of its displacement range, the flange 2220 of the trigger body 2002 may be advanced clear of the canted panels 2266 of the bias member retainer 2000. This may allow the canted panels 2266 to restore to a resting state. In the resting state, the canted panels 2266 may overhang the flange 2220 of the trigger body 2002. Thus, the canted panels 2266 may lock the trigger body 2002 in a forward state substantially preventing further displacement of the trigger body 2002. This may help to prevent inadvertent contact with the insertion sharp 132 and reuse of the inserter assembly 100. Bias member 2136 may still be slightly distorted when the trigger body 2002 is against the latch plate 2270.

Referring now to FIGS. 117A-117B, two cross-sectional views of the example inserter assembly 100 of FIG. 105 are shown. The example inserter assembly 100 is depicted in a retracted state. When the retraction release latch is disengaged (see, e.g., FIG. 116B), bias member 2138 may propel the sharp shuttle 2130 toward the closed end of the inserter assembly 100, at least partially through the opening 2254 in the bias member retainer 2000, and into a retracted state. The guide projections 2224 of the trigger body 2002 may dictate the displacement path of the sharp shuttle 2130 for a first portion of the retraction stroke and a concluding portion of the retraction stroke may be unguided. The stem body 2208 of the sharp shuttle 2130 may also be guided by features of the barrel 2226 during an initial portion of the retraction stroke. As shown, the position of the sharp shuttle 2130 in the retracted state is different from the position of the sharp shuttle 2130 in the storage state. In the retracted state, the insertion sharp 132 may not project through the orifice 2236 in the barrel 2226 of the trigger body 2002. The tip of the insertion sharp 132 may be disposed within the barrel 2226 of the trigger body 2002. Thus, the insertion sharp 132 may be rendered inaccessible to a user and the barrel 2226 may serve as a guard or sharp receptacle after the inserter assembly 100 has been used. Additionally, as best shown in FIG. 116A, the sharp shuttle 2130 may include a wall 2204 with an extended section 2206. As the sharp shuttle 2130 is driven to the retracted state, the extended section 2206 may contact the closed end of the exterior housing 2116 blocking further travel of that portion of the sharp shuttle 2130. The sharp shuttle 2130 may begin to tip as the bias member 2138 continues to restore to a less distorted state. Thus, the extended section 2206 of the wall 2204 may act as a tipping projection which may cause the insertion sharp 132 to tilt away from the long axis of the inserter assembly 100 during the retraction stroke of the sharp shuttle 2130. The retraction bias member 2138 may still be in a partially distorted state when the sharp shuttle 2130 is in the retracted position. This may help to hold the sharp shuttle 2130 in the retracted state and inhibit rattling of the sharp shuttle 2130 within the inserter assembly 100 after use.

Referring now to FIG. 118, in some examples, an inserter assembly 1000 may be reusable. After actuation, certain inserter assembly 1000 embodiments, may be reset and used to install a next infusion set 102 (or analyte sensor in certain examples). Thus, the same inserter assembly 1000 may be used to install a plurality of different infusion sets 102 (or other patient care assemblies). For example, a container of infusion sets 102 may include a single inserter assembly 1000 (or a number of inserter assemblies 1000 which is less than the number of infusion sets 102). The single inserter assembly 1000 may be intended to be used to install each of the infusion sets 102 in the container onto the patient. Thus, the waste and cost associated with site changes may be reduced. In embodiments where the inserter assembly 1000 is a multi-use device, infusion sets 102 may be provided in separate set cartridges 1002. Similarly, where the inserter assembly 100 is configured to apply a sensor to the patient, sensors may be provided in sensor cartridges which are separate from the inserter assembly 1000. As in other embodiments described herein, the infusion set 102 may be provided partially assembled within the set cartridges 1002. A set cartridge 1002 is depicted separate from the inserter assembly 1000 in FIG. 118. The set cartridge 1002 may be coupled to the inserter assembly 1000. Once coupled, the inserter assembly 1000 may be actuated to install the infusion set 102 at a desired infusion site. After actuation, the spent cartridge 1002 may be separated from the inserter assembly 1000 and disposed of. The inserter assembly 1000 may be reset when another set cartridge 1002 is coupled thereto and used to install another infusion set 102.

Depending on the embodiment, actuation of the inserter assembly 1000 may also cause assembly of the infusion set 102 to be completed. The infusion set 102 or other patient care assembly may be provided as a number of portions (e.g. separate components, subassemblies, or combinations thereof) within a set cartridge 1002. Actuation of the inserter assembly 1000 may cause each portion of the infusion set 102 to be coupled together to complete the assembly of an infusion set 102. For example, assemblage of an infusion set 102 may occur as an initial stage of the actuation of the inserter assembly 1000 or may occur as part of an insertion stage of inserter assembly 1000 actuation which results in the cannula 104 being introduced into the patient.

Referring now to FIGS. 119A-120B, exploded views of exemplary set cartridges 1002 are depicted. As shown, the set cartridge 1002 may include an exterior housing 1004. When the set cartridge 1002 is assembled, the exterior housing 1004 may contain the other components of the set cartridge 1002. The exterior housing 1004 may thus also be referred to herein as a container. In the examples, the exterior housing 1004 is shown as a cup and includes an open top. Depending on the embodiment, when fully assembled, the open top of the exterior housing 1004 may be covered by a barrier member so as to completely enclose the components of the set cartridge 1002. This barrier member may be permeable to a sterilizing agent to allow for sterilization of the set cartridge 1002 after assembly. A barrier member may also help minimize contact of components in the exterior housing 1004 with the surrounding environment or a user.

As shown, an infusion set 102 (or other patient care assembly) may be contained within the set cartridge 1002 as a first portion and a second portion which are separate from one another, but coupled together during actuation of the inserter assembly 1000 to form the infusion set 102. The first portion may include a base 106 which may be applied to the skin of a patient and may couple to a fluid pathway (e.g. via a terminal connector on the pathway such as connector 368 shown in FIGS. 15A-F) which is part of or extends from an infusion pump. An adhesive backing, film, or liner 111 may be included and may be applied over adhesive 374 included on the infusion set base 106. The infusion set base 106 may seat within a receiving bay 1006 of an interior housing 1008 of the set cartridge 1002. The receiving bay 1006 may include notches 1010 which may accept tube retainers 184 included on the infusion set base 106. In the example embodiment, the notches 1010 may also serve to ensure that the base 106 may only be installed within the receiving bay 1006 in a desired orientation or orientations (see, e.g. FIGS. 120A-120B). As shown in FIGS. 119A-B, the interior housing 1008 may include an indention 1012. The indention 1012 may be sized so as to accept pull tabs 410 included on the adhesive liner 111. As the indention 1012 may be visible to the user, the indention 1012 may be used as an orientation indicator. This may help the user install the infusion set 102 in a manner which accommodates their planned routing pathway for infusion tubing which is to be coupled to the infusion set 102. Indicators which show the orientation of the infusion set 102 may be included on portions of the inserter assembly 1000 as well. This may be particularly true in embodiments where the set cartridge 1002 may only be coupled to the inserter assembly 1000 in a single orientation.

The second portion of the infusion set 102 may be a subassembly 114 of two or more components of the infusion set 102. The second portion may include a cannula 104, septum housing 108, septum 110, and septum retainer 112 for example (an exemplary cannula subassembly 114 is shown exploded apart in FIG. 1A). Any cannula subassembly 114 described herein may be used. The cannula 104 and the septum housing 108 are shown a single continuous unitary part in the example embodiments though as described elsewhere herein this need not be so in all embodiments. The example cannulated housing may be a molded part which is constructed of a single material such as, PTFE, Teflon, polypropylene, etc. for example. When the set cartridge 1002 is assembled, the insertion sharp 132 may extend through the cannula subassembly 114 and the cannula subassembly 114 may be disposed against the sharp holder 130. In sensor cartridge embodiments, the cannula subassembly 114 and infusion set base 106 may be replaced by a sensor assembly.

A set cartridge 1002 may further include a sharp holder 130. The sharp holder 130 may retain an insertion sharp 132 thereon. The insertion sharp 132 may be glued or otherwise bonded into the sharp holder 130 so as to be fixedly located relative to the sharp holder 130. The insertion sharp 132 may alternatively be press fit into the sharp holder 130 or the sharp holder 130 and insertion sharp 132 may be joined in an overmolding process. Any suitable type of sharp 132 may be used. For example, the sharp 132 may be a hollow or solid needle, stylet, or other pointed member which may be made of a metal material such as steel.

Referring now primarily to FIG. 121, an infusion base retainer 1014 may also be included in a set cartridge 1002. The example infusion base retainer of FIGS. 119A-B is depicted in FIG. 121. The infusion base retainer 1014 may include a set of retainer arms 1016. The retainer arms 1016 may extend from an end plate 1028 of the infusion base retainer 1014. The arms 1016 may be separated from a wall 1018 defining the central cavity 1020 of the infusion base retainer 1014 by interrupt regions included in the wall 1018. The wall 1018 may also include a set of protuberances 1030. The protuberances 1030 may be disposed opposite one another on the wall 1018 and may be roughly spaced 90° from the arms 1016. The protuberances 1030 may include a ramped face 1032 on a portion of each protuberance 1032 most distal to the end plate 1028. The protuberances 1030 may also define a catch face 1034 on a portion of the protuberances 1030 most proximal to the end plate 1028.

Referring now also to FIG. 122, during assembly of the infusion base retainer 1014 into the interior housing 1008, the protuberances 1030 may travel along respective channels 1036 defined in the interior housing 1008. As shown, a terminus of the channels 1036 may be closed by a stop wall 1038. As the protuberances 1030 are driven into the stop wall 1038 the portions of the wall 1018 on which the protuberances 1030 are included may resiliently deflect inward so as to allow passage of the protuberances 1030 beyond the stop wall 1038. The ramped face 1032 may facilitate this deflection. Once the protuberances 1030 have passed the stop wall 1038, the portions of the wall 1018 may restore back to an unstressed state. When the portions of the wall 1018 are in the unstressed state, the catch faces 1034 of the protuberances 1030 may be latched against the stop walls 1038 of the channels 1036 preventing the infusion base retainer 1014 from being pushed out of the interior housing 1008. The end plate 1028 of the infusion base retainer 1014 may abut a rim 1040 which prevents further displacement of the infusion base retainer 1014 into the interior housing 1008. Thus the infusion base retainer 1014 may be fixed in place within the interior housing 1008.

Referring now to FIGS. 123-124 (respectively depicting views of the infusion base retainer 1014 and interior housing 1008 of FIGS. 120A-120B), in some embodiments, protuberances 1030 on the wall 1018 of the infusion base retainer 1014 may be omitted. In some such examples, the infusion base retainer 1014 may be installed into the cartridge 1002 via the receiving bay 1006 of the interior housing 1008. A set of retention members may project into the bay 1006 such that the end plate 1028 of the infusion base retainer 1014 may be captured between the rim 1040 and the ends of the retention members. For example, the sidewall of the receiving bay 1006 may include a set of cantilevered fingers 1007. The cantilevered fingers 1007 may be disposed on the wall in opposition to one another and may extend to points slightly below the rim 1040. Thus, the unsupported ends of the cantilevered fingers 1007 may be spaced from the rim 1040 by a small gap. As the infusion base retainer 1014 is advanced into the receiving bay 1006 toward the rim 1040, the end plate 1028 of the infusion base retainer 1014 may cause the cantilevered fingers 1007 to splay apart to accommodate the infusion base retainer 1014. As the end plate 1028 is displaced against the rim 1040 and into the gap between the rim 1040 and the unsupported ends of the cantilevered fingers 1007, the end plate 1028 may clear the unsupported ends of the cantilevered fingers 1007. The cantilevered fingers 1007 may restore to an undeflected state. Upon restoration to the undeflected state, the infusion base retainer 1014 may be fixed in place within the interior housing 1008. A face of the end plate 1028 may rest upon the unsupported ends of the cantilevered fingers 1007 and the cantilevered fingers 1007 may block removal of the infusion base retainer 1014 from the receiving bay 1006 (best shown in FIG. 128B). The rim 1040 may robustly prevent removal of the infusion base retainer 1014 from the opposing side of the interior housing 1008.

Referring now primarily to FIG. 121 and FIG. 123, the set of arms 1016 of the example infusion base retainers 1014 may be disposed in opposing relationship to one another and may be cantilevered from the end plate 1028. Each of the arms 1016 may include a protuberance 1022 disposed at an unsupported end thereof. Each protuberance 1022 may form a ledge 1024 on the arm 1016 on which it is included. Additionally, the arms 1016 may include a nub 1026 or raised ramp which increases in thickness as distance from the cavity 1020 (see, e.g., FIG. 119A) increases. The nub 1026 may be disposed intermediate the unsupported end of the arm 1016 and its attachment point to the remainder of the infusion base retainer 1014.

Referring now to FIGS. 125-128B and as best shown in FIG. 126B and FIG. 128B, each ledge 1024 may capture a portion of the infusion set base 106. Specifically, the ledges 1024 may catch on an outcropped portion of the infusion set base 106. The base 106 may include rails, step features, nubs or any other suitable protrusions to provide a complimentary catch surface for the ledges 1024. In certain embodiments, the ledges 1024 may catch on guides 172 of the infusion set base 106 (see, e.g., FIG. 126B). In other examples, walls of cutouts (see, e.g. breaks 181 of the example infusion set base 106 shown in FIGS. 21A-F) in an infusion set base 106 may provide a catch with the ledges 1024 may engage. Thus the infusion set base 106 may be retained within the set cartridge 1002. Ledges 1024 may be angled with respect to the cantilevered arm 1016 on which they are included such that the undercut has a triangular cross section. The portion of, for example, the guides 172 (or any other catch feature) on which each ledge 1024 catches may be angled in a cooperating manner to help ensure a robust engagement.

In certain embodiments, only one arm 1016 may be included. In some embodiments, the interior housing 1008 may also or instead include latch which may interface with the guide 172 or another cooperative portion of the infusion set base 106 to retain the infusion set base 106 in place.

With the infusion set base 106 retained by the arms 1016, the infusion set base 106 may also act as a protective barrier. As the cannula subassembly 114 and insertion sharp 132 may be internal to the set cartridge 1002, when the infusion set base 106 is in the initial retained position, the user may be protected from accidental contact with the insertion sharp 132. This may additionally help to keep the cannula 104 or insertion sharp 132 from coming into contact with contaminants. Though a void for receipt of the cannula subassembly 114 may extend through the entirety of the infusion set base 106, the void may be sized to prevent finger ingress (e.g. have a cross-section smaller than that of a finger). Thus the infusion set base 106 may present an obstacle which blocks unintentional access to the insertion sharp 132 and cannula 104. Additionally, as the cannula subassembly 114 is internal to the set cartridge 1002, any adhesive backing 111 provided on the infusion set base 106 need not include an interruption to allow for passage of the cannula 104 therethrough. Thus, the void in the infusion set base 106 for the cannula subassembly 114 may be blocked by the adhesive backing 111 until just prior to use. This may further prevent finger ingress and may mitigate potential for detritus to enter the set cartridge 1002. The exterior housing 1004 may also present a barrier which inhibits a user from interacting with the insertion sharp 132 and/or cannula 104.

As shown in FIGS. 126A-126B and FIGS. 128A-128B, the infusion base retainer 1014 may include at least one guide in various embodiments. In the example embodiments, the infusion base retainer 1014 includes a set of sharp holder guides 1042 (see, e.g., FIG. 126A). The sharp holder guides 1042 may be recessed into a cavity facing side of the wall 1018 of the infusion base retainer 1014. The sharp holder 130 may include fins 1044 which may ride within the sharp holder guides 1042 during displacement of the sharp holder 130 within the set cartridge 1002. In alternative embodiments, the sharp holder 130 may include recesses and the wall may include rails projecting from the cavity facing side of the wall 1018. The rails may be received within the recesses of the sharp holder 130 and guide displacement of the sharp holder 130 as it displaces within the set cartridge 1002.

The infusion base retainer 1014 may also include a set of septum housing guides 1046. The septum housing guides 1046 may be recessed into the cavity facing sides of the arms 1016 (see, e.g., FIG. 126B). Alternatively, the arms 1016 may include guide passages (such as slots shown in FIG. 123) which extend through the arms 1016 to form the septum housing guides 1046. Ears 204 of the septum housing 108 may ride within the septum housing guides 1046 during displacement of the cannula subassembly 114 within the set cartridge 1002. As shown, the sharp holder 130 may also include fins 1048 which are in line with the ears 204 and which may also ride within the septum housing guides 1046. Where the fins 1048 are included in embodiments where the septum housing guides 1048 are defined by guide passages through the arms 1016, the fins 1048 may extend through the slots and beyond the outer surface of the walls 1018. As best shown in FIG. 128B, the lateral tip regions of the fins 1048 may abut a portion of the rim 1040 when the cartridge 1002 is in a storage state. The cannula subassembly 114 may rest on a standoff in the outer housing 1004. This may inhibit movement of the sharp holder 130 and cannula subassembly 114 within the cartridge 1002 in the storage state. The lateral tip regions of the fins 1048 may be unable to pass through the rim 1040 inhibiting removal of the sharp holder 130 and insertion sharp 132 from the cartridge 1002.

Referring to FIGS. 125-128B, when the cannula subassembly 114 latches into the base 106, the ears 204 on the cannula subassembly 114 may press against the nubs 1026 included on the arms 1016. This may cause the arms 1016 to be splayed apart resulting in disengagement of the arms 1016 from the infusion set base 106. In turn, this may free the now assembled infusion set 102 from the set cartridge 1002.

Referring now to FIGS. 129A-131B, exploded views of various example embodiments of inserter assemblies 1000 are depicted. Inserter assemblies such as those shown in FIGS. 129A-131B may be coupled to set cartridges 1002 (see, e.g., FIGS. 119A-128B) and subsequently used to place an infusion set 102 onto an infusion site of a patient and introduce a cannula 104 of an infusion set 102 into the patient's body. As mentioned elsewhere, some inserter assemblies 1000 may be used to place other patient care assemblies onto the body of a patient. For example, certain inserter assemblies 1000 may be operated to place physiological monitors or analyte sensors into working relationship with a patient's body. Blood sugar monitors such as continuous glucose sensors may be placed using an inserter assembly 1000. In certain embodiments, the same inserter assembly 1000 may be mated with a set cartridge 1002 or sensor cartridge depending on the type of device a patient intends to place on their body. In some embodiments, inserter assemblies 1000 may also be coupled to lancet cartridges (e.g. a set cartridge 1002 without a cannula subassembly and infusion set base 106) to create a skin puncture for collection of a body sample with an analyte testing strip.

As shown in the exploded views in FIGS. 129A-131B, an insertion assembly 1000 may include an exterior housing 116. The exterior housing 116 may enclose various components of the inserter assembly 1000 and serve as the portion of the inserter assembly 1000 which the user grips during operation. The exterior housing 116 in the example embodiment of FIGS. 129A-129B has a cross sectional shape which is round, though other embodiments may have different shapes such as any type of polygonal shape. In certain examples, a rectangular or obround cross-sectional shape such as that shown in FIGS. 130A-130B may be used. Such a shape may more easily fit within a pocket or may more easily fit into smaller pockets which may, for example, be more typical of women's clothing. The cross sectional area in the example embodiments also vary with the bottom section (that most proximal the skin when in use) of the exterior housing 116 being wider or having a greater cross-sectional area than the top. An exterior housing 116 may include various ergonomic features which facilitate grasping of the inserter assembly 1000 in which it is included. For example, texturing or a finger or thumb depression may be included on the outer surface of the exterior housing 116. Alternatively or additionally, a region of the external housing 116 may be thinner in width than the remaining portion of the external housing 116. This may make firm grasping of the inserter assembly 1000 easier.

Example exterior housings 116 may include a marking, tab, embossed section, recess section, textured section, protuberance, color coding, appliqué, or other indicia which serves to indicate position and/or orientation of the infusion set 102 within the insertion assembly 1000. A raised rib 118 such as that shown in FIG. 1A for example, may be included. This may allow a user to position the inserter assembly 1000 in a desired orientation so as to allow for a run of infusion tubing 366 (see, e.g. FIG. 6) to be routed in a planned manner once the infusion set 102 is attached to the user.

A retainer cap 406 may serve to couple to a top portion of the inserter assembly 1000 to hold the various components in place within the inserter assembly 1000. In the examples shown in FIGS. 129A-131B, the retainer caps 406 include cantilevered retainer bodies 408 which may snap into retaining interfaces 411 (see, e.g. FIG. 129A) included on the exterior housing 116. Other couplings are also possible such as a bayonet mount, interference fit, snap fit, adhesive, glue, threads, solvent bonding, welding, etc.

As various inserter assemblies 1000 may be tugged away from the infusion site to trigger placement of an infusion set 102, it may be desirable that the coupling between the retainer cap 406 and the exterior housing 116 be particularly robust. In certain examples, and referring now primarily to FIG. 132, in certain examples, the retainer bodies 408 may each be deflected in a first direction and second direction before snapping into respective retention interfaces. The first and second direction may be substantially perpendicular. Retention interfaces 411 may be included on opposing sides of the interior surface of the exterior housing 116 and may be defined as slots. The slots may include a central ramp 409 which projects further into the slot as distance from the end face 407 of the exterior housing 116 increases. The retainer bodies 408 may be provided in pairs on opposing sides of the retainer cap 406. The lateral edges of the unsupported ends of the retainer bodies 408 may include a ramped protuberance 413 defining a ledge 415. As the retainer bodies 408 are advanced into respective slots, the cantilevered retainer bodies 408 may be deflected toward one another due to the slope of the ramped protuberances 413. Further advancement may drive the unsupported ends of the retainer bodies 408 into the central ramps 409 of each slot. This may deflect the retainer arms 408 toward the sidewalls of the slots opposite the ramps 409. When fully advanced into the slots, the ledges 415 may clear past the ends of the slot allowing the retainer bodies 408 to restore away from one another to a less stressed state. As the retainer bodies 408 restore away from one another they may be displaced out of contact with the ramps 409 and also restore toward the wall of the slots from which the ramps 409 project. When in the coupled state, the ledges 415 may seat against the bottom end of the respective slots and the ramps 409 may be disposed intermediate each pair of cantilevered retainer bodies 408. The ramps 409 may thus present an interference inhibiting displacement the retainer bodies 408 of each pair in a direction toward one another. This may assist preventing inadvertent disassociation of the retainer cap 406 and exterior housing 116.

Referring again primarily to FIGS. 129A-131B, when coupled together, the exterior housing 116 and retainer cap 406 may form a casing of the inserter assembly 1000. The exterior housing 116 and the retainer cap 406 together may form a first unit of the inserter assembly 1000. The remaining components of the inserter assembly 1000 may be referred to as a second unit of the inserter assembly 1000.

Still referring to FIGS. 129A-130B, an inserter assembly 1000 may also include an interior housing 120. The interior housing 120 may be disposed inside of the external housing 116 when the inserter assembly 1000 is assembled. The first unit of the inserter assembly 1000 may be displaceable relative to the interior housing 120 and other components of the second unit of the inserter assembly 1000 contained therein. Various exterior housings 116 may have at least one keying feature which constrains the interior housing 120 such that it may only be installed in a limited number of orientations within the exterior housing 116. The cross-sectional shape may be chosen so as to dictate such a constraint (see, e.g., FIGS. 130A-130B). Alternatively, the exterior housing 116 may include at least one rail 1090 (see, e.g., FIGS. 129A-129B). In the exemplary embodiment shown in FIGS. 129A-129B, two rails 1090 are included directly opposite one another (only one is visible) on the interior facing surfaces of the exterior housing 116. The rails 1090 extend substantially parallel to one another. If it is desired to limit the interior housing 116 to a single installation orientation, the rails 1090 may be of different widths. The exterior face of the interior housing 120 may include tracks 1092 which cooperate with the rails 1090. The interior housing 120 may be inhibited from displacing into the exterior housing 116 until the rails 1090 are aligned with the tracks 1092. The interaction of the rails 1090 within the tracks 1092 may also inhibit rotation of the interior housing 120 and exterior housing 116 relative to the other. Though rails 1090 are shown on the exterior housing 116 in the example, the rails 1090 may instead be present on the exterior face of the interior housing 120 in some embodiments. In such examples, the tracks 1092 may be located on the exterior housing 116.

As shown in FIGS. 129A-129B, the exterior housing 116 may also include stop protrusions 1094 on the interior face of the exterior housing 116. The stop protrusions 1094 may be nubs, pins, rails or any suitable feature. The stop protrusions 1094 may limit the travel of the interior housing 120 along the axis of the exterior housing 116. In the example embodiment, the stop protrusions 1094 extend from an end of the exterior housing 116 in a direction parallel to the rails 1090. In certain examples, the retainer arms 408 of the retainer cap 406 may also act as stops which limit travel of the interior housing 120 relative to the exterior housing 116.

A receptacle body 1060 (described in greater detail in relation to FIGS. 134-136, and FIG. 142) may serve to couple to a bottom portion of the inserter assembly 1000 to hold the various components in place within the inserter assembly 1000. In the examples shown in FIGS. 129A-131B, the receptacle bodies 1060 include cantilevered retention arms 1096 which may snap into retainer interfaces 1098 included on the interior housing 120. Other couplings are also possible such as a bayonet mount, interference fit, snap fit, adhesive, glue, threads, solvent bonding, welding, etc. Lock members 1112A, B which may be part of another component (e.g. the retraction latch body 1100 in FIG. 129A-129B) or as individual separate components (see, e.g., FIG. 130A-130B) may be included and may project through the receptacle body 1060.

A retraction latch body 1100 and a retracting spring retainer 1102 may also be included. As will be further described later in the specification, the retraction latch body 1100 and retraction spring retainer 1102 may engage with one another to hold a bias member such as spring 1104 (or springs 1104A, B of FIGS. 130A-130B) and spring 1108 in an energy storing state during portions of the inserter assembly 1000 actuation. The retraction latch body 1100 may be coupled in place on the receptacle body 1060 via interaction of latch fingers 1097 of the receptacle body 1060 with catch bodies 1099 on the retraction latch body 1100. Alternatively, and as shown in FIGS. 131A-131B, the receptacle body 1060 may include a number of retainer arms 1095 which may snap in place over a face of the retraction latch body 1100 when the retraction latch body 1100 is installed in the receptacle body 1060.

An insertion driver 1062 may also be included in an inserter assembly 1000. As will be further described later in the specification, the insertion driver 1062 may have a plunger 1106 and a spring 1108 housed in a portion of the insertion driver 1062. Alternatively, the plunger 1106 may be omitted and the spring 1108 may not be housed within the insertion driver 1062 (see, e.g., FIGS. 131A-131B). An assembly resetting body 1110 may be included. As further described later in the specification, the resetting body 1110 may act on various components of the inserter assembly 1000 to place the components in a ready state in preparation for an actuation. When freed to transition from an energy storing state to a relaxed state, the spring 1108, may displace the insertion driver 1062 to cause insertion of a cannula 104 from an attached set cartridge 1002 and complete assembly of the infusion set 102 of the set cartridge 1002. Retraction of the sharp 132 into the set cartridge 1002 may also occur as spring 1104 (or springs 1104A, B of FIGS. 130A-130B) is freed to transition from an energy storing state to a relaxed state. During this transition, the spring 1104 may in some embodiments, drive the retraction spring retainer 1102 towards a retracted state within the inserter assembly 1000. This may cause the insertion driver 1062 (which may be attached to the sharp holder 130, see e.g. discussion of FIG. 134) to be driven to a retracted state.

Referring FIG. 133, a cross-sectional view of the inserter assembly 1000 of FIGS. 130A-130B is depicted. The inserter assembly 1000 is depicted in a relaxed or storage state. As shown, no set cartridge 1002 is attached to the inserter assembly 1000. In some embodiments, an end cover may be included for storage and may be placed over the end of the inserter assembly 1000 to which a cartridge 1002 may be coupled. Additionally, in FIG. 133, all of the bias members 1108, 1104A, B are shown in a relaxed or unstressed state. The inserter assembly 1000 may be in the relaxed state between usages of the inserter assembly 1000. As the inserter assembly 1000 may typically only be used during site changes (e.g. every three days), the inserter assembly 1000 may be in the relaxed state for the vast majority of its usage life. Thus, the bias members 1108, 1104A, B may only be required to be in an energy storing state or stressed state (a compressed state in the example embodiments) for short periods of time. Bias members 1108 and 1104 of the inserter assembly 1000 of FIGS. 129A-129B may similarly be in a substantially unstressed state when the inserter assembly 1000 is in its storage state. In alternative embodiments, the bias members 1008, 1104A, B may be in an at least partially stressed state when the inserter assembly 1000 is in a storage state.

A storage state in which bias members 1108, 1104A, B are in an unstressed state may facilitate use of a wide variety different of bias members 1108, 1104A, B or bias member 1108, 1104A, B materials. For example, spring relaxation and/or creep may be less of a concern allowing materials such as various polymers to more easily be utilized in construction of the bias members 1108, 1104A, B. Additionally, other components of an inserter assembly 1000 may not be subjected to sustained stress exerted by bias members of the inserter assembly 1000 being in a stressed state when the inserter assembly 1000 is being stored (e.g. during shipping or when sitting in stock). Consequentially, any creep engendered by this sustained stress may be removed. This in turn may allow for greater design flexibility in other components of the inserter assembly 1000. For example, a greater variety of materials may be used or certain components may be made smaller. It should be noted that in certain examples, the set cartridge 1002 (or sensor cartridge or lancet cartridge) may not include any bias members. Instead, all bias members may be included in the inserter assembly 1000. As a result, the components of the set cartridge 1002 may also be stored in a state where they are not subjected to sustained stress. This may similarly assist in providing greater design flexibility for components of cartridges 1002.

Referring now to FIG. 134, a view of an example cartridge 1002 exploded away from an exemplary inserter assembly 1000 is depicted. The example cartridge 1002 is that shown in FIGS. 119A-126B, however, any example cartridge 1002 described herein may be used. Additionally, the inserter assembly 1000 shown is that depicted in FIGS. 129A-B, however, any inserter assembly 1000 could be used. As shown, the end plate 1028 of infusion base retainer 1014 (see, e.g., FIG. 121) may include at least one mating pin 1050. In the example embodiment two mating pins 1050 are included. The mating pins 1050 may be disposed opposite one another on the top plate 1028 and in the example are shown 180° apart from one another. The mating pins 1050 may include an enlarged head portion 1052 which is connected to the end plate 1028 via a pin body 1054. A portion of the sharp holder 130 is also visible in FIG. 134. As best shown in the detailed view in FIG. 135, the sharp holder 130 may include a mating section 1056. The mating section 1056 may include a thinned region 1058 which is adjacent a terminal flange 1059 that forms an end of the sharp holder 130. The terminal flange 1059 may have a length dimension which is longer than its width dimension. In the example embodiment, the top flange 1059 is obround in shape.

To couple the cartridge 1002 to the inserter assembly 1000, the cartridge 1002 may be placed against a receptacle body 1060 included within the inserter assembly 1000. A sharp driver 1062 including a port 1064 for the mating section 1056 of the sharp holder 130 may be accessible through the receptacle body 1060. In an initial coupling state, the mating section 1056 may be oriented in an aligned position with the port 1064 such that the mating section 1056 may pass into the port 1064. The mating pins 1050 may act as standoffs which limit the amount that the mating section 1056 may be displaced into the port 1064. In the example embodiment, the mating pins 1050 may limit displacement of the mating section 1056 into the port 1064 such that the thinned section 1058 is in line with a rim 1066 surrounding the port 1064. The cartridge 1002 may then be rotated from the initial coupling state to a fully coupled state. As the thinned section 1058 is in line with the rim 1066, the mating section 1056 may be free to rotate. During coupling, the terminal flange 1059 may be swept over an interior face of the rim 1066 into an orientation in which it may no longer pass through the port 1064. The top flange 1059 may be biased against the interior face of the rim 1066 by at least one bias member 1108 in some examples (see, e.g. FIG. 142). This may aid in inhibiting additional rotation of the terminal flange 1059. The mating pins 1050 may also be displaced into a mating interface such as retention shoes 1068 included on the receptacle body 1060. The retention shoes 1068 may be formed as “U” shaped bodies which are raised proud of the receptacle body 1060. The “U” shaped bodies may vary in width in a stepwise fashion as distance from the receptacle body 1060 increases. Adjacent the receptacle body 1060, the width may be sized to accept the heads 1052 of the mating pins 1050. The portion of the shoes 1068 most distal to the receptacle body 1060 may have a width sized to accept the pin body 1054 of the mating pins 1050. Thus, when the cartridge 1002 is rotated to the fully coupled state, the heads 1052 of the mating pins 1050 may be overhung by a portion of the shoes 1068 such that the mating pins 1050 may not be translationally displaced out of the shoes 1068 in a direction parallel to the longitudinal axis of the inserter assembly 1000. In alternative embodiments, the mating pins 1050 (or another mating projection) may be included on the receptacle body 1060. Retention shoes 1068 (or another mating interface) may be included as part of the cartridge 1002.

In some examples, and referring now to FIGS. 137A-B, the “U” shaped bodies may be swept in an arc around a portion of the port 1064 (see also, e.g., FIG. 131B). This may prevent the mating pins 1050 from entering the retention shoes 1068 unless the mating section 1056 of the sharp holder 130 is first in the aligned position with respect to the port 1064. Additionally, in some examples and as shown in FIGS. 137A-B, the portions of the shoes 1068 which overhang the heads 1052 of the mating pins 1050 may include a ramped surface 1069 (best shown in FIG. 137B). Thus, as the mating pins 1050 are introduced and advanced along the initial portions of the respective shoes 1068, the shoes 1068 may act as cam features. The cartridge 1002 may be translationally displaced against the receptacle body 1060 as the mating pins 1050 are displaced into a fully mated position within the shoes 1068. This may further help ensure that the mating section 1056 of the sharp holder 130 is properly aligned with the port 1064 before the cartridge 1002 is rotated to a fully coupled state. As shown, the angle of the ramped surfaces 1069 may alter (continuously or in stepwise fashion) along the extent of each shoe 1068 and may generally be steeper near the open end of the shoes 1068. This may help ensure that the thinned section 1058 of the mating section 1056 is at a proper depth within the port 1068 before significant rotation of the cartridge 1002 has occurred. In certain embodiments, a ramp 1071 may extend from the end of the each shoe 1068 opposite the open end. In the event that a user attempts to rotate the cartridge 1002 in the inappropriate direction 1071, the mating pins 1050 may ride along the ramps 1071 and the ramps 1071 may force the cartridge 1002 away from the receptacle body 1060. This may also ensure that the mating section 1056 will be brought out of alignment with and not coupled into the port 1064 in such a scenario. Such ramps 1071 may be included on any receptacle body 1060 embodiments described herein.

Referring now to FIGS. 138A-B, there may be variability in respect to the firmness with which users press a cartridge 1002 and inserter assembly 1000 together as the cartridge 1002 is brought to the coupled state. Preferably the coupling interfaces of a cartridge 1002 and the receptacle body 1060 may be arranged such that a cartridge 1002 is reliably coupled irrespective of user to user variability. In certain examples, an inserter assembly 1000 may include a receptacle body 1060 with a set of mating tracks such as shoes 1068 which are swept around the axis of the port 1064 of the insertion driver 1062. The port 1064 may be flanked on opposing sides by portions of a port rim 1066. The port rim 1066 may define ledges which flank the port 1064. When a cartridge 1002 is placed in an aligned position against the receptacle body 1060, the cartridge 1002 may be rotated to couple the cartridge 1002 to the receptacle body 1060 of the inserter assembly 1000. Mating projections (see, e.g., mating pins 1050 of FIG. 134) of the cartridge 1002 may be rotated into an open end of the mating tracks and advanced to a closed end of the mating tracks when the cartridge 1002 is rotated to the coupled state. Additionally, a sharp holder 130 of the cartridge 1002 may be advanced into the port 1064 and rotated such that a portion of the sharp holder 130 overhangs the ledges formed by the port rim 1066. This may couple the sharp holder 130 to the insertion driver 1062. The ledges may have a thickness sufficient to substantially fill the notch forming the thinned region 1058 of the sharp holder 130 when the sharp holder 130 is in the coupled state.

The mating tracks may extend over a substantial majority (e.g. at least 80%, 85% in some specific implementations) of the rotational displacement range of the mating projections. In certain examples, during a mating projection capture displacement range or first portion of the displacement range of the cartridge 1002, cartridge 1002 rotation may result in translational displacement the cartridge 1002 in the direction of the receptacle body 1060. That is, the cartridge 1002 may be cinched up against the receptacle body 1060 during coupling of the cartridge 1002 and inserter assembly 1000. As best shown in FIG. 138B, the example mating tracks each include a ramped surface 1069 along which a portion (e.g. mating pin head 1052) of a respective mating projection may ride for at least part of the first portion of the displacement range. In various examples, the slope of the ramped surface 1069 may be greatest adjacent the open end of the mating track such that a disproportionate amount of the translational displacement of the cartridge 1002 occurs at the beginning of the first portion of the displacement range. In certain alternative embodiments, the ramped surface 1069 may be replaced by a stop defined in each mating track. When the mating projections encounter the respective stops, the stops may inhibit further rotation of the cartridge 1002. By firmly pressing the cartridge 1002 against the receptacle body 1060, the mating projections may be displaced clear of the stop allowing for further rotation of the cartridge 1002.

Referring now also to FIG. 139, during the first portion of the displacement range, the mating section 1056 or end of the sharp holder 130 opposite the insertion sharp 132 may be advanced into the port 1064 as the mating projections travel along the ramped surfaces 1069 (or are pressed clear of the stops). This may also be accomplished when the cartridge 1002 is in the aligned position depending on user variability. At the end of the first portion of the displacement range, however, the mating tracks will have ensured the thinned section 1058 of the mating section 1056 of the sharp holder 130 is aligned with or level with the port rim 1066. Thus, rotation of the cartridge 1002 through the first portion of the displacement range may leave the sharp holder 130 appropriately positioned to be coupled to the port 1064 as rotation of the cartridge 1002 continues. The mating section 1056 may be considered aligned if further rotation in the same direction will result in coupling of the sharp holder 130 into the port 1064. Translational displacement of the cartridge 1002 may be absent in the event that the cartridge 1002 is pressed firmly enough against the receptacle body 1060 during the first portion of the displacement range.

To rotate the cartridge 1002 to the fully coupled position, the cartridge 1002 may be rotated through a subsequent sharp holder capture displacement range. The segment of the mating tracks traversed by the mating projections may be substantially flat or ramp free over the sharp holder capture displacement range. At the end of the sharp holder capture displacement range, the terminal flange 1059 at the first end of the sharp holder 130 may be out of alignment with the port 1064 and may rest on the ledges or shelves defined by the port rim 1066. The port rim 1066 may substantially fill (the ledges may be slightly smaller to allot for tolerances) the recess defining the thinned section 1058 when the cartridge 1002 is in the fully coupled position. This may inhibit any jostling of the sharp holder 130 once retained in the port 1064. In alternative embodiments, the port 1064 and sharp holder 130 may include cooperating thread features and the sharp holder 130 may thread into the port 1064 as the cartridge 1002 is rotated.

Referring now to FIGS. 140A-B, a block diagram representation of an example insertion driver 1062 and portion of an example sharp holder 130 are respectively depicted. The sharp holder 130 may include a set of slots 1073 which may each include a serif 1075 at one end. The insertion driver 1062 may include a set of ears 1077 disposed opposite one another at an end region of the insertion driver 1062 including the port 1064. The most outboard portion of each ear 1077 may define a leg section 1079. When the sharp holder 130 coupled into the port 1064 of the insertion driver 1064 (described in greater detail above) the legs 1079 may be advanced through the serifs 1075 of the slots 1073 and to an opposing side of a flange of the sharp holder 130. A stem portion 1081 of each ear 1077 may be located in each slot 1073. As a cartridge 1002 is rotated to the fully coupled position, the slots 1073 may displace relative to respective stem portions 1081 until the stem portions 1081 are adjacent the end of a respective slot 1073 opposite the serif 1075. The leg 1079 may sweep along the underside of the flange. In the event that the cartridge 1002 is pressed against the inserter assembly 1000 with insufficient firmness, the leg portion 1079 of each ear 1077 would not be advanced through the serif 1075 and rotation of the cartridge 1002 would be inhibited by the legs 1079 colliding against the wall of the respective serif 1075. Thus, including cooperating bayonet mount type coupling features on the insertion driver 1062 and sharp holder 130 may help to ensure that components of the cartridge 1002 properly couple to the inserter assembly 1000 as a cartridge 1002 is rotated to the coupled state.

The exterior housing 1004 may include receiving slots or ledges 1072 (see, e.g., FIG. 126B and FIG. 128A) with which housing tabs 1070 of the interior housing 1008 may engage to hold the interior housing 1008 in place within the exterior housing 1004. Referring now also to FIG. 136, in some embodiments, rotation of the cartridge 1002 to the fully coupled state may actuate housing tabs 1070 of the interior housing 1008 out of engagement with the exterior housing 1004. In the example embodiment, the housing tabs 1070 each include a ramped projection 1074 which may be disposed on the medial portions of the housing tabs 1070. As best shown in FIG. 122, each housing tab 1070 may be disposed on a cantilevered arm 1076. During coupling of the cartridge 1002 to the inserter assembly 1000, a portion of the receptacle body 1060 may interact with the housing tab 1070 and deflect the cantilevered arm 1076 toward the center of the cartridge 1002. This deflection may cause the housing tab 1070 to be displaced out of the receiving slot 1072 (best shown in FIG. 126B) of the exterior housing 1004. In the example embodiment, the receptacle body 1060 includes a set of deflector members 1078 which are raised from the receptacle body 1060. The deflector members 1078 may include a ramped portion 1080. As the cartridge 1002 is rotated to the fully coupled state, the ramped portions 1080 of the deflector members 1078 may be displaced into abutment with the ramped projections 1074 of the housing tabs 1070. As further rotation occurs the deflector members 1078 may push the ramped projections 1074 out of the displacement path of the deflector members 1078 by bending the cantilevered arms 1076. In turn, this may actuate the housing tabs 1070 out of the receiving slots 1072. The exterior housing 1004 may then be separated from the set cartridge 1002.

Still referring primarily to FIG. 134, the inserter assembly 1000 may include one or more lock members 1112A, B. In the example embodiment, two lock members 1112A, B which are diametrically opposed or spaced 180° from one another are included on the inserter assembly 1000. Other embodiments may include a greater or lesser number of lock members 1112A, B. When a cartridge 1002 is coupled to the inserter assembly 1000 and the exterior housing 1004 is removed, the lock members 1112A, B may be in a state in which they project from the receptacle body 1060. When in the projecting state, the lock members 1112A, B may be positioned between a portion of the edge walls 1084 on either side of the cantilevered arms 1076. This may inhibit rotation of the interior housing 1008 of the cartridge 1002 relative to the inserter assembly 1000 as the edge walls 1084 may act as stop surfaces which present a mechanical interference blocking displacement of the lock members 1112A, B. Thus, the inserter assembly 1000 and interior housing 1008 may be locked together in the fully coupled orientation as rotational displacement of the mating pins 1050 out of the retention shoes 1068 is prevented. Sensor cartridges or lancet cartridges may similarly couple to an inserter assembly 1000.

Referring now to FIG. 141, in certain embodiments, the cartridge 1002 (or other cartridge) may couple to an inserter assembly 1000 in the same manner, but may not have the same cross sectional shape as the inserter assembly 1000. In the example shown in FIG. 141, the inserter assembly 1000 as a roughly obround cross sectional shape while the set cartridge 1002 has a substantially circular shape. In some examples, various different types of a cartridges may have differing cross sectional shapes so that they are readily differentiable upon visual inspection. Different types of cartridges may also be different colors or have different textures, surface finishes, indicia, labeling, etc. The cross-sectional shape of a cartridge 1002 may be selected such that at least some sidewalls of the cartridge 1002 are even with the exterior surface of the exterior housing 116 when the cartridge 1002 is fully coupled to the inserter assembly 1000. The cartridge 1002 may, for example, have an obround cross-sectional shape such that, when coupled to the inserter assembly 1000, the flat sides of the cartridge 1002 are even with the exterior surface of an inserter assembly 1000 (such as that shown in FIGS. 130A-B or FIGS. 131A-B).

Referring now to FIG. 142, another cross-sectional view of the inserter assembly 1000 of FIGS. 130A-130B is depicted. The inserter assembly 1000 is coupled to an example set cartridge 1002 in FIG. 142. For purposes of example, the set cartridge 1002 of FIGS. 119A-119B and FIGS. 125-126B is shown, however, other set cartridges 1002 such as any of those described herein may be used. Mating pins 1050 of the set cartridge 1002 may be retained within the retention shoes 1068 of the receptacle body 1060 of the inserter assembly 1000. The deflector members 1078 of the receptacle body 1060 have deflected the cantilevered arms 1076 of the interior housing 1008. This in turn has pushed the housing tabs 1070 out of engagement with the receiving slots 1072 of the exterior housing 1004. Thus, the exterior housing 1004 of the set cartridge 1002 may be disassociated with the set cartridge 1002 to expose the infusion set base 106.

Still referring to FIG. 142, during coupling of a set cartridge 1002 to an inserter assembly 1000, a portion of the set cartridge 1002 may displace the lock members 1112A, B from a projecting state to a retracted state. As shown in FIG. 142, the exterior housing 1004 of the set cartridge 1002 may force the lock members 1112A, B into the retracted state when the set cartridge 1002 is docked against the inserter assembly 1000. When in the retracted state, the lock members 1112A, B may permit rotation of the set cartridge 1002.

Referring now to FIG. 143, a lock member 1112A of the inserter assembly 1000 of FIG. 142 is depicted in isolation. As shown, the lock member 1112A may include a lock projection 1114 which may be the portion of the lock member 1112A which extends out of the receptacle body 1060. The lock projection 1114 may extend from a first end 1124 of a locating plate 1116 at a substantially perpendicular angle to the locating plate 1116. The locating plate 1116 may include one or more orifices 1118, 1120 which may allow the locating plate 1116 to be slid over portions of another component of the inserter assembly 1000 to hold the locating plate 1116 in a prescribed location within the inserter assembly 1000. The locating plate 1116 may slide over portions of the retraction latch body 1100 as, for example, shown in FIG. 142. A second end 1126 of the locating plate 1116 opposite the attachment point of the lock projection 1114 may be rounded.

As shown, the locating plate 1116 may include ridges 1122 which may be disposed on the sides of the locating plate 1116. Other components of the inserter assembly 1000 may also include ridges along their side edges (see e.g. the exploded views in FIGS. 130A-130B). These ridges 1122 may be provided as stiffeners which add rigidity to the lock members 1112A, B and any other components on which they are included. In some embodiments, the ridges 1122 may also help to guide or locate other components as they are displaced within an inserter assembly 1000.

As shown in FIG. 142, the lock members 1112A, B may be biased towards the projecting state. In the example, the lock members 1112A, B are disposed between a respective bias member 1104A, B and a face of the retraction latch body 1100. The rounded end 1126 of each lock member 1112A, B may allow the lock member 1112A, B to pivot as they are actuated to the retracted state. The orifices 1118, 1120 may also be dimensioned so as to allow such pivoting. When pivoted, the lock members 1112A, B may stress their associated bias member 1104A, B. Thus, when the exterior housing 1004 of the set cartridge 1002 is doffed, the lock members 1112A, B may automatically displace back to the projecting state as the bias members 1104A, B restore to their unstressed state (see, e.g. FIG. 146). This may, for example, lock an interior housing 1008 of a set cartridge 1002 in place on the inserter assembly 1000.

In alternative examples, and as shown in FIGS. 131A-131B, the lock members 1112A, B may be included on opposing ends of a single, monolithic plate 1113 which is spring biased against the receptacle body 1060 (e.g. by spring 1104). The entire plate 1113 may translate with respect to the receptacle body 1060 when the lock members 1112A, B are displaced between the projecting and retracted states. The spring bias may hold the lock members 1112A, B in a projecting state unless force is applied to the lock members 1112A, B to compress the spring 1104.

Referring now to FIG. 144, in other certain alternative embodiments (see, e.g. FIGS. 129A-129B) the lock members 1112A, B may be integrated into another component. As shown, the lock members 1112A, B are formed as projections which extend from an arcuate member 1128 which may, for example, be cantilevered to the retraction latch body 1100. When an inserter assembly 1000 including such lock members 1112A, B is assembled, the lock members 1112A, B may extend out of the receptacle body 1060 as shown in FIG. 134. When the lock members 1112A, B are displaced to the retracted state, the cantilevered arcuate members 1128 may resiliently deflect. The cantilevered arcuate members 1128 may resiliently restore to their unstressed state when, for example, the exterior housing 1004 is removed. This may cause the lock members 1112A, B to return to the projecting state and lock the interior housing 1008 in place on the inserter assembly 1000.

In still other embodiments, and referring now to FIG. 145, the lock members 1112A, B may be formed integrally with another component of the inserter assembly 1000. For example, the lock members 1112A, B may be formed as a portion of the receptacle body 1060 as shown or the interior housing 120. The lock members 1112A, B may be disposed at an end of a flexure 1115 which may be monolithically formed with the remainder of, for instance, the receptacle body 1060 (e.g. during an injection molding process). The flexures 1115 may have a resting state in which the lock members 1112A, B extend proud of the major surface 1117 of the exterior face of the receptacle body 1060. When an exterior housing 1004 of a set cartridge 1002 is pressed against the lock members 1112A, B the flexures 1115 may deform and the lock members 1112A, B may be pressed to the retracted state. The flexures 1115 may be free to restore to a less distorted state when the exterior housing 1004 is removed. As the flexures 1115 restore, the lock members 1112A, B may automatically return to their projecting state locking the interior housing 1008 in place on the receptacle body 1060. Any suitable geometry may be utilized to form the flexures 1115.

Referring now to FIG. 146, after removal of the adhesive backing 111 (see, e.g. FIG. 119A) by pulling on pull tabs 410, the set cartridge 1002 may be placed against the skin 356. The inserter assembly 1000 may then be actuated to a ready or armed state. As the storage state of the example inserter assembly 1000 is a state in which all bias members 1104A, B, 1108 are in a relaxed or unstressed state (in the example shown in FIG. 146), the inserter assembly 1000 may be actuated through a setting stage in order to place the inserter assembly 1000 in the ready state. In the setting stage, the bias members 1104A, B, 1108 of the inserter assembly 1000 may be transitioned (e.g. compressed) into a stressed state. To accomplish this, a user may press a first unit (e.g. exterior housing 116 and retainer cap 406) of the inserter assembly 1000 toward the remainder of the inserter assembly 1000 (or second unit of the inserter assembly 1000) and the skin 356. In addition to actuating the inserter assembly 1000 to the ready state, the pressure exerted by the user may help to ensure that the adhesive 374 on the infusion set base 106 is soundly adhered to the skin 356. Though FIG. 146 depicts the inserter assembly 1000 illustrated in FIGS. 130A-130B, the example inserter assembly 1000 of FIGS. 129A-129B may also be progressed through a setting stage by pressing on its exterior housing 116 and retainer cap 406. The example inserter assembly 1000 in FIGS. 131A-131B may similarly be progressed through a setting stage by pressing on the casing formed by the exterior housing 116 and the retainer cap 406. The bias members 1104, 1108 may be in a partially stressed state in the storage state and may be transitioned to a more stressed state as the inserter assembly 1000 is progressed through the setting stage.

The inserter assembly 1000 may be considered to have progressed through the setting stage and into a ready state once the first unit of the inserter assembly 1000 has been displaced at least a threshold distance to a ready position. Once progressed through the setting stage, and as described in greater detail elsewhere herein, at least one retainer may engage with at least one latch to hold the bias members 1104A, B, 1108 in a stressed state.

Referring now to FIG. 147, in the example embodiment, as the user displaces the exterior housing 116 toward the skin 356, the bias members 1108, 1104A, B (or bias member 1104 of the example shown in FIGS. 129A-129B) may begin to compress. As shown, the retainer cap 406 may include a set of standoffs 1130. The standoffs 1130 may surround a barrel 1132 of a reset body 1110 of the inserter assembly 1000. As the exterior housing 116 is displaced, the standoffs 1130 may be driven into contact with a flange 1134 of the reset body 1110. In the example embodiment, the flange 1134 is disposed in a central region of the barrel 1132 and extends substantially perpendicularly thereto. Further displacement of the exterior housing 116 may cause the standoffs 1130 to push against the flange 1134 such that the reset body 1110 moves together with the exterior housing 116. This may cause the barrel 1132 to advance along the plunger 1106 such that an increasing amount of the plunger 1106 is disposed within the bore of the barrel 1132. As bias member 1108 is captured between an end of the barrel 1132 and a flange 1136 of the plunger 1106, the advancement of the barrel 1132 over the plunger 1106 may cause the bias member 1108 to be compressed.

Referring now to FIG. 148, the example inserter assembly 1000 of FIGS. 131A-131B is depicted in a storage state. The reset body 1110 may include a locating cup 1125 for bias member 1108. The locating cup 1125 may include a central post 1127 and a surrounding cup wall 1123. Bias member 1108 may be placed in the locating cup 1125 such that the central post 1127 projects through the bias member 1108 (e.g. a compression spring) and the bias member 1108 is at least partially surrounded by the cup wall 1123. The example bias member 1108 is shown in a compressed state in FIG. 148 for ease of illustration, however, as would be understood by one of skill, the bias member 1108 would, in practice, be in a less compressed state with an end in contact with the closed end of the locating cup 1125. The retainer cap 406 may include a pin 1129 which may project into a passage 1121 (e.g. a bore extending through the length of the post 1127) defined in the locating cup 1125. As the casing is displaced toward a ready position, the retainer cap 406 may press against the closed end of the locating cup 1125 and the reset body 1110 may begin to displace in tandem with the casing. This may cause the central post 1127 to advance into the insertion driver 1062. The insertion driver 1062 may be engaged with an insertion driver latch and held substantially static during the setting stage as further described in relation to FIG. 164. The bias member 1108 may be captured between the closed end of the locating cup 1125 and a face of the insertion driver 1062. As the post 1127 is displaced into the insertion driver 1062, the bias member 1108 may become increasingly distorted. The central post 1127 may hold the bias member 1108 in place as the bias member 1108 becomes increasingly stressed.

Referring to FIG. 147-148, as the reset body 1110 is displaced, bias members 1104A, B (FIG. 147), 1104 (FIG. 148 or FIGS. 129A-129B) may also be compressed. In example embodiments, the retraction spring retainer 1102 may be coupled to the reset body 1110 such that the reset body 1110 and retraction spring retainer 1102 displace together as a unit. To illustrate this, an example reset body 1110 and retraction spring retainer 1102 are depicted coupled together and isolated from a remainder of the inserter assembly 1000 in FIG. 149. Referring to each of FIGS. 147-149, in the example embodiment, the retraction spring retainer 1102 includes a set of retainer arms 1138. The retainer arms 1138 may be cantilevered to a base 1140 of the retraction spring retainer 1102 which in the example embodiment is depicted as a planar body. Each of the retainer arms 1138 may include a protuberance 1142 disposed at an unsupported or terminal end thereof. A ledge section 1144 may be defined by a portion of each of the protuberances 1142. The flange 1134 of the reset body 1110 may include passages 1146 through which the protuberances 1142 may be displaced to couple the reset body 1110 and retainer arms 1138 via a snap fit engagement. The protuberances 1142 may include ramped portions to facilitate deflection of the retainer arms 1138 as the reset body 1110 and the retraction spring retainer 1102 are coupled to one another. When coupled together, a bottom face of the flange 1134 may rest against at least one step 1148 included on each retainer arm 1138. The retainer arm 1138 widths may change at the step 1148. The portion of the retainer arms 1138 proximal to the base 1140 with respect to the step 1148 may have a width which is greater than the width of the passages 1146. Thus, the flange 1136 may be captured between the ledge 1144 and step 1148 of each retainer arm 1138 and be unable to substantially displace relative to the ledge 1144 and step 1148. With the reset body 1110 and retraction spring retainer 1102 coupled together they may be displaced as a unit. The reset body 1110 and retraction spring retainer 1102 may be collectively referred to as a retainer herein.

Referring primarily to FIG. 147, bias members 1104A, B may be captured between the retraction spring retainer 1102 and the retraction latch body 1100. One end of the bias members 1104A, B may contact the retraction spring retainer 1102 and the other may contact the lock members 1112A, B. In the example embodiment, the bias members 1104A, B are disposed surrounding guide projections 1150 included on the retraction latch body 1100. The guide projections 1150 may thus serve as locator projections which hold the bias members 1104A, B in place within the inserter assembly 1000. The retraction spring retainer 1102 and the insertion driver 1062 may include guide apertures 1152 through which the guide projections 1150 may extend. As the user pushes down on the exterior housing 116, the retraction spring retainer 1102 may displace toward the retraction latch body 1100 along the guide projections 1150. Since the bias members 1104A, B are captured between the retraction spring retainer 1102 and the retraction latch body 1100, the advancement of retraction spring retainer 1102 may cause the bias members 1104A, B to be compressed.

With reference to FIG. 148, the retraction bias member 1104 is depicted in a compressed state. In practice, the bias member 1104 would be captured between and press against the retraction spring retainer 1102 and the plate 1113 bearing the lock members 1112A, B. The retraction spring retainer 1102 and the receptacle body 1060 each include a seat body 1105 which project toward one another. The retraction latch body 1100 and plate 1113 may include an aperture through which the seat body 1105 of the receptacle body 1060 extends. Opposing ends of bias member 1104 are seated around the seat bodies 1105. The shaft 1063 of the insertion driver 1062 may extend through the seats 1105 and be surrounded by the bias member 1104. As a user presses down on the casing, the retraction spring retainer 1102 may displace toward the retraction latch body 1100. The bias member 1104 may become compressed as the retraction spring retainer 1102 is displaced toward the retraction latch body 1100.

Referring now to FIGS. 150-151, in some embodiments, additional guide projections 1150 may be included, or guide projections 1150 may be included on another component of the inserter assembly 1000. FIG. 151 depicts a three-quarter section view (taken along line 140-140 of FIG. 150) of the example interior housing 120 of the inserter assembly 1000 shown in FIGS. 129A-129B. As shown, the interior housing 120 may include four guide projections 1150 (one is cut away) which extend from the top of the interior housing 120. The guide projections 1150 may be spaced at even angular intervals from one another though the spacing and number of guide projections 1150 may differ in alternative embodiments. The retraction spring retainer 1102 and insertion driver 1062 may have cooperating guide apertures 1152 (see, FIGS. 129A-129B) and may displace along the guide projections 1150.

Referring now to FIG. 152, as the exterior housing 116 of an inserter assembly 1000 continues to displace and the bias members 1104A, B, 1108 continue to compress, the base 1140 of the retraction spring retainer 1102 may contact latch arms 1190 of the retraction latch body 1100. As shown, the latch arms 1190 may be cantilevered from a base 1196 of the retraction latch body 1100. The latch arms 1190 may each include a first portion 1192 which is proximal to the base 1196. The first portions 1192 may, when unstressed, extend substantially perpendicular from the base 1196 and parallel to one another. Each latch arm 1190 may also include a second portion 1194 distal to the base 1196 which may be angled with respect to the first portion 1192. In the example, the second portions 1194 are angled such that distance between the latch arms 1190 increases with distance from the base 1196. A catch 1198 may be included where the second portion 1194 meets the first portion 1192 of each latch arm 1190.

Referring now to FIG. 153 (a cross-section view of a ready state of the example inserter assembly 1000 shown in FIGS. 131A-131B), in alternative embodiments, the retraction latch arms 1190 may each include a third portion 1195. The third portions 1195 may extend from the second portions 1194 and may be the segments of the latch arms 1190 most distal to the base 1196. The third portions 1195 may extend substantially parallel to one another and may be perpendicular to the base 1196. The third portions 1195 may be spaced a greater distance apart than the first portions 1192 of the latch arms 1190. A catch 1198 is provided as a step in the width of each latch arm 1190 where the first and second portions 1192, 1194 meet. A second catch 1199 is included in the third portion 1195 and may be provided as a second step in the width of each latch arm 1190. The retraction spring retainer 1102 may include variable width notches 1189 on opposing sides thereof. The latch arms 1190 may extend into the notches 1189 and the retraction spring retainer 1102 may travel along the latch arms 1190 as the inserter assembly 1000 is transitioned to the ready state and the casing is displaced to a ready position. The retraction spring retainer 1102 may be disposed between the latch arms 1190 in the storage state.

During assembly, the retraction spring retainer 1102 may be advanced between the third portions 1195 of the latch arms 1190. The latch arms 1190 may be resiliently deflected as this occurs. Further displacement of the retraction spring retainer 1102 toward the base 1196 of the retraction latch body 1100 may cause the retraction spring retainer 1102 to advance past the second catches 1199. Due to the change in width of the latch arms 1190 at the second catch 1199, the latch arms 1190 may restore into the variable width notches 1189 and the second catches 1199 may over hang portions of the base 1140 of the retraction spring retainer 1102. The bias member 1104 may press the retraction spring retainer 1102 against the second catches 1199 holding the components in place as other assembly operations are performed. Thus the second catches 1199 may be referred to herein as assembly catches 1199 and may assist in allowing an inserter assembly 1000 to be built up in various subassemblies which may later be combined.

Referring now also to FIGS. 154-156, views of the example inserter assemblies 1000 of FIGS. 129A-129B and FIGS. 130A-130B in a ready state are depicted. As the retraction spring retainer 1102 is driven into contact with the second portion 1194 of each latch arm 1190, the latch arms 1190 may be spread apart from one another as shown in, for example, FIG. 152. Once the retraction spring retainer 1102 has been displaced below the second portion 1194 of each latch arm 1190, the latch arms 1190 may resiliently restore from their spread state. The change in width of the latch arms 1190 at catches 1198 in the example shown in FIG. 153 may allow the latch arms 1190 to restore into the narrowest portions of the variable width notches 1189 of the retraction spring retainer 1102. Thus the latch arms 1190 and the retainer formed by the retraction spring retainer 1102 and reset body 1110 may form a latch arrangement in the inserter assembly 1000. When the latch arms 1190 restore to their unstressed state, the catches 1198 may overhang the base 1140 of the retraction spring retainer 1102. In turn, the catches 1198 may hold the retraction spring retainer 1102 in place with the bias members 1104A, B, 1108 compressed. The inserter assembly 1000 may then be ready to be actuated in order to drive installation of the infusion set 102 to the chosen infusion site on the patient. The exterior housing 116 and retainer cap 406 may be considered in a ready position in FIG. 153-156.

In alternative embodiments, and referring now to FIGS. 157A-D, the retraction latch arms 1190 may be arranged to pinch together or toward one another instead of spread apart as the retraction spring retainer 1102 is driven to its ready state position. An example of an inserter assembly 1000 with such retraction latch arms 1190 is cross-sectioned in the storage state in FIG. 157A. FIG. 157B depicts a perspective view of the inserter assembly 1000 in this state with the casing, interior housing 120, and receptacle body 1060 removed. Each of the insertion driver 1062 and the retraction spring retainer 1102 may respectively include a set of apertures 1061, 1103 through which the retraction latch arms 1190 extend. As shown, the tip regions of the retraction latch arms 1190 most distal the base 1196 of the retraction latch body 1100 may include a ledge 1191. The ledge 1191 may overhang the portion of the insertion driver 1062 lateral to the aperture 1061 inhibiting displacement of the insertion driver 1062 and the retraction spring retainer 1102 in the direction of the retainer cap 406 or closed end of the inserter assembly 1000. The abutment of the insertion driver 1062 against the ledge 1191 may also act similarly to assembly catches 1199 described above in relation to FIG. 153.

A cross-sectional view of the inserter assembly 1000 of FIG. 157A in the ready state is shown in FIG. 157C. FIG. 157D depicts a perspective view of the inserter assembly 1000 in the ready state with the casing, interior housing 120, and receptacle body 1060 removed. As the inserter assembly 1000 is transitioned to the ready state, the insertion driver 1062 may be held static via engagement with an inserter driver latch arrangement (further described, e.g., in relation to FIG. 164). The retainer formed by the retraction spring retainer 1102 and reset body 1110 may displace toward the open end of the inserter assembly 1000. Each of the retraction latch arms 1190 may include a catch 1193 defined on their lateral faces. A portion of the catch 1193 most distal to the base 1196 of the retraction latch body 1100 may be ramped. As the retraction spring retainer 1102 is driven into the ramped portions of the catches 1193, the retraction latch arms 1190 may be forced to deflect or pinch towards a midplane of the inserter assembly 1000. Upon reaching the ready state, the retraction spring retainer 1102 may clear the catches 1193 and the retraction latch arms 1190 may restore from the inwardly deflected state. As the retraction latch arms 1190 restore, a catch face 1197 of each catch 1193 may displace over a portion of the retraction spring retainer 1102 lateral to the aperture 1103. Thus, the retraction spring retainer 1102 may be captured by the catches 1193 holding the spring 1104 in a distorted state (note both springs 1104, 1108 are shown in a compressed state for ease of illustration). In some examples, the retraction latch arms 1190 may be molded in an exaggerated outwardly deflected state such that the retraction latch arms 1190 are deflected inward when the inserter assembly 1000 is assembled. This may create a preload which helps to hold the catches 1193 firmly engaged with the retraction spring retainer 1102 when the inserter assembly 1000 is in the ready state. When the inserter driver latch arrangement is disengaged (further described, e.g., in relation to FIGS. 164-166), the insertion driver 1062 may displace toward the open end of the inserter assembly 1000 and collide with the ramped portions of the catches 1193. This may deflect or pinch the retraction latch arms 1190 inward releasing the retraction spring retainer 1102 from engagement with the catch faces 1197 of the catches 1193 allowing a retraction stroke to occur.

Referring now to FIGS. 158 and 159, a cross-sectional view (FIG. 158) of an example inserter assembly 1000 and a detailed view (FIG. 159) of an indicated region thereof are shown. The example inserter assembly 1000 depicted is that shown in FIGS. 130A-130B. As the exterior housing 116 of the exemplary inserter assembly 1000 is pressed toward the skin 356 (see, e.g. FIG. 147) during the setting stage, release fingers 1154 extending from the retainer cap 406 may deflect around director wedges 1156 included on the interior housing 120. Each of the release fingers 1154 may be connected to a base portion 1174 of the retainer cap 406 in a cantilevered manner. At an unsupported end 1162 of each release finger 1154, a paddle body 1164 having a projection 1166 may be included. The paddle bodies 1164 may have a width greater than the remainder of the release fingers 1154. In some embodiments, the width may be 2-3 times (e.g. 2.15-2.30 or in some examples 2.25 times) the width of the rest of the release finger 1154. The paddle body 1164 may be disposed such that a center region of the paddle body 1164 is connected to the rest of the associated release finger 1154. Thus, the paddle body 1164 may include two evenly sized portions (only one is visible in the FIG. 158 cross-section) which flank the release finger 1154.

Each paddle body 1164 may include a medial face 1168 proximal to the longitudinal axis or midplane of the inserter assembly 1000 and a lateral face 1170 on a side of the paddle body 1164 opposite the medial face 1168. The projection 1166 may be disposed on the lateral face 1170 of each paddle body 1164. The projection 1166 may be centrally disposed on each paddle body 1164 such that the projection 1166 may be displaced without contacting the director wedges 1156 during actuation. The lateral face 1170 of each paddle body 1164 may include a lateral ramp portion 1172 on the flanking portions of the paddle body 1164. The lateral ramp portions 1172 may be included on a section of the paddle body 1164 most distal to the base portion 1174 of the retainer cap 406. The lateral ramp portions 1172 may slope toward the medial face 1168 as distance from the base portion 1174 of the retainer cap 406 increases. The medial face 1168 of the paddle body 1164 may also include a medial ramp portion 1176 on the flanking portions of the paddle body 1164. The medial ramp portions 1176 may be included on a portion of the paddle body 1164 most proximal to the base portion 1174 of the retainer cap 406. The medial ramp portions 1176 may slope toward the lateral face 1170 as distance to the base portion 1174 of the retainer cap 406 decreases.

Referring now also to FIG. 160, in the example embodiment, the director wedges 1156 extend from the side wall 1160 of a passage 1158 through the top of the interior housing 120 (shown in isolation in FIG. 160). The director wedges 1156 are included in pairs. The director wedges 1156 of each pair extend from opposing side walls 1160 of the passage toward one another. The director wedges 1156 include a top face 1180 which slopes toward the midplane of the inserter assembly 1000 as distance from the top of the interior housing 120 increases. The director wedges 1156 also include a bottom face 1182 which is parallel to the top face 1180. The ends of the top and bottom faces 1180, 1182 most distal to the top of the interior housing 120 may be rounded or chamfered to form a point (as shown in FIGS. 158-160). As the exterior housing 116 is displaced toward the body during the setting phase, the release fingers 1154 and paddle bodies 1164 may displace along displacement paths into which the director wedges 1156 extend. The lateral ramp portions 1172 of the paddle body 1164 of each release finger 1154 may contact the top faces 1180 of a pair director wedges 1156 during this displacement. Further displacement may cause the lateral ramp portions 1172 to slide along the top faces 1180 of the director wedges 1156. This may generate deflection of the associated release finger 1154 and movement of the projection 1166 of the paddle body 1164 toward the midplane (see, e.g., FIG. 147) of the inserter assembly 1000. The projection 1166 of the paddle body 1164 may pass through the gap between the associated pair of director wedges 1156 as this displacement occurs. Once the paddle body 1164 has been displaced below the director wedges 1156, the release finger 1154 may be free to resiliently restore to its undeflected state (see, e.g., FIG. 152).

As will be described in greater depth later in the specification, the exterior housing 116 may be displaced relative to the interior housing 120 in the opposite direction to fire the inserter assembly 1000. As this occurs, the medial ramp portions 1176 of the paddle body 1164 of each release finger 1154 may contact the bottom face or underside 1182 of the associated director wedges 1156. Further displacement may cause the medial ramp portion 1176 to slide along the underside 1182 of the director wedges 1156. This may generate deflection of the release finger 1154 and projection 1166 of the paddle body 1164 away from the midplane of the inserter assembly 1000. The projection 1166 of the paddle body 1164 may pass through the gap between the associated pair of director wedges 1156 as the exterior housing 116 is displaced.

As the release fingers 1154 are deflected away from the midplane of the inserter assembly 1000, the projections 1166 may deflect toward cantilevered arms 1184 on the insertion driver 1062. The arms 1184 may form resilient projections which may deflect if sufficient force is exerted against them. The unsupported end of the arms 1184 may include a curved or ramped section. A notch or pair of notches 1188 may also be present on each of the cantilevered arms 1184. In the example, each arm 1184 includes a pair of notches 1188 located near the unsupported ends of the arms 1184. The notches 1188 may be disposed similarly to the notches 342 shown in FIG. 71 for example. Each of the one or more notches 1188 may engage with a cooperating projection 1200. The cooperating projection 1200 may be included on the interior housing 120 and may project from the side wall 1160 of the passage 1158 through the top of the interior housing 120. The interaction of the notch(es) 1188 and cooperating projection(s) 1200 may maintain the bias member 1108 under compression and serve as an insertion prevention latch or insertion driver latch.

With the release fingers 1154 deflected toward the arms 1184, further displacement of the exterior housing 116 away from the skin 356 may cause the projections 1166 on the paddle bodies 1164 to collide with protrusions 1202 on the cantilevered arms 1184. This may dislodge the notches 1188 of the cantilevered arms 1184 from cooperating projections 1200 of the interior housing 120. Thus, once the first unit of the inserter assembly 1000 (e.g. exterior housing 116 and retainer cap 406) has been pulled away from the remainder of the inserter assembly 1000 (second unit of the inserter assembly 1000) beyond a threshold distance (which may be measured from the ready position), the insertion driver 1062 may be dislodged from the insertion driver latch. This may free the spring 1108 to transition to its unstressed state and displace the insertion driver 1062 toward the skin 356. As the spring 1108 transitions from its stressed state to a relaxed state, the inserter driver 1062 may displace from its stowed state to an extended position in which at least a portion of the insertion driver 1062 projects out of the inserter assembly 1000 and into the cartridge 1002. As shown in best in FIG. 160, a ridge 1201 which blocks displacement of the cantilevered arms 1184 may be included medial to each of the cooperating projections 1200. This may help to ensure that the cantilevered arms 1184 may only be released from the cooperating projections 1200 when intended by the user.

Referring now to FIG. 161, a cross section of the inserter assembly 1000 shown in FIGS. 129A-129B is depicted. In some embodiments, and as shown in FIG. 161, the release fingers 1154 may be disposed outboard (with respect to the midplane) as opposed to inboard (see e.g. embodiment of FIGS. 130A-130B) of the cantilevered arms 1184 of the insertion driver 1062. In such embodiments, to be displaced off their respective cooperating projections 1200 of the interior housing 120, they may be displaced toward the midplane of the inserter assembly 1000. In such embodiments, the standoffs 1130 included on the retainer cap 406 may include an enlarged section 1131. The enlarged sections 1131 may block the cantilevered arms 1184 from being dislodged until the inserter assembly 1000 has been withdrawn from the skin 356 more than a certain amount.

Referring also to FIG. 162B, a detailed view of the indicated region of FIG. 162A, the release fingers 1154 may have paddle bodies 1164 configured to deflect the release fingers 1154 in opposite directions to those described in relation to FIGS. 158-160. Each paddle body 1164 may include a medial face 1168 proximal to the longitudinal axis or midplane of the inserter assembly 1000 and a lateral face 1170 on a side of the paddle body 1164 opposite the medial face 1168. A projection 1166 may be disposed on the medial face 1170 of each paddle body 1164. The projection 1166 may be centrally disposed on each paddle body 1164 such that the projection 1166 may be displaced without contacting the director wedges 1156 during actuation. The lateral face 1170 of each paddle body 1164 may include a lateral ramp portion 1172 on the flanking portions of the paddle body 1164. The lateral ramp portions 1172 may be included on a section of the paddle body 1164 most proximal to the base portion 1174 (see, e.g., FIG. 162A) of the retainer cap 406. The lateral ramp portions 1172 may slope toward the medial face 1168 as distance from the base portion 1174 of the retainer cap 406 decreases. The medical face 1168 of the paddle body 1164 may also include a medial ramp portion 1176 on the flanking portions of the paddle body 1164. The medial ramp portions 1176 may be included on a portion of the paddle body 1164 most distal from the base portion 1174 of the retainer cap 406. The medial ramp portions 1176 may slope toward the lateral face 1170 as distance to the base portion 1174 of the retainer cap 406 increases.

As the exterior housing 116 is pressed toward the skin 356 during the setting stage, the medial ramped portions 1176 may deflect the paddle bodies 1164 of the release fingers 1154 outwardly around the director wedges 1156. As the inserter assembly 1000 is lifted from the skin 356 to trigger insertion, the lateral ramped portions 1172 may deflect the release fingers 1154 inwardly around the director wedges 1156 and towards the cantilevered arms 1184. With the release fingers 1154 deflected toward the arms 1184, further displacement of the exterior housing 116 away from the skin 356 may cause the projections 1166 on the paddle bodies 1164 to collide with protrusions 1202 on the cantilevered arms 1184. This may dislodge the notches 1188 (described above) of the cantilevered arms 1184 from cooperating projections 1200 (described above) of the interior housing 120. This may free the spring 1108 to transition to its unstressed state and displace the insertion driver 1062 toward the skin 356.

A cut away view (taken at the indicated cut line of FIG. 163) of the example inserter assembly 1000 of FIGS. 131A-131B is depicted in FIG. 152. In embodiments such as the inserter assembly 1000 shown in FIGS. 131A-131B, no director wedges 1156 (see, e.g., FIG. 160) may be included. Projections 1166 (see, e.g., FIG. 159) on paddle bodies 1164 may also be omitted. The cantilevered arms 1184 (only one shown in the cutaway view of FIG. 164) may include a catch body 1185 at their unsupported ends. The catch bodies 1185 may engage with respective latches included as part of the interior housing 120. Interaction of the catch bodies 1185 with these latches may form an insertion prevention latch arrangement or insertion driver latch arrangement. The interior housing 120 may, for example, include shelves 1187 upon which the catch bodies 1185 engage. When the catch bodies 1185 are latched in place on the insertion driver latches of the interior housing 120, the insertion driver 1062 may be inhibited from displacing toward the receptacle body 1060. As the casing is displaced toward the skin 356 (see, e.g., FIG. 167) and to the ready position during the setting stage, the insertion driver 1062 may be held substantially static in its initial position as the reset body 1110 and the retraction spring retainer 1102 are displaced toward their ready state positions. Such an insertion driver latch arrangement may also be provided in the inserter assembly depicted and described in relation to FIGS. 157A-D. Thus, the bias members 1104, 1108 may both be increasingly distorted as the inserter assembly 1000 is brought to the ready state. With the insertion driver 1062 engaged with the insertion driver latch, both of the bias members 1104, 1108 may be held in a distorted state once the retraction spring retainer 1102 enters into engagement with the catches 1198 of the latch arms 1190 (see, e.g., FIG. 153).

Referring now also to FIGS. 165-166, the retainer cap 406 may include opposing sets of release fingers 1154 projecting from sides of the base 1174 of the retainer cap 406. The unsupported ends 1162 of each release finger 1154 may include a paddle body 1164. Each paddle body 1164 may include a medial face 1168 proximal to the midplane of the inserter assembly 1000 and a lateral face 1170 on a side of the paddle body 1164 opposite the medial face 1168. The lateral face 1170 of each paddle body 1164 may include a lateral ramp portion 1172 on the flanking portions of the paddle body 1164. The lateral ramp portions 1172 may be included on a section of the paddle body 1164 most distal to the base portion 1174 of the retainer cap 406. The lateral ramp portions 1172 may slope toward the medial face 1168 as distance from the base portion 1174 of the retainer cap 406 increases. The medial face 1168 of the paddle body 1164 may also include a medial ramp portion 1176 on the flanking portions of the paddle body 1164. The medial ramp portions 1176 may be included on a portion of the paddle body 1164 most proximal to the base portion 1174 of the retainer cap 406. The medial ramp portions 1176 may slope toward the lateral face 1170 as distance to the base portion 1174 of the retainer cap 406 decreases. Such a retainer cap 406 may be included in the example inserter assembly embodiment 1000 depicted in FIGS. 157A-D.

The cantilevered arms 1184 of the insertion driver 1062 may include routing bodies or fins 1183. The routing fins 1183 may project from opposing sides of each arm 1184 at a point intermediate the catch body 1185 and the attachment points of the arms 1184 to the remainder of the insertion driver 1062. The routing fins 1183 may be disposed substantially perpendicular to the long axis of each arm 1184 and may be in the displacement path of at least a portion of the paddle bodies 1164 as the casing is displaced relative to the rest of the inserter assembly 1000. Each routing fin 1183 may include a medial face 1171 proximal to the midplane of the inserter assembly 1000 and a lateral face 1173 on a side of the routing fin 1183 opposite the medial face 1171. The lateral face 1173 of each routing fin 1183 may include a lateral ramp portion 1175. The lateral ramp portions 1175 may be included on a section of the routing fin 1183 most distal to the catch bodies 1185. The lateral ramp portions 1175 may slope toward the medial face 1171 as distance from the respective catch body 1185 of the arm 1184 increases. The medial face 1171 of the routing fin 1183 may also include a medial ramp portion 1177. The medial ramp portions 1177 may be included on a portion of the routing fin 1183 most proximal to the catch body 1185. The medial ramp portions 1177 may slope toward the lateral face 1173 as distance to the catch body 1185 decreases. Such fins 1183 may also be included on the insertion driver 1062 of the inserter assembly 1000 depicted in FIGS. 157A-D.

As the exterior housing 116 and retainer cap 406 are displaced toward the body during the setting phase, the release fingers 1154 may hold the insertion driver 1062 in engagement with the insertion driver latches. The release fingers 1154 may deflect around the routing fins 1183 and the resiliency of the release fingers 1154 may lead the release fingers 1154 press against the routing fins 1183 in a setting direction. This may press against the routing fins 1183 in a manner which reinforces the engagement of the catch bodies 1185 with the insertion driver latches. The wall of the interior housing 120 may inhibit deflection of the cantilevered arms 1184 as this occurs.

For example, the paddle bodies 1164 may displace along displacement paths into which the routing fins 1183 extend. The lateral ramp portions 1172 of the paddle body 1164 of each release finger 1154 may contact the medial ramped portions 1177 of respective routing fins 1183 during this displacement. Further displacement may cause the lateral ramp portions 1172 to slide along the medial ramped portions 1177 of the routing fins 1183 resulting in deflection of the associated release finger 1154 toward a midplane of the inserter assembly 1000. Due to the resiliency of the material forming the release fingers 1154, the deflected release fingers 1154 may press the cantilevered arms 1184 outward against the interior face of the internal housing 120 as the paddle bodies 1164 of each release finger 1154 pass along the routing fins 1183. This may tend to hold the catch bodies 1185 in engagement with the shelves 1187 on the interior housing 120 inhibiting movement of the insertion driver 1062 during this portion of the setting phase. Once the paddle body 1164 has been displaced below the routing fin 1183, the release finger 1154 may be free to resiliently restore to its undeflected state (see, e.g., FIG. 164).

As will be described in greater depth later in the specification, the exterior housing 116 and retainer cap 406 may be displaced relative to the interior housing 120 in the opposite direction to a trigger position to fire the inserter assembly 1000. As this occurs, the release fingers 1154 may collide with the routing fins 1183 and the release fingers 1154 may press in a release direction on the routing fins 1183 resulting in deflection of the cantilevered arms 1184. This may disassociate the insertion driver 1062 from the insertion driver latches. The interior housing 120 may inhibit deflection of the release fingers 1154 as the casing is displaced toward the trigger position.

For example, the medial ramp portions 1176 of the paddle body 1164 of each release finger 1154 may contact the lateral ramped portion 1175 of respective routing fins 1183 as the casing is displaced toward the trigger position. Further displacement may cause the medial ramp portion 1176 to slide along the lateral ramped portions 1175 of the routing fins 1183. As the interior surface of the interior housing 120 may prohibit deflection of the release fingers 1154 in an outward direction, this further displacement may force the cantilevered arms 1184 to deflect toward a midplane of the inserter assembly 1000 to permit passage of the paddle bodies 1164 between the interior housing 120 and lateral faces 1173 of the routing fins 1183.

As the interior housing 120 prevents outward deflection of the release fingers 1154, greater freedom adjusting the stiffness and flexibility of the release fingers 1154 may be allotted. Similarly, a greater range of stiffnesses and flexibilities may be available for the cantilevered arms 1184. The stiffness of the release fingers 1154 may be relatively low so as to allow the release fingers 1154 to easily deflect toward the midplane of the inserter assembly 1000 during the setting stage. A relatively low stiffness of the release fingers 1154 or increased stiffness of the cantilevered arms 1184, however, may not hinder reliable firing of the inserter assembly 1000. Since the release fingers 1154 are constrained from outward deflection by the interior housing 120 during the triggering movement of the casing, the cantilever arms 1184 are forced to deflect to disengage the insertion prevention latch arrangement as the casing is displaced.

Referring primarily to FIG. 164, the interior housing 120 may also define stop bodies 1179. The stop bodies 1179 may block displacement of outboard portions of the paddle bodies 1164 as the casing is displaced away from the skin 356 (see, e.g., FIG. 167). The stop bodies 1179 may also prevent disassociation of the casing from the interior housing 120. The stop bodies 1179 may include a sloped surface nearest the retainer cap 406. This surface may interact with the medial ramped portion 1776 of the paddle bodies 1164 during assembly to assist in deflecting the release fingers 1154 as the casing is assembled.

Referring to FIGS. 164-166, in various examples, as the cantilevered arms 1184 are deflected toward the midplane of the inserter assembly 1000, the catch bodies 1185 may be disengaged from the interior housing 120. The catch bodies 1185 may, for example, be slid off the shelves 1187 in the example embodiment shown in FIG. 164. Thus, once the first unit of the inserter assembly 1000 (e.g. exterior housing 116 and retainer cap 406) has been pulled away from the remainder of the inserter assembly 1000 (second unit of the inserter assembly 1000) beyond a threshold distance (which may be measured from the ready position) to a trigger position, the insertion driver 1062 may be dislodged from the insertion driver latch. This may free the spring 1108 (see, e.g., FIG. 153) to transition to its unstressed state and displace the insertion driver 1062 toward the skin 356. As the spring 1108 transitions from its stressed state to a relaxed state, the inserter driver 1062 may displace from its stowed state to an extended position in which at least a portion of the insertion driver 1062 projects out of the inserter assembly 1000 and into the cartridge 1002.

As shown, for example, in FIG. 167 (a cross-section of the inserter assembly 1000 of FIGS. 130A-130B), actuation of an inserter assembly 1000 may be triggered as the inserter assembly 1000 is lifted up from the skin 356 so as to be removed from the patient. No other depression, twisting, squeezing, etc. of a trigger, button, housing sleeve or other portion of an inserter assembly 100 by a user may be needed to provoke the actuation, however, the actuation may still be under the control of the user. In alternative embodiments, and as discussed elsewhere herein, a discrete manual triggering action may be employed to trigger actuation of an inserter assembly 1000. Where triggering occurs automatically as the inserter assembly 1000 is withdrawn from the skin 356, relative movement of the free component(s) of the inserter assembly 1000 with respect to the restricted component(s) may trigger actuation. As described above, actuation may be triggered by, for example, displacing or dislodging a latch and freeing one or more bias members to begin driving actuation. Thus, one or more trigger internal to the inserter assembly 1000 may be actuated as a result of the removal action of the inserter assembly 1000 from the body. From the perspective of a user, such an inserter assembly 1000 may simply be placed on the skin 356 and then withdrawn to execute placement of the infusion set 102. This may be advantageous for a number of reasons which are detailed elsewhere in the specification.

FIG. 167 depicts the example inserter assembly 1000 of FIGS. 130A-130B coupled set cartridge 1002 and as it is being withdrawn from the skin 356. As shown, the adhesive 374 on the infusion set base 106 may adhere to the skin 356 resulting in the skin 356 being tugged upward as the inserter assembly 1000 and set cartridge 1002 are withdrawn. The exterior housing 116 and retainer cap 406 may displace together as a unit with the hand of the user as the user removes the inserter assembly 1000 from their body. This may also be true of the exterior housing 116 and retainer cap 406 of the example inserter assembly 1000 shown in FIGS. 129A-129B and FIGS. 131A-131B. The other components of the example inserter assemblies 1000 and set cartridges 1002 may not be constrained to displace as a unit with the exterior housing 116 and retainer cap 406. These components may form a second unit which maybe held behind, unable to displace relative to the patch of skin 356 adhered to the adhesive 374. In certain embodiments, a disarm lock may be included to prevent relative displacement of the first and second units (see, e.g., FIGS. 174A-175B and related description). In such embodiments, a disarming lock or actuator may allow a user to remove the inserter assembly 1000 and set cartridge 1002 without placement of the infusion set 102 (e.g. user desires to place the infusion set 102 at a different site).

During removal of the inserter assembly 1000 and set cartridge 1002, the exterior housing 116 and retainer cap 406 may displace away from the skin 356 substantially along the axis of the insertion sharp 132. This displacement relative to the other components may cause the release fingers 1154 to deflect towards the cantilevered arms 1184 of the insertion drive 1062 as described above. Alternatively, as described in relation to the inserter assembly 1000 of FIGS. 131A-131B (see, e.g., discussion relating to FIG. 164), this displacement may case the cantilevered arms 1184 to deflect and disengage an insertion prevention latch arrangement. Depending on the embodiment, the resiliency of release fingers 1154 or cantilevered arms 1184 may cause the entire inserter assembly 1000 and set cartridge 1002 to move together for at least a portion of the inserter assembly 1000 withdrawal motion from the skin 356. During this portion of the removal action of the inserter assembly 1000, the skin 356 may be lifted off underlying body structures. Portions of the inserter assembly 1000 may again displace relative to one another once the force exerted by the elasticity of the skin exceeds a force threshold and the release fingers 1154 fully deflect around the deflector wedges 1158 or routing fins 1183 depending on the embodiment.

Referring now to FIG. 168, as the exterior housing 116 and retainer cap 406 continue to displace relative to the rest of the inserter assembly 1000 and set cartridge 1002, the cantilevered arms 1184 of the insertion driver 1062 may be dislodged off the associated cooperating projections 1200 (or shelves 1187, see, e.g., FIG. 164) of the interior housing 120. As described above with respect to FIGS. 158-160 or FIGS. 161-162B, this may be caused by the projections 1166 of the paddle bodies 1164 on the release fingers 1154 colliding with protrusions 1202 at the unsupported ends of the cantilevered arms 1184. Alternatively and as described above with respect to FIG. 164, this may be caused by paddle bodies 1164 on the release fingers 1154 wedging the catch bodies 1185 of the cantilevered arms 1184 out of engagement with the interior housing 120. In certain examples a disarm lock may be included and may block deflection the cantilevered arms 1184 of the respective embodiment (see, e.g., FIGS. 176-177B). This may allow a user to remove the inserter assembly 1000 and set cartridge 1002, without placing the infusion set 102.

Referring now to FIG. 169, with the cantilevered arms 1184 freed from engagement with the interior housing 120, this may allow the bias member 1108 between the reset body 1110 and the plunger 1106 to transition to its uncompressed state. As the bias member 1108 transitions to its relaxed state, the plunger 1106 and insertion driver 1062 (or alternatively, solely the insertion driver 1062, see, e.g., FIG. 48) may be propelled towards the skin 356. As the sharp holder 130 is coupled into the port 1064 of the insertion driver 1062, the sharp holder 130 and cannula subassembly 114 coupled thereto may also be shot towards the skin 356 along an insertion path. As shown in FIG. 169, which depicts the inserter assembly 1000 of FIGS. 130A-130B for sake of example, the insertion sharp 132 and cannula 104 have just punctured through the skin 356. During puncture, the skin 356 may still be in a state in which it is tugged up away from muscle and other underlying body structures. The cannula subassembly 114 has begun to be advanced toward the infusion set base 106 as well. Also as shown, the retainer cap 406 of the inserter assembly 1000 may include one or more stop arms 1204 which prevent relative movement beyond a certain point between the interior housing 120 and the casing formed by the exterior housing 116 and retainer cap 406. The stop arms 1204 may catch on a portion of the top of the interior housing 120 inhibiting further relative displacement. The stop arms 1204 may be engaged as the insertion of the cannula 104 begins or is in progress. In alternative embodiments, and as described above in relation to FIG. 164, stop arms 1204 may be omitted and the paddle bodies 1164 may include outboard portions which engage with stop bodies 1179 defined in the interior housing 120. Thus, additional lifting of the skin 356 may occur during the cannula 104 insertion movement.

In some embodiments, a bias member may be included such that the stop arms 1204 must compress the bias member prior to the cantilevered arms 1184 of the insertion driver 1062 being dislodged from the cooperating projections 1200. This may aid in further lifting the skin 356 before insertion is triggered. In some embodiments, the portions of the interior housing 120 which the stop arms 1204 contact or on which stop bodies 1179 are disposed may be resiliently cantilevered in the path of the stop arms 1204 or paddle bodies 1164 respectively. Thus, as the inserter assembly 1000 is withdrawn, the cantilevered portions of the interior housing 120 may be deflected by the stop arms 1204 or paddle bodies 1164 before the cantilevered arms 1184 are dislodged. The resiliency of these cantilevered portions may be chosen to ensure that the skin is lifted at least a certain amount. In other embodiments, springs (e.g. compression springs, leaf type springs, etc.) may be placed in the path of the stop arms 1204 or paddle bodies 1164. These springs may need to be brought to a stressed state via displacement of the stop arms 1204 or paddle bodies 1164 before the cantilevered arms 1184 are released. Again, the springs may be chosen such that at least a desired amount of skin lifting occurs prior to the cantilevered arms 1184 being freed from the cooperating projections 1200 or disengaged from shelves 1187 of the interior housing 120.

Referring now to FIG. 170, another cross sectional view of an example inserter assembly 1000 and set cartridge 1002 are shown. As shown, the spring 1108 has restored to a relaxed state and completed the insertion movement of the sharp holder 130, insertion sharp 132, and cannula subassembly 114 toward the skin 356. The relaxed state may be a completely relaxed state or a comparatively relaxed state where the spring 1108 is still exerting some pressure against the sharp holder 130 to prevent it from jostling about. Similarly to as shown in FIG. 77B, a notch 184 of the cannula subassembly 114 may be in engagement with a protuberance 182 of the infusion set base 106 locking the cannula subassembly 114 in place and completing assembly of the infusion set 102. As shown, when the cannula subassembly 114 latches into the base 106, the ears 204 on the cannula subassembly 114 may press against the nubs 1026 included on the retainer arms 1016. This may cause the retainer arms 1016 to be splayed apart resulting in disengagement of the retainer arms 1016 from the infusion set base 106. Thus, the assembled infusion set 102 may be installed at the infusion site and released from the set cartridge 1002.

As also shown in FIG. 170, the insertion driver 1062 may collide with the latch arms 1190 of the retraction latch body 1100 as the now assembled infusion set 102 is released. This collision may cause the latch arms 1190 to spread apart freeing the retraction spring retainer 1102 from engagement with the catch 1198 of the latch arms 1190. Thus, FIG. 170 depicts the inserter assembly 1000 at a retraction release state. The example inserter assembly 1000 of FIGS. 129A-129B is shown in the retraction release state in FIGS. 171A-171B. The example inserter assembly 1000 of FIGS. 131A-131B would also free the retraction spring retainer 1102 from engagement with the latch arms 1190 as a result of the insertion driver 1062 colliding with the latch arms 1190. In certain embodiments, (see, e.g. FIGS. 157A-D) the latch arms 1190 may be pinched together as opposed to spread in order to free the retraction spring retainer 1102.

In some embodiments, inserter assemblies 1000 may include a disarming actuator which may be displaced to drive the latch arms 1190 out of engagement with the retraction spring retainer 1102 (see, e.g., FIGS. 178A-183B). This may allow an inserter assembly 1000 and set cartridge 1002 to be removed from a user without placement of an infusion set 102.

In some examples, there may be a dwell period where retraction of the insertion sharp 132 has been triggered and the retraction spring retainer 1102 is displacing, however, the insertion sharp 132 remains substantially static. During this dwell period, spring 1108 may continue to exert pressure on the cannula subassembly 114 through the sharp holder 130. This may block any possible tendency of the cannula subassembly 114 to bounce or rebound as it is propelled into the infusion set base 106 and ensure it is firmly retained in the base 106. Referring to FIG. 153, there is a short span of retraction latch arm 1190 intermediate the catches 1198 of the arms 1190 and the proximate ends of the second portions 1194 of retraction latch arms 1190. The insertion driver 1062 may free retraction spring retainer 1102 from the latch arms 1190 after reaching the end of the second portions 1194 of the latch arms 1190. Bias member 1104 may begin to restore to a less distorted state displacing the retraction spring retainer 1102 in a retraction direction. Due to the presence of the above mentioned short span, there will be a small gap between the base 1140 of the retraction spring retainer 1102 and the plate 1057 of the insertion driver 1062 when the retraction spring retainer 1102 is freed. The insertion driver 1062 will not begin to retract until this gap has been closed in the initial moments of the retraction process.

Referring now to FIG. 172, with the retraction spring retainer 1102 freed from the catches 1198, the bias members 1104A, B (or bias member 1104 for the inserter assembly 1000 of FIGS. 129A-129B, FIGS. 131A-131B, and FIGS. 157A-D) may transition to their unstressed state driving the retraction spring retainer 1102 toward the retainer cap 406 of the exterior housing 116. As a portion of the insertion driver 1062 is between the retraction spring retainer 1102 and the retainer cap 406, the insertion driver 1062 may also be displaced along with the retraction spring retainer 1102 as the bias members 1104A, B relax. Since the sharp holder 130 is coupled to the insertion driver 1062, displacement of the insertion driver 1062 may cause the insertion sharp 132 to be removed from the skin 356 and retracted back into the set cartridge 1002. With reference to the embodiment in FIG. 164, the catch bodies 1185 of the insertion driver 1062 of FIGS. 131A-131B (and FIGS. 157A-D) may re-engage with the shelves 1187 of the interior housing 120 as the bias member 1104 relaxes.

In certain alternative embodiments, retraction of the insertion sharp 132 may not be automatic and/or may not be spring biased. For example, the insertion sharp 132 may remain in the advanced position and the removal action of the user may manually pull the insertion sharp 132 out of the cannula 104. In such embodiments, bias members 1104A, B (or bias member 1104 depending on the embodiment) may be omitted. In some embodiments, a button press or similar interaction may be required to trigger a spring biased retraction of the insertion sharp 132.

Referring now to FIG. 173, the exterior housing 1004 is shown separated from the remainder of a spent set cartridge 1002 which is installed on an inserter assembly 1000. Once the infusion set 102 is installed at the desired infusion site, the exterior housing 1004 may be used as a removal and containment tool for the spent set cartridge 1002. As shown, the cantilevered arms 1076 of the interior housing 1008 may be recessed with respect to the external face 1082 of the interior housing 1008. A recess edge wall 1084 may be present on each side of the cantilevered arms 1076. The exterior housing 1004 may include a set of stops 1086 which may fit within the recesses formed in the interior housing 1008. After insertion of the infusion set 102, the exterior housing 1004 may be slid over the interior housing 1008 and the spent set cartridge 1002 may be rotated to an uncoupled state. The stops 1086 may catch against the recess edge walls 1084 and ensure that the interior housing 1008 rotates in tandem with the exterior housing 1004. Referring now also to FIG. 134, this may displace the ramped projections 1074 of the housing tabs 1070 out of abutment with the deflector members 1078 of the receptacle body 1060. Due to the resiliency of the cantilevered arms 1076, the housing tabs 1070 may restore back into engagement with the receiver slots 1072 in the exterior housing 1004. The spent set cartridge 1002 may then be removed from the inserter assembly 1000.

After use, the exterior housing 1004 may serve as a containment for the remaining components of the spent set cartridge 1002. This may ensure that the used insertion sharp 132 is enclosed within the set cartridge 1002. Thus, the point of the insertion sharp 132 may be inaccessible to the user. The engagement of the housing tabs 1070 with the receiver slots 1072 may lock the insertion sharp 132 within the spent set cartridge 1002. In certain embodiments, placement of the infusion set 102 on the infusion site via the inserter assembly 1000 may be performed with one hand. Thus, after removing the exterior housing 1004, the user may be encouraged to hold the exterior housing 1004 in their free hand as the infusion set 102 is applied with the inserter assembly 1000. The user may then remove the spent set cartridge 1002 by reattaching the exterior housing 1004 to the interior housing 1008 and separating the set cartridge 1002 from the inserter 1000. Occupying both hands of the user during the process may aid in limiting opportunity for a user to inadvertently come into contact with the insertion sharp 132.

Referring now to FIGS. 174A-183B, in certain examples, various inserter assemblies 1000 depicted herein may include a lock or actuator which may be engaged or displaced to disarm an inserter assembly 1000. For purposes of example, disarming locks 1298 and actuators 1310 are depicted in relation to the example embodiment of FIGS. 131A-B, though may be incorporated into the other embodiments of inserter assemblies 1000 described herein. Such disarming locks 1298 and actuators 1310 may allow for a user to place the adhesive 374 in contact with the skin 356 and subsequently remove the inserter assembly 1000 without triggering it. This may be true even if the inserter assembly 1000 has been brought to an armed or ready state by the user. Depending on the embodiment, the inserter assembly 1000 may be maintained in the ready state or may be transitioned from the ready state to the storage state by a disarming lock 1298 or disarming actuator 1310. Thus, if a user desires to place an infusion set 102 at another location or otherwise decides they do not want to place an infusion set 102 at a particular site, the inserter assembly 1000 may be separated from the user without consuming the set cartridge 1002.

For inserter assemblies 1000 where actuation to place an infusion set 102 is triggered as a result of relative displacement of a first unit (e.g. casing) and second unit or the inserter assembly 1000, example disarming locks 1298 may be transitioned from an inactive state to an activated state in which they inhibit this displacement. In other embodiments, example disarming locks 1298 may prevent an insertion prevention latch arrangement or insertion driver latch arrangement from being disengaged. Again, such disarming locks 1298 may be actuated from an inactive state to an activated or disarming state in which this disengagement is inhibited.

In still other examples, a disarming actuator 1310 may be displaced by a user to trigger retraction of the retraction latch retainer 1102 and reset body 1110. For example, a disarming actuator 1310 may be displaced to an actuated state to drive the retraction latch arms 1190 out of engagement with the retraction spring retainer 1102. In some embodiments, this may be accomplished while preventing the insertion driver 1062 of the inserter assembly 1000 from being released from an insertion driver latch arrangement. In other examples, the retraction spring retainer 1102 may be released via displacement of the disarming actuator 1310 prior to disengagement of the insertion driver latch arrangement. In such examples, the insertion driver latch arrangement may be released and the insertion driver 1062 may displace toward an insertion position, however, movement of the insertion driver 1062 may be halted and reversed by the retraction stroke of the retraction spring retainer 1102. This may occur before the insertion driver 1062 displaces a distance sufficient for a user to come into contact with any insertion sharp 132 coupled to the insertion driver 1062. Likewise, displacement of the insertion driver 1062 may be halted and reversed by the retraction stroke of the retraction spring retainer 1102 prior to release of the infusion set base 102 from the retainer arms 1016 of the set cartridge 1002 (see, e.g., FIG. 170).

Referring now to FIGS. 174A-175B, example embodiments of inserter assemblies 1000 with disarming locks 1298 are depicted. As shown, the exterior housings 116 may include at least one button 1300. The at least one button 1300 may be displaceable relative to the remainder of the exterior housing 116. Though any suitable button 1300 may be used, in various examples, the button 1300 may be formed as a monolithic part of the exterior housing 116 during molding. In the examples shown, the buttons 1300 are cantilevered from the remainder of the exterior housing 116. The buttons 1300 may deflect into apertures 1302 included in the exterior housing 116 in response to force applied to the buttons 1300 by a user. Buttons 1300 may include thumb or finger press surfaces 1304 to facilitate use of the buttons 1300. Though each embodiment includes a set of buttons 1300 on opposing sides of the inserter assembly 1000, alternative embodiments may only include a single button 1300.

The interior housing 120 may include respective windows 1306 for each button 1300. The windows 1306 may align with the displacement paths of at least a portion of the respective buttons 1300 when the inserter assembly 1000 is in a ready state. To utilize the disarming lock 1298, at least one of the buttons 1300 may be displaced at least partially into the window 1306 in the interior housing 120. Thus, as the casing of the inserter assembly 1000 is pulled in a direction away from the skin 356, relative displacement of the first unit or casing of the inserter assembly 1000 relative to the remainder or second unit of the inserter assembly 1000 may be blocked by the presence of the button 1300 within the window 1306. As the first and second unit of the inserter assembly 1000 are inhibited from displacing relative to one another, the inserter assembly 1000 may be pulled until the adhesive 374 disengages the skin 356 without triggering actuation of the inserter assembly 1000. The inserter assembly 1000 may remain in the ready state as this occurs. When a user releases a button 1300, the button 1300 may automatically restore to an unobstructing, resting position. Thus, the inserter assembly 1000 may easily be used again as desired without further user interaction. Alternatively, the button 1300 may snap into engagement with the interior housing 120 as the button 1300 is driven into the window 1306. The user may pry against the press surfaces 1304 to dislodge the button 1300 out of engagement with the interior housing 120 when it is desired to use the inserter assembly 1000 again. Though described in relation to reusable inserter assemblies 1000 described herein, it should be understood that the disarming locks 1298 shown in FIGS. 174A-175B may be included in the various example embodiment of inserter assemblies 100 described above.

Referring now to FIGS. 176A-176C, various views of another example embodiment of an inserter assembly 1000 with an example disarming lock 1298 are depicted. The inserter assembly 1000 is depicted in the ready state in FIGS. 176A-176C. As shown, the disarming lock 1298 may include a base 1350 from which a set of barrier bodies 1352 project. The retainer cap 406 of the inserter assembly 1000 may include a corresponding set of arced apertures 1358 through which the barrier bodies 1352 may be advanced into the inserter assembly 1000. As shown, the barrier bodies 1352 include a stem portion 1354 and a barrier segment 1356 at the end of the stem portion 1354 most distal to the base 1350. When installed in the inserter assembly 1000, the stem portions 1354 of the barrier bodies 1352 may be disposed within the apertures 1358. The disarming lock 1298 may be rotated and the stem portions 1354 may traverse within the apertures 1358 as this occurs. The rotational displacement range of the disarming lock 1298 may be defined by the ends of the apertures 1358.

The position of the apertures 1358 may constrain the disarming lock 1298 to be installed into the inserter assembly 1000 in a first position which may be an inactive position (FIG. 176B). In the inactive position, the disarming lock 1298 may not interfere with normal operation of the inserter assembly 1000. The disarming lock 1298 may be rotated to a second or disarm position (FIG. 176C). In the disarm position, the barrier segments 1356 of the barrier bodies 1352 may be swung into a position in which they are disposed between the cantilevered arms 1184 of the insertion driver 1062 and the cup wall 1123 of the locating cup 1125 of the reset body 1110. The presence of the barrier bodies 1352 may block the cantilevered arms 1184 from displacing in a medial direction. The sidewall of the interior housing 120 with which the cantilevered arms 1184 are be engaged may block outward or lateral displacement of the cantilevered arms 1184. This may mechanically lock the cantilevered arms 1184 from deflection within the inserter assembly 1000 when the disarming lock 1298 is in the disarm position. As the cantilevered arms 1184 are blocked from deflecting, the casing of the inserter assembly 1000 may be pulled on to disassociate adhesive 374 (see, e.g., FIG. 167) of an attached set cartridge 1002 from the skin 356 of a user. The insertion driver 1062 may be firmly held in engagement with the insertion driver latch arrangement (e.g. shelfs 1187 on the interior housing 120 see, e.g., FIG. 164) as this occurs, preventing the inserter assembly 1000 from actuating. To place the infusion set 102 of the attached set cartridge 1002 at another site, the adhesive 374 may be pressed into engagement with the skin 356 and the disarming lock 1298 may be returned to the inactive position (or removed). With the disarming lock 1298 in the inactive position (or removed) the inserter assembly 1000 may be fired from the ready state as described above in relation to FIG. 168.

In other embodiments, and referring now to FIGS. 177A-177B, the cantilevered arms 1184 may be similarly locked in place via translational displacement of a disarming lock 1298. As shown, the disarming lock may include a post 1355 having a fork portion 1357 at an end thereof. The post 1355 may be accessible from the exterior of the inserter assembly 1000 and may be depressed by a user to drive the arms 1359 of the fork portion 1357 between the cantilevered arms 1184 and the cup wall 1123. This may transition the disarming lock 1298 from an inactive to an active state. Though not shown, a bias member may be included to spring bias the disarming lock 1298 to an inactive state. In other examples, a bias member may be built into the disarming lock 1298. For example, the disarming lock 1298 may include one or more flexure (not shown) which is integrally molded with the remainder of the disarming lock 1298. The flexure(s) may be distorted when the disarming lock 1298 is transitioned to the active state and may restore toward a non-distorted rest state absent user interaction. As the flexure(s) restore, the disarming lock 1298 may be returned to an inactive state.

Referring now to FIGS. 178A-178D, in various examples, a disarming actuator 1310 (shown in isolation in FIG. 178D)

may be included in an inserter assembly 1000. A disarming actuator 1310 may be displaced by a user to prompt a retraction stroke of the retraction spring retainer 1102 absent firing of the inserter assembly 1000. This may return the inserter assembly 1000 to a storage or unarmed state. For example, some disarming actuators 1310 may be operated to cause retraction of the retraction spring retainer 1102 absent disengagement of an insertion prevention latch arrangement. A disarming actuator 1310 may include at least one segment which may be accessible from the exterior of the inserter assembly 1000. A user may displace the external segment to actuate a trigger within the inserter assembly 1000 which initiates the retraction stroke. In certain embodiments, when the disarming actuator 1310 is transitioned to an actuated state, at least one portion of the disarming actuator 1310 may drive retraction latch arms 1190 out of engagement with a retraction spring retainer 1102 of the inserter assembly 1000.

As shown best shown in FIG. 178D, exemplary disarming actuators 1310 may include a button portion 1370. The button portion 1370 may extend through the interior housing 120 and exterior housing 116 and form the external segment of the disarming actuator 1310. Two flanking bodies 1372A, B may extend from opposing sides of the button portion 1370. Each of the flanking bodies 1372A, B may include a post portion 1374 and a clip portion 1376. The clip portion 1376 may couple the disarming actuator 1310 to the retraction latch retainer 1102 such that the disarming actuator 1310 moves in unison with the retraction latch retainer 1102. The clip portion 1376 may include a set of guides 1378 and a set of prongs 1380. The guides 1378 may be disposed within tracks 1382 (see, e.g., FIG. 178C) of the retraction latch retainer 1102. As the disarming actuator 1310 is displaced toward an actuated state, the guides 1378 may ride within the tracks 1382 and the prongs 1380 may displace into contact with the retraction latch arms 1190. As the disarming actuator 1310 reaches the actuated state, the prongs 1380 may splay the retraction latch arms 1190 to a point at which the retraction latch arms 1190 disengage from the retraction latch retainer 1102.

As described elsewhere herein, the retraction latch retainer 1102 may be coupled to the reset body 1110. The reset body 1110 may be in abutment with the interior surface of the retainer cap 406. With the retraction latch arms 1190 disengaged from the retraction latch retainer 1102, spring 1104 may be freed, propelling the retraction latch retainer 1102, reset body 1110, and the casing (e.g. exterior housing 116 and retainer cap 406) through a disarming stroke. At the conclusion of the disarming stroke, the inserter assembly 1000 may be returned to the storage state. As spring 1108 is held in a distorted state between the insertion driver 1062 and the closed end of the cup 1125 of the reset body 1110, spring 1108 may assist in powering the driving the retraction stroke by restoring against the closed end of the cup 1125.

As the disarming stroke occurs, the post portions 1374 of the disarming actuator 1310, which may be coupled to the retraction latch retainer 1102 via the clip portions 1356, may contact and deflect the release fingers 1154 on the retainer cap 406 in a medial direction. This may move paddle bodies 1164 of the release fingers 1154 out of alignment with the routing fins 1183 of the cantilevered bodies 1184 of the insertion driver 1062. Thus, the insertion driver latch arrangement may remain in an engaged state as the disarming stroke transpires. The post portions 1374 of the disarming actuator 1310 may also be spaced apart by a distance greater than the width of the cantilevered arm 1184 at the routing fin 1183. This spacing may ensure that the disarming actuator 1310 will not contact the routing fins 1183 as the disarming actuator 1310 displaces during the disarming stroke. As shown best in FIG. 178B, the interior housing 120 may include a guide aperture 1384 which may accommodate displacement of the disarming actuator 1310 as the inserter assembly 1000 is returned to the storage state via the disarming stroke.

The interior side of the button portion 1370 may include a ramped face 1386. The ramped face 1386 may collide with the underside of the plate 1057 of the insertion driver 1062 as the inserter assembly 1000 returns to the storage state. This may automatically restore the disarming actuator 1310 to an unactuated state. As shown best in FIGS. 178B-178C, a tooth 1388 may be included on the underside of the plate 1057 to assist in returning the disarming actuator 1310 to the unactuated state. Though only one disarming actuator 1310 is shown, disarming actuators 1310 may be included on opposing sides of the inserter assembly 1000 in various embodiments.

In some examples, the post portions 1354 of a disarming actuator 1310 may be omitted as shown in the embodiment depicted in FIGS. 179A-179B. In such embodiments, when the inserter assembly 1000 is in a ready state (shown in FIGS. 179A-179B), transition of the disarming actuator 1310 to the actuated state may splay retraction latch arms 1190 out of an engaged state with the retraction latch retainer 1102. The spring 1104 may drive the retraction spring retainer 1102, reset body 1110, and casing through a disarming stroke. As with FIGS. 178A-178D, the disarming actuator 1310 may displace along with these components as the retraction stroke transpires. The paddle bodies 1164 of the release fingers 1154 may contact the routing fins 1183 of the insertion driver 1062 as the disarming stroke progresses. As a result, the insertion driver 1062 may be disengaged from the insertion driver latch arrangement (e.g. the cantilevered arms 1184 may be wedged off shelves 1187, see FIG. 164). As the in-progress disarming stroke triggers release of the insertion driver 1062, the retraction spring retainer 1102 may rapidly collide with the plate 1057 of the insertion driver 1062. Displacement of the insertion driver 1062 under urging of spring 1108 may quickly be halted and reversed. This may occur before the insertion driver 1062 displaces a distance sufficient for a user to come into contact with any insertion sharp 132 and prior to release of the infusion set base 102 from the retainer arms 1016 of the set cartridge 1002 (see, e.g., FIG. 170).

Referring now to FIGS. 180A-180D, in certain other example embodiments, a disarming actuator 1310 may remain stationary as the retraction stroke occurs. As shown, the disarming actuator 1310 may include a base member 1381 having legs 1383 extending therefrom. As best shown in the cross-section depicted in FIG. 180D, the legs 1383 may extend through the interior housing 120 and into guides 1385 flanking a thickened region 1387 of the retraction latch arms 1190. The disarming actuator 1310 may be pressed toward the interior of the inserter assembly 1000 via a deflectable or deformable section 1379 of the exterior housing 116. The legs 1383 of the disarming actuator 1310 may collide with the thickened regions 1387. The retraction latch arms 1190 may splay out of engagement with the retraction spring retainer 1102 to accommodate the advance of the legs 1383 triggering initiation of a disarming stroke. As with the embodiment of FIGS. 179A-179B, the insertion driver 1062 may be disengaged from the insertion driver latch arrangement, but the retraction spring retainer 1102 may quickly block and reverse travel of the insertion driver 1062 as the retraction spring retainer 1102 progresses through the disarming stroke.

Referring now also to FIGS. 181A-181D, in some examples, the disarming actuator 1310 may be a button 1390 (shown in isolation in FIG. 181C) which may include a set of tines 1392 that extend through slots 1394 in the retaining cap 406 of the inserter assembly 1000. The button 1390 may include an aperture 1396 within which a post 1398 of the retainer cap 406 may be disposed. The button 1390 may be depressed into contact with the exterior surface of the retainer cap 406 by a user to trigger a disarming stroke of the inserter assembly 1000. The post 1398 may interact with the aperture 1396 to guide displacement of the button 1390. At least one of the tines 1392 may include a set of nubs 1400. When the disarming actuator 1310 is in an unactuated position, the nubs 1400 may rest on a set of flexures 1402 defined on the interior housing 120 (best shown in FIG. 181D). The flexures 1402 may hold the disarming actuator 1310 in the unactuated position. The flexures 1402 may deflect out of an obstructing position when pressure is exerted on the button 1390 allowing the disarming actuator 1310 to transition to the actuated state. As best shown in FIG. 181B, the tips 1404 of the tines 1392 may include ramped faces which may collide with the retainer latch arms 1190 spreading them apart from one another. The tines 1392 may be blocked from deflecting medially by the presence of the flange 1134 of the reset body 1110. With the retainer latch arms 1190 splayed apart, the retraction latch body 1102 may be released initiating the disarming stroke. The flexures 1402 may be sufficiently compliant to allow return of the nubs 1400 past the flexures 1402 as the disarming stroke transpires.

Referring now primarily to FIGS. 182A-182B, in certain exemplary embodiments, the exterior segments of the disarming actuator 1310 may be coupled to the retraction latch arms 1190 and directly displace the latch arms 1190 out of engagement with a retraction spring retainer 1102. The exterior housing 116 and interior housing 120 may include respective channels 1312A, B. The channels 1312A, B may be disposed outboard of the retraction latch arms 1190 of the inserter assembly 1000. Each of the retraction latch arms 1190 may include a projection 1314 which extends through the channels 1312A, B to the exterior of the inserter assembly 1000. The projections 1314 may be depressed to deflect the retraction latch arms 1190 out of engagement with the retraction spring retainer 1102. This may mimic the deflection of the retraction latch arms 1190 caused by the insertion drive 1062 when the inserter assembly 1000 is in a retraction release state (further described in relation to, e.g., FIGS. 171A-B). With the retraction latch arms 1190 freed from engagement with the retraction spring retainer 1102, a disarming stroke may occur bringing the inserter assembly 1000 back to the storage state.

Referring now to FIGS. 183A-183B, disarming actuators 1310 may also be included on embodiments in which the retraction latch arms 1190 are pinched inward instead of spread outward to release the retraction spring retainer 1102. An example of the inserter assembly 1000 depicted in FIGS. 157A-D including disarming actuators 1310 is shown in FIGS. 183A-183B. As shown, the exterior housing 116 of the inserter assembly 1000 may include a set of buttons 1410. The buttons 1410 may be formed integrally with the remainder of the exterior housing 116 and may be deflectable with respect to apertures 1414 surrounding the buttons 1410. The buttons 1410 may be formed as cantilevered panels which have an exterior surface that is flush with and mimics the curvature of the exterior housing 116. This may limit potential for the buttons 1410 to be accidentally pressed and may increase comfort when the inserter assembly 1000 is held. As shown, a protuberance 1412 may extend from the interior face of each button 1410. When the inserter assembly 1000 is in a ready state, the protuberances 1412 may be in alignment with the catches 1193 defined on the retraction latch arms 1190. Upon deflection of the buttons 1410 into the inserter assembly 1000, the protuberances 1412 may be driven into the catches 1193 forcing the retraction latch arms 1190 toward one another. As the retraction latch arms 1190 are deflected, the catch 1193 may disengage from the retraction spring retainer 1102 initiating a disarming stroke. The retraction spring retainer 1102 and the insertion driver 1062 may include clearance passages 1416 (best shown in FIG. 157D) which allow the retraction spring retainer 1102 and insertion driver 1062 to displace within the inserter assembly 1000 without colliding with the protuberances 1412.

Referring now to FIGS. 184-188, an example tubing connector 368 (FIGS. 184-185B) and a fixture 480 (FIGS. 186-187) for assembling a tubing connector 368 are depicted. The fixture 480 may aid in assembly of a sharp 482 and infusion tubing 366 (see, e.g. FIG. 6) into a tubing connector 368. The fixture 480 may ensure that the sharp 482 is positioned so as to have an exposed portion 484 of a prescribed length. In various embodiments, this may aid in ensuring that the sharp 482 extends a desired distance into a septum 110 (see e.g. FIG. 5B) when the tubing connector 368 is coupled to an infusion set 102 (see, e.g. FIG. 6). For example, the length of the exposed portion 484 may be sized so as to extend into a fluid introduction volume of the cannula subassembly 114 as described elsewhere herein.

In the example, the sharp 482 is depicted with a lancet tip though other types of sharps may be used. For example, a sharp 482 with a back bevel may be used in certain embodiments. The exemplary sharp 482 (see FIG. 185B) includes a primary grind region 487 which is at an angle (e.g. an angle between 10-20° such as 15.5°) with respect to the longitudinal axis of the sharp 482. A set of secondary grinds 489 are also included and form the point 485 of the sharp 482.

Additionally, the fixture 480 may ensure that the sharp 482 is brought into a prescribed rotational orientation. This may be achieved through the use of magnetism. Thus, tips 486 of sharps 482 of tubing connectors 368 may be uniformly oriented across tubing connectors 368. This may be desirable for a variety of reasons. For example, during the typical usage life of an infusion set 102, the tubing connector 368 may be disconnected and reconnected a number of times. As the tip 486 is ramped, there may be a tendency for the sharp 482 to veer from the axis of insertion as the tubing connector 368 is advanced into engagement with the infusion set base 106. This tendency may be exaggerated with repeated connection and disconnection. By ensuring the tip 486 is always oriented in a particular orientation any veering of the sharp 482 may occur in a predictable direction and the septum 110 may be designed to accommodate such veering. This may allow for the septum 110 to be made smaller in portions where veering of the sharp 482 is not expected to occur. The septum 110 may be made smaller in footprint or height and with less material. Additionally, the fluid introduction volume formed by the septum recess 196 (see, e.g. FIG. 5B) may be made smaller. This would minimize any hold up volume in the infusion set 102 and minimize an amount of drug or agent expended filling this volume. Such rotational alignment of the sharp 482 may allow for a wider variety of tip 486 bevels to be used. It may also minimize any potential for occlusion due to the tip 486 being entirely surround by septum 110 material after a connection is made. Alternatively, it may allow for connection between the infusion set 102 and tubing connector 368 to be made in a more forgiving manner. As a result, the range of acceptable tolerances on various features of the infusion set 102 and tubing connector 368 may be greater. Likewise, the amount of material needed to form guides 172 (see, e.g. FIG. 6) or flanking projection 372 of the tubing connector 368 may be lessened.

As best shown in FIG. 188, the fixture 480 may include a dock 490 for a tubing connector 368. The dock 490 may mimic the mating interface of an infusion set base 106 (see, e.g. FIG. 6) and may, for example, include guides 172' and connector receivers 170'. Thus, the tubing connector 368 may engage the fixture 480 and be retained in fixture 480. The dock 490 may also position the tubing connector 368 in a desired location and orientation on the fixture 480.

The fixture 480 may include an adhesive port 510 (best shown in FIG. 187) which may allow glue, epoxy, or adhesive to be introduced into the tubing connector 368 such that the sharp 482 may be retained in the tubing connector 368 once properly positioned therein. A UV cure adhesive may be used in certain embodiments.

Referring now to FIGS. 189-190, two cross-sectional views of a tubing connector 368 installed on a dock 490 are shown. A sharp 482 is shown being installed into the tubing connector 368 in FIG. 189. The sharp 482 is in place within the tubing connector 368 and rotationally clocked such that the point 485 of the sharp 482 is in a specified position which in the example embodiment is a 12 o'clock position. In the example embodiment, the point 485 of the tip 486 of the sharp 482 is positioned to be substantially in line with and perpendicular to the axis of a lumen 202 of a cannula 104 of the infusion set 102 when the tubing connector 368 is connected thereto. The primary grind 487 and secondary grinds 489 on the tip 486 are also in a downward facing position.

As shown, the fixture 480 includes a first body 498 and a second body 500. The bodies 498, 500 may be coupled together via any suitable method including bonding, welding, adhesive, fasteners, etc. In the example, screws 502 are used to couple the first body 498 and second body 500. The second body 500 may fit within a cavity or slot 504 in the first body 498 which may serve to position the second body 500 with respect to the first body 498. As shown, the second body 500 may include a sloped face 506. The sloped face 506 may have an angle with respect to the axis of the sharp 482 which is substantially equal to the angle of one of the grinds 487, 489 on the sharp 482. In the example, the angle is about 15.5° which is the angle of the primary grind 487 of the sharp 482. The sloped face 506 may include a portion which is in line with a sharp receiving bore 508 of the first body 498. This portion may act as a support surface for a primary grind 487 of a sharp 482. The second body 500 may be constructed of a hard, non-metallic material.

As shown, the fixture 480 may include a first magnet 492 and a second magnet 494. The first magnet 492 may be larger than the second magnet 494. The dimensions of each edge of the second magnet 494 may be half the size of the dimensions of the respective sides of the first magnet 492. In some embodiments, the first magnet 492 may be a ⅛ in×⅛ in×½ in NdFeB magnet. The second magnet 494 may be a 1/16 in×1/16 in×¼ in NdFeB magnet. In alternative embodiments electromagnets which may, for example, be equivalent to the permanent magnets just described may be used. The first magnet 492 and second magnet 494 may be located in channels 496 included in the fixture 480. The channel 496 for the second magnet 494 may be at an angle with respect to the channel 496 for the first magnet 492. In the example embodiment the angle is about 15.5°. The angle may reflect the angle of one of the grinds 487, 489 of the sharp 482. The angle may be the same as that of the sloped face 506 of the second body 500. The first magnet 492 may be oriented such that each of its poles are respectively most proximal to the opposing pole of the second magnet 494. The ends of the magnets 492, 494 are set back from the support surface portion of the sloped face 506. In the example embodiment, the ends of the magnets 492, 494 are set back about 0.060 inches.

As a sharp 482 is introduced into the tubing connector 368, the magnetic fields generated by the magnets 492, 494 may rotate and guide the sharp 482 into the desired rotational orientation. The magnetic fields may also draw the sharp 482 into contact with the sloped face 506 setting the length of the exposed portion 484 of the sharp 482. During introduction of the sharp 482, the sharp 482 may be displaced into the desired position and orientation with no or minimal contact of the point 485 or secondary grinds 489 with any material of the tubing connector 368 or the fixture 480. Only the primary grind 487 of the sharp 482 may rest against the sloped face 506. The beveled sections formed by the secondary grinds 489 as well as the point 485 may not be in contact with the sloped face 506. This may help to ensure that the tip 486 remains sharp and may help prevent any attenuation of the piercing capabilities of the tip 486.

With the sharp 482 in place, infusion tubing 366 may be coupled to the tubing connector 368. The tubing 366 may be introduced into a tubing receptacle 512 of the tubing connector 368. The lumen 514 of the tubing 336 may be placed into fluid communication with the lumen 516 of the sharp 482. The tubing receptacle 512 of the tubing connector 368 may include at least one tapered region 518 which may aid in funneling the tubing 366 into the tubing receptacle 512. Any force exerted on the sharp 482 as the tubing 366 is slid into place may be transmitted into the sloped face 506 through the primary grind 487 of the sharp 482. This may help to ensure the tip 486 of the sharp 482 is protected as the tubing 366 is assembled onto the tubing connector 368.

Once the tubing 366 is in place, an applicator may be advanced into the port 510. Glue or adhesive may be dispensed into an aperture 520 of the tubing connector 368. In some embodiments a UV curing adhesive may be used. UV light may be emitted toward the tubing connector 368 to cure the adhesive and fixedly retain the sharp 482 and tubing 366 onto the tubing connector 368. In some embodiments, UV emitting LEDS (no shown) may be included in the fixture 480 for this purpose, though an external light source may also be utilized. The tubing connector 368 may then be removed from the fixture 480.

Referring now also to FIG. 191, a flowchart 530 depicting a number of example actions which may be executed to assemble a tubing connector 368 is shown. In block 532, a tubing connector 368 may be coupled to a fixture 480. A sharp 482 may be introduced into the tubing connector 368 in block 534. The fixture 480 may be oriented such that the sharp 482 is introduced into the tubing connector 368 along the direction of acceleration due to gravity to allow gravity to assist in the introduction. Magnets 492, 494 in the fixture 480 may orient the sharp 482 in a desired position as the sharp 482 is introduced. In block 536, infusion tubing 366 may be inserted into a tubing receptacle 512 of the tubing connector 368. Adhesive may be applied into the tubing connector 540 in block 538. The adhesive may be cured in block 540. In block 542, the completed tubing connector 368 may be removed from the fixture 480.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. The drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A patient care assembly placement system comprising:

an inserter assembly including a port and a receptacle body, the port having a central slot flanked on opposing sides by segments of a port rim, the receptacle body including a set of shoes each swept about a portion of the port from a closed shoe end to an open shoe end, the shoes each having an overhang region most distal a main section of the receptacle body;

a cartridge including a retainer, a patient care assembly coupled to the retainer, a sharp bearing body from which an insertion sharp projects, the retainer including a set of mating pins each having a stem portion and a wider head portion, the sharp bearing body including a first end opposite a second end from which the insertion sharp projects, the sharp bearing body including a thinned region intermediate the first and second end;

wherein when the cartridge is placed in an aligned position relative the receptacle body and rotated to a coupled state, each mating pin displaces from the open shoe end to the closed shoe end of a respective shoe, the cartridge translationally displacing to a position in which the first end of the sharp bearing body is advanced into the port to a depth where thinned region is aligned with the port rim over a mating pin capture displacement range, the head portion of each mating pin displacing along a ramp of the overhang region of the respective shoe in the mating pin capture displacement range, the first end of the sharp bearing body subsequently being rotated over the port rim in a sharp bearing body capture displacement range.

2. A patient care assembly placement system comprising:

an inserter assembly including a port flanked on opposing sides by shelves and a receptacle body including a set of mating tracks partially swept around the axis of the port;

a cartridge including a retainer, a patient care assembly coupled to the retainer, a sharp holder from which an insertion sharp projects, the retainer including a set of mating projections, the sharp holder including a thinned region intermediate a first end opposite a second end from which the insertion sharp projects;

wherein when the cartridge is placed in an aligned position relative the receptacle body and rotated to a coupled state, the mating projections displace along a ramped region of a respective mating track in a mating projection capture displacement range translationally driving the cartridge to a position in which the first end of the sharp holder is advanced into the port to a depth where thinned region is aligned with the shelves, the first end of the sharp holder subsequently being rotated over the shelves in a sharp holder capture displacement range of the cartridge.

3. The system of claim 2, wherein the mating tracks include shoes with overhanging shoulder segments at a portion of each mating track most distal a main section of the receptacle body.

4. The system of claim 2, wherein the mating projections are each mating pins having a head portion and a relatively thinner stem portion connecting the head portion to the rest of the retainer.

5. The system of claim 2, wherein the port is shaped to accept the first end of the sharp holder when the cartridge is within a rotational position within the mating projection capture displacement range.

6. The system of claim 2, wherein the first end of the sharp holder has an elongate cross-sectional shape and the thinned region has a cross-sectional shape which is less elongate than that of the first end.

7. The system of claim 2, wherein the thinned region is formed by a notch recessed into the sharp holder at an angle which is substantially perpendicular to the axis of the insertion sharp.

8. The system of claim 7, wherein the shelves have a thickness sufficient to substantially fill the notch when the cartridge has been rotated through the sharp holder capture displacement range.

9. The system of claim 2, wherein the ramped region of each respective mating track begins at an open end of that mating track, the mating projections being at a closed end of respective mating tracks when the cartridge is rotated to the coupled state.

10. The system of claim 9, wherein the ramped region of each respective mating track includes a steepest portion along a segment of the ramped region most proximal the open end.

11. The system of claim 2, wherein the patient care assembly is selected from a list consisting of an infusion set and an analyte sensor.

12. The system of claim 2, wherein the patient care assembly includes a first portion and a second portion spaced from the first portion within the cartridge.

13. A patient care assembly placement system comprising:

an inserter assembly including a port having a port coupling interface and a receptacle body including a set of mating tracks partially swept around the axis of the port;

a cartridge including a retainer, a patient care assembly coupled to the retainer, a sharp holder from which an insertion sharp projects, the retainer including a set of projections, the sharp holder including a sharp holder coupling interface disposed opposite a first end of the sharp holder from which the insertion sharp projects;

wherein when the cartridge is placed in an aligned position relative the receptacle body and rotated to a coupled state, the projections displace along a ramped region of a respective mating track in a first displacement range translationally driving the cartridge to a position in which the sharp holder coupling interface is aligned with the port coupling interface, the sharp holder coupling interface being into engagement with the port coupling interface in a second displacement range of the cartridge.

14. The system of claim 13, wherein the port coupling interface and sharp holder coupling interface are threaded interfaces.

15. The system of claim 13, wherein the port coupling interface includes a set of shelves disposed on opposing sides of the port and the sharp holder coupling interface includes a projection having a thinned region which is disposed intermediate the first end and a second end of the sharp holder opposite the first end.

16. The system of claim 15, wherein the second end of the sharp holder is rotated over the set of shelves when the cartridge is rotated through the second displacement range.

17. The system of claim 16, wherein the shelves have a thickness sufficient to substantially fill the notch when the cartridge has been rotated through the second displacement range.

18. The system of claim 13, wherein the cartridge further comprises a housing and a container, the retainer, patient care assembly, and sharp holder being at least partially disposed in the housing.

19. The system of claim 18, wherein the housing includes a set of arms deflectable from a container engaging state in which a portion of each of the set of arms is disposed in a respective recess in the container, and a container release state in which the portion of each of the set of arms is displaced out of the respective recess, the container being disassociated from the remainder of the cartridge when the set of arms are in the container release state.

20. The system of claim 19, wherein the receptacle body includes a set of ramped deflectors positioned to collide with and deflect the set of arms from the container engaging state to the container release state as the cartridge is rotated from the aligned position to the coupled state.

21. The system of claim 20, wherein the receptacle body includes a set of protrusions proud of a main surface of the receptacle body and connected to the remainder of the receptacle body via respective flexures, the flexures configured to permit the projections to be depressed by the container as the cartridge is rotated from the aligned position to the coupled state, the flexures restoring between sets of stop surfaces of the housing when the container is disassociated from the rest of the cartridge and the cartridge is in the coupled state.

22. The system of claim 13, wherein the ramped region of each respective mating track begins at an open end of that mating track, the mating projections being at a closed end of respective mating tracks when the cartridge is rotated to the coupled state.

23. The system of claim 13, wherein the ramped region of each respective mating track includes a steepest portion along a segment of the ramped region most proximal the open end.

* * * * *